US010195288B2

(12) United States Patent
Masuda et al.

(10) Patent No.: US 10,195,288 B2
(45) Date of Patent: *Feb. 5, 2019

(54) ANTIBODY-DRUG CONJUGATE

(71) Applicant: Daiichi Sankyo Company, Limited, Tokyo (JP)

(72) Inventors: Takeshi Masuda, Tokyo (JP); Hiroyuki Naito, Tokyo (JP); Takashi Nakada, Tokyo (JP); Masao Yoshida, Tokyo (JP); Shinji Ashida, Tokyo (JP); Hideki Miyazaki, Tokyo (JP); Yuji Kasuya, Tokyo (JP); Koji Morita, Tokyo (JP); Yuki Abe, Tokyo (JP); Yusuke Ogitani, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/435,114

(22) PCT Filed: Oct. 10, 2013

(86) PCT No.: PCT/JP2013/006069
§ 371 (c)(1),
(2) Date: Apr. 10, 2015

(87) PCT Pub. No.: WO2014/057687
PCT Pub. Date: Apr. 17, 2014

(65) Prior Publication Data
US 2015/0297748 A1    Oct. 22, 2015

(30) Foreign Application Priority Data
Oct. 11, 2012  (JP) ................................. 2012-225887

(51) Int. Cl.
A61K 47/68      (2017.01)
A61K 31/4745    (2006.01)
A61K 31/48      (2006.01)
C07K 16/30      (2006.01)
C07K 16/28      (2006.01)

(52) U.S. Cl.
CPC ...... *A61K 47/6803* (2017.08); *A61K 31/4745* (2013.01); *A61K 31/48* (2013.01); *C07K 16/2803* (2013.01); *C07K 16/2827* (2013.01); *C07K 16/2851* (2013.01); *C07K 16/2875* (2013.01); *C07K 16/2878* (2013.01); *C07K 16/30* (2013.01); *C07K 2317/30* (2013.01); *C07K 2317/77* (2013.01)

(58) Field of Classification Search
None
See application file for complete search history.

(56) References Cited

U.S. PATENT DOCUMENTS

| 5,834,476 | A | 11/1998 | Terasawa et al. |
|---|---|---|---|
| 5,837,673 | A | 11/1998 | Tsujihara et al. |
| 5,892,043 | A | 4/1999 | Tsujihara et al. |
| 6,214,345 | B1 | 4/2001 | Firestone et al. |
| 6,291,671 | B1 | 9/2001 | Inoue et al. |
| 6,835,807 | B1 * | 12/2004 | Susaki ............. A61K 47/48169 530/322 |
| 7,585,491 | B2 | 9/2009 | Govindan |
| 7,833,979 | B2 | 11/2010 | Sullivan et al. |
| 7,837,980 | B2 | 11/2010 | Alley et al. |
| 8,226,945 | B2 | 7/2012 | Ebens, Jr. et al. |
| 8,268,319 | B2 | 9/2012 | Govindan |
| 8,394,607 | B2 | 3/2013 | Ebens, Jr. et al. |
| 8,425,912 | B2 | 4/2013 | Govindan |
| 8,524,865 | B2 | 9/2013 | Ebens, Jr. et al. |
| 8,741,291 | B2 | 6/2014 | Bhat et al. |
| 8,907,071 | B2 | 12/2014 | Sullivan et al. |
| 8,968,741 | B2 | 3/2015 | Ebens et al. |
| 2003/0148931 | A1 | 8/2003 | Takahashi et al. |
| 2003/0166513 | A1 | 9/2003 | Imura et al. |
| 2004/0185053 | A1 | 9/2004 | Govindan |
| 2005/0123536 | A1 | 6/2005 | Law et al. |
| 2005/0228007 | A1 | 10/2005 | Jagtap et al. |
| 2006/0193865 | A1 | 8/2006 | Govindan |

(Continued)

FOREIGN PATENT DOCUMENTS

| CA | 2927832 A1 | 11/2011 |
|---|---|---|
| CA | 2859255 A1 | 6/2013 |

(Continued)

OTHER PUBLICATIONS

Loo et al. ("Loo", Clin. Cancer Res. Jul. 15, 2012, 18, 3834-3845.*
F. Dosio et al., "Antibody-targeted leucinostatin A", Journal of Controlled Release, No. 32, (1994), pp. 37-44.
L. Ducry et al., "Antibody-Drug Conjugates: Linking Cytotoxic Payloads to Monoclonal Antibodies", Bioconjugate Chem., No. 21, (2009), pp. 5-13.
S. Alley et al., "Antibody-drug conjugates: targeted drug delivery for cancer", Current Opinion in Chemical Biology, No. 14, (2010), pp. 529-537.

(Continued)

*Primary Examiner* — Mark Halvorson
*Assistant Examiner* — Kauser M Akhoon
(74) *Attorney, Agent, or Firm* — Foley & Lardner LLP

(57) ABSTRACT

As an antitumor drug which is excellent in terms of antitumor effect and safety, there is provided an antibody-drug conjugate in which an antitumor compound represented by the following formula is conjugated to an antibody via a linker having a structure represented by the following formula:

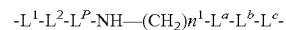

$-L^1-L^2-L^P-NH-(CH_2)n^1-L^a-L^b-L^c-$ wherein the antibody is connected to the terminal of $L^1$, and the antitumor compound is connected to the terminal of $L^c$ with the nitrogen atom of the amino group at position 1 as a connecting position.

35 Claims, 22 Drawing Sheets

Specification includes a Sequence Listing.

(56) References Cited

U.S. PATENT DOCUMENTS

| | | | |
|---|---|---|---|
| 2007/0071764 | A1 | 3/2007 | Sullivan et al. |
| 2008/0050310 | A1 | 2/2008 | Ebens, Jr. et al. |
| 2008/0161245 | A1 | 7/2008 | Kratz et al. |
| 2008/0305044 | A1 | 12/2008 | McDonagh et al. |
| 2009/0274713 | A1 | 11/2009 | Chari et al. |
| 2009/0291093 | A1 | 11/2009 | Govindan |
| 2010/0068181 | A1 | 3/2010 | Paliwal et al. |
| 2010/0120816 | A1 | 5/2010 | Fontana et al. |
| 2011/0045587 | A1 | 2/2011 | Sullivan et al. |
| 2011/0070248 | A1 | 3/2011 | Ichikawa et al. |
| 2011/0293513 | A1 | 12/2011 | Govindan et al. |
| 2012/0121615 | A1 | 5/2012 | Flygare et al. |
| 2012/0201809 | A1 | 8/2012 | Bhat et al. |
| 2012/0328634 | A1 | 12/2012 | Govindan |
| 2013/0123178 | A1 | 5/2013 | Dimarchi et al. |
| 2013/0216561 | A1 | 8/2013 | Govindan |
| 2014/0004078 | A1 | 1/2014 | Govindan |
| 2016/0287722 | A1 | 10/2016 | Govindan |

FOREIGN PATENT DOCUMENTS

| | | | |
|---|---|---|---|
| CN | 101490087 A | 7/2009 | |
| EP | 0 495 432 A1 | 7/1992 | |
| EP | 0 737 686 A1 | 10/1996 | |
| EP | 0 916 348 A1 | 5/1999 | |
| EP | 1 155 702 A1 | 11/2001 | |
| JP | 05-059061 A | 3/1993 | |
| JP | 06-087746 A | 3/1994 | |
| JP | 08-337584 A | 12/1996 | |
| JP | 10-095802 A | 4/1998 | |
| JP | 11-092405 A | 4/1999 | |
| JP | 2002-060351 A | 2/2002 | |
| JP | 2005-511627 A | 4/2005 | |
| JP | 2006-511526 A | 4/2006 | |
| JP | 2007-527872 A | 10/2007 | |
| JP | 2008-521828 A | 6/2008 | |
| JP | 2009-538629 A | 11/2009 | |
| JP | 2010-513524 A | 4/2010 | |
| JP | 2012-100671 A | 5/2012 | |
| JP | 2013-534535 A | 9/2013 | |
| JP | 2013-534906 A | 9/2013 | |
| RU | 2450008 C2 | 7/2010 | |
| TW | 1232930 | 5/2005 | |
| TW | 200817434 A | 4/2008 | |
| WO | WO 1997/46260 A1 | 12/1997 | |
| WO | WO 2000/25825 A1 | 5/2000 | |
| WO | WO 2002/00734 A1 | 1/2002 | |
| WO | WO 03/0156826 A1 | 2/2003 | |
| WO | WO 03/043583 A2 | 5/2003 | |
| WO | WO 2005112919 A2 * | 12/2005 | ........... A61K 31/403 |
| WO | WO 2006/065533 A2 | 6/2006 | |
| WO | WO 2006/092230 A2 | 9/2006 | |
| WO | WO 2011/021397 A1 | 2/2011 | |
| WO | WO 2013/163229 A1 | 10/2013 | |
| WO | WO 2013/188740 A1 | 12/2013 | |
| WO | WO 2014/057687 A1 | 4/2014 | |
| WO | WO 2014/061277 A1 | 4/2014 | |
| WO | WO 2014/107024 A1 | 7/2014 | |

OTHER PUBLICATIONS

N. Damlie, "Tumour-targeted chemotherapy with immunoconjugates of calicheamicin", Expert Opinion, Vacinese & Antibodies, No. 4(9), (2004), pp. 1445-1452.
P. Senter et al., "The discovery and development of brentuximab vedotin for use in relapsed Hodgkin lymphoma and systemic anaplastic large cell lymphoma", Nature Biotechnology, vol. 30, No. 7 (Jul. 2012), pp. 631-637.
E. Kumazawa et al., "Antitumor activity of DX-8951f: a new camptothecin derivative". Expert Opinion Invest Drugs. No. 7(4), (1998), pp. 625-632.
I. Mitsui, "A New Water-soluble Camptothecin Derivative, DX-8951f, Exhibits Potent Antitumor Activity against Human Tumors in vitro and invivo", Japan J. Cancer Res., No. 86, (Aug. 1995), pp. 776-782.
S. Takiguchi et al., "Antitumor Effect of DX-8951, a Novel Camptothecin Analog, on Human Pancreatic Tumor Cells and Their CPT-11-resistant Variants Cultured in vitro and Xenografted into Nude Mice", Japan J. Cancer Res., No. 88 (Aug. 1997), pp. 760-769.
N. Joto et al., "DX-6951f, A water-soluble camptothecin analog, exhibits potent antitumor activity against a human lung cancer call line and its SN-38-resistant variant", Japan J. Cancer, No. 72, (1997), pp. 680-686.
E. Kumazawa et al., "Potent and broad antitumor effects of DX-8951f, a water-soluble camptotecin derivative, against various human tumors xenografted in nude mice", Cancer Chemother Pharmacol, No. 42, (1998), pp. 210-220.
R. De Jager et al., "DX-8951f: summary of phase I clinical trials", Annals New York Academy of Sciences, pp. 260-273.
K. Inoue et al., "CM-Dextran-Polyalcohol-Camptothecin Conjugate", Polymer Drugs in the Clinical Stage, (2003), pp. 145-153.
E. Kumazawa et al., "DE-310, a novel macromolecular carrier system for the camptothecin analog DX-8951f: Potent antitumor activities in various murine tumor models", Cancer Sci, vol. 95, No. 2, (Feb. 2004), pp. 168-175.
O. Soepenberg et al., "PHASE I and Pharmacokinetic Study of DE-310 in Patients with Advanced Solid Tumors", Clinical Cancer Research, vol. 11, (Jan. 15, 2005), pp. 703-711.
M. Wente et al., "DE-310, a Macromolecular prodrug of the topoisomerase-I-inhibitor exatecan (DX-8951), in patients with operable solid tumors", Investigational New Drugs, No. 23 (2005), pp. 339-347.
International Search Report for PCT/JP2013/006069, dated Dec. 17, 2013, 6 pages.
E. Kumazawa et al., "Antitumour activity of DX-8951f: a new camptothecin derivative", Expert Opinion Invest. Drugs, No. 7(4), (1998), pp. 625-632.
N. Joto et al., "DX-8951F, A water-soluble camptothecin analog, exhibits potent antitumor activity against a human lung cancer call line and its SN-38-resistant variant", Japan J. Cancer, No. 72, (1997), pp. 680-686.
International Search Report for PCT/JP2013/006069, dated Dec. 17, 2013, 3 pages.
International Search Report for PCT/JP2013/006178, dated Dec. 17, 2013, 3 pages.
Office Action dated Apr. 22, 2016, in Singapore Application No. 11201502887W.
Supplementary European Search Report dated May 6, 2016, in EP 13845596.9.
Supplementary European Search Report dated May 13, 2016, in EP 13847461.4.
Barginear et al., "Trastuzumab-DM1: A Review of the Novel Immuno-Conjugate for HER2-Overexpressing Breast Cancer," The Open Breast Cancer Journal, Dec. 31, 2009, 1:25-30.
Beck et al., "The Next Generation of Antibody-Drug Conjugates Comes of Age," Discovery Medicine, Oct. 16, 2010, 10(53):329-339.
Nakada et al., "Novel antibody drug conjugates containing exatecan derivative-based cytotoxic payloads," Bioorganic & Medicinal Chemistry Letters, Feb. 8, 2016, 26(6):1542-1545.
Shiose et al., "Relationship between Drug Release of DE-310, Macromolecular Prodrug of DX-8951f, and Cathepsins Activity in Several Tumors," Biol. Pharm. Bull., 2007, 30(12):2365-2370.
Office Action dated Nov. 1, 2016, in Chinese Application No. 201380053256.2.
Office Action dated Dec. 6, 2016, in Japanese Application No. 2016-540705.
Non-Final Office Action dated Oct. 21, 2016, in U.S. Appl. No. 15/187,179.
Decision to Grant dated Oct. 18, 2016, in Japanese Patent Application No. 2016-166850.
Allowance dated Jul. 4, 2017, in JP 2016-117096.

(56) References Cited

OTHER PUBLICATIONS

Burke et al., "Design, Synthesis, and Biological Evaluation of Antibody-Drug Conjugates Comprised of Potent Camptothecin Analogues," Bioconjugate Chemistry, Jun. 17, 2009, 20(6):1242-1250.
Gomez-Monterrey et al., "Design, Synthesis, and Cytotoxic Evaluation of Acyl Derivatives of 3-Aminonaphtho[2,3-b]thiophene-4,9-dione, a Quinone-Based System," Journal of Medicinal Chemistry, 2011, 54(12):4077-4091, abstract.
Interview summary dated Mar. 28, 2017, in CA 2885800.
Masabuchi, N., "Pharmacokinetics of DE-310, a novel macromolecular carrier system for the camptothecin analog DX-8951f, in tumor-bearing mice," Pharmazie, 2004, 59:374-377.
McDonagh et al., "Engineered antibody-drug conjugates with defined sites and stoichiometries of drug attachment," Protein Engineering, Design & Selection, 2006, 19(7):299-307.
Ochi et al., "A possible mechanism for the long-lasting antitumor effect of the macromolecular conjugate DE-310: mediation by cellular uptake and drug release of its active camptothecin analog DX-8951," Cancer Chemotherapy and Pharmacology, Apr. 1, 2005, 55(4):323-332.
Office Action dated May 15, 2017, in TW 102136742.
Office Action with Search Report dated Aug. 29, 2017, in RU 2015113767.
Opposition dated May 3, 2017, against CO NC2016/0000187, with partial English translation.
Shiose et al., "Systematic Research of Peptide Spacers Controlling Drug Release from Macromolecular Prodrug System, Carboxymethyldextran Polyalcohol-Peptide-Drug Conjugates," Bioconjuqate Chem., Jan. 1, 2009, 20(1):60-70.
Soepenberg et al., "Liquid chromatographic assays for DE-310, a novel camptothecin analog, and two major enzymatic products in human matrices," Journal of Chromatography B, 2004, 799:15-22.
Supplementary European Search Report dated Aug. 11, 2017, in EP 15776810.2.
Supplementary European Search Report dated Aug. 9, 2017, in EP 15743738.5.
Supplementary European Search Report dated May 10, 2017 in EP 14874745.4.
Office Action dated Apr. 13, 2018, in Canadian Application No. 2939802.
Office Action dated Jul. 30, 2018, in TW 104111534.
Behrens et al., "Methods for site-specific drug conjugation to antibodies," mAbs, 2014 (online Sep. 27, 2013), 6(1):46-53.
Shen et al., "Conjugation site modulates the in vivo stability and therapeutic activity of antibody-drug conjugates," Nature Biotechnology, 2012, 30:184-189.
Office Action dated Oct. 11, 2018, in RU 2016123597, with English translation.
Barok et al., "Trastuzumab-DM1 is highly effective in preclinical models of HER2-positive gastric cancer," Cancer Letters, Jul. 28, 2011, 306(2):171-179.
Oguma et al., "Validation study of a method for assaying DE-310, a macromolecular carrier conjugate containing an anti-tumor camptothecin derivative, and the free drug in tumor tissue by high performance liquid chromatography/atmospheric pressure chemical ionization tandem mass spectrometry," Biomedical Chromatography, 2005 (online Oct. 13, 2004), 19(1):19-26.

\* cited by examiner

Fig. 1

Amino acid sequence of B7-H3 variant 1 (SEQ ID NO: 1)

MLRRRGSPGMGVHVGAALGALWFCLTGALEVQVPEDPVVALVGTD
ATLCCSFSPEPGFSLAQLNLIWQLTDTKQLVHSFAEGQDQGSAYA
NRTALFPDLLAQGNASLRLQRVRVADEGSFTCFVSIRDFGSAAVS
LQVAAPYSKPSMTLEPNKDLRPGDTVTITCSSYQGYPEAEVFWQD
GQGVPLTGNVTTSQMANEQGLFDVHSILRVVLGANGTYSCLVRNP
VLQQDAHSSVTITPQRSPTGAVEVQVPEDPVVALVGTDATLRCSF
SPEPGFSLAQLNLIWQLTDTKQLVHSFTEGRDQGSAYANRTALFP
DLLAQGNASLRLQRVRVADEGSFTCFVSIRDFGSAAVSLQVAAPY
SKPSMTLEPNKDLRPGDTVTITCSSYRGYPEAEVFWQDGQGVPLT
GNVTTSQMANEQGLFDVHSVLRVVLGANGTYSCLVRNPVLQQDAH
GSVTITGQPMTFPPEALWVTVGLSVCLIALLVALAFVCWRKIKQS
CEEENAGAEDQDGEGEGSKTALQPLKHSDSKEDDGQEIA

Fig. 2

Amino acid sequence of B7-H3 variant 2 (SEQ ID NO: 2)

MLRRRGSPGMGVHVGAALGALWFCLTGALEVQVPEDPVVALVGTD
ATLCCSFSPEPGFSLAQLNLIWQLTDTKQLVHSFAEGQDQGSAYA
NRTALFPDLLAQGNASLRLQRVRVADEGSFTCFVSIRDFGSAAVS
LQVAAPYSKPSMTLEPNKDLRPGDTVTITCSSYRGYPEAEVFWQD
GQGVPLTGNVTTSQMANEQGLFDVHSVLRVVLGANGTYSCLVRNP
VLQQDAHGSVTITGQPMTFPPEALWVTVGLSVCLIALLVALAFVC
WRKIKQSCEEENAGAEDQDGEGEGSKTALQPLKHSDSKEDDGQEI
A

Fig. 3

Amino acid sequence of M30-H1-type heavy chain (SEQ ID NO: 9)

MKHLWFFLLLVAAPRWVLSQVQLVQSGAEVKKPGSSVKVSCKASG
YTFTNYVMHWVRQAPGQGLEWMGYINPYNDDVKYNEKFKGRVTIT
ADESTSTAYMELSSLRSEDTAVYYCARWGYYGSPLYYFDYWGQGT
LVTVSSASTKGPSVFPLAPSSKSTSGGTAALGCLVKDYFPEPVTV
SWNSGALTSGVHTFPAVLQSSGLYSLSSVVTVPSSSLGTQTYICN
VNHKPSNTKVDKRVEPKSCDKTHTCPPCPAPELLGGPSVFLFPPK
PKDTLMISRTPEVTCVVVDVSHEDPEVKFNWYVDGVEVHNAKTKP
REEQYNSTYRVVSVLTVLHQDWLNGKEYKCKVSNKALPAPIEKTI
SKAKGQPREPQVYTLPPSREEMTKNQVSLTCLVKGFYPSDIAVEW
ESNGQPENNYKTTPPVLDSDGSFFLYSKLTVDKSRWQQGNVFSCS
VMHEALHNHYTQKSLSLSPGK

Fig. 4

Amino acid sequence of M30-H2-type heavy chain (SEQ ID NO: 10)

MKHLWFFLLLVAAPRWVLSQVQLVQSGAEVKKPGSSVKVSCKASG
YTFTNYVMHWVRQAPGQGLEWIGYINPYNDDVKYNEKFKGRVTIT
ADESTSTAYMELSSLRSEDTAVYYCARWGYYGSPLYYFDYWGQGT
LVTVSSASTKGPSVFPLAPSSKSTSGGTAALGCLVKDYFPEPVTV
SWNSGALTSGVHTFPAVLQSSGLYSLSSVVTVPSSSLGTQTYICN
VNHKPSNTKVDKRVEPKSCDKTHTCPPCPAPELLGGPSVFLFPPK
PKDTLMISRTPEVTCVVVDVSHEDPEVKFNWYVDGVEVHNAKTKP
REEQYNSTYRVVSVLTVLHQDWLNGKEYKCKVSNKALPAPIEKTI
SKAKGQPREPQVYTLPPSREEMTKNQVSLTCLVKGFYPSDIAVEW
ESNGQPENNYKTTPPVLDSDGSFFLYSKLTVDKSRWQQGNVFSCS
VMHEALHNHYTQKSLSLSPGK

Fig. 5

Amino acid sequence of M30-H3-type heavy chain (SEQ ID NO: 11)

MKHLWFFLLLVAAPRWVLSEVQLVQSGAEVKKPGSSVKVSCKASG
YTFTNYVMHWVKQAPGQGLEWIGYINPYNDDVKYNEKFKGKATIT
ADESTSTAYMELSSLRSEDTAVYYCARWGYYGSPLYYFDYWGQGT
LVTVSSASTKGPSVFPLAPSSKSTSGGTAALGCLVKDYFPEPVTV
SWNSGALTSGVHTFPAVLQSSGLYSLSSVVTVPSSSLGTQTYICN
VNHKPSNTKVDKRVEPKSCDKTHTCPPCPAPELLGGPSVFLFPPK
PKDTLMISRTPEVTCVVVDVSHEDPEVKFNWYVDGVEVHNAKTKP
REEQYNSTYRVVSVLTVLHQDWLNGKEYKCKVSNKALPAPIEKTI
SKAKGQPREPQVYTLPPSREEMTKNQVSLTCLVKGFYPSDIAVEW
ESNGQPENNYKTTPPVLDSDGSFFLYSKLTVDKSRWQQGNVFSCS
VMHEALHNHYTQKSLSLSPGK

Fig. 6

Amino acid sequence of M30-H4-type heavy chain (SEQ ID NO: 12)

MKHLWFFLLLVAAPRWVLSEVQLVQSGAEVKKPGSSVKVSCKASG
YTFTNYVMHWVKQAPGQGLEWIGYINPYNDDVKYNEKFKGKATQT
SDKSTSTAYMELSSLRSEDTAVYYCARWGYYGSPLYYFDYWGQGT
LVTVSSASTKGPSVFPLAPSSKSTSGGTAALGCLVKDYFPEPVTV
SWNSGALTSGVHTFPAVLQSSGLYSLSSVVTVPSSSLGTQTYICN
VNHKPSNTKVDKRVEPKSCDKTHTCPPCPAPELLGGPSVFLFPPK
PKDTLMISRTPEVTCVVVDVSHEDPEVKFNWYVDGVEVHNAKTKP
REEQYNSTYRVVSVLTVLHQDWLNGKEYKCKVSNKALPAPIEKTI
SKAKGQPREPQVYTLPPSREEMTKNQVSLTCLVKGFYPSDIAVEW
ESNGQPENNYKTTPPVLDSDGSFFLYSKLTVDKSRWQQGNVFSCS
VMHEALHNHYTQKSLSLSPGK

Fig. 7

Amino acid sequence of M30-L1-type light chain (SEQ ID NO: 13)

MVLQTQVFISLLLWISGAYGEIVLTQSPATLSLSPGERATLSCRA
SSRLIYMHWYQQKPGQAPRLLIYATSNLASGIPARFSGSGSGTDF
TLTISRLEPEDFAVYYCQQWNSNPPTFGQGTKVEIKRTVAAPSVF
IFPPSDEQLKSGTASVVCLLNNFYPREAKVQWKVDNALQSGNSQE
SVTEQDSKDSTYSLSSTLTLSKADYEKHKVYACEVTHQGLSSPVT
KSFNRGEC

Fig. 8

Amino acid sequence of M30-L2-type light chain (SEQ ID NO: 14)

MVLQTQVFISLLLWISGAYGEIVLTQSPATLSLSPGERATLSCRA
SSRLIYMHWYQQKPGQAPRLWIYATSNLASGIPARFSGSGSGTDY
TLTISRLEPEDFAVYYCQQWNSNPPTFGQGTKVEIKRTVAAPSVF
IFPPSDEQLKSGTASVVCLLNNFYPREAKVQWKVDNALQSGNSQE
SVTEQDSKDSTYSLSSTLTLSKADYEKHKVYACEVTHQGLSSPVT
KSFNRGEC

Fig. 9

Amino acid sequence of M30-L3-type light chain (SEQ ID NO: 15)

MVLQTQVFISLLLWISGAYGQIVLSQSPATLSLSPGERATLTCRA
SSRLIYMHWYQQKPGSAPKLWIYATSNLASGIPARFSGSGSGTSY
TLTISRLEPEDFAVYYCQQWNSNPPTFGQGTKVEIKRTVAAPSVF
IFPPSDEQLKSGTASVVCLLNNFYPREAKVQWKVDNALQSGNSQE
SVTEQDSKDSTYSLSSTLTLSKADYEKHKVYACEVTHQGLSSPVT
KSFNRGEC

Fig. 10

Amino acid sequence of M30-L4-type light chain (SEQ ID NO: 16)

MVLQTQVFISLLLWISGAYGEIVLTQSPATLSLSPGERATLSCRA
SSRLIYMHWYQQKPGQAPRPLIYATSNLASGIPARFSGSGSGTDF
TLTISSLEPEDFAVYYCQQWNSNPPTFGQGTKVEIKRTVAAPSVF
IFPPSDEQLKSGTASVVCLLNNFYPREAKVQWKVDNALQSGNSQE
SVTEQDSKDSTYSLSSTLTLSKADYEKHKVYACEVTHQGLSSPVT
KSFNRGEC

Fig. 11

Amino acid sequence of M30-L5-type light chain (SEQ ID NO: 17)

MVLQTQVFISLLLWISGAYGQIVLSQSPATLSLSPGERATLTCRA
SSRLIYMHWYQQKPGSAPKPWIYATSNLASGIPARFSGSGSGTSY
TLTISRLEPEDFAVYYCQQWNSNPPTFGQGTKVEIKRTVAAPSVF
IFPPSDEQLKSGTASVVCLLNNFYPREAKVQWKVDNALQSGNSQE
SVTEQDSKDSTYSLSSTLTLSKADYEKHKVYACEVTHQGLSSPVT
KSFNRGEC

Fig. 12

Amino acid sequence of M30-L6-type light chain (SEQ ID NO: 18)

MVLQTQVFISLLLWISGAYGEIVLTQSPATLSLSPGERATLSCRA
SSRLIYMHWYQQKPGQAPRPLIYATSNLASGIPARFSGSGSGTDF
TLTISRLEPEDFAVYYCQQWNSNPPTFGQGTKVEIKRTVAAPSVF
IFPPSDEQLKSGTASVVCLLNNFYPREAKVQWKVDNALQSGNSQE
SVTEQDSKDSTYSLSSTLTLSKADYEKHKVYACEVTHQGLSSPVT
KSFNRGEC

Fig. 13

Amino acid sequence of M30-L7-type light chain (SEQ ID NO: 19)

MVLQTQVFISLLLWISGAYGEIVLTQSPATLSLSPGERATLSCRA
SSRLIYMHWYQQKPGQAPRPLIYATSNLASGIPARFSGSGSGTDY
TLTISRLEPEDFAVYYCQQWNSNPPTFGQGTKVEIKRTVAAPSVF
IFPPSDEQLKSGTASVVCLLNNFYPREAKVQWKVDNALQSGNSQE
SVTEQDSKDSTYSLSSTLTLSKADYEKHKVYACEVTHQGLSSPVT
KSFNRGEC

Fig. 14

Amino acid sequence of M30 antibody heavy chain (SEQ ID NO: 20)

MEWSWIFLFLLSGTAGVHSEVQLQQSGPELVKPGASVKMSCKASG
YTFTNYVMHWVKQKPGQGLEWIGYINPYNDDVKYNEKFKGKATQT
SDKSSSTAYMELSSLTSEDSAVYYCARWGYYGSPLYYFDYWGQGT
TLTVSSAKTTAPSVYPLAPVCGDTTGSSVTLGCLVKGYFPEPVTL
TWNSGSLSSGVHTFPAVLQSDLYTLSSSVTVTSSTWPSQSITCNV
AHPASSTKVDKKIEPRGPTIKPCPPCKCPAPNLLGGPSVFIFPPK
IKDVLMISLSPIVTCVVVDVSEDDPDVQISWFVNNVEVHTAQTQT
HREDYNSTLRVVSALPIQHQDWMSGKEFKCKVNNKDLPAPIERTI
SKPKGSVRAPQVYVLPPPEEEMTKKQVTLTCMVTDFMPEDIYVEW
TNNGKTELNYKNTEPVLDSDGSYFMYSKLRVEKKNWVERNSYSCS
VVHEGLHNHHTTKSFSRTPGK

Fig. 15

Amino acid sequence of M30 antibody light chain (SEQ ID NO: 21)

MDFLVQIFSFLLISASVIMSRGQIVLSQSPTILSASPGEKVTMTC
RASSRLIYMHWYQQKPGSSPKPWIYATSNLASGVPARFSGSGSGT
SYSLTISRVEAEDAATYYCQQWNSNPPTFGTGTKLELKRADAAPT
VSIFPPSSEQLTSGGASVVCFLNNFYPKDINVKWKIDGSERQNGV
LNSWTDQDSKDSTYSMSSTLTLTKDEYERHNSYTCEATHKTSTSP
IVKSFNRNEC

Fig. 16

Nucleotide sequence of B7-H3 variant 1 (SEQ ID NO: 26)

atgctgcgtcggcggggcagccctggcatgggtgtgcatgtgggt
gcagccctgggagcactgtggttctgcctcacaggagccctggag
gtccaggtccctgaagacccagtggtggcactggtgggcaccgat
gccaccctgtgctgctccttctccctgagcctggcttcagcctg
gcacagctcaacctcatctggcagctgacagataccaaacagctg
gtgcacagctttgctgagggcaggaccagggcagcgcctatgcc
aaccgcacggccctcttcccggacctgctggcacagggcaacgca
tccctgaggctgcagcgcgtgcgtgtggcggacgagggcagcttc
acctgcttcgtgagcatccgggatttcggcagcgctgccgtcagc
ctgcaggtggccgctccctactcgaagcccagcatgaccctggag
cccaacaaggacctgcggccaggggacacggtgaccatcacgtgc
tccagctaccagggctaccctgaggctgaggtgttctggcaggat
gggcagggtgtgcccctgactggcaacgtgaccacgtcgcagatg
gccaacgagcagggcttgtttgatgtgcacagcatcctgcgggtg
gtgctgggtgcaaatggcacctacagctgcctggtgcgcaaccct
gtgctgcagcaggatgcgcacagctctgtcaccatcacacccccag
agaagcccacaggagccgtggaggtccaggtccctgaggacccg
gtggtggccctagtgggcaccgatgccaccctgcgctgctccttc
tccccgagcctggcttcagcctggcacagctcaacctcatctgg
cagctgacagacaccaaacagctggtgcacagtttcaccgaaggc
cggaccagggcagcgcctatgccaaccgcacggccctcttcccg
gacctgctggcacaaggcaatgcatccctgaggctgcagcgcgtg
cgtgtggcggacgagggcagcttcacctgcttcgtgagcatccgg
gatttcggcagcgctgccgtcagcctgcaggtggccgctccctac
tcgaagcccagcatgaccctggagcccaacaaggacctgcggcca
gggacacggtgaccatcacgtgctccagctaccggggctaccct
gaggctgaggtgttctggcaggatgggcagggtgtgcccctgact
ggcaacgtgaccacgtcgcagatggccaacgagcagggcttgttt
gatgtgcacagcgtcctgcgggtggtgctgggtgcgaatggcacc
tacagctgcctggtgcgcaaccccgtgctgcagcaggatgcgcac
ggctctgtcaccatcacagggcagcctatgacattccccccagag
gccctgtgggtgaccgtggggctgtctgtctgtctcattgcactg
ctggtggccctggcttcgtgtgctggagaaagatcaaacagagc
tgtgaggaggagaatgcaggagctgaggaccaggatggggaggga
gaaggctccaagacagccctgcagcctctgaaacactctgacagc
aaagaagatgatgggcaagaaatagccgagcggccgcactgtg
ctggatatctgcagaattccaccacactggactagtggatccgag
ctcggtaccaagcttaagtttaaaccgctgatcagcctcgactgt
ttccttgacccctggaaggtgccactcccactgtcctttcctaata
aaatgaggaaattgc

ANTIBODY-DRUG CONJUGATE

CROSS-REFERENCE TO RELATED APPLICATIONS

This application is the National Phase of PCT/JP2013/006069, filed Oct. 10, 2013, which claims priority to Japanese Application No. 2012-225887, filed Oct. 11, 2012.

The instant application contains a Sequence Listing which has been submitted in ASCII format via EFS-WEB and is hereby incorporated by reference in its entirety. Said ASCII copy, created on Jun. 29, 2015, is named Revised_sequence.txt and is 68.1 KB.

TECHNICAL FIELD

The present invention relates to an antibody-drug conjugate having an antitumor drug conjugated to an antibody capable of targeting tumor cells via a linker structure moiety, the conjugate being useful as an antitumor drug.

BACKGROUND ART

An antibody-drug conjugate (ADC) having a drug with cytotoxicity conjugated to an antibody, whose antigen is expressed on a surface of cancer cells and which also binds to an antigen capable of cellular internalization, and therefore can deliver the drug selectively to cancer cells and is thus expected to cause accumulation of the drug within cancer cells and to kill the cancer cells (see, Non Patent Literatures 1 to 3). As an ADC, Mylotarg (Gemtuzumab ozogamicin) in which calicheamicin is conjugated to an anti-CD33 antibody is approved as a therapeutic agent for acute myeloid leukemia. Further, Adcetris (Brentuximab vedotin), in which auristatin E is conjugated to an anti-CD30 antibody, has recently been approved as a therapeutic agent for Hodgkin's lymphoma and anaplastic large cell lymphoma (see, Non Patent Literature 4). The drugs contained in ADCs which have been approved until now target DNA or tubulin.

With regard to an antitumor, low-molecular-weight compounds, camptothecin derivatives, compounds that inhibit topoisomerase I to exhibit an antitumor effect, are known. Among them, an antitumor compound represented by the formula below

[Formula 1]

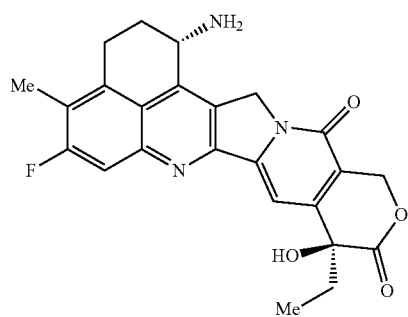

(exatecan, chemical name: (1S,9S)-1-amino-9-ethyl-5-fluoro-2,3-dihydro-9-hydroxy-4-methyl-1H,12H-benzo[de]pyrano[3',4':6,7]indolizino[1,2-b]quinolin-10,13(9H,15H)-dione) is a water soluble derivative of camptothecin (Patent Literature 1 and 2). Unlike irinotecan currently used in clinical settings, an activation by an enzyme is unnecessary. Further, the inhibitory activity on topoisomerase I is higher than SN-38 which is a main pharmaceutically active substance of irinotecan and topotecan also used in clinical settings, and higher in vitro cytocidal activity is obtained for against various cancer cells. In particular, it exhibits the effect against cancer cells which have resistance to SN-38 or the like due to expression of P-glycoprotein. Further, in a human tumor subcutaneously transplanted mouse model, it exhibited a potent antitumor effect, and thus has undergone the clinical studies, but has not been put on the market yet (see, Non Patent Literatures 5 to 10). It remains unclear whether or not exatecan functions effectively as an ADC.

DE-310 is a complex in which exatecan is conjugated to a biodegradable carboxymethyldextran polyalcohol polymer via a GGFG peptide spacer (Patent Literature 3). By converting exatecan into a form of a polymer prodrug, so that a high blood retention property can be maintained and also a high targetable property to a tumor area is passively increased by utilizing the increased permeability of newly formed blood vessels within tumor and retention property in tumor tissues. With DE-310, through a cleavage of the peptide spacer by enzyme, exatecan and exatecan with glycine connected to an amino group are continuously released as a main active substance. As a result, the pharmacokinetics are improved and DE-310 was found to have higher effectiveness than exatecan administered alone even though the dosage of exatecan is lower than the case of administration of exatecan alone according to various tumor evaluation models in non-clinical studies. A clinical study was conducted for DE-310, and effective cases were confirmed in humans, in which a report suggesting that the main active substance accumulates in a tumor than in normal tissues was present, however, there is also a report indicating that the accumulation of DE-310 and the main active substance in a tumor is not much different from the accumulation in normal tissues in humans, and thus no passive targeting is observed in humans (see, Non Patent Literatures 11 to 14). As a result, DE-310 was not also commercialized, and it remains unclear whether or not exatecan effectively functions as a drug oriented for such targeting.

As a compound relating to DE-310, a complex in which a structure moiety represented by —NH(CH$_2$)$_4$C(=O)— is inserted between -GGFG-spacer and exatecan to form -GGFG-NH(CH$_2$)$_4$C(=O)— used as a spacer structure is also known (Patent Literature 4). However, the antitumor effect of the complex is not known at all.

CITATION LIST

Patent Literature

[Patent Literature 1] Japanese Patent Laid-Open No. 5-59061
[Patent Literature 2] Japanese Patent Laid-Open No. 8-337584
[Patent Literature 3] International Publication No. WO 1997/46260
[Patent Literature 4] International Publication No. WO 2000/25825

Non Patent Literature

[Non Patent Literature 1] Ducry, L., et al. Bioconjugate Chem. (2010) 21, 5-13; Antibody-Drug Conjugates: Linking cytotoxic payloads to monoclonal antibodies.

[Non Patent Literature 2] Alley, S. C., et al. Current Opinion in Chemical Biology (2010) 14, 529-537; Antibody-drug conjugates: targeted drug delivery for cancer.

[Non Patent Literature 3] Damle N. K. Expert Opin. Biol. Ther. (2004) 4, 1445-1452; Tumour-targeted chemotherapy with immunoconjugates of calicheamicin.

[Non Patent Literature 4] Senter P. D., et al. Nature Biotechnology (2012) 30, 631-637; The discovery and development of brentuximab vedotin for use in relapsed Hodgkin lymphoma and systemic anaplastic large cell lymphoma.

[Non Patent Literature 5] Kumazawa, E., Tohgo, A., Exp. Opin. Invest. Drugs (1998) 7, 625-632; Antitumour activity of DX-8951f: a new camptothecin derivative.

[Non Patent Literature 6] Mitsui, I., Kumazawa, E., Hirota, Y., et al. Jpn J. Cancer Res. (1995) 86, 776-782; A new water-soluble camptothecin derivative, DX-8951f, exhibits potent antitumor activity against human tumors in vitro and in vivo.

[Non Patent Literature 7] Takiguchi, S., Tohgo, A., et al. Jpn J. Cancer Res. (1997) 88, 760-769; Antitumor effect of DX-8951, a novel camptothecin analog, on human pancreatic tumor cells and their CPT-11-resistant variants cultured in vitro and xenografted into nude mice.

[Non Patent Literature 8] Joto, N. et al. Int J Cancer (1997) 72, 680-686; DX-8951f, a water-soluble camptothecin analog, exhibits potent antitumor activity against a human lung cancer cell line and its SN-38-resistant variant.

[Non Patent Literature 9] Kumazawa, E. et al. Cancer Chemother. Pharmacol. (1998) 42, 210-220; Potent and broad antitumor effects of DX-8951f, a water-soluble camptothecin derivative, against various human tumors xenografted in nude mice.

[Non Patent Literature 10] De Jager, R., et al. Ann N Y Acad Sci (2000) 922, 260-273; DX-8951f: summary of phase I clinical trials.

[Non Patent Literature 11] Inoue, K. et al. Polymer Drugs in the Clinical Stage, Edited by Maeda et al. (2003), 145-153; CM-dextran-polyalcohol-camptothecin conjugate, DE-310 with a novel carrier system and its preclinical data.

[Non Patent Literature 12] Kumazawa, E. et al. Cancer Sci (2004) 95, 168-175; DE-310, a novel macromolecular carrier system for the camptothecin analog DX-8951f: Potent antitumor activities in various murine tumor models.

[Non Patent Literature 13] Soepenberg, O. et al. Clinical Cancer Research, (2005) 11, 703-711; Phase I and pharmacokinetic study of DE-310 in Patients with Advanced Solid Tumors.

[Non Patent Literature 14] Wente M. N. et al. Investigational New Drugs (2005) 23, 339-347; DE-310, a macromolecular prodrug of the topoisomerase-I-inhibitor exatecan (DX-8951), in patients with operable solid tumors.

SUMMARY OF INVENTION

Technical Problem

With regard to the treatment of tumor by an antibody, an insufficient antitumor effect may be observed even when the antibody recognizes an antigen and binds to tumor cells, and there is a case in which a more effective antitumor antibody is needed. Further, many antitumor low-molecular-weight compounds have a problem in safety like side effect and toxicity even the compounds have an excellent antitumor effect, it remains as a subject to achieve a superior therapeutic effect by further enhancing the safety. Thus, an object of the present invention is to obtain to provide an antitumor drug having an excellent therapeutic effect, which is excellent in terms of antitumor effect and safety.

Means to Solve the Problem

The inventors thought that, when an antitumor compound exatecan is converted into an antibody-drug conjugate, via a linker structure moiety, by conjugation to the antibody, which is capable of targeting tumor cells, that is having a property of recognizing tumor cells, a property of binding to tumor cells, a property of internalizing within tumor cells, a cytocidal activity against tumor cells, or the like, the antitumor compound can be more surely delivered to tumor cells to specifically exhibit the antitumor effect of the compound in tumor cells, and thus the antitumor effect can be surely exhibited and also an enhanced cytocidal effect of the antibody is expected, and a dose of the antitumor compound can be reduced compared to a case of administering the compound alone, and thus an influence of the antitumor compound on normal cells can be alleviated so that higher safety can be achieved.

In this connection, the inventors created a linker with a specific structure and succeeded in obtaining an antibody-drug conjugate in which the antibody and exatecan are conjugated to each other via the linker, and confirmed an excellent antitumor effect exhibited by the conjugate to thereby complete the present invention.

Specifically, the present invention relates to the followings.

[1] An antibody-drug conjugate wherein an antitumor compound represented by the following formula:

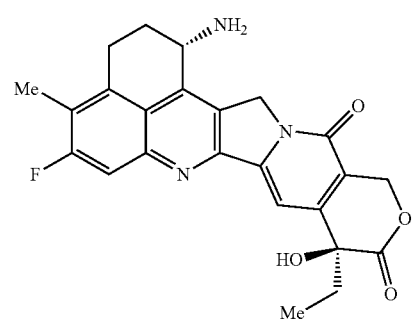

[Formula 2]

is conjugated to an antibody via a linker having a structure represented by the following formula:

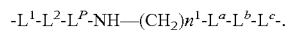

Here, the antibody is connected to the terminal of $L^1$, the antitumor compound is connected to the terminal of $L^c$ with the nitrogen atom of the amino group at position 1 as connecting position, wherein $n^1$ represents an integer of 0 to 6, $L^1$ represents -(Succinimid-3-yl-N)—$(CH_2)n^2$-C(=O)—, —$CH_2$—C(=O)—NH—$(CH_2)n^3$-C(=O)—, —C(=O)-cyc.Hex(1,4)-$CH_2$—(N-ly-3-diminiccuS)-, or —C(=O)—$(CH_2)n^4$-C(=O)—, wherein $n^2$ represents an integer of 2 to 8, $n^3$ represents an integer of 1 to 8, $n^4$ represents an integer of 1 to 8, $L^2$ represents —NH—$(CH_2$—$CH_2$—O)$n^5$-$CH_2$—$CH_2$—C(=O)—, —S—$(CH_2)n^6$-C(=O)—, or a single bond, wherein $n^5$ represents an integer of 1 to 6, $n^6$ represents an integer of 1 to 6, $L^P$ represents a peptide residue consisting of 2 to 7 amino acids, $L^a$ represents —C(=O)—NH—, —NR$^1$—(CH$_2$)n$^7$-, —O—, or a single bond, wherein $n^7$ represents an integer of 1 to 6, $R^1$ represents a hydrogen atom, an alkyl group having 1 to 6 carbon atoms, —(CH$_2$)n$^8$-COOH, or —(CH$_2$)n$^9$-OH, $n^8$ represents an integer of 1 to 4, $n^9$ represents an integer of 1 to 6, $L^b$ represents —CR$^2$(—R$^3$)—, —O—, —NR$^4$—, or a single bond, wherein $R^2$ and $R^3$ each independently represents a hydrogen atom, an alkyl group having 1 to 6 carbon atoms, —(CH$_2$)n$^a$-NH$_2$, —(CH$_2$)n$^b$-COOH, or —(CH$_2$)n$^c$-OH, $R^4$ represents a hydrogen atom or an alkyl group having 1 to 6 carbon atoms, $n^a$ represents an integer of 0 to 6, $n^b$ represents an integer of 1 to 4, $n^c$ represents an integer of 1 to 4, provided that when $n^a$ is 0, $R^2$ and $R^3$ are not the same as each other, $L^c$ represents —CH$_2$— or —C(=O)—, -(Succinimid-3-yl-N)— has a structure represented by the following formula:

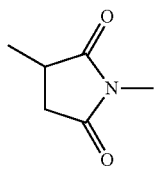

[Formula 3]

which is connected to the antibody at position 3 thereof and is connected to a methylene group in the linker structure containing this structure on the nitrogen atom at position 1, —(N-ly-3-diminiccuS)- has a structure represented by the following formula:

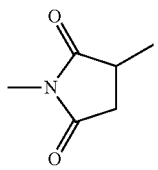

[Formula 4]

which is connected to $L^2$ at position 3 thereof and is connected to a methylene group in the linker structure containing this structure on the nitrogen atom at position 1, cyc.Hex(1,4) represents a 1,4-cyclohexylene group, and when $L^2$ is —S—(CH$_2$)n$^6$-C(=O)—, $L^1$ is —C(=O)-cyc.Hex(1,4)-CH$_2$—(N-ly-3-diminiccuS)-.

The present invention further relates to each of the followings.

[2] The antibody-drug conjugate according to [1], wherein $L^c$ is —C(=O)—.

[3] The antibody-drug conjugate according to [1] or [2], wherein the bond between the antibody and $L^1$ is a thioether bond which is formed at a disulfide bond site present in a hinge part of the antibody, a disulfide bond which is formed at a disulfide bond site present in a hinge part of the antibody, or an amide bond which is formed at an amino group present on a side chain of an amino acid constituting the antibody or at the terminal amino group.

[4] The antibody-drug conjugate according to any one of [1] to [3], wherein the peptide residue of $L^P$ is an amino acid residue comprising an amino acid selected from phenylalanine, glycine, valine, lysine, citrulline, serine, glutamic acid, and aspartic acid.

[5] The antibody-drug conjugate according to any one of [1] to [3], wherein $L^P$ is a peptide residue consisting of 4 amino acids.

[6] The antibody-drug conjugate according to any one of [1] to [3], wherein $L^P$ is -GGFG-.

[7] An antibody-drug conjugate wherein an antitumor compound represented by the following formula:

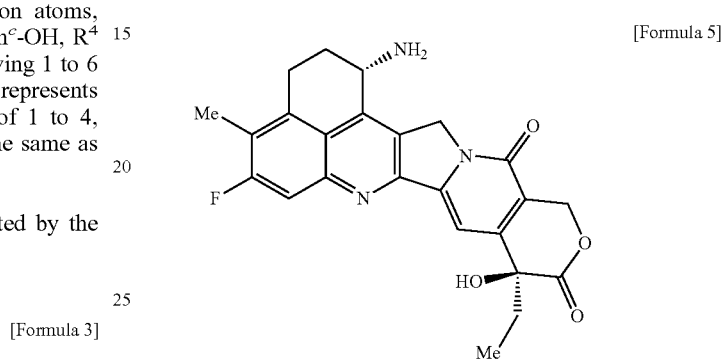

[Formula 5]

is conjugated to an antibody via a linker having a structure represented by the following formula:

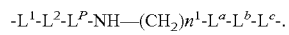

-$L^1$-$L^2$-$L^P$-NH—(CH$_2$)$n^1$-$L^a$-$L^b$-$L^c$-.

Here, the antibody is connected to the terminal of $L^1$, the antitumor compound is connected to the terminal of $L^c$ with the nitrogen atom of the amino group at position 1 as a connecting position, wherein $n^1$ represents an integer of 0 to 6, $L^1$ represents -(Succinimid-3-yl-N)—(CH$_2$)n$^2$-C(=O)—, —CH$_2$—C(=O)—NH—(CH$_2$)n$^3$-C(=O)—, —C(=O)-cyc.Hex(1,4)-CH$_2$—(N-ly-3-diminiccuS)-, or —C(=O)—(CH$_2$)n$^4$-C(=O)—, wherein $n^2$ represents an integer of 2 to 8, $n^3$ represents an integer of 1 to 8, $n^4$ represents an integer of 1 to 8, $L^2$ represents —NH—(CH$_2$—CH$_2$—O)n$^5$-CH$_2$—CH$_2$—C(=O)—, —S—(CH$_2$)n$^6$-C(=O)—, or a single bond, wherein $n^5$ represents an integer of 1 to 6, $n^6$ represents an integer of 1 to 6, $L^P$ represents a tetrapeptide residue of GGFG, $L^a$ represents —O— or a single bond, $L^b$ represents —CR$^2$(—R$^3$)— or a single bond, wherein $R^2$ and $R^3$ each represents a hydrogen atom, $L^c$ represents —C(=O)—, -(Succinimid-3-yl-N)— has a structure represented by the following formula:

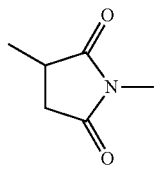

[Formula 6]

which is connected to the antibody at position 3 thereof and is connected to a methylene group in the linker structure containing this structure on the nitrogen atom at position 1, —(N-ly-3-diminiccuS)- has a structure represented by the following formula:

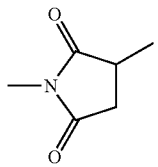

[Formula 7]

which is connected to L² at position 3 thereof and is connected to a methylene group in the linker structure containing this structure on the nitrogen atom at position 1, cyc.Hex(1,4) represents a 1,4-cyclohexylene group, and when L² is —S—(CH₂)n⁶-C(=O)—, L¹ is —C(=O)-cyc.Hex(1,4)-CH₂—(N-ly-3-diminiccuS)-.

[8] The antibody-drug conjugate according to any one of [1] to [7], wherein L¹ is -(Succinimid-3-yl-N)—(CH₂)n²-C(=O)— or —CH₂—C(=O)—NH—(CH₂)n³-C(=O)—.

[9] The antibody-drug conjugate according to any one of [1] to [7], wherein L¹ is -(Succinimid-3-yl-N)—(CH₂)n²-C(=O)—.

[10] The antibody-drug conjugate according to any one of [1] to [7], wherein L¹ is —C(=O)-cyc.Hex(1,4)-CH₂—(N-ly-3-diminiccuS)— or —C(=O)—(CH₂)n⁴-C(=O)—.

[11] The antibody-drug conjugate according to any one of [1] to [9], wherein n² is an integer of 2 to 5, and L² is a single bond.

[12] The antibody-drug conjugate according to any one of [1] to [9], wherein n² is an integer of 2 to 5, L² is —NH—(CH₂CH₂O)n⁵-CH₂—CH₂—C(=O)—, and n⁵ is 2 or 4.

[13] The antibody-drug conjugate according to any one of [1] to [12], wherein —NH—(CH₂)n¹-Lᵃ-Lᵇ-Lᶜ- is a partial structure having a chain length of 4 to 7 atoms.

[14] The antibody-drug conjugate according to any one of [1] to [12], wherein —NH—(CH₂)n¹-Lᵃ-Lᵇ-Lᶜ- is a partial structure having a chain length of 5 or 6 atoms.

[15] The antibody-drug conjugate according to any one of [1] to [14], wherein —NH—(CH₂)n¹-Lᵃ-Lᵇ-Lᶜ- is
—NH—(CH₂)₃—C(=O)—,
—NH—CH₂—O—CH₂—C(=O)—, or
—NH—(CH₂)₂—O—CH₂—C(=O)—.

[16] The antibody-drug conjugate according to any one of [1] to [15], wherein the drug-linker structure moiety is one drug-linker structure selected from the group consisting of the following drug-linker structures:

-(Succinimid-3-yl-N)—CH₂CH₂—C(=O)-GGFG-NH—CH₂CH₂—C(=O)—(NH-DX)

-(Succinimid-3-yl-N)—CH₂CH₂—C(=O)-GGFG-NH—CH₂CH₂CH₂—C(=O)—(NH-DX)

-(Succinimid-3-yl-N)—CH₂CH₂CH₂CH₂—C(=O)-GGFG-NH—CH₂CH₂—C(=O)—(NH-DX)

-(Succinimid-3-yl-N)—CH₂CH₂CH₂CH₂—C(=O)-GGFG-NH—CH₂CH₂CH₂—C(=O)—(NH-DX)

-(Succinimid-3-yl-N)—CH₂CH₂CH₂CH₂CH₂—C(=O)-GGFG-NH—CH₂CH₂CH₂CH₂—C(=O)—(NH-DX)

-(Succinimid-3-yl-N)—CH₂CH₂CH₂CH₂CH₂—C(=O)-GGFG-NH—CH₂—O—CH₂—C(=O)—(NH-DX)

-(Succinimid-3-yl-N)—CH₂CH₂CH₂CH₂CH₂—C(=O)-GGFG-NH—CH₂CH₂—O—CH₂—C(=O)—(NH-DX)

-(Succinimid-3-yl-N)—CH₂CH₂—C(=O)—NH—CH₂CH₂O—CH₂CH₂O—CH₂CH₂—C(=O)-GGFG-NH—CH₂CH₂CH₂—C(=O)—(NH-DX)

-(Succinimid-3-yl-N)—CH₂CH₂—C(=O)—NH—CH₂CH₂O—CH₂CH₂O—CH₂CH₂—C(=O)-GGFG-NH—CH₂CH₂—C(=O)—(NH-DX)

-(Succinimid-3-yl-N)—CH₂CH₂—C(=O)—NH—CH₂CH₂O—CH₂CH₂O—CH₂CH₂O—CH₂CH₂O—CH₂CH₂—C(=O)-GGFG-NH—CH₂CH₂CH₂—C(=O)—(NH-DX)

-(Succinimid-3-yl-N)—CH₂CH₂—C(=O)—NH—CH₂CH₂O—CH₂CH₂O—CH₂CH₂O—CH₂CH₂O—CH₂CH₂—C(=O)-GGFG-NH—CH₂CH₂—C(=O)—(NH-DX)

—CH₂—C(=O)—NH—CH₂CH₂—C(=O)-GGFG-NH—CH₂CH₂CH₂—C(=O)—(NH-DX)

—C(=O)—CH₂CH₂CH₂CH₂CH₂—C(=O)-GGFG-NH—CH₂CH₂CH₂—C(=O)—(NH-DX)

—C(=O)-cyc.Hex(1,4)-CH₂—(N-ly-3-diminiccuS)-S—CH₂CH₂—C(=O)-GGFG-NH—CH₂CH₂CH₂—C(=O)—(NH-DX)

Wherein, -(Succinimid-3-yl-N)— has a structure represented by the following formula:

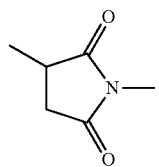

[Formula 8]

which is connected to the antibody at position 3 thereof and is connected to a methylene group in the linker structure containing this structure on the nitrogen atom at position 1, —(N-ly-3-diminiccuS)- has a structure represented by the following formula:

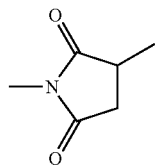

[Formula 9]

which is connected to L² at position 3 thereof and is connected to a methylene group in the linker structure containing this structure on the nitrogen atom at position 1, cyc.Hex(1,4) represents a 1,4-cyclohexylene group, —(NH-DX) represents a group represented by the following formula:

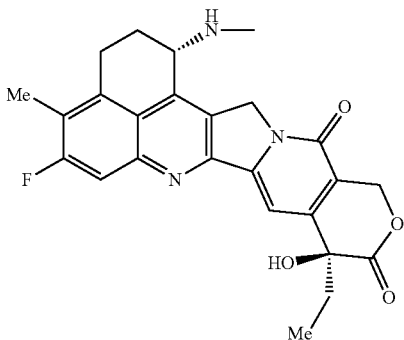

[Formula 10]

wherein the nitrogen atom of the amino group at position 1 is the connecting position, and
-GGFG- represents a peptide residue of -Gly-Gly-Phe-Gly-.

[17] The antibody-drug conjugate according to any one of [1] to [9] and [11] to [14], wherein the drug-linker structure moiety having a drug connected to -L$^1$-L$^2$-L$^P$-NH—(CH$_2$)n$^1$-L$^a$-L$^b$-L$^c$- is one drug-linker structure selected from the following group:
-(Succinimid-3-yl-N)—CH$_2$CH$_2$CH$_2$CH$_2$CH$_2$—C(=O)-GGFG-NH—CH$_2$—O—CH$_2$—C(=O)—(NH-DX)
-(Succinimid-3-yl-N)—CH$_2$CH$_2$CH$_2$CH$_2$CH$_2$—C(=O)-GGFG-NH—CH$_2$CH$_2$—O—CH$_2$—C(=O)—(NH-DX)
-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX).

In the above, -(Succinimid-3-yl-N)— has a structure represented by the following formula:

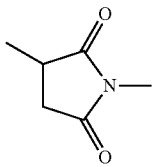

[Formula 11]

which is connected to the antibody at position 3 thereof and connected to a methylene group in the linker structure containing this structure on the nitrogen atom at position 1, and
—(NH-DX) represents a group represented by the following formula:

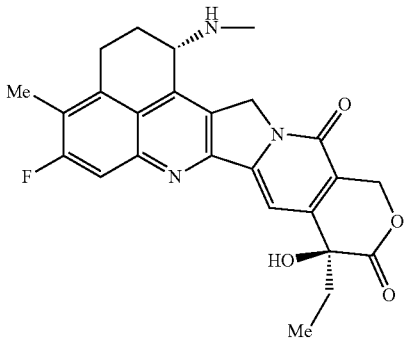

[Formula 12]

wherein the nitrogen atom of the amino group at position 1 is a connecting position.

[18] An antibody-drug conjugate wherein an antitumor compound represented by the following formula:

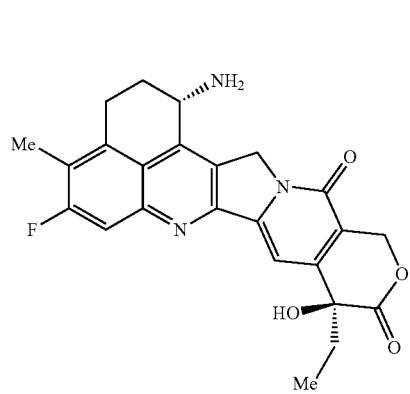

[Formula 13]

is conjugated to an antibody via a linker having a structure represented by the following formula:

-L$^1$-L$^2$-L$^P$-NH—(CH$_2$)n$^1$-L$^a$-L$^b$-L$^c$-.

Here, the antibody is connected to the terminal of L$^1$, the antitumor compound is connected to the terminal of L$^c$, wherein
n$^1$ represents an integer of 0 to 6,
L$^1$ represents -(Succinimid-3-yl-N)—(CH$_2$)n$^2$-C(=O)— and is connected to the antibody via a thioether bond which is formed at a disulfide bond site present in a hinge part of the antibody,
wherein n$^2$ represents an integer of 2 to 8,
L$^2$ represents —NH—(CH$_2$—CH$_2$—O) n$^5$-CH$_2$—CH$_2$—C(=O)— or a single bond,
wherein
n$^5$ represents an integer of 1 to 6,
L$^P$ represents a tetrapeptide residue of GGFG,
L$^a$ represents —O— or a single bond,
L$^b$ represents —CR$^2$(—R$^3$)— or a single bond,
wherein R$^2$ and R$^3$ each represents a hydrogen atom,
L$^c$ represents —C(=O)—, and
-(Succinimid-3-yl-N)— has a structure represented by the following formula:

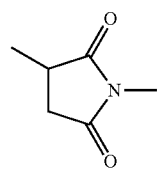

[Formula 14]

which is connected to the antibody at position 3 thereof and is connected to a methylene group in the linker structure containing this structure on the nitrogen atom at position 1.

[19] The antibody-drug conjugate according to [18], wherein
n$^2$ is 2, L$^2$ is —NH—(CH$_2$—CH$_2$—O)n$^5$-CH$_2$—CH$_2$—C(=O)—, n$^5$ is 2,
n$^1$ is 3, and both of L$^a$ and L$^b$ are single bonds,
n$^2$ is 5, L$^2$ is a single bond, n$^1$ is 1, L$^a$ is —O—, and L$^b$ is —CR$^2$(—R$^3$)—, or
n$^2$ is 5, L$^2$ is a single bond, n$^1$ is 2, L$^a$ is —O—, and L$^b$ is —CR$^2$(—R$^3$)—.

[20] The antibody-drug conjugate according to [18] or [19], wherein $n^2$ is an integer of 2 to 5, and $L^2$ is a single bond.

[21] The antibody-drug conjugate according to [18] or [19], wherein $n^2$ is an integer of 2 to 5, $L^2$ is —NH—(CH$_2$CH$_2$O)n$^5$-CH$_2$—CH$_2$—C(=O)—, and $n^5$ is 2 or 4.

[22] The antibody-drug conjugate according to any one of [18] to [21], wherein —NH—(CH$_2$)n$^1$-L$^a$-L$^b$-L$^c$- is
—NH—(CH$_2$)$_3$—C(=O)—,
—NH—CH$_2$—O—CH$_2$—C(=O)—, or
—NH—(CH$_2$)$_2$—O—CH$_2$—C(=O)—.

[23] The antibody-drug conjugate according to any one of [18] to [22], wherein the drug-linker structure moiety is one drug-linker structure selected from the group consisting of the following drug-linker structures:

-(Succinimid-3-yl-N)—CH$_2$CH$_2$—C(=O)-GGFG-NH—CH$_2$CH$_2$—C(=O)—(NH-DX)

-(Succinimid-3-yl-N)—CH$_2$CH$_2$—C(=O)-GGFG-NH—CH$_2$CH$_2$CH$_2$—C(=O)—(NH-DX)

-(Succinimid-3-yl-N)—CH$_2$CH$_2$CH$_2$CH$_2$CH$_2$—C(=O)-GGFG-NH—CH$_2$CH$_2$—C(=O)—(NH-DX)

-(Succinimid-3-yl-N)—CH$_2$CH$_2$CH$_2$CH$_2$CH$_2$—C(=O)-GGFG-NH—CH$_2$CH$_2$CH$_2$—C(=O)—(NH-DX)

-(Succinimid-3-yl-N)—CH$_2$CH$_2$CH$_2$CH$_2$CH$_2$—C(=O)-GGFG-NH—CH$_2$CH$_2$CH$_2$CH$_2$CH$_2$—C(=O)—(NH-DX)

-(Succinimid-3-yl-N)—CH$_2$CH$_2$CH$_2$CH$_2$CH$_2$—C(=O)-GGFG-NH—CH$_2$—O—CH$_2$—C(=O)—(NH-DX)

-(Succinimid-3-yl-N)—CH$_2$CH$_2$CH$_2$CH$_2$CH$_2$—C(=O)-GGFG-NH—CH$_2$CH$_2$—O—CH$_2$—C(=O)—(NH-DX)

-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX)

-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$—C(=O)—(NH-DX)

-(Succinimid-3-yl-N)—CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—(NH-DX)

-(Succinimid-3-yl-N)—CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$—C(=O)—(NH-DX)

In the above, -(Succinimid-3-yl-N)— has a structure represented by the following formula:

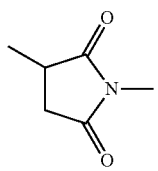

[Formula 15]

which is connected to the antibody at position 3 thereof and is connected to a methylene group in the linker structure containing this structure on the nitrogen atom at position 1, and —(NH-DX) represents a group represented by the following formula:

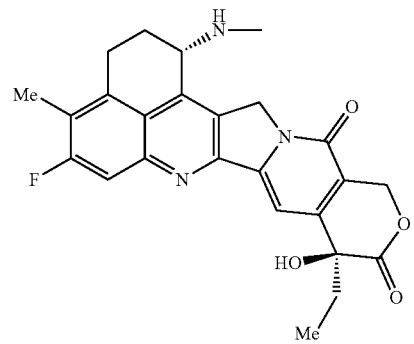

[Formula 16]

wherein the nitrogen atom of the amino group at position 1 is a connection position.

[24] The antibody-drug conjugate according to [23], wherein the drug-linker structure moiety having a drug connected to -L$^1$-L$^2$-L$^P$-NH—(CH$_2$)n$^1$-L$^a$-L$^b$-L$^c$- is one drug-linker structure selected from the following group:

-(Succinimid-3-yl-N)—CH$_2$CH$_2$CH$_2$CH$_2$CH$_2$—C(=O)-GGFG-NH—CH$_2$—O—CH$_2$—C(=O)—(NH-DX)

-(Succinimid-3-yl-N)—CH$_2$CH$_2$CH$_2$CH$_2$CH$_2$—C(=O)-GGFG-NH—CH$_2$CH$_2$—O—CH$_2$—C(=O)—(NH-DX)

-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX).

In the above, -(Succinimid-3-yl-N)— has a structure represented by the following formula:

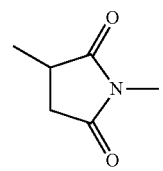

[Formula 17]

which is connected to the antibody at position 3 thereof and is connected to a methylene group in the linker structure containing this structure on the nitrogen atom at position 1, and —(NH-DX) represents a group represented by the following formula:

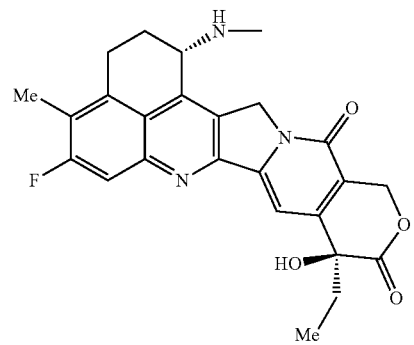

[Formula 18]

wherein the nitrogen atom of the amino group at position 1 is a connecting position.

[25] The antibody-drug conjugate according to any one of [1] to [24], wherein an average number of units of the selected one drug-linker structure conjugated per antibody is in a range of from 1 to 10.
[26] The antibody-drug conjugate according to any one of [1] to [24], wherein an average number of units of the selected one drug-linker structure conjugated per antibody is in a range of from 2 to 8.
[27] The antibody-drug conjugate according to any one of [1] to [24], wherein an average number of units of the selected one drug-linker structure conjugated per antibody is in a range of from 3 to 8.
[28] The antibody-drug conjugate according to any one of [1] to [27], wherein the antibody is an antibody having one or more of a property of recognizing a target cell, a property of binding to a target cell, a property of internalizing in a target cell, and a property of damaging a target cell.
[29] The antibody-drug conjugate according to any one of [1] to [27], wherein a cell which is targeted by the antibody-drug conjugate is a tumor cell.
[30] The antibody-drug conjugate according to any one of [1] to [27], wherein the antibody is an anti-A33 antibody, an anti-B7-H3 antibody, an anti-CanAg antibody, an anti-CD20 antibody, an anti-CD22 antibody, an anti-CD30 antibody, an anti-CD33 antibody, an anti-CD56 antibody, an anti-CD70 antibody, an anti-CEA antibody, an anti-Cripto antibody, an anti-EphA2 antibody, an anti-G250 antibody, an anti-MUC1 antibody, an anti-GPNMB antibody, an anti-integrin antibody, an anti-PSMA antibody, an anti-tenascin-C antibody, an anti-SLC44A4 antibody, or an anti-mesothelin antibody.
[31] The antibody-drug conjugate according to any one of [1] to [27], wherein the antibody is an anti-B7-H3 antibody, an anti-CD30 antibody, an anti-CD33 antibody, or an anti-CD70 antibody.
[32] The antibody-drug conjugate according to any one of [1] to [27], wherein the antibody is an anti-B7-H3 antibody.
[33] A drug containing the antibody-drug conjugate according to any one of [1] to [32], a salt thereof or a hydrate thereof.
[34] An antitumor drug and/or anticancer drug containing the antibody-drug conjugate according to any one of [1] to [32], a salt thereof or a hydrate thereof.
[35] The antitumor drug and/or anticancer drug according to [34], which is applied to lung cancer, kidney cancer, urothelial cancer, colorectal cancer, prostate cancer, glioblastoma multiforme, ovarian cancer, pancreatic cancer, breast cancer, melanoma, liver cancer, bladder cancer, stomach cancer, or esophageal cancer.
[36] A pharmaceutical composition containing the antibody-drug conjugate according to any one of [1] to [32], a salt thereof or a hydrate thereof as an active component, and a pharmaceutically acceptable formulation component.
[37] The pharmaceutical composition according to [36], which is applied to lung cancer, kidney cancer, urothelial cancer, colorectal cancer, prostate cancer, glioblastoma multiforme, ovarian cancer, pancreatic cancer, breast cancer, melanoma, liver cancer, bladder cancer, stomach cancer, or esophageal cancer.
[38] A method for treating tumor and/or cancer comprising administering the antibody-drug conjugate according to any one of [1] to [32], a salt thereof or a hydrate thereof.
[39] A drug-linker intermediate compound represented by the following formula:

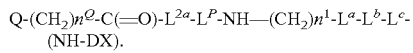

In the formula, Q represents (maleimid-N-yl)-, HS—, X—CH$_2$—C(=O)—NH—, or (Pyrrolidine-2,5-dione-N-yl)-O—C(=O)—, X represents a bromine atom or an iodine atom, $n^Q$ represents an integer of 2 to 8, $L^{2a}$ represents —NH—(CH$_2$—CH$_2$—O) $n^5$-CH$_2$—CH$_2$—C(=O)— or a single bond, wherein $n^5$ represents an integer of 1 to 6, $L^P$ represents a peptide residue consisting of 2 to 7 amino acids selected from phenylalanine, glycine, valine, lysine, citrulline, serine, glutamic acid, and aspartic acid, $n^1$ represents an integer of 0 to 6, $L^a$ represents —C(=O)—NH—, —NR$^1$—(CH$_2$)n$^7$-, —O—, or a single bond, wherein $n^7$ represents an integer of 1 to 6, R$^1$ represents a hydrogen atom, an alkyl group having 1 to 6 carbon atoms, —(CH$_2$)n$^8$-COOH, or —(CH$_2$)n$^9$-OH, $n^8$ represents an integer of 1 to 4, $n^9$ represents an integer of 1 to 6, $L^b$ represents —CR$^2$(—R$^3$)—, —O—, —NR$^4$—, or a single bond, wherein R$^2$ and R$^3$ each independently represent a hydrogen atom, an alkyl group having 1 to 6 carbon atoms, —(CH$_2$)n$^a$-NH$_2$, —(CH$_2$)n$^b$-COOH, or —(CH$_2$)n$^c$-OH, R$^4$ represents a hydrogen atom or an alkyl group having 1 to 6 carbon atoms, $n^a$ represents an integer of 0 to 6, $n^b$ represents an integer of 1 to 4, $n^c$ represents an integer of 1 to 4, provided that when $n^a$ is 0, R$^2$ and R$^3$ are not the same as each other, $L^c$ represents —CH$_2$— or —C(=O)—, (maleimid-N-yl)- is a group represented by the following formula:

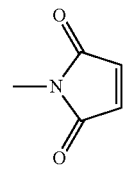

[Formula 19]

wherein the nitrogen atom is a connecting position, (Pyrrolidine-2,5-dione-N-yl) is a group represented by the following formula:

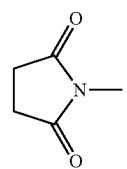

[Formula 20]

wherein the nitrogen atom is a connecting position, and —(NH-DX) is a group represented by the following formula:

[Formula 21]

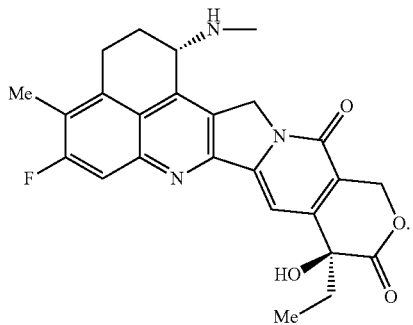

wherein the nitrogen atom of the amino group at position 1 is a connecting position.

[40] The drug-linker intermediate compound according to [39], wherein $L^c$ is —C(=O)—.

[41] The drug-linker intermediate compound according to [39] or [40], wherein $L^P$ is a peptide residue consisting of 4 amino acids.

[42] The drug-linker intermediate compound according to any one of [39] to [41], wherein $L^P$ is -GGFG-.

[43] The drug-linker intermediate compound according to any one of [39] to [42], wherein —NH—$(CH_2)n^1$-$L^a$-$L^b$- is
—NH—$CH_2CH_2$—,
—NH—$CH_2CH_2CH_2$—,
—NH—$CH_2CH_2CH_2CH_2$—,
—NH—$CH_2CH_2CH_2CH_2CH_2$—,
—NH—$CH_2$—O—$CH_2$—, or
—NH—$CH_2CH_2$—O—$CH_2$—.

[44] The drug-linker intermediate compound according to any one of [39] to [42], wherein —NH—$(CH_2)n^1$-$L^a$-$L^b$- is
—NH—$CH_2CH_2CH_2$—,
—NH—$CH_2$—O—$CH_2$—, or
—NH—$(CH_2)_2$—O—$CH_2$—.

[45] The drug-linker intermediate compound according to any one of [39] to [44], wherein $n^Q$ is an integer of 2 to 6.

[46] The drug-linker intermediate compound according to [43], wherein
Q is (maleimid-N-yl)-,
$n^Q$ is an integer of 2 to 5, and
$L^{2a}$ is a single bond.

[47] The drug-linker intermediate compound according to [44], wherein
Q is (maleimid-N-yl)-,
$n^Q$ is an integer of 2 to 5, and
$L^{2a}$ is a single bond.

[48] The drug-linker intermediate compound according to any one of [39] to [42], wherein
Q is (maleimid-N-yl)-,
$n^Q$ is an integer of 2 to 5,
$L^{2a}$ is —NH—$(CH_2$—$CH_2$—O)$n^5$-$CH_2$—$CH_2$—C(=O)—,
$n^5$ is an integer of 2 to 4, and
—NH—$(CH_2)n^1$-$L^a$-$L^b$- is
—NH—$CH_2CH_2$—,
—NH—$CH_2CH_2CH_2$—,
—NH—$CH_2CH_2CH_2CH_2$—,
—NH—$CH_2CH_2CH_2CH_2CH_2$—,
—NH—$CH_2$—O—$CH_2$—, or
—NH—$CH_2CH_2$—O—$CH_2$—.

[49] The drug-linker intermediate compound according to [48], wherein
$n^5$ is an integer of 2 or 4, and
—NH—$(CH_2)n^1$-$L^a$-$L^b$- is —NH—$CH_2CH_2CH_2$—,
—NH—$CH_2$—O—$CH_2$—, or
—NH—$CH_2CH_2$—O—$CH_2$—.

[50] A compound of the following:
(maleimid-N-yl)-$CH_2CH_2$—C(=O)-GGFG-NH—$CH_2CH_2$—C(=O)—(NH-DX)
(maleimid-N-yl)-$CH_2CH_2CH_2$—C(=O)-GGFG-NH—$CH_2CH_2$—C(O)—(NH-DX)
(maleimid-N-yl)-$CH_2CH_2CH_2CH_2$—C(=O)-GGFG-NH—$CH_2CH_2$—C(=O)—(NH-DX)
(maleimid-N-yl)-$CH_2CH_2CH_2CH_2$—C(=O)-GGFG-NH—$CH_2CH_2$—C(=O)—(NH-DX)
(maleimid-N-yl)-$CH_2CH_2$—C(=O)-GGFG-NH—$CH_2CH_2CH_2$—C(=O)—(NH-DX)
(maleimid-N-yl)-$CH_2CH_2CH_2$—C(=O)-GGFG-NH—$CH_2CH_2CH_2$—C(=O)—(NH-DX)
(maleimid-N-yl)-$CH_2CH_2CH_2CH_2$—C(=O)-GGFG-NH—$CH_2CH_2CH_2$—C(=O)—(NH-DX)
(maleimid-N-yl)-$CH_2CH_2CH_2CH_2CH_2$—C(=O)-GGFG-NH—$CH_2CH_2CH_2$—C(=O)—(NH-DX)
(maleimid-N-yl)-$CH_2CH_2$—C(=O)-GGFG-NH—$CH_2CH_2CH_2CH_2$—C(=O)—(NH-DX)
(maleimid-N-yl)-$CH_2CH_2CH_2$—C(=O)-GGFG-NH—$CH_2CH_2CH_2CH_2$—C(=O)—(NH-DX)
(maleimid-N-yl)-$CH_2CH_2CH_2CH_2$—C(=O)-GGFG-NH—$CH_2CH_2CH_2CH_2$—C(=O)—(NH-DX)
(maleimid-N-yl)-$CH_2CH_2CH_2CH_2CH_2$—C(=O)-GGFG-NH—$CH_2CH_2CH_2CH_2CH_2$—C(=O)—(NH-DX)
(maleimid-N-yl)-$CH_2CH_2$—C(=O)-GGFG-NH—$CH_2$—O—$CH_2$—C(=O)—(NH-DX)
(maleimid-N-yl)-$CH_2CH_2CH_2$—C(=O)-GGFG-NH—$CH_2$—O—$CH_2$—C(=O)—(NH-DX)
(maleimid-N-yl)-$CH_2CH_2CH_2CH_2$—C(=O)-GGFG-NH—$CH_2$—O—$CH_2$—C(=O)—(NH-DX)
(maleimid-N-yl)-$CH_2CH_2CH_2CH_2CH_2$—C(=O)-GGFG-NH—$CH_2$—O—$CH_2$—C(=O)—(NH-DX)
(maleimid-N-yl)-$CH_2CH_2$—C(=O)-GGFG-NH—$CH_2CH_2$—O—$CH_2$—C(=O)—(NH-DX)
(maleimid-N-yl)-$CH_2CH_2CH_2$—C(=O)-GGFG-NH—$CH_2CH_2$—O—$CH_2$—C(=O)—(NH-DX)
(maleimid-N-yl)-$CH_2CH_2CH_2CH_2$—C(=O)-GGFG-NH—$CH_2CH_2$—O—$CH_2$—C(=O)—(NH-DX)
(maleimid-N-yl)-$CH_2CH_2CH_2CH_2CH_2$—C(=O)-GGFG-NH—$CH_2CH_2$—O—$CH_2$—C(=O)—(NH-DX)
(maleimid-N-yl)-$CH_2CH_2$—C(=O)—NH—$CH_2CH_2O$—$CH_2CH_2O$—$CH_2CH_2$—C(=O)-GGFG-NH—$CH_2CH_2$—C(=O)—(NH-DX)
(maleimid-N-yl)-$CH_2CH_2$—C(=O)—NH—$CH_2CH_2O$—$CH_2CH_2O$—$CH_2CH_2O$—$CH_2CH_2$—C(=O)-GGFG-NH—$CH_2CH_2$—C(=O)—(NH-DX)
(maleimid-N-yl)-$CH_2CH_2$—C(=O)—NH—$CH_2CH_2O$—$CH_2CH_2O$—$CH_2CH_2O$—$CH_2CH_2$—C(=O)-GGFG-NH—$CH_2CH_2$—C(=O)—(NH-DX)
(maleimid-N-yl)-$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—(NH-DX)
(maleimid-N-yl)-$CH_2CH_2$—C(=O)—NH—$CH_2CH_2O$—$CH_2CH_2O$—$CH_2CH_2O$—$CH_2CH_2$—C(=O)-GGFG-NH—$CH_2CH_2CH_2$—C(=O)—(NH-DX)
(maleimid-N-yl)-$CH_2CH_2$—C(=O)—NH—$CH_2CH_2O$—$CH_2CH_2O$—$CH_2CH_2O$—$CH_2CH_2O$—$CH_2CH_2$—C(=O)-GGFG-NH—$CH_2CH_2CH_2$—C(=O)—(NH-DX)
(maleimid-N-yl)-$CH_2CH_2$—C(=O)—NH—$CH_2CH_2O$—$CH_2CH_2O$—$CH_2CH_2$—C(=O)-GGFG-NH—$CH_2$—O—$CH_2$—C(=O)—(NH-DX)

(maleimid-N-yl)-CH₂CH₂—C(=O)—NH—CH₂CH₂O—CH₂CH₂O—CH₂CH₂O—CH₂CH₂—C(=O)-GGFG-NH—CH₂—O—CH₂—C(=O)—(NH-DX)
(maleimid-N-yl)-CH₂CH₂—C(=O)—NH—CH₂CH₂O—CH₂CH₂O—CH₂CH₂O—CH₂CH₂—C(=O)-GGFG-NH—CH₂—O—CH₂—C(=O)—(NH-DX)
(maleimid-N-yl)-CH₂CH₂—C(=O)—NH—CH₂CH₂O—CH₂CH₂O—CH₂CH₂—C(=O)-GGFG-NH—CH₂CH₂—O—CH₂—C(=O)—(NH-DX)
(maleimid-N-yl)-CH₂CH₂—C(=O)—NH—CH₂CH₂O—CH₂CH₂O—CH₂CH₂O—CH₂CH₂—C(=O)-GGFG-NH—CH₂CH₂—O—CH₂—C(=O)—(NH-DX)
(maleimid-N-yl)-CH₂CH₂—C(=O)—NH—CH₂CH₂O—CH₂CH₂O—CH₂CH₂O—CH₂CH₂—C(=O)-GGFG-NH—CH₂CH₂—O—CH₂—C(=O)—(NH-DX)
X—CH₂—C(=O)—NH—CH₂CH₂—C(=O)-GGFG-NH—CH₂CH₂—C(=O)—(NH-DX)
X—CH₂—C(=O)—NH—CH₂CH₂—C(=O)-GGFG-NH—CH₂CH₂CH₂—C(=O)—(NH-DX)
X—CH₂—C(=O)—NH—CH₂CH₂—C(=O)-GGFG-NH—CH₂—O—CH₂—C(=O)—(NH-DX)
X—CH₂—C(=O)—NH—CH₂CH₂—C(=O)-GGFG-NH—CH₂CH₂—O—CH₂—C(=O)—(NH-DX)
X—CH₂—C(=O)—NH—CH₂CH₂CH₂—C(=O)-GGFG-NH—CH₂CH₂—C(=O)—(NH-DX)
X—CH₂—C(=O)—NH—CH₂CH₂CH₂—C(=O)-GGFG-NH—CH₂CH₂CH₂—C(=O)—(NH-DX)
X—CH₂—C(=O)—NH—CH₂CH₂CH₂—C(=O)-GGFG-NH—CH₂—O—CH₂—C(=O)—(NH-DX)
X—CH₂—C(=O)—NH—CH₂CH₂CH₂—C(=O)-GGFG-NH—CH₂CH₂—O—CH₂—C(=O)—(NH-DX)
X—CH₂—C(=O)—NH—CH₂CH₂CH₂CH₂—C(=O)-GGFG-NH—CH₂CH₂—C(=O)—(NH-DX)
X—CH₂—C(=O)—NH—CH₂CH₂CH₂CH₂—C(=O)-GGFG-NH—CH₂CH₂CH₂—C(=O)—(NH-DX)
X—CH₂—C(=O)—NH—CH₂CH₂CH₂CH₂—C(=O)-GGFG-NH—CH₂—O—CH₂—C(=O)—(NH-DX)
X—CH₂—C(=O)—NH—CH₂CH₂CH₂CH₂—C(=O)-GGFG-NH—CH₂CH₂—O—CH₂—C(=O)—(NH-DX)
X—CH₂—C(=O)—NH—CH₂CH₂CH₂CH₂CH₂—C(=O)-GGFG-NH—CH₂CH₂—C(=O)—(NH-DX)
X—CH₂—C(=O)—NH—CH₂CH₂CH₂CH₂CH₂—C(=O)-GGFG-NH—CH₂CH₂CH₂—C(=O)—(NH-DX)
X—CH₂—C(=O)—NH—CH₂CH₂CH₂CH₂CH₂—C(=O)-GGFG-NH—CH₂—O—CH₂—C(=O)—(NH-DX)
X—CH₂—C(=O)—NH—CH₂CH₂CH₂CH₂CH₂—C(=O)-GGFG-NH—CH₂CH₂—O—CH₂—C(=O)—(NH-DX)
X—CH₂—C(=O)—NH—CH₂CH₂—C(=O)—NH—CH₂CH₂O—CH₂CH₂O—CH₂CH₂—C(=O)-GGFG-NH—CH₂CH₂—C(=O)—(NH-DX)
X—CH₂—C(=O)—NH—CH₂CH₂—C(=O)—NH—CH₂CH₂O—CH₂CH₂—CH₂CH₂—C(=O)-GGFG-NH—CH₂CH₂CH₂—C(=O)—(NH-DX)
X—CH₂—C(=O)—NH—CH₂CH₂—C(=O)—NH—CH₂CH₂—CH₂CH₂—CH₂CH₂—C(=O)-GGFG-NH—CH₂—O—CH₂—C(=O)—(NH-DX)
X—CH₂—C(=O)—NH—CH₂CH₂—C(=O)—NH—CH₂CH₂O—CH₂CH₂O—CH₂CH₂—C(=O)-GGFG-NH—CH₂CH₂—O—CH₂—C(=O)—(NH-DX)
HS—CH₂CH₂—C(=O)-GGFG-NH—CH₂CH₂—C(=O)—(NH-DX)
HS—CH₂CH₂CH₂—C(=O)-GGFG-NH—CH₂CH₂—C(=O)—(NH-DX)
HS—CH₂CH₂CH₂CH₂—C(=O)-GGFG-NH—CH₂CH₂—C(=O)—(NH-DX)
HS—CH₂CH₂CH₂CH₂CH₂—C(=O)-GGFG-NH—CH₂CH₂—C(=O)—(NH—HS—CH₂CH₂—C(=O)-GGFG-NH—CH₂CH₂CH₂—C(=O)—(NH-DX)
HS—CH₂CH₂CH₂—C(=O)-GGFG-NH—CH₂CH₂CH₂—C(=O)—(NH-DX)
HS—CH₂CH₂CH₂CH₂—C(=O)-GGFG-NH—CH₂CH₂CH₂—C(=O)—(NH—HS—CH₂CH₂CH₂CH₂CH₂—C(=O)-GGFG-NH—CH₂CH₂CH₂—C(=O)—(NH-DX)
HS—CH₂CH₂—C(=O)-GGFG-NH—CH₂—O—CH₂—C(=O)—(NH-DX)
HS—CH₂CH₂CH₂—C(=O)-GGFG-NH—CH₂—CH₂—C(=O)—(NH-DX)
HS—CH₂CH₂CH₂CH₂—C(=O)-GGFG-NH—CH₂—O—CH₂—C(=O)—(NH-DX)
HS—CH₂CH₂CH₂CH₂CH₂—C(=O)-GGFG-NH—CH₂—CH₂—C(=O)—(NH-DX)
HS—CH₂CH₂—C(=O)-GGFG-NH—CH₂CH₂—O—CH₂—C(=O)—(NH-DX)
HS—CH₂CH₂CH₂—C(=O)-GGFG-NH—CH₂CH₂—O—CH₂—C(=O)—(NH-DX)
HS—CH₂CH₂CH₂CH₂—C(=O)-GGFG-NH—CH₂CH₂—C(=O)—(NH-DX)
HS—CH₂CH₂CH₂CH₂CH₂—C(=O)-GGFG-NH—CH₂CH₂—O—CH₂—C(=O)—(NH-DX)
HS—CH₂CH₂—C(=O)—NH—CH₂CH₂O—CH₂CH₂O—CH₂CH₂—C(=O)-GGFG-NH—CH₂CH₂—C(=O)—(NH-DX)
HS—CH₂CH₂—C(=O)—NH—CH₂CH₂O—CH₂CH₂O—CH₂CH₂O—CH₂CH₂—C(=O)-GGFG-NH—CH₂CH₂—C(=O)—(NH-DX)
HS—CH₂CH₂—C(=O)—NH—CH₂CH₂O—CH₂CH₂O—CH₂CH₂—CH₂CH₂—CH₂CH₂—C(=O)-GGFG-NH—CH₂CH₂—C(=O)—(NH-DX)
HS—CH₂CH₂—C(=O)—NH—CH₂CH₂O—CH₂CH₂O—CH₂CH₂—C(=O)-GGFG-NH—CH₂CH₂CH₂—C(=O)—(NH-DX)
HS—CH₂CH₂—C(=O)—NH—CH₂CH₂—CH₂CH₂O—CH₂CH₂—CH₂CH₂—C(=O)-GGFG-NH—CH₂CH₂CH₂—C(=O)—(NH-DX)
HS—CH₂CH₂—C(=O)—NH—CH₂CH₂O—CH₂CH₂O—CH₂CH₂O—CH₂CH₂—C(=O)-GGFG-NH—CH₂CH₂CH₂—C(=O)—(NH-DX)
HS—CH₂CH₂—C(=O)—NH—CH₂CH₂O—CH₂CH₂—CH₂CH₂—C(=O)-GGFG-NH—CH₂—O—CH₂—C(=O)—(NH-DX)
HS—CH₂CH₂—C(=O)—NH—CH₂CH₂O—CH₂CH₂O—CH₂CH₂—C(=O)-GGFG-NH—CH₂—O—CH₂—C(=O)—(NH-DX)
HS—CH₂CH₂—C(=O)—NH—CH₂CH₂O—CH₂CH₂O—CH₂CH₂—CH₂CH₂—CH₂CH₂—C(=O)-GGFG-NH—CH₂—O—CH₂—C(=O)—(NH-DX)
(Pyrrolidine-2,5-dione-N-yl)-O—C(=O)—CH₂CH₂—C(=O)-GGFG-NH—CH₂CH₂—C(=O)—(NH-DX)
(Pyrrolidine-2,5-dione-N-yl)-O—C(=O)—CH₂CH₂CH₂—C(=O)-GGFG-NH—CH₂CH₂—C(=O)—(NH-DX)
(Pyrrolidine-2,5-dione-N-yl)-O—C(=O)—CH₂CH₂CH₂CH₂—C(=O)-GGFG-NH—CH₂CH₂—C(=O)—(NH-DX)
(Pyrrolidine-2,5-dione-N-yl)-O—C(=O)—CH₂CH₂CH₂CH₂CH₂—C(=O)-GGFG-NH—CH₂CH₂—C(=O)—(NH-DX)
(Pyrrolidine-2,5-dione-N-yl)-O—C(=O)—CH₂CH₂CH₂CH₂CH₂CH₂—C(=O)-GGFG-NH—CH₂CH₂—C(=O)—(NH-DX)

(Pyrrolidine-2,5-dione-N-yl)-O—C(=O)—CH₂CH₂—C(=O)-GGFG-NH—CH₂CH₂CH₂—C(=O)—(NH-DX)
(Pyrrolidine-2,5-dione-N-yl)-O—C(=O)—CH₂CH₂CH₂—C(=O) GGFG-NH—CH₂CH₂CH₂—C(=O)—(NH-DX)
(Pyrrolidine-2,5-dione-N-yl)-O—C(=O)—CH₂CH₂CH₂CH₂—C(=O)-GGFG-NH—CH₂CH₂CH₂—C(=O)—(NH-DX)
(Pyrrolidine-2,5-dione-N-yl)-O—C(=O)—CH₂CH₂CH₂CH₂CH₂—C(=O)-GGFG-NH—CH₂CH₂CH₂—C(=O)—(NH-DX)
(Pyrrolidine-2,5-dione-N-yl)-O—C(=O)—CH₂CH₂CH₂CH₂CH₂CH₂—C(=O)-GGFG-NH—CH₂CH₂CH₂—C(=O)—(NH-DX)
(Pyrrolidine-2,5-dione-N-yl)-O—C(=O)—CH₂CH₂—C(=O)-GGFG-NH—CH₂—O—CH₂—C(=O)—(NH-DX)
(Pyrrolidine-2,5-dione-N-yl)-O—C(=O)—CH₂CH₂CH₂—C(=O)-GGFG-NH—CH₂—O—CH₂—C(=O)—(NH-DX)
(Pyrrolidine-2,5-dione-N-yl)-O—C(=O)—CH₂CH₂CH₂CH₂—C(=O)-GGFG-NH—CH₂—O—CH₂—C(=O)—(NH-DX)
(Pyrrolidine-2,5-dione-N-yl)-O—C(=O)—CH₂CH₂CH₂CH₂CH₂—C(=O)-GGFG-NH—CH₂—O—CH₂—C(=O)—(NH-DX)
(Pyrrolidine-2,5-dione-N-yl)-O—C(=O)—CH₂CH₂CH₂CH₂CH₂CH₂—C(=O)-GGFG-NH—CH₂—O—CH₂—C(=O)—(NH-DX)
(Pyrrolidine-2,5-dione-N-yl)-O—C(=O)—CH₂CH₂—C(=O)-GGFG-NH—CH₂CH₂—O—CH₂—C(=O)—(NH-DX)
(Pyrrolidine-2,5-dione-N-yl)-O—C(=O)—CH₂CH₂CH₂—C(=O)-GGFG-NH—CH₂CH₂—O—CH₂—C(=O)—(NH-DX)
(Pyrrolidine-2,5-dione-N-yl)-O—C(=O)—CH₂CH₂CH₂CH₂—C(=O)-GGFG-NH—CH₂CH₂—O—CH₂—C(=O)—(NH-DX)
(Pyrrolidine-2,5-dione-N-yl)-O—C(=O)—CH₂CH₂CH₂CH₂CH₂—C(=O)-GGFG-NH—CH₂CH₂—O—CH₂—C(=O)—(NH-DX)
(Pyrrolidine-2,5-dione-N-yl)-O—C(=O)—CH₂CH₂CH₂CH₂CH₂CH₂—C(=O)-GGFG-NH—CH₂CH₂—O—CH₂—C(=O)—(NH-DX)
(Pyrrolidine-2,5-dione-N-yl)-O—C(=O)—CH₂CH₂—C(=O)—NH—CH₂CH₂O—CH₂CH₂O—CH₂CH₂—C(=O)-GGFG-NH—CH₂CH₂—C(=O)—(NH-DX)
(Pyrrolidine-2,5-dione-N-yl)-O—C(=O)—CH₂CH₂—C(=O)—NH—CH₂CH₂O—CH₂CH₂O—CH₂CH₂O—CH₂CH₂—C(=O)-GGFG-NH—CH₂CH₂—C(=O)—(NH-DX)
(Pyrrolidine-2,5-dione-N-yl)-O—C(=O)—CH₂CH₂—C(=O)—NH—CH₂CH₂—CH₂CH₂O—CH₂CH₂CH₂—CH₂CH₂—C(=O)-GGFG-NH—CH₂CH₂—C(=O)—(NH-DX)
(Pyrrolidine-2,5-dione-N-yl)-O—C(=O)—CH₂CH₂—C(=O)—NH—CH₂CH₂O—CH₂CH₂O+CH₂CH₂—C(=O)-GGFG-NH—CH₂CH₂CH₂—C(=O)—NH-DX)
(Pyrrolidine-2,5-dione-N-yl)-O—C(=O)—CH₂CH₂—C(=O)—NH—CH₂CH₂O—CH₂CH₂O—CH₂CH₂—C(=O)-GGFG-NH—CH₂CH₂CH₂—C(=O)—(NH-DX)
(Pyrrolidine-2,5-dione-N-yl)-O—C(=O)—CH₂CH₂—C(=O)—NH—CH₂CH₂O—CH₂CH₂O—CH₂CH₂O—CH₂CH₂O—CH₂CH₂—C(=O)-GGFG-NH—CH₂CH₂CH₂—C(=O)—(NH-DX)
(Pyrrolidine-2,5-dione-N-yl)-O—(=O)—CH₂CH₂—C(=O)—NH—CH₂CH₂O—CH₂CH₂O—CH₂CH₂—C(=O)-GGFG-NH—CH₂—O—CH₂—C(=O)—(NH-DX)
(Pyrrolidine-2,5-dione-N-yl)-O—C(=O)—CH₂CH₂—C(=O)—NH—CH₂CH₂O—CH₂CH₂O—CH₂CH₂O—CH₂CH₂—C(=O)-GGFG-NH—CH₂—O—CH₂—C(=O)—(NH-DX)
(Pyrrolidine-2,5-dione-N-yl)-O—C(=O)—CH₂CH₂—C(=O)—NH—CH₂CH₂O—CH₂CH₂O—CH₂CH₂O—CH₂CH₂O—CH₂CH₂—C(=O)-GGFG-NH—CH₂—O—CH₂—C(=O)—(NH-DX)
(Pyrrolidine-2,5-dione-N-yl)-O—C(=O)—CH₂CH₂—C(=O)—NH—CH₂CH₂O—CH₂CH₂O—CH₂CH₂—C(=O)-GGFG-NH—CH₂CH₂—O—CH₂—C(=O)—(NH-DX)
(Pyrrolidine-2,5-dione-N-yl)-O—C(=O)—CH₂CH₂—C(=O)—NH—CH₂CH₂O—CH₂CH₂O—CH₂CH₂O—CH₂CH₂—C(=O)-GGFG-NH—CH₂CH₂—O—CH₂—C(=O)—(NH-DX), or
(Pyrrolidine-2,5-dione-N-yl)-O—C(=O)—CH₂CH₂—C(=O)—NH—CH₂CH₂O—CH₂CH₂O—CH₂CH₂O—CH₂CH₂O—CH₂CH₂—C(=O)-GGFG-NH—CH₂CH₂—O—CH₂—C(=O)—(NH-DX).

In the above, (maleimid-N-yl)- is a group represented by the following formula:

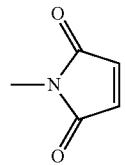

[Formula 22]

wherein the nitrogen atom is a connecting position,
X represents a halogen atom,
(Pyrrolidine-2,5-dione-N-yl)- is a group represented by the following formula:

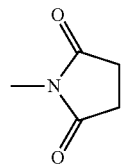

[Formula 23]

wherein the nitrogen atom is a connecting position, and
—(NH-DX) is a group represented by the following formula:

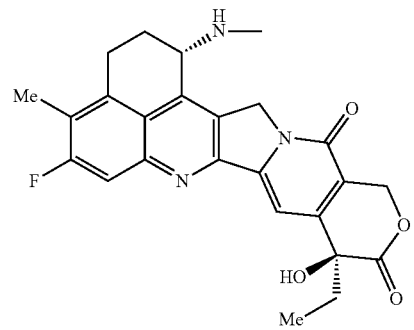

[Formula 24]

wherein the nitrogen atom of the amino group at position 1 is a connecting position.

[51] A compound of the following:
(maleimid-N-yl)-CH$_2$CH$_2$—C(=O)-GGFG-NH—CH$_2$—C(=O)—(NH-DX)
(maleimid-N-yl)-CH$_2$CH$_2$CH$_2$—C(=O)-GGFG-NH—CH$_2$CH$_2$—C(=O)—(NH-DX)
(maleimid-N-yl)-CH$_2$CH$_2$CH$_2$CH$_2$—C(=O)-GGFG-NH—CH$_2$CH$_2$—C(=O)—(NH-DX)
(maleimid-N-yl)-CH$_2$CH$_2$CH$_2$CH$_2$CH$_2$—C(=O)-GGFG-NH—CH$_2$CH$_2$—C(=O)—(NH-DX)
(maleimid-N-yl)-CH$_2$CH$_2$—C(=O)-GGFG-NH—CH$_2$CH$_2$CH$_2$—C(=O)—(NH-DX)
(maleimid-N-yl)-CH$_2$CH$_2$CH$_2$—C(=O)-GGFG-NH—CH$_2$CH$_2$CH$_2$—C(=O)—(NH-DX)
(maleimid-N-yl)-CH$_2$CH$_2$CH$_2$CH$_2$—C(=O)-GGFG-NH—CH$_2$CH$_2$CH$_2$—C(=O)—(NH-DX)
(maleimid-N-yl)-CH$_2$CH$_2$CH$_2$CH$_2$CH$_2$—C(=O)-GGFG-NH—CH$_2$CH$_2$CH$_2$—C(=O)—(NH-DX)
(maleimid-N-yl)-CH$_2$CH$_2$—C(=O)-GGFG-NH—CH$_2$CH$_2$CH$_2$CH$_2$CH$_2$—C(=O)—(NH-DX)
(maleimid-N-yl)-CH$_2$CH$_2$CH$_2$—C(=O)-GGFG-NH—CH$_2$CH$_2$CH$_2$CH$_2$—C(=O)—(NH-DX)
(maleimid-N-yl)-CH$_2$CH$_2$CH$_2$CH$_2$—C(=O)-GGFG-NH—CH$_2$CH$_2$CH$_2$CH$_2$—C(=O)—(NH-DX)
(maleimid-N-yl)-CH$_2$CH$_2$CH$_2$CH$_2$CH$_2$—C(=O)-GGFG-NH—CH$_2$CH$_2$CH$_2$CH$_2$CH$_2$—C(=O)—(NH-DX)
(maleimid-N-yl)-CH$_2$CH$_2$—C(=O)-GGFG-NH—CH$_2$—O—CH$_2$—C(=O)—(NH-DX)
(maleimid-N-yl)-CH$_2$CH$_2$CH$_2$—C(=O)-GGFG-NH—CH$_2$—O—CH$_2$—C(=O)—(NH-DX)
(maleimid-N-yl)-CH$_2$CH$_2$CH$_2$CH$_2$—C(=O)-GGFG-NH—CH$_2$—O—CH$_2$—C(=O)—(NH-DX)
(maleimid-N-yl)-CH$_2$CH$_2$CH$_2$CH$_2$CH$_2$—C(=O)-GGFG-NH—CH$_2$—O—CH$_2$—C(=O)—(NH-DX)
(maleimid-N-yl)-CH$_2$CH$_2$—C(=O)-GGFG-NH—CH$_2$CH$_2$—O—CH$_2$—C(=O)—(NH-DX)
(maleimid-N-yl)-CH$_2$CH$_2$CH$_2$—C(=O)-GGFG-NH—CH$_2$CH$_2$—O—CH$_2$—C(=O)—(NH-DX)
(maleimid-N-yl)-CH$_2$CH$_2$CH$_2$CH$_2$—C(=O)-GGFG-NH—CH$_2$CH$_2$—O—CH$_2$—C(=O)—(NH-DX)
(maleimid-N-yl)-CH$_2$CH$_2$CH$_2$CH$_2$CH$_2$—C(=O)-GGFG-NH—CH$_2$CH$_2$—O—CH$_2$—C(=O)—(NH-DX)
(maleimid-N-yl)-CH$_2$CH$_2$—C(=O)—NH—CH$_2$CH$_2$O—CH$_2$CH$_2$—CH$_2$CH$_2$—C(=O)-GGFG-NH—CH$_2$CH$_2$—C(=O)—(NH-DX)
(maleimid-N-yl)-CH$_2$CH$_2$—C(=O)—NH—CH$_2$CH$_2$O—CH$_2$CH$_2$O—CH$_2$CH$_2$O—CH$_2$CH$_2$—C(=O)-GGFG-NH—CH$_2$CH$_2$—C(=O)—(NH-DX)
(maleimid-N-yl)-CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$—C(=O)—(NH-DX)
(maleimid-N-yl)-CH$_2$CH$_2$—C(=O)—NH—CH$_2$CH$_2$O—CH$_2$CH$_2$—CH$_2$CH$_2$—C(=O)-GGFG-NH—CH$_2$CH$_2$CH$_2$—C(=O)—(NH-DX)
(maleimid-N-yl)-CH$_2$CH$_2$—C(=O)—NH—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—(NH-DX)
(maleimid-N-yl)-CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—(NH-DX)
(maleimid-N-yl)-CH$_2$CH$_2$—C(=O)—NH—CH$_2$CH$_2$O—CH$_2$CH$_2$O—CH$_2$CH$_2$—C(=O)-GGFG-NH—CH$_2$—O—CH$_2$—C(=O)—(NH-DX)
(maleimid-N-yl)-CH$_2$CH$_2$—C(=O)—NH—CH$_2$CH$_2$O—CH$_2$CH$_2$O—CH$_2$CH$_2$O—CH$_2$CH$_2$—C(=O)-GGFG-NH—CH$_2$—O—CH$_2$—C(=O)—(NH-DX)
(maleimid-N-yl)-CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$—O—CH$_2$—C(=O)—(NH-DX)
(maleimid-N-yl)-CH$_2$CH$_2$—C(=O)—NH—CH$_2$CH$_2$O—CH$_2$CH$_2$O—CH$_2$CH$_2$—C(=O)-GGFG-NH—CH$_2$CH$_2$—O—CH$_2$—C(=O)—(NH-DX)
(maleimid-N-yl)-CH$_2$CH$_2$—C(=O)—NH—CH$_2$CH$_2$O—CH$_2$CH$_2$O—CH$_2$CH$_2$O—CH$_2$CH$_2$—C(=O)-GGFG-NH—CH$_2$CH$_2$—O—CH$_2$—C(=O)—(NH-DX), or
(maleimid-N-yl)-CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$—O—CH$_2$—C(=O)—(NH-DX).

In the above, (maleimid-N-yl)- is a group represented by the following formula:

[Formula 25]

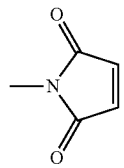

wherein the nitrogen atom is a connecting position, and —(NH-DX) is a group represented by the following formula:

[Formula 26]


wherein the nitrogen atom of the amino group at position 1 is a connecting position.

[52] A compound of the following:
(maleimid-N-yl)-CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX),
(maleimid-N-yl)-CH$_2$CH$_2$CH$_2$CH$_2$CH$_2$—C(=O)-GGFG-NH—CH$_2$—O—CH$_2$—C(=O)—(NH-DX) or
(maleimid-N-yl)-CH$_2$CH$_2$CH$_2$CH$_2$—C(=O)-GGFG-NH—CH$_2$CH$_2$—O—CH$_2$—C(=O)—(NH-DX).

In the above, (maleimid-N-yl)- is a group represented by the following formula:

[Formula 27]

wherein the nitrogen atom is a connecting position, and —(NH-DX) is a group represented by the following formula:

[Formula 28]

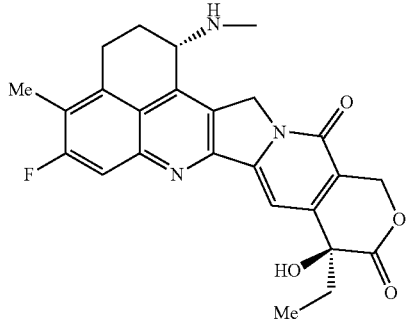

wherein the nitrogen atom of the amino group at position 1 is a connecting position.

[53] A compound selected from the following group:
NH₂—CH₂CH₂—C(=O)—(NH-DX),
NH₂—CH₂CH₂CH₂—C(=O)—(NH-DX),
NH₂—CH₂—O—CH₂—C(=O)—(NH-DX),
NH₂—CH₂CH₂—O—CH₂—C(=O)—(NH-DX), and
HO—CH₂—C(=O)—(NH-DX)

wherein —(NH-DX) is a group represented by the following formula:

[Formula 29]

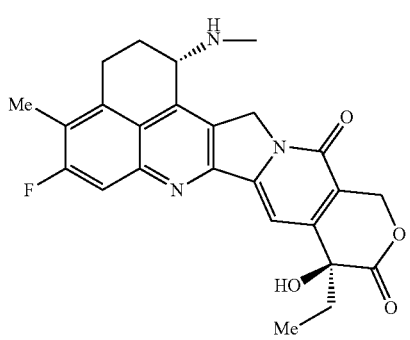

wherein the nitrogen atom of the amino group at position 1 is a connecting position.

[54] A compound represented by the following formula:

[Formula 30]

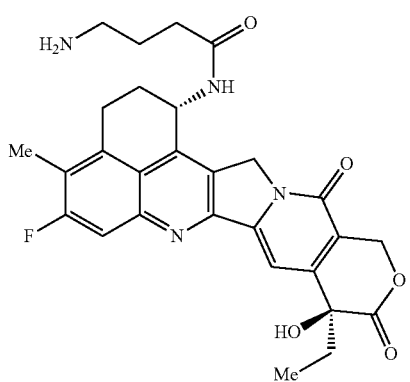

[55] A compound represented by the following formula:

[Formula 31]

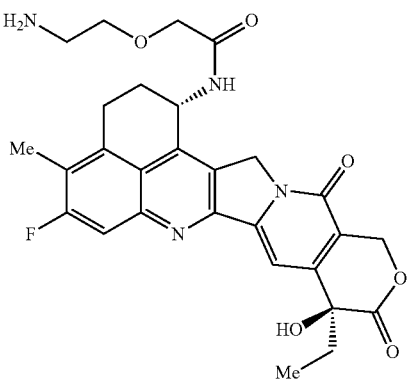

[56] A compound represented by the following formula:

[Formula 32]

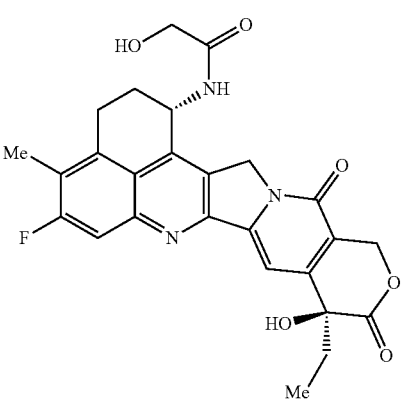

[57] A method for producing an antibody-drug conjugate comprising reacting a compound represented by the following formula:

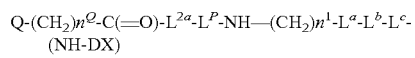

Q-(CH₂)n^Q-C(=O)-L^{2a}-L^P-NH—(CH₂)n¹-L^a-L^b-L^c-(NH-DX)

with an antibody or a reactive derivative thereof and conjugating a drug-linker moiety to the antibody by a method for forming a thioether bond at a disulfide bond site present in a hinge part of the antibody, or by a method for forming an amide bond at an amino group present on a side chain of an amino acid constituting the antibody or at the terminal amino group.

In the formula, Q represents (maleimid-N-yl)-, HS—, X—CH₂—C(=O)—NH—, or (Pyrrolidine-2,5-dione-N-yl)-O—C(=O)—, X represents a bromine atom or an iodine atom, $n^Q$ represents an integer of 2 to 8, $L^{2a}$ represents —NH—(CH₂—CH₂—O)n⁵-CH₂—CH₂—C(=O)— or a single bond, wherein n⁵ represents an integer of 1 to 6, $L^P$ represents a peptide residue consisting of 2 to 7 amino acids selected from phenylalanine, glycine, valine, lysine, citrulline, serine, glutamic acid, and aspartic acid, n¹ represents an integer of 0 to 6, $L^a$ represents —C(=O)—NH—, —NR¹—(CH₂)n⁷-, —O—, or a single bond, wherein $n^7$ represents an integer of 1 to 6, $R^1$ represents a hydrogen atom, an alkyl group having 1 to 6 carbon atoms, —(CH$_2$)n$^8$-COOH, or —(CH$_2$)n$^9$-OH, $n^8$ represents an integer of 1 to 4, $n^9$ represents an integer of 1 to 6,
$L^b$ represents —CR$^2$(—R$^3$)—, —O—, —NR$^4$—, or a single bond,
wherein $R^2$ and $R^3$ each independently represents a hydrogen atom, an alkyl group having 1 to 6 carbon atoms, —(CH$_2$)n$^a$-NH$_2$, —(CH$_2$)n$^b$-COOH, or —(CH$_2$)n$^c$-OH, $R^4$ represents a hydrogen atom or an alkyl group having 1 to 6 carbon atoms, $n^a$ represents an integer of 0 to 6, $n^b$ represents an integer of 1 to 4, $n^c$ represents an integer of 1 to 4, provided that when $n^a$ is 0, $R^2$ and $R^3$ are not the same as each other,
$L^c$ represents —CH$_2$— or —C(=O)—,
(maleimid-N-yl)- is a group represented by the following formula:

[Formula 33]

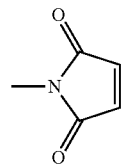

wherein the nitrogen atom is a connecting position, (Pyrrolidine-2,5-dione-N-yl) is a group represented by the following formula:

[Formula 34]

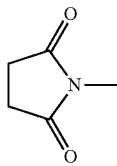

wherein the nitrogen atom is a connecting position, and —(NH-DX) is a group represented by the following formula:

[Formula 35]

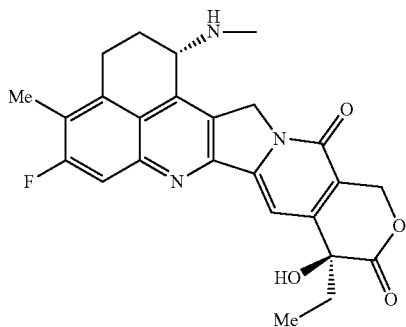

wherein the nitrogen atom of the amino group at position 1 is a connecting position.

[58] The production method according to [57], wherein the method for conjugating a drug-linker moiety to an antibody is
a method of reducing the antibody and thereafter forming a thioether bond by the reaction with the compound in which Q is a maleimidyl group or X—CH$_2$—C(=O)—NH—,
a method of forming an amide bond by the reaction with the compound in which Q is (Pyrrolidine-2,5-dione-N-yl)-O—C(=O)—, or
a method of reacting the antibody with a compound represented by the formula Q$^1$-L$^{1a}$-Q$^2$
[wherein Q$^1$ represents (Pyrrolidine-2,5-dione-N-yl)-O—C(=O)—, (3-Sulfo-pyrrolidine-2,5-dione-N-yl)-O—C(=O)—, $R^Q$—O—C(=N)—, or O=C=N—,
$L^{1a}$- represents -cyc.Hex(1,4)-CH$_2$—, an alkylene group having 1 to 10 carbon atoms, a phenylene group, —(CH$_2$)n$^4$-C(=O)—, —(CH$_2$)n$^{4a}$-NH—C(=O)—(CH$_2$)n$^{4b}$-, or —(CH$_2$)n$^{4a}$-NH—C(=O)-cyc.Hex(1,4)-CH$_2$—,
Q$^2$ represents (maleimid-N-yl), a halogen atom, or —S—S-(2-Pyridyl),
$R^Q$ represents an alkyl group having 1 to 6 carbon atoms,
$n^4$ represents an integer of 1 to 8,
$n^{4a}$ represents an integer of 0 to 6, $n^{4b}$ represents an integer of 1 to 6,
(3-Sulfo-pyrrolidine-2,5-dione-N-yl)- is a group represented by the following formula:

[Formula 36]

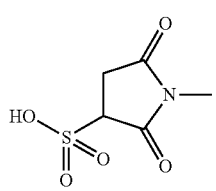

wherein the nitrogen atom is a connecting position, and this sulfonic acid is capable of forming a lithium salt, sodium salt, or potassium salt,
cyc.Hex(1,4) represents a 1,4-cyclohexylene group, and (2-Pyridyl) represents a 2-pyridyl group] and thereafter reacting with the compound in which Q is SH to form a drug-linker structure by an amide bond.

[59] The production method according to [57] or [58], wherein an average number of units of the selected one drug-linker structure conjugated per antibody is in a range of from 1 to 10.

[60] The production method according to [57] or [58], wherein an average number of units of the selected one drug-linker structure conjugated per antibody is in a range of from 2 to 8.

[61] The production method according to [57] or [58], wherein an average number of units of the selected one drug-linker structure conjugated per antibody is in a range of from 3 to 8.

[62] The production method according to any one of [57] to [61], wherein a cell which is targeted by the antibody-drug conjugate is a tumor cell.

[63] The production method according to any one of [57] to [61], wherein the antibody is an anti-A33 antibody, an anti-B7-H3 antibody, an anti-CanAg antibody, an anti-CD20 antibody, an anti-CD22 antibody, an anti-CD30 antibody, an anti-CD33 antibody, an anti-CD56 antibody, an anti-CD70 antibody, an anti-CEA antibody, an anti-Cripto antibody, an anti-EphA2 antibody, an anti-G250 antibody, an anti-MUC1 antibody, an anti-GPNMB antibody, an anti-integrin antibody, an anti-PSMA antibody, an anti-tenascin-C antibody, an anti-SLC44A4 antibody, or an anti-mesothelin antibody.

[64] The production method according to any one of [57] to [61], wherein the antibody is an anti-B7-H3 antibody, an anti-CD30 antibody, an anti-CD33 antibody, or an anti-CD70 antibody.

[65] The production method according to any one of [57] to [61], wherein the antibody is an anti-B7-H3 antibody.
[66] An antibody-drug conjugate obtained by the production method according to any of [57] to [65].
[67] An antibody-drug conjugate obtained by forming a thioether bond at a sulfide bond site in a hinge part of an antibody, wherein the antibody is treated in a reducing condition and thereafter reacted with a compound selected from the compound group shown below:
(maleimid-N-yl)-CH₂CH₂—C(=O)-GGFG-NH—CH₂CH₂—C(=O)—(NH-DX)
(maleimid-N-yl)-CH₂CH₂CH₂—C(=O)-GGFG-NH—CH₂CH₂—C(=O)—(NH-DX)
(maleimid-N-yl)-CH₂CH₂CH₂CH₂—C(=O)-GGFG-NH—CH₂CH₂—C(=O)—(NH-DX)
(maleimid-N-yl)-CH₂CH₂CH₂CH₂CH₂—C(=O)-GGFG-NH—CH₂CH₂—C(=O)—(NH-DX)
(maleimid-N-yl)-CH₂CH₂—C(=O)-GGFG-NH—CH₂CH₂CH₂—C(=O)—(NH-DX)
(maleimid-N-yl)-CH₂CH₂CH₂—C(=O)-GGFG-NH—CH₂CH₂CH₂—C(=O)—(NH-DX)
(maleimid-N-yl)-CH₂CH₂CH₂CH₂—C(=O)-GGFG-NH—CH₂CH₂CH₂—C(=O)—(NH-DX)
(maleimid-N-yl)-CH₂CH₂CH₂CH₂CH₂—C(=O)-GGFG-NH—CH₂CH₂CH₂—C(=O)—(NH-DX)
(maleimid-N-yl)-CH₂CH₂—C(=O)-GGFG-NH—CH₂CH₂CH₂CH₂CH₂—C(=O)—(NH-DX)
(maleimid-N-yl)-CH₂CH₂CH₂—C(=O)-GGFG-NH—CH₂CH₂CH₂CH₂CH₂—C(=O)—(NH-DX)
(maleimid-N-yl)-CH₂CH₂CH₂CH₂—C(=O)-GGFG-NH—CH₂CH₂CH₂CH₂CH₂—C(=O)—(NH-DX)
(maleimid-N-yl)-CH₂CH₂CH₂CH₂CH₂—C(=O)-GGFG-NH—CH₂CH₂CH₂CH₂CH₂—C(=O)—(NH-DX)
(maleimid-N-yl)-CH₂CH₂—C(=O)-GGFG-NH—CH₂—O—CH₂—C(=O)—(NH-DX)
(maleimid-N-yl)-CH₂CH₂CH₂—C(=O)-GGFG-NH—CH₂—O—CH₂—C(=O)—(NH-DX)
(maleimid-N-yl)-CH₂CH₂CH₂CH₂—C(=O)-GGFG-NH—CH₂—O—CH₂—C(=O)—(NH-DX)
(maleimid-N-yl)-CH₂CH₂CH₂CH₂CH₂—C(=O)-GGFG-NH—CH₂—O—CH₂—C(=O)—(NH-DX)
(maleimid-N-yl)-CH₂CH₂—C(=O)-GGFG-NH—CH₂CH₂—O—CH₂—C(=O)—(NH-DX)
(maleimid-N-yl)-CH₂CH₂CH₂—C(=O)-GGFG-NH—CH₂CH₂—O—CH₂—C(=O)—(NH-DX)
(maleimid-N-yl)-CH₂CH₂CH₂CH₂—C(=O)-GGFG-NH—CH₂CH₂—O—CH₂—C(=O)—(NH-DX)
(maleimid-N-yl)-CH₂CH₂CH₂CH₂CH₂—C(=O)-GGFG-NH—CH₂CH₂—O—CH₂—C(=O)—(NH-DX)
(maleimid-N-yl)-CH₂CH₂—C(=O)—NH—CH₂CH₂O—CH₂CH₂O—CH₂CH₂—C(=O)-GGFG-NH—CH₂CH₂—C(=O)—(NH-DX)
(maleimid-N-yl)-CH₂CH₂—C(=O)—NH—CH₂CH₂O—CH₂CH₂O—CH₂CH₂O—CH₂CH₂—C(=O)-GGFG-NH—CH₂CH₂—C(=O)—(NH-DX)
(maleimid-N-yl)-CH₂CH₂—C(=O)—NH—CH₂CH₂O—CH₂CH₂O—CH₂CH₂O—CH₂CH₂O—CH₂CH₂—C(=O)-GGFG-NH—CH₂CH₂—C(=O)—(NH-DX)
(maleimid-N-yl)-CH₂CH₂—C(=O)—NH—CH₂CH₂O—CH₂CH₂O—CH₂CH₂—C(=O)-GGFG-NH—CH₂CH₂CH₂—C(=O)—(NH-DX)
(maleimid-N-yl)-CH₂CH₂—C(=O)—NH—CH₂CH₂O—CH₂CH₂O—CH₂CH₂O—CH₂CH₂—C(=O)-GGFG-NH—CH₂CH₂CH₂—C(=O)—(NH-DX)
(maleimid-N-yl)-CH₂CH₂—C(=O)—NH—CH₂CH₂O—CH₂CH₂O—CH₂CH₂O—CH₂CH₂O—CH₂CH₂—C(=O)-GGFG-NH—CH₂CH₂CH₂—C(=O)—(NH-DX)
(maleimid-N-yl)-CH₂CH₂—C(=O)—NH—CH₂CH₂O—CH₂CH₂O—CH₂CH₂—C(=O)-GGFG-NH—CH₂—O—CH₂—C(=O)—(NH-DX)
(maleimid-N-yl)-CH₂CH₂—C(=O)—NH—CH₂CH₂O—CH₂CH₂O—CH₂CH₂O—CH₂CH₂—C(=O)-GGFG-NH—CH₂—O—CH₂—C(=O)—(NH-DX)
(maleimid-N-yl)-CH₂CH₂—C(=O)—NH—CH₂CH₂O—CH₂CH₂O—CH₂CH₂O—CH₂CH₂O—CH₂CH₂—C(=O)-GGFG-NH—CH₂—O—CH₂—C(=O)—(NH-DX)
(maleimid-N-yl)-CH₂CH₂—C(=O)—NH—CH₂CH₂O—CH₂CH₂O—CH₂CH₂—C(=O)-GGFG-NH—CH₂CH₂—O—CH₂—C(=O)—(NH-DX)
(maleimid-N-yl)-CH₂CH₂—C(=O)—NH—CH₂CH₂O—CH₂CH₂O—CH₂CH₂O—CH₂CH₂—C(=O)-GGFG-NH—CH₂CH₂—O—CH₂—C(=O)—(NH-DX), or
(maleimid-N-yl)-CH₂CH₂—C(=O)—NH—CH₂CH₂O—CH₂CH₂O—CH₂CH₂O—CH₂CH₂O—CH₂CH₂—C(=O)-GGFG-NH—CH₂CH₂—O—CH₂—C(=O)—(NH-DX).

In the above, (maleimid-N-yl)- is a group represented by the following formula:

[Formula 37]

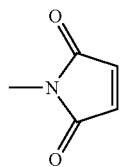

wherein the nitrogen atom is a connecting position, and —(NH-DX) is a group represented by the following formula:

[Formula 38]

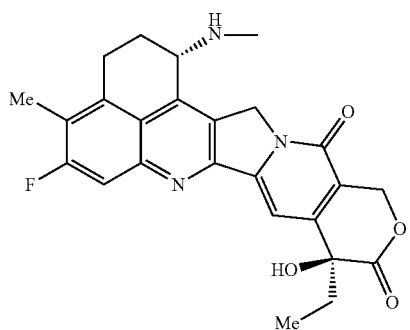

wherein the nitrogen atom of the amino group at position 1 is a connecting position.

[68] An antibody-drug conjugate obtained by forming a thioether bond at a sulfide bond site present in a hinge part of an antibody, wherein the antibody is treated in a reducing condition and thereafter reacted with a compound selected from the compound group shown below:
(maleimid-N-yl)-CH₂CH₂—C(=O)—NH—CH₂CH₂O—CH₂CH₂O—CH₂CH₂—C(=O)-GGFG-NH—CH₂CH₂CH₂—C(=O)—(NH-DX),
(maleimid-N-yl)-CH₂CH₂CH₂CH₂CH₂—C(=O)-GGFG-NH—CH₂—O—CH₂—C(=O)—(NH-DX), or
(maleimid-N-yl)-CH₂CH₂CH₂CH₂CH₂—C(=O)-GGFG-NH—CH₂CH₂—O—CH₂—C(=O)—(NH-DX).

In the above, (maleimid-N-yl)- is a group represented by the following formula:

[Formula 39]

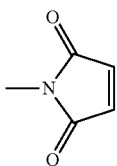

wherein the nitrogen atom is a connecting position, and —(NH-DX) is a group represented by the following formula:

[Formula 40]

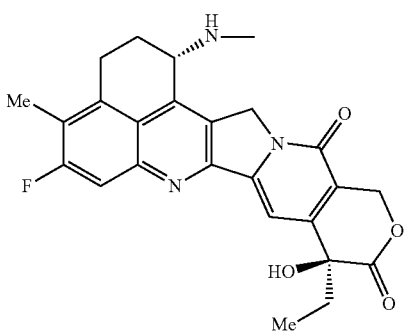

wherein the nitrogen atom of the amino group at position 1 is a connecting position.

[69] The antibody-drug conjugate according to [67] or [68], wherein an average number of units of the selected one drug-linker structure conjugated per antibody is in a range of from 1 to 10.

[70] The antibody-drug conjugate according to [67] or [68], wherein an average number of units of the selected one drug-linker structure conjugated per antibody is in a range of from 2 to 8.

[71] The antibody-drug conjugate according to [67] or [68], wherein an average number of units of the selected one drug-linker structure conjugated per antibody is in a range of from 3 to 8.

[72] The antibody-drug conjugate according to any one of [67] to [71], wherein a cell which is targeted by the antibody-drug conjugate is a tumor cell.

[73] The antibody-drug conjugate according to any one of [67] to [71], wherein the antibody is an anti-A33 antibody, an anti-B7-H3 antibody, an anti-CanAg antibody, an anti-CD20 antibody, an anti-CD22 antibody, an anti-CD30 antibody, an anti-CD33 antibody, an anti-CD56 antibody, an anti-CD70 antibody, an anti-CEA antibody, an anti-Cripto antibody, an anti-EphA2 antibody, an anti-G250 antibody, an anti-MUC1 antibody, an anti-GPNMB antibody, an anti-integrin antibody, an anti-PSMA antibody, an anti-tenascin-C antibody, an anti-SLC44A4 antibody, or an anti-mesothelin antibody.

[74] The antibody-drug conjugate according to any one of [67] to [71], wherein the antibody is an anti-B7-H3 antibody, an anti-CD30 antibody, an anti-CD33 antibody, or an anti-CD70 antibody.

[75] The antibody-drug conjugate according to any one of [67] to [71], wherein the antibody is an anti-B7-H3 antibody.

[76] A linker represented by the following formula:

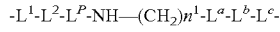

for obtaining an antibody-drug conjugate in which a drug is conjugated to an antibody via the linker.

In the above, $L^1$ is a connecting position for the antibody, $L^c$ is a connecting position for an antitumor compound, wherein $n^1$ represents an integer of 0 to 6, $L^1$ represents -(Succinimid-3-yl-N)—$(CH_2)n^2$-C(=O)—, —$CH_2$—C(=O)—NH—$(CH_2)n^3$-C(=O)—, —C(=O)-cyc.Hex(1,4)-$CH_2$—(N-ly-3-diminiccuS)-, or —C(=O)—$(CH_2)n^4$-C(=O)—, wherein $n^2$ represents an integer of 2 to 8, $n^3$ represents an integer of 1 to 8, $n^4$ represents an integer of 1 to 8, $L^2$ represents —NH—$(CH_2$—$CH_2$—O$)n^5$-$CH_2$—$CH_2$—C(=O)—, —S—$(CH_2)n^6$-C(=O)—, or a single bond, wherein $n^5$ represents an integer of 1 to 6, $n^6$ represents an integer of 1 to 6, $L^P$ represents a peptide residue consisting of 2 to 7 amino acids, $L^a$ represents —C(=O)—NH—, —NR$^1$—$(CH_2)n^7$-, —O—, or a single bond, wherein $n^7$ represents an integer of 1 to 6, $R^1$ represents a hydrogen atom, an alkyl group having 1 to 6 carbon atoms, —$(CH_2)n^8$-COOH, or —$(CH_2)n^9$-OH, no represents an integer of 1 to 4, $n^9$ represents an integer of 1 to 6, $L^b$ represents —CR$^2$(—R$^3$)—, —O—, —NR$^4$—, or a single bond, wherein $R^2$ and $R^3$ each independently represents a hydrogen atom, an alkyl group having 1 to 6 carbon atoms, —$(CH_2)n^a$-$NH_2$, —$(CH_2)n^b$-COOH, or —$(CH_2)n^c$-OH, $R^4$ represents a hydrogen atom or an alkyl group having 1 to 6 carbon atoms, $n^a$ represents an integer of 0 to 6, $n^b$ represents an integer of 1 to 4, $n^c$ represents an integer of 1 to 4, provided that when $n^a$ is 0, $R^2$ and $R^3$ are not the same each other, $L^c$ represents —$CH_2$— or —C(=O)—, -(Succinimid-3-yl-N)— has a structure represented by the following formula:

[Formula 41]

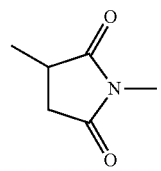

which is connected to the antibody at position 3 thereof and is connected to a methylene group in the linker structure containing this structure on the nitrogen atom at position 1, —(N-ly-3-diminiccuS)- has a structure represented by the following formula:

[Formula 42]

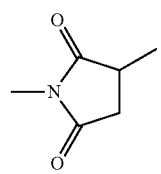

which is connected to $L^2$ at position 3 thereof and is connected to a methylene group in the linker structure containing this structure on the nitrogen atom at position 1, cyc.Hex(1,4) represents a 1,4-cyclohexylene group, and when $L^2$ is —S—$(CH_2)n^6$-C(=O)—, $L^1$ is —C(=O)-cyc.Hex(1,4)-$CH_2$—(N-ly-3-diminiccuS)-.

[77] The linker according to [76], which is selected from the following group, provided that the left terminal is a connecting position with the antibody and the right terminal is a connecting position with the antitumor compound:

-(Succinimid-3-yl-N)—$CH_2CH_2$—C(=O)-GGFG-NH—$CH_2CH_2$—C(=O)—
-(Succinimid-3-yl-N)—$CH_2CH_2CH_2$—C(=O)-GGFG-NH—$CH_2CH_2$—C(=O)—
-(Succinimid-3-yl-N)—$CH_2CH_2CH_2CH_2$—C(=O)-GGFG-NH—$CH_2CH_2$—C(=O)—
-(Succinimid-3-yl-N)—$CH_2CH_2CH_2CH_2CH_2$—C(=O)-GGFG-NH—$CH_2CH_2$—C(=O)—
-(Succinimid-3-yl-N)—$CH_2CH_2$—C(=O)-GGFG-NH—$CH_2CH_2CH_2$—C(=O)—
-(Succinimid-3-yl-N)—$CH_2CH_2CH_2$—C(=O)-GGFG-NH—$CH_2CH_2CH_2$—C(=O)—
-(Succinimid-3-yl-N)—$CH_2CH_2CH_2CH_2$—C(=O)-GGFG-NH—$CH_2CH_2CH_2$—C(=O)—
-(Succinimid-3-yl-N)—$CH_2CH_2CH_2CH_2CH_2$—C(=O)-GGFG-NH—$CH_2CH_2CH_2$—C(=O)—
-(Succinimid-3-yl-N)—$CH_2CH_2$—C(=O)-GGFG-NH—$CH_2CH_2CH_2CH_2CH_2$—C(=O)—
-(Succinimid-3-yl-N)—$CH_2CH_2CH_2$—C(=O)-GGFG-NH—$CH_2CH_2CH_2CH_2CH_2$—C(=O)—
-(Succinimid-3-yl-N)—$CH_2CH_2CH_2CH_2$—C(=O)-GGFG-NH—$CH_2CH_2CH_2CH_2CH_2$—C(=O)—
-(Succinimid-3-yl-N)—$CH_2CH_2CH_2CH_2CH_2$—C(=O)-GGFG-NH—$CH_2CH_2CH_2CH_2CH_2$—C(=O)—
-(Succinimid-3-yl-N)—$CH_2CH_2$—C(=O)-GGFG-NH—$CH_2$—O—$CH_2$—C(=O)—
-(Succinimid-3-yl-N)—$CH_2CH_2CH_2$—C(=O)-GGFG-NH—$CH_2$—O—$CH_2$—C(=O)—
-(Succinimid-3-yl-N)—$CH_2CH_2CH_2CH_2$—C(=O)-GGFG-NH—$CH_2$—O—$CH_2$—C(=O)—
-(Succinimid-3-yl-N)—$CH_2CH_2CH_2CH_2CH_2$—C(=O)-GGFG-NH—$CH_2$—O—$CH_2$—C(=O)—
-(Succinimid-3-yl-N)—$CH_2CH_2$—C(=O)-GGFG-NH—$CH_2CH_2$—O—$CH_2$—C(=O)—
-(Succinimid-3-yl-N)—$CH_2CH_2CH_2$—C(=O)-GGFG-NH—$CH_2CH_2$—O—$CH_2$—C(=O)—
-(Succinimid-3-yl-N)—$CH_2CH_2CH_2CH_2$—C(=O)-GGFG-NH—$CH_2CH_2$—O—$CH_2$—C(=O)—
-(Succinimid-3-yl-N)—$CH_2CH_2CH_2CH_2CH_2$—C(=O)-GGFG-NH—$CH_2CH_2$—O—$CH_2$—C(=O)—
-(Succinimid-3-yl-N)—$CH_2CH_2$—C(=O)—NH—$CH_2CH_2O$—$CH_2CH_2O$—$CH_2CH_2$—C(=O)-GGFG-NH—$CH_2CH_2$—C(=O)—
-(Succinimid-3-yl-N)—$CH_2CH_2$—C(=O)—NH—$CH_2CH_2O$—$CH_2CH_2O$—$CH_2CH_2O$—$CH_2CH_2$—C(=O)-GGFG-NH—$CH_2CH_2$—C(=O)—
-(Succinimid-3-yl-N)—$CH_2CH_2$—C(=O)—NH—$CH_2CH_2O$—$CH_2CH_2O$—$CH_2CH_2O$—$CH_2CH_2O$—$CH_2CH_2$—C(=O)-GGFG-NH—$CH_2CH_2$—C(=O)—
-(Succinimid-3-yl-N)—$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—
-(Succinimid-3-yl-N)—$CH_2CH_2$—C(=O)—NH—$CH_2CH_2O$—$CH_2CH_2O$—$CH_2CH_2O$—$CH_2CH_2$—C(=O)-GGFG-NH—$CH_2CH_2CH_2$—C(=O)—
-(Succinimid-3-yl-N)—$CH_2CH_2$—C(=O)—NH—$CH_2CH_2O$—$CH_2CH_2O$—$CH_2CH_2$—C(=O)-GGFG-NH—$CH_2$—O—$CH_2$—C(=O)—
-(Succinimid-3-yl-N)—$CH_2CH_2$—C(=O)—NH—$CH_2CH_2O$—$CH_2CH_2O$—$CH_2CH_2O$—$CH_2CH_2$—C(=O)-GGFG-NH—$CH_2$—O—$CH_2$—C(=O)—
-(Succinimid-3-yl-N)—$CH_2CH_2$—C(=O)—NH—$CH_2CH_2O$—$CH_2CH_2O$—$CH_2CH_2O$—$CH_2CH_2O$—$CH_2CH_2$—C(=O)-GGFG-NH—$CH_2$—O—$CH_2$—C(=O)—
-(Succinimid-3-yl-N)—$CH_2CH_2$—C(=O)—NH—$CH_2CH_2O$—$CH_2CH_2O$—$CH_2CH_2$—C(=O)-GGFG-NH—$CH_2CH_2$—O—$CH_2$—C(=O)—
-(Succinimid-3-yl-N)—$CH_2CH_2$—C(=O)—NH—$CH_2CH_2O$—$CH_2CH_2O$—$CH_2CH_2O$—$CH_2CH_2$—C(=O)-GGFG-NH—$CH_2CH_2$—O—$CH_2$—C(=O)—
-(Succinimid-3-yl-N)—$CH_2CH_2$—C(=O)—NH—$CH_2CH_2O$—$CH_2CH_2O$—$CH_2CH_2O$—$CH_2CH_2O$—$CH_2CH_2$—C(=O)-GGFG-NH—$CH_2CH_2$—O—$CH_2$—C(=O)—
—$CH_2$—C(=O)—NH—$CH_2CH_2$—C(=O)-GGFG-NH—$CH_2CH_2$—C(=O)—
—$CH_2$—C(=O)—NH—$CH_2CH_2$—C(=O)-GGFG-NH—$CH_2CH_2CH_2$—C(=O)—
—$CH_2$—C(=O)—NH—$CH_2CH_2$—C(=O)-GGFG-NH—$CH_2$—O—$CH_2$—C(=O)—
—$CH_2$—C(=O)—NH—$CH_2CH_2$—C(=O)-GGFG-NH—$CH_2CH_2$—O—$CH_2$—C(=O)—
—$CH_2$—C(=O)—NH—$CH_2CH_2CH_2$—C(=O)-GGFG-NH—$CH_2CH_2$—C(=O)—
—$CH_2$—C(=O)—NH—$CH_2CH_2CH_2$—C(=O)-GGFG-NH—$CH_2CH_2CH_2$—C(=O)—
—$CH_2$—C(=O)—NH—$CH_2CH_2CH_2$—C(=O)-GGFG-NH—$CH_2$—O—$CH_2$—C(=O)—
—$CH_2$—C(=O)—NH—$CH_2CH_2CH_2$—C(=O)-GGFG-NH—$CH_2CH_2$—O—$CH_2$—C(=O)—
—$CH_2$—C(=O)—NH—$CH_2CH_2CH_2CH_2$—C(=O)-GGFG-NH—$CH_2CH_2$—C(=O)—
—$CH_2$—C(=O)—NH—$CH_2CH_2CH_2CH_2$—C(=O)-GGFG-NH—$CH_2CH_2CH_2$—C(=O)—
—$CH_2$—C(=O)—NH—$CH_2CH_2CH_2CH_2$—C(=O)-GGFG-NH—$CH_2$—O—$CH_2$—C(=O)—
—$CH_2$—C(=O)—NH—$CH_2CH_2CH_2CH_2$—C(=O)-GGFG-NH—$CH_2CH_2$—O—$CH_2$—C(=O)—
—$CH_2$—C(=O)—NH—$CH_2CH_2CH_2CH_2CH_2$—C(=O)-GGFG-NH—$CH_2CH_2$—C(=O)—
—$CH_2$—C(=O)—NH—$CH_2CH_2CH_2CH_2CH_2$—C(=O)-GGFG-NH—$CH_2CH_2CH_2$—C(=O)—
—$CH_2$—C(=O)—NH—$CH_2CH_2CH_2CH_2CH_2$—C(=O)-GGFG-NH—$CH_2$—O—$CH_2$—C(=O)—
—$CH_2$—C(=O)—NH—$CH_2CH_2CH_2CH_2CH_2$—C(=O)-GGFG-NH—$CH_2CH_2$—O—$CH_2$—C(=O)—
—$CH_2$—C(=O) 20-NH—$CH_2CH_2$—C(=O)—$CH_2CH_2$—$CH_2CH_2$—$CH_2CH_2$—C(=O)-GGFG-NH—$CH_2CH_2$—C(=O)—
—$CH_2$—C(=O)—NH—$CH_2CH_2$—C(=O)—$CH_2CH_2O$—$CH_2CH_2$—$CH_2CH_2$—$CH_2CH_2$—C(=O)-GGFG-NH—$CH_2CH_2$—C(=O)—
—$CH_2$—C(=O)—NH—$CH_2CH_2$—C(=O)—$CH_2CH_2O$—$CH_2CH_2O$—$CH_2CH_2O$—$CH_2CH_2O$—$CH_2CH_2$—C(=O)-GGFG-NH—$CH_2CH_2$—C(=O)—
—$CH_2$—C(=O)—NH—$CH_2CH_2$—C(=O)—$CH_2CH_2O$—$CH_2CH_2O$—C(=O)-GGFG-NH—$CH_2CH_2CH_2$—C(=O)—
—$CH_2$—C(=O)—NH—$CH_2CH_2$—C(=O)—$CH_2CH_2$—$CH_2CH_2$—$CH_2CH_2$—C(=O)-GGFG-NH—$CH_2CH_2CH_2$—C(=O)—

—CH$_2$—C(=O)—NH—CH$_2$CH$_2$—C(=O)—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—
—CH$_2$—C(=O)—NH—CH$_2$CH$_2$—C(=O)—CH$_2$CH$_2$O—CH$_2$CH$_2$O—CH$_2$CH$_2$—C(=O)-GGFG-NH—CH$_2$—O—CH$_2$—C(=O)—
—CH$_2$—C(=O)—NH—CH$_2$CH$_2$—CH$_2$CH$_2$O—CH$_2$CH$_2$—C(=O)-GGFG-NH—CH$_2$—O—CH$_2$—C(=O)—
—CH$_2$—C(=O)—NH—CH$_2$CH$_2$—C(=O)—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$—O—CH$_2$—C(=O)—
—CH$_2$—C(=O)—NH—CH$_2$CH$_2$—C(=O)—CH$_2$CH$_2$O—CH$_2$CH$_2$O—CH$_2$CH$_2$—C(=O)-GGFG-NH—CH$_2$CH$_2$—O—CH$_2$—C(=O)—
—CH$_2$—C(=O)—NH—CH$_2$CH$_2$—C(=O)—CH$_2$CH$_2$O—CH$_2$CH$_2$—CH$_2$CH$_2$—CH$_2$CH$_2$—C(=O)-GGFG-NH—CH$_2$CH$_2$—O—CH$_2$—C(=O)—
—CH$_2$—C(=O)—NH—CH$_2$CH$_2$—C(=O)—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$—O—CH$_2$—C(=O)—
—C(=O)—CH$_2$CH$_2$—C(=O)-GGFG-NH—CH$_2$CH$_2$—C(=O)—
—C(=O)—CH$_2$CH$_2$CH$_2$—C(=O)-GGFG-NH—CH$_2$CH$_2$—C(=O)—
—C(=O)—CH$_2$CH$_2$CH$_2$CH$_2$—C(=O)-GGFG-NH—CH$_2$CH$_2$—C(=O)—
—C(=O)—CH$_2$CH$_2$CH$_2$CH$_2$CH$_2$—C(=O)-GGFG-NH—CH$_2$CH$_2$—C(=O)—
—C(=O)—CH$_2$CH$_2$CH$_2$CH$_2$CH$_2$CH$_2$—C(=O)-GGFG-NH—CH$_2$CH$_2$—C(=O)—
—C(=O)—CH$_2$CH$_2$—C(=O)-GGFG-NH—CH$_2$CH$_2$CH$_2$—C(=O)—
—C(=O)—CH$_2$CH$_2$CH$_2$—C(=O)-GGFG-NH—CH$_2$CH$_2$CH$_2$—C(=O)—
—C(=O)—CH$_2$CH$_2$CH$_2$CH$_2$—C(=O)-GGFG-NH—CH$_2$CH$_2$CH$_2$—C(=O)—
—C(=O)—CH$_2$CH$_2$CH$_2$CH$_2$CH$_2$—C(=O)-GGFG-NH—CH$_2$CH$_2$CH$_2$—C(=O)—
—C(=O)—CH$_2$CH$_2$CH$_2$CH$_2$CH$_2$CH$_2$—C(=O)-GGFG-NH—CH$_2$CH$_2$CH$_2$—C(=O)—
—C(=O)—CH$_2$CH$_2$—C(=O)-GGFG-NH—CH$_2$—O—CH$_2$—C(=O)—
—C(=O)—CH$_2$CH$_2$CH$_2$—C(=O)-GGFG-NH—CH$_2$—O—CH$_2$—C(=O)—
—C(=O)—CH$_2$CH$_2$CH$_2$CH$_2$—C(=O)-GGFG-NH—CH$_2$—O—CH$_2$—C(=O)—
—C(=O)—CH$_2$CH$_2$CH$_2$CH$_2$CH$_2$—C(=O)-GGFG-NH—CH$_2$—O—CH$_2$—C(=O)—
—C(=O)—CH$_2$CH$_2$CH$_2$CH$_2$CH$_2$CH$_2$—C(=O)-GGFG-NH—CH$_2$—O—CH$_2$—C(=O)—
—C(=O)—CH$_2$CH$_2$—C(=O)-GGFG-NH—CH$_2$CH$_2$—O—CH$_2$—C(=O)—
—C(=O)—CH$_2$CH$_2$CH$_2$—C(=O)-GGFG-NH—CH$_2$CH$_2$—O—CH$_2$—C(=O)—
—C(=O)—CH$_2$CH$_2$CH$_2$CH$_2$—C(=O)-GGFG-NH—CH$_2$CH$_2$—O—CH$_2$—C(=O)—
—C(=O)—CH$_2$CH$_2$CH$_2$CH$_2$CH$_2$—C(=O)-GGFG-NH—CH$_2$CH$_2$—O—CH$_2$—C(=O)—
—C(=O)—CH$_2$CH$_2$CH$_2$CH$_2$CH$_2$CH$_2$—C(=O)-GGFG-NH—CH$_2$CH$_2$-O—CH$_2$—C(=O)—
—C(=O)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—
—C(=O)—CH$_2$CH$_2$—C(=O)—NH—CH$_2$CH$_2$O—CH$_2$CH$_2$O+CH$_2$CH$_2$—CH$_2$CH$_2$—C(=O)-GGFG-NH—CH$_2$CH$_2$CH$_2$—C(=O)—
—C(=O)—CH$_2$CH$_2$—C(=O)—NH—CH$_2$CH$_2$O—CH$_2$CH$_2$O—CH$_2$CH$_2$—CH$_2$CH$_2$—C(=O)-GGFG-NH—CH$_2$CH$_2$CH$_2$—C(=O)—
—C(=O)-cyc.Hex(1,4)-CH$_2$—(N-ly-3-diminiccuS)-S—CH$_2$—C(=O)-GGFG-NH—CH$_2$CH$_2$—C(=O)—
—C(=O)-cyc.Hex(1,4)-CH$_2$—(N-ly-3-diminiccuS)-S—CH$_2$CH$_2$—C(=O)-GGFG-NH—CH$_2$CH$_2$—C(=O)—
—C(=O)-cyc.Hex(1,4)—CH$_2$—(N-ly-3-diminiccuS)-S—CH$_2$CH$_2$CH$_2$—C(=O)-GGFG-NH—CH$_2$CH$_2$—C(=O)—
—C(=O)-cyc.Hex(1,4)-CH$_2$—(N-ly-3-diminiccuS)-S—CH$_2$CH$_2$CH$_2$CH$_2$—C(=O)-GGFG-NH—CH$_2$CH$_2$—C(=O)—
—C(=O)-cyc.Hex(1,4)-CH$_2$—(N-ly-3-diminiccuS)-S—CH$_2$CH$_2$CH$_2$CH$_2$CH$_2$—C(=O)-GGFG-NH—CH$_2$CH$_2$—C(=O)—
—C(=O)-cyc.Hex(1,4)-CH$_2$—(N-ly-3-diminiccuS)-S—CH$_2$CH$_2$CH$_2$CH$_2$CH$_2$CH$_2$—C(=O)-GGFG-NH—CH$_2$CH$_2$—C(=O)—
—C(=O)-cyc.Hex(1,4)-CH$_2$—(N-ly-3-diminiccuS)-S—CH$_2$—C(=O)-GGFG-NH—CH$_2$CH$_2$CH$_2$—C(=O)—
—C(=O)-cyc.Hex(1,4)-CH$_2$—(N-ly-3-diminiccuS)-S—CH$_2$CH$_2$—C(=O)-GGFG-NH—CH$_2$CH$_2$CH$_2$—C(=O)—
—C(=O)-cyc.Hex (1,4)-CH$_2$—(N-ly-3-diminiccuS)-S—CH$_2$CH$_2$CH$_2$—C(=O)-GGFG-NH—CH$_2$CH$_2$CH$_2$—C(=O)—
—C(=O)-cyc.Hex(1,4)-CH$_2$—(N-ly-3-diminiccuS)-S—CH$_2$CH$_2$CH$_2$CH$_2$—C(=O)-GGFG-NH—CH$_2$CH$_2$CH$_2$—C(=O)—
—C(=O)-cyc.Hex(1,4)-CH$_2$—(N-ly-3-diminiccuS)-S—CH$_2$CH$_2$CH$_2$CH$_2$CH$_2$—C(=O)-GGFG-NH—CH$_2$CH$_2$CH$_2$—C(=O)—
—C(=O)-cyc.Hex(1,4)-CH$_2$—(N-ly-3-diminiccuS)-S—CH$_2$CH$_2$CH$_2$CH$_2$CH$_2$CH$_2$—C(=O)-GGFG-NH—CH$_2$CH$_2$CH$_2$—C(=O)—.

[78] The linker according to [76], which is selected from the following group, provided that the left terminal is a connecting position with the antibody and the right terminal is a connecting position with the antitumor compound:
-(Succinimid-3-yl-N)—CH$_2$CH$_2$—C(=O)-GGFG-NH—CH$_2$CH$_2$—C(=O)—
-(Succinimid-3-yl-N)—CH$_2$CH$_2$CH$_2$—C(=O)-GGFG-NH—CH$_2$CH$_2$—C(=O)—
-(Succinimid-3-yl-N)—CH$_2$CH$_2$CH$_2$CH$_2$—C(=O)-GGFG-NH—CH$_2$CH$_2$—C(=O)—
-(Succinimid-3-yl-N)—CH$_2$CH$_2$CH$_2$CH$_2$CH$_2$—C(=O)-GGFG-NH—CH$_2$CH$_2$—C(=O)—
-(Succinimid-3-yl-N)—CH$_2$CH$_2$—C(=O)-GGFG-NH—CH$_2$CH$_2$CH$_2$—C(=O)—
-(Succinimid-3-yl-N)—CH$_2$CH$_2$CH$_2$—C(=O)-GGFG-NH—CH$_2$CH$_2$CH$_2$—C(=O)—
-(Succinimid-3-yl-N)—CH$_2$CH$_2$CH$_2$CH$_2$—C(=O)-GGFG-NH—CH$_2$CH$_2$CH$_2$—C(=O)—
-(Succinimid-3-yl-N)—CH$_2$CH$_2$CH$_2$CH$_2$CH$_2$—C(=O)-GGFG-NH—CH$_2$CH$_2$CH$_2$—C(=O)—
-(Succinimid-3-yl-N)—CH$_2$CH$_2$—C(=O)-GGFG-NH—CH$_2$CH$_2$CH$_2$CH$_2$—C(=O)—
-(Succinimid-3-yl-N)—CH$_2$CH$_2$CH$_2$—C(=O)-GGFG-NH—CH$_2$CH$_2$CH$_2$CH$_2$CH$_2$—C(=O)—
-(Succinimid-3-yl-N)—CH$_2$CH$_2$CH$_2$—C(=O)-GGFG-NH—CH$_2$CH$_2$CH$_2$CH$_2$CH$_2$—C(=O)—
-(Succinimid-3-yl-N)—CH$_2$CH$_2$CH$_2$CH$_2$CH$_2$—C(=O)-GGFG-NH—CH$_2$CH$_2$CH$_2$CH$_2$CH$_2$—C(=O)—
-(Succinimid-3-yl-N)—CH$_2$CH$_2$—C(=O)-GGFG-NH—CH$_2$—O—CH$_2$—C(=O)—

-(Succinimid-3-yl-N)—CH₂CH₂CH₂—C(=O)-GGFG-NH—CH₂—O—CH₂—C(=O)—
-(Succinimid-3-yl-N)—CH₂CH₂CH₂CH₂—C(=O)-GGFG-NH—CH₂—O—CH₂—C(=O)—
-(Succinimid-3-yl-N)—CH₂CH₂CH₂CH₂CH₂—C(=O)-GGFG-NH—CH₂—O—CH₂—C(=O)—
-(Succinimid-3-yl-N)—CH₂CH₂—C(=O)-GGFG-NH—CH₂CH₂—O—CH₂—C(=O)—
-(Succinimid-3-yl-N)—CH₂CH₂CH₂—C(=O)-GGFG-NH—CH₂CH₂—O—CH₂—C(=O)—
  (Succinimid-3-yl-N)—CH₂CH₂CH₂CH₂—C(=O)-GGFG-NH—CH₂CH₂—O—CH₂—C(=O)—
-(Succinimid-3-yl-N)—CH₂CH₂CH₂CH₂CH₂—C(=O)-GGFG-NH—CH₂CH₂—O—CH₂—C(=O)—
-(Succinimid-3-yl-N)—CH₂CH₂—C(=O)—NH—CH₂CH₂O—CH₂CH₂O—CH₂CH₂—C(=O)-GGFG-NH—CH₂CH₂CH₂—C(=O)—
-(Succinimid-3-yl-N)—CH₂CH₂—C(=O)—NH—CH₂CH₂O—CH₂CH₂O—CH₂CH₂O—CH₂CH₂—C(=O)-GGFG-NH—CH₂CH₂CH₂—C(=O)—
-(Succinimid-3-yl-N)—CH₂CH₂—C(=O)—NH—CH₂CH₂O—CH₂CH₂O—CH₂CH₂O—CH₂CH₂O—CH₂CH₂—C(=O)-GGFG-NH—CH₂CH₂CH₂—C(=O)—.

[79] The linker according to [76], which is selected from the following group, provided that the left terminal is a connecting position with the antibody and the right terminal is a connecting position with the antitumor compound:
-(Succinimid-3-yl-N)—CH₂CH₂—C(=O)-GGFG-NH—CH₂CH₂—C(=O)—
-(Succinimid-3-yl-N)—CH₂CH₂—C(=O)-GGFG-NH—CH₂CH₂CH₂—C(=O)—
-(Succinimid-3-yl-N)—CH₂CH₂CH₂CH₂—C(=O)-GGFG-NH—CH₂CH₂—C(=O)—
-(Succinimid-3-yl-N)—CH₂CH₂CH₂CH₂—C(=O)-GGFG-NH—CH₂CH₂CH₂—C(=O)—
-(Succinimid-3-yl-N)—CH₂CH₂CH₂CH₂—C(=O)-GGFG-NH—CH₂CH₂CH₂CH₂—C(=O)—
-(Succinimid-3-yl-N)—CH₂CH₂CH₂CH₂CH₂—C(=O)-GGFG-NH—CH₂CH₂CH₂CH₂CH₂—C(=O)—
-(Succinimid-3-yl-N)—CH₂CH₂CH₂CH₂CH₂—C(=O)-GGFG-NH—CH₂—O—CH₂—C(=O)—
-(Succinimid-3-yl-N)—CH₂CH₂CH₂CH₂CH₂—C(=O)-GGFG-NH—CH₂CH₂—O—CH₂—C(=O)—
-(Succinimid-3-yl-N)—CH₂CH₂—C(=O)—NH—CH₂CH₂O—CH₂CH₂O—CH₂CH₂—C(=O)-GGFG-NH—CH₂CH₂CH₂—C(=O)—
-(Succinimid-3-yl-N)—CH₂CH₂—C(=O)—NH—CH₂CH₂O—CH₂CH₂O—CH₂CH₂—C(=O)-GGFG-NH—CH₂CH₂—C(=O)—
-(Succinimid-3-yl-N)—CH₂CH₂—C(=O)—NH—CH₂CH₂O—CH₂CH₂O—CH₂CH₂O—CH₂CH₂—C(=O)-GGFG-NH—CH₂CH₂CH₂—C(=O)—
-(Succinimid-3-yl-N)—CH₂CH₂—C(=O)-GGFG-NH—CH₂CH₂CH₂—C(=O)—
—CH₂—C(=O)—NH—CH₂CH₂—C(=O)-GGFG-NH—CH₂CH₂—C(=O)—
—C(=O)—CH₂CH₂CH₂CH₂CH₂—C(=O)-GGFG-NH—CH₂CH₂CH₂—C(=O)—.

[80] The linker according to [76], which is selected from the following group, provided that the left terminal is a connecting position with the antibody and the right terminal is a connecting position with the antitumor compound:
-(Succinimid-3-yl-N)—CH₂CH₂CH₂CH₂CH₂—C(=O)-GGFG-NH—CH₂—O—CH₂—C(=O)—
-(Succinimid-3-yl-N)—CH₂CH₂CH₂CH₂CH₂—C(=O)-GGFG-NH—CH₂CH₂—O—CH₂—C(=O)—
-(Succinimid-3-yl-N)—CH₂CH₂—C(=O)—NH—CH₂CH₂O—CH₂CH₂O—CH₂CH₂—C(=O)-GGFG-NH—CH₂CH₂CH₂—C(=O)—.

Advantageous Effects of Invention

With an antibody-drug conjugate having an antitumor compound exatecan conjugated via a linker with a specific structure, an excellent antitumor effect and safety can be achieved.

BRIEF DESCRIPTION OF DRAWINGS

FIG. 1 shows an amino acid sequence of B7-H3 variant 1 (SEQ ID NO: 1).
FIG. 2 shows an amino acid sequence of B7-H3 variant 2 (SEQ ID NO: 2).
FIG. 3 shows an amino acid sequence of an M30-H1-type heavy chain (SEQ ID NO: 9).
FIG. 4 shows an amino acid sequence of an M30-H2-type heavy chain (SEQ ID NO: 10).
FIG. 5 shows an amino acid sequence of an M30-H3-type heavy chain (SEQ ID NO: 11).
FIG. 6 shows an amino acid sequence of an M30-H4-type heavy chain (SEQ ID NO: 12).
FIG. 7 shows an amino acid sequence of an M30-L1-type light chain (SEQ ID NO: 13).
FIG. 8 shows an amino acid sequence of an M30-L2-type light chain (SEQ ID NO: 14).
FIG. 9 shows an amino acid sequence of an M30-L3-type light chain (SEQ ID NO: 15).
FIG. 10 shows an amino acid sequence of an M30-L4-type light chain (SEQ ID NO: 16).
FIG. 11 shows an amino acid sequence of an M30-L5-type light chain (SEQ ID NO: 17).
FIG. 12 shows an amino acid sequence of an M30-L6-type light chain (SEQ ID NO: 18).
FIG. 13 shows an amino acid sequence of an M30-L7-type light chain (SEQ ID NO: 19).
FIG. 14 shows an amino acid sequence of an M30 antibody heavy chain (SEQ ID NO: 20).
FIG. 15 shows an amino acid sequence of an M30 antibody light chain (SEQ ID NO: 21).
FIG. 16 shows a nucleotide sequence of B7-H3 variant 1 (SEQ ID NO: 26).

DESCRIPTION OF EMBODIMENTS

Figure 17:
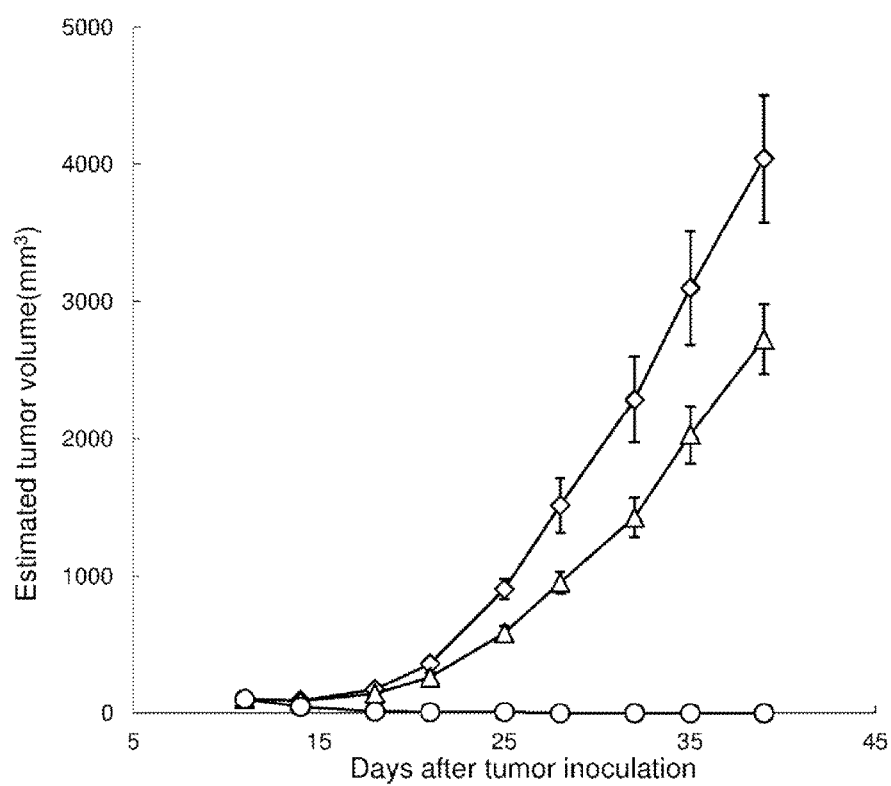
FIG. 17 shows the effect of an antibody-drug conjugate (2) on subcutaneously transplanted human melanoma line A375 cells. In the drawing, the line with open rhombuses depicts results about untreated tumor, the line with open triangles depicts the effect of an M30-H1-L4P antibody, and the line with open circles depicts the effect of the antibody-drug conjugate (2).

The antibody-drug conjugate of the present invention is an antitumor drug in which an antitumor antibody is conjugated to an antitumor compound via a linker structure moiety and explained in detail hereinbelow.

[Antibody]

The antibody used in the antibody-drug conjugate of the present invention means an immunoglobulin and is a molecule containing an antigen-binding site immunospecifically binding to an antigen. The class of the antibody of the present invention may be any of IgG, IgE, IgM, IgD, IgA, and IgY and is preferably IgG. The subclass of the antibody of the present invention may be any of IgG1, IgG2, IgG3, IgG4, IgA1, and IgA2 and is preferably IgG1 or IgG2. The antibody may be derived from any species, and preferred examples of the species can include humans, rats, mice, and rabbits. In case when derived from other than human species, it is preferably chimerized or humanized using a well known technique. The antibody of the present invention may be a polyclonal antibody or a monoclonal antibody and is preferably a monoclonal antibody.

The antibody of the present invention may be those which is capable of targeting tumor cells. Since the antibody of the present invention is conjugated with a drug having antitumor activity via a linker, the antibody preferably possesses one or more of a property of recognizing a tumor cell, a property of binding to a tumor cell, a property of internalizing in a tumor cell, and a property of damaging a tumor cell.

The binding activity of the antibody against tumor cells can be confirmed using flow cytometry. The internalization of the antibody into tumor cells can be confirmed using (1) an assay of visualizing an antibody incorporated in cells under a fluorescence microscope using a secondary antibody (fluorescently labeled) binding to the therapeutic antibody (Cell Death and Differentiation (2008) 15, 751-761), (2) an assay of measuring the amount of fluorescence incorporated in cells using a secondary antibody (fluorescently labeled) binding to the therapeutic antibody (Molecular Biology of the Cell, Vol. 15, 5268-5282, December 2004), or (3) a Mab-ZAP assay using an immunotoxin binding to the therapeutic antibody wherein the toxin is released upon incorporation into cells to inhibit cell growth (Bio Techniques 28: 162-165, January 2000).

The antitumor activity of the antibody refers to a cytotoxic activity or cytocidal effect against tumor cells and can be confirmed in vitro by determining inhibitory activity against cell growth. For example, a cancer cell line overexpressing a target protein for the antibody is cultured, and the antibody is added at varying concentrations into the culture system to determine an inhibitory activity against focus formation, colony formation, and spheroid growth. The antitumor activity can be confirmed in vivo, for example, by administering the antibody to a nude mouse with a transplanted tumor cell line highly expressing the target protein, and determining change in the cancer cell. Since the drug conjugated in the antibody-drug conjugate exerts an antitumor effect, it is more preferred but not essential that the antibody itself should have an antitumor effect. For exerting the antitumor effect and also for specifically and selectively damaging tumor cells by the drug, it is important and also preferred that the antibody should have the property of internalizing to migrate into tumor cells.

Examples of such an antibody can include, but not limited to, an anti-A33 antibody, an anti-B7-H3 antibody, an anti-CanAg antibody, an anti-CD20 antibody, an anti-CD22 antibody, an anti-CD30 antibody, an anti-CD33 antibody, an anti-CD56 antibody, an anti-CD70 antibody, an anti-CEA antibody, an anti-Cripto antibody, an anti-EphA2 antibody, an anti-G250 antibody, an anti-MUC1 antibody, an anti-GPNMB antibody, an anti-integrin antibody, an anti-PSMA antibody, an anti-tenascin-C antibody, an anti-SLC44A4 antibody, and an anti-mesothelin antibody.

The antibody of the present invention is preferably an anti-CD30 antibody, an anti-CD33 antibody, an anti-CD70 antibody, or an anti-B7-H3 antibody, and more preferably an anti-B7-H3 antibody.

The antibody of the present invention can be obtained using a method usually carried out in the art, which involves immunizing animals with an antigenic polypeptide and collecting and purifying antibodies produced in vivo. The origin of the antigen is not limited to humans, and the animals may be immunized with an antigen derived from a non-human animal such as a mouse, a rat and the like. In this case, the cross-reactivity of antibodies binding to the obtained heterologous antigen with human antigens can be tested to screen for an antibody applicable to a human disease.

Alternatively, antibody-producing cells which produce antibodies against the antigen are fused with myeloma cells according to a method known in the art (e.g., Kohler and Milstein, Nature (1975) 256, p. 495-497; and Kennet, R. ed., Monoclonal Antibodies, p. 365-367, Plenum Press, N.Y. (1980)) to establish hybridomas, from which monoclonal antibodies can in turn be obtained.

The antigen can be obtained by genetically engineering host cells to produce a gene encoding the antigenic protein. Specifically, vectors that permit expression of the antigen gene are prepared and transferred to host cells so that the gene is expressed. The antigen thus expressed can be purified.

The anti-CD30 antibody, the anti-CD33 antibody, and the anti-CD70 antibody can obtained by an approach known in the art with reference to WO2002/043661, U.S. Pat. No. 5,773,001, and WO2006/113909, respectively.

The B7-H3 antibody used in the present invention is preferably those having properties as described below.

(1) An antibody having the following properties:
   (a) specifically binding to B7-H3,
   (b) having antibody-dependent cell-mediated phagocytosis (ADCP) activity, and
   (c) having antitumor activity in vivo.
(2) The antibody according to (1), wherein B7-H3 is a molecule comprising the amino acid sequence represented by SEQ ID NO: 1 or 2.
(3) The antibody according to (1) or (2), wherein the antibody has CDRH1 comprising the amino acid sequence represented by SEQ ID NO: 3, CDRH2 comprising the amino acid sequence represented by SEQ ID NO: 4, and CDRH3 comprising the amino acid sequence represented by SEQ ID NO: 5 as heavy chain complementarity determining regions, and CDRL1 comprising the amino acid sequence represented by SEQ ID NO: 6, CDRL2 comprising the amino acid sequence represented by SEQ ID NO: 7, and CDRL3 comprising the amino acid sequence represented by SEQ ID NO: 8 as light chain complementarity determining regions.
(4) The antibody according to any of (1) to (3), wherein the constant region thereof is a human-derived constant region.
(5) The antibody according to any of (1) to (4), wherein the antibody is a humanized antibody.
(6) The antibody according to (5), wherein the antibody has a heavy chain variable region comprising an amino acid sequence selected from the group consisting of (a) an amino acid sequence described in amino acid positions 20 to 141 in SEQ ID NO: 9, (b) an amino acid sequence described in amino acid positions 20 to 141 in SEQ ID NO: 10, (c) an amino acid sequence described in amino acid positions 20 to 141 in SEQ ID NO: 11, (d) an amino acid sequence described in amino acid positions 20 to 141 in SEQ ID NO: 12, (e) an amino acid sequence having at least 95% or higher homology to any of the sequences (a) to (d), and (f) an amino acid sequence derived from any of the sequences (a) to (d) by the deletions, replacements, or additions of at least one amino acid, and a light chain variable region comprising an amino acid sequence selected from the group consisting of (g) an amino acid sequence described in amino acid positions 21 to 128 in SEQ ID NO: 13, (h) an amino acid sequence described in amino acid positions 21 to 128 in SEQ ID NO: 14, (i) an amino acid sequence described in amino acid positions 21 to 128 in SEQ ID NO: 15, (j) an amino acid sequence described in amino acid positions 21 to 128 in SEQ ID NO: 16, (k) an amino acid sequence described in amino acid positions 21 to 128 in SEQ ID NO: 17, (l) an amino acid sequence described in amino acid positions 21 to 128 in SEQ ID NO: 18, (m) an amino acid sequence described in amino acid positions 21 to 128 in SEQ ID NO: 19, (n) an amino acid sequence having at least 95% or higher homology to any of the sequences (g) to (m), and (o) an amino acid sequence derived from any of the sequences (g) to (m) by the deletions, replacements, or additions of at least one amino acid.
(7) The antibody according to (6), wherein the antibody has a heavy chain variable region and a light chain variable region selected from the group consisting of a heavy chain variable region comprising an amino acid sequence described in amino acid positions 20 to 141 in SEQ ID NO: 9 and a light chain variable region comprising an amino acid sequence described in amino acid positions 21 to 128 in SEQ ID NO: 13, a heavy chain variable region comprising an amino acid sequence described in amino acid positions 20 to 141 in SEQ ID NO: 9 and a light chain variable region comprising an amino acid sequence described in amino acid positions 21 to 128 in SEQ ID NO: 14, a heavy chain variable region comprising an amino acid sequence described in amino acid positions 20 to 141 in SEQ ID NO: 9 and a light chain variable region comprising an amino acid sequence described in amino acid positions 21 to 128 in SEQ ID NO: 15, a heavy chain variable region comprising an amino acid sequence described in amino acid positions 20 to 141 in SEQ ID NO: 9 and a light chain variable region comprising an amino acid sequence described in amino acid positions 21 to 128 in SEQ ID NO: 16, a heavy chain variable region comprising an amino acid sequence described in amino acid positions 20 to 141 in SEQ ID NO: 9 and a light chain variable region comprising an amino acid sequence described in amino acid positions 21 to 128 in SEQ ID NO: 17, a heavy chain variable region comprising an amino acid sequence described in amino acid positions 20 to 141 in SEQ ID NO: 9 and a light chain variable region comprising an amino acid sequence described in amino acid positions 21 to 128 in SEQ ID NO: 18, a heavy chain variable region comprising an amino acid sequence described in amino acid positions 20 to 141 in SEQ ID NO: 9 and a light chain variable region comprising an amino acid sequence described in amino acid positions 21 to 128 in SEQ ID NO: 19, a heavy chain variable region comprising an amino acid sequence described in amino acid positions 20 to 141 in SEQ ID NO: 12 and a light chain variable region comprising an amino acid sequence described in amino acid positions 21 to 128 in SEQ ID NO: 13, a heavy chain variable region comprising an amino acid sequence described in amino acid positions 20 to 141 in SEQ ID NO: 12 and a light chain variable region comprising an amino acid sequence described in amino acid positions 21 to 128 in SEQ ID NO: 14, a heavy chain variable region comprising an amino acid sequence described in amino acid positions 20 to 141 in SEQ ID NO: 12 and a light chain variable region comprising an amino acid sequence described in amino acid positions 21 to 128 in SEQ ID NO: 15, and a heavy chain variable region comprising an amino acid sequence described in amino acid positions 20 to 141 in SEQ ID NO: 12 and a light chain variable region comprising an amino acid sequence described in amino acid positions 21 to 128 in SEQ ID NO: 16.
(8) The antibody according to (6) or (7), wherein the antibody comprises a heavy chain and a light chain selected from the group consisting of a heavy chain comprising an amino acid sequence described in amino acid positions 20 to 471 in SEQ ID NO: 9 and a light chain comprising an amino acid sequence described in amino acid positions 21 to 233 in SEQ ID NO: 13, a heavy chain comprising an amino acid sequence described in amino acid positions 20 to 471 in SEQ ID NO: 9 and a light chain comprising an amino acid sequence described in amino acid positions 21 to 233 in SEQ ID NO: 14, a heavy chain comprising an amino acid sequence described in amino acid positions 20 to 471 in SEQ ID NO: 9 and a light chain comprising an amino acid sequence described in amino acid positions 21 to 233 in SEQ ID NO: 15, a heavy chain comprising an amino acid sequence described in amino acid positions 20 to 471 in SEQ ID NO: 9 and a light chain comprising an amino acid sequence described in amino acid positions 21 to 233 in SEQ ID NO: 16, a heavy chain comprising an amino acid sequence described in amino acid positions 20 to 471 in SEQ ID NO: 9 and a light chain comprising an amino acid sequence described in amino acid positions 21 to 233 in SEQ ID NO: 17, a heavy chain comprising an amino acid sequence described in amino acid positions 20 to 471 in SEQ ID NO: 9 and a light chain comprising an amino acid sequence described in amino acid positions 21 to 233 in SEQ ID NO: 18, a heavy chain comprising an amino acid sequence described in amino acid positions 20 to 471 in SEQ ID NO: 9 and a light chain comprising an amino acid sequence described in amino acid positions 21 to 233 in SEQ ID NO: 19, a heavy chain comprising an amino acid sequence described in amino acid positions 20 to 471 in SEQ ID NO: 12 and a light chain comprising an amino acid sequence described in amino acid positions 21 to 233 in SEQ ID NO: 13, a heavy chain comprising an amino acid sequence described in amino acid positions 20 to 471 in SEQ ID NO: 12 and a light chain comprising an amino acid sequence described in amino acid positions 21 to 233 in SEQ ID NO: 14, a heavy chain comprising an amino acid sequence described in amino acid positions 20 to 471 in SEQ ID NO: 12 and a light chain comprising an amino acid sequence described in amino acid positions 21 to 233 in SEQ ID NO: 15, and a heavy chain comprising an amino acid sequence described in amino acid positions 20 to 471 in SEQ ID NO: 12 and a light chain comprising an amino acid sequence described in amino acid positions 21 to 233 in SEQ ID NO: 16.

(9) The antibody according to any of (6) to (8), wherein the antibody comprises a heavy chain and a light chain selected from the group consisting of a heavy chain comprising the amino acid sequence represented by SEQ ID NO: 9 and a light chain comprising the amino acid sequence represented by SEQ ID NO: 13, a heavy chain comprising the amino acid sequence represented by SEQ ID NO: 9 and a light chain comprising the amino acid sequence represented by SEQ ID NO: 14, a heavy chain comprising the amino acid sequence represented by SEQ ID NO: 9 and a light chain comprising the amino acid sequence represented by SEQ ID NO: 15, a heavy chain comprising the amino acid sequence represented by SEQ ID NO: 9 and a light chain comprising the amino acid sequence represented by SEQ ID NO: 16, a heavy chain comprising the amino acid sequence represented by SEQ ID NO: 9 and a light chain comprising the amino acid sequence represented by SEQ ID NO: 17, a heavy chain comprising the amino acid sequence represented by SEQ ID NO: 9 and a light chain comprising the amino acid sequence represented by SEQ ID NO: 18, a heavy chain comprising the amino acid sequence represented by SEQ ID NO: 9 and a light chain comprising the amino acid sequence represented by SEQ ID NO: 19, a heavy chain comprising the amino acid sequence represented by SEQ ID NO: 12 and a light chain comprising the amino acid sequence represented by SEQ ID NO: 13, a heavy chain comprising the amino acid sequence represented by SEQ ID NO: 12 and a light chain comprising the amino acid sequence represented by SEQ ID NO: 14, a heavy chain comprising the amino acid sequence represented by SEQ ID NO: 12 and a light chain comprising the amino acid sequence represented by SEQ ID NO: 15, and a heavy chain comprising the amino acid sequence represented by SEQ ID NO: 12 and a light chain comprising the amino acid sequence represented by SEQ ID NO: 16.

(10) The antibody according to (8) or (9), wherein the antibody lacks an amino acid at the carboxy terminus of the amino acid sequence represented by SEQ ID NO: 9 or 12 in the heavy chain.

(11) An antibody obtained by a method for producing the antibody according to any of (1) to (10), the method comprising the steps of: culturing a host cell transformed with an expression vector containing a polynucleotide encoding the antibody; and collecting the antibody of interest from the cultures obtained in the preceding step.

(12) The antibody according to any of (1) to (11), wherein the modification of a glycan is regulated in order to enhance antibody-dependent cytotoxic activity.

Hereinafter, the B7-H3 antibody used in the invention is described.

The terms "cancer" and "tumor" as used herein are used with the same meaning.

The term "gene" as used herein includes not only DNA, but also mRNA thereof, cDNA thereof and cRNA thereof.

The term "polynucleotide" as used herein is used with the same meaning as a nucleic acid and also includes DNA, RNA, probes, oligonucleotides, and primers.

The terms "polypeptide" and "protein" as used herein are used without distinction.

The term "cell" as used herein also includes cells in an animal individual and cultured cells.

The term "B7-H3" as used herein is used in the same meaning as B7-H3 protein, and also refers to B7-H3 variant 1 and/or B7-H3 variant 2.

The term "CDR" as used herein refers to a complementarity determining region (CDR), and it is known that each heavy and light chain of an antibody molecule has three complementarity determining regions (CDRs). The CDR is also called the hypervariable region, and is present in a variable region of each heavy and light chain of an antibody. It is a site which has unusually high variability in its primary structure, and there are three separate CDRs in the primary structure of each heavy and light polypeptide chain. In this specification, as for the CDRs of an antibody, the CDRs of the heavy chain are represented by CDRH1, CDRH2, and CDRH3 from the amino-terminal side of the amino acid sequence of the heavy chain, and the CDRs of the light chain are represented by CDRL1, CDRL2, and CDRL3 from the amino-terminal side of the amino acid sequence of the light chain. These sites are proximate to one another in the tertiary structure and determine the specificity for an antigen to which the antibody binds.

The phrase "hybridization is performed under stringent conditions" as used herein refers to a process in which hybridization is performed under conditions under which identification can be achieved by performing hybridization at 68° C. in a commercially available hybridization solution ExpressHyb Hybridization Solution (manufactured by Clontech, Inc.) or by performing hybridization at 68° C. in the presence of 0.7 to 1.0 M NaCl using a filter having DNA immobilized thereon, followed by performing washing at 68° C. using 0.1 to 2×SSC solution (1×SSC solution is composed of 150 mM NaCl and 15 mM sodium citrate) or under conditions equivalent thereto.

1. B7-H3

B7-H3 is a member of the B7 family expressed on antigen-presenting cells as a co-stimulatory molecule, and is considered to act on a receptor on T cells to enhance or suppress immune activity.

B7-H3 is a protein having a single-pass transmembrane structure, and the N-terminal extracellular domain of B7-H3 contains two variants.

The B7-H3 variant 1 (4Ig-B7-H3) contains a V-like or C-like Ig domain at two sites, respectively, and the B7-H3 variant 2 (2Ig-B7-H3) contains a V-like or C-like Ig domain at one site, respectively.

As for B7-H3 to be used in the invention, B7-H3 can be directly purified from B7-H3-expressing cells of a human or a non-human mammal (such as a rat or a mouse) and used, or a cell membrane fraction of the above-described cells can be prepared and used. Further, B7-H3 can be obtained by in vitro synthesis thereof or production thereof in a host cell through genetic engineering. In the genetic engineering, specifically, after B7-H3 cDNA is integrated into a vector capable of expressing B7-H3 cDNA, B7-H3 can be obtained by synthesizing it in a solution containing an enzyme, a substrate and an energy substance required for transcription and translation, or by expressing B7-H3 in another prokaryotic or eucaryotic transformed host cell.

The amino acid sequence of an open reading frame (ORF) of a human B7-H3 variant 1 gene is represented by SEQ ID NO: 1 in the Sequence Listing. Further, the sequence of SEQ ID NO: 1 is shown in FIG. 1.

The amino acid sequence of an ORF of a human B7-H3 variant 2 gene is represented by SEQ ID NO: 2 in the Sequence Listing. Further, the sequence of SEQ ID NO: 2 is shown in FIG. 2.

Further, a protein which consists of an amino acid sequence wherein one or several amino acids are substituted, deleted and/or added in any of the above-described amino acid sequences of B7-H3 and also has a biological activity equivalent to that of the protein is also included in B7-H3.

Mature human B7-H3 variant 1 from which the signal sequence has been removed corresponds to an amino acid sequence consisting of amino acid residues 27 to 534 of the amino acid sequence represented by SEQ ID NO: 1. Further, mature human B7-H3 variant 2 from which the signal sequence has been removed corresponds to an amino acid sequence consisting of amino acid residues 27 to 316 of the amino acid sequence represented by SEQ ID NO: 2.

2. Production of Anti-B7-H3 Antibody

The antibody against B7-H3 of the invention can be obtained by immunizing an animal with B7-H3 or an arbitrary polypeptide selected from the amino acid sequence of B7-H3, and collecting and purifying the antibody produced in vivo according to a common procedure. The biological species of B7-H3 to be used as an antigen is not limited to being human, and an animal can be immunized with B7-H3 derived from an animal other than humans such as a mouse or a rat. In this case, by examining the cross-reactivity between an antibody binding to the obtained heterologous B7-H3 and human B7-H3, an antibody applicable to a human disease can be selected.

Further, a monoclonal antibody can be obtained from a hybridoma established by fusing antibody-producing cells which produce an antibody against B7-H3 with myeloma cells according to a known method (for example, Kohler and Milstein, Nature, (1975) 256, pp. 495-497; Kennet, R. ed., Monoclonal Antibodies, pp. 365-367, Plenum Press, N.Y. (1980)).

B7-H3 to be used as an antigen can be obtained by expressing B7-H3 gene in a host cell using genetic engineering.

Specifically, a vector capable of expressing B7-H3 gene is produced, and the resulting vector is transfected into a host cell to express the gene, and then, the expressed B7-H3 is purified. Hereinafter, a method of obtaining an antibody against B7-H3 is specifically described.

(1) Preparation of antigen

Examples of the antigen to be used for producing the anti-B7-H3 antibody include B7-H3, a polypeptide consisting of a partial amino acid sequence comprising at least 6 consecutive amino acids of B7-H3, and a derivative obtained by adding a given amino acid sequence or carrier thereto.

B7-H3 can be purified directly from human tumor tissues or tumor cells and used. Further, B7-H3 can be obtained by synthesizing it in vitro or by producing it in a host cell by genetic engineering.

With respect to the genetic engineering, specifically, after B7-H3cDNA is integrated into a vector capable of expressing B7-H3 cDNA, B7-H3 can be obtained by synthesizing it in a solution containing an enzyme, a substrate and an energy substance required for transcription and translation, or by expressing B7-H3 in another prokaryotic or eucaryotic transformed host cell.

Further, the antigen can also be obtained as a secretory protein by expressing a fusion protein obtained by ligating the extracellular domain of B7-H3, which is a membrane protein, to the constant region of an antibody in an appropriate host-vector system.

B7-H3 cDNA can be obtained by, for example, a so-called PCR method in which a polymerase chain reaction (hereinafter referred to as "PCR") is performed using a cDNA library expressing B7-H3 cDNA as a template and primers which specifically amplify B7-H3 cDNA (see Saiki, R. K., et al., Science, (1988) 239, pp. 487-489).

As the in vitro synthesis of the polypeptide, for example, Rapid Translation System (RTS) manufactured by Roche Diagnostics, Inc. can be exemplified, but it is not limited thereto.

Examples of the prokaryotic host cells include *Escherichia coli* and *Bacillus subtilis*. In order to transform the host cells with a target gene, the host cells are transformed by a plasmid vector comprising a replicon, i.e., a replication origin derived from a species compatible with the host, and a regulatory sequence. Further, the vector preferably has a sequence capable of imposing phenotypic selectivity on the transformed cell.

Examples of the eucaryotic host cells include vertebrate cells, insect cells, and yeast cells. As the vertebrate cells, for example, simian COS cells (Gluzman, Y., Cell, (1981) 23, pp. 175-182, ATCC CRL-1650), murine fibroblasts NIH3T3 (ATCC No. CRL-1658), and dihydrofolate reductase-deficient strains (Urlaub, G. and Chasin, L. A., Proc. Natl. Acad. Sci. USA (1980) 77, pp. 4126-4220) of Chinese hamster ovarian cells (CHO cells; ATCC: CCL-61); and the like are often used, however, the cells are not limited thereto.

The thus obtained transformant can be cultured according to a common procedure, and by the culturing of the transformant, a target polypeptide is produced intracellularly or extracellularly.

A suitable medium to be used for the culturing can be selected from various commonly used culture media depending on the employed host cells. If *Escherichia coli* is employed, for example, an LB medium supplemented with an antibiotic such as ampicillin or IPMG as needed can be used.

A recombinant protein produced intracellularly or extracellularly by the transformant through such culturing can be separated and purified by any of various known separation methods utilizing the physical or chemical property of the protein.

Specific examples of the methods include treatment with a common protein precipitant, ultrafiltration, various types of liquid chromatography such as molecular sieve chromatography (gel filtration), adsorption chromatography, ion exchange chromatography, and affinity chromatography, dialysis, and a combination thereof.

Further, by attaching a tag of six histidine residues to a recombinant protein to be expressed, the protein can be efficiently purified with a nickel affinity column. Alternatively, by attaching the IgG Fc region to a recombinant protein to be expressed, the protein can be efficiently purified with a protein A column.

By combining the above-described methods, a large amount of a target polypeptide can be easily produced in high yield and high purity.

(2) Production of Anti-B7-H3 Monoclonal Antibody

Examples of the antibody specific binding to B7-H3 include a monoclonal antibody specific binding to B7-H3, and a method of obtaining the antibody is as described below.

The production of a monoclonal antibody generally requires the following operational steps of:

(a) purifying a biopolymer to be used as an antigen;
(b) preparing antibody-producing cells by immunizing an animal by injection of the antigen, collecting the blood, assaying its antibody titer to determine when the spleen is excised;
(c) preparing myeloma cells (hereinafter referred to as "myeloma");
(d) fusing the antibody-producing cells with the myeloma;
(e) screening a group of hybridomas producing a desired antibody;
(f) dividing the hybridomas into single cell clones (cloning);
(g) optionally, culturing the hybridoma or rearing an animal implanted with the hybridoma for producing a large amount of a monoclonal antibody;
(h) examining the thus produced monoclonal antibody for biological activity and binding specificity, or assaying the same for properties as a labeled reagent; and the like.

Hereinafter, the method of producing a monoclonal antibody will be described in detail following the above steps, however, the method is not limited thereto, and, for example, antibody-producing cells other than spleen cells and myeloma can be used.

(a) Purification of Antigen

As the antigen, B7-H3 prepared by the method as described above or a partial peptide thereof can be used.

Further, a membrane fraction prepared from recombinant cells expressing B7-H3 or the recombinant cells expressing B7-H3 themselves, and also a partial peptide of the protein of the invention chemically synthesized by a method known to those skilled in the art can also be used as the antigen.

(b) Preparation of Antibody-Producing Cells

The antigen obtained in the step (a) is mixed with an adjuvant such as Freund's complete or incomplete adjuvant or aluminum potassium sulfate and the resulting mixture is used as an immunogen to immunize an experimental animal. As the experimental animal, any animal used in a known hybridoma production method can be used without any trouble. Specifically, for example, a mouse, a rat, a goat, sheep, cattle, a horse, or the like can be used. However, from the viewpoint of ease of availability of myeloma cells to be fused with the extracted antibody-producing cells, a mouse or a rat is preferably used as the animal to be immunized.

Further, the strain of a mouse or a rat to be used is not particularly limited, and in the case of a mouse, for example, various strains such as A, AKR, BALB/c, BDP, BA, CE, C3H, 57BL, C57BL, C57L, DBA, FL, HTH, HT1, LP, NZB, NZW, RF, R III, SJL, SWR, WB, and 129 and the like can be used, and in the case of a rat, for example, Wistar, Low, Lewis, Sprague, Dawley, ACI, BN, Fischer and the like can be used.

These mice and rats are commercially available from breeders/distributors of experimental animals, for example, CLEA Japan, Inc. and Charles River Laboratories Japan, Inc.

Among these, in consideration of compatibility of fusing with myeloma cells described below, in the case of a mouse, BALB/c strain, and in the case of a rat, Wistar and Low strains are particularly preferred as the animal to be immunized.

Further, in consideration of antigenic homology between humans and mice, it is also preferred to use a mouse having decreased biological function to remove auto-antibodies, that is, a mouse with an autoimmune disease.

The age of such mouse or rat at the time of immunization is preferably 5 to 12 weeks of age, more preferably 6 to 8 weeks of age.

In order to immunize an animal with B7-H3 or a recombinant thereof, for example, a known method described in detail in, for example, Weir, D. M., Handbook of Experimental Immunology Vol. I. II. III., Blackwell Scientific Publications, Oxford (1987), Kabat, E. A. and Mayer, M. M., Experimental Immunochemistry, Charles C Thomas Publisher Springfield, Ill. (1964) or the like can be used.

Among these immunization methods, a preferred specific method in the invention is, for example, as follows.

That is, first, a membrane protein fraction serving as the antigen or cells caused to express the antigen is/are intradermally or intraperitoneally administrated to an animal.

However, the combination of both routes of administration is preferred for increasing the immunization efficiency, and when intradermal administration is performed in the first half and intraperitoneal administration is performed in the latter half or only at the last dosing, the immunization efficiency can be particularly increased.

The administration schedule of the antigen varies depending on the type of animal to be immunized, individual difference or the like. However, in general, an administration schedule in which the frequency of administration of the antigen is 3 to 6 times and the dosing interval is 2 to 6 weeks is preferred, and an administration schedule in which the frequency of administration of the antigen is 3 to 4 times and the dosing interval is 2 to 4 weeks is more preferred.

Further, the dose of the antigen varies depending on the type of animal, individual differences or the like, however, the dose is generally set to 0.05 to 5 mg, preferably about 0.1 to 0.5 mg.

A booster immunization is performed 1 to 6 weeks, preferably 2 to 4 weeks, more preferably 2 to 3 weeks after the administration of the antigen as described above.

The dose of the antigen at the time of performing the booster immunization varies depending on the type or size of animal or the like, however, in the case of, for example, a mouse, the dose is generally set to 0.05 to 5 mg, preferably 0.1 to 0.5 mg, more preferably about 0.1 to 0.2 mg.

Spleen cells or lymphocytes including antibody-producing cells are aseptically removed from the immunized animal 1 to 10 days, preferably 2 to 5 days, more preferably 2 to 3 days after the booster immunization. At this time, the antibody titer is measured, and if an animal having a sufficiently increased antibody titer is used as a supply source of the antibody-producing cells, the subsequent procedure can be carried out more efficiently.

Examples of the method of measuring the antibody titer to be used here include an RIA method and an ELISA method, but the method is not limited thereto.

For example, if an ELISA method is employed, the measurement of the antibody titer in the invention can be carried out according to the procedures as described below.

First, a purified or partially purified antigen is adsorbed to the surface of a solid phase such as a 96-well plate for ELISA, and the surface of the solid phase having no antigen adsorbed thereto is covered with a protein unrelated to the antigen such as bovine serum albumin (hereinafter referred to as "BSA"). After washing the surface, the surface is brought into contact with a serially-diluted sample (for example, mouse serum) as a primary antibody to allow the antibody in the sample to bind to the antigen.

Further, as a secondary antibody, an antibody labeled with an enzyme against a mouse antibody is added and is allowed to bind to the mouse antibody.

After washing, a substrate for the enzyme is added and a change in absorbance which occurs due to color development induced by degradation of the substrate or the like is measured and the antibody titer is calculated based on the measurement.

The separation of the antibody-producing cells from the spleen cells or lymphocytes of the immunized animal can be carried out according to a known method (for example, Kohler et al., Nature (1975), 256, p. 495; Kohler et al., Eur. J. Immunol. (1977), 6, p. 511; Milstein et al., Nature (1977), 266, p. 550; Walsh, Nature (1977), 266, p. 495). For example, in the case of spleen cells, a general method in which the antibody-producing cells are separated by homogenizing the spleen to obtain the cells through filtration with a stainless steel mesh and suspending the cells in Eagle's Minimum Essential Medium (MEM) can be employed.

(c) Preparation of Myeloma Cells (Hereinafter Referred to as "Myeloma")

The myeloma cells to be used for cell fusion are not particularly limited and suitable cells can be selected from known cell lines. However, in consideration of convenience when a hybridoma is selected from fused cells, it is preferred to use an HGPRT (hypoxanthine-guanine phosphoribosyl transferase) deficient strain whose selection procedure has been established.

More specifically, examples of the HGPRT-deficient strain include X63-Ag8(X63), NS1-ANS/1(NS1), P3X63-Ag8.U1(P3U1), X63-Ag8.653(X63.653), SP2/0-Agl4(SP2/0), MPC11-45.6TG1.7(45.6TG), FO, S149/5XXO, and BU.1 derived from mice; 210.RSY3.Ag.1.2.3(Y3) derived from rats; and U266AR(SKO-007), GM1500.GTG-A12 (GM1500), UC729-6, LICR-LOW-HMy2(HMy2) and 8226AR/NIP4-1(NP41) derived from humans. These HGPRT-deficient strains are available from, for example, the American Type Culture Collection (ATCC) or the like.

These cell strains are subcultured in an appropriate medium such as an 8-azaguanine medium [a medium obtained by adding 8-azaguanine to an RPMI 1640 medium supplemented with glutamine, 2-mercaptoethanol, gentamicin, and fetal calf serum (hereinafter referred to as "FCS")], Iscove's Modified Dulbecco's Medium (hereinafter referred to as "IMDM"), or Dulbecco's Modified Eagle Medium (hereinafter referred to as "DMEM"). In this case, 3 to 4 days before performing cell fusion, the cells are subcultured in a normal medium [for example, an ASF104 medium (manufactured by Ajinomoto Co., Ltd.) containing 10% FCS] to ensure not less than $2 \times 10^7$ cells on the day of cell fusion.

(d) Cell Fusion

Fusion between the antibody-producing cells and the myeloma cells can be appropriately performed according to a known method (Weir, D. M. Handbook of Experimental Immunology Vol. T. TI. III., Blackwell Scientific Publications, Oxford (1987), Kabat, E. A. and Mayer, M. M., Experimental Immunochemistry, Charles C Thomas Publisher, Springfield, Ill. (1964), etc.), under conditions such that the survival rate of cells is not excessively reduced.

As such a method, for example, a chemical method in which the antibody-producing cells and the myeloma cells are mixed in a solution containing a polymer such as polyethylene glycol at a high concentration, a physical method using electric stimulation, or the like can be used. Among these methods, a specific example of the chemical method is as described below.

That is, in the case where polyethylene glycol is used in the solution containing a polymer at a high concentration, the antibody-producing cells and the myeloma cells are mixed in a solution of polyethylene glycol having a molecular weight of 1500 to 6000, more preferably 2000 to 4000 at a temperature of from 30 to 40° C., preferably from 35 to 38° C. for 1 to 10 minutes, preferably 5 to 8 minutes.

(e) Selection of a Group of Hybridomas

The method of selecting hybridomas obtained by the above-described cell fusion is not particularly limited. Usually, an HAT (hypoxanthine, aminopterin, thymidine) selection method (Kohler et al., Nature (1975), 256, p. 495; Milstein et al., Nature (1977), 266, p. 550) is used.

This method is effective when hybridomas are obtained using the myeloma cells of an HGPRT-deficient strain which cannot survive in the presence of aminopterin.

That is, by culturing unfused cells and hybridomas in an HAT medium, only hybridomas resistant to aminopterin are selectively allowed to survive and proliferate.

(f) Division into Single Cell Clone (Cloning)

As a cloning method for hybridomas, a known method such as a methylcellulose method, a soft agarose method, or a limiting dilution method can be used (see, for example, Barbara, B. M. and Stanley, M. S.: Selected Methods in Cellular Immunology, W. H. Freeman and Company, San Francisco (1980)). Among these methods, particularly, a three-dimensional culture method such as a methylcellulose method is preferred. For example, the group of hybridomas produced by cell fusion are suspended in a methylcellulose medium such as ClonaCell-HY Selection Medium D (manufactured by StemCell Technologies, inc., #03804) and cultured. Then, the formed hybridoma colonies are collected, whereby monoclonal hybridomas can be obtained. The collected respective hybridoma colonies are cultured, and a hybridoma which has been confirmed to have a stable antibody titer in an obtained hybridoma culture supernatant is selected as a B7-H3 monoclonal antibody-producing hybridoma strain.

Examples of the thus established hybridoma strain include B7-H3 hybridoma M30. In this specification, an antibody produced by the B7-H3 hybridoma M30 is referred to as "M30 antibody" or simply "M30".

The heavy chain of the M30 antibody has an amino acid sequence represented by SEQ ID NO: 20 in the Sequence Listing. Further, the light chain of the M30 antibody has an amino acid sequence represented by SEQ ID NO: 21 in the Sequence Listing. In the heavy chain amino acid sequence represented by SEQ ID NO: 20 in the Sequence Listing, an amino acid sequence consisting of amino acid residues 1 to 19 is a signal sequence, an amino acid sequence consisting of amino acid residues 20 to 141 is a variable region, and an amino acid sequence consisting of amino acid residues 142 to 471 is a constant region. Further, in the light chain amino acid sequence represented by SEQ ID NO: 21 in the Sequence Listing, an amino acid sequence consisting of amino acid residues 1 to 22 is a signal sequence, an amino acid sequence consisting of amino acid residues 23 to 130 is a variable region, and an amino acid sequence consisting of amino acid residues 131 to 235 is a constant region.

(g) Preparation of Monoclonal Antibody by Culturing Hybridoma

By culturing the thus selected hybridoma, a monoclonal antibody can be efficiently obtained. However, prior to culturing, it is preferred to perform screening of a hybridoma which produces a target monoclonal antibody.

In such screening, a known method can be employed.

The measurement of the antibody titer in the invention can be carried out by, for example, an ELISA method explained in item (b) described above.

The hybridoma obtained by the method described above can be stored in a frozen state in liquid nitrogen or in a freezer at −80° C. or below.

After completion of cloning, the medium is changed from an HT medium to a normal medium, and the hybridoma is cultured.

Large-scale culture is performed by rotation culture using a large culture bottle or by spinner culture. From the supernatant obtained by the large-scale culture, a monoclonal antibody which specifically binds to the protein of the invention can be obtained by purification using a method known to those skilled in the art such as gel filtration.

Further, the hybridoma is injected into the abdominal cavity of a mouse of the same strain as the hybridoma (for example, the above-described BALB/c) or a Nu/Nu mouse to proliferate the hybridoma, whereby the ascites containing a large amount of the monoclonal antibody of the invention can be obtained.

In the case where the hybridoma is administered in the abdominal cavity, if a mineral oil such as 2,6,10,14-tetramethyl pentadecane (pristane) is administered 3 to 7 days prior thereto, a larger amount of the ascites can be obtained.

For example, an immunosuppressant is previously injected into the abdominal cavity of a mouse of the same strain as the hybridoma to inactivate T cells. 20 days thereafter, $10^6$ to $10^7$ hybridoma clone cells are suspended in a serum-free medium (0.5 ml), and the suspension is administrated in the abdominal cavity of the mouse. In general, when the abdomen is expanded and filled with the ascites, the ascites is collected from the mouse. By this method, the monoclonal antibody can be obtained at a concentration which is about 100 times or much higher than that in the culture solution.

The monoclonal antibody obtained by the above-described method can be purified by a method described in, for example, Weir, D. M.: Handbook of Experimental Immunology Vol. I, II, III, Blackwell Scientific Publications, Oxford (1978).

The thus obtained monoclonal antibody has high antigen specificity for B7-H3.

(h) Assay of Monoclonal Antibody

The isotype and subclass of the thus obtained monoclonal antibody can be determined as follows.

First, examples of the identification method include an Ouchterlony method, an ELISA method, and an RIA method.

An Ouchterlony method is simple, but when the concentration of the monoclonal antibody is low, a condensation operation is required.

On the other hand, when an ELISA method or an RIA method is used, by directly reacting the culture supernatant with an antigen-adsorbed solid phase and using antibodies corresponding to various types of immunoglobulin isotypes and subclasses as secondary antibodies, the isotype and subclass of the monoclonal antibody can be identified.

In addition, as a simpler method, a commercially available identification kit (for example, Mouse Typer Kit manufactured by Bio-Rad Laboratories, Inc.) or the like can also be used.

Further, the quantitative determination of a protein can be performed by the Folin Lowry method and a method of calculation based on the absorbance at 280 nm [1.4 (OD 280)=Immunoglobulin 1 mg/ml].

Further, even when the monoclonal antibody is separately and independently obtained by performing again the steps of (a) to (h) in (2), it is possible to obtain an antibody having a cytotoxic activity equivalent to that of the M30 antibody. As one example of such an antibody, an antibody which binds to the same epitope as the M30 antibody can be exemplified. The M30 recognizes an epitope in the IgC1 or IgC2 domain, which is a domain in the B7-H3 extracellular domain, and binds to the IgC1 domain or the IgC2 domain or both. Therefore, as the epitope for the antibody of the invention, particularly, an epitope present in the IgC1 or IgC2 domain of B7-H3 can be exemplified. If a newly produced monoclonal antibody binds to a partial peptide or a partial tertiary structure to which the M30 antibody binds, it can be determined that the monoclonal antibody binds to the same epitope as the M30 antibody. Further, by confirming that the monoclonal antibody competes with the M30 antibody for the binding to B7-H3 (that is, the monoclonal antibody inhibits the binding between the M30 antibody and B7-H3), it can be determined that the monoclonal antibody binds to the same epitope as the M30 antibody even if the specific epitope sequence or structure has not been determined. When it is confirmed that the monoclonal antibody binds to the same epitope as the M30 antibody, the monoclonal antibody is strongly expected to have a cytotoxic activity equivalent to that of the M30 antibody.

(3) Other Antibodies

The antibody of the invention includes not only the above-described monoclonal antibody against B7-H3 but also a recombinant antibody obtained by artificial modification for the purpose of decreasing heterologous antigenicity to humans such as a chimeric antibody, a humanized antibody and a human antibody. These antibodies can be produced using a known method.

As the chimeric antibody, an antibody in which antibody variable and constant regions are derived from different species, for example, a chimeric antibody in which a mouse- or rat-derived antibody variable region is connected to a human-derived antibody constant region can be exemplified (see Proc. Natl. Acad. Sci. USA, 81, 6851-6855, (1984)).

As the humanized antibody, an antibody obtained by integrating only a complementarity determining region (CDR) into a human-derived antibody (see Nature (1986) 321, pp. 522-525), and an antibody obtained by grafting a part of the amino acid residues of the framework as well as the CDR sequence to a human antibody by a CDR-grafting method (WO 90/07861) can be exemplified.

However, the humanized antibody derived from the M30 antibody is not limited to a specific humanized antibody as long as the humanized antibody has all 6 types of CDR sequences of the M30 antibody and has an antitumor activity. The heavy chain variable region of the M30 antibody has CDRH1 (NYVMH) consisting of an amino acid sequence represented by SEQ ID NO: 3 in the Sequence Listing, CDRH2 (YINPYNDDVKYNEKFKG) consisting of an amino acid sequence represented by SEQ ID NO: 4 in the Sequence Listing, and CDRH3 (WGYYGSPLYYFDY) consisting of an amino acid sequence represented by SEQ ID NO: 5 in the Sequence Listing. Further, the light chain variable region of the M30 antibody has CDRL1 (RASSR-LIYMH) consisting of an amino acid sequence represented by SEQ ID NO: 6 in the Sequence Listing, CDRL2 (ATSN-LAS) consisting of an amino acid sequence represented by SEQ ID NO: 7 in the Sequence Listing, and CDRL3 (QQWNSNPPT) consisting of an amino acid sequence represented by SEQ ID NO: 8 in the Sequence Listing.

As an example of the humanized antibody of a mouse antibody M30, an arbitrary combination of a heavy chain comprising a heavy chain variable region consisting of any one of (1) an amino acid sequence consisting of amino acid residues 20 to 141 of SEQ ID NO: 9, 10, 11, or 12 in the Sequence Listing, (2) an amino acid sequence having a homology of at least 95% or more with the amino acid sequence (1) described above, and (3) an amino acid sequence wherein one or several amino acids in the amino acid sequence (1) described above are deleted, substituted or added and a light chain comprising a light chain variable region consisting of any one of (4) an amino acid sequence consisting of amino acid residues 21 to 128 of SEQ ID NO: 13, 14, 15, 16, 17, 18, or 19 in the Sequence Listing, (5) an amino acid sequence having a homology of at least 95% or more with the amino acid sequence (4) described above, and (6) an amino acid sequence wherein one or several amino acids in the amino acid sequence (4) described above are deleted, substituted or added can be exemplified.

The term "several" as used herein refers to 1 to 10, 1 to 9, 1 to 8, 1 to 7, 1 to 6, 1 to 5, 1 to 4, 1 to 3, or 1 or 2.

As the amino acid substitution in this specification, a conservative amino acid substitution is preferred. The conservative amino acid substitution refers to a substitution occurring within a group of amino acids related to amino acid side chains. Preferred amino acid groups are as follows: an acidic group (aspartic acid and glutamic acid); a basic group (lysine, arginine, and histidine); a non-polar group (alanine, valine, leucine, isoleucine, proline, phenylalanine, methionine, and tryptophan); and an uncharged polar family (glycine, asparagine, glutamine, cysteine, serine, threonine, and tyrosine). More preferred amino acid groups are as follows: an aliphatic hydroxy group (serine and threonine); an amide-containing group (asparagine and glutamine); an aliphatic group (alanine, valine, leucine, and isoleucine); and an aromatic group (phenylalanine, tryptophan, and tyrosine). Such an amino acid substitution is preferably performed within a range which does not impair the properties of a substance having the original amino acid sequence.

As an antibody which has a preferred combination of a heavy chain and a light chain described above, an antibody consisting of a heavy chain comprising a heavy chain variable region consisting of an amino acid sequence consisting of amino acid residues 20 to 141 of SEQ ID NO: 9 and a light chain comprising a light chain variable region consisting of an amino acid sequence consisting of amino acid residues 21 to 128 of SEQ ID NO: 13; an antibody consisting of a heavy chain comprising a heavy chain variable region consisting of an amino acid sequence consisting of amino acid residues 20 to 141 of SEQ ID NO: 9 and a light chain comprising a light chain variable region consisting of an amino acid sequence consisting of amino acid residues 21 to 128 of SEQ ID NO: 14; an antibody consisting of a heavy chain comprising a heavy chain variable region consisting of an amino acid sequence consisting of amino acid residues 20 to 141 of SEQ ID NO: 9 and a light chain comprising a light chain variable region consisting of an amino acid sequence consisting of amino acid residues 21 to 128 of SEQ ID NO: 15; an antibody consisting of a heavy chain comprising a heavy chain variable region consisting of an amino acid sequence consisting of amino acid residues 20 to 141 of SEQ ID NO: 9 and a light chain comprising a light chain variable region consisting of an amino acid sequence consisting of amino acid residues 21 to 128 of SEQ ID NO: 16; an antibody consisting of a heavy chain comprising a heavy chain variable region consisting of an amino acid sequence consisting of amino acid residues 20 to 141 of SEQ ID NO: 9 and a light chain comprising a light chain variable region consisting of an amino acid sequence consisting of amino acid residues 21 to 128 of SEQ ID NO: 17; an antibody consisting of a heavy chain comprising a heavy chain variable region consisting of an amino acid sequence consisting of amino acid residues 20 to 141 of SEQ ID NO: 9 and a light chain comprising a light chain variable region consisting of an amino acid sequence consisting of amino acid residues 21 to 128 of SEQ ID NO: 18; an antibody consisting of a heavy chain comprising a heavy chain variable region consisting of an amino acid sequence consisting of amino acid residues 20 to 141 of SEQ ID NO: 9 and a light chain comprising a light chain variable region consisting of an amino acid sequence consisting of amino acid residues 21 to 128 of SEQ ID NO: 19; an antibody consisting of a heavy chain comprising a heavy chain variable region consisting of an amino acid sequence consisting of amino acid residues 20 to 141 of SEQ ID NO: 12 and a light chain comprising a light chain variable region consisting of an amino acid sequence consisting of amino acid residues 21 to 128 of SEQ ID NO: 13; an antibody consisting of a heavy chain comprising a heavy chain variable region consisting of an amino acid sequence consisting of amino acid residues 20 to 141 of SEQ ID NO: 12 and a light chain comprising a light chain variable region consisting of an amino acid sequence consisting of amino acid residues 21 to 128 of SEQ ID NO: 14; an antibody consisting of a heavy chain comprising a heavy chain variable region consisting of an amino acid sequence consisting of amino acid residues 20 to 141 of SEQ ID NO: 12 and a light chain comprising a light chain variable region consisting of an amino acid sequence consisting of amino acid residues 21 to 128 of SEQ ID NO: 15; and an antibody consisting of a heavy chain comprising a heavy chain variable region consisting of an amino acid sequence consisting of amino acid residues 20 to 141 of SEQ ID NO: 12 and a light chain comprising a light chain variable region consisting of an amino acid sequence consisting of amino acid residues 21 to 128 of SEQ ID NO: 16 can be exemplified.

Further, as an antibody which has a more preferred combination of a heavy chain and a light chain described above, an antibody consisting of a heavy chain consisting of an amino acid sequence consisting of amino acid residues 20 to 471 of SEQ ID NO: 9 and a light chain consisting of an amino acid sequence consisting of amino acid residues 21 to 233 of SEQ ID NO: 13; an antibody consisting of a heavy chain consisting of an amino acid sequence consisting of amino acid residues 20 to 471 of SEQ ID NO: 9 and a light chain consisting of an amino acid sequence consisting of amino acid residues 21 to 233 of SEQ ID NO: 14; an antibody consisting of a heavy chain consisting of an amino acid sequence consisting of amino acid residues 20 to 471 of SEQ ID NO: 9 and a light chain consisting of an amino acid sequence consisting of amino acid residues 21 to 233 of SEQ ID NO: 15; an antibody consisting of a heavy chain consisting of an amino acid sequence consisting of amino acid residues 20 to 471 of SEQ ID NO: 9 and a light chain consisting of an amino acid sequence consisting of amino acid residues 21 to 233 of SEQ ID NO: 16; an antibody consisting of a heavy chain consisting of an amino acid sequence consisting of amino acid residues 20 to 471 of SEQ ID NO: 9 and a light chain consisting of an amino acid sequence consisting of amino acid residues 21 to 233 of SEQ ID NO: 17; an antibody consisting of a heavy chain consisting of an amino acid sequence consisting of amino acid residues 20 to 471 of SEQ ID NO: 9 and a light chain consisting of an amino acid sequence consisting of amino acid residues 21 to 233 of SEQ ID NO: 18; an antibody consisting of a heavy chain consisting of an amino acid sequence consisting of amino acid residues 20 to 471 of SEQ ID NO: 9 and a light chain consisting of an amino acid sequence consisting of amino acid residues 21 to 233 of SEQ ID NO: 19; an antibody consisting of a heavy chain consisting of an amino acid sequence consisting of amino acid residues 20 to 471 of SEQ ID NO: 12 and a light chain consisting of an amino, acid sequence consisting of amino acid residues 21 to 233 of SEQ ID NO: 13; an antibody consisting of a heavy chain consisting of an amino acid sequence consisting of amino acid residues 20 to 471 of SEQ ID NO: 12 and a light chain consisting of an amino acid sequence consisting of amino acid residues 21 to 233 of SEQ ID NO: 14; an antibody consisting of a heavy chain consisting of an amino acid sequence consisting of amino acid residues 20 to 471 of SEQ ID NO: 12 and a light chain consisting of an amino acid sequence consisting of amino acid residues 21 to 233 of SEQ ID NO: 15; and an antibody consisting of a heavy chain consisting of an amino acid sequence consisting of amino acid residues 20 to 471 of SEQ ID NO: 12 and a light chain consisting of an amino acid sequence consisting of amino acid residues 21 to 233 of SEQ ID NO: 16 can be exemplified.

Furthermore, as an antibody which has another more preferred combination of a heavy chain and a light chain described above, an antibody consisting of a heavy chain consisting of an amino acid sequence of SEQ ID NO: 9 and a light chain consisting of an amino acid sequence of SEQ ID NO: 13; an antibody consisting of a heavy chain consisting of an amino acid sequence of SEQ ID NO: 9 and a light chain consisting of an amino acid sequence of SEQ ID NO: 14; an antibody consisting of a heavy chain consisting of an amino acid sequence of SEQ ID NO: 9 and a light chain consisting of an amino acid sequence of SEQ ID NO: 15; an antibody consisting of a heavy chain consisting of an amino acid sequence of SEQ ID NO: 9 and a light chain consisting of an amino acid sequence of SEQ ID NO: 16; an antibody consisting of a heavy chain consisting of an amino acid sequence of SEQ ID NO: 9 and a light chain consisting of an amino acid sequence of SEQ ID NO: 17; an antibody consisting of a heavy chain consisting of an amino acid sequence of SEQ ID NO: 9 and a light chain consisting of an amino acid sequence of SEQ ID NO: 18; an antibody consisting of a heavy chain consisting of an amino acid sequence of SEQ ID NO: 9 and a light chain consisting of an amino acid sequence of SEQ ID NO: 19; an antibody consisting of a heavy chain consisting of an amino acid sequence of SEQ ID NO: 12 and a light chain consisting of an amino acid sequence of SEQ ID NO: 13; an antibody consisting of a heavy chain consisting of an amino acid sequence of SEQ ID NO: 12 and a light chain consisting of an amino acid sequence of SEQ ID NO: 14; an antibody consisting of a heavy chain consisting of an amino acid sequence of SEQ ID NO: 12 and a light chain consisting of an amino acid sequence of SEQ ID NO: 15; and an antibody consisting of a heavy chain consisting of an amino acid sequence of SEQ ID NO: 12 and a light chain consisting of an amino acid sequence of SEQ ID NO: 16 can be exemplified.

By combining a sequence having a high homology with the above-described heavy chain amino acid sequence with a sequence having a high homology with the above-described light chain amino acid sequence, it is possible to select an antibody having a cytotoxic activity equivalent to that of each of the above-described antibodies. Such a homology is generally a homology of 80% or more, preferably a homology of 90% or more, more preferably a homology of 95% or more, most preferably a homology of 99% or more. Further, by combining an amino acid sequence wherein one to several amino acid residues are substituted, deleted or added in the heavy chain or light chain amino acid sequence, it is also possible to select an antibody having a cytotoxic activity equivalent to that of each of the above-described antibodies.

The homology between two amino acid sequences can be determined using default parameters of Blast algorithm version 2.2.2 (Altschul, Stephen F., Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25: 3389-3402). The Blast algorithm can be used also through the Internet by accessing the site www.ncbi.nlm.nih.gov/blast.

In the heavy chain amino acid sequence represented by SEQ ID NO: 9, 10, 11 or 12 in the Sequence Listing, an amino acid sequence consisting of amino acid residues 1 to 19 is a signal sequence, an amino acid sequence consisting of amino acid residues 20 to 141 is a variable region, and an amino acid sequence consisting of amino acid residues 142 to 471 is a constant region. The sequence of SEQ ID NO: 9, 10, 11 and 12 are shown in FIGS. 3, 4, 5 and 6 respectively.

Further, in the light chain amino acid sequence represented by SEQ ID NO: 13, 14, 15, 16, 17, 18 or 19 in the Sequence Listing, an amino acid sequence consisting of amino acid residues 1 to 20 is a signal sequence, an amino acid sequence consisting of amino acid residues 21 to 128 is a variable region, and an amino acid sequence consisting of amino acid residues 129 to 233 is a constant region. The sequence of SEQ ID NO: 13, 14, 15, 16, 17, 18 and 19 are shown in FIGS. 7, 8, 9, 10, 11, 12 and 13 respectively.

Further, the antibody of the invention includes a human antibody which binds to the same epitope as the M30 antibody. An anti-B7-H3 human antibody refers to a human antibody having only a sequence of an antibody derived from a human chromosome. The anti-B7-H3 human antibody can be obtained by a method using a human antibody-producing mouse having a human chromosome fragment comprising heavy and light chain genes of a human antibody (see Tomizuka, K. et al., Nature Genetics (1997) 16, pp. 133-143; Kuroiwa, Y. et al., Nucl. Acids Res. (1998) 26, pp. 3447-3448; Yoshida, H. et al., Animal Cell Technology: Basic and Applied Aspects vol. 10, pp. 69-73 (Kitagawa, Y., Matuda, T. and Iijima, S. eds.), Kluwer Academic Publishers, 1999; Tomizuka, K. et al., Proc. Natl. Acad. Sci. USA (2000) 97, pp. 722-727, etc.).

Such a human antibody-producing mouse can be created specifically as follows. A genetically modified animal in which endogenous immunoglobulin heavy and light chain gene loci have been disrupted, and instead, human immunoglobulin heavy and light chain gene loci have been introduced via a yeast artificial chromosome (YAC) vector or the like is created by producing a knockout animal and a transgenic animal and mating these animals.

Further, according to a recombinant DNA technique, by using cDNAs encoding each of such a heavy chain and a light chain of a human antibody, and preferably a vector comprising such cDNAs, eukaryotic cells are transformed, and a transformant cell which produces a recombinant human monoclonal antibody is cultured, whereby the antibody can also be obtained from the culture supernatant.

Here, as the host, for example, eukaryotic cells, preferably mammalian cells such as CHO cells, lymphocytes, or myeloma cells can be used.

Further, a method of obtaining a phage display-derived human antibody selected from a human antibody library (see Wormstone, I. M. et al., Investigative Ophthalmology & Visual Science. (2002) 43 (7), pp. 2301-2308; Carmen, S. et al., Briefings in Functional Genomics and Proteomics (2002), 1 (2), pp. 189-203; Siriwardena, D. et al., Ophthalmology (2002) 109 (3), pp. 427-431, etc.) is also known.

For example, a phage display method in which a variable region of a human antibody is expressed on the surface of a phage as a single-chain antibody (scFv), and a phage which binds to an antigen is selected (Nature Biotechnology (2005), 23, (9), pp. 1105-1116) can be used.

By analyzing the gene of the phage selected based on the binding to an antigen, a DNA sequence encoding the variable region of a human antibody which binds to an antigen can be determined.

If the DNA sequence of scFv which binds to an antigen is determined, a human antibody can be obtained by preparing an expression vector comprising the sequence and introducing the vector into an appropriate host to express it (WO 92/01047, WO 92/20791, WO 93/06213, WO 93/11236, WO 93/19172, WO 95/01438, WO 95/15388, Annu. Rev. Immunol. (1994) 12, pp. 433-455, Nature Biotechnology (2005) 23 (9), pp. 1105-1116).

If a newly produced human antibody binds to a partial peptide or a partial tertiary structure to which the M30 antibody binds, it can be determined that the human antibody binds to the same epitope as the M30 antibody. Further, by confirming that the human antibody competes with the M30 antibody for the binding to B7-H3 (that is, the human antibody inhibits the binding between the M30 antibody and B7-H3), it can be determined that the human antibody binds to the same epitope as the M30 antibody even if the specific epitope sequence or structure has not been determined.

When it is confirmed that the human antibody binds to the same epitope as the M30 antibody, the human antibody is strongly expected to have a cytotoxic activity equivalent to that of the M30 antibody.

The chimeric antibodies, humanized antibodies, or human antibodies obtained by the above-described method are evaluated for the binding property to an antigen by a known method or the like, and a preferred antibody can be selected.

As one example of another index for use in the comparison of the properties of antibodies, the stability of antibodies can be exemplified. The differential scanning calorimetry (DSC) is a device capable of quickly and accurately measuring a thermal denaturation midpoint temperature (Tm) to be used as a favorable index of the relative conformational stability of proteins. By measuring the Tm values using DSC and comparing the values, a difference in thermal stability can be compared. It is known that the storage stability of antibodies shows some correlation with the thermal stability of antibodies (Lori Burton, et. al., Pharmaceutical Development and Technology (2007) 12, pp. 265-273), and a preferred antibody can be selected by using thermal stability as an index. Examples of other indices for selecting antibodies include the following features: the yield in an appropriate host cell is high; and the aggregability in an aqueous solution is low. For example, an antibody which shows the highest yield does not always show the highest thermal stability, and therefore, it is necessary to select an antibody most suitable for the administration to humans by making comprehensive evaluation based on the above-described indices.

In the invention, a modified variant of the antibody is also included. The modified variant refers to a variant obtained by subjecting the antibody of the invention to chemical or biological modification.

Examples of the chemically modified variant include variants chemically modified by linking a chemical moiety to an amino acid skeleton, variants chemically modified with an N-linked or O-linked carbohydrate chain, etc. Examples of the biologically modified variant include variants obtained by post-translational modification (such as N-linked or O-linked glycosylation, N- or C-terminal processing, deamidation, isomerization of aspartic acid, or oxidation of methionine), and variants in which a methionine residue has been added to the N terminus by being expressed in a prokaryotic host cell.

Further, an antibody labeled so as to enable the detection or isolation of the antibody or an antigen of the invention, for example, an enzyme-labeled antibody, a fluorescence-labeled antibody, and an affinity-labeled antibody are also included in the meaning of the modified variant. Such a modified variant of the antibody of the invention is useful for improving the stability and blood retention of the original antibody of the invention, reducing the antigenicity thereof, detecting or isolating such an antibody or an antigen, and so on.

Further, by regulating the modification of a glycan which is linked to the antibody of the invention (glycosylation, defucosylation, etc.), it is possible to enhance an antibody-dependent cellular cytotoxic activity. As the technique for regulating the modification of a glycan of antibodies, WO 99/54342, WO 00/61739, WO 02/31140, etc. are known. However, the technique is not limited thereto. In the antibody of the invention, an antibody in which the modification of a glycan is regulated is also included.

In the case where an antibody is produced by first isolating an antibody gene and then introducing the gene into an appropriate host, a combination of an appropriate host and an appropriate expression vector can be used. Specific examples of the antibody gene include a combination of a gene encoding a heavy chain sequence of an antibody described in this specification and a gene encoding a light chain sequence thereof. When a host cell is transformed, it is possible to insert the heavy chain sequence gene and the light chain sequence gene into the same expression vector, and also into different expression vectors separately.

In the case where eukaryotic cells are used as the host, animal cells, plant cells, and eukaryotic microorganisms can be used. As the animal cells, mammalian cells, for example, simian COS cells (Gluzman, Y., Cell, (1981) 23, pp. 175-182, ATCC CRL-1650), murine fibroblasts NIH3T3 (ATCC No. CRL-1658), and dihydrofolate reductase-deficient strains (Urlaub, G. and Chasin, L. A., Proc. Natl. Acad. Sci. USA (1980) 77, pp. 4126-4220) of Chinese hamster ovarian cells (CHO cells; ATCC: CCL-61) can be exemplified.

In the case where prokaryotic cells are used, for example, *Escherichia coli* and *Bacillus subtilis* can be exemplified.

By introducing a desired antibody gene into these cells through transformation, and culturing the thus transformed cells in vitro, the antibody can be obtained. In the above-described culture method, the yield may sometimes vary depending on the sequence of the antibody, and therefore, it is possible to select an antibody which is easily produced as a pharmaceutical by using the yield as an index among the antibodies having an equivalent binding activity. Therefore, in the antibody of the invention, an antibody obtained by a method of producing an antibody, characterized by including a step of culturing the transformed host cell and a step of collecting a desired antibody from a cultured product obtained in the culturing step is also included.

It is known that a lysine residue at the carboxyl terminus of the heavy chain of an antibody produced in a cultured mammalian cell is deleted (Journal of Chromatography A, 705: 129-134 (1995)), and it is also known that two amino acid residues (glycine and lysine) at the carboxyl terminus of the heavy chain of an antibody produced in a cultured mammalian cell are deleted and a proline residue newly located at the carboxyl terminus is amidated (Analytical Biochemistry, 360: 75-83 (2007)). However, such deletion and modification of the heavy chain sequence do not affect the antigen-binding affinity and the effector function (the activation of a complement, the antibody-dependent cellular cytotoxicity, etc.) of the antibody. Therefore, in the invention, an antibody subjected to such modification is also included, and a deletion variant in which one or two amino acids have been deleted at the carboxyl terminus of the heavy chain, a variant obtained by amidation of the deletion variant (for example, a heavy chain in which the carboxyl terminal proline residue has been amidated), and the like can be exemplified. The type of deletion variant having a deletion at the carboxyl terminus of the heavy chain of the antibody according to the invention is not limited to the above variants as long as the antigen-binding affinity and the effector function are conserved. The two heavy chains constituting the antibody according to the invention may be of one type selected from the group consisting of a full-length heavy chain and the above-described deletion variant, or may be of two types in combination selected therefrom. The ratio of the amount of each deletion variant can be affected by the type of cultured mammalian cells which produce the antibody according to the invention and the culture conditions, however, a case where one amino acid residue at the carboxyl terminus has been deleted in both of the two heavy chains contained as main components in the antibody according to the invention can be exemplified.

As isotype of the antibody of the invention, for example, IgG (IgG1, IgG2, IgG3, IgG4) can be exemplified, and IgG1 or IgG2 can be exemplified preferably.

As the function of the antibody, generally an antigen-binding activity, an activity of neutralizing the activity of an antigen, an activity of enhancing the activity of an antigen, an antibody-dependent cellular cytotoxicity (ADCC) activity and a complement-dependent cytotoxicity (CDC) activity can be exemplified. The function of the antibody of the invention is a binding activity to B7-H3, preferably an antibody-dependent cell-mediated phagocytosis (ADCP) activity, more preferably a cytotoxicity activity (antitumor activity) to tumor cell mediated by an ADCP activity. Further, the antibody of the invention may have an ADCC activity and/or a CDC activity in addition to an ADCP activity.

The obtained antibody can be purified to homogeneity. The separation and purification of the antibody may be performed employing a conventional protein separation and purification method. For example, the antibody can be separated and purified by appropriately selecting and combining column chromatography, filter filtration, ultrafiltration, salt precipitation, dialysis, preparative polyacrylamide gel electrophoresis, isoelectric focusing electrophoresis, and the like (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)), but the method is not limited thereto.

Examples of such chromatography include affinity chromatography, ion exchange chromatography, hydrophobic chromatography, gel filtration chromatography, reverse phase chromatography, and adsorption chromatography.

Such chromatography can be performed employing liquid chromatography such as HPLC or FPLC.

As a column to be used in affinity chromatography, a Protein A column and a Protein G column can be exemplified. For example, as a column using a Protein A column, Hyper D, POROS, Sepharose FF (Pharmacia) and the like can be exemplified.

Further, by using a carrier having an antigen immobilized thereon, the antibody can also be purified utilizing the binding property of the antibody to the antigen.

[Antitumor Compound]

The antitumor compound to be conjugated to the antibody-drug conjugate of the present invention is explained. The antitumor compound is not particularly limited if it is a compound having an antitumor effect and a substituent group or a partial structure allowing connecting to a linker structure. When a part or whole linker is cleaved in tumor cells, the antitumor compound moiety is released to exhibit the antitumor effect of the antitumor compound. As the linker is cleaved at a connecting position to drug, the antitumor compound is released in its intrinsic structure to exhibit its intrinsic antitumor effect.

Examples of the antitumor compound can include doxorubicin, daunorubicin, mitomycin C, bleomycin, cyclocytidine, vincristine, vinblastine, methotrexate, platinum-based antitumor agent (cisplatin or derivatives thereof), taxol or derivatives thereof, and camptothecin or derivatives thereof (antitumor agent described in Japanese Patent Laid-Open No. 6-87746). In the antibody-drug conjugate of the present invention, exatecan as a camptothecin derivative (((1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione; shown in the following formula) can be preferably used.

[Formula 43]

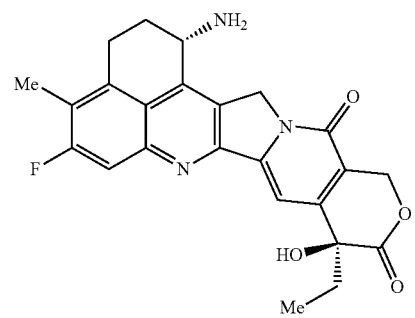

Although having an excellent antitumor effect, exatecan has not been commercialized as an antitumor drug. The compound can be easily obtained by a known method and the amino group at position 1 can be preferably used as a connecting position to the linker structure. Further, although exatecan can be also released in tumor cells while part of the linker is still attached thereto, it is an excellent compound exhibiting an excellent antitumor effect even in such case.

With regard to the antibody-drug conjugate, the number of conjugated drug molecules per antibody molecule is a key factor having an influence on the efficacy and safety. Production of the antibody-drug conjugate is performed by defining the reaction condition including the amounts of use of raw materials and reagents for reaction so as to have a constant number of conjugated drug molecules, a mixture containing different numbers of conjugated drug molecules is generally obtained unlike the chemical reaction of a low-molecular-weight compound. The number of drugs conjugated in an antibody molecule is expressed or specified by the average value, that is, the average number of conjugated drug molecules. Unless specifically described otherwise as a principle, the number of conjugated drug molecules means an average value except in a case in which it represents an antibody-drug conjugate having a specific number of conjugated drug molecules that is included in an antibody-drug conjugate mixture having different number of conjugated drug molecules. The number of exatecan molecules conjugated to an antibody molecule is controllable, and as an average number of conjugated drug molecules per antibody, about 1 to 10 exatecans can be bound. Preferably, it is 2 to 8, and more preferably 3 to 8. Meanwhile, a person skilled in the art can design a reaction for conjugating a required number of drug molecules to an antibody molecule based on the description of the Examples of the present application and can obtain an antibody conjugated with a controlled number of exatecan molecules.

Because exatecan has a camptothecin structure, it is known that the equilibrium shifts to a structure with a closed lactone ring (closed ring) in an aqueous acidic medium (for example, pH 3 or so) but it shifts to a structure with an open lactone ring (open ring) in an aqueous basic medium (for example, pH 10 or so). A drug conjugate being introduced with an exatecan residue corresponding to the closed ring structure and the open ring structure is also expected to have the same antitumor effect and it is needless to say that any of them is within the scope of the present invention.

[Linker Structure]

With regard to the antibody-drug conjugate of the present invention, the linker structure for conjugating an antitumor drug to the antibody is explained. The linker has a structure of the following structure: -$L^1$-$L^2$-$L^P$-NH—$(CH_2)$ $n^1$-$L^a$-$L^b$-$L^c$-.

The antibody is connected to the terminal of $L^1$ (terminal opposite to the connection to $L^2$), and the antitumor drug is connected to the terminal of $L^c$ (terminal opposite to the connection to $L^b$).

$n^1$ represents an integer of 0 to 6 and is preferably an integer of 1 to 5, and more preferably 1 to 3.

1. $L_1$ $L^1$ is a moiety in the linker represented by the following structure:
-(Succinimid-3-yl-N)—$(CH_2)n^2$-C(=O)—,
—$CH_2$—C(=O)—NH—$(CH_2)n^3$-C(=O)—,
—C(=O)-cyc.Hex(1,4)-$CH_2$—(N-ly-3-diminiccuS)-, or
—C(=O)—$(CH_2)n^4$-C(=O)—
In the above, $n^2$ is an integer of 2 to 8, $n^3$ is an integer of 1 to 8, and $n^4$ is an integer of 1 to 8.

In the linker having a structure represented by -(Succinimid-3-yl-N)—$(CH_2)n^2$-C(=O)— of $L^1$, "-(Succinimid-3-yl-N)—" has a structure represented by the following formula:

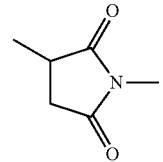

[Formula 44]

Position 3 of the above partial structure is a connecting position to the antibody. The bond to the antibody at position 3 is characterized by bonding with thioether formation. On the other hand, the nitrogen atom at position 1 of the structure moiety is connected to the carbon atom of methylene which is present within the linker including the structure. Specifically, -(Succinimid-3-yl-N)—$(CH_2)n^2$-C(=O)-$L^2$- is a structure represented by the following formula (herein, "antibody-S-" originates from an antibody).

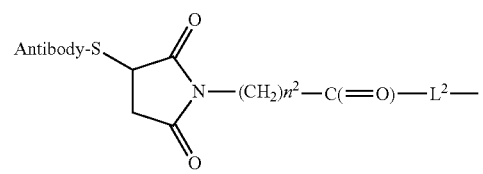

[Formula 45]

In the formula, $n^2$ is an integer of 2 to 8, and preferably 2 to 5.

In the linker having a structure represented by —$CH_2$—C(=O)—NH—$(CH_2)n^3$-C(=O)— of $L^1$, $n^3$ is an integer of 1 to 8, preferably 2 to 6. This linker is connected to the antibody at its carbon atom of terminal methylene and has the following structure for connecting by thioether formation, as with the preceding linker (herein, "antibody-S-" originates from an antibody). Antibody-S—$CH_2$—C(=O)—NH—$(CH_2)n^3$-C(=O)-$L^2$-.

In the linker having a structure represented by —C(=O)-cyc.Hex(1,4)-$CH_2$—(N-ly-3-diminiccuS)- of $L^1$, "—(N-ly-3-diminiccuS)-" has a structure represented by the following formula:

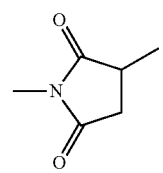

[Formula 46]

In this structure moiety, the nitrogen atom at position 1 is connected to the carbon atom of methylene present in the linker structure containing this structure. The carbon atom at position 3 is connected to the terminal sulfur atom of —S—$(CH_2)n^6$-C(=O)— of $L^2$ in the linker. This moiety —S—$(CH_2)n^6$-C(=O)— of $L^2$ in the linker forms a combined linker structure only with —C(=O)-cyc.Hex(1,4)-$CH_2$—(N-ly-3-diminiccuS)- of $L^1$ in the linker. In the above, "-cyc.Hex(1,4)-" contained in the linker represents a 1,4-cyclohexylene group. In the linker, —C(=O)-cyc.Hex(1,4)-CH$_2$—(N-ly-3-diminiccuS)- is connected to the antibody with amide bond formation at its terminal carbonyl carbon (herein, "antibody-NH—" originates from an antibody).

$L^2$ may not be present, and in such a case, $L^2$ is a single bond. In the above, $n^5$ is an integer of 1 to 6, and $n^6$ is an integer of 1 to 6.

In the linker having a structure of —NH—(CH$_2$CH$_2$O)n$^5$-CH$_2$—CH$_2$—C(=O)— as $L^2$, $n^5$ is an integer of 1 to 6,

[Formula 47]

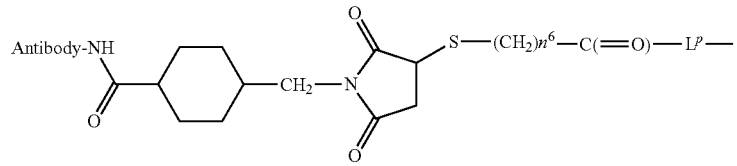

The amino group of the antibody for this amide bond formation is the terminal amino group of a side chain of a lysine residue in the antibody or an amino group at the N terminal of the antibody. Said linker of a structure can connect by forming ester bond with the hydroxy group of an amino acid in the antibody other than such amide bond.

The structure moiety "-cyc.Hex(1,4)-" contained in said linker may be a divalent saturated cyclic alkylene group other than the 1,4-cyclohexylene group, i.e., a divalent cyclic saturated hydrocarbon group such as a cyclobutylene group, a cyclopentylene group, a cycloheptalene group, or a cyclooctalene group, a divalent aromatic hydrocarbon group such as a phenylene group or a naphthylene group, or a 5- or 6-membered saturated, partially saturated, or aromatic divalent heterocyclic group containing 1 or 2 heteroatoms. Alternatively, this moiety may be a divalent alkylene group having 1 to 4 carbon atoms. The connection to the divalent group may occur at adjacent positions or at distant positions.

In the linker having a structure represented by —C(=O)—(CH$_2$)n$^4$-C(=O)— as $L^1$, $n^4$ is an integer of 1 to 8, and preferably 2 to 6. This linker is also connected by amide bond formation at its terminal carbonyl group with an amino group of the antibody, as with the linkers mentioned above (see the following formula; in the structure thereof, "antibody-NH-" originates from an antibody).
Antibody-NH—C(=O)—(CH$_2$)n$^4$-C(=O)-$L^2$-.

Specific examples of $L^1$ in the linker can include
-(Succinimid-3-yl-N)—CH$_2$CH$_2$—C(=O)—
-(Succinimid-3-yl-N)—CH$_2$CH$_2$CH$_2$—C(=O)—
-(Succinimid-3-yl-N)—CH$_2$CH$_2$CH$_2$CH$_2$—C(=O)—
-(Succinimid-3-yl-N)—CH$_2$CH$_2$CH$_2$CH$_2$CH$_2$—C(=O)—
—CH$_2$C(=O)NH—CH$_2$—C(=O)—,
—CH$_2$C(=O)NH—CH$_2$CH$_2$—C(=O)—
—CH$_2$C(=O)NH—CH$_2$CH$_2$CH$_2$—C(=O)—
—CH$_2$C(=O)NH—CH$_2$CH$_2$CH$_2$CH$_2$—C(=O)—
—CH$_2$C(=O)NH—CH$_2$CH$_2$CH$_2$CH$_2$CH$_2$—C(=O)—
—C(=O)-cyc.Hex(1,4)-CH$_2$—(N-ly-3-diminiccuS)-
—C(=O)-Aryl-CH$_2$—(N-ly-3-diminiccuS)-
—C(=O)-cyc.Het-CH$_2$—(N-ly-3-diminiccuS)-
—C(=O)—CH$_2$CH$_2$—C(=O)—
—C(=O)—CH$_2$CH$_2$CH$_2$—C(=O)—
—C(=O)—CH$_2$CH$_2$CH$_2$CH$_2$—C(=O)—
—C(=O)—CH$_2$CH$_2$CH$_2$CH$_2$CH$_2$—C(=O)—
—C(=O)—CH$_2$CH$_2$CH$_2$CH$_2$CH$_2$CH$_2$—C(=O)—.
(Aryl represents a divalent aromatic hydrocarbon group, and cyc.Het represents a divalent cyclic heterocyclic group).

2. $L^2$ $L^2$ is a linker represented by the following structure:
—NH—(CH$_2$CH$_2$O)n$^5$-CH$_2$—CH$_2$—C(=O)—, or
—S—(CH$_2$)n$^6$-C(=O)—, and preferably 2 to 4. This moiety in the linker is connected to $L^1$ at its terminal amino group and is connected to $L^P$ at its carbonyl group at the other terminal.

In the linker having a structure of —S—(CH$_2$)n$^6$-C(=O)— as $L^2$, $n^6$ is an integer of 1 to 6, and preferably 2 to 4.

Specific examples of $L^2$ can include
—NH—CH$_2$CH$_2$O—CH$_2$CH$_2$—C(=O)—,
—NH—CH$_2$CH$_2$O—CH$_2$CH$_2$O—CH$_2$CH$_2$—C(=O)—,
—NH—CH$_2$CH$_2$O—CH$_2$CH$_2$—CH$_2$CH$_2$O—CH$_2$CH$_2$—C(=O)—,
—NH—CH$_2$CH$_2$O—CH$_2$CH$_2$O—CH$_2$CH$_2$O—CH$_2$CH$_2$O—CH$_2$CH$_2$—C(=O)—,
—NH—CH$_2$CH$_2$O—CH$_2$CH$_2$O—CH$_2$CH$_2$O—CH$_2$CH$_2$O—CH$_2$CH$_2$O—CH$_2$CH$_2$—C(=O)—,
—NH—CH$_2$CH$_2$O—CH$_2$CH$_2$O—CH$_2$CH$_2$O—CH$_2$CH$_2$O—CH$_2$CH$_2$O—CH$_2$CH$_2$—C(=O)—.

When $L^2$ is —S—(CH$_2$)n$^6$-C(=O)—, $L^1$ to be combined therewith is —C(=O)-cyc.Hex(1,4)-CH$_2$—(N-ly-3-diminiccuS)-. Specific examples of -$L^1$-$L^2$- can include
—C(=O)-cyc.Hex(1,4)-CH$_2$—(N-ly-3-diminiccuS)-S—CH$_2$—C(=O)—
—C(=O)-cyc.Hex(1,4)-CH$_2$—(N-ly-3-diminiccuS)-S—CH$_2$CH$_2$-C—(=O)—
—C(=O)-cyc.Hex(1,4)-CH$_2$—(N-ly-3-diminiccuS)-S—CH$_2$CH$_2$CH$_2$—C(=O)—
—C(=O)-cyc.Hex(1,4)-CH$_2$—(N-ly-3-diminiccuS)-S—CH$_2$CH$_2$CH$_2$CH$_2$—C(=O)—
—C(=O)-cyc.Hex(1,4)-CH$_2$—(N-ly-3-diminiccuS)-S—CH$_2$CH$_2$CH$_2$CH$_2$CH$_2$—C(=O)—
—C(=O)-cyc.Hex(1,4)-CH$_2$—(N-ly-3-diminiccuS)-S—CH$_2$CH$_2$CH$_2$CH$_2$CH$_2$CH$_2$—C(=O)—.

3. $L^P$

The linker $L^P$ is a peptide residue consisting of 2 to 7 amino acids. Specifically, it consists of an oligopeptide residue in which 2 to 6 amino acids are linked by a peptide bonding. The linker $L^P$ is connected to $L^2$ at its N terminal and is connected to the amino group of —NH—(CH$_2$)n$^1$-$L^a$-$L^b$-$L^c$-moiety of the linker at its C terminal. The amino acid constituting $L^P$ in the linker is not particularly limited, however, examples thereof include an L- or a D-amino acid, preferably an L-amino acid. And, it can be an amino acid having a structure such as β-alanine, ε-aminocaproic acid, or γ-aminobutyric acid in addition to an α-amino acid, further, it can be a non-natural type amino acid such as N-methylated amino acid.

The amino acid sequence of $L^P$ is not particularly limited, but examples of the constituting amino acid include phenylalanine (Phe; F), tyrosine (Tyr; Y), leucine (Leu; L), glycine (Gly; G), alanine (Ala; A), valine (Val; V), lysine (Lys; K), citrulline (Cit), serine (Ser; S), glutamic acid (Glu;

E), and aspartic acid (Asp; D). Among them, preferred examples include phenylalanine, glycine, valine, lysine, citrulline, serine, glutamic acid, and aspartic acid. Depending on the type of the amino acid, drug release pattern can be controlled. The number of the amino acid can be between 2 to 7.

Specific examples of $L^P$ can include
-GGF-
-DGGF-
-(D-)D-GGF-
-EGGF-
-GGFG-
-SGGF-
-KGGF-
-DGGFG-
-GGFGG-
-DDGGFG-
-KDGGFG-
-GGFGGGF-
[in the above, "(D-)D" represents a D-aspartic acid]. Particularly preferred examples of $L^P$ for the antibody-drug conjugate of the present invention can include -GGFG-.

In the structure represented by —NH—$(CH_2)n^1$- within the linker, $n^1$ is an integer of 0 to 6 and is preferably an integer of 1 to 5, and more preferably 1 to 3. The amino group of this moiety is connected to the C terminal of $L^P$ in the linker.

4. $L^a$

The linker $L^a$ is represented by any of structures —C(=O)—NH—, —$NR^1$—$(CH_2)n^7$-, and —O— or is a single bond. In the above, $n^7$ is an integer of 1 to 6, $R^1$ is a hydrogen atom, an alkyl group having 1 to 6 carbon atoms, —$(CH_2)n^8$-COOH, or —$(CH_2)n^9$-OH, no is an integer of 1 to 4, and $n^9$ is an integer of 1 to 6.

The amide structure —C(=O)—NH— within linker $L^a$ is connected to $L^b$ at its nitrogen atom side. In the structure moiety of —$NR^1$—$(CH_2)n^7$- within $L^a$, $n^7$ is an integer of 1 to 6, and preferably 1 to 3. This moiety is connected to $L^b$ at its methylene side. $R^1$ is a hydrogen atom or an alkyl group having 1 to 6 carbon atoms. The alkyl group having 1 to 6 carbon atoms may be linear or branched. Examples thereof can include a methyl group, an ethyl group, a propyl group, an isopropyl group, a butyl group, an isobutyl group, a sec-butyl group, a tert-butyl group, a pentyl group, an isopentyl group, a 2-methylbutyl group, a neopentyl group, a 1-ethylpropyl group, a hexyl group, an isohexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, and a 2-ethylbutyl group. Of them, a methyl group or an ethyl group is preferred. When $R^1$ has a structure represented by —$(CH_2)n^8$-COOH, no is an integer of 1 to 4, and preferably 1 or 2. When $R^1$ has a structure represented by —$(CH_2)n^9$-OH, $n^9$ is an integer of 1 to 6, and preferably 1 or 2. $R^1$ is preferably a hydrogen atom, a methyl group, an ethyl group, —$CH_2COOH$, —$CH_2CH_2$—COOH, or —$CH_2CH_2$—OH, and more preferably a hydrogen atom, a methyl group, or —$CH_2COOH$. It is further preferably a hydrogen atom. The $L^a$ moiety of the linker may be —O— or a single bond.

5. $L^b$

The linker $L^b$ is any of structures —$CR^2(-R^3)$—, —O—, and —$NR^4$— or is a single bond. In the above, $R^2$ and $R^3$ each independently represents a hydrogen atom, an alkyl group having 1 to 6 carbon atoms, —$(CH_2)n^a$-$NH_2$, —$(CH_2)n^b$-COOH, or —$(CH_2)n^c$-OH, $R^4$ is a hydrogen atom or an alkyl group having 1 to 6 carbon atoms, $n^a$ is an integer of 0 to 6, $n^b$ is an integer of 1 to 4, and $n^c$ is an integer of 0 to 4. When $n^a$ or $n^c$ is 0, $R^2$ and $R^3$ are not the same each other.

When each of $R^2$ and $R^3$ is an alkyl group, this alkyl group is interpreted as defined in the alkyl group of $R^1$. When $R^2$ and $R^3$ has a structure of —$(CH_2)n^a$-$NH_2$, $n^a$ is an integer of 0 to 6, and preferably 0, or is 3 to 5. When $n^a$ is 0, $R^2$ and $R^3$ are not the same as each other. When $R^2$ and $R^3$ has a structure of —$(CH_2)n^b$-COOH, $n^b$ is an integer of 1 to 4, and preferably 1 or 2. When $R^2$ and $R^3$ has a structure of —$(CH_2)n^c$-OH, $n^c$ is an integer of 0 to 4, and preferably 1 or 2.

Each of $R^2$ and $R^3$ is preferably a hydrogen atom, a methyl group, an ethyl group, —$NH_2$, —$CH_2CH_2CH_2NH_2$, —$CH_2CH_2CH_2CH_2NH_2$, —$CH_2CH_2CH_2CH_2CH_2CH_2NH_2$, —$CH_2COOH$, —$CH_2CH_2$—COOH, —$CH_2OH$, or —$CH_2CH_2$—OH, and more preferably a hydrogen atom, a methyl group, —$NH_2$, —$CH_2CH_2CH_2CH_2NH_2$, —$CH_2COOH$, —$CH_2CH_2$—COOH, —$CH_2OH$, or —$CH_2CH_2$—OH. They are further preferably hydrogen atoms.

When $R^4$ is an alkyl group having 1 to 6 carbon atoms, this alkyl group is interpreted as defined in the alkyl group of $R^1$. $R^4$ is preferably a hydrogen atom or a methyl group, and more preferably a hydrogen atom.

Specific examples of the structure represented by —NH—$(CH_2)n^1$-$L^a$-$L^b$- as the linker can include
—NH—$CH_2$—
—NH—CH(-Me)-
—NH—C(-Me)$_2$-
—NH—$CH_2$—CHMe-
—NH—CH(—$CH_2OH$)—
—NH—CH(—$CH_2COOH$)—
—NH—CH(—$CH_2CH_2COOH$)—
—NH—CH(—$CH_2CH_2CH_2CH_2NH_2$)—
—NH—$CH_2CH_2$—
—NH—$CH_2$—O—$CH_2$—
—NH—$CH_2CH_2$—O—
—NH—$CH_2CH_2$—O—$CH_2$—
—NH—$CH_2CH_2C$(-Me)$_2$-
—NH—$CH_2CH_2NH$—
—NH—$CH_2CH_2NH$—$CH_2$—
—NH—$CH_2CH_2NMe$-$CH_2$—
—NH—$CH_2CH_2NH$—$CH_2CH_2$—
—NH—$CH_2CH_2NMe$-$CH_2CH_2$—
—NH—$CH_2CH_2N$(—$CH_2COOH$)—$CH_2$—
—NH—$CH_2CH_2N$(—$CH_2CH_2OH$)—$CH_2$—
—NH—$CH_2CH_2N$(—$CH_2CH_2OH$)—$CH_2CH_2$—
—NH—$CH_2CH_2CH_2C$(=O)—NHCH(—$CH_2OH$)—
—NH—$CH_2CH_2CH_2C$(=O)—NHCH(—$CH_2COOH$)—
—NH—$CH_2CH_2CH_2C$(=O)—NHCH(—$CH_2CH_2CH_2CH_2NH_2$)—
—NH—$CH_2CH_2CH_2$—
—NH—$CH_2CH_2CH_2CH_2$—
—NH—$CH_2CH_2CH_2CH_2CH_2$—
—NH—$CH_2CH_2CH_2CH_2CH(NH_2)$—.

Of them, preferred examples thereof can include
—NH—$CH_2$—
—NH—$CH_2$—CH(Me)-
—NH—CH(—$CH_2OH$)—
—NH—CH(—$CH_2CH_2COOH$)—
—NH—$CH_2CH_2$—
—NH—$CH_2$—O—$CH_2$—
—NH—$CH_2CH_2$—O—
—NH—$CH_2CH_2$—O—$CH_2$—
—NH—$CH_2CH_2C$(-Me)$_2$-
—NH—$CH_2CH_2NH$—

—NH—CH₂CH₂NH—CH₂—
—NH—CH₂CH₂NMe-CH₂—
—NH—CH₂CH₂NMe-CH₂CH₂—
—NH—CH₂CH₂N(—CH₂COOH)—CH₂—
—NH—CH₂CH₂N(—CH₂CH₂OH)—CH₂—
—NH—CH₂CH₂N(—CH₂CH₂OH)—CH₂CH₂—
—NH—CH₂CH₂CH₂C(=O)—NHCH(—CH₂OH)—
—NH—CH₂CH₂CH₂C(=O)—NHCH(—CH₂COOH)—
—NH—CH₂CH₂CH₂—
—NH—CH₂CH₂CH₂CH₂—
—NH—CH₂CH₂CH₂CH₂CH₂—.

More preferred examples thereof can include
—NH—CH₂—
—NH—CH₂CH₂—
—NH—CH₂—O—CH₂—
—NH—CH₂CH₂—O—
—NH—CH₂CH₂—O—CH₂—
—NH—CH₂CH₂NH—
—NH—CH₂CH₂NH—CH₂—
—NH—CH₂CH₂N(—CH₂COOH)—CH₂—
—NH—CH₂CH₂N(—CH₂CH₂OH)—CH₂CH₂—
—NH—CH₂CH₂CH₂C(=O)—NHCH(—CH₂COOH)—
—NH—CH₂CH₂CH₂—
—NH—CH₂CH₂CH₂CH₂—
—NH—CH₂CH₂CH₂CH₂CH₂—.

Further preferred examples thereof can include
—NH—CH₂—O—CH₂—, and
—NH—(CH₂)₂—O—CH₂—.

6. $L^c$

The linker $L^c$ is —CH₂— or —C(=O)—. Said linker is connected to the antitumor compound. L of the linker is more preferably —C(=O)—.

In the linker, the chain length of —NH—(CH₂)n¹-$L^a$-$L^b$-$L^c$ is preferably a chain length of 4 to 7 atoms, and more preferably a chain length of 5 or 6 atoms.

With regard to the antibody-drug conjugate of the present invention, when it is transferred to the inside of tumor cells, the linker moiety is cleaved and the drug derivative having a structure represented by NH₂—(CH₂)n¹-$L^a$-$L^b$-$L^c$-(NH-DX) is released to express an antitumor action. Examples of the antitumor derivative exhibiting an antitumor effect by releasing from the antibody-drug conjugate of the present invention include an antitumor derivative having a structure moiety in which the structure represented by —NH—(CH₂)n¹-$L^a$-$L^b$- of the linker is bound with $L^c$ and has a terminal amino group, and the particularly preferred include the followings.
NH₂—CH₂CH₂—C(=O)—(NH-DX)
NH₂—CH₂CH₂CH₂—C(=O)—(NH-DX)
NH₂—CH₂—O—CH₂—C(=O)—(NH-DX)
NH₂—CH₂CH₂—O—CH₂—C(=O)—(NH-DX)

Meanwhile, in case of NH₂—CH₂—O—CH₂—C(=O)—(NH-DX), it was confirmed that, as the aminal structure in the molecule is unstable, it again undergoes a self-degradation to release the following HO—CH₂—C(=O)—(NH-DX). Those compounds can be also preferably used as a production intermediate of the antibody-drug conjugate of the present invention.

For the antibody-drug conjugate of the present invention in which exatecan is used as a drug, it is preferable that the drug-linker structure moiety having the following structure [-$L^1$-$L^2$-$L^P$-NH—(CH₂)n¹-$L^a$-$L^b$-$L^c$-(NH-DX)] is connected to an antibody. The average conjugated number of the drug-linker structure moiety per antibody can be 1 to 10. Preferably, it is 2 to 8, and more preferably 3 to 8.
-(Succinimid-3-yl-N)—CH₂CH₂—C(=O)-GGFG-NH—CH₂CH₂—C(=O)—(NH-DX)
-(Succinimid-3-yl-N)—CH₂CH₂—C(=O)-GGFG-NH—CH₂CH₂CH₂—C(=O)—(NH-DX)
-(Succinimid-3-yl-N)—CH₂CH₂CH₂—C(=O)-GGFG-NH—CH₂CH₂—C(=O)—(NH-DX)
-(Succinimid-3-yl-N)—CH₂CH₂CH₂—C(=O)-GGFG-NH—CH₂CH₂CH₂—C(=O)—(NH-DX)
-(Succinimid-3-yl-N)—CH₂CH₂CH₂CH₂—C(=O)-GGFG-NH—CH₂CH₂CH₂—C(=O)—(NH-DX)
-(Succinimid-3-yl-N)—CH₂CH₂CH₂CH₂CH₂—C(=O)-GGFG-NH—CH₂CH₂CH₂—C(=O)—(NH-DX)
-(Succinimid-3-yl-N)—CH₂CH₂CH₂CH₂CH₂—C(=O)-GGFG-NH—CH₂—O—CH₂—C(=O)—(NH-DX)
-(Succinimid-3-yl-N)—CH₂CH₂CH₂CH₂CH₂—C(=O)-GGFG-NH—CH₂CH₂—O—CH₂—C(=O)—(NH-DX)
-(Succinimid-3-yl-N)—CH₂CH₂—C(=O)—NH—CH₂CH₂O—CH₂CH₂O—CH₂CH₂—C(=O)-GGFG-NH—CH₂CH₂CH₂—C(=O)—(NH-DX)
-(Succinimid-3-yl-N)—CH₂CH₂—C(=O)—NH—CH₂CH₂O—CH₂CH₂O—CH₂CH₂—C(=O)-GGFG-NH—CH₂CH₂—C(=O)—(NH-DX)
-(Succinimid-3-yl-N)—CH₂CH₂—C(=O)—NH—CH₂CH₂O—CH₂CH₂O—CH₂CH₂O—CH₂CH₂O—CH₂CH₂—C(=O)-GGFG-NH—CH₂CH₂CH₂—C(=O)—(NH-DX)
-(Succinimid-3-yl-N)—CH₂CH₂—C(=O)—NH—CH₂CH₂O—CH₂CH₂O—CH₂CH₂O—CH₂CH₂O—CH₂CH₂—C(=O)-GGFG-NH—CH₂CH₂—C(=O)—(NH-DX)
—CH₂—C(=O)—NH—CH₂CH₂—C(=O)-GGFG-NH—CH₂CH₂CH₂—C(=O)—(NH-DX)
—C(=O)—CH₂CH₂CH₂CH₂CH₂—C(=O)-GGFG-NH—CH₂CH₂CH₂—C(=O)—(NH-DX)
—C(=O)-cyc.Hex(1,4)-CH₂—(N-ly-3-diminiccuS)-S—CH₂CH₂—C(=O)-GGFG-NH—CH₂CH₂—C(=O)—(NH-DX)

Among them, the more preferred are the followings.
-(Succinimid-3-yl-N)—CH₂CH₂—C(=O)-GGFG-NH—CH₂CH₂CH₂—C(=O)—(NH-DX)
-(Succinimid-3-yl-N)—CH₂CH₂CH₂CH₂—C(=O)-GGFG-NH—CH₂CH₂CH₂—C(=O)—(NH-DX)
-(Succinimid-3-yl-N)—CH₂CH₂CH₂CH₂CH₂—C(=O)-GGFG-NH—CH₂—O—CH₂—C(=O)—(NH-DX)
-(Succinimid-3-yl-N)—CH₂CH₂CH₂CH₂CH₂—C(=O)-GGFG-NH—CH₂CH₂—O—CH₂—C(=O)—(NH-DX)
-(Succinimid-3-yl-N)—CH₂CH₂—C(=O)—NH—CH₂CH₂O—CH₂CH₂O—CH₂CH₂—C(=O)-GGFG-NH—CH₂CH₂CH₂—C(=O)—(NH-DX)
-(Succinimid-3-yl-N)—CH₂CH₂—C(=O)—NH—CH₂CH₂O—CH₂CH₂O—CH₂CH₂O—CH₂CH₂O—CH₂CH₂—C(=O)-GGFG-NH—CH₂CH₂CH₂—C(=O)—(NH-DX)
—CH₂—C(=O)—NH—CH₂CH₂—C(=O)-GGFG-NH—CH₂CH₂CH₂—C(=O)—(NH-DX)
—C(=O)—CH₂CH₂CH₂CH₂CH₂—C(=O)-GGFG-NH—CH₂CH₂CH₂—C(=O)—(NH-DX)
—C(=O)-cyc.Hex(1,4)-CH₂—(N-ly-3-diminiccuS)-S—CH₂CH₂—C(=O)-GGFG-NH—CH₂CH₂CH₂—C(=O)—(NH-DX).

The particularly preferred are the followings.
-(Succinimid-3-yl-N)—CH₂CH₂CH₂CH₂CH₂—C(=O)-GGFG-NH—CH₂—O—CH₂—C(=O)—(NH-DX)
-(Succinimid-3-yl-N)—CH₂CH₂CH₂CH₂CH₂—C(=O)-GGFG-NH—CH₂CH₂—O—CH₂—C(=O)—(NH-DX)
-(Succinimid-3-yl-N)—CH₂CH₂—C(=O)—NH—CH₂CH₂O—CH₂CH₂O—CH₂CH₂—C(=O)-GGFG-NH—CH₂CH₂CH₂—C(=O)—(NH-DX).

With regard to the linker structure for conjugating the antibody and a drug in the antibody-drug conjugate of the present application, the preferred linker can be constructed by connecting preferred structures shown for each part of the linker explained above. As for the linker structure, those with the following structure can be preferably used.

Meanwhile, the left terminal of the structure is a connecting position with the antibody and the right terminal is a connecting position with the drug.

-(Succinimid-3-yl-N)—CH$_2$CH$_2$—C(=O)-GGFG-NH—CH$_2$CH$_2$—C(=O)—

-(Succinimid-3-yl-N)—CH$_2$CH$_2$—C(=O)-GGFG-NH—CH$_2$CH$_2$CH$_2$—C(=O)—

-(Succinimid-3-yl-N)—CH$_2$CH$_2$CH$_2$CH$_2$CH$_2$—C(=O)-GGFG-NH—CH$_2$CH$_2$—C(=O)—

-(Succinimid-3-yl-N)—CH$_2$CH$_2$CH$_2$CH$_2$CH$_2$—C(=O)-GGFG-NH—CH$_2$CH$_2$CH$_2$—C(=O)—

-(Succinimid-3-yl-N)—CH$_2$CH$_2$CH$_2$CH$_2$CH$_2$—C(=O)-GGFG-NH—CH$_2$CH$_2$CH$_2$CH$_2$CH$_2$—C(=O)—

-(Succinimid-3-yl-N)—CH$_2$CH$_2$CH$_2$CH$_2$CH$_2$—C(=O)-GGFG-NH—CH$_2$—O—CH$_2$—C(=O)—

-(Succinimid-3-yl-N)—CH$_2$CH$_2$CH$_2$CH$_2$CH$_2$—C(=O)-GGFG-NH—CH$_2$CH$_2$—O—CH$_2$—C(=O)—

-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—

-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$—C(=O)—

-(Succinimid-3-yl-N)—CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—

-(Succinimid-3-yl-N)—CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$—C(=O)—

—CH$_2$—C(=O)—NH—CH$_2$CH$_2$—C(=O)-GGFG-NH—CH$_2$CH$_2$CH$_2$—C(=O)—

—C(=O)—CH$_2$CH$_2$CH$_2$CH$_2$CH$_2$—C(=O)-GGFG-NH—CH$_2$CH$_2$CH$_2$—C(=O)—

—C(=O)-cyc.Hex(1,4)-CH$_2$—(N-ly-3-diminiccuS)-S—CH$_2$CH$_2$—C(=O)-GGFG-NH—CH$_2$CH$_2$CH$_2$—C(=O)—

Among them, the more preferred are the followings.

-(Succinimid-3-yl-N)—CH$_2$CH$_2$—C(=O)-GGFG-NH—CH$_2$CH$_2$CH$_2$—C(=O)—

-(Succinimid-3-yl-N)—CH$_2$CH$_2$CH$_2$CH$_2$CH$_2$—C(=O)-GGFG-NH—CH$_2$CH$_2$CH$_2$—C(=O)—

-(Succinimid-3-yl-N)—CH$_2$CH$_2$CH$_2$CH$_2$CH$_2$—C(=O)-GGFG-NH—CH$_2$—O—CH$_2$—C(=O)—

-(Succinimid-3-yl-N)—CH$_2$CH$_2$CH$_2$CH$_2$CH$_2$—C(=O)-GGFG-NH—CH$_2$CH$_2$—O—CH$_2$—C(=O)—

-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—

-(Succinimid-3-yl-N)—CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—

—CH$_2$—C(=O)—NH—CH$_2$CH$_2$—C(=O)-GGFG-NH—CH$_2$CH$_2$CH$_2$—C(=O)—

—C(=O)—CH$_2$CH$_2$CH$_2$CH$_2$CH$_2$—C(=O)-GGFG-NH—CH$_2$CH$_2$CH$_2$—C(=O)—

—C(=O)-cyc.Hex(1,4)-CH$_2$—(N-ly-3-diminiccuS)-S—CH$_2$CH$_2$—C(=O)-GGFG-NH—CH$_2$CH$_2$CH$_2$—C(=O)—.

The particularly preferred include the followings.

-(Succinimid-3-yl-N)—CH$_2$CH$_2$CH$_2$CH$_2$CH$_2$—C(=O)-GGFG-NH—CH$_2$—O—CH$_2$—C(=O)—

-(Succinimid-3-yl-N)—CH$_2$CH$_2$CH$_2$CH$_2$CH$_2$—C(=O)-GGFG-NH—CH$_2$CH$_2$—O—CH$_2$—C(=O)—

-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—.

[Production Method]

Next, explanations are given for the representative method for producing the antibody-drug conjugate of the present invention or a production intermediate thereof. Meanwhile, the compounds are hereinbelow described with the compound number shown in each reaction formula. Specifically, they are referred to as a "compound of the formula (1)", a "compound (1)", or the like. The compounds with numbers other than those are also described similarly.

1. Production Method 1

The antibody-drug conjugate represented by the formula (1) in which the antibody is bound to the linker structure via thioether can be produced by the following method, for example.

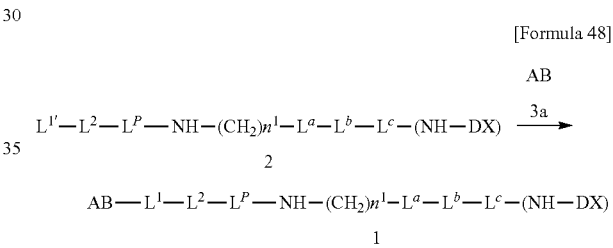

[Formula 48]

[In the formula, AB represents an antibody with a sulfhydryl group, and $L^{1'}$ represents $L^1$ linker structure in which the linker terminal is a maleimidyl group (formula shown below)

[Formula 49]

(in the formula, the nitrogen atom is the connecting position) or the terminal is halogen, and represents a group in which the -(Succinimid-3-yl-N)- moiety in -(Succinimid-3-yl-N)—(CH$_2$)n$^2$-C(=O)— of $L^1$ is a maleimidyl group or a halogen-CH$_2$C(=O)NH—(CH$_2$)n$^3$-C(=O)— group in which terminal methylene in —CH$_2$C(=O) NH—(CH$_2$)n$^3$-C(=O)— of L is halogenated to form haloacetamide. Further, the —(NH-DX) represents a structure represented by the following formula:

[Formula 50]

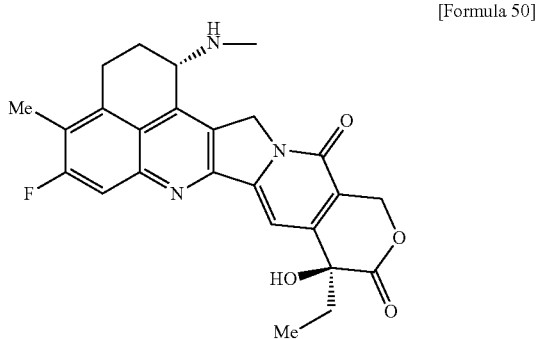 [SMILES: CC[C@@]1(O)C(=O)OCc2c1cc1n(c2=O)Cc2c-1nc1cc(F)c(C)c3c1c2[C@@H](NC)CC3]

and it represents a group that is derived by removing one hydrogen atom of the amino group at position 1 of exatecan. Further, the compound of the formula (1) in the above reaction formula is described as a structure in which one structure moiety from drug to the linker terminal connects to one antibody. However, it is only the description given for the sake of convenience, and there are actually many cases in which a plurality of the structure moieties are connected to one antibody molecule. The same applies to the explanation of the production method described below.]

Specifically, the antibody-drug conjugate (1) can be produced by reacting the compound (2), which is obtainable by the method described below, with the antibody (3a) having a sulfhydryl group.

The antibody (3a) having a sulfhydryl group can be obtained by a method well known in the art (Hermanson, G. T, Bioconjugate Techniques, pp. 56-136, pp. 456-493, Academic Press (1996)). Examples include: Traut's reagent is reacted with the amino group of the antibody; N-succinimidyl S-acetylthioalkanoates are reacted with the amino group of the antibody followed by reaction with hydroxylamine; after reacting with N-succinimidyl 3-(pyridyldithio)propionate, the antibody is reacted with a reducing agent; the antibody is reacted with a reducing agent such as dithiothreitol, 2-mercaptoethanol, and tris(2-carboxyethyl)phosphine hydrochloride (TCEP) to reduce the disulfide bond in a hinge part in the antibody to form a sulfhydryl group, but it is not limited thereto.

Specifically, using 0.3 to 3 molar equivalents of TCEP as a reducing agent per disulfide in hinge part in the antibody and reacting with the antibody in a buffer solution containing a chelating agent, the antibody with partially or completely reduced disulfide in hinge part in the antibody can be obtained. Examples of the chelating agent include ethylenediamine tetraacetic acid (EDTA) and diethylenetriamine pentaacetic acid (DTPA). It can be used at concentration of 1 mM to 20 mM. Examples of the buffer solution which may be Used include a solution of sodium phosphate, sodium borate, or sodium acetate. As a specific example, by reacting the antibody with TCEP at 4° C. to 37° C. for 1 to 4 hours, the antibody (3a) having partially or completely reduced sulfhydryl group can be obtained.

Meanwhile, by performing the reaction for adding a sulfhydryl group to a drug-linker moiety, the drug-linker moiety can be conjugated by a thioether bond.

Next, using 2 to 20 molar equivalents of the compound (2) per the antibody (3a) having a sulfhydryl group, the antibody-drug conjugate (1) in which 2 to 8 drug molecules are conjugated per antibody can be produced. Specifically, it is sufficient that the solution containing the compound (2) dissolved therein is added to a buffer solution containing the antibody (3a) having a sulfhydryl group for the reaction. Herein, examples of the buffer solution which may be used include sodium acetate solution, sodium phosphate, and sodium borate. pH for the reaction is 5 to 9, and more preferably the reaction is performed near pH 7. Examples of the solvent for dissolving the compound (2) include an organic solvent such as dimethyl sulfoxide (DMSO), dimethylformamide (DMF), dimethyl acetamide (DMA), and N-methyl-2-pyridone (NMP). It is sufficient that the organic solvent solution containing the compound (2) dissolved therein is added at 1 to 20% v/v to a buffer solution containing the antibody (3a) having a sulfhydryl group for the reaction. The reaction temperature is 0 to 37° C., more preferably 10 to 25° C., and the reaction time is 0.5 to 2 hours. The reaction can be terminated by deactivating the reactivity of unreacted compound (2) with a thiol-containing reagent. Examples of the thiol-containing reagent include cysteine and N-acetyl-L-cysteine (NAC). More specifically, 1 to 2 molar equivalents of NAC are added to the compound (2) used and, by incubating at room temperature for 10 to 30 minutes, the reaction can be terminated.

The produced antibody-drug conjugate (1) can be subjected to, after concentration, buffer exchange, purification, and measurement of antibody concentration and average number of conjugated drug molecules per antibody molecule according to common procedures described below, identification of the antibody-drug conjugate (1)

Common Procedure A: Concentration of Aqueous Solution of Antibody or Antibody-Drug Conjugate To a Amicon Ultra (50,000 MWCO, Millipore Corporation) container, a solution of antibody or antibody-drug conjugate was added and the solution of the antibody or antibody-drug conjugate was concentrated by centrifugation (centrifuge for 5 to 20 minutes at 2000 G to 3800 G) using a centrifuge (Allegra X-15R, Beckman Coulter, Inc.).

Common Procedure B: Measurement of Antibody Concentration

Using a UV detector (Nanodrop 1000, Thermo Fisher Scientific Inc.), measurement of the antibody concentration was performed according to the method defined by the manufacturer. At that time, 280 nm absorption coefficient different for each antibody was used (1.3 mLmg$^{-1}$ cm$^{-1}$ to 1.8 mLmg$^{-1}$ cm$^{-1}$).

Common Procedure C-1: Buffer Exchange for Antibody

NAP-25 column (Cat. No. 17-0852-02, GE Healthcare Japan Corporation) using Sephadex G-25 carrier was equilibrated with phosphate buffer (10 mM, pH 6.0) (it is referred to as PBS6.0/EDTA in the specification) containing sodium chloride (137 mM) and ethylene diamine tetraacetic acid (EDTA, 5 mM) according to the method defined by the manufacturer's instruction manual. Aqueous solution of the antibody was applied in an amount of 2.5 mL to single NAP-25 column, and then the fraction (3.5 mL) eluted with 3.5 mL of PBS6.0/EDTA was collected. The resulting fraction was concentrated by the Common procedure A. After measuring the concentration of the antibody using the Common procedure B, the antibody concentration was adjusted to 10 mg/mL using PBS6.0/EDTA.

Common Procedure C-2: Buffer Exchange for Antibody

NAP-25 column (Cat. No. 17-0852-02, GE Healthcare Japan Corporation) using Sephadex G-25 carrier was equilibrated with phosphate buffer (50 mM, pH 6.5) (it is referred to as PBS6.5/EDTA in the specification) containing sodium chloride (50 mM) and EDTA (2 mM) according to the method defined by the manufacturer. Aqueous solution of the antibody was applied in an amount of 2.5 mL to single NAP-25 column, and then the fraction (3.5 mL) eluted with 3.5 mL of PBS6.5/EDTA was collected. The resulting fraction was concentrated by the Common procedure A. After measuring the concentration of the antibody using the Common procedure B, the antibody concentration was adjusted to 20 mg/mL using PBS6.5/EDTA.

Common Procedure D-1: Purification of Antibody-Drug Conjugate

NAP-25 column was equilibrated with any buffer selected from commercially available phosphate buffer (PBS7.4, Cat. No. 10010-023, Invitrogen), sodium phosphate buffer (10 mM, pH 6.0; it is referred to as PBS6.0) containing sodium chloride (137 mM), and acetate buffer containing sorbitol (5%) (10 mM, pH 5.5; it is referred to as ABS in the specification). Aqueous solution of the antibody-drug conjugate reaction was applied in an amount of about 1.5 mL to the NAP-25 column, and then eluted with the buffer in an amount defined by the manufacturer to collect the antibody fraction. The collected fraction was again applied to the NAP-25 column and, by repeating 2 to 3 times in total the gel filtration purification process for eluting with buffer, the antibody-drug conjugate excluding non-conjugated drug linker and a low-molecular-weight compound (tris(2-carboxyethyl)phosphine hydrochloride (TCEP), N-acetyl-L-cysteine (NAC), and dimethyl sulfoxide (DMSO)) was obtained.

Common Procedure E: Measurement of Antibody Concentration in Antibody-Drug Conjugate and Average Number of Conjugated Drug Molecules Per Antibody Molecule.

The conjugated drug concentration in the antibody-drug conjugate can be calculated by measuring UV absorbance of an aqueous solution of the antibody-drug conjugate at two wavelengths of 280 nm and 370 nm, followed by performing the calculation shown below.

Because the total absorbance at any wavelength is equal to the sum of the absorbance of every light-absorbing chemical species that are present in a system [additivity of absorbance], when the molar absorption coefficients of the antibody and the drug remain the same before and after conjugation between the antibody and the drug, the antibody concentration and the drug concentration in the antibody-drug conjugate are expressed with the following equations.

$$A_{280}=A_{D,280}+A_{A,280}=\varepsilon_{D,280}C_D+\varepsilon_{A,280}C_A \quad \text{Equation (1)}$$

$$A_{370}=A_{D,370}+A_{A,370}=\varepsilon_{D,370}C_D+\varepsilon_{A,370}C_A \quad \text{Equation (2)}$$

In the above, $A_{280}$ represents the absorbance of an aqueous solution of the antibody-drug conjugate at 280 nm, $A_{370}$ represents the absorbance of an aqueous solution of the antibody-drug conjugate at 370 nm, $A_{A,280}$ represents the absorbance of an antibody at 280 nm, $A_{A,370}$ represents the absorbance of an antibody at 370 nm, $A_{D,280}$ represents the absorbance of a conjugate precursor at 280 nm, $A_{D,370}$ represents the absorbance of a conjugate precursor at 370 nm, $C_{A,280}$ represents the molar absorption coefficient of an antibody at 280 nm, $\varepsilon_{A,370}$ represents the molar absorption coefficient of an antibody at 370 nm, $\varepsilon_{D,280}$ represents the molar absorption coefficient of a conjugate precursor at 280 nm, $\varepsilon_{D,370}$ represents the molar absorption coefficient of a conjugate precursor at 370 nm, $C_A$ represents the antibody concentration in an antibody-drug conjugate, and $C_D$ represent the drug concentration in an antibody-drug conjugate.

As for $\varepsilon_{A,280}$, $\varepsilon_{A,370}$, $\varepsilon_{D,280}$, and $\varepsilon_{D,370}$ in the above, previously prepared values (estimated value based on calculation or measurement value obtained by UV measurement of the compound) are used. For example, $\varepsilon_{A,280}$ can be estimated from the amino acid sequence of an antibody using a known calculation method (Protein Science, 1995, vol. 4, 2411-2423). $\varepsilon_{A,370}$ is generally zero. $\varepsilon_{D,280}$ and $\varepsilon_{D,370}$ can be obtained based on Lambert-Beer's law (Absorbance=molar concentration×molar absorption coefficient×cell path length) by measuring the absorbance of a solution in which the conjugate precursor to be used is dissolved at a certain molar concentration. By measuring $A_{280}$ and $A_{370}$ of an aqueous solution of the antibody-drug conjugate and solving the simultaneous equations (1) and (2) using the values, $C_A$ and $C_D$ can be obtained. Further, by diving $C_D$ by $C_A$, the average number of conjugated drug per antibody can be obtained.

The compound represented by the formula (2) in Production method 1 is any compound represented by the following formula:

[Formula 51]

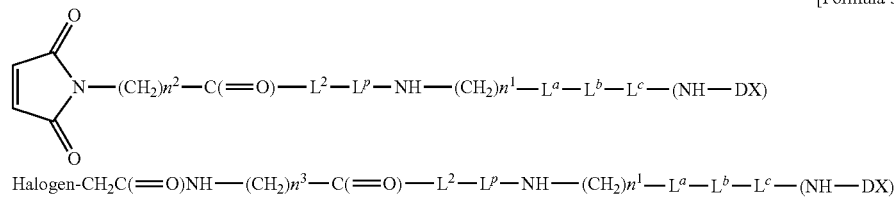

In the formula, $n^1$, $n^2$, $n^3$, $L^2$, $L^P$, $L^a$, $L^b$, and $L^c$ are as already defined, and $L^c$ is a connecting position for the drug.

In an intermediate useful in producing such a compound of the present invention, preferably, $n^2$ is an integer of 2 to 5, $L^2$ is $—NH—(CH_2CH_2O)n^5-CH_2CH_2—C(=O)—$ or a single bond, $n^5$ is an integer of 2 to 4, $L^P$ is GGFG, and $—NH—(CH_2)n^1-L^a-L^b-L^c-$ is a partial structure of $—NH—CH_2CH_2—C(=O)—$, $NH—CH_2CH_2CH_2—C(=O)—$, $—NH—CH_2—O—CH_2—C(=O)—$, or $—NH—CH_2CH_2—O—CH_2—C(=O)—$. Halogen is preferably bromine or iodine. Specific examples of these compounds can include the followings [herein, (maleimid-N-yl) represents a maleimidyl group (2,5-dioxo-2,5-dihydro-1H-pyrrol-1-yl group)].

(maleimid-N-yl)-$CH_2CH_2$—C(=O)-GGFG-NH—$CH_2CH_2$—C(=O)—(NH-DX)

(maleimid-N-yl)-$CH_2CH_2CH_2$—C(=O)-GGFG-NH—$CH_2CH_2$—C(=O)—(NH-DX)

(maleimid-N-yl)-$CH_2CH_2CH_2CH_2$—C(=O)-GGFG-NH—$CH_2CH_2$—C(=O)—(NH-DX)

(maleimid-N-yl)-$CH_2CH_2CH_2CH_2CH_2$—C(=O)-GGFG-NH—$CH_2CH_2$—C(=O)—(NH-DX)

(maleimid-N-yl)-$CH_2CH_2$—C(=O)-GGFG-NH—$CH_2CH_2CH_2$—C(=O)—(NH-DX)

(maleimid-N-yl)-$CH_2CH_2CH_2$—C(=O)-GGFG-NH—$CH_2CH_2CH_2$—C(=O)—(NH-DX)

(maleimid-N-yl)-$CH_2CH_2CH_2CH_2$—C(=O)-GGFG-NH—$CH_2CH_2CH_2$—C(=O)—(NH-DX)

(maleimid-N-yl)-CH$_2$CH$_2$CH$_2$CH$_2$CH$_2$—C(=O)-GGFG-NH—CH$_2$CH$_2$CH$_2$—C(=O)—(NH-DX)
(maleimid-N-yl)-CH$_2$CH$_2$—C(=O)-GGFG-NH—CH$_2$CH$_2$CH$_2$CH$_2$—C(=O)—(NH-DX)
(maleimid-N-yl)-CH$_2$CH$_2$CH$_2$—C(=O)-GGFG-NH—CH$_2$CH$_{22}$CH$_2$—C(=O)—(NH-DX)
(maleimid-N-yl)-CH$_2$CH$_2$CH$_2$CH$_2$—C(=O)-GGFG-NH—CH$_2$CH$_2$CH$_2$CH$_2$—C(=O)—(NH-DX)
(maleimid-N-yl)-CH$_2$CH$_2$CH$_2$CH$_2$CH$_2$—C(=O)-GGFG-NH—CH$_2$CH$_2$CH$_2$CH$_2$—C(=O)—(NH-DX)
(maleimid-N-yl)-CH$_2$CH$_2$—C(=O)-GGFG-NH—CH$_2$CH$_2$CH$_2$CH$_2$CH$_2$—C(=O)—(NH-DX)
(maleimid-N-yl)-CH$_2$CH$_2$CH$_2$—C(=O)-GGFG-NH—CH$_2$CH$_2$CH$_2$CH$_2$CH$_2$—C(=O)—(NH-DX)
(maleimid-N-yl)-CH$_2$CH$_2$CH$_2$CH$_2$—C(=O)-GGFG-NH—CH$_2$CH$_2$CH$_2$CH$_2$CH$_2$—C(=O)—(NH-DX)
(maleimid-N-yl)-CH$_2$CH$_2$CH$_2$CH$_2$CH$_2$—C(=O)-GGFG-NH—CH$_2$CH$_2$CH$_2$CH$_2$CH$_2$—C(=O)—(NH-DX)
(maleimid-N-yl)-CH$_2$CH$_2$—C(=O)-GGFG-NH—CH$_2$—O—CH$_2$—C(=O)—(NH-DX)
(maleimid-N-yl)-CH$_2$CH$_2$CH$_2$—C(=O)-GGFG-NH—CH$_2$—O—CH$_2$—C(=O)—(NH-DX)
(maleimid-N-yl)-CH$_2$CH$_2$CH$_2$CH$_2$—C(=O)-GGFG-NH—CH$_2$—O—CH$_2$—C(=O)—(NH-DX)
(maleimid-N-yl)-CH$_2$CH$_2$CH$_2$CH$_2$CH$_2$—C(=O)-GGFG-NH—CH$_2$—O—CH$_2$—C(=O)—(NH-DX)
(maleimid-N-yl)-CH$_2$CH$_2$—C(=O)-GGFG-NH—CH$_2$CH$_2$—O—CH$_2$—C(=O)—(NH-DX)
(maleimid-N-yl)-CH$_2$CH$_2$CH$_2$—C(=O)-GGFG-NH—CH$_2$CH$_2$—O—CH$_2$—C(=O)—(NH-DX)
(maleimid-N-yl)-CH$_2$CH$_2$CH$_2$CH$_2$—C(=O)-GGFG-NH—CH$_2$CH$_2$—O—CH$_2$—C(=O)—(NH-DX)
(maleimid-N-yl)-CH$_2$CH$_2$CH$_2$CH$_2$CH$_2$—C(=O)-GGFG-NH—CH$_2$CH$_2$—O—CH$_2$—C(=O)—(NH-DX)
(maleimid-N-yl)-CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX)
(maleimid-N-yl)-CH$_2$CH$_2$—C(=O)—NH—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—(NH-DX)
(maleimid-N-yl)-CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—(NH-DX)
X—CH$_2$—C(=O)—NH—CH$_2$CH$_2$—C(=O)-GGFG-NH—CH$_2$CH$_2$—C(=O)—(NH-DX)
X—CH$_2$—C(=O)—NH—CH$_2$CH$_2$CH$_2$—C(=O)-GGFG-NH—CH$_2$CH$_2$CH$_2$—C(=O)—(NH-DX)
X—CH$_2$—C(=O)—NH—CH$_2$CH$_2$—C(=O)-GGFG-NH—CH$_2$—O—CH$_2$—C(=O)—(NH-DX)
X—CH$_2$—C(=O)—NH—CH$_2$CH$_2$—C(=O)-GGFG-NH—CH$_2$CH$_2$—O—CH$_2$—C(=O)—(NH-DX)
X—CH$_2$—C(=O)—NH—CH$_2$CH$_2$CH$_2$—C(=O)-GGFG-NH—CH$_2$CH$_2$—C(=O)—(NH-DX)
X—CH$_2$—C(=O)—NH—CH$_2$CH$_2$CH$_2$—C(=O)-GGFG-NH—CH$_2$CH$_2$CH$_2$—C(=O)—(NH-DX)
X—CH$_2$—C(=O)—NH—CH$_2$CH$_2$CH$_2$—C(=O)-GGFG-NH—CH$_2$—O—CH$_2$—C(=O)—(NH-DX)
X—CH$_2$—C(=O)—NH—CH$_2$CH$_2$CH$_2$—C(=O)-GGFG-NH—CH$_2$CH$_2$—O—CH$_2$—C(=O)—(NH-DX)
X—CH$_2$—C(=O)—NH—CH$_2$CH$_2$CH$_2$CH$_2$—C(=O)-GGFG-NH—CH$_2$CH$_2$—C(=O)—(NH-DX)
X—CH$_2$—C(=O)—NH—CH$_2$CH$_2$CH$_2$CH$_2$—C(=O)-GGFG-NH—CH$_2$CH$_2$CH$_2$—C(=O)—(NH-DX)
X—CH$_2$—C(=O)—NH—CH$_2$CH$_2$CH$_2$CH$_2$—C(=O)-GGFG-NH—CH$_2$—O—CH$_2$—C(=O)—(NH-DX)
X—CH$_2$—C(=O)—NH—CH$_2$CH$_2$CH$_2$CH$_2$—C(=O)-GGFG-NH—CH$_2$CH$_2$—O—CH$_2$—C(=O)—(NH-DX)
X—CH$_2$—C(=O)—NH—CH$_2$CH$_2$CH$_2$CH$_2$CH$_2$—C(=O)-GGFG-NH—CH$_2$CH$_2$—C(=O)—(NH-DX)
X—CH$_2$—C(=O)—NH—CH$_2$CH$_2$CH$_2$CH$_2$CH$_2$—C(=O)-GGFG-NH—CH$_2$CH$_2$CH$_2$—C(=O)—(NH-DX)
X—CH$_2$—C(=O)—NH—CH$_2$CH$_2$CH$_2$CH$_2$CH$_2$—C(=O)-GGFG-NH—CH$_2$—O—CH$_2$—C(=O)—(NH-DX)
X—CH$_2$—C(=O)—NH—CH$_2$CH$_2$CH$_2$CH$_2$CH$_2$—C(=O)-GGFG-NH—CH$_2$CH$_2$—O—CH$_2$—C(=O)—(NH-DX)

In the formula, X represents a bromine atom or an iodine atom. All of these bromine and iodine compounds can be preferably used as production intermediates.

In order to secure the amount of the conjugate, a plurality of conjugates obtained under similar production conditions to have an equivalent number of drugs (e.g., about ±1) can be mixed to prepare new lots. In this case, the average number of drugs falls between the average numbers of drugs in the conjugates before the mixing.

2. Production Method 2

The antibody-drug conjugate represented by the formula (1) in which the antibody is connected via an amide group to a linker and having a thioether bond within the linker, specifically, a structure in which -L$^1$-L$^2$- is —C(=O)-cyc.Hex(1,4)-CH$_2$—(N-ly-3-diminiccuS)-S—(CH$_2$)n$^6$-C(=O)—, can be also produced by the following method.

[Formula 52]

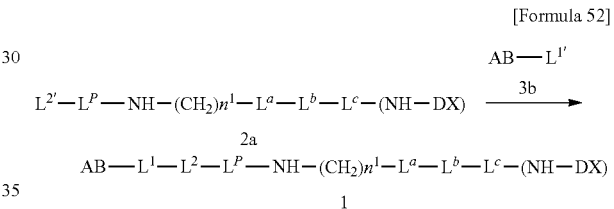

In the formula, AB-L$^{1'}$ represents a group which the antibody and linker L$^1$ are connected and, further, the terminal of L$^1$ is converted to a N-maleimidyl group. This group specifically has a structure in which —(N-ly-3-diminiccuS)- in AB—C(=O)-cyc.Hex(1,4)-CH$_2$—(N-ly-3-diminiccuS)- is converted to a maleimidyl group. L$^{2'}$ represents a HS—(CH$_2$)n$^6$-C(=O)— group in which the terminal is a mercapto group, and AB represents the antibody.

Specifically, the antibody-drug conjugate (1) can be produced by reacting the compound (2a), which is obtainable by the method described below, with the antibody (3b) which is connected to the linker having a maleimidyl group.

The antibody (3b) having a maleimidyl group can be also obtained by a method well known in the art (Hermanson, G. T, Bioconjugate Techniques, pp. 56-136, pp. 456-493, Academic Press (1996)). Examples include: a bifunctional linker, such as succinimidyl-4-(N-maleimidomethyl)cyclohexane-1-carboxylate (SMCC), which is capable of bonding to an amino group or a hydroxyl group and has a maleimidyl group is allowed to react on the amino group of the ligand to introduce a maleimidyl group, but it is not limited thereto.

For example, a compound having an amino group-reactive moiety and a thiol group-reactive moiety bound via a linker can be preferably used. Here, the amino group-reactive moiety can be active ester, imide ester, or the like, and the thiol-reactive moiety can be maleimidyl, acetyl halide, alkyl halide, dithiopyridyl, or the like.

As a method for constructing the linker with amino group or hydroxy group of an amino acid constituting the antibody, particularly via an amide bond with the amino group, the compound to be first reacted with the antibody can be a compound represented by the following formula:

$Q^1$-$L^{1a}$-$Q^2$.

[In the formula, $Q^1$ represents (Pyrrolidine-2,5-dione-N-yl)-O—C(=O)—, (3-Sulfo-pyrrolidine-2,5-dione-N-yl)-O—C(=O)—, $R^Q$—O—C(=N)—, or O=C=N—,
$L^{1a}$- represents -cyc.Hex(1,4)-CH$_2$—, an alkylene group having 1 to 10 carbon atoms, a phenylene group, —(CH$_2$)$n^4$-C(=O)—, —(CH$_2$)$n^{4a}$-NH—C(=O)—(CH$_2$)$n^{4b}$-, or —(CH$_2$)$n^{4a}$-NH—C(=O)-cyc.Hex(1,4)—CH$_2$—,
$Q^2$ represents (maleimid-N-yl), a halogen atom, or —S—S-(2-Pyridyl),
$R^Q$ represents an alkyl group having 1 to 6 carbon atoms, $n^4$ represents an integer of 1 to 8, $n^{4a}$ represents an integer of 0 to 6, and $n^{4b}$ represents an integer of 1 to 6.]

In the above, $R^Q$ is an alkyl group having 1 to 6 carbon atoms, and more preferably a methyl group or an ethyl group.

The alkylene group of $L^{1a}$ may be those having 1 to 10 carbon atoms. The phenylene group may be any of ortho, meta, and para configurations and is more preferably a para- or meta-phenylene group.

Preferred examples of $L^{1a}$ can include -cyc.Hex(1,4)-CH$_2$—, —(CH$_2$)$_5$—NH—C(=O)-cyc.Hex(1,4)-CH$_2$—, —(CH$_2$)$_2$—NH—C(=O)—CH$_2$—, —(CH$_2$)$_5$—NH—C(=O)—(CH$_2$)$_2$—, —CH$_2$—, —(CH$_2$)$_2$—, —(CH$_2$)$_3$—, —(CH$_2$)$_5$—, —(CH$_2$)$_{10}$—, -(para-Ph)-, -(meta-Ph)-, -(para-Ph)-CH(—CH$_3$)—, —(CH$_2$)$_3$-(meta-Ph)-, and -(meta-Ph)—NH—C(=O)—CH$_2$—.

$Q^1$ is preferably (Pyrrolidine-2,5-dione-N-yl)-O—C(=O)—, $Q^2$ is preferably (maleimid-N-yl), or —S—S-(2-Pyridyl) can be used when a disulfide bond is to be formed.

In the above, (Pyrrolidine-2,5-dione-N-yl)-is a group represented by the following formula:

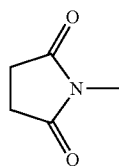

[Formula 53]

wherein the nitrogen atom as a connecting position, and (3-Sulfo-pyrrolidine-2,5-dione-N-yl)- is a group represented by the following formula:

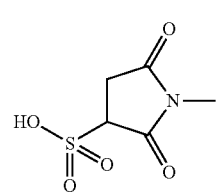

[Formula 54]

wherein the nitrogen atom is a connecting position, and this sulfonic acid is capable of forming a lithium salt, sodium salt, or potassium salt, and preferably sodium salt, cyc.Hex(1,4) represents a 1,4-cyclohexylene group, (maleimid-N-yl) is a group represented by the following formula:

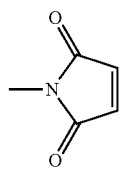

[Formula 55]

wherein the nitrogen atom is a connecting position, (2-Pyridyl) represents a 2-pyridyl group, (para-Ph) represents a para-phenylene group, and (meta-Ph) represents a meta-phenylene group.

Examples of such a compound include sulfosuccinimidyl-4-(N-maleimidylmethyl)cyclohexane-1-carboxylate (sulfo-SMCC), N-succinimidyl-4-(N-maleimidylmethyl)-cyclohexane-1-carboxy-(6-amidocaproate) (LC-SMCC), κ-maleimidyl undecanoic acid N-succinimidyl ester (KMUA), γ-maleimidyl butyric acid N-succinimidyl ester (GMBS), ε-maleimidyl caproic acid N-hydroxysuccinimide ester (EMCS), m-maleimidylbenzoyl-N-hydroxysuccinimide ester (MBS), N-(α-maleimidylacetoxy)-succinimide ester (AMAS), succinimidyl-6-(β-maleimidylpropionamide)hexanoate (SMPH), N-succinimidyl 4-(p-maleimidyl-phenyl)-butyrate (SMPB), N-(p-maleimidylphenyl)isocyanate (PMPI), N-succinimidyl-4-(iodoacetyl)-aminobenzoate (SIAB), N-succinimidyl iodoacetate (SIA), N-succinimidyl bromoacetate (SBA), N-succinimidyl 3-(bromoacetamide) propionate (SBAP), N-succinimidyl-3-(2-pyridodithio)propionate (SPDP), and succinimidyloxycarbonyl-α-methyl-α-(2-pyridyldithio)toluene (SMPT).

Specifically, for example, by reacting 2 to 6 equivalents of SMCC with the antibody (3) in a phosphate buffer of pH 6 to 7 at room temperature for 1 to 6 hours, the active ester of SMCC can react with the antibody to yield the antibody (3b) having a maleimidyl group. The obtained antibody (3b) can be purified by Common procedure D-2 described below, and used for the next reaction with the compound (2a).

Common Procedure D-2: Purification of Succinimidyl 4-(N-Maleimidylmethyl)-Cyclohexane-1-Carboxylate (SMCC)-Derivatized Antibody NAP-25 column was equilibrated with PBS6.5/EDTA. Reaction solution containing the succinimidyl 4-(N-maleimidylmethyl)-cyclohexane-1-carboxylate (herein, referred to as SMCC)-derivatized antibody was applied in an amount of about 0.5 mL to the NAP-25 column, and then eluted with the buffer in an amount defined by the manufacturer to collect the antibody fraction for purification.

The amino group of the antibody for connecting to the linker can be a N-terminal amino group and/or an amino group carried by a lysine residue, but it is not limited thereto. Alternatively, the antibody may be connected to the linker with ester bond formation by use of a hydroxy group carried by a serine residue.

The reaction of the compound (2a) with the antibody (3b) connected to the linker having a maleimidyl group can be performed in the same manner as the method for reacting the compound (2) with the antibody (3a) having a sulfhydryl group as mentioned in Production method 1.

For the antibody-drug conjugate (1) prepared, concentration, buffer exchange, purification, and identification of the antibody-drug conjugate (1) by the measurement of antibody concentration and an average number of conjugated drug molecules per antibody molecule can be performed in the same manner as Production method 1.

The compound represented by the formula (3b) in Production method 2 has the following structure (see the following formula; in the structure thereof, "antibody —NH—" originates from an antibody).

[Formula 56]

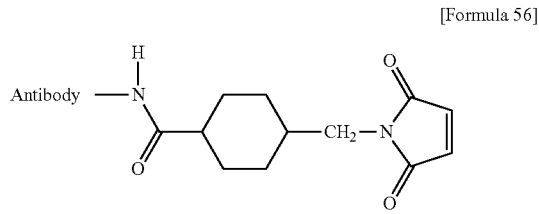 [SMILES: CNC(=O)C1CCC(CN2C(=O)C=CC2=O)CC1]

A compound which is an intermediate for producing the antibody-drug conjugate of the present invention and has the above structure is as described below (in the formula, n is an integer of 1 to 10, preferably 2 to 8, and more preferably 3 to 8).

[Formula 57]

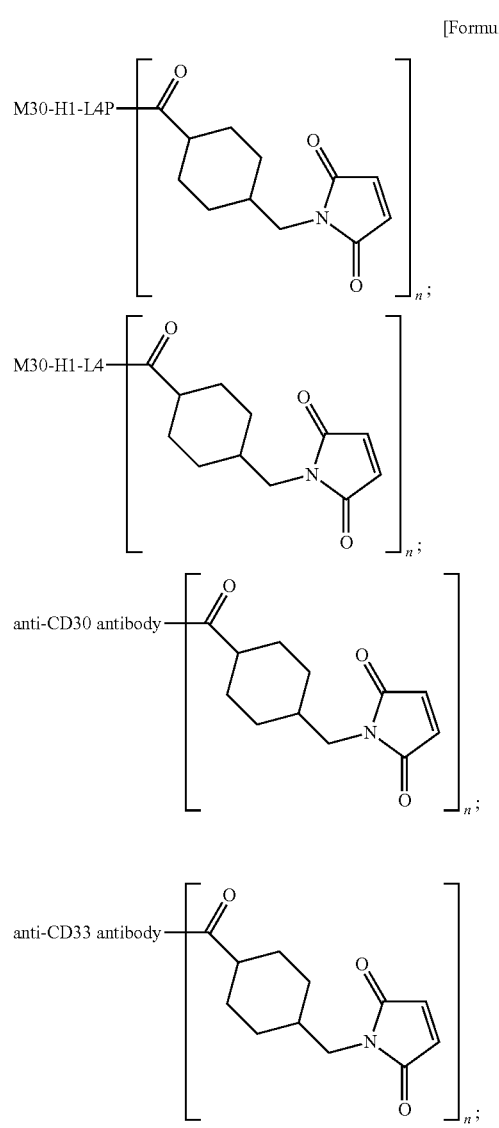

Further, examples of the compound of the present invention in which the terminal is a mercapto group can include the followings.

HS—$CH_2CH_2$—C(=O)-GGFG-NH—$CH_2CH_2$—C(=O)—(NH-DX)
HS—$CH_2CH_2CH_2$—C(=O)-GGFG-NH—$CH_2CH_2$—C(=O)—(NH-DX)
HS—$CH_2CH_2CH_2CH_2$—C(=O)-GGFG-NH—$CH_2CH_2$—C(=O)—(NH-DX)
HS—$CH_2CH_2CH_2CH_2CH_2$—C(=O)-GGFG-NH—$CH_2CH_2$—C(=O)—(NH-DX)
HS—$CH_2CH_2$—C(=O)-GGFG-NH—$CH_2CH_2$—C(=O)—(NH-DX)
HS—$CH_2CH_2CH_2$—C(=O)-GGFG-NH—$CH_2CH_2CH_2$—C(=O)—(NH-DX)
HS—$CH_2CH_2CH_2CH_2$—C(=O)-GGFG-NH—$CH_2CH_2CH_2$CC(=O)—(NH-DX)
HS—$CH_2CH_2CH_2CH_2CH_2$—C(=O)-GGFG-NH—$CH_2CH_2CH_2$—C(=O)—(NH-DX)
HS—$CH_2CH_2$—C(=O)-GGFG-NH—$CH_2$—O—$CH_2$—C(=O)—(NH-DX)
HS—$CH_2CH_2CH_2$—C(=O)-GGFG-NH—$CH_2$—O—$CH_2$—C(=O)—(NH-DX)
HS—$CH_2CH_2CH_2CH_2$—C(=O)-GGFG-NH—$CH_2$—O—$CH_2$—C(=O)—(NH-DX)
HS—$CH_2CH_2CH_2CH_2CH_2$—C(=O)-GGFG-NH—$CH_2$—O—$CH_2$—C(=O)—(NH-DX)
HS—$CH_2CH_2$—C(=O)-GGFG-NH—$CH_2CH_2$—O—$CH_2$—C(=O)—(NH-DX)
HS—$CH_2CH_2CH_2$—C(=O)-GGFG-NH—$CH_2CH_2$—O—$CH_2$—C(=O)—(NH-DX)
HS—$CH_2CH_2CH_2CH_2$—C(=O)-GGFG-NH—$CH_2CH_2$—O—$CH_2$—C(=O)—(NH-DX)
HS—$CH_2CH_2CH_2CH_2CH_2$—C(=O)-GGFG-NH—$CH_2CH_2$—O—$CH_2$—C(=O)—(NH-DX)
HS—$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—(NH-DX)
HS—$CH_2CH_2$—C(=O)—NH—$CH_2CH_2O$—$CH_2CH_2O$—$CH_2CH_2O$—$CH_2CH_2$—C(=O)-GGFG-NH—$CH_2CH_2CH_2$—C(=O)—(NH-DX)
HS—$CH_2CH_2$—C(=O)—NH—$CH_2CH_2O$—$CH_2CH_2O$—$CH_2CH_2O$—$CH_2CH_2O$—$CH_2CH_2$—C(=O)-GGFG-NH—$CH_2CH_2CH_2$—C(=O)—(NH-DX)

3. Production Method 3

The antibody-drug conjugate represented by the formula (1) in which the antibody is conjugated to the drug linker moiety via an amide bond can be produced by a method described below. For example, as for —C(=O)—$(CH_2)n^4$-C(=O)— of $L^1$, its active ester $L^{1i}$, for example, (Pyrrolidine-2,5-dione-N-yl)-O—C(=O)—$(CH_2)n^4$C(=O)—, can be preferably used. When $L^2$ is a single bond, the antibody-drug conjugate (1) can be produced by the following method, for example.

[Formula 58]

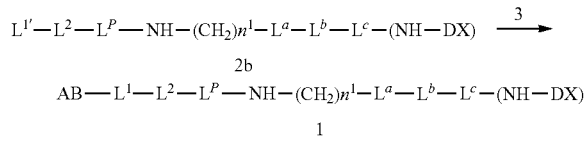

Specifically, the antibody-drug conjugate (1) can be produced by reacting the compound (2b), which is obtainable by the method described below, with the antibody (3).

The compound (2b) is capable of connecting to the amino group or hydroxyl group of the antibody. The amino group and hydroxyl group of the antibody refer to, as described in Production method 2, for example, a N-terminal amino group carried by the antibody and/or an amino group carried by a lysine residue and a hydroxy group carried by a serine residue, respectively, but they are not limited thereto.

The compound (2b) is active ester composed of a N-hydroxysuccinimidyl ester group. Alternatively, other active esters, for example, a sulfosuccinimidyl ester group, N-hydroxyphthalimidyl ester, N-hydroxysulfophthalimidyl ester, ortho-nitrophenyl ester, para-nitrophenyl ester, 2,4-dinitrophenyl ester, 3-sulfonyl-4-nitrophenyl ester, 3-carboxy-4-nitrophenyl ester, and pentafluorophenyl ester, may be used.

By using 2 to 20 molar equivalents of the compound (2b) per the antibody (3) in the reaction of the compound (2b) with the antibody (3), the antibody-drug conjugate (1) in which 1 to 10 drug molecules are conjugated per antibody can be produced. Specifically, the solution containing the compound (2b) dissolved therein can be added to a buffer solution containing the antibody (3) for the reaction to yield the antibody-drug conjugate (1). Herein, examples of the buffer solution which may be used include sodium acetate solution, sodium phosphate, and sodium borate. pH for the reaction can be 5 to 9, and more preferably the reaction is performed near pH 7. Examples of the solvent for dissolving the compound (2b) include an organic solvent such as dimethyl sulfoxide (DMSO), dimethylformamide (DMF), dimethyl acetamide (DMA), and N-methyl-2-pyridone (NMP). It is sufficient that the organic solvent solution containing the compound (2b) dissolved therein is added at 1 to 20% v/v to a buffer solution containing the antibody (3) for the reaction. The reaction temperature is 0 to 37° C., more preferably 10 to 25° C., and the reaction time is 0.5 to 20 hours.

For the produced antibody-drug conjugate (1), concentration, buffer exchange, purification, and identification of the antibody-drug conjugate (1) by the measurement of antibody concentration and an average number of conjugated drug molecules per antibody molecule can be performed in the same manner as Production method 1.

The moiety (Pyrrolidine-2,5-dione-N-yl)-O—C(=O)—$(CH_2)n^4$-C(=O)— in Production method 3 has the following structure.

[Formula 59]

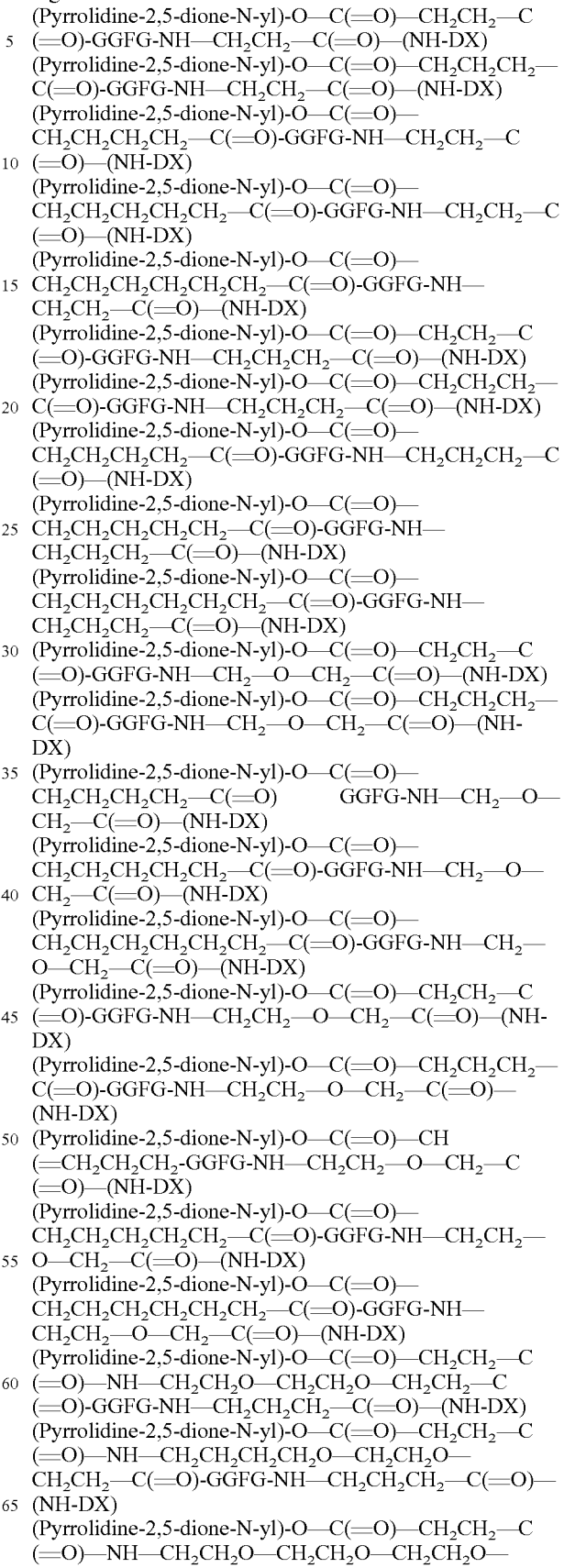

Examples of the compound of the present invention having the above partial structure can include the followings.

(Pyrrolidine-2,5-dione-N-yl)-O—C(=O)—$CH_2CH_2$—C(=O)-GGFG-NH—$CH_2CH_2$—C(=O)—(NH-DX)
(Pyrrolidine-2,5-dione-N-yl)-O—C(=O)—$CH_2CH_2CH_2$—C(=O)-GGFG-NH—$CH_2CH_2$—C(=O)—(NH-DX)
(Pyrrolidine-2,5-dione-N-yl)-O—C(=O)—$CH_2CH_2CH_2CH_2$—C(=O)-GGFG-NH—$CH_2CH_2$—C(=O)—(NH-DX)
(Pyrrolidine-2,5-dione-N-yl)-O—C(=O)—$CH_2CH_2CH_2CH_2CH_2$—C(=O)-GGFG-NH—$CH_2CH_2$—C(=O)—(NH-DX)
(Pyrrolidine-2,5-dione-N-yl)-O—C(=O)—$CH_2CH_2CH_2CH_2CH_2CH_2$—C(=O)-GGFG-NH—$CH_2CH_2$—C(=O)—(NH-DX)
(Pyrrolidine-2,5-dione-N-yl)-O—C(=O)—$CH_2CH_2$—C(=O)-GGFG-NH—$CH_2CH_2CH_2$—C(=O)—(NH-DX)
(Pyrrolidine-2,5-dione-N-yl)-O—C(=O)—$CH_2CH_2CH_2$—C(=O)-GGFG-NH—$CH_2CH_2CH_2$—C(=O)—(NH-DX)
(Pyrrolidine-2,5-dione-N-yl)-O—C(=O)—$CH_2CH_2CH_2CH_2$—C(=O)-GGFG-NH—$CH_2CH_2CH_2$—C(=O)—(NH-DX)
(Pyrrolidine-2,5-dione-N-yl)-O—C(=O)—$CH_2CH_2CH_2CH_2CH_2$—C(=O)-GGFG-NH—$CH_2CH_2CH_2$—C(=O)—(NH-DX)
(Pyrrolidine-2,5-dione-N-yl)-O—C(=O)—$CH_2CH_2CH_2CH_2CH_2CH_2$—C(=O)-GGFG-NH—$CH_2CH_2CH_2$—C(=O)—(NH-DX)
(Pyrrolidine-2,5-dione-N-yl)-O—C(=O)—$CH_2CH_2$—C(=O)-GGFG-NH—$CH_2$—O—$CH_2$—C(=O)—(NH-DX)
(Pyrrolidine-2,5-dione-N-yl)-O—C(=O)—$CH_2CH_2CH_2$—C(=O)-GGFG-NH—$CH_2$—O—$CH_2$—C(=O)—(NH-DX)
(Pyrrolidine-2,5-dione-N-yl)-O—C(=O)—$CH_2CH_2CH_2CH_2$—C(=O) GGFG-NH—$CH_2$—O—$CH_2$—C(=O)—(NH-DX)
(Pyrrolidine-2,5-dione-N-yl)-O—C(=O)—$CH_2CH_2CH_2CH_2CH_2$—C(=O)-GGFG-NH—$CH_2$—O—$CH_2$—C(=O)—(NH-DX)
(Pyrrolidine-2,5-dione-N-yl)-O—C(=O)—$CH_2CH_2CH_2CH_2CH_2CH_2$—C(=O)-GGFG-NH—$CH_2$—O—$CH_2$—C(=O)—(NH-DX)
(Pyrrolidine-2,5-dione-N-yl)-O—C(=O)—$CH_2CH_2$—C(=O)-GGFG-NH—$CH_2CH_2$—O—$CH_2$—C(=O)—(NH-DX)
(Pyrrolidine-2,5-dione-N-yl)-O—C(=O)—$CH_2CH_2CH_2$—C(=O)-GGFG-NH—$CH_2CH_2$—O—$CH_2$—C(=O)—(NH-DX)
(Pyrrolidine-2,5-dione-N-yl)-O—C(=O)—CH(=$CH_2CH_2CH_2$-GGFG-NH—$CH_2CH_2$—O—$CH_2$—C(=O)—(NH-DX)
(Pyrrolidine-2,5-dione-N-yl)-O—C(=O)—$CH_2CH_2CH_2CH_2$—C(=O)-GGFG-NH—$CH_2CH_2$—O—$CH_2$—C(=O)—(NH-DX)
(Pyrrolidine-2,5-dione-N-yl)-O—C(=O)—$CH_2CH_2CH_2CH_2CH_2CH_2$—C(=O)-GGFG-NH—$CH_2CH_2$—O—$CH_2$—C(=O)—(NH-DX)
(Pyrrolidine-2,5-dione-N-yl)-O—C(=O)—$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—(NH-DX)
(Pyrrolidine-2,5-dione-N-yl)-O—C(=O)—$CH_2CH_2$—C(=O)—NH—$CH_2CH_2CH_2CH_2O$—$CH_2CH_2O$—$CH_2CH_2$—C(=O)-GGFG-NH—$CH_2CH_2CH_2$—C(=O)—(NH-DX)
(Pyrrolidine-2,5-dione-N-yl)-O—C(=O)—$CH_2CH_2$—C(=O)—NH—$CH_2CH_2O$—$CH_2CH_2O$—$CH_2CH_2O$—

CH$_2$CH$_2$O—CH$_2$CH$_2$—C(=O)-GGFG-NH—CH$_2$CH$_2$CH$_2$—C(=O)—(NH-DX)

4. Production Method 4

The compound represented by the formula (2) or (2b) as an intermediate used in the previous production method and a pharmacologically acceptable salt thereof can be produced by the following method, for example.

[Formula 60]

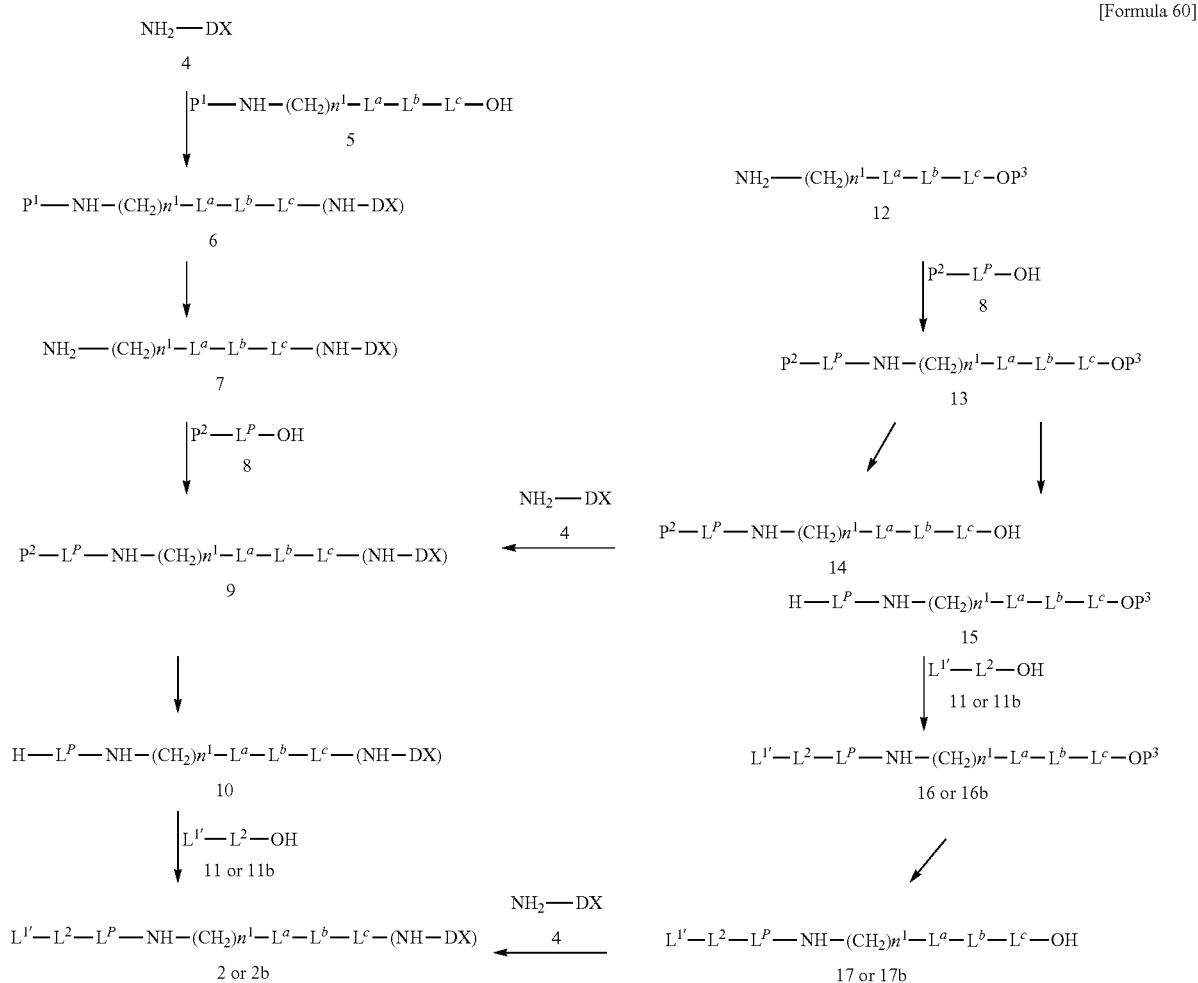

In the formula, L$^c$ is —C(=O)— and is connected to —(NH-DX) with formation of amide bond, L$^{1'}$ represents L$^1$ structure in which the terminal is converted to a maleimidyl group or a haloacetyl group, or to (Pyrrolidine-2,5-dione-N-yl)-O—C(=O)—(CH$_2$)n$^4$-C(=O)—, and P$^1$, P$^2$, and P$^3$ each represents a protecting group.

The compound (6) can be produced by derivatizing the carboxylic acid (5) into an active ester, mixed acid anhydride, acid halide, or the like and reacting it with NH$_2$-DX [indicating exatecan; chemical name: (1S,9S)-1-amino-9-ethyl-5-fluoro-2,3-dihydro-9-hydroxy-4-methyl-1H,12H-benzo[de]pyrano[3',4':6,7]indolizino[1,2-b]quinolin-10,13 (9H,15H)-dione](4) or a pharmacologically acceptable salt thereof.

Reaction reagents and conditions that are commonly used for peptide synthesis can be employed for the reaction. There are various kinds of active ester.

For example, it can be produced by reacting phenols such as p-nitrophenol, N-hydroxy benzotriazole, N-hydroxy suc-cinimide, or the like, with the carboxylic acid (5) using a condensing agent such as N,N'-dicyclohexylcarbodiimide or 1-ethyl-3-(3-dimethylaminopropyl)carbodiimide hydrochloride. Further, the active ester can be also produced by a reaction of the carboxylic acid (5) with pentafluorophenyl trifluoroacetate or the like; a reaction of the carboxylic acid (5) with 1-benzotriazolyl oxytripyrrolidinophosphonium hexafluorophosphite; a reaction of the carboxylic acid (5) with diethyl cyanophosphonate (salting-in method); a reaction of the carboxylic acid (5) with triphenylphosphine and 2,2'-dipyridyl disulfide (Mukaiyama's method); a reaction of the carboxylic acid (5) with a triazine derivative such as 4-(4,6-dimethoxy-1,3,5-triazin-2-yl)-4-methylmorpholinium chloride (DMTMM); or the like. Further, the reaction can be also performed by, e.g., an acid halide method by which the carboxylic acid (5) is treated with acid halide such as thionyl chloride and oxalyl chloride in the presence of a base. By reacting the active ester, mixed acid anhydride, or acid halide of the carboxylic acid (5) obtained accordingly with the compound (4) in the presence of a suitable base in an inert solvent at −78° C. to 150° C., the compound (6) can be produced. (Meanwhile, "inert solvent" indicates a solvent which does not inhibit a reaction for which the solvent is used.)

Specific examples of the base used for each step described above include carbonate of an alkali metal or an alkali earth metal, an alkali metal alkoxide, hydroxide or hydride of an alkali metal including sodium carbonate, potassium carbonate, sodium ethoxide, potassium butoxide, sodium hydroxide, potassium hydroxide, sodium hydride, and potassium hydride, organometallic base represented by an alkyl lithium including n-butyl lithium, dialkylamino lithium including lithium diisopropylamide; organometallic base of bissilylamine including lithium bis(trimethylsilyl)amide; and organic base- including pyridine, 2,6-lutidine, collidine, 4-dimethylaminopyridine, triethylamine, N-methylmorpholine, diisopropylethylamine, and diazabicyclo[5.4.0]undec-7-ene (DBU).

Examples of the inert solvent which is used for the reaction of the present invention include a halogenated hydrocarbon solvent such as dichloromethane, chloroform, and carbon tetrachloride; an ether solvent such as tetrahydrofuran, 1,2-dimethoxyethane, and dioxane; an aromatic hydrocarbon solvent such as benzene and toluene; and an amide solvent such as N,N-dimethylformamide, N,N-dimethylacetamide, and N-methylpyrrolidin-2-one. In addition to them, a sulfoxide solvent such as dimethyl sulfoxide and sulfolane; and a ketone solvent such as acetone and methyl ethyl ketone may be used depending on a case.

The hydroxy group, carboxy group, amino group, or the like of $L^a$ and $L^b$ in the compound (6) may be protected with a protecting group which is commonly used in organic compound synthesis, as mentioned later. Specifically, examples of the protecting group for a hydroxyl group include an alkoxymethyl group such as methoxymethyl group; an arylmethyl group such as benzyl group, 4-methoxybenzyl group, and triphenylmethyl group; an alkanoyl group such as acetyl group; an aroyl group such as benzoyl group; and a silyl group such as tert-butyl diphenylsilyl group. Carboxy group can be protected, e.g., as an ester with an alkyl group such as methyl group, ethyl group, and tert-butyl group, an allyl group, or an arylmethyl group such as benzyl group. Amino group can be protected with a protecting group for an amino group which is generally used for peptide synthesis, for example, an alkyloxy carbonyl group such as tert-butyloxy carbonyl group, methoxycarbonyl group, and ethoxycarbonyl group; an arylmethyl group such as allyloxycarbonyl, 9-fluorenylmethyloxy carbonyl group, benzyloxy carbonyl group, paramethoxybenzyloxy carbonyl group, and para (or ortho)nitroybenzyloxy carbonyl group; an alkanoyl group such as acetyl group; an arylmethyl group such as benzyl group and triphenyl methyl group; an aroyl group such as benzoyl group; and an aryl sulfonyl group such as 2,4-dinitrobenzene sulfonyl group or orthonitrobenzene sulfonyl group. Protection with and deprotection of the protecting group can be performed according to a method commonly carried out.

As for the protecting group $P^1$ for the terminal amino group of the compound (6), a protecting group for an amino group which is generally used for peptide synthesis, for example, tert-butyloxy carbonyl group, 9-fluorenylmethyloxy carbonyl group, and benzyloxy carbonyl group, can be used. Examples of the other protecting group for an amino group include an alkanoyl group such as acetyl group; an alkoxycarbonyl group such as methoxycarbonyl group and ethoxycarbonyl group; an arylmethoxy carbonyl group such as paramethoxybenzyloxy carbonyl group, and para (or ortho)nitroybenzyloxy carbonyl group; an arylmethyl group such as benzyl group and triphenyl methyl group; an aroyl group such as benzoyl group; and an aryl sulfonyl group such as 2,4-dinitrobenzene sulfonyl group and orthonitrobenzene sulfonyl group. The protecting group $P^1$ can be selected depending on, e.g., properties of a compound having an amino group to be protected.

By deprotecting the protecting group $P^1$ for the terminal amino group of the compound (6) obtained, the compound (7) can be produced. Reagents and conditions can be selected depending on the protecting group.

The compound (9) can be produced by derivatizing the peptide carboxylic acid (8) having the N terminal protected with $P^2$ into an active ester, mixed acid anhydride, or the like and reacting it with the compound (7) obtained. The reaction conditions, reagents, base, and inert solvent used for forming a peptide bond between the peptide carboxylic acid (8) and the compound (7) can be suitably selected from those described for the synthesis of the compound (6). The protecting group $P^2$ can be suitably selected from those described for the protecting group of the compound (6), and the selection can be made based on, e.g., the properties of the compound having an amino group to be protected. As it is generally used for peptide synthesis, by repeating sequentially the reaction and deprotection of the amino acid or peptide constituting the peptide carboxylic acid (8) for elongation, the compound (9) can be also produced.

By deprotecting $P^2$ as the protecting group for the amino group of the compound (9) obtained, the compound (10) can be produced. Reagents and conditions can be selected depending on the protecting group.

It is possible to produce the compound (2) or (2b) by derivatizing the carboxylic acid (11) or (11b) into an active ester, mixed acid anhydride, acid halide, or the like and reacting it with the compound (10) obtained. The reaction conditions, reagents, base, and inert solvent used for forming a peptide bond between the carboxylic acid (11) or (11b) and the compound (10) can be suitably selected from those described for the synthesis of the compound (6).

The compound (9) can be also produced by the following method, for example.

The compound (13) can be produced by derivatizing the peptide carboxylic acid (8) having the N terminal protected with $P^2$ into active ester, mixed acid anhydride, or the like and reacting it with the amine compound (12) having the carboxy group protected with $P^3$ in the presence of a base. The reaction conditions, reagents, base, and inert solvent used for forming a peptide bond between the peptide carboxylic acid (8) and the compound (12) can be suitably selected from those described for the synthesis of the compound (6). The protecting group $P^2$ for the amino group of the compound (13) can be suitably selected from those described for the protecting group of the compound (6). As for the protecting group $P^3$ for a carboxy group, a protecting group commonly used as a protecting group for a carboxy group in organic synthetic chemistry, in particular, peptide synthesis can be used. Specifically, it can be suitably selected from those described for the protecting group of the compound (6), for example, esters with an alkyl group such as a methyl group, an ethyl group, or a tert-butyl, allyl esters, and benzyl esters. In such case, it is necessary that the protecting group for an amino group and the protecting group for a carboxy group can be removed by a different method or different conditions. For example, a representative example includes a combination in which $P^2$ is a tert-butyloxy carbonyl group and $P^3$ is a benzyl group. The protecting groups can be selected from the aforementioned ones depending on, e.g., the properties of a compound having an amino group and a carboxy group to be protected. For removal of the protecting groups, reagents and conditions can be selected depending on the protecting group.

By deprotecting the protecting group $P^3$ for the carboxy group of the compound (13) obtained, the compound (14) can be produced. Reagents and conditions are selected depending on the protecting group.

The compound (9) can be produced by derivatizing the compound (14) obtained into active ester, mixed acid anhydride, acid halide, or the like and reacting with the compound (4) in the presence of a base. For the reaction, reaction reagents and conditions that are generally used for peptide synthesis can be also used, and the reaction conditions, reagents, base, and inert solvent used for the reaction can be suitably selected from those described for the synthesis of the compound (6).

The compound (2) or (2b) can be also produced by the following method, for example.

By deprotecting the protecting group $P^2$ for the amino group of the compound (13), the compound (15) can be produced. Reagents and conditions can be selected depending on the protecting group.

The compound (16) or (16b) can be produced by derivatizing the carboxylic acid derivative (11) or (11b) into active ester, mixed acid anhydride, acid halide, or the like and reacting it with the compound (15) obtained in the presence of a base. The reaction conditions, reagents, base, and inert solvent used for forming an amide bond between the peptide carboxylic acid (11) or (11b) and the compound (15) can be suitably selected from those described for the synthesis of the compound (6).

By deprotecting the protecting group for the carboxy group of the compound (16) or (16b) obtained, the compound (17) or (17b) can be produced. It can be carried out similar to deprotecting carboxy group for producing the compound (14).

The compound (2) or (2b) can be produced by derivatizing the compound (17) or (17b) into active ester, mixed acid anhydride, acid halide, or the like and reacting it with the compound (4) in the presence of a base. For the reaction, reaction reagents and conditions that are generally used for peptide synthesis can be also used, and the reaction conditions, reagents, base, and inert solvent used for the reaction can be suitably selected from those described for the synthesis of the compound (6).

5. Production Method 5

The compound represented by the formula (2) of an intermediate can be also produced by the following method.

[Formula 61]

$$H—L^P—OP^4$$
18

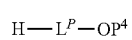
11

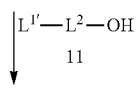

-continued $$L^{1'}—L^2—L^P—OP^4$$
19

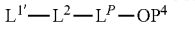

$$L^{1'}—L^2—L^P—OH$$
20

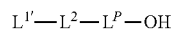

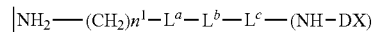

$$L^{1'}—L^2—L^P—NH—(CH_2)n^1—L^a—L^b—L^c—(NH—DX)$$
2

In the formula, $L^{1'}$ corresponds to $L^1$ having a structure in which the terminal is converted to a maleimidyl group or a haloacetyl group, and $P^4$ represents a protecting group.

The compound (19) can be produced by derivatizing the compound (11) into active ester, mixed acid anhydride, or the like and reacting it with the peptide carboxylic acid (18) having the C terminal protected with $P^4$ in the presence of a base. The reaction conditions, reagents, base, and inert solvent used for forming a peptide bond between the peptide carboxylic acid (18) and the compound (11) can be suitably selected from those described for the synthesis of the compound (6). The protecting group $P^4$ for the carboxy group of the compound (18) can be suitably selected from those described for the protecting group of the compound (6).

By deprotecting the protecting group for the carboxy group of the compound (19) obtained, the compound (20) can be produced. It can be performed similar to the deprotection of the carboxy group for producing the compound (14).

The compound (2) can be produced by derivatizing the compound (20) obtained into active ester, mixed acid anhydride, or the like and reacting it with the compound (7). For the reaction, reaction reagents and conditions that are generally used for peptide synthesis can be also used, and the reaction conditions, reagents, base, and inert solvent used for the reaction can be suitably selected from those described for the synthesis of the compound (6).

6. Production Method 6

The production intermediate (2a) described in Production method 2 in which $L^2$ corresponds to $L^2$ having a structure in which the terminal is converted to a mercaptoalkanoyl group can be produced by the following method.

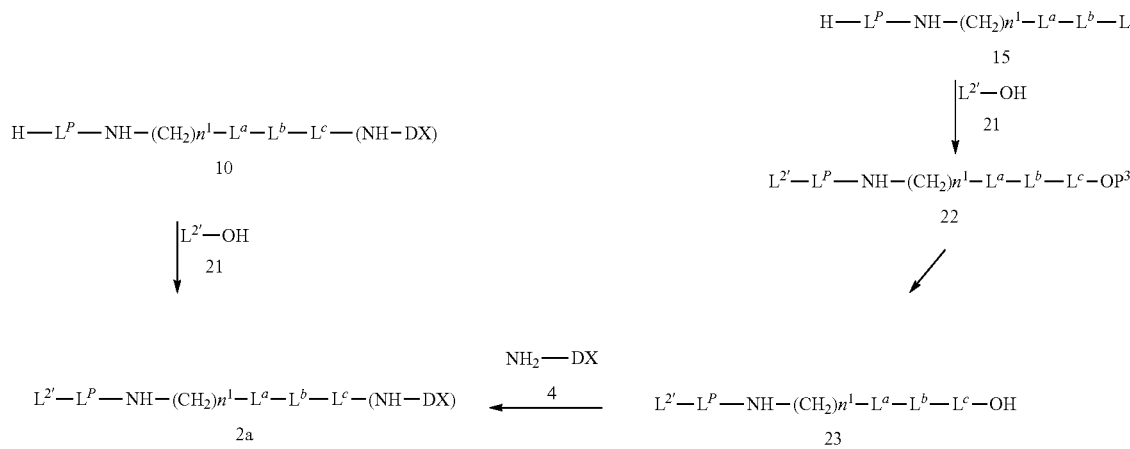

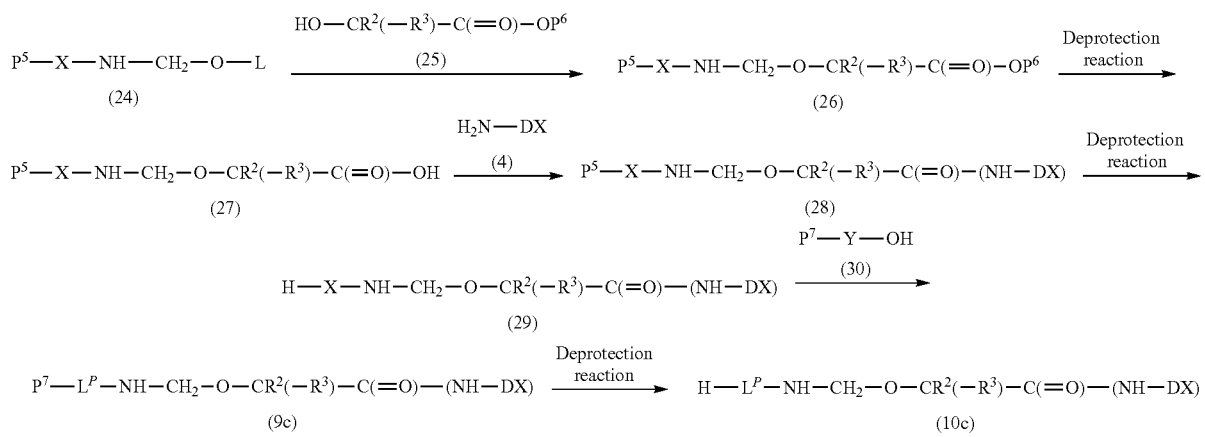

The compound (2a) can be produced by derivatizing the carboxylic acid (21) having a terminal mercapto group into active ester, mixed acid anhydride, or the like and reacting it with the compound (10). For the reaction, reaction reagents and conditions that are generally used for peptide synthesis can be also used, and the reaction conditions, reagents, base, and inert solvent used for the reaction can be suitably selected from those described for the synthesis of the compound (4).

Further, the compound (23) can be produced by derivatizing the compound (21) into active ester, mixed acid anhydride, acid halide, or the like, reacting it with the compound (15), and deprotecting the protecting group for the carboxy group of the compound (22) obtained.

The compound (2a) can be produced by derivatizing the compound (23) into active ester, mixed acid anhydride, acid halide, or the like and reacting it with the compound (4) in the presence of a base. For the reaction, reaction reagents and conditions that are generally used for peptide synthesis can be also used, and the reaction conditions, reagents, base, and inert solvent used for the reaction can be suitably selected from those described for the synthesis of the compound (6).

7. Production Method 7

Hereinbelow, the method for producing the compound (10c) having $n^1=1$, $L^a=O$, and $L^b=CR^2(-R^3)$ in the production intermediate (10) described in Production method 4 is described in detail. The compound represented by the formula (10c), a salt or a solvate thereof can be produced according to the following method, for example.

In the formula, $L^P$, $R^2$, and $R^3$ are as defined above, L represents an acetyl group, a hydrogen atom, or the like, X and Y each represent an oligopeptide consisting of 1 to 3 amino acids, $P^5$ and $P^7$ each represent a protecting group for an amino group, and $P^6$ represents a protecting group for a carboxy group.

A compound represented by the formula (24) can be produced by using or applying the method described in Japanese Patent Laid-Open No. 2002-60351 or the literature (J. Org. Chem., Vol. 51, page 3196, 1986), and if necessary, by removing the protecting groups or modifying the functional groups. Alternatively, it can be also obtained by treating an amino acid with a protected terminal amino group or acid amide of oligopeptide with protected amino group with aldehyde or ketone.

By reacting the compound (24) with the compound (25) having a hydroxyl group at a temperature ranging from under cooling to room temperature in an inert solvent in the presence of an acid or a base, the compound (26) can be produced. Examples of the acid which may be used include inorganic acid such as hydrofluoric acid, hydrochloric acid, sulfuric acid, nitric acid, phosphoric acid, and boric acid; an organic acid such as acetic acid, citric acid, paratoluene sulfonic acid, and methane sulfonic acid; and a Lewis acid such as tetrafluoroborate, zinc chloride, tin chloride, aluminum chloride, and iron chloride. Paratoluene sulfonic acid is particularly preferable. As for the base to be used, any one of the aforementioned base can be suitably selected and used. Preferred examples thereof include an alkali metal alkoxide such as potassium tert-butoxide, an alkali metal hydroxide such as sodium hydroxide and potassium hydroxide; alkali metal hydride such as sodium hydride and potassium hydride; organometallic base represented by dialkylamino lithium such as lithium diisopropylamide; and organometallic base of bissilylamine such as lithium bis(trimethylsilyl)amide. Examples of the solvent to be used for the reaction include an ether solvent such as tetrahydrofuran and 1,4-dioxane; and an aromatic hydrocarbon solvent such as benzene and toluene. Those solvents can be prepared as a mixture with water. Further, the protecting group for an amino group as exemplified by $P^5$ is not particularly limited if it is a group commonly used for protection of an amino group. Representative examples include the protecting groups for an amino group that are described in Production method 4. However, in the present reaction, the protecting group for an amino group as exemplified by $P^5$ may be cleaved off. In such case, it is necessary to perform a reaction with a suitable reagent for protecting an amino group as it may be required.

The compound (27) can be produced by removing the protecting group $P^6$ of the compound (26). Herein, although the representative examples of the protecting group for a carboxy group as exemplified by $P^6$ are described in Production method 4, it is desirable in this case that the protecting group $P^5$ for an amino group and the protecting group $P^6$ for a carboxy group are the protecting groups that can be removed by a different method or different conditions. For example, a representative example includes a combination in which $P^5$ is a 9-fluorenylmethyloxy carbonyl group and $P^6$ is a benzyl group. The protecting groups can be selected depending on, e.g., the properties of a compound having an amino group and a carboxy group to be protected. For removal of the protecting groups, reagents and conditions are selected depending on the protecting group.

The compound (29) can be produced by derivatizing the carboxylic acid (27) into active ester, mixed acid anhydride, acid halide, or the like and reacting it with the compound (4) and a pharmacologically acceptable salt thereof to produce the compound (28) followed by removing the protecting group $P^5$ of the compound (28) obtained. For the reaction between the compound (4) and the carboxylic acid (27) and the reaction for removing the protecting group $P^6$, the same reagents and reaction conditions as those described for Production method 4 can be used.

The compound (10c) can be produced by reacting the compound (29) with an amino acid with protected terminal amino group or the oligopeptide (30) with protected amino group to produce the compound (9c) and removing the protecting group $P^7$ of the compound (9c) obtained. The protecting group for an amino group as exemplified by $P^7$ is not particularly limited if it is generally used for protection of an amino group. Representative examples thereof include the protecting groups for an amino group that are described in Production method 4. For removing the protecting group, reagents and conditions are selected depending on the protecting group. For the reaction between the compound (29) and the compound (30), reaction reagents and conditions that are commonly used for peptide synthesis can be employed. The compound (10c) produced by the aforementioned method can be derivatized into the compound (1) of the present invention according to the method described above.

8. Production Method 8

Hereinbelow, the method for producing the compound (2c) having $n^1=1$, $L^a=O$, and $L^b=CR^2(-R^3)$ in the production intermediate (2) described in Production method 4 is described in detail. The compound represented by the formula (2c), a salt or a solvate thereof can be produced according to the following method, for example.

[Formula 64]

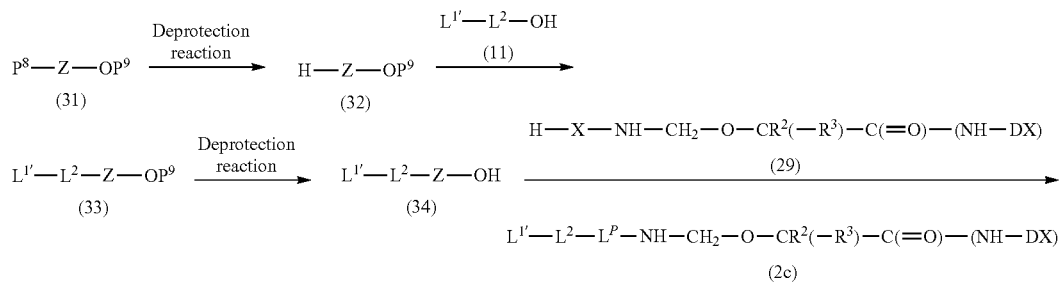

In the formula, $L^1$, $L^2$, $L^P$, $R^2$, and $R^3$ are as defined above, Z represents an oligopeptide consisting of 1 to 3 amino acids, $P^8$ represents a protecting group for an amino group, and $P^9$ represents a protecting group for a carboxy group.

The compound (33) can be produced by removing the protecting group $P^8$ of the amino acid or oligopeptide (31) with protected terminal amino group and carboxy group to produce the compound (32) and reacting the obtained amine form (32) with the compound (11). The protecting group for an amino group as exemplified by $P^8$ is not particularly limited if it is a group commonly used for protection of an amino group. Representative examples include the protecting groups for an amino group that are described in Production method 4. Further, for removing the protecting group P⁸, reagents and conditions can be selected depending on the protecting group. For the reaction between the compound (32) and the carboxylic acid (11), the same reagents and reaction conditions as those described for Production method 4 can be used.

The production intermediate (2c) can be produced by removing the protecting group P⁹ of the compound (33) to produce the compound (34) and reacting the obtained carboxylic acid (34) with the compound (29) The representative examples of the protecting group for a carboxy group as exemplified by P⁹ are described in Production method 4. For the deprotection reaction thereof, the same reagents and reaction conditions as those described for Production method 4 can be used. For the reaction between the compound (29) and the carboxylic acid (34), reaction reagents and conditions that are generally used for peptide synthesis can be also used. The compound (2c) produced by the aforementioned method can be derivatized into the compound (1) of the present invention according to the method described above.

9. Production Method 9

Hereinbelow, the method for producing the compound (17c) having $n^1=1$, $L^a=O$, and $L^b=CR^2(-R^3)$ in the production intermediate (17) described in Production method 4 is described in detail. The compound represented by the formula (17c), a salt or a solvate thereof can be also produced according to the following method, for example.

[Formula 65]

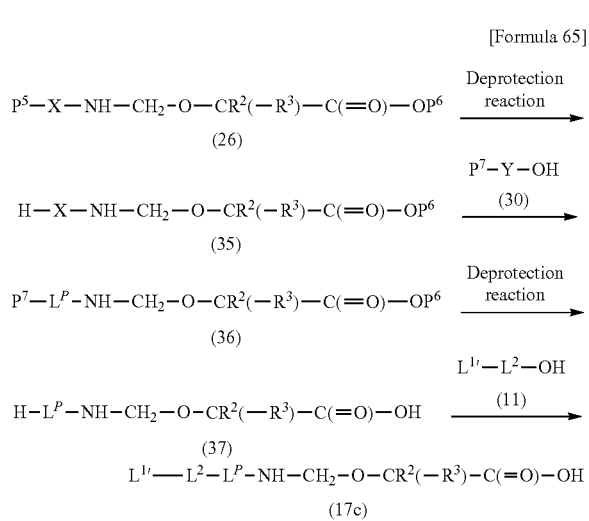

In the formula, $L^{1'}$, $L^2$, $L^P$, $R^2$, $R^3$, X, Y, $P^5$, $P^6$ and $P^7$ are as defined above.

The compound (36) can be produced by deprotecting the protecting group $P^5$ for the amino group of the compound (26) with protected terminal amino group and carboxy group to produce the compound (35) and reacting the obtained amine form (35) with the oligopeptide (30) with protected terminal amino group or protected amino group. The protecting group for an amino group as exemplified by $P^5$ is not particularly limited if it is a group commonly used for protection of an amino group. Representative examples include the protecting groups for an amino group that are described in Production method 4. Further, for removing the protecting group $P^5$, reagents and conditions can be selected depending on the protecting group. Herein, although representative examples of the protecting group for a carboxy group as exemplified by $P^6$ and the protecting group for an amino group as exemplified by $P^7$ include the protecting groups for a carboxy group and an amino group that are described in Production method 4, it is desirable that the protecting group $P^6$ for a carboxy group and the protecting group $P^7$ for an amino group are the protecting groups that can be removed by the same method or the same conditions. For example, a representative example includes a combination in which $P^6$ is a benzyl ester group and $P^7$ is a benzyloxy carbonyl group.

The compound (37) can be produced by removing the protecting group $P^6$ for the carboxy group of the compound (36) and the protecting group $P^7$ for the amino group of the compound (36). The compound (37) can be also produced by sequentially removing the protecting group $P^6$ for the carboxy group and the protecting group $P^7$ for the amino group, or the compound (37) can be produced by removing at once both of the protecting groups $P^6$ and $P^7$ that can be removed by the same method or the same conditions.

The compound (17c) can be produced by reacting the obtained compound (37) with the compound (11). For the reaction between the compound (37) and the compound (11), the same reagents and reaction conditions as those described for Production method 4 can be used.

In the foregoing, the compound represented by the following formula:

[Formula 66]

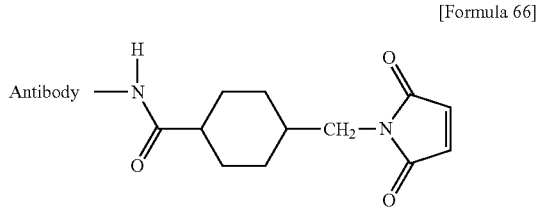 [SMILES: CNC(=O)C1CCC(CN2C(=O)C=CC2=O)CC1]

is described as a production intermediate useful for producing the antibody-drug conjugate of the present invention. In addition, a group of compounds represented by the following formula:

Q-(CH₂)n^Q-C(=O)-L^{2a}-L^P-NH—(CH₂)n¹-L^a-L^b-L^c-(NH-DX)

are also compounds that serve as production intermediates useful for producing the antibody-drug conjugate of the present invention.

Specifically, in the above formula, Q is (maleimid-N-yl)-, HS—, X—CH₂—C(=O)—NH—, or (pyrrolidine-2,5-dione-N-yl)-O—C(=O)—, X is a bromine atom or an iodine atom, $n^Q$ is an integer of 2 to 8, $L^{2a}$ represents —NH—(CH₂—CH₂—O)n⁵-CH₂—CH₂—C(=O)— or a single bond, wherein $n^5$ represents an integer of 1 to 6, $L^P$ represents a peptide residue consisting of 2 to 7 amino acids, $n^1$ represents an integer of 0 to 6, $L^a$ represents —C(=O)—NH—, —NR¹—(CH₂)n⁷-, —O—, or a single bond, wherein $n^7$ represents an integer of 1 to 6, $R^1$ represents a hydrogen atom, an alkyl group having 1 to 6 carbon atoms, —(CH₂)n⁸-COOH, or —(CH₂)n⁹-OH, $n^8$ represents an integer of 1 to 4, $n^9$ represents an integer of 1 to 6, $L^b$ represents —CR²(—R³)—, —O—, —NR⁴—, or a single bond, wherein $R^2$ and $R^3$ each independently represent a hydrogen atom, an alkyl group having 1 to 6 carbon atoms, —(CH$_2$)n$^a$-NH$_2$, —(CH$_2$)n$^b$-COOH, or —(CH$_2$)n$^c$-OH, R$^4$ represents a hydrogen atom or an alkyl group having 1 to 6 carbon atoms, n$^a$ represents an integer of 0 to 6, n$^b$ represents an integer of 1 to 4, n$^c$ represents an integer of 1 to 4, provided that when n$^a$ is 0, R$^2$ and R$^3$ are not the same as each other, L$^c$ represents —CH$_2$— or —C(=O)—, (maleimid-N-yl)- is a group having a structure represented by the following formula:

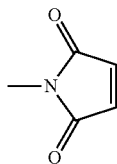

[Formula 67]

(in the formula, the nitrogen atom is the connecting position), (Pyrrolidine-2,5-dione-N-yl)- is a group having a structure represented by the following formula:

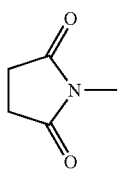

[Formula 68]

(in the formula, the nitrogen atom is the connecting position), —(NH-DX) is a group having a structure represented by the following formula:

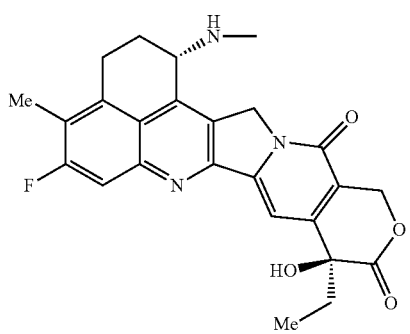

[Formula 69]

(in the formula, the nitrogen atom of the amino group at position 1 is the connecting position).

A compound in which L$^c$ is —C(=O)— is preferred as a production intermediate.

As for the peptide residue of L$^P$, a compound of an amino acid residue consisting of an amino acid selected from phenylalanine, glycine, valine, lysine, citrulline, serine, glutamic acid, and aspartic acid is preferred as a production intermediate. Among those peptide residues, a compound in which L$^P$ is a peptide residue consisting of 4 amino acids is preferred as a production intermediate. More specifically, a compound in which L$^P$ is -GGFG- is preferred as a production intermediate.

Further, as for the —NH—(CH$_2$)n$^1$-L$^a$-L$^b$-, a compound of —NH—CH$_2$CH$_2$—, —NH—CH$_2$CH$_2$CH$_2$—, —NH—CH$_2$CH$_2$CH$_2$CH$_2$—, —NH—CH$_2$CH$_2$CH$_2$CH$_2$CH$_2$—, —NH—CH$_2$—O—CH$_2$—, or —NH—CH$_2$CH$_2$—O—CH$_2$— is preferred as a production intermediate. A compound of NH—CH$_2$CH$_2$CH$_2$—, —NH—CH$_2$—O—CH$_2$—, or —NH—(CH$_2$)$_2$—O—CH$_2$—C(=O)— is more preferred.

As for n$^Q$, a compound in which it is an integer of 2 to 6 is preferred as a production intermediate.

A compound in which L$^{2a}$ is a single bond or n$^5$ is an integer of 2 to 4 is preferred as a production intermediate.

When Q is (maleimid-N-yl)-, a compound in which n$^Q$ is an integer of 2 to 5, L$^{2a}$ is a single bond, and —NH—(CH$_2$)n$^1$-L$^a$-L$^b$- is —NH—CH$_2$CH$_2$—, —NH—CH$_2$CH$_2$CH$_2$—, —NH—CH$_2$CH$_2$CH$_2$CH$_2$—, —NH—CH$_2$CH$_2$CH$_2$CH$_2$CH$_2$—, —NH—CH$_2$—O—CH$_2$—, or —NH—CH$_2$CH$_2$—O—CH$_2$— is preferred as a production intermediate. A compound in which —NH—(CH$_2$)n$^1$-L$^a$-L$^b$- is —NH—CH$_2$CH$_2$—, —NH—CH$_2$CH$_2$CH$_2$—, —NH—CH$_2$—O—CH$_2$—, or —NH—CH$_2$CH$_2$—O—CH$_2$— is more preferred. A compound in which n$^Q$ is an integer of 2 or 5 is further preferred.

Also, when Q is (maleimid-N-yl)-, a compound in which n$^Q$ is an integer of 2 to 5, L$^{2a}$ is —NH—(CH$_2$—CH$_2$-0)n$^5$-CH$_2$—CH$_2$—C(=O)—, n$^5$ is an integer of 2 to 4, and —NH—(CH$_2$)n$^1$-L$^a$-L$^b$- is —NH—CH$_2$CH$_2$—, —NH—CH$_2$CH$_2$CH$_2$—, —NH—CH$_2$CH$_2$CH$_2$CH$_2$—, —NH—CH$_2$CH$_2$CH$_2$CH$_2$CH$_2$—, —NH—CH$_2$—O—CH$_2$—, or —NH—CH$_2$CH$_2$—O—CH$_2$— is preferred as a production intermediate. A compound in which n$^5$ is an integer of 2 or 4 is more preferred. A compound in which —NH—(CH$_2$)n$^1$-L$^a$-L$^b$- is —NH—CH$_2$CH$_2$CH$_2$—, —NH—CH$_2$—O—CH$_2$—, or —NH—CH$_2$CH$_2$—O—CH$_2$— is further preferred.

When Q is HS—, a compound in which n$^Q$ is an integer of 2 to 5, L$^{2a}$ is a single bond, and —NH—(CH$_2$)n$^1$-L$^a$-L$^b$- is —NH—CH$_2$CH$_2$—, —NH—CH$_2$CH$_2$CH$_2$—, —NH—CH$_2$CH$_2$CH$_2$CH$_2$—, —NH—CH$_2$CH$_2$CH$_2$CH$_2$CH$_2$—, —NH—CH$_2$—O—CH$_2$—, or —NH—CH$_2$CH$_2$—O—CH$_2$— is preferred as a production intermediate. A compound in which —NH—(CH$_2$)n$^1$-L$^a$-L$^b$- is —NH—CH$_2$CH$_2$CH$_2$—, —NH—CH$_2$—O—CH$_2$—, or —NH—CH$_2$CH$_2$—O—CH$_2$— is more preferred.

When Q is X—CH$_2$—C(=O)—NH—, a compound in which X is a bromine atom is preferred as a production intermediate. A compound in which n$^Q$ is an integer of 2 to 8 is preferred, also a compound in which L$^{2a}$ is a single bond is preferred, and a compound in which —NH—(CH$_2$)n$^1$-L$^a$-L$^b$- is —NH—CH$_2$CH$_2$CH$_2$—, —NH—CH$_2$—O—CH$_2$—, or —NH—CH$_2$CH$_2$—O—CH$_2$— is preferred as a production intermediate.

When Q is (Pyrrolidine-2,5-dione-N-yl)-O—C(=O)—, a compound in which n$^Q$ is an integer of 2 to 5, L$^{2a}$ is a single bond, and —NH—(CH$_2$)n$^1$-L$^a$-L$^b$- is —NH—CH$_2$CH$_2$—, —NH—CH$_2$CH$_2$CH$_2$—, —NH—CH$_2$CH$_2$CH$_2$CH$_2$—, —NH—CH$_2$CH$_2$CH$_2$CH$_2$CH$_2$—, —NH—CH$_2$—O—CH$_2$—, or —NH—CH$_2$CH$_2$—O—CH$_2$— is preferred as a production intermediate. A compound in which —NH—(CH$_2$)n$^1$-L$^a$-L$^b$- is —NH—CH$_2$CH$_2$CH$_2$—, —NH—CH$_2$—O—CH$_2$—, or —NH—CH$_2$CH$_2$—O—CH$_2$— is more preferred.

More specifically, the followings are compounds preferred as production intermediates.

(maleimid-N-yl)-CH$_2$CH$_2$—C(=O)-GGFG-NH—CH$_2$CH$_2$—C(=O)—(NH-DX)

(maleimid-N-yl)-CH$_2$CH$_2$—C(=O)-GGFG-NH—CH$_2$CH$_2$CH$_2$—C(=O)—(NH-DX)

(maleimid-N-yl)-CH$_2$CH$_2$CH$_2$CH$_2$CH$_2$—C(=O)-GGFG-NH—CH$_2$CH$_2$—C(=O)—(NH-DX)
(maleimid-N-yl)-CH$_2$CH$_2$CH$_2$CH$_2$CH$_2$—C(=O)-GGFG-NH—CH$_2$CH$_2$CH$_2$—C(=O)—(NH-DX)
(maleimid-N-yl)-CH$_2$CH$_2$CH$_2$CH$_2$CH$_2$—C(=O)-GGFG-NH—CH$_2$CH$_2$CH$_2$CH$_2$CH$_2$—C(=O)—(NH-DX)
(maleimid-N-yl)-CH$_2$CH$_2$CH$_2$CH$_2$CH$_2$—C(=O)-GGFG-NH—CH$_2$—O—CH$_2$—C(=O)—(NH-DX)
(maleimid-N-yl)-CH$_2$CH$_2$CH$_2$CH$_2$CH$_2$—C(=O)-GGFG-NH—CH$_2$CH$_2$O—CH$_2$—C(=O)—(NH-DX)
(maleimid-N-yl)-CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX)
(maleimid-N-yl)-CH$_2$CH$_2$—C(=O)—NH—CH$_2$CH$_2$O—CH$_2$CH$_2$O—CH$_2$CH$_2$—C(=O)-GGFG-NH—CH$_2$CH$_2$—C(=O)—(NH-DX)
(maleimid-N-yl)-CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—(NH-DX)
HS—CH$_2$CH$_2$—C(=O)-GGFG-NH—CH$_2$CH$_2$CH$_2$—C(=O)—(NH-DX)
Br—CH$_2$—C(=O)—NH—CH$_2$CH$_2$—C(=O)-GGFG-NH—CH$_2$CH$_2$CH$_2$—C(=O)—(NH-DX)
(Pyrrolidine-2,5-dione-N-yl)-O—C(=O)—CH$_2$CH$_2$CH$_2$CH$_2$CH$_2$—C(=O)-GGFG-NH—CH$_2$CH$_2$CH$_2$—C(=O)—(NH-DX)

Meanwhile, the antibody-drug conjugate of the present invention, when it is left in air or recrystallized, may absorb moisture to have adsorption water or turn into a hydrate, and such a compound and a salt containing water are also included in the present invention.

A compound labeled with various radioactive or non-radioactive isotopes is also included in the present invention. One or more atoms constituting the antibody-drug conjugate of the present invention may contain an atomic isotope at non-natural ratio. Examples of the atomic isotope include deuterium ($^2$H), tritium ($^3$H), iodine-125 ($^{125}$I), and carbon-14 ($^{14}$C). Further, the compound of the present invention may be radioactive-labeled with a radioactive isotope such as tritium ($^3$H), iodine-125 ($^{125}$I), carbon-14 ($^{14}$C), copper-64 ($^{64}$Cu), zirconium-89 ($^{89}$Zr), iodine-124 ($^{124}$I), fluorine-18 ($^{18}$F), indium-111 ($^{111}$I), carbon-11 ($^{11}$C) and iodine-131 ($^{131}$I). The compound labeled with a radioactive isotope is useful as a therapeutic or prophylactic agent, a reagent for research such as an assay reagent and an agent for diagnosis such as an in vivo diagnostic imaging agent. Without being related to radioactivity, any isotope variant type of the antibody-drug conjugate of the present invention is within the scope of the present invention.

[Drugs]

The antibody-drug conjugate of the present invention exhibits a cytotoxic activity against cancer cells, and thus, it can be used as a drug, particularly as a therapeutic agent and/or prophylactic agent for cancer.

Examples of the cancer type to which the antibody-drug conjugate of the present invention is applied include lung cancer, kidney cancer, urothelial cancer, colorectal cancer, prostate cancer, glioblastoma multiforme, ovarian cancer, pancreatic cancer, breast cancer, melanoma, liver cancer, bladder cancer, stomach cancer, or esophageal cancer, however, it is not limited to them as long as it is a cancer cell expressing, in a cancer cell as a treatment subject, a protein which the antibody within the antibody-drug conjugate can recognize.

The antibody-drug conjugate of the present invention can be preferably administered to a mammal, but it is more preferably administered to a human.

Substances used in a pharmaceutical composition containing antibody-drug conjugate of the present invention can be suitably selected and applied from formulation additives or the like that are generally used in the art, in view of the dosage or administration concentration.

The antibody-drug conjugate of the present invention can be administered as a pharmaceutical composition containing at least one pharmaceutically suitable ingredient.

For example, the pharmaceutical composition above typically contains at least one pharmaceutical carrier (for example, sterilized liquid). for example, water and oil (petroleum oil and oil of animal origin, plant origin, or synthetic origin (the oil may be, for example, peanut oil, soybean oil, mineral oil, sesame oil or the like)). Water is a more typical carrier when the pharmaceutical composition above is intravenously administered. Saline solution, an aqueous dextrose solution, and an aqueous glycerol solution can be also used as a liquid carrier, in particular, for an injection solution. A suitable pharmaceutical vehicle is known in the art. If desired, the composition above may also contain a trace amount of a moisturizing agent, an emulsifying agent, or a pH buffering agent. Examples of suitable pharmaceutical carrier are disclosed in "Remington's Pharmaceutical Sciences" by E. W. Martin. The formulations correspond to an administration mode.

Various delivery systems are known and they can be used for administering the antibody-drug conjugate of the present invention. Examples of the administration route include intradermal, intramuscular, intraperitoneal, intravenous, and subcutaneous routes, but not limited thereto. The administration can be made by injection or bolus injection, for example. According to a specific preferred embodiment, the administration of the antibody-drug conjugate is performed by injection. Parenteral administration is a preferred administration route.

According to a representative embodiment, the pharmaceutical composition is prescribed, as a pharmaceutical composition suitable for intravenous administration to human, according to the conventional procedures. The composition for intravenous administration is typically a solution in a sterile and isotonic aqueous buffer solution. If necessary, the drug may contain a solubilizing agent and local anesthetics to alleviate pain at injection site (for example, lignocaine). Generally, the ingredient above is provided individually as any one of lyophilized powder or an anhydrous concentrate contained in a container which is obtained by sealing in an ampoule or a sachet having an amount of the active agent or as a mixture in a unit dosage form. When the drug is to be administered by injection, it may be administered from an injection bottle containing water or saline of sterile pharmaceutical grade. When the drug is administered by injection, an ampoule of sterile water or saline for injection may be provided such that the aforementioned ingredients are admixed with each other before administration.

The pharmaceutical composition of the present invention may be a pharmaceutical composition containing only the antibody-drug conjugate of the present invention or a pharmaceutical composition containing the antibody-drug conjugate and at least one cancer treating agent other than the conjugate. The antibody-drug conjugate of the present invention can be administered with other cancer treating agent. The anti-cancer effect may be enhanced accordingly. Another anti-cancer agent used for such purpose may be administered to an individual simultaneously with, separately from, or subsequently to the antibody-drug conjugate, and it may be administered while varying the administration interval for each. Examples of the cancer treating agent include abraxane, carboplatin, cisplatin, gemcitabine, irinotecan (CPT-11), paclitaxel, pemetrexed, sorafenib, vinorelbine, drugs described in International Publication No. WO 2003/038043, LH-RH analogues (leuprorelin, goserelin, or the like), estramustine phosphate, estrogen antagonist (tamoxifen, raloxifene, or the like), and an aromatase inhibitor (anastrozole, letrozole, exemestane, or the like), but it is not limited as long as it is a drug having an antitumor activity.

The pharmaceutical composition can be formulated into a lyophilization formulation or a liquid formulation as a formulation having desired composition and required purity. When formulated as a lyophilization formulation, it may be a formulation containing suitable formulation additives that are used in the art. Also for a liquid formulation, it can be formulated as a liquid formulation containing various formulation additives that are used in the art.

Composition and concentration of the pharmaceutical composition may vary depending on administration method. However, the antibody-drug conjugate contained in the pharmaceutical composition of the present invention can exhibit the pharmaceutical effect even at a small dosage when the antibody-drug conjugate has higher affinity for an antigen, that is, higher affinity (=lower Kd value) in terms of the dissociation constant (that is, Kd value) for the antigen. Thus, for determining dosage of the antibody-drug conjugate, the dosage can be determined in view of a situation relating to the affinity between the antibody-drug conjugate and antigen. When the antibody-drug conjugate of the present invention is administered to a human, for example, about 0.001 to 100 mg/kg can be administered once or administered several times with an interval of one time for 1 to 180 days.

EXAMPLES

The present invention is specifically described in view of the examples shown below. However, the present invention is not limited to them. Further, it is by no means interpreted in a limited sense. Further, unless specifically described otherwise, the reagent, solvent, and starting material described in the specification can be easily obtained from a commercial supplier.

Reference Example 1 M30-H1-L4 Antibody

Of humanized antibodies of an anti-B7-H3 antibody, an antibody composed of a heavy chain consisting of an amino acid sequence described in amino acid positions 20 to 471 in SEQ ID NO: 9 and a light chain consisting of an amino acid sequence described in amino acid positions 21 to 233 in SEQ ID NO: 16 was produced in accordance with a method known in the art to yield humanized anti-B7-H3 antibody designated as an M30-H1-L4 antibody (or simply referred to as "M30-H1-L4").

Reference Example 2 M30-H1-L4P Antibody

The modification of a glycan bonded to the M30-H1-L4 antibody obtained above was regulated by defucosylation in accordance with a method known in the art to yield antibody with the regulated modification of a glycan designated as an M30-H1-L4P antibody (or simply referred to as "M30-H1-L4P").

Reference Example 3 Anti-CD30 Antibody

An anti-CD30 antibody was produced with reference to National Publication of International Patent Application No. 2005-506035. Its sequence is shown in SEQ ID NOs: 27 and 28.

Reference Example 4 Anti-CD33 Antibody

An anti-CD33 antibody was produced with reference to Japanese Patent Laid-Open No. 8-48637. Its sequence is shown in SEQ ID NOs: 29 and 30.

Reference Example 5 Anti-CD70 Antibody

An anti-CD70 antibody was produced with reference to National Publication of International Patent Application No. 2008-538292. Its sequence is shown in SEQ ID NOs: 31 and 32.

Example 1 4-Amino-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]butanamide

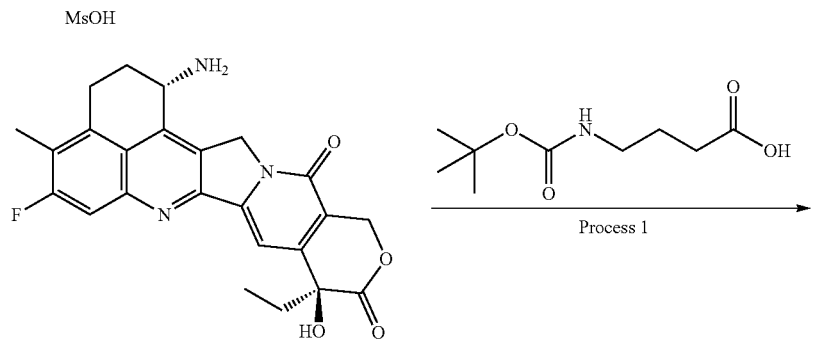

[Formula 70]

-continued

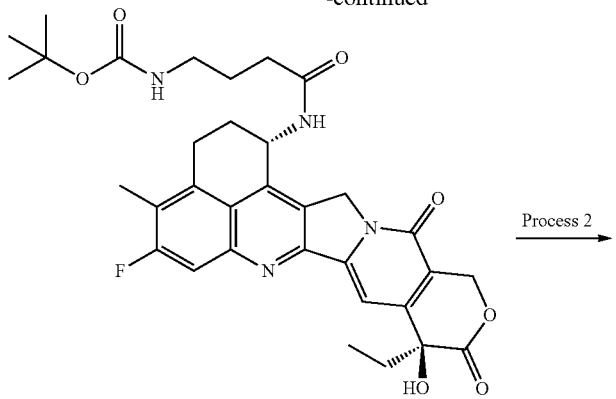

Process 2

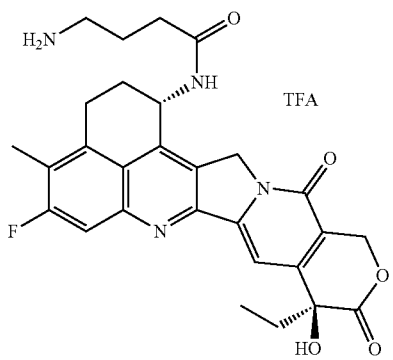

Process 1: tert-Butyl (4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)carbamate 4-(tert-Butoxycarbonylamino)butanoic acid (0.237 g, 1.13 mmol) was dissolved in dichloromethane (10 mL), N-hydroxysuccinimide (0.130 g, 1.13 mmol) and 1-ethyl-3-(3-dimethylaminopropyl)carbodiimide hydrochloride (0.216 g, 1.13 mmol) were added, and stirred for 1 hour. The reaction solution was added dropwise to an N,N-dimethylformamide solution (10 mL) charged with mesylate of the compound (4) (0.500 g, 0.94 mmol) and triethylamine (0.157 mL, 1.13 mmol), and stirred at room temperature for 1 day. The solvent was removed under reduced pressure and the residue obtained were purified by silica gel column chromatography [chloroform-chloroform:methanol=8:2 (v/v)] to yield the titled compound (0.595 g, quantitative).

$^1$H-NMR (400 MHz, DMSO-$d_6$) δ: 0.87 (3H, t, J=7.2 Hz), 1.31 (9H, s), 1.58 (1H, t, J=7.2 Hz), 1.66 (2H, t, J=7.2 Hz), 1.82-1.89 (2H, m), 2.12-2.21 (3H, m), 2.39 (3H, s), 2.92 (2H, t, J=6.5 Hz), 3.17 (2H, s), 5.16 (1H, d, J=18.8 Hz), 5.24 (1H, d, J=18.8 Hz), 5.42 (2H, s), 5.59-5.55 (1H, m), 6.53 (1H, s), 6.78 (1H, t, J=6.3 Hz), 7.30 (1H, s), 7.79 (1H, d, J=11.0 Hz), 8.40 (1H, d, J=8.6 Hz).

MS (APCI) m/z: 621 (M+H)$^+$

Process 2: 4-Amino-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]butanamide The compound (0.388 g, 0.61 mmol) obtained in Process 1 above was dissolved in dichloromethane (9 mL). Trifluoroacetic acid (9 mL) was added and it was stirred for 4 hours. The solvent was removed under reduced pressure and the residues obtained were purified by silica gel column chromatography [chloroform-partitioned organic layer of chloroform:methanol:water=7:3:1 (v/v/v)] to yield trifluoroacetate of the titled compound (0.343 g, quantitative). This compound was confirmed in the tumor of a cancer-bearing mouse that received the antibody-drug conjugate (13) or (14).

$^1$H-NMR (400 MHz, DMSO-$d_6$) δ: 0.87 (3H, t, J=7.2 Hz), 1.79-1.92 (4H, m), 2.10-2.17 (2H, m), 2.27 (2H, t, J=7.0 Hz), 2.40 (3H, s), 2.80-2.86 (2H, m), 3.15-3.20 (2H, m), 5.15 (1H, d, J=18.8 Hz), 5.26 (1H, d, J=18.8 Hz), 5.42 (2H, s), 5.54-5.61 (1H, m), 6.55 (1H, s), 7.32 (1H, s), 7.72 (3H, brs), 7.82 (1H, d, J=11.0 Hz), 8.54 (1H, d, J=8.6 Hz).

MS (APCI) m/z: 521 (M+H)$^+$

101
Example 2 Antibody-Drug Conjugate (1)
[Formula 71]
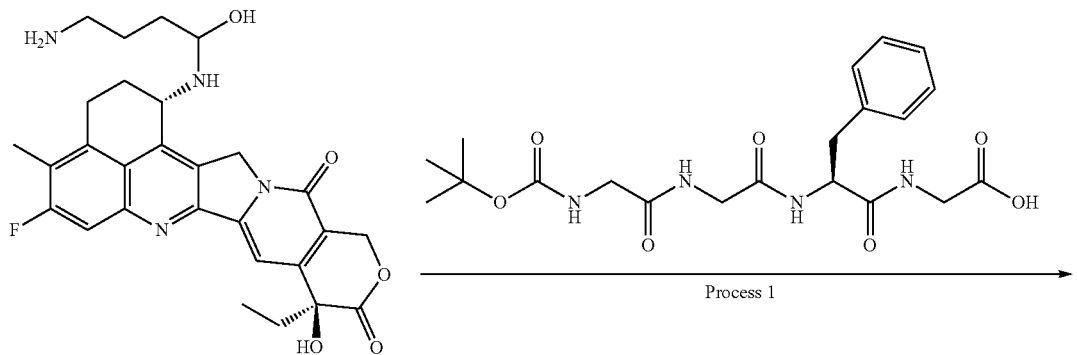
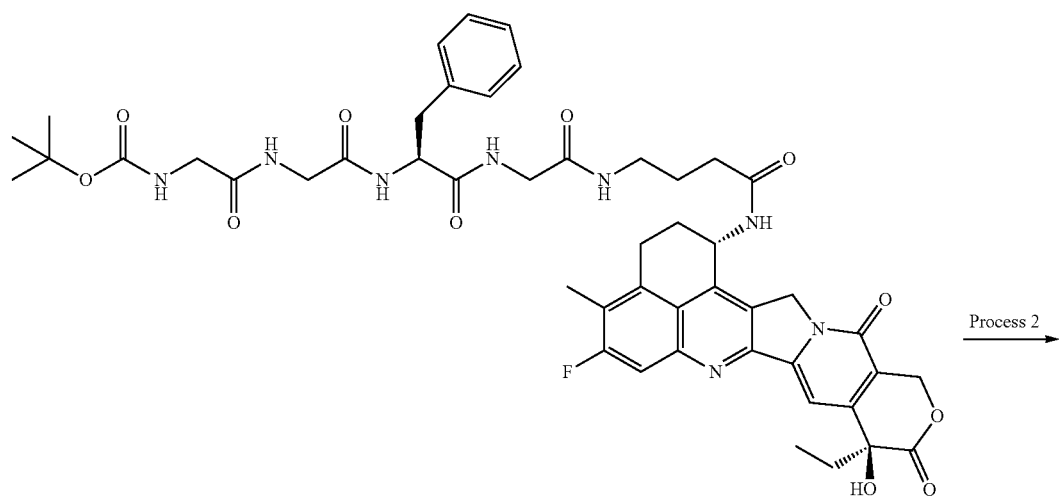
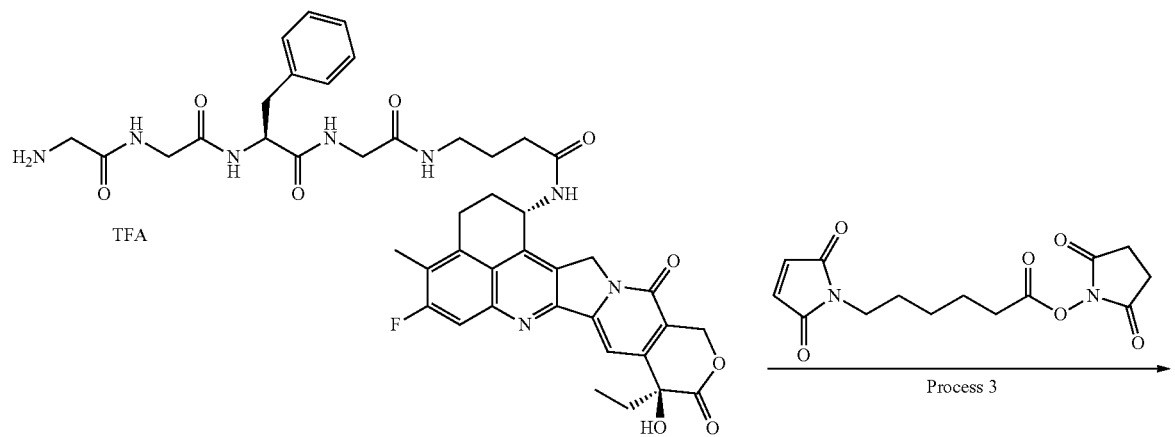

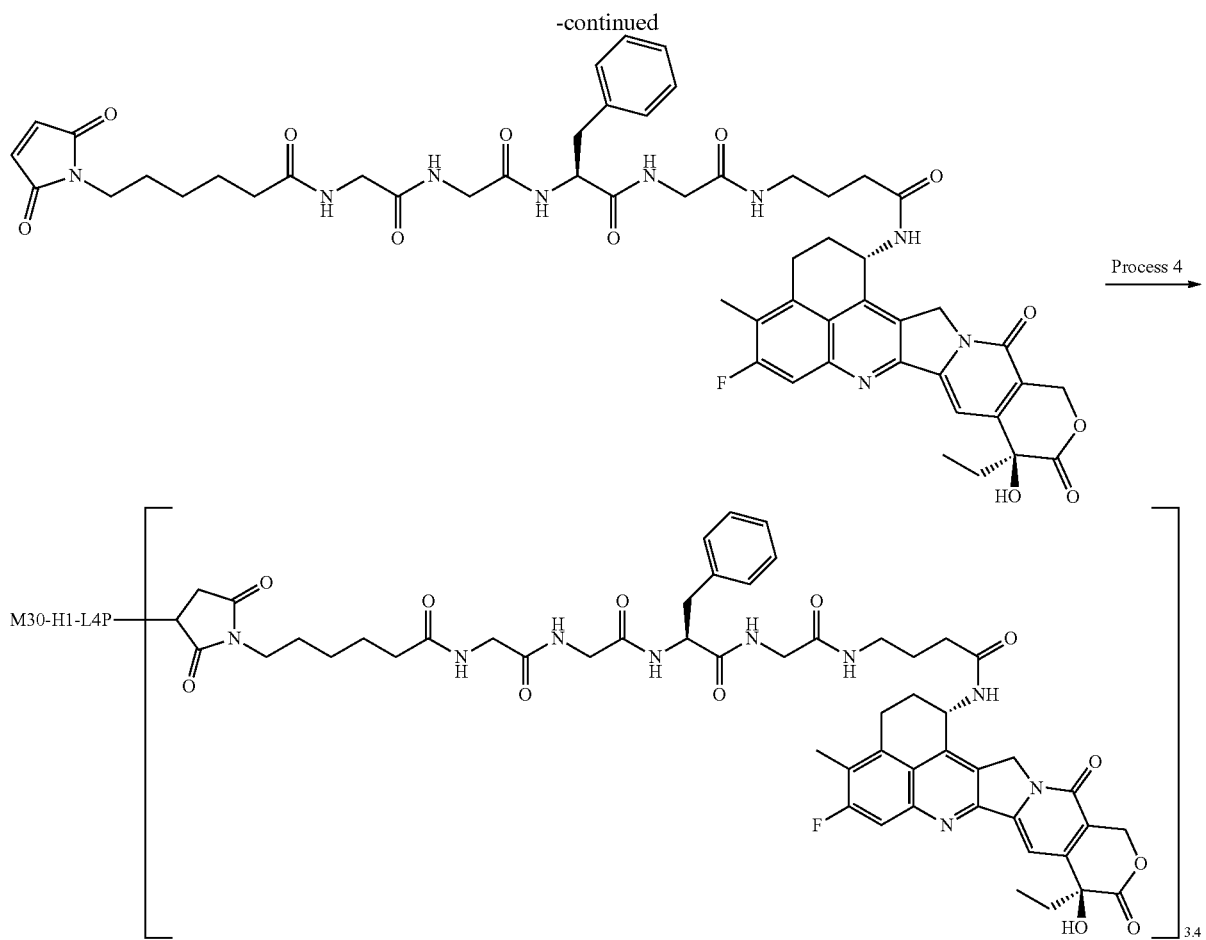

Process 1: N-(tert-butoxycarbonyl)glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide N-(tert-butoxycarbonyl)glycylglycyl-L-phenylalanylglycine (0.081 g, 0.19 mmol) was dissolved in dichloromethane (3 mL), N-hydroxysuccinimide (0.021 g, 0.19 mmol) and 1-ethyl-3-(3-dimethylaminopropyl)carbodiimide hydrochloride (0.036 g, 0.19 mmol) were added and then stirred for 3.5 hours. The reaction solution was added dropwise to an N,N-dimethylformamide solution (1.5 mL) charged with the compound (0.080 g, 0.15 mmol) of Example 1, and stirred at room temperature for 4 hours. The solvent was removed under reduced pressure and the residues obtained were purified by silica gel column chromatography [chloroform-chloroform:methanol=8:2 (v/v)] to yield the titled compound (0.106 g, 73%).

$^1$H-NMR (400 MHz, DMSO-$d_6$) δ: 0.87 (3H, t, J=7.4 Hz), 1.36 (9H, s), 1.71 (2H, m), 1.86 (2H, t, J=7.8 Hz), 2.15-2.19 (4H, m), 2.40 (3H, s), 2.77 (1H, dd, J=12.7, 8.8 Hz), 3.02 (1H, dd, J=14.1, 4.7 Hz), 3.08-3.11 (2H, m), 3.16-3.19 (2H, m), 3.54 (2H, d, J=5.9 Hz), 3.57-3.77 (4H, m), 4.46-4.48 (1H, m), 5.16 (1H, d, J=19.2 Hz), 5.25 (1H, d, J=18.8 Hz), 5.42 (2H, s), 5.55-5.60 (1H, m), 6.53 (1H, s), 7.00 (1H, t, J=6.3 Hz), 7.17-7.26 (5H, m), 7.31 (1H, s), 7.71 (1H, t, J=5.7 Hz), 7.80 (1H, d, J=11.0 Hz), 7.92 (1H, t, J=5.7 Hz), 8.15 (1H, d, J=8.2 Hz), 8.27 (1H, t, J=5.5 Hz), 8.46 (1H, d, J=8.2 Hz).

MS (APCI) m/z: 939 (M+H)$^+$

Process 2: Glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide trifluoroacetate The compound (1.97 g, 2.10 mmol) obtained in Process 1 above was dissolved in dichloromethane (7 mL). After adding trifluoroacetic acid (7 mL), it was stirred for 1 hour. The solvent was removed under reduced pressure, and it was charged with toluene for azeotropic distillation. The residues obtained were purified by silica gel column chromatography [chloroform-partitioned organic layer of chloroform:methanol:water=7:3:1 (v/v/v)] to yield the titled compound (1.97 g, 99%).

$^1$H-NMR (400 MHz, DMSO-$d_6$) δ: 0.87 (3H, t, J=7.4 Hz), 1.71-1.73 (2H, m), 1.82-1.90 (2H, m), 2.12-2.20 (4H, m), 2.40 (3H, s), 2.75 (1H, dd, J=13.7, 9.4 Hz), 3.03-3.09 (3H, m), 3.18-3.19 (2H, m), 3.58-3.60 (2H, m), 3.64 (1H, d, J=5.9 Hz), 3.69 (1H, d, J=5.9 Hz), 3.72 (1H, d, J=5.5 Hz), 3.87 (1H, dd, J=16.8, 5.9 Hz), 4.50-4.56 (1H, m), 5.16 (1H, d, J=19.2 Hz), 5.25 (1H, d, J=18.8 Hz), 5.42 (2H, s), 5.55-5.60 (1H, m), 7.17-7.27 (5H, m), 7.32 (1H, s), 7.78-7.81 (2H, m), 7.95-7.97 (3H, m), 8.33-8.35 (2H, m), 8.48-8.51 (2H, m).

MS (APCI) m/z: 839 (M+H)$^+$

Process 3: N-[6-(2,5-dioxo-2,5-dihydro-1H-pyrrol-1-yl)hexanoyl]glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide To an N,N-dimethylformamide (1.2 mL) solution of the compound (337 mg, 0.353 mmol) obtained in Process 2 above, triethylamine (44.3 mL, 0.318 mmol) and N-succinimidyl 6-maleimide hexanoate (119.7 mg, 0.388 mmol) were added and stirred at room temperature for 1 hour. The solvent was removed under reduced pressure and the residues obtained were purified by silica gel column chromatography [chloroform-chloroform:methanol=5:1 (v/v)] to yield the titled compound as a pale yellow solid (278.0 mg, 76%).

$^1$H-NMR (400 MHz, DMSO-$d_6$) δ: 0.87 (3H, t, J=7.3 Hz), 1.12-1.22 (2H, m), 1.40-1.51 (4H, m), 1.66-1.76 (2H, m), 1.80-1.91 (2H, m), 2.05-2.21 (6H, m), 2.39 (3H, s), 2.79 (1H, dd, J=14.0, 9.8 Hz), 2.98-3.21 (5H, m), 3.55-3.77 (8H, m), 4.41-4.48 (1H, m), 5.15 (1H, d, J=18.9 Hz), 5.24 (1H, d, J=18.9 Hz), 5.40 (1H, d, J=17.1 Hz), 5.44 (1H, d, J=17.1 Hz), 5.54-5.60 (1H, m), 6.53 (1H, s), 6.99 (2H, s), 7.20-7.27 (5H, m), 7.30 (1H, s), 7.70 (1H, t, J=5.5 Hz), 7.80 (1H, d, J=11.0 Hz), 8.03 (1H, t, J=5.8 Hz), 8.08 (1H, t, J=5.5 Hz), 8.14 (1H, d, J=7.9 Hz), 8.25 (1H, t, J=6.1 Hz), 8.46 (1H, d, J=8.5 Hz).

MS (APCI) m/z: 1032 (M+H)$^+$

Process 4: Antibody-Drug Conjugate (1)

Reduction of the antibody: The M30-H1-L4P antibody produced in Reference Example 2 was prepared to have antibody concentration of 10 mg/mL by replacing the medium with PBS6.0/EDTA by using the Common procedure C-1 and Common procedure B (as absorption coefficient at 280 nm, 1.61 mLmg$^{-1}$ cm$^{-1}$ was used) described in Production method 1. The solution (1.25 mL) was placed in a 1.5 mL polypropylene tube and charged with an aqueous solution of 10 mM TCEP (Tokyo Chemical Industry Co., Ltd.) (0.025 mL; 3.0 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding dimethyl sulfoxide (Sigma-Aldrich Co. LLC; 0.109 mL) and a dimethyl sulfoxide solution containing 10 mM of the compound obtained in above Process 3 (0.039 mL; 4.6 equivalents per antibody molecule) to the above solution at room temperature, it was stirred by using a tube rotator (MTR-103, manufactured by AS ONE Corporation) for conjugating the drug linker to the antibody at room temperature for 40 minutes. Next, an aqueous solution (0.008 mL) of 100 mM NAC (Sigma-Aldrich Co. LLC) was added thereto and stirred at room temperature to terminate the raction of drug linker for another 20 minutes.

Purification: The above solution was subjected to purification using the Common procedure D-1 (ABS was used as buffer solution) described in Production method 1 to yield 6 mL of a solution containing the titled antibody-drug conjugate. After that, the solution was concentrated by the Common procedure A.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,280}$=5000 (measured average value), and $\varepsilon_{D,370}$=19000 (measured average value) were used), the following characteristic values were obtained.

Antibody concentration: 13.02 mg/mL, antibody yield: 9.1 mg (73%), and average number of conjugated drug molecules (n) per antibody molecule: 3.4.

Example 3 Antibody-Drug Conjugate (2)

[Formula 72]

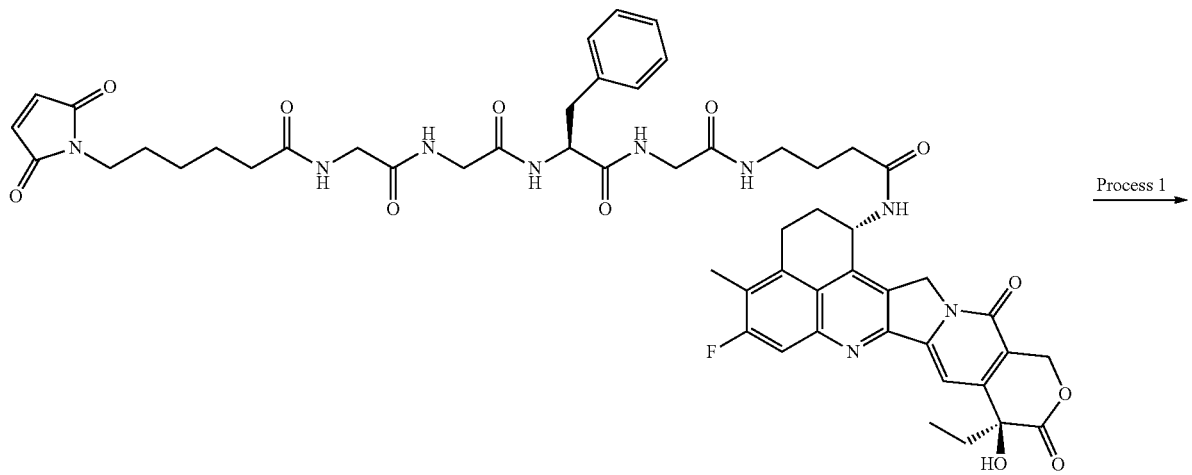

Process 1

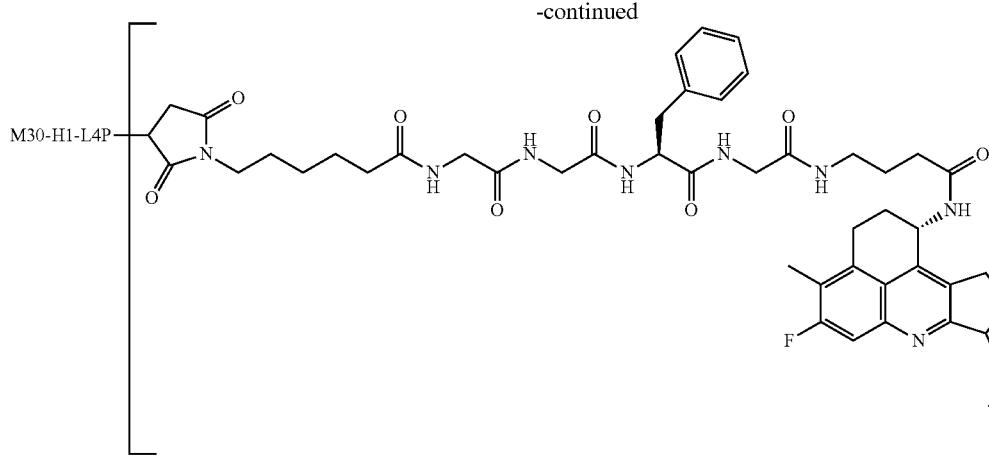

Process 1: Antibody-Drug Conjugate (2)

Reduction of the antibody: The M30-H1-L4P antibody produced in Reference Example 2 was prepared to have antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (4.0 mL) was collected into a 15 mL tube and charged with an aqueous solution of 10 mM TCEP (Tokyo Chemical Industry Co., Ltd.) (0.118 mL; 4.6 equivalents per antibody molecule) and an aqueous solution of 1 M dipotassium hydrogen phosphate (Nacalai Tesque, Inc.; 0.200 mL). After confirming that the solution had pH of 7.4±0.1, the disulfide bond at hinge part in the antibody was reduced by incubating at 37° C. for 1 hour. Conjugation between antibody and drug linker: After incubating the above solution for 10 minutes at 22° C., a dimethyl sulfoxide solution (0.236 mL; 9.2 equivalents per antibody molecule) containing 10 mM of the compound obtained in Process 3 of Example 2 was added thereto and incubated for conjugating the drug linker to the antibody at 22° C. for 40 minutes. Next, an aqueous solution (0.00471 mL) of 100 mM NAC (Sigma-Aldrich Co. LLC) was added thereto and incubated to terminate the raction of drug linker at 22° C. for another 20 minutes.

Purification: The above solution was subjected to purification using the Common procedure D-1 (ABS was used as buffer solution) described in Production method 1 to yield 17.5 mL of a solution containing the titled antibody-drug conjugate.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,280}$=5000 (measured average value), and $\varepsilon_{D,370}$=19000 (measured average value) were used), the following characteristic values were obtained.

Antibody concentration: 1.80 mg/mL, antibody yield: 26.1 mg (65%), and average number of conjugated drug molecules (n) per antibody molecule: 5.9.

Example 4 Antibody-Drug Conjugate (3)

[Formula 73]

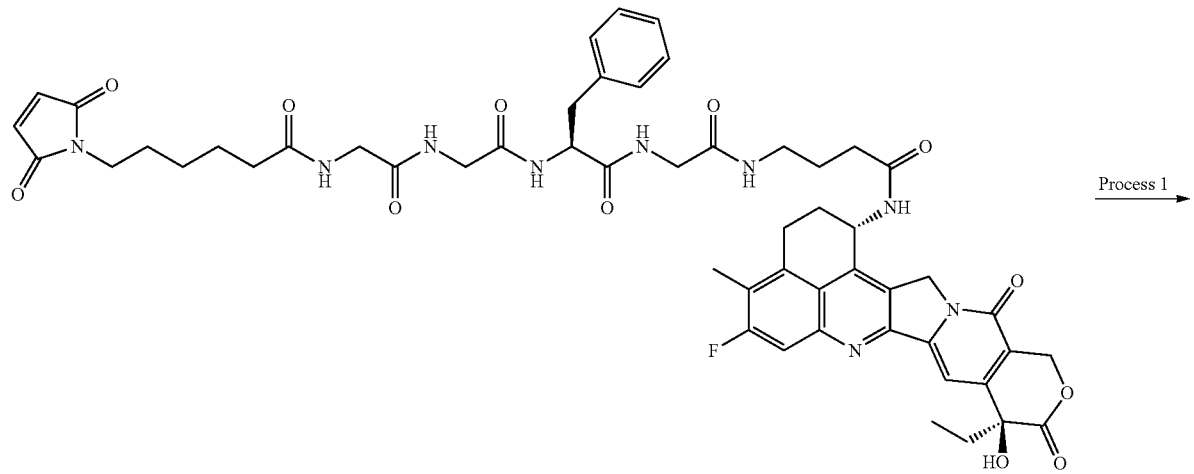

Process 1

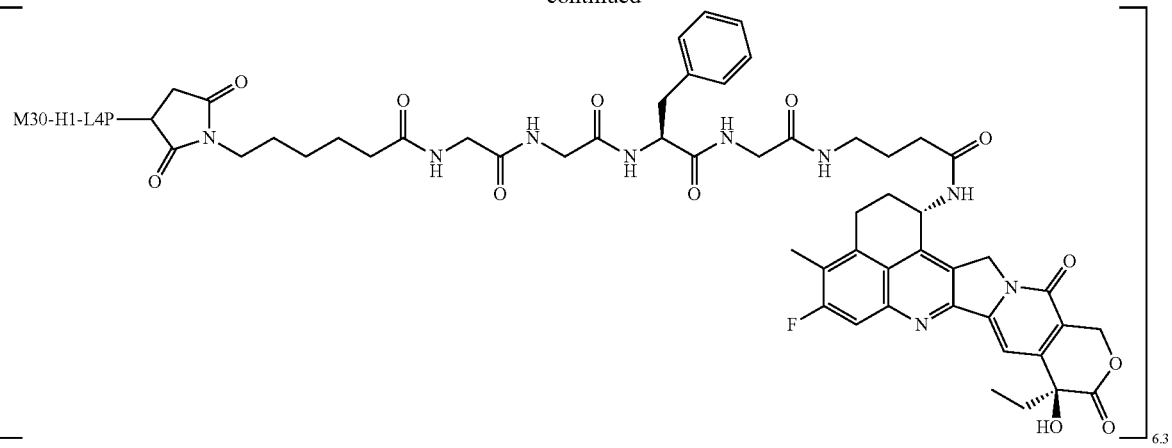

Process 1: Antibody-Drug Conjugate (3)

Reduction of the antibody: The M30-H1-L4P antibody produced in Reference Example 2 was prepared to have antibody concentration of 10 mg/mL by replacing the medium with PBS6.0/EDTA by using the Common procedure C-1 and Common procedure B (as absorption coefficient at 280 nm, 1.61 mLmg$^{-1}$ cm$^{-1}$ was used) described in Production method 1. The solution (1.25 mL) was placed in a 1.5 mL polypropylene tube and charged with an aqueous solution of 10 mM TCEP (Tokyo Chemical Industry Co., Ltd.) (0.051 mL; 6.0 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding dimethyl sulfoxide (Sigma-Aldrich Co. LLC; 0.067 mL) and a dimethyl sulfoxide solution containing 10 mM of the compound obtained in Process 3 of Example 2 (0.085 mL; 10.0 equivalents per antibody molecule) to the above solution at room temperature, it was stirred by using a tube rotator (MTR-103, manufactured by AS ONE Corporation) for conjugating the drug linker to the antibody at room temperature for 60 minutes. Next, an aqueous solution (0.013 mL) of 100 mM NAC (Sigma-Aldrich Co. LLC) was added thereto and stirred to terminate the raction of drug linker at room temperature for another 20 minutes.

Purification: The above solution was subjected to purification using the Common procedure D-1 (ABS was used as buffer solution) described in Production method 1 to yield 6 mL of a solution containing the titled antibody-drug conjugate.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,280}$=5000 (measured average value), and $\varepsilon_{D,370}$=19000 (measured average value) were used), the following characteristic values were obtained.

Antibody concentration: 1.67 mg/mL, antibody yield: 10.02 mg (80%), and average number of conjugated drug molecules (n) per antibody molecule: 6.3.

Example 5 Antibody-Drug Conjugate (4)

[Formula 74]

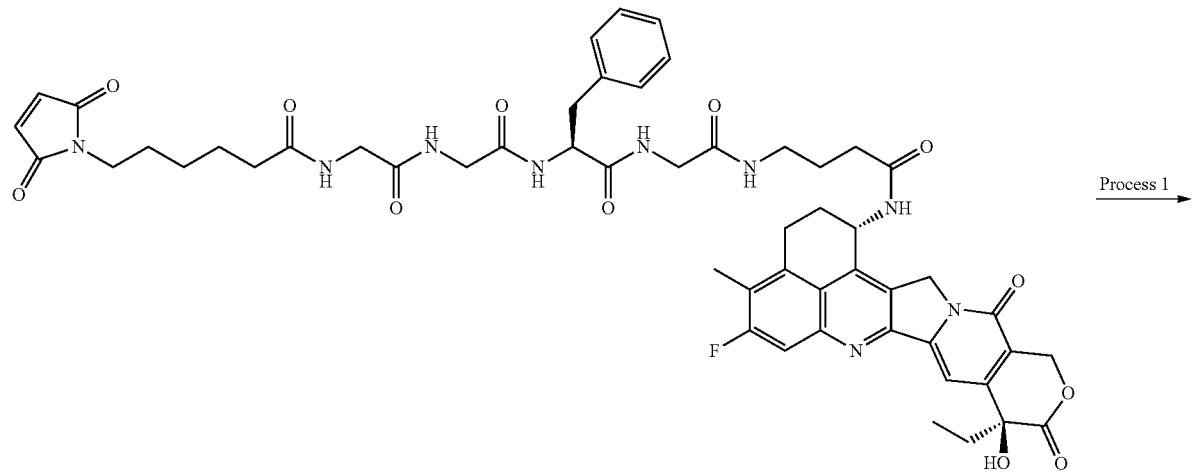

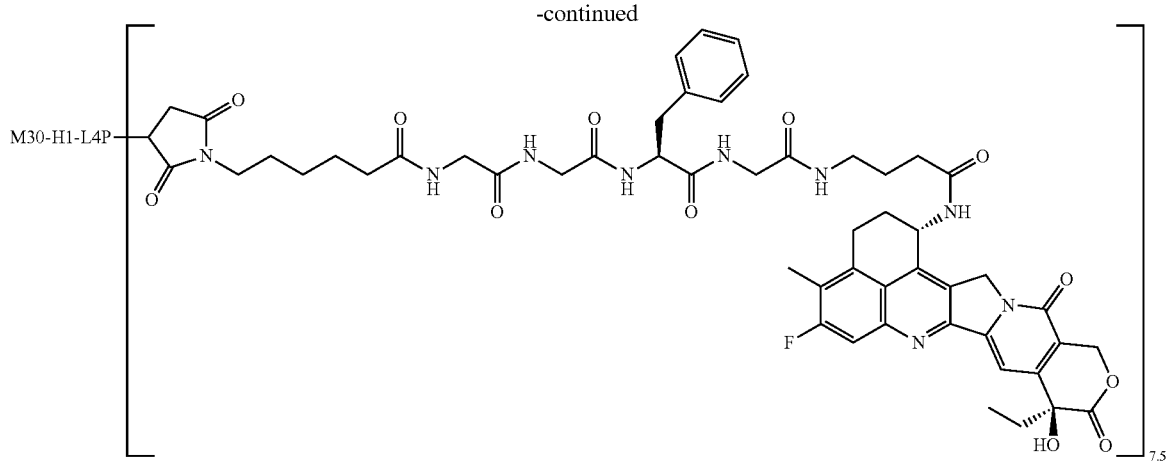

Process 1: Antibody-Drug Conjugate (4)

Reduction of the antibody: The M30-H1-L4P antibody produced in Reference Example 2 was prepared to have antibody concentration of 10 mg/mL by replacing the medium with PBS6.0/EDTA by using the Common procedure C-1 and Common procedure B (as absorption coefficient at 280 nm, 1.61 mLmg$^{-1}$ cm$^{-1}$ was used) described in Production method 1. The solution (1.25 mL) was placed in a 1.5 mL polypropylene tube and charged with an aqueous solution of 10 mM TCEP (Tokyo Chemical Industry Co., Ltd.) (0.051 mL; 6.0 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding dimethyl sulfoxide (Sigma-Aldrich Co. LLC; 0.025 mL) and a dimethyl sulfoxide solution containing 10 mM of the compound obtained in Process 3 of Example 2 (0.127 mL; 15.0 equivalents per antibody molecule) to the above solution at room temperature, it was stirred by using a tube rotator (MTR-103, manufactured by AS ONE Corporation) for conjugating the drug linker to the antibody at room temperature for 60 minutes. Next, an aqueous solution (0.019 mL) of 100 mM NAC (Sigma-Aldrich Co. LLC) was added thereto and stirred to terminate the raction of drug linker at room temperature for another 20 minutes.

Purification: The above solution was subjected to purification using the Common procedure D-1 (ABS was used as buffer solution) described in Production method 1 to yield 6 mL of a solution containing the titled antibody-drug conjugate. After that, the solution was concentrated by the Common procedure A.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,280}$=5000 (measured average value), and $\varepsilon_{D,370}$=19000 (measured average value) were used), the following characteristic values were obtained.

Antibody concentration: 1.19 mg/mL, antibody yield: 7.14 mg (57%), and average number of conjugated drug molecules (n) per antibody molecule: 7.5.

Example 6 Antibody-Drug Conjugate (5)

[Formula 75]

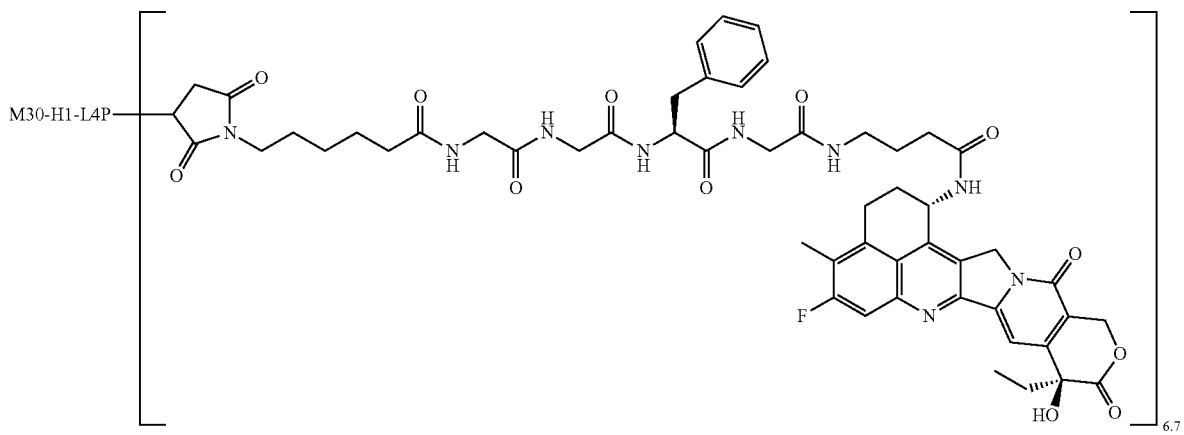

Almost the whole amounts of the antibody-drug conjugates of Examples 4 and 5 were mixed and the solution was concentrated by the Common procedure A to yield the titled antibody-drug conjugate.

Antibody concentration: 10.0 mg/mL, antibody yield: 15.37 mg, and average number of conjugated drug molecules (n) per antibody molecule: 6.7.

Example 7 Antibody-Drug Conjugate (6)

dimethyl sulfoxide solution (0.0593 mL; 9.2 equivalents per antibody molecule) containing 10 mM of the compound obtained in Process 3 of Example 2 was added thereto and incubated for conjugating the drug linker to the antibody at 22° C. for 40 minutes. Next, an aqueous solution (0.0119 mL; 18.4 equivalents per antibody molecule) of 100 mM NAC (Sigma-Aldrich Co. LLC) was added thereto and incubated to terminate the raction of drug linker at 22° C. for another 20 minutes.

[Formula 76]

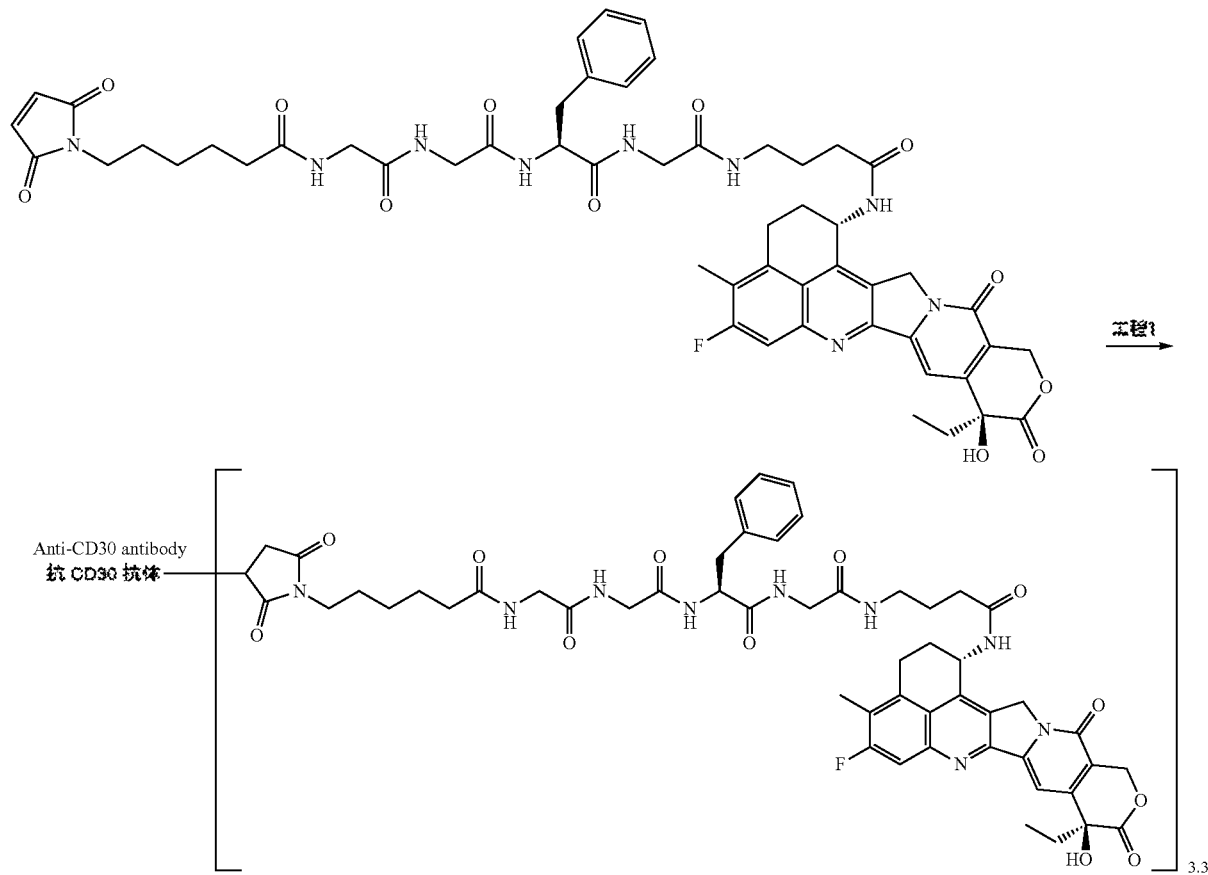

Process 1: Antibody-Drug Conjugate (6)

Reduction of the antibody: The anti-CD30 antibody produced in Reference Example 3 was prepared to have antibody concentration of 10 mg/mL with PBS6.0/EDTA by using the Common procedure B (as absorption coefficient at 280 nm, 1.75 was used) and Common procedure C-1 described in Production method 1. The solution (1.0 mL) was collected into a 2 mL tube and charged with an aqueous solution of 10 mM TCEP (Tokyo Chemical Industry Co., Ltd.) (0.0297 mL; 4.6 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a Purification: The above solution was subjected to purification using the Common procedure D-1 (ABS was used as buffer solution) described in Production method 1 to yield 6 mL of a solution containing the titled antibody-drug conjugate.

Physicochemical characterization: By using the Common procedure E described in Production method 1 (as molar absorption coefficient, $\varepsilon_{A,280}=270400$ (estimated calculation value), $\varepsilon_{A,370}=0$ (estimated calculation value), $\varepsilon_{D,280}=5000$ (measured average value), and $\varepsilon_{D,370}=19000$ (measured average value) were used), the following characteristic values were obtained.

Antibody concentration: 0.99 mg/mL, antibody yield: 5.94 mg (59%), and average number of conjugated drug molecules (n) per antibody molecule: 3.3.

Example 8 Antibody-Drug Conjugate (7)

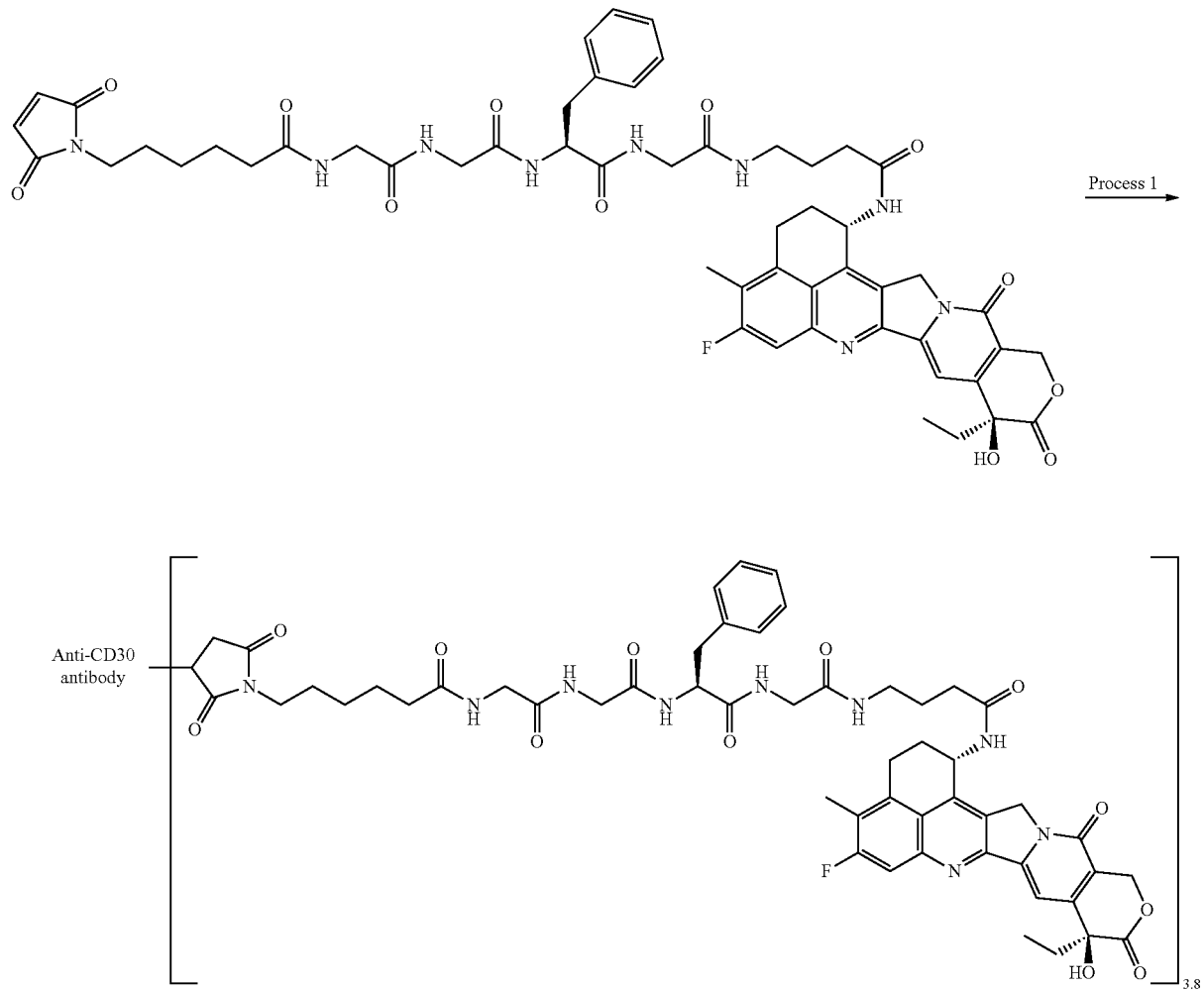

[Formula 77]

Process 1: Antibody-Drug Conjugate (7)

Reduction of the antibody: The anti-CD30 antibody produced in Reference Example 3 was prepared to have antibody concentration of 10 mg/mL with PBS6.0/EDTA by using the Common procedure B (as absorption coefficient at 280 nm, 1.75 was used) and Common procedure C-1 described in Production method 1. The solution (1.0 mL) was collected into a 2 mL tube and charged with an aqueous solution of 30 mM TCEP (Tokyo Chemical Industry Co., Ltd.) (0.0148 mL; 6.9 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution for 10 minutes at 22° C., a dimethyl sulfoxide solution (0.0297 mL; 13.8 equivalents per antibody molecule) containing 30 mM of the compound obtained in Process 3 of Example 2 was added thereto and incubated for 40 minutes at 22° C. for conjugating the drug linker to the antibody. Next, an aqueous solution (0.0178 mL; 27.6 equivalents per antibody molecule) of 100 mM NAC (Sigma-Aldrich Co. LLC) was added thereto and incubated to terminate the raction of drug linker at 22° C. for another 20 minutes.

Purification: The above solution was subjected to purification using the Common procedure D-1 (ABS was used as buffer solution) described in Production method 1 to yield 6 mL of a solution containing the titled antibody-drug conjugate.

Physicochemical characterization: By using the Common procedure E described in Production method 1 (as molar absorption coefficient, $\varepsilon_{A,280}$=270400 (estimated calculation value), $\varepsilon_{A,370}$=0 (estimated calculation value), $\varepsilon_{D,280}$=5000 (measured average value), and $\varepsilon_{D,370}$=19000 (measured average value) were used), the following characteristic values were obtained.

Antibody concentration: 0.99 mg/mL, antibody yield: 5.94 mg (59%), and average number of conjugated drug molecules (n) per antibody molecule: 3.8.

Example 9 Antibody-Drug Conjugate (8)

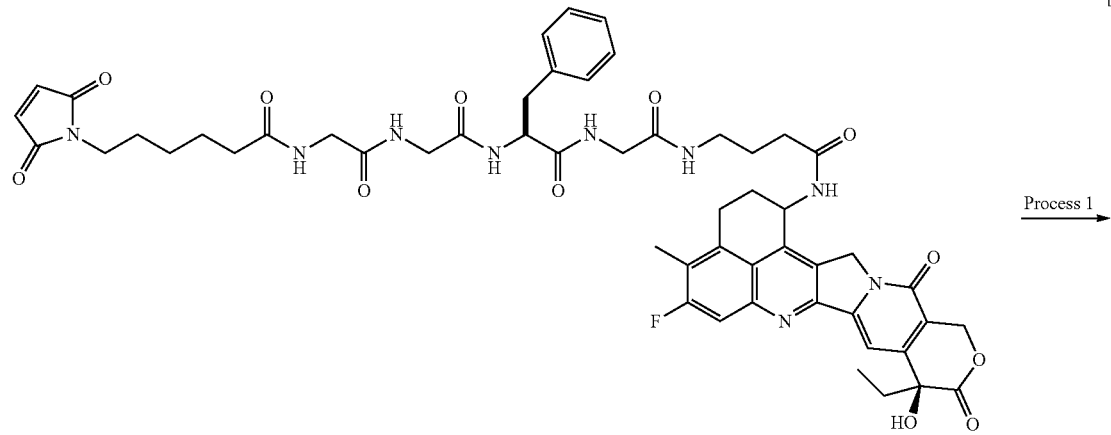

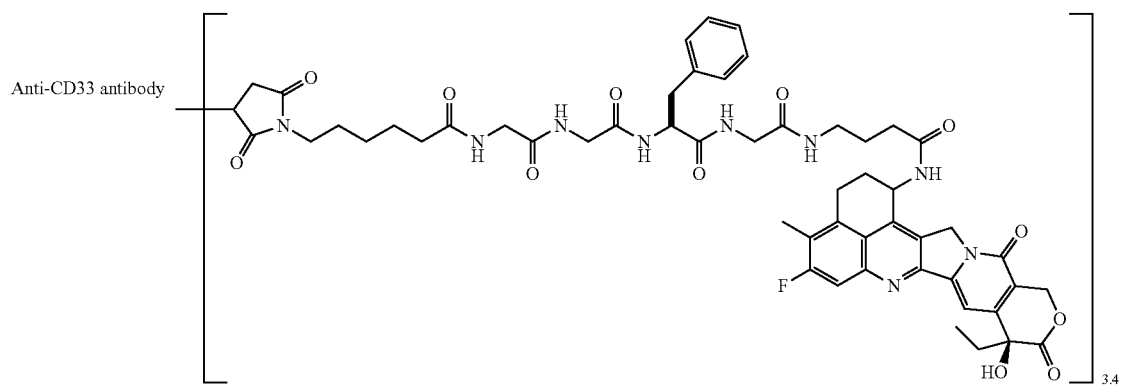

Process 1: Antibody-Drug Conjugate (8)

Reduction of the antibody: The anti-CD33 antibody produced in Reference Example 4 was prepared to have antibody concentration of 10 mg/mL with PBS6.0/EDTA by using the Common procedure B (as absorption coefficient at 280 nm, 1.66 was used) and Common procedure C-1 described in Production method 1. The solution (1.0 mL) was collected into a 2 mL tube and charged with an aqueous solution of 10 mM TCEP (Tokyo Chemical Industry Co., Ltd.) (0.0297 mL; 4.6 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution for 10 minutes at 22° C., a dimethyl sulfoxide solution (0.0593 mL; 9.2 equivalents per antibody molecule) containing 10 mM of the compound obtained in Process 3 of Example 2 was added thereto and incubated for conjugating the drug linker to the antibody at 22° C. for 40 minutes. Next, an aqueous solution (0.0119 mL; 18.4 equivalents per antibody molecule) of 100 mM NAC (Sigma-Aldrich Co. LLC) was added thereto and incubated to terminate the raction of drug linker at 22° C. for another 20 minutes.

Purification: The above solution was subjected to purification using the Common procedure D-1 (ABS was used as buffer solution) described in Production method 1 to yield 6 mL of a solution containing the titled antibody-drug conjugate.

Physicochemical characterization: By using the Common procedure E described in Production method 1 (as molar absorption coefficient, $\varepsilon_{A,280}=256400$ (estimated calculation value), $\varepsilon_{A,370}=0$ (estimated calculation value), $\varepsilon_{D,280}=5000$ (measured average value), and $\varepsilon_{D,370}=19000$ (measured average value) were used), the following characteristic values were obtained.

Antibody concentration: 1.06 mg/mL, antibody yield: 6.36 mg (64%), and average number of conjugated drug molecules (n) per antibody molecule: 3.4.

Example 10 Antibody-Drug Conjugate (9)

[Formula 79]

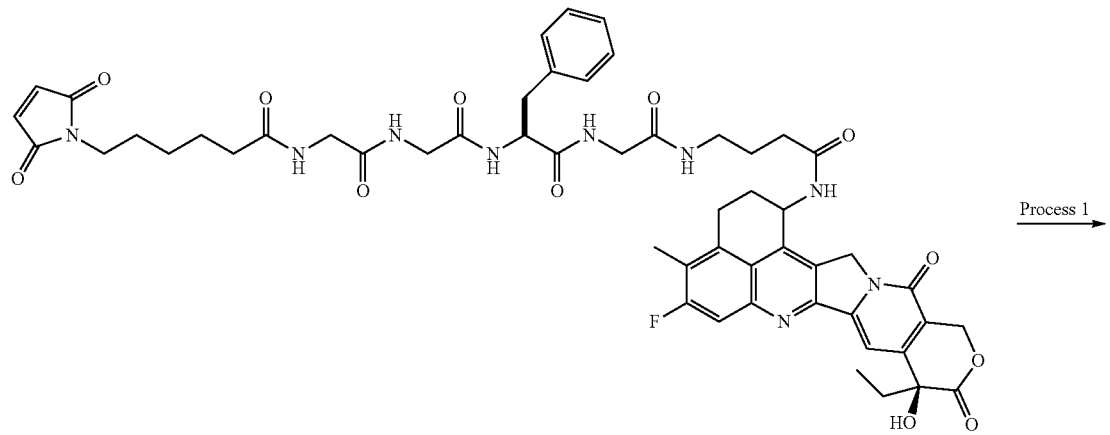

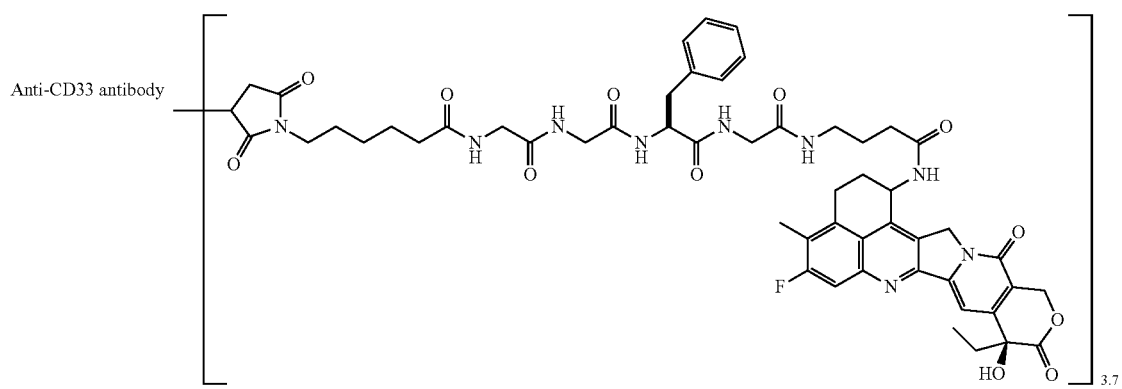

Process 1: Antibody-Drug Conjugate (9)

Reduction of the antibody: The anti-CD33 antibody produced in Reference Example 4 was prepared to have antibody concentration of 10 mg/mL with PBS6.0/EDTA by using the Common procedure B (as absorption coefficient at 280 nm, 1.66 was used) and Common procedure C-1 described in Production method 1. The solution (1.0 mL) was collected into a 2 mL tube and charged with an aqueous solution of 30 mM TCEP (Tokyo Chemical Industry Co., Ltd.) (0.0148 mL; 6.9 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution for 10 minutes at 22° C., a dimethyl sulfoxide solution (0.0297 mL; 13.8 equivalents per antibody molecule) containing 30 mM of the compound obtained in Process 3 of Example 2 was added thereto and incubated for conjugating the drug linker to the antibody at 22° C. for 40 minutes. Next, an aqueous solution (0.0178 mL; 27.6 equivalents per antibody molecule) of 100 mM NAC (Sigma-Aldrich Co. LLC) was added thereto and incubated to terminate the raction of drug linker at 22° C. for another 20 minutes.

Purification: The above solution was subjected to purification using the Common procedure D-1 (ABS was used as buffer solution) described in Production method 1 to yield 6 mL of a solution containing the titled antibody-drug conjugate.

Physicochemical characterization: By using the Common procedure E described in Production method 1 (as molar absorption coefficient, $\varepsilon_{A, 280}$=256400 (estimated calculation value), $\varepsilon_{A,370}$=0 (estimated calculation value), $\varepsilon_{D,280}$=5000 (measured average value), and $\varepsilon_{D,370}$=19000 (measured average value) were used), the following characteristic values were obtained.

Antibody concentration: 0.95 mg/mL, antibody yield: 5.70 mg (57%), and average number of conjugated drug molecules (n) per antibody molecule: 3.7.

Example 11 Antibody-Drug Conjugate (10)

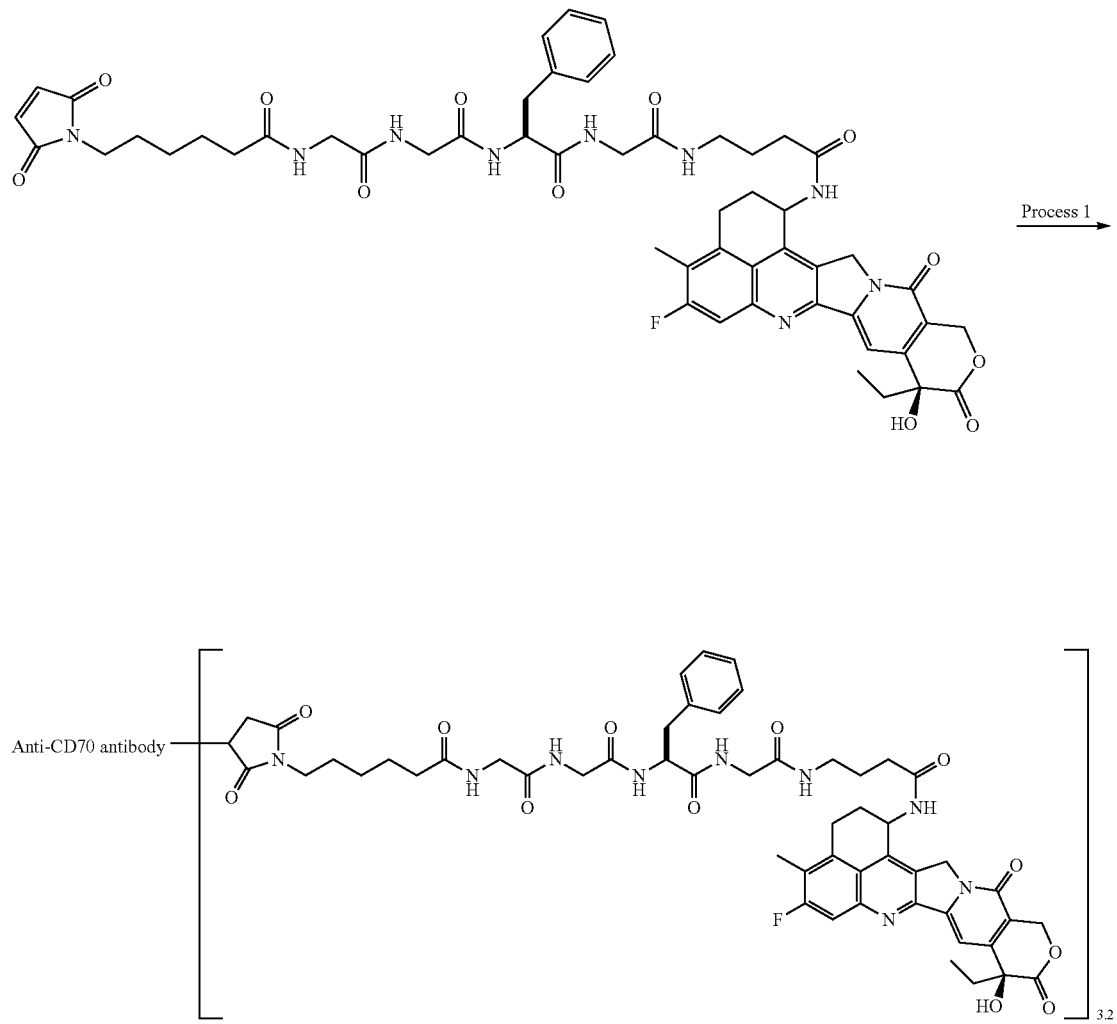

Process 1: Antibody-Drug Conjugate (10)

Reduction of the antibody: The anti-CD70 antibody produced in Reference Example 5 was prepared to have antibody concentration of 10 mg/mL with PBS6.0/EDTA by using the Common procedure B (as absorption coefficient at 280 nm, 1.69 was used) and Common procedure C-1 described in Production method 1. The solution (1.0 mL) was collected into a 2 mL tube and charged with an aqueous solution of 10 mM TCEP (Tokyo Chemical Industry Co., Ltd.) (0.0297 mL; 4.6 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.0593 mL; 9.2 equivalents per antibody molecule) containing 10 mM of the compound obtained in Process 3 of Example 2 was added thereto and incubated for conjugating the drug linker to the antibody at 22° C. for 40 minutes. Next, an aqueous solution (0.0119 mL; 18.4 equivalents per antibody molecule) of 100 mM NAC (Sigma-Aldrich Co. LLC) was added thereto and incubated to terminate the raction of drug linker at 22° C. for another 20 minutes.

Purification: The above solution was subjected to purification using the Common procedure D-1 (ABS was used as buffer solution) described in Production method 1 to yield 6 mL of a solution containing the titled antibody-drug conjugate.

Physicochemical characterization: By using the Common procedure E described in Production method 1 (as molar absorption coefficient, $\varepsilon_{A,280}=262400$ (estimated calculation value), $\varepsilon_{A,370}=0$ (estimated calculation value), $\varepsilon_{D,280}=5000$ (measured average value), and $\varepsilon_{D,370}=19000$ (measured average value) were used), the following characteristic values were obtained.

Antibody concentration: 1.00 mg/mL, antibody yield: 6.00 mg (60%), and average number of conjugated drug molecules (n) per antibody molecule: 3.2.

Example 12 Antibody-Drug Conjugate (11)

[Formula 81]

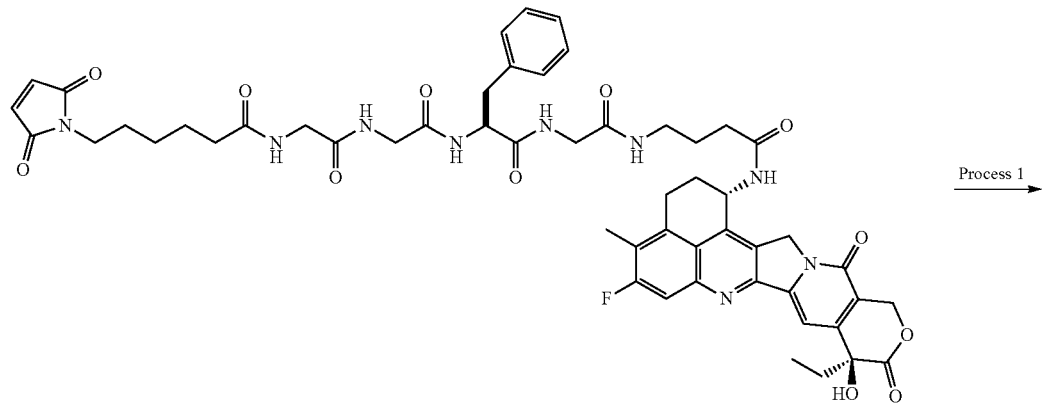

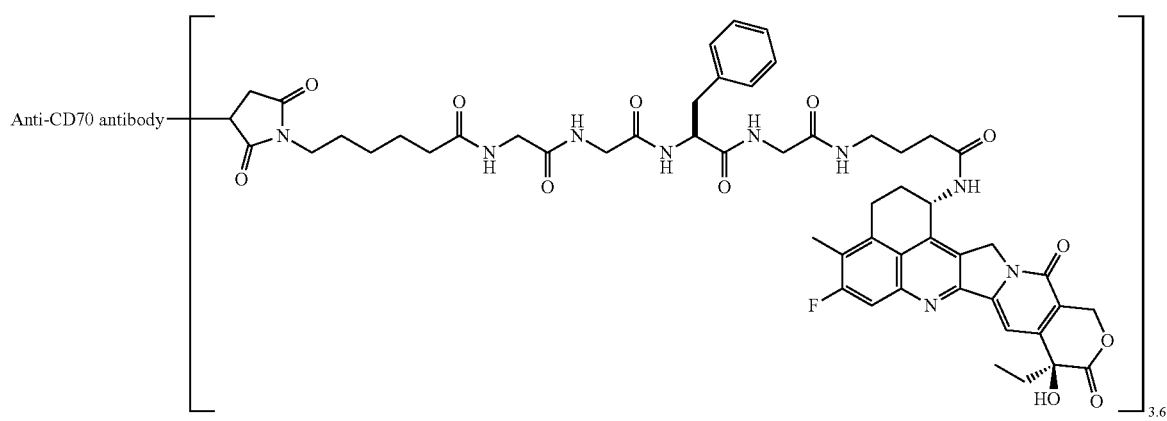

Process 1: Antibody-Drug Conjugate (11)

Reduction of the antibody: The anti-CD70 antibody produced in Reference Example 5 was prepared to have antibody concentration of 10 mg/mL with PBS6.0/EDTA by using the Common procedure B (as absorption coefficient at 280 nm, 1.69 was used) and Common procedure C-1 described in Production method 1. The solution (1.0 mL) was collected into a 2 mL tube and charged with an aqueous solution of 30 mM TCEP (Tokyo Chemical Industry Co., Ltd.) (0.0148 mL; 6.9 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour.

Conjugation between antibody and drug linker: After incubating the above solution at 22° C. for 10 minutes, a dimethyl sulfoxide solution (0.0297 mL; 13.8 equivalents per antibody molecule) containing 30 mM of the compound obtained in Process 3 of Example 2 was added thereto and incubated for 40 minutes at 22° C. for conjugating the drug linker to the antibody. Next, an aqueous solution (0.0178 mL; 27.6 equivalents per antibody molecule) of 100 mM NAC (Sigma-Aldrich Co. LLC) was added thereto and incubated to terminate the raction of drug linker at 22° C. for another 20 minutes.

Purification: The above solution was subjected to purification using the Common procedure D-1 (ABS was used as buffer solution) described in Production method 1 to yield 6 mL of a solution containing the titled antibody-drug conjugate.

Physicochemical characterization: By using the Common procedure E described in Production method 1 (as molar absorption coefficient, $\varepsilon_{A,280}=262400$ (estimated calculation value), $\varepsilon_{A,370}=0$ (estimated calculation value), $\varepsilon_{D,280}=5000$ (measured average value), and $\varepsilon_{D,370}=19000$ (measured average value) were used), the following characteristic values were obtained.

Antibody concentration: 0.96 mg/mL, antibody yield: 5.76 mg (58%), and average number of conjugated drug molecules (n) per antibody molecule: 3.6.

Example 13 Antibody-Drug Conjugate (12)

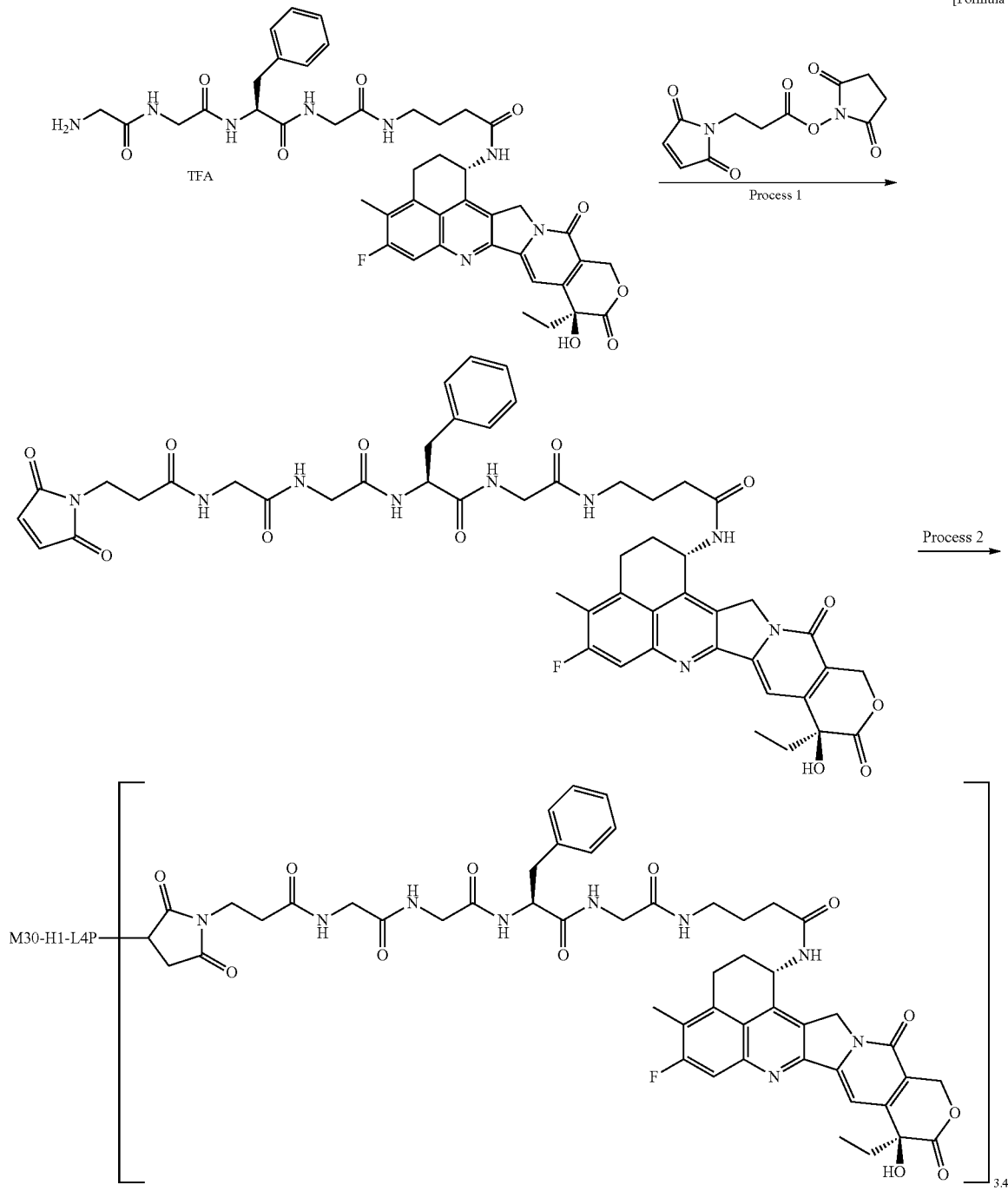

Process 1: N-[3-(2,5-dioxo-2,5-dihydro-1H-pyrrol-1-yl)propanoyl]glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (80 mg, 0.084 mmol) obtained in Process 2 of Example 2 was reacted in the same manner as Process 3 of Example 2 by using N-succinimidyl 3-maleimide propioate (24.6 mg, 0.0924 mmol) instead of N-succinimidyl 6-maleimide hexanoate to yield the titled compound as a pale yellow solid (60.0 mg, 73%).

$^1$H-NMR (400 MHz, DMSO-d$_6$) δ: 0.89 (3H, t, J=7.3 Hz), 1.70-1.78 (2H, m), 1.81-1.94 (2H, m), 2.12-2.23 (4H, m), 2.42 (3H, s), 2.81 (1H, dd, J=13.7, 9.8 Hz), 3.01-3.15 (3H, m), 3.16-3.23 (2H, m), 3.30-3.35 (1H, m), 3.58-3.71 (6H, m), 3.71-3.79 (1H, m), 4.44-4.51 (1H, m), 5.19 (1H, d, J=19.0 Hz), 5.27 (1H, d, J=19.0 Hz), 5.43 (1H, d, J=17.6 Hz), 5.47 (1H, d, J=17.6 Hz), 5.57-5.63 (1H, m), 6.56 (1H, s), 7.02 (2H, s), 7.17-7.22 (1H, m), 7.22-7.30 (5H, m), 7.34 (1H, s), 7.73 (1H, t, J=5.6 Hz), 7.83 (1H, d, J=10.7 Hz), 8.08 (1H, t, J=5.6 Hz), 8.15 (1H, d, J=7.8 Hz), 8.30 (2H, dt, J=18.7, 5.7 Hz), 8.49 (1H, d, J=8.8 Hz).

MS (APCI) m/z: 990 (M+H)$^+$

Process 2: Antibody-Drug Conjugate (12)

By using the M30-H1-L4P antibody produced in Reference Example 2 and the compound obtained in Process 1 above, the titled antibody-drug conjugate was obtained in the same manner as Process 4 of Example 2. Antibody concentration: 12.16 mg/mL, antibody yield: 8.5 mg (68%), and average number of conjugated drug molecules (n) per antibody molecule: 3.4.

Example 14 Antibody-Drug Conjugate (13)

Process 1: N-{3-[2-(2-{[3-(2,5-dioxo-2,5-dihydro-1H-pyrrol-1-yl)propanoyl]amino}ethoxy)ethoxy]propanoyl}glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (100 mg, 0.119 mmol) obtained in Process 2 of Example 2 was reacted in the same manner as Process 3 of Example 2 by using diisopropylethylamine (20.8 µL, 0.119 mmol) instead of triethylamine and N-succinimidyl 3-(2-(2-(3-maleinimidepropanamide)ethoxy)ethoxy)propanoate (50.7 mg, 0.119 mmol) instead of N-succinimidyl 6-maleimide hexanoate to yield the titled compound as a pale yellow solid (66.5 mg, 48%).

$^1$H-NMR (400 MHz, DMSO-d$_6$) δ: 0.85 (3H, t, J=7.4 Hz), 1.65-1.74 (2H, m), 1.77-1.90 (2H, m), 2.07-2.19 (4H, m),

[Formula 99]

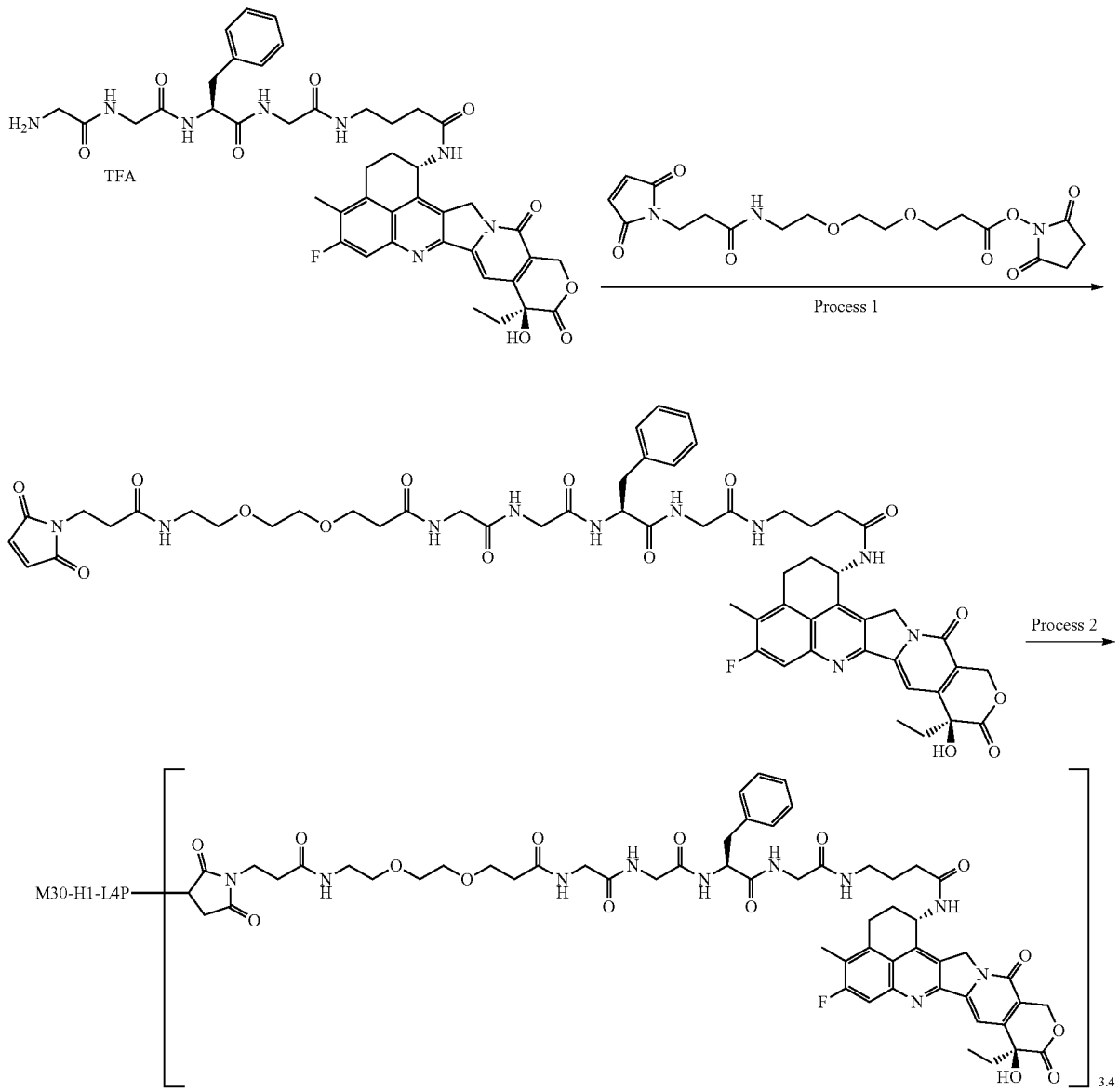

2.30 (2H, t, J=7.2 Hz), 2.33-2.36 (2H, m), 2.38 (3H, s), 2.76 (1H, dd, J=13.7, 9.8 Hz), 2.96-3.18 (9H, m), 3.42-3.44 (4H, m), 3.53-3.76 (10H, m), 4.43 (1H, td, J=8.6, 4.7 Hz), 5.14 (1H, d, J=18.8 Hz), 5.23 (1H, d, J=18.8 Hz), 5.38 (1H, d, J=17.2 Hz), 5.42 (1H, d, J=17.2 Hz), 5.52-5.58 (1H, m), 6.52 (1H, s), 6.98 (2H, s), 7.12-7.17 (1H, m), 7.18-7.25 (4H, m), 7.29 (1H, s), 7.69 (1H, t, J=5.5 Hz), 7.78 (1H, d, J=11.3 Hz), 7.98-8.03 (2H, m), 8.11 (1H, d, J=7.8 Hz), 8.16 (1H, t, J=5.7 Hz), 8.23 (1H, t, J=5.9 Hz), 8.44 (1H, d, J=9.0 Hz).

MS (APCI) m/z: 1149 $(M+H)^+$

Process 2: Antibody-Drug Conjugate (13)

By using the M30-H1-L4P antibody produced in Reference Example 2 and the compound obtained in Process 1 above, the titled antibody-drug conjugate was obtained in the same manner as Process 4 of Example 2. Antibody concentration: 12.76 mg/mL, antibody yield: 8.9 mg (71%), and average number of conjugated drug molecules (n) per antibody molecule: 3.4.

Example 15 Antibody-Drug Conjugate (14)

[Formula 84]
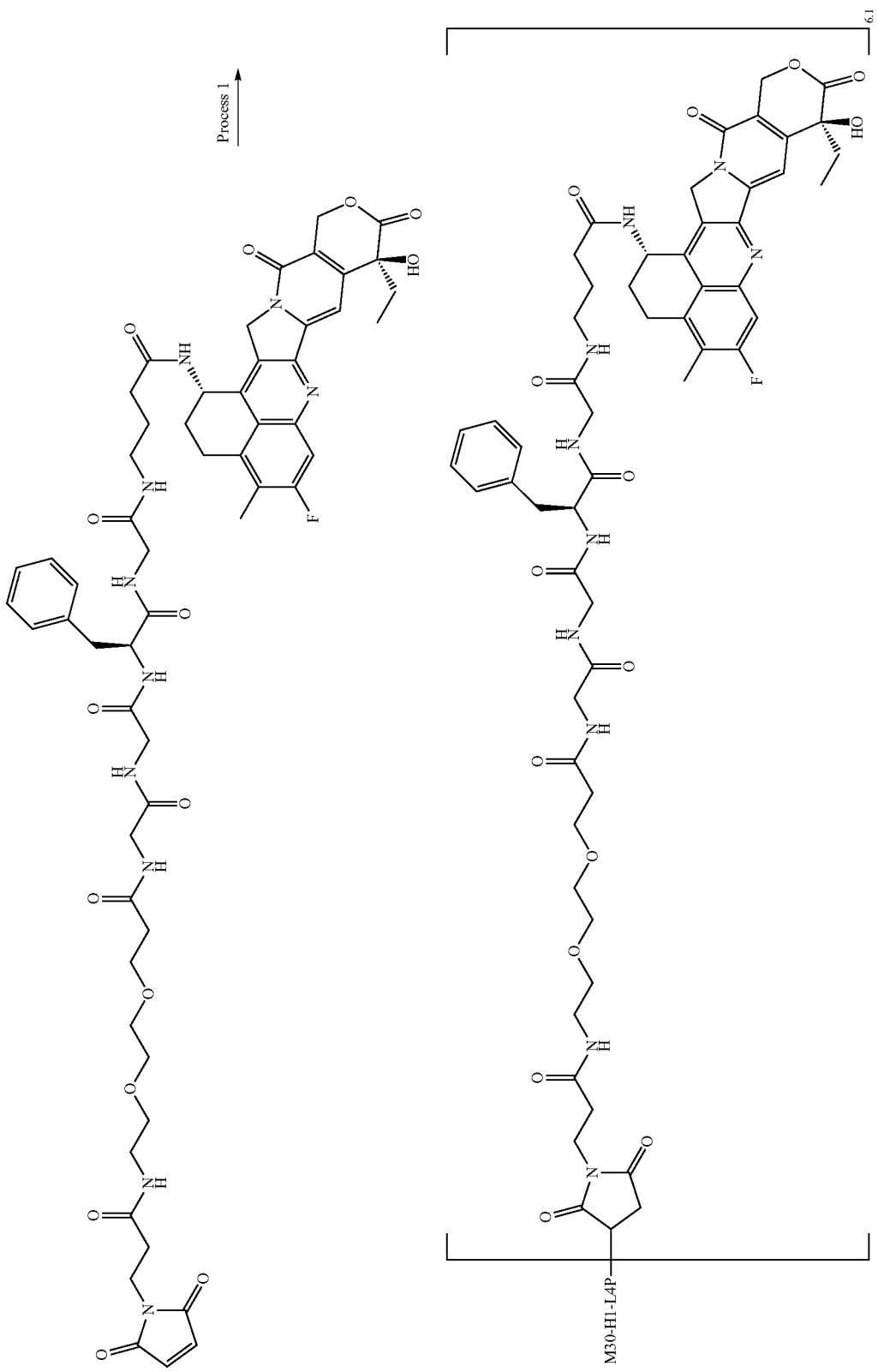

Process 1: Antibody-Drug Conjugate (14)

By using the M30-H1-L4P antibody produced in Reference Example 2 and the compound obtained in Process 1 of Example 14, the titled antibody-drug conjugate was obtained in the same manner as Process 1 of Example 4.

Antibody concentration: 1.60 mg/mL, antibody yield: 9.60 mg (77%), and average number of conjugated drug molecules (n) per antibody molecule: 6.1.

Example 16 Antibody-Drug Conjugate (15)

[Formula 85]

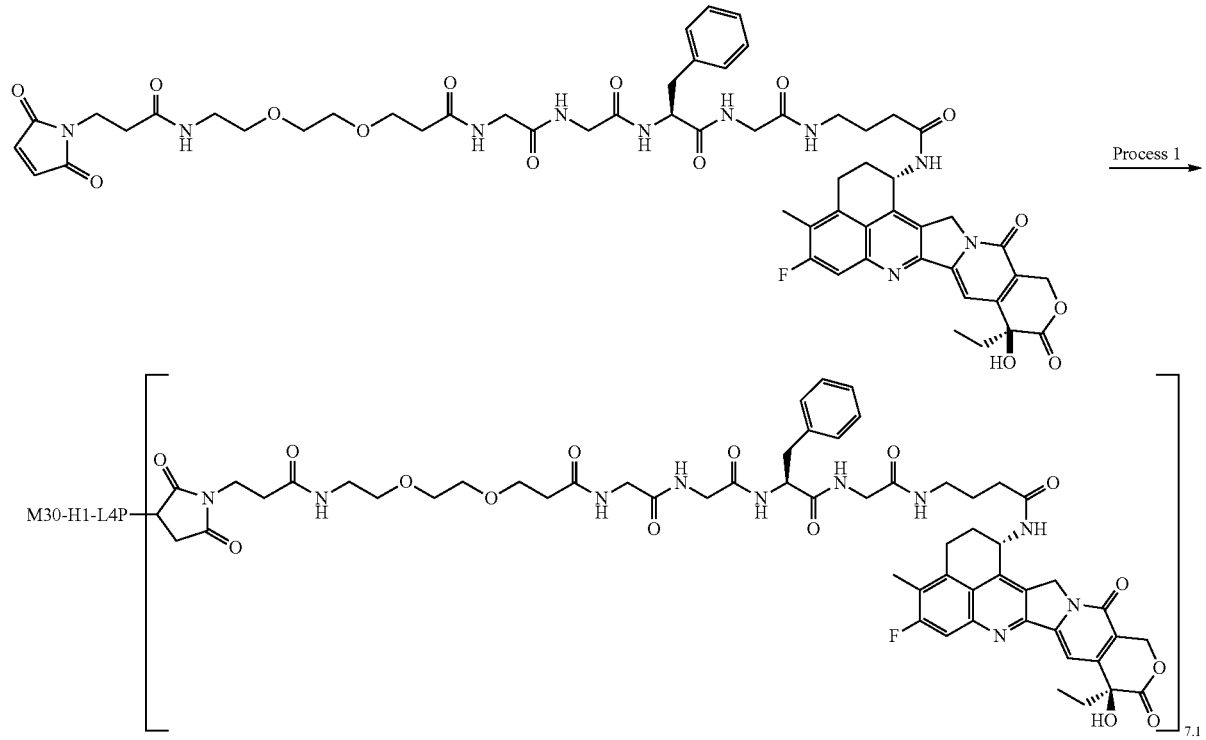

Process 1: Antibody-Drug Conjugate (15)

By using the M30-H1-L4P antibody produced in Reference Example 2 and the compound obtained in Process 1 of Example 14, the titled antibody-drug conjugate was obtained in the same manner as Process 1 of Example 5.

Antibody concentration: 1.64 mg/mL, antibody yield: 9.84 mg (79%), and average number of conjugated drug molecules (n) per antibody molecule: 7.1.

Example 17 Antibody-Drug Conjugate (16)

[Formula 86]

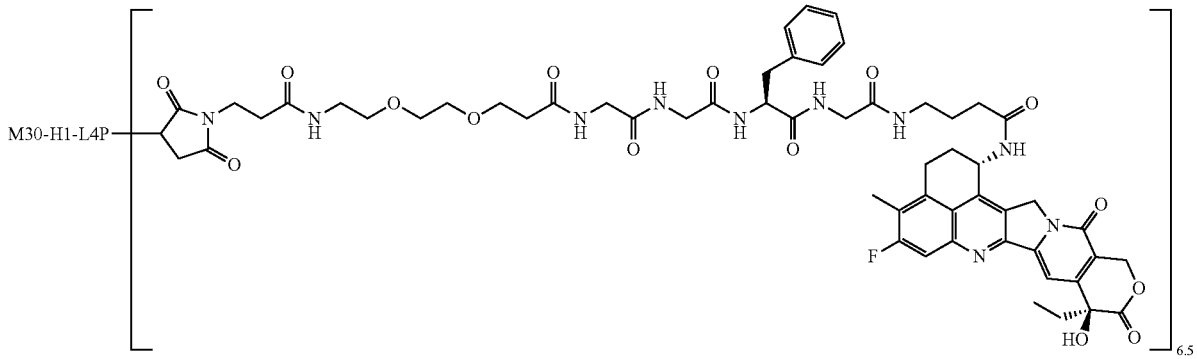

Almost the whole amounts of the antibody-drug conjugates of Examples 15 and 16 were mixed and the solution was concentrated by the Common procedure A to yield the titled antibody-drug conjugate.

Antibody concentration: 10.0 mg/mL, antibody yield: 17.30 mg, and average number of conjugated drug molecules (n) per antibody molecule: 6.5.

Example 18 Antibody-Drug Conjugate (17)

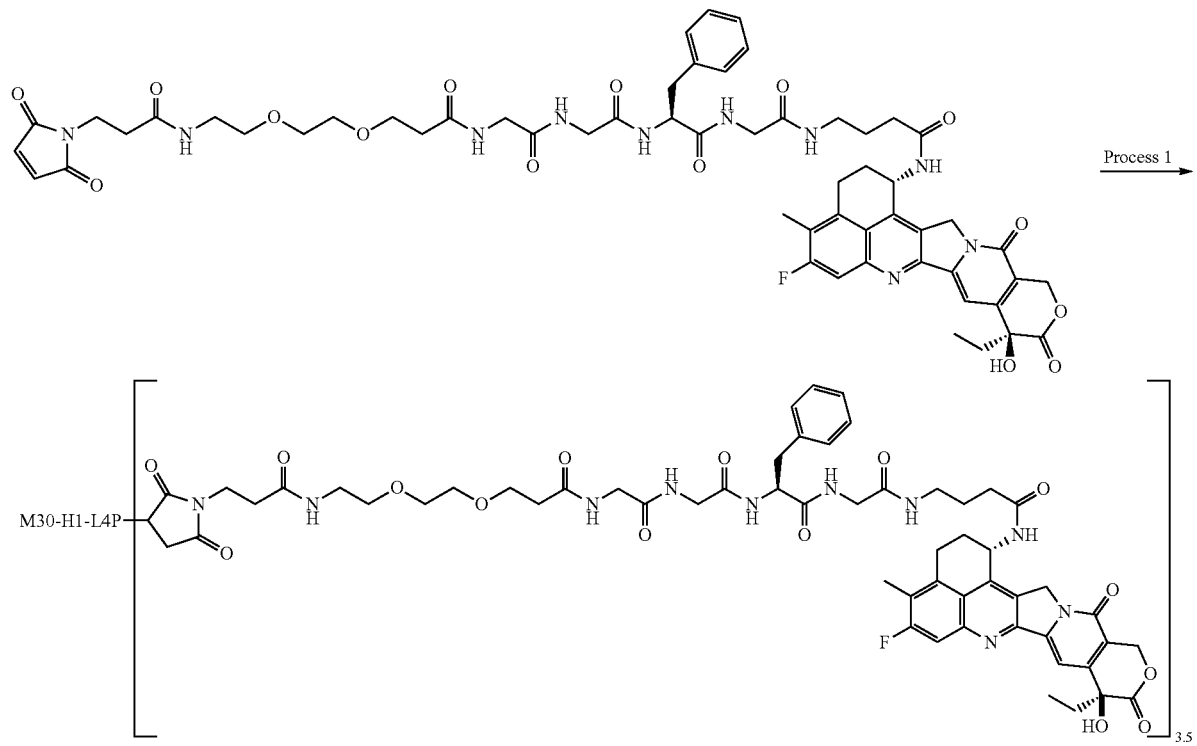

Process 1: Antibody-Drug Conjugate (17)

Reduction of the antibody: The M30-H1-L4P antibody produced in Reference Example 2 was prepared to have antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (100 mL, 1 g of the antibody) was placed in a 250 mL flask and charged with an aqueous solution of 10 mM TCEP (Tokyo Chemical Industry Co., Ltd.) (2.43 mL; 3.6 equivalents per antibody molecule) and further with an aqueous solution of 1 M dipotassium hydrogen phosphate (5 mL). After confirming that the solution had pH near 7.4 by using a pH meter, the disulfide bond at hinge part in the antibody was reduced by incubating at 37° C. for 1 hour.

Conjugation between antibody and drug linker: After adding dimethyl sulfoxide (2.14 mL) and a dimethyl sulfoxide solution containing 10 mM of the compound obtained in Process 1 of Example 14 (3.51 mL; 5.2 equivalents per antibody molecule) to the above solution at room temperature, it was stirred with a stirrer for conjugating the drug linker to the antibody in a water bath at 15° C. for 130 minutes. Next, an aqueous solution (0.547 mL) of 100 mM NAC was added thereto and further incubated to terminate the raction of drug linker at room temperature for 20 minutes.

Purification: The above solution was subjected to ultrafiltration purification using an ultrafiltration apparatus composed of an ultrafiltration membrane (Merck Japan, Pellicon XL Cassette, Biomax 50 KDa), a tube pump (Cole-Parmer International, MasterFlex Pump model 77521-40, Pump Head model 7518-00), and a tube (Cole-Parmer International, MasterFlex Tube L/S16). Specifically, while ABS was added dropwise (a total of 800 mL) as a buffer solution for purification to the reaction solution, ultrafiltration purification was performed for removing unconjugated drug linkers and other low-molecular-weight reagents, also replacing the buffer solution with ABS, and further concentrating the solution, to yield about 70 mL of a solution containing the titled antibody-drug conjugate.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,280}$=4964 (measured value), and $\varepsilon_{D,370}$=18982 (measured value) were used), the following characteristic values were obtained.

Antibody concentration: 14.5 mg/mL, antibody yield: 1.0 g (about 100%), and average number of conjugated drug molecules (n) per antibody molecule: 3.5.

Example 19 Antibody-Drug Conjugate (18)

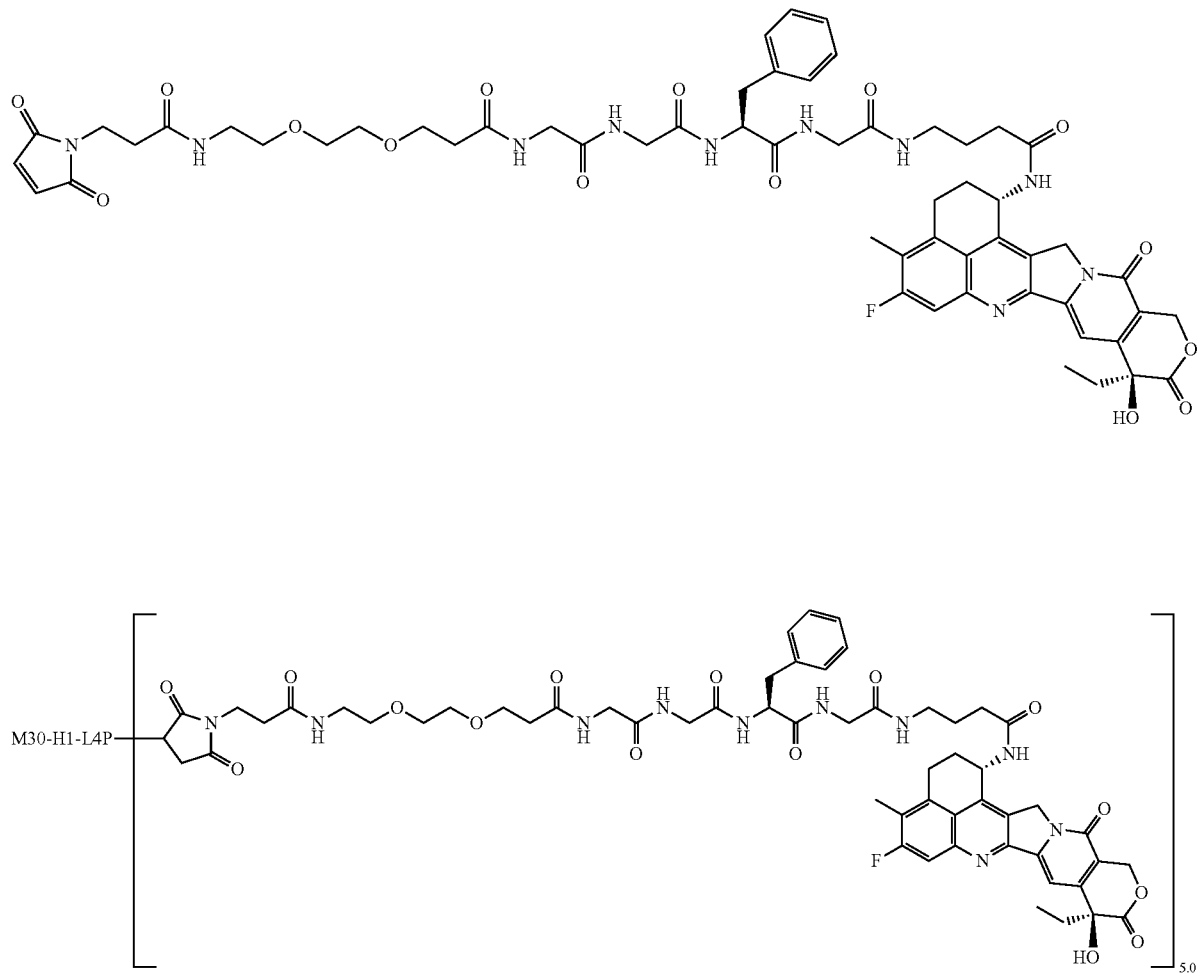

Process 1: Antibody-Drug Conjugate (18)

Reduction of the antibody: The M30-H1-L4P antibody produced in Reference Example 2 was prepared to have antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (5 mL, 50 mg of the antibody) was placed in a 15 mL tube and charged with an aqueous solution of 10 mM TCEP (Tokyo Chemical Industry Co., Ltd.) (0.135 mL; 4 equivalents per antibody molecule). After confirming that the solution had pH near 7.4 by using a pH meter, the disulfide bond at hinge part in the antibody was reduced by incubating at 37° C. for 1 hour.

Conjugation between antibody and drug linker: After adding dimethyl sulfoxide (0.064 mL) and a dimethyl sulfoxide solution containing 10 mM of the compound obtained in Process 1 of Example 14 (0.219 mL; 6.5 equivalents per antibody molecule) to the above solution, it was incubated for conjugating the drug linker to the antibody in a water bath at 15° C. for 90 minutes. Next, an aqueous solution (0.033 mL; 9.8 equivalents per antibody molecule) of 100 mM NAC was added thereto and incubated to terminate the raction of drug linker at room temperature for another 20 minutes. Purification: The above solution was subjected to purification using the Common procedure D-1 (ABS was used as buffer solution) described in Production method 1 to yield 19 mL of a solution containing the titled antibody-drug conjugate.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,280}$=4964 (measured value), and $\varepsilon_{D,370}$=18982 (measured value) were used), the following characteristic values were obtained.

Antibody concentration: 2.17 mg/mL, antibody yield: 41 mg (82%), and average number of conjugated drug molecules (n) per antibody molecule: 5.0.

Example 20 Antibody-Drug Conjugate (19)

[Formula 89]
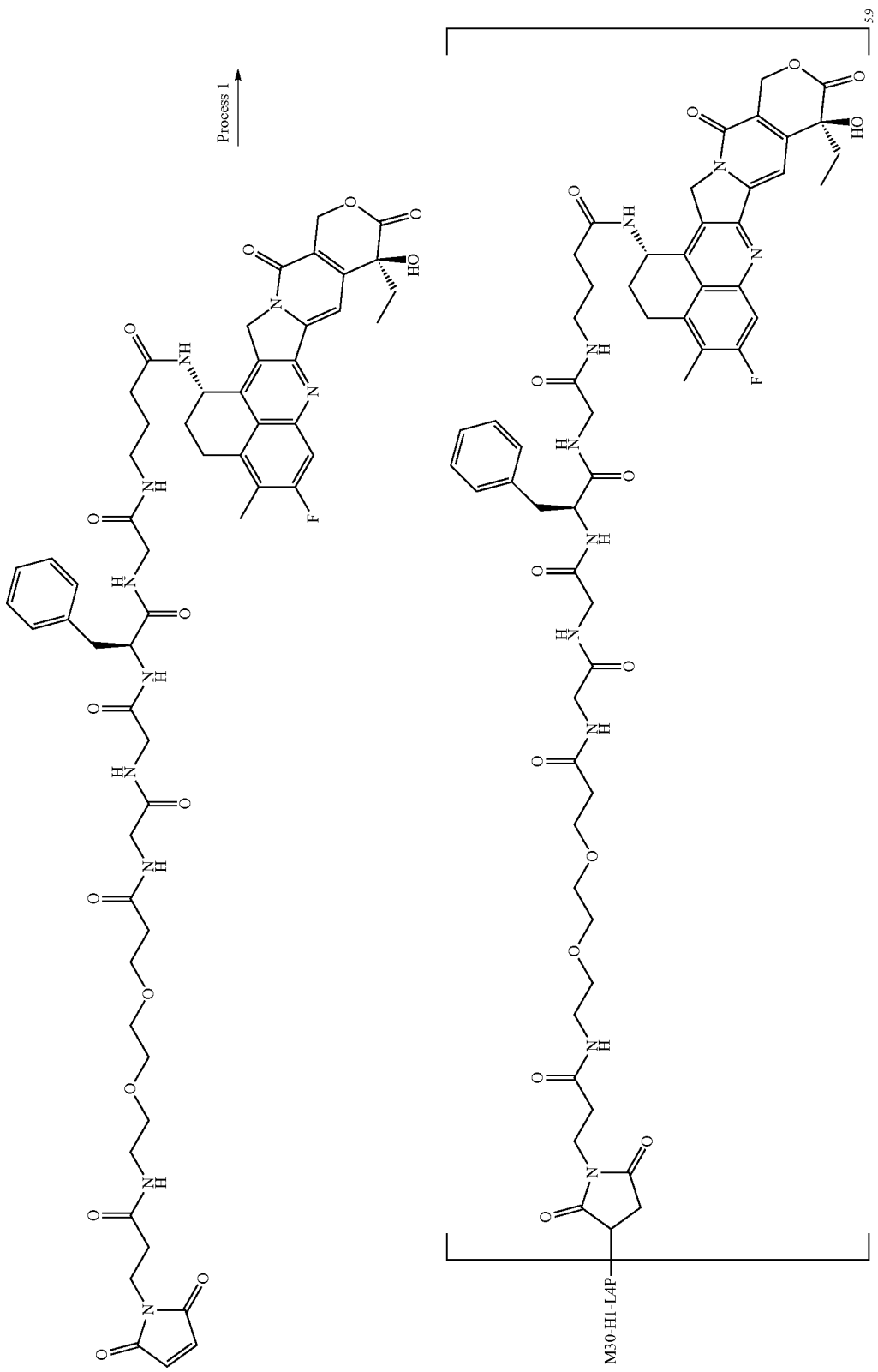

Process 1: Antibody-Drug Conjugate (19)

Reduction of the antibody: The M30-H1-L4P antibody produced in Reference Example 2 was prepared to have antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (4 mL, 40 mg of the antibody) was placed in a 15 mL tube and charged with an aqueous solution of 10 mM TCEP (Tokyo Chemical Industry Co., Ltd.) (0.140 mL; 5.2 equivalents per antibody molecule). After confirming that the solution had pH near 7.4 by using a pH meter, the disulfide bond at hinge part in the antibody was reduced by incubating at 37° C. for 1 hour. Conjugation between antibody and drug linker: After adding a dimethyl sulfoxide solution containing 10 mM of the compound obtained in Process 1 of Example 14 (0.232 mL; 8.6 equivalents per antibody molecule) to the above solution, it was incubated for conjugating the drug linker to the antibody in a water bath at 15° C. for 90 minutes. Next, an aqueous solution (0.035 mL; 12.9 equivalents per antibody molecule) of 100 mM NAC was added thereto and incubated to terminate the raction of drug linker at room temperature for another 20 minutes.

Purification: The above solution was subjected to purification using the Common procedure D-1 (ABS was used as buffer solution) described in Production method 1 to yield 13 mL of a solution containing the titled antibody-drug conjugate.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,280}$=4964 (measured value), and $\varepsilon_{D,370}$=18982 (measured value) were used), the following characteristic values were obtained.

Antibody concentration: 2.36 mg/mL, antibody yield: 31 mg (77%), and average number of conjugated drug molecules (n) per antibody molecule: 5.9.

Example 21 Antibody-Drug Conjugate (20)

[Formula 90]
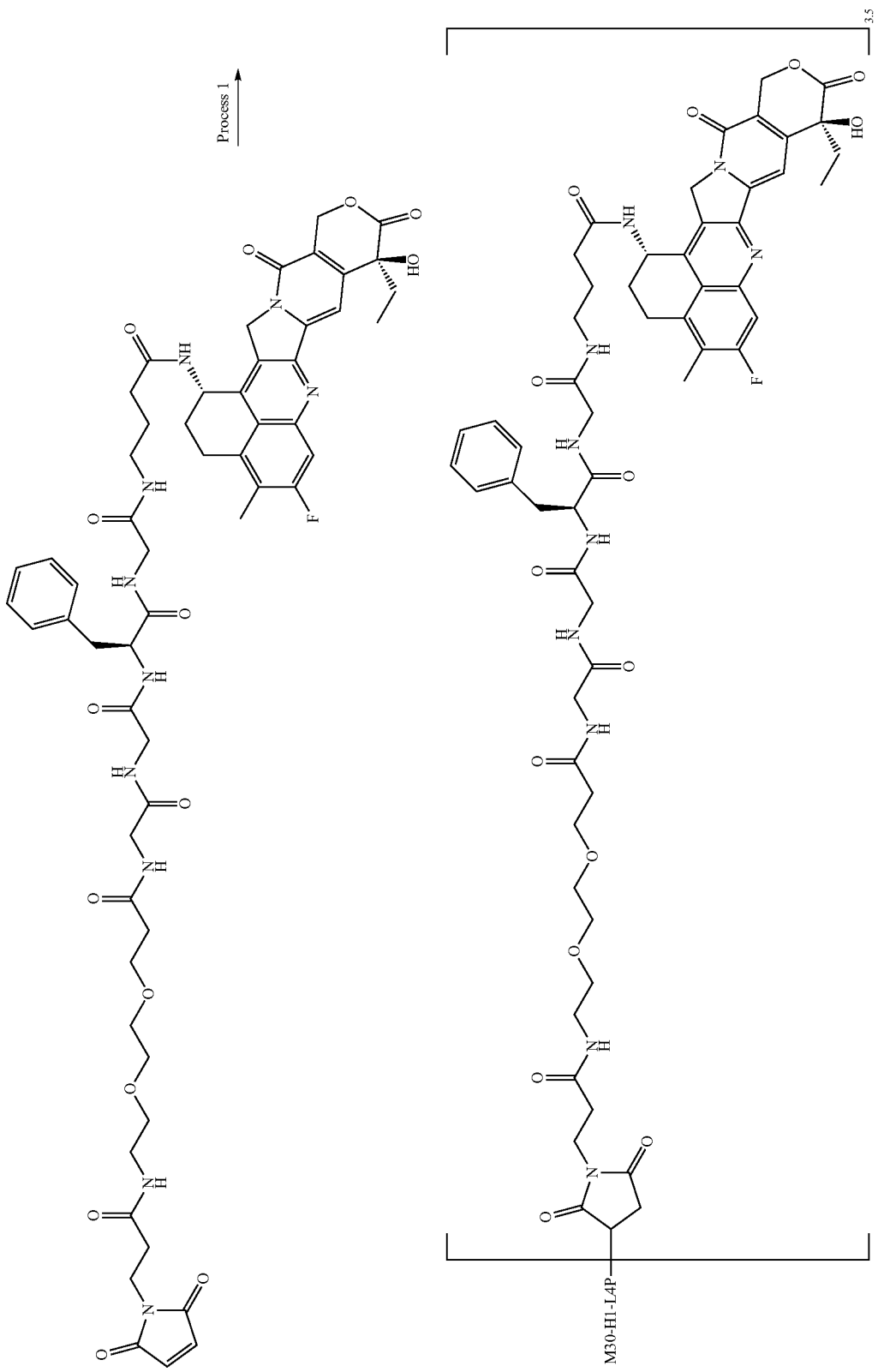

Process 1: Antibody-Drug Conjugate (20)

Reduction of the antibody: The M30-H1-L4 antibody produced in Reference Example 1 was prepared to have antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (1.25 mL, 12.5 mg of the antibody) was placed in a 1.5 mL tube and charged with an aqueous solution of 10 mM TCEP (Tokyo Chemical Industry Co., Ltd.) (0.0287 mL; 3.4 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding dimethyl sulfoxide (0.0267 mL) and a dimethyl sulfoxide solution containing 10 mM of the compound obtained in Process 1 of Example 14 (0.0439 mL; 5.2 equivalents per antibody molecule) to the above solution at room temperature, it was incubated for conjugating the drug linker to the antibody in a water bath at 15° C. for 1 hour. Next, an aqueous solution (0.0066 mL) of 100 mM NAC (Sigma-Aldrich Co. LLC) was added thereto and incubated to terminate the raction of drug linker at room temperature for another 20 minutes. Purification: The above solution was subjected to purification using the Common procedure D-1 (ABS was used as buffer solution) described in Production method 1 to yield 6 mL of a solution containing the titled antibody-drug conjugate. After that, the solution was concentrated by the Common procedure A.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,280}$=4964 (measured value), and $\varepsilon_{D,370}$=18982 (measured value) were used), the following characteristic values were obtained.

Antibody concentration: 10.0 mg/mL, antibody yield: 8.7 mg (70%), and average number of conjugated drug molecules (n) per antibody molecule: 3.5.

Example 22 Antibody-Drug Conjugate (21)

Process 1

[Formula 91]

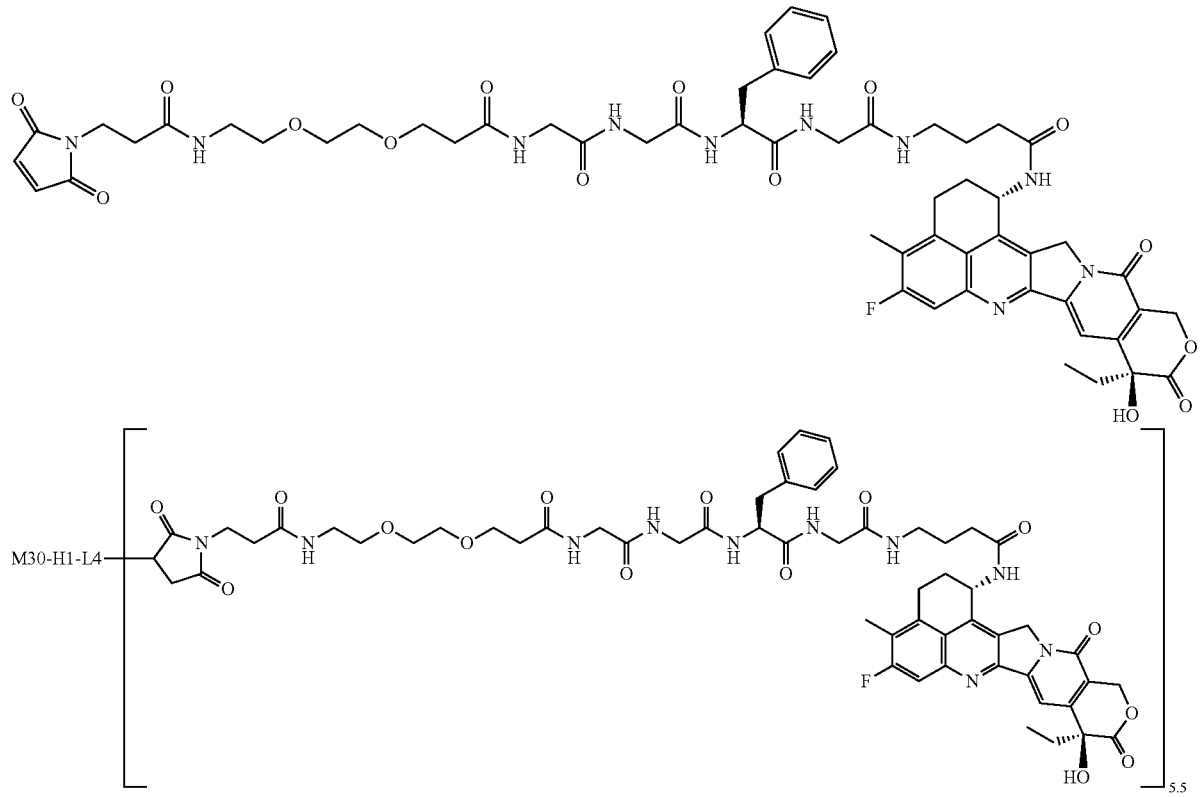

Process 1: Antibody-Drug Conjugate (21)

Reduction of the antibody: The M30-H1-L4 antibody produced in Reference Example 1 was prepared to have antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (1.25 mL, 12.5 mg of the antibody) was placed in a 1.5 mL tube and charged with an aqueous solution of 10 mM TCEP (Tokyo Chemical Industry Co., Ltd.) (0.0439 mL; 5.2 equivalents per antibody molecule) (0.0287 mL; 3.4 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding a dimethyl sulfoxide solution containing 10 mM of the compound obtained in Process 1 of Example 14 (0.0726 mL; 8.6 equivalents per antibody molecule) to the above solution at room temperature, it was incubated for conjugating the drug linker to the antibody in a water bath at 15° C. for 1 hour. Next, an aqueous solution (0.011 mL) of 100 mM NAC (Sigma-Aldrich Co. LLC) was added thereto and incubated to terminate the raction of drug linker at room temperature for another 20 minutes.

Purification: The above solution was subjected to purification using the Common procedure D-1 (ABS was used as buffer solution) described in Production method 1 to yield 6 mL of a solution containing the titled antibody-drug conjugate. After that, the solution was concentrated by the Common procedure A.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,280}$=4964 (measured value), and $\varepsilon_{D,370}$=18982 (measured value) were used), the following characteristic values were obtained.

Antibody concentration: 10.0 mg/mL, antibody yield: 8.3 mg (66%), and average number of conjugated drug molecules (n) per antibody molecule: 5.5.

Example 23 Antibody-Drug Conjugate (22)

Process 1: Antibody-Drug Conjugate (22)

Reduction of the antibody: The anti-CD30 antibody produced in Reference Example 3 was prepared to have antibody concentration of 10 mg/mL with PBS6.0/EDTA by using the Common procedure B (as absorption coefficient at 280 nm, 1.75 mLmg$^{-1}$ cm$^{-1}$ was used) and Common procedure C-1 described in Production method 1. The solution (0.4 mL, 4 mg of the antibody) was placed in a 1.5 mL tube and charged with an aqueous solution of 10 mM TCEP (Tokyo Chemical Industry Co., Ltd.) (0.0065 mL; 2.5 equivalents per antibody molecule). The disulfide bond at hinge part in the antibody was reduced by incubating at 37° C. for 1 hour.

Conjugation between antibody and drug linker: After adding dimethyl sulfoxide (0.0098 mL) and a dimethyl sulfoxide solution containing 10 mM of the compound obtained in Process 1 of Example 14 (0.0116 mL; 4.5 equivalents per antibody molecule) to the above solution at room temperature, it was stirred by using a tube rotator (MTR-103, manufactured by AS ONE Corporation) for conjugating the drug linker to the antibody at room temperature for 1 hour. Next, an aqueous solution (0.0017 mL) of 100 mM NAC (Sigma-Aldrich Co. LLC) was added thereto and further incubated to terminate the raction of drug linker at room temperature for 20 minutes.

Purification: The above solution was subjected to purification using the Common procedure D-1 (ABS was used as buffer solution) described in Production method 1 to yield 2.5 mL of a solution containing the titled antibody-drug conjugate.

Process 1

[Formula 92]

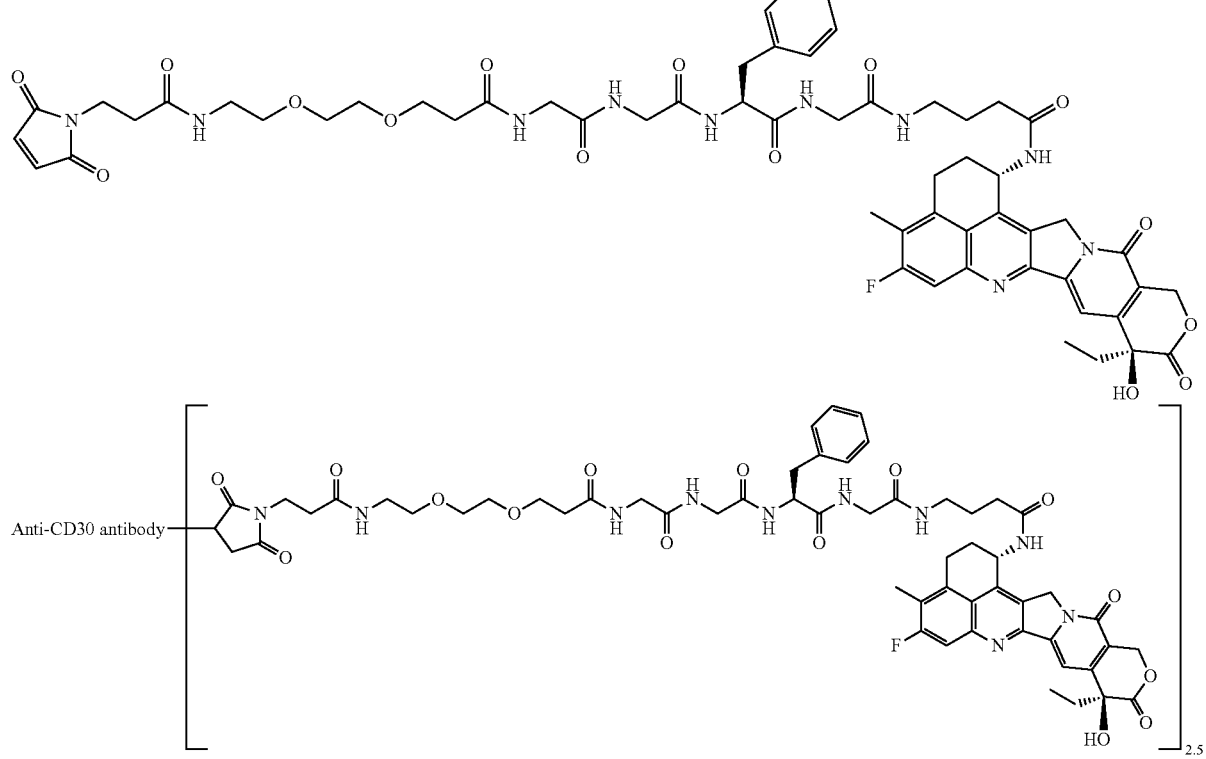

Physicochemical characterization: By using the Common procedure E described in Production method 1 (as molar absorption coefficient, $\varepsilon_{A,280}$=270400 (estimated calculation value), $\varepsilon_{A,370}$=0 (estimated calculation value), $\varepsilon_{D,280}$=4964 (measured value), and $\varepsilon_{D,370}$=18982 (measured value) were used), the following characteristic values were obtained.

Antibody concentration: 0.86 mg/mL, antibody yield: 2.2 mg (54%), and average number of conjugated drug molecules (n) per antibody molecule: 2.5.

Example 24 Antibody-Drug Conjugate (23)

the compound obtained in Process 1 of Example 14 (0.0204 mL; 9 equivalents per antibody molecule) and propylene glycol (Kanto Chemical Co., Inc., 0.18 mL) to the above solution at room temperature, it was stirred by using a tube rotator (MTR-103, manufactured by AS ONE Corporation) for conjugating the drug linker to the antibody at room temperature for 1 hour. Next, an aqueous solution (0.0031 mL) of 100 mM NAC (Sigma-Aldrich Co. LLC) was added thereto and further incubated to terminate the raction of drug linker at room temperature for 20 minutes.

Process 1

[Formula 93]

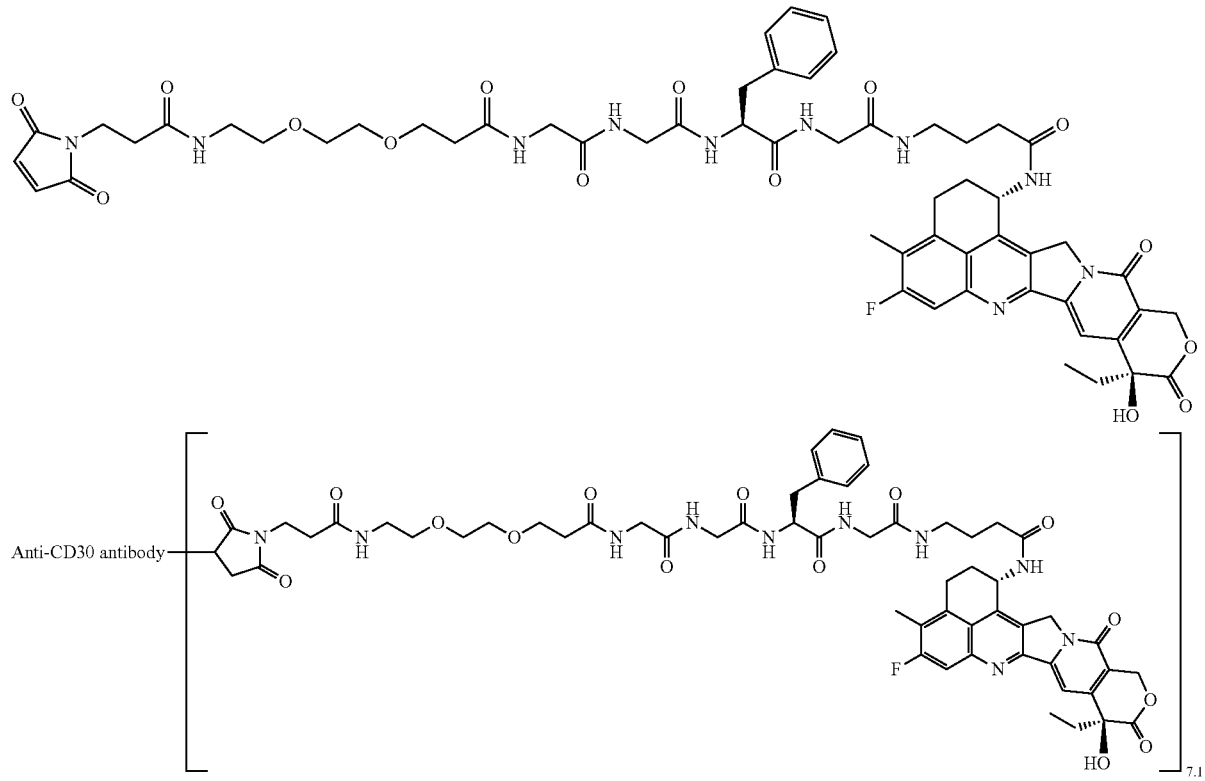

Process 1: Antibody-Drug Conjugate (23)

Reduction of the antibody: The anti-CD30 antibody produced in Reference Example 3 was prepared to have antibody concentration of 10 mg/mL with PBS6.0/EDTA by using the Common procedure B (as absorption coefficient at 280 nm, 1.75 mLmg$^{-1}$ cm$^{-1}$ was used) and Common procedure C-1 described in Production method 1. The solution (0.35 mL, 3.5 mg of the antibody) was placed in a 1.5 mL tube and charged with an aqueous solution of 10 mM TCEP (Tokyo Chemical Industry Co., Ltd.) (0.0113 mL; 5 equivalents per antibody molecule). The disulfide bond at hinge part in the antibody was reduced by incubating at 37° C. for 1 hour.

Conjugation between antibody and drug linker: After adding a dimethyl sulfoxide solution containing 10 mM of Purification: The above solution was subjected to purification using the Common procedure D-1 (ABS was used as buffer solution) described in Production method 1 to yield 2.5 mL of a solution containing the titled antibody-drug conjugate.

Physicochemical characterization: By using the Common procedure E described in Production method 1 (as molar absorption coefficient, $\varepsilon_{A,280}$=270400 (estimated calculation value), $\varepsilon_{A,370}$=0 (estimated calculation value), $\varepsilon_{D,280}$=4964 (measured value), and $\varepsilon_{D,370}$=18982 (measured value) were used), the following characteristic values were obtained.

Antibody concentration: 0.41 mg/mL, antibody yield: 1.0 mg (29%), and average number of conjugated drug molecules (n) per antibody molecule: 7.1.

Example 25 Antibody-Drug Conjugate (24)

Process 1

[Formula 94]

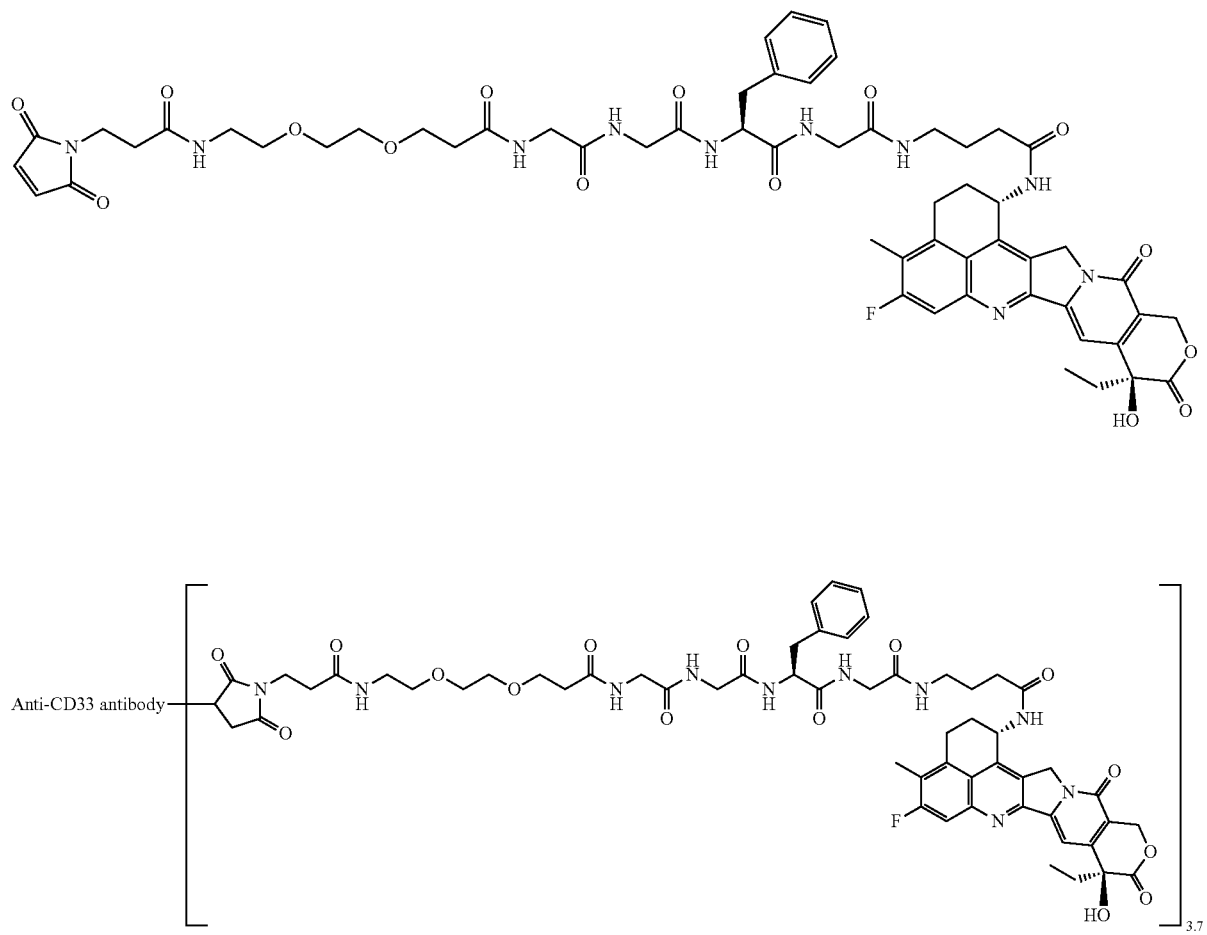

Process 1: Antibody-Drug Conjugate (24)

Reduction of the antibody: The anti-CD33 antibody produced in Reference Example 4 was prepared to have antibody concentration of 10 mg/mL with PBS6.0/EDTA by using the Common procedure B (as absorption coefficient at 280 nm, 1.66 mLmg$^{-1}$ cm$^{-1}$ was used) and Common procedure C-1 described in Production method 1. The solution (0.4 mL, 4 mg of the antibody) was placed in a 1.5 mL tube and charged with an aqueous solution of 10 mM TCEP (Tokyo Chemical Industry Co., Ltd.) (0.0065 mL; 2.5 equivalents per antibody molecule) and an aqueous solution of 1 M dipotassium hydrogen phosphate (Nacalai Tesque, Inc.; 0.0058 mL). After confirming that the solution had pH of 7.0±0.1, the disulfide bond at hinge part in the antibody was reduced by incubating at 37° C. for 1 hour.

Conjugation between antibody and drug linker: After adding dimethyl sulfoxide (0.0101 mL) and a dimethyl sulfoxide solution containing 10 mM of the compound obtained in Process 1 of Example 14 (0.0116 mL; 4.5 equivalents per antibody molecule) to the above solution at room temperature, it was stirred by using a tube rotator (MTR-103, manufactured by AS ONE Corporation) for conjugating the drug linker to the antibody at room temperature for 1 hour. Next, an aqueous solution (0.0017 mL) of 100 mM NAC (Sigma-Aldrich Co. LLC) was added thereto and further incubated to terminate the raction of drug linker at room temperature for 20 minutes.

Purification: The above solution was subjected to purification using the Common procedure D-1 (ABS was used as buffer solution) described in Production method 1 to yield 2.5 mL of a solution containing the titled antibody-drug conjugate.

Physicochemical characterization: By using the Common procedure E described in Production method 1 (as molar absorption coefficient, $\varepsilon_{A,280}$=256400 (estimated calculation value), $\varepsilon_{A,370}$=0 (estimated calculation value), $\varepsilon_{D,280}$=4964 (measured value), and $\varepsilon_{D,370}$=18982 (measured value) were used), the following characteristic values were obtained.

Antibody concentration: 1.25 mg/mL, antibody yield: 3.1 mg (78%), and average number of conjugated drug molecules (n) per antibody molecule: 3.7.

Example 26 Antibody-Drug Conjugate (25)

[Formula 95]
Process 1
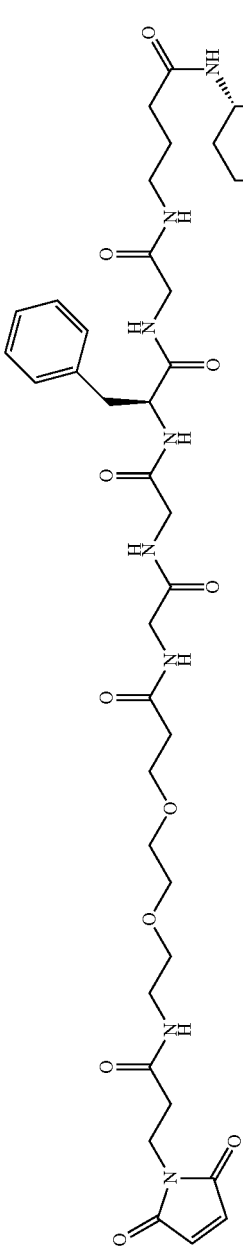
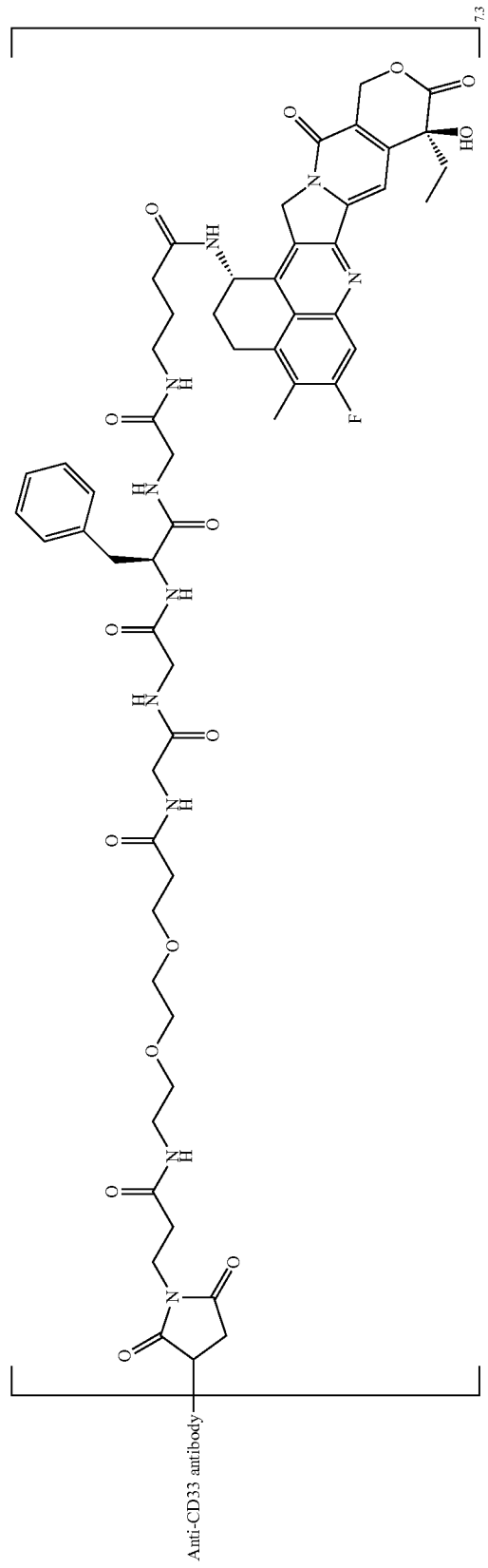

Process 1: Antibody-Drug Conjugate (25)

Reduction of the antibody: The anti-CD33 antibody produced in Reference Example 4 was prepared to have antibody concentration of 10 mg/mL with PBS6.0/EDTA by using the Common procedure B (as absorption coefficient at 280 nm, 1.66 mLmg$^{-1}$ cm$^{-1}$ was used) and Common procedure C-1 described in Production method 1. The solution (0.4 mL, 4 mg of the antibody) was placed in a 1.5 mL tube and charged with an aqueous solution of 10 mM TCEP (Tokyo Chemical Industry Co., Ltd.) (0.0129 mL; 5 equivalents per antibody molecule) and an aqueous solution of 1 M dipotassium hydrogen phosphate (Nacalai Tesque, Inc.; 0.006 mL). After confirming that the solution had pH of 7.0 f 0.1, the disulfide bond at hinge part in the antibody was reduced by incubating at 37° C. for 1 hour.

Conjugation between antibody and drug linker: After adding a dimethyl sulfoxide solution containing 10 mM of the compound obtained in Process 1 of Example 14 (0.0233 mL; 9 equivalents per antibody molecule) to the above solution at room temperature, it was stirred by using a tube rotator (MTR-103, manufactured by AS ONE Corporation) for conjugating the drug linker to the antibody at room temperature for 1 hour. Next, an aqueous solution (0.0035 mL) of 100 mM NAC (Sigma-Aldrich Co. LLC) was added thereto and further incubated to terminate the raction of drug linker at room temperature for 20 minutes.

Purification: The above solution was subjected to purification using the Common procedure D-1 (ABS was used as buffer solution) described in Production method 1 to yield 2.5 mL of a solution containing the titled antibody-drug conjugate.

Physicochemical characterization: By using the Common procedure E described in Production method 1 (as molar absorption coefficient, $\varepsilon_{A,280}=256400$ (estimated calculation value), $\varepsilon_{A,370}=0$ (estimated calculation value), $\varepsilon_{D,280}=4964$ (measured value), and $\varepsilon_{D,370}=18982$ (measured value) were used), the following characteristic values were obtained.

Antibody concentration: 1.17 mg/mL, antibody yield: 2.9 mg (73%), and average number of conjugated drug molecules (n) per antibody molecule: 7.3.

Example 27 Antibody-Drug Conjugate (26)

[Formula 96]
Process 1
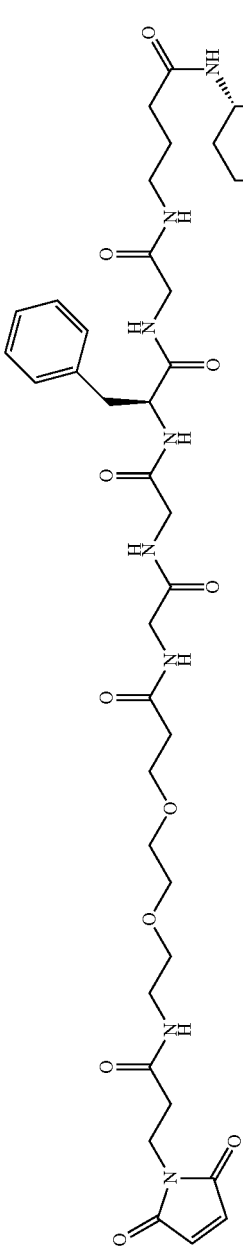
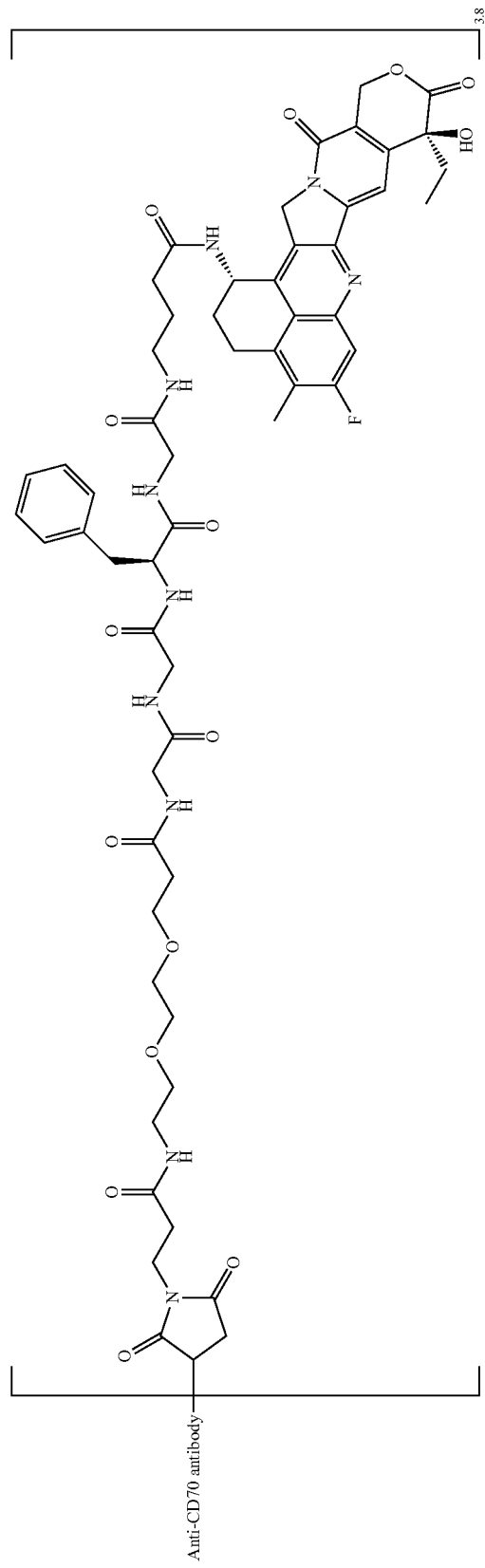

Process 1: Antibody-Drug Conjugate (26)

Reduction of the antibody: The anti-CD70 antibody produced in Reference Example 5 was prepared to have antibody concentration of 10 mg/mL with PBS6.0/EDTA by using the Common procedure B (as absorption coefficient at 280 nm, 1.69 mLmg$^{-1}$ cm$^{-1}$ was used) and Common procedure C-1 described in Production method 1. The solution (0.4 mL, 4 mg of the antibody) was placed in a 1.5 mL tube and charged with an aqueous solution of 10 mM TCEP (Tokyo Chemical Industry Co., Ltd.) (0.0065 mL; 2.5 equivalents per antibody molecule) and an aqueous solution of 1 M dipotassium hydrogen phosphate (Nacalai Tesque, Inc.; 0.0058 mL). After confirming that the solution had pH of 7.0±0.1, the disulfide bond at hinge part in the antibody was reduced by incubating at 37° C. for 1 hour.

Conjugation between antibody and drug linker: After adding dimethyl sulfoxide (0.0101 mL) and a dimethyl sulfoxide solution containing 10 mM of the compound obtained in Process 1 of Example 14 (0.0116 mL; 4.5 equivalents per antibody molecule) to the above solution at room temperature, it was stirred by using a tube rotator (MTR-103, manufactured by AS ONE Corporation) for conjugating the drug linker to the antibody at room temperature for 1 hour. Next, an aqueous solution (0.0017 mL) of 100 mM NAC (Sigma-Aldrich Co. LLC) was added thereto and further incubated to terminate the raction of drug linker at room temperature for 20 minutes.

Purification: The above solution was subjected to purification using the Common procedure D-1 (ABS was used as buffer solution) described in Production method 1 to yield 2.5 mL of a solution containing the titled antibody-drug conjugate.

Physicochemical characterization: By using the Common procedure E described in Production method 1 (as molar absorption coefficient, $\varepsilon_{A,280}$=262400 (estimated calculation value), $\varepsilon_{A,370}$=0 (estimated calculation value), $\varepsilon_{D,280}$=4964 (measured value), and $\varepsilon_{D,370}$=18982 (measured value) were used), the following characteristic values were obtained.

Antibody concentration: 1.14 mg/mL, antibody yield: 2.9 mg (71%), and average number of conjugated drug molecules (n) per antibody molecule: 3.8.

Example 28 Antibody-Drug Conjugate (27)

[Formula 97]
Process 1
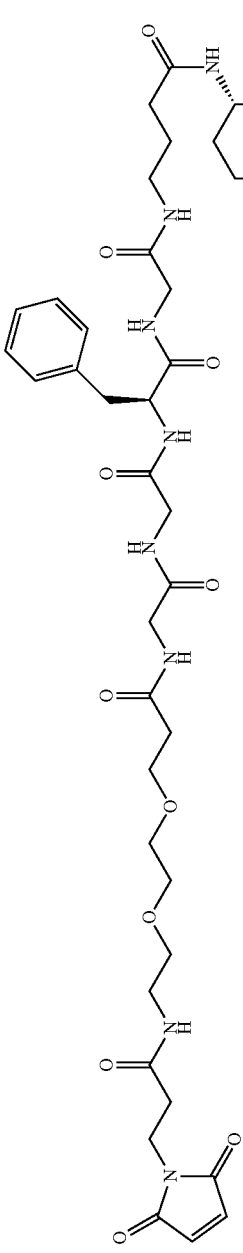
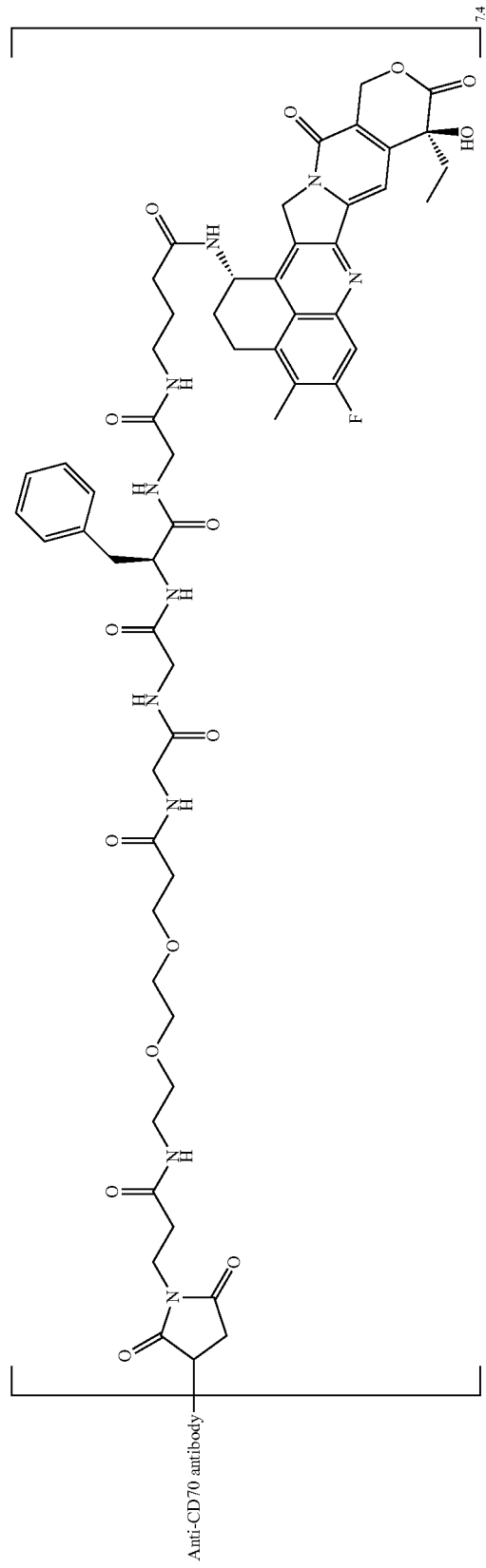

Process 1: Antibody-Drug Conjugate (27)

Reduction of the antibody: The anti-CD70 antibody produced in Reference Example 5 was prepared to have antibody concentration of 10 mg/mL with PBS6.0/EDTA by using the Common procedure B (as absorption coefficient at 280 nm, 1.69 mLmg$^{-1}$ cm$^{-1}$ was used) and Common procedure C-1 described in Production method 1. The solution (0.4 mL, 4 mg of the antibody) was placed in a 1.5 mL tube and charged with an aqueous solution of 10 mM TCEP (Tokyo Chemical Industry Co., Ltd.) (0.0129 mL; 5 equivalents per antibody molecule) and an aqueous solution of 1 M dipotassium hydrogen phosphate (Nacalai Tesque, Inc.; 0.006 mL). After confirming that the solution had pH of 7.0±0.1, the disulfide bond at hinge part in the antibody was reduced by incubating at 37° C. for 1 hour.

Conjugation between antibody and drug linker: After adding a dimethyl sulfoxide solution (0.0233 mL; 9 equivalents per antibody molecule) containing 10 mM of the compound obtained in Process 1 of Example 14 to the above solution at room temperature, it was stirred by using a tube rotator (MTR-103, manufactured by AS ONE Corporation) for conjugating the drug linker to the antibody at room temperature for 1 hour. Next, an aqueous solution (0.0035 mL) of 100 mM NAC (Sigma-Aldrich Co. LLC) was added thereto and further incubated to terminate the raction of drug linker at room temperature for 20 minutes.

Purification: The above solution was subjected to purification using the Common procedure D-1 (ABS was used as buffer solution) described in Production method 1 to yield 2.5 mL of a solution containing the titled antibody-drug conjugate.

Physicochemical characterization: By using the Common procedure E described in Production method 1 (as molar absorption coefficient, $\varepsilon_{A,280}$=262400 (estimated calculation value), $\varepsilon_{A,370}$=0 (estimated calculation value), $\varepsilon_{D,280}$=4964 (measured value), and $\varepsilon_{D,370}$=18982 (measured value) were used), the following characteristic values were obtained.

Antibody concentration: 1.13 mg/mL, antibody yield: 2.8 mg (71%), and average number of conjugated drug molecules (n) per antibody molecule: 7.4.

Example 29 Antibody-Drug Conjugate (28)

[Formula 98]

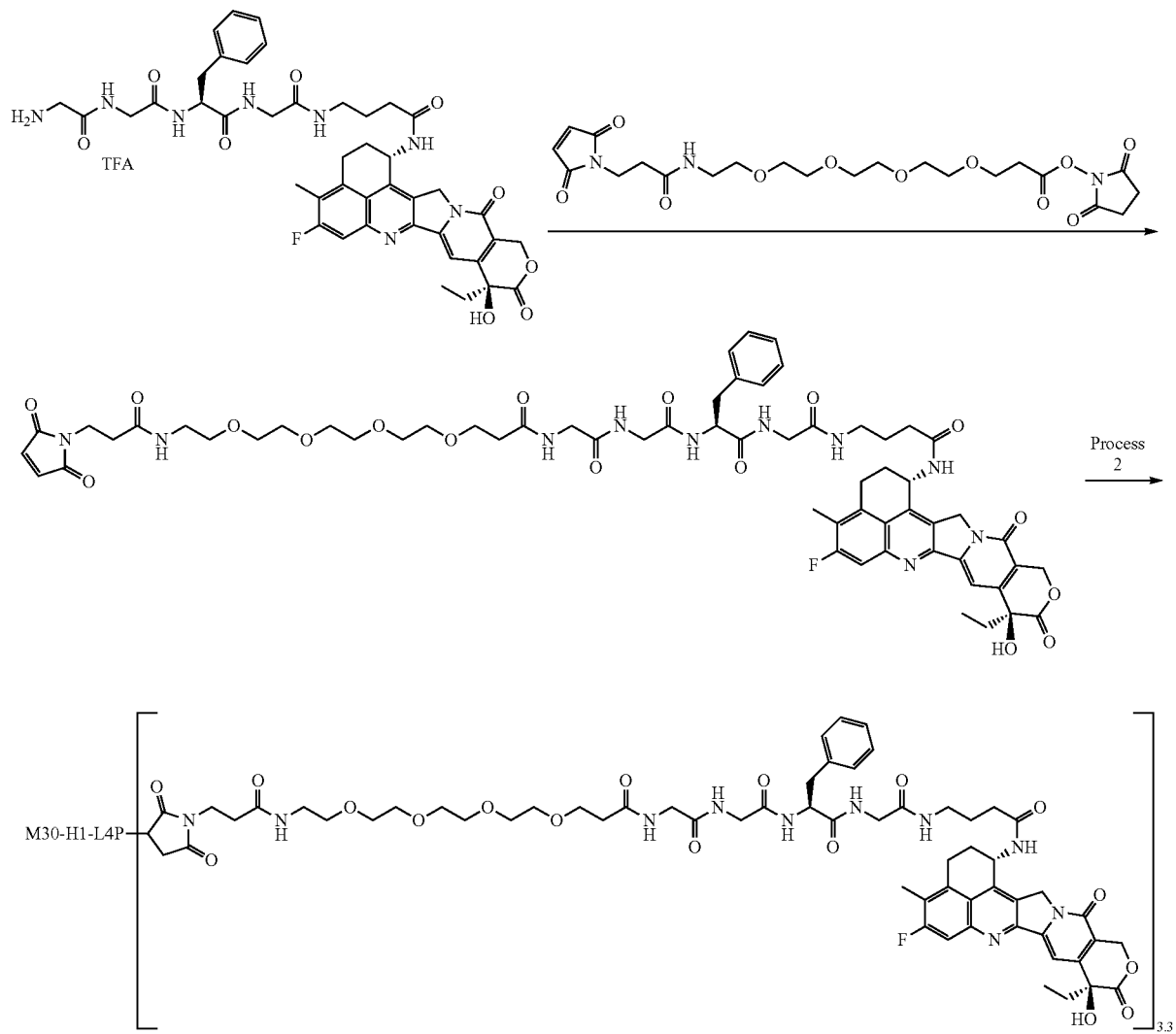

Process 1: N-[19-(2,5-dioxo-2,5-dihydro-1H-pyrrol-1-yl)-17-oxo-4,7,10,13-tetraoxo-16-azanonadecan-1-oyl]glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (90 mg, 0.107 mmol) obtained in Process 2 of Example 2 was reacted in the same manner as Process 3 of Example 2 by using diisopropylethylamine (18.7 μL, 0.107 mmol) instead of triethylamine and N-succinimidyl 1-maleinimide-3-oxo-7,10,13,16-tetraoxa-4-azanonadecan-19-oate (55.1 mg, 0.107 mmol) instead of N-succinimidyl 6-maleimide hexanoate to yield the titled compound as a pale yellow solid (50 mg, 37%).

$^1$H-NMR (400 MHz, DMSO-$d_6$) δ: 0.85 (3H, t, J=7.2 Hz), 1.64-1.74 (2H, m), 1.77-1.90 (2H, m), 2.06-2.19 (4H, m), 2.27-2.32 (2H, m), 2.33-2.37 (2H, m), 2.38 (3H, s), 2.72-2.80 (3H, m), 2.96-3.19 (6H, m), 3.39-3.48 (10H, m), 3.52-3.75 (10H, m), 4.39-4.48 (1H, m), 5.14 (1H, d, J=18.8 Hz), 5.23 (1H, d, J=18.8 Hz), 5.38 (1H, d, J=17.0 Hz), 5.42 (1H, d, J=17.0 Hz), 5.52-5.58 (1H, m), 6.52 (1H, s), 6.98 (1H, s), 7.13-7.24 (5H, m), 7.29 (1H, s), 7.69 (1H, t, J=5.5 Hz), 7.78 (1H, d, J=10.9 Hz), 7.98-8.03 (2H, m), 8.10 (1H, d, J=7.8 Hz), 8.16 (1H, t, J=5.7 Hz), 8.23 (1H, t, J=5.7 Hz), 8.44 (1H, d, J=8.6 Hz).

MS (APCI) m/z: 1237 (M+H)$^+$

Process 2: Antibody-Drug Conjugate (28)

Reduction of the antibody: The M30-H1-L4P antibody produced in Reference Example 2 was prepared to have antibody concentration of 10 mg/mL by replacing the medium with PBS6.0/EDTA by using the Common procedure C-1 and Common procedure B (as absorption coefficient at 280 nm, 1.61 mLmg$^{-1}$ cm$^{-1}$ was used) described in Production method 1. The solution (1.25 mL) was placed in a 1.5 mL polypropylene tube and charged with an aqueous solution of 10 mM TCEP (Tokyo Chemical Industry Co., Ltd.) (0.025 mL; 3.0 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding dimethyl sulfoxide (Sigma-Aldrich Co. LLC; 0.102 mL) and a dimethyl sulfoxide solution containing 10 mM of the compound obtained in above Process 1 (0.047 mL; 5.5 equivalents per antibody molecule) to the above solution at room temperature, it was stirred by using a tube rotator (MTR-103, manufactured by AS ONE Corporation) for conjugating the drug linker to the antibody at room temperature for 40 minutes. Next, an aqueous solution (0.009 mL) of 100 mM NAC (Sigma-Aldrich Co. LLC) was added thereto and stirred to terminate the raction of drug linker at room temperature for another 20 minutes.

Purification: The above solution was subjected to purification using the Common procedure D-1 (ABS was used as buffer solution) described in Production method 1 to yield 6 mL of a solution containing the titled antibody-drug conjugate. After that, the solution was concentrated by the Common procedure A.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\alpha_{D,280}$=5000 (measured average value), and $\varepsilon_{D,370}$=19000 (measured average value) were used), the following characteristic values were obtained.

Antibody concentration: 13.60 mg/mL, antibody yield: 9.5 mg (76%), and average number of conjugated drug molecules (n) per antibody molecule: 3.3.

Example 30 Antibody-Drug Conjugate (29)

[Formula 99]

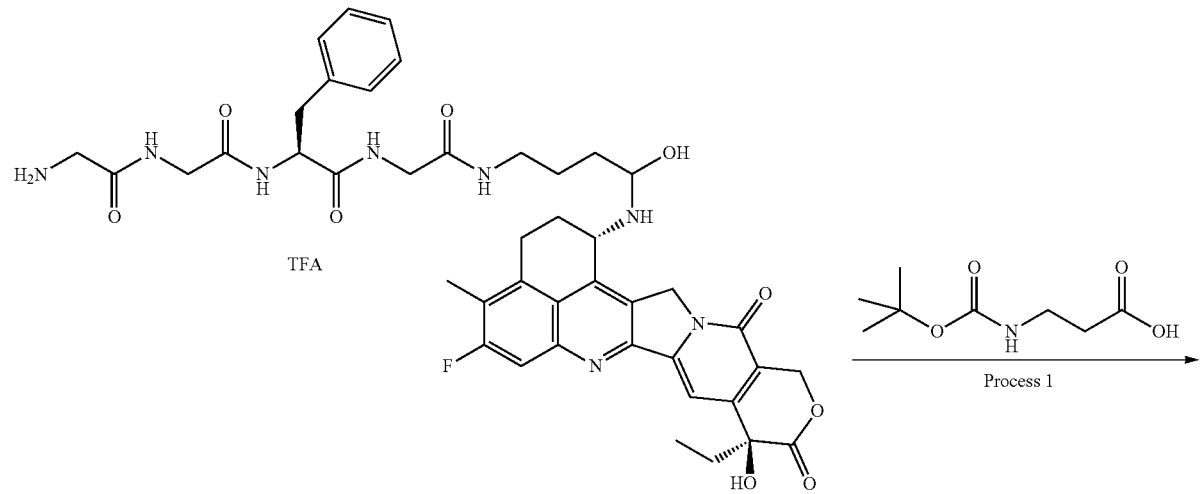

-continued
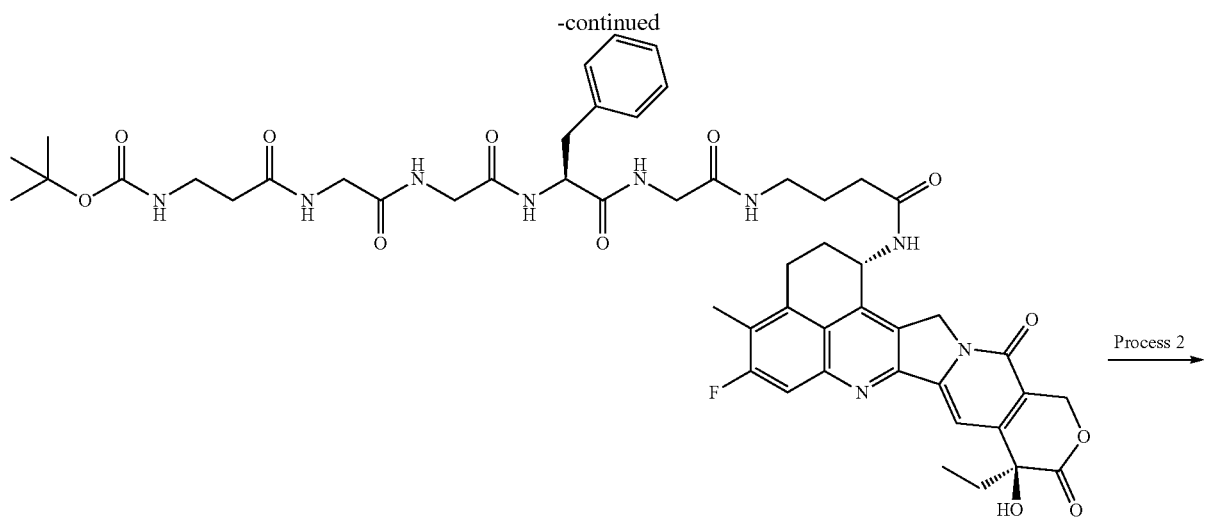
Process 2 →
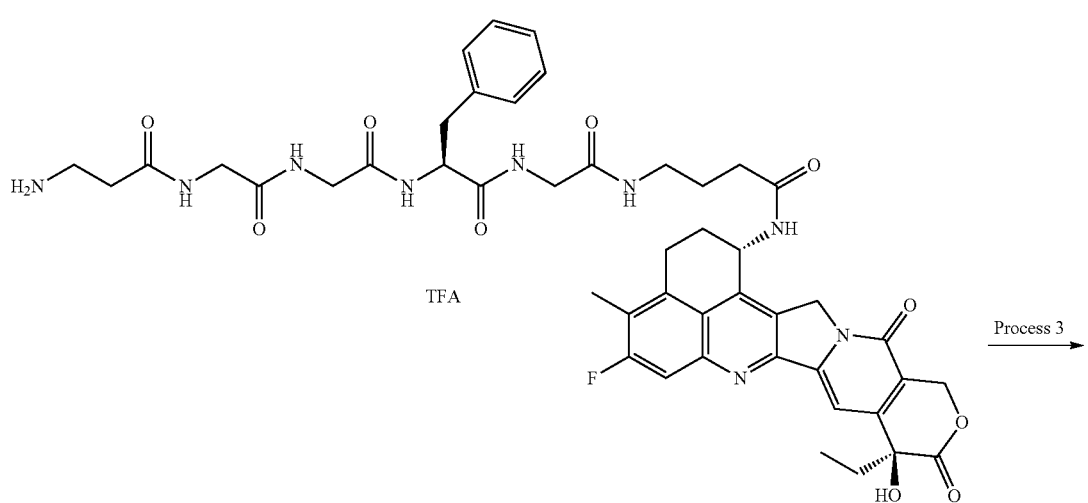
TFA
Process 3 →
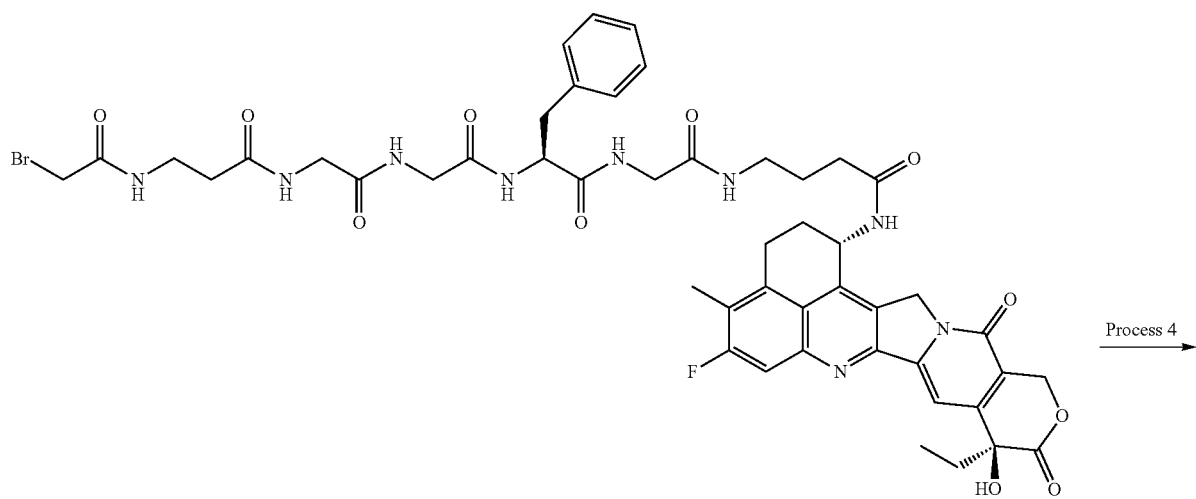
Process 4 →

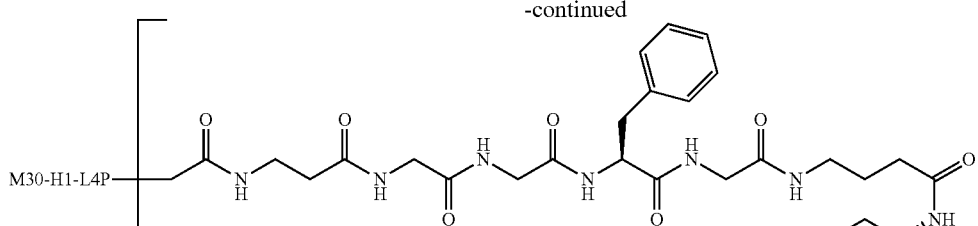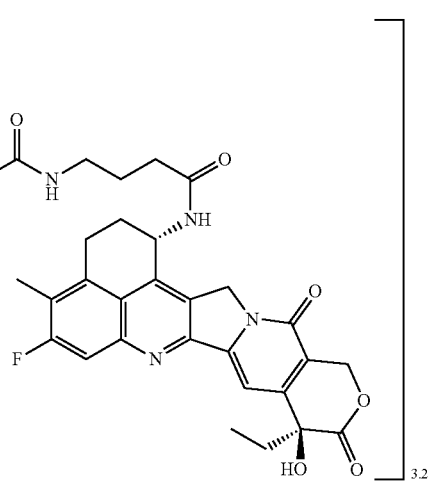

Process 1: N-(tert-butoxycarbonyl)-β-alanylglycyl-glycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (0.839 g, 1.00 mmol) obtained in Process 2 of Example 2 was reacted in the same manner as Process 1 of Example 1 by using N-(tert-butoxycarbonyl)-β-alanine instead of 4-(tert-butoxycarbonylamino)butanoic acid. The crude product obtained was used in the next process without purification.

Process 2: 3-Alanylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The crude product obtained in Process 1 above was reacted in the same manner as Process 2 of Example 2 to yield the titled compound as a pale yellow solid (0.610 g, 67%).

$^1$H-NMR (400 MHz, DMSO-d$_6$) δ: 0.87 (3H, t, J=7.4 Hz), 1.67-1.77 (2H, m), 1.79-1.92 (2H, m), 2.09-2.22 (4H, m), 2.40 (3H, s), 2.46-2.55 (2H, m), 2.82-2.73 (1H, m), 2.95-3.13 (5H, m), 3.14-3.21 (2H, m), 3.55-3.80 (6H, m), 4.44-4.52 (1H, m), 5.20 (2H, dd, J=35.0, 19.0 Hz), 5.42 (2H, s), 5.53-5.60 (1H, m), 6.54 (1H, s), 7.14-7.28 (5H, m), 7.31 (1H, s), 7.67 (2H, brs), 7.72-7.78 (1H, m), 7.80 (1H, d, J=11.0 Hz), 8.10-8.17 (2H, m), 8.29 (1H, t, J=5.9 Hz), 8.42 (1H, t, J=5.7 Hz), 8.47 (1H, d, J=8.6 Hz).

Process 3: N-(bromoacetyl)-β-alanylglycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide To a dichloromethane (4.5 mL) solution of 2-bromoacetic acid (96.3 mg, 0.693 mmol), N-hydroxysuccinimide (79.7 mg, 0.693 mmol) and 1,3-diisopropylcarbodiimide (0.107 mL, 0.693 mmol) were added and stirred at room temperature. The reaction solution was added to an N,N-dimethylformamide (4.5 mL) solution of the compound (473 mg, 0.462 mmol) obtained in Process 2 above and triethylamine (0.154 mL, 1.11 mmol) at 0° C. and stirred at room temperature for 1 hour.

The reaction solution was purified by silica gel column chromatography [elution solvent:chloroform-chloroform:methanol=85:15 (v/v)]. The obtained solid was washed with chloroform:methanol:diethyl ether mixed solvent to yield the titled compound as a pale yellow solid (191 mg, 40%).

$^1$H-NMR (400 MHz, DMSO-d$_6$) δ: 0.87 (3H, t, J=7.4 Hz), 1.67-1.77 (2H, m), 1.79-1.92 (2H, m), 2.08-2.22 (4H, m), 2.33 (2H, t, J=7.0 Hz), 2.40 (3H, s), 2.74-2.83 (1H, m), 2.99-3.12 (3H, m), 3.14-3.21 (2H, m), 3.24-3.30 (2H, m), 3.56-3.77 (6H, m), 3.82 (2H, s), 4.41-4.51 (1H, m), 5.20 (2H, q, J=18.9 Hz), 5.42 (2H, s), 5.54-5.60 (1H, m), 6.54 (1H, s), 7.15-7.27 (5H, m), 7.31 (1H, s), 7.69-7.74 (1H, m), 7.80 (1H, d, J=10.9 Hz), 8.06 (1H, t, J=5.7 Hz), 8.13 (1H, d, J=7.8 Hz), 8.21-8.34 (3H, m), 8.46 (1H, d, J=8.6 Hz).

MS (ESI) m/z: 1030, 1032 (M+H)$^+$

Process 4: Antibody-Drug Conjugate (29)

Reduction of the antibody: The M30-H1-L4P antibody produced in Reference Example 2 was prepared to have antibody concentration of 10 mg/mL by replacing the medium with PBS6.0/EDTA by using the Common procedure C-1 and Common procedure B (as absorption coefficient at 280 nm, 1.61 mLmg$^{-1}$ cm$^{-1}$ was used) described in Production method 1. The solution (1.25 mL) was placed in a 1.5 mL polypropylene tube and charged with an aqueous solution of 10 mM TCEP (Tokyo Chemical Industry Co., Ltd.) (0.025 mL; 3.0 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding dimethyl sulfoxide (Sigma-Aldrich Co. LLC; 0.09 mL) and a dimethyl sulfoxide solution containing 10 mM of the compound obtained in Process 3 (0.059 mL; 7.0 equivalents per antibody molecule) to the above solution at room temperature, it was stirred by using a tube rotator (MTR-103, manufactured by AS ONE Corporation) for conjugating the drug linker to the antibody at room temperature for 40 minutes. Next, an aqueous solution (0.009 mL) of 100 mM NAC (Sigma-Aldrich Co. LLC) was added thereto and stirred to terminate the raction of drug linker at room temperature for another 20 minutes.

Purification: The above solution was subjected to purification using the Common procedure D-1 (ABS was used as buffer solution) described in Production method 1 to yield 6 mL of a solution containing the titled antibody-drug conjugate. After that, the solution was concentrated by the Common procedure A.

Physicochemical characterization: By using the Common procedure E described in Production method 1 (as molar absorption coefficient, $\varepsilon_{A,260}=235300$ (estimated calculation value), $\varepsilon_{A,370}=0$ (estimated calculation value), $\varepsilon_{D,280}=5000$ (measured average value), and $\varepsilon_{D,370}=19000$ (measured average value) were used), the following characteristic values were obtained.

Antibody concentration: 13.9 mg/mL, antibody yield: 9.7 mg (78%), and average number of conjugated drug molecules (n) per antibody molecule: 3.2.

Example 31 Antibody-Drug Conjugate (30)

Process 1

[Formula 100]

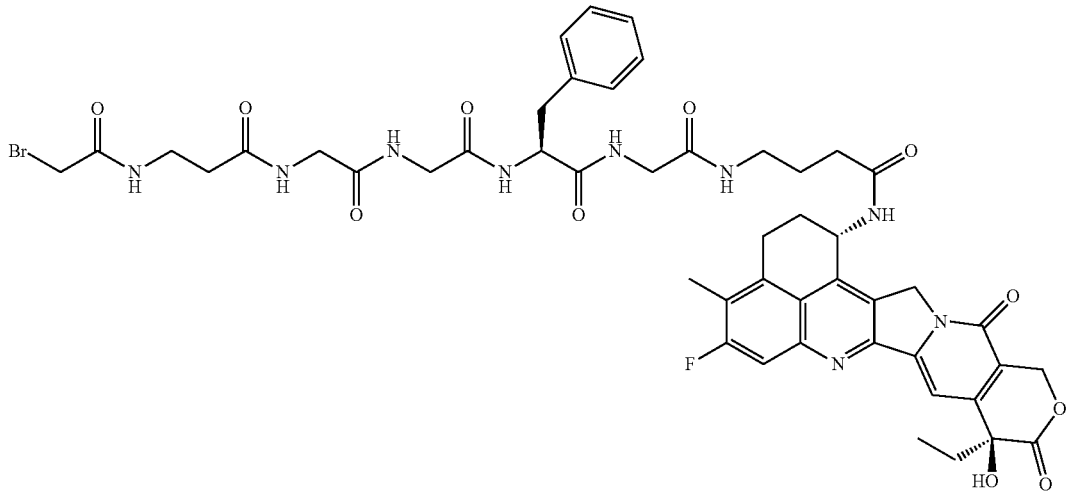

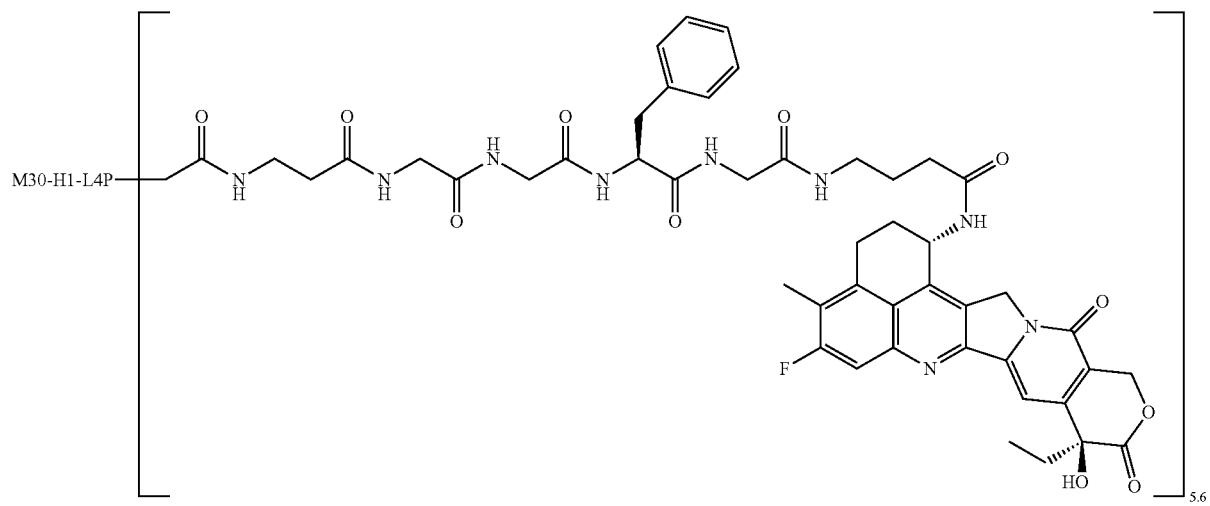

By using the M30-H1-L4P antibody produced in Reference Example 2 and the compound obtained in Process 3 of Example 30, the titled antibody-drug conjugate was obtained in the same manner as Process 1 of Example 4.

Antibody concentration: 1.94 mg/mL, antibody yield: 11.64 mg (93%), and average number of conjugated drug molecules (n) per antibody molecule: 5.6.

Example 32 Antibody-Drug Conjugate (31)

Process 1

[Formula 101]

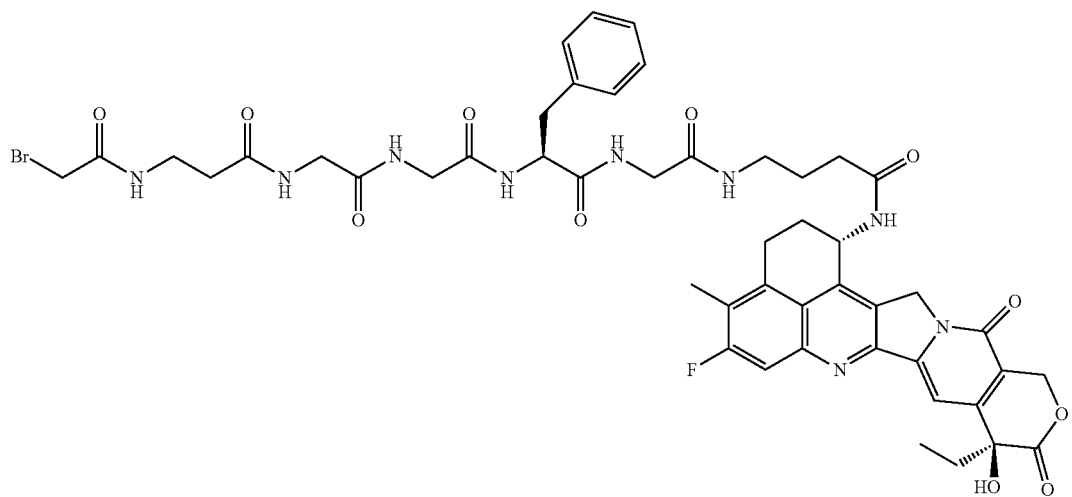

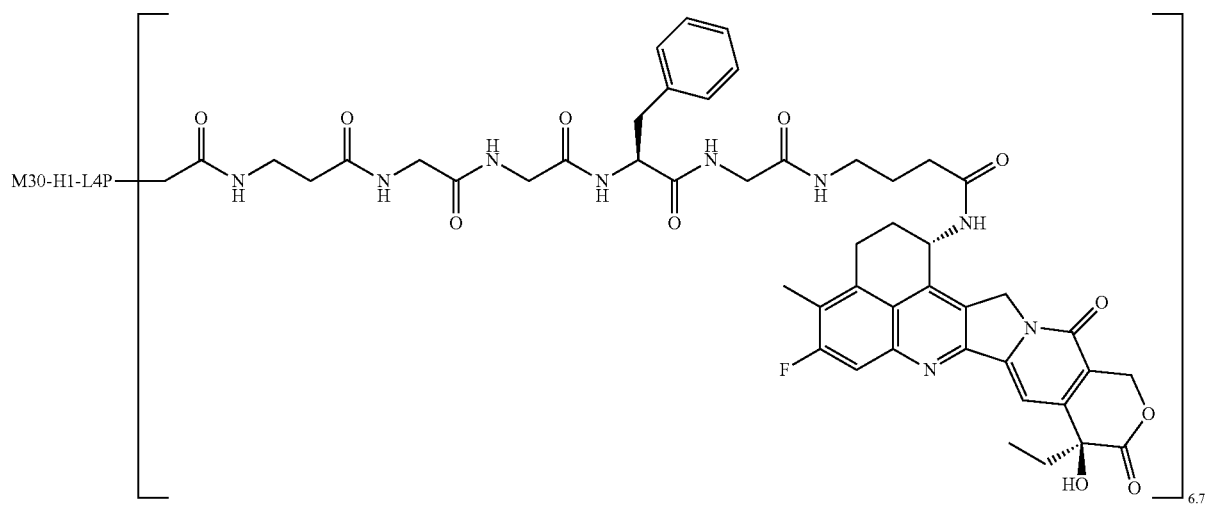

Process 1: Antibody-Drug Conjugate (31)

By using the M30-H1-L4P antibody produced in Reference Example 2 and the compound obtained in Process 3 of Example 30, the titled antibody-drug conjugate was obtained in the same manner as Process 1 of Example 5.

Antibody concentration: 1.90 mg/mL, antibody yield: 11.40 mg (91%), and average number of conjugated drug molecules (n) per antibody molecule: 6.7.

Example 33 Antibody-Drug Conjugate (32)

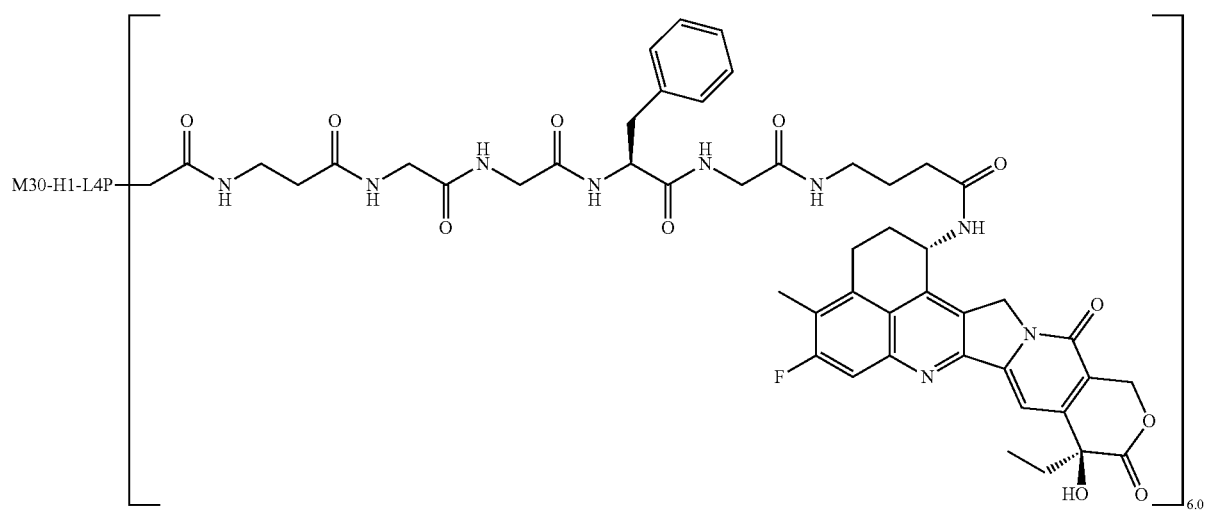

[Formula 102]

Almost the whole amounts of the antibody-drug conjugates of Examples 31 and 32 were mixed and the solution was concentrated by the Common procedure A to yield the titled antibody-drug conjugate.

Antibody concentration: 10.0 mg/mL, antibody yield: 21.06 mg, and average number of conjugated drug molecules (n) per antibody molecule: 6.0.

Example 34 Antibody-Drug Conjugate (33)

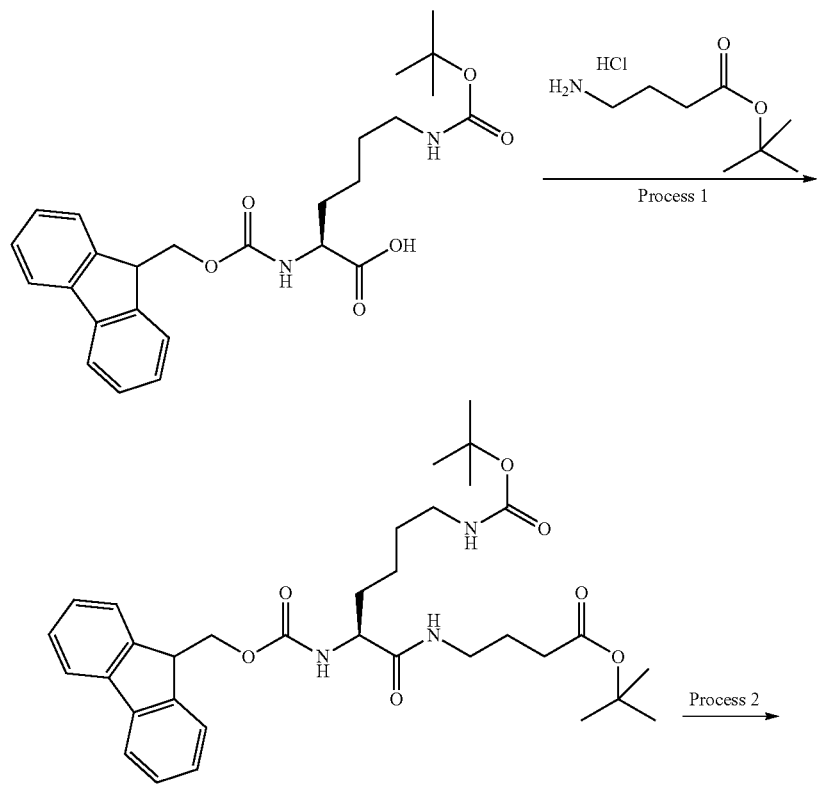

[Formula 103]

-continued
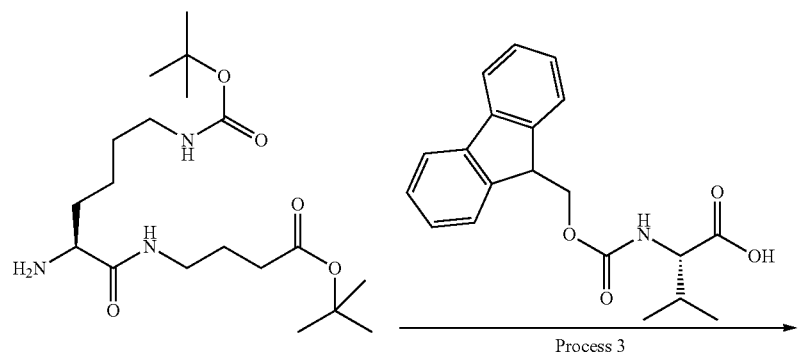
Process 3
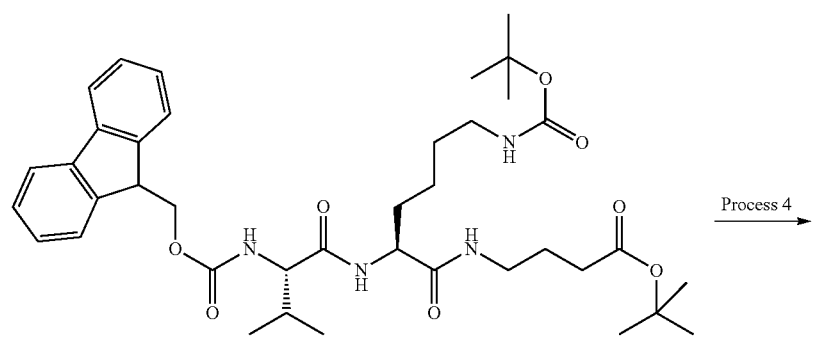
Process 4
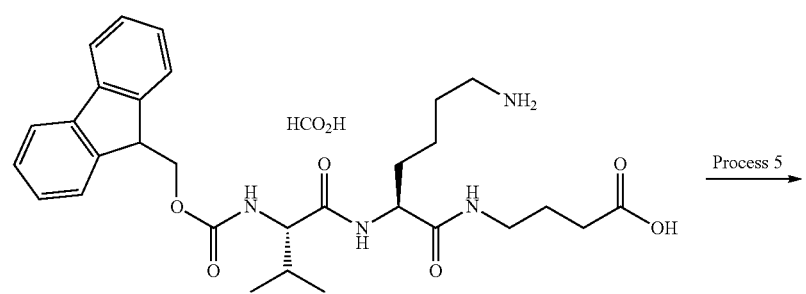
Process 5
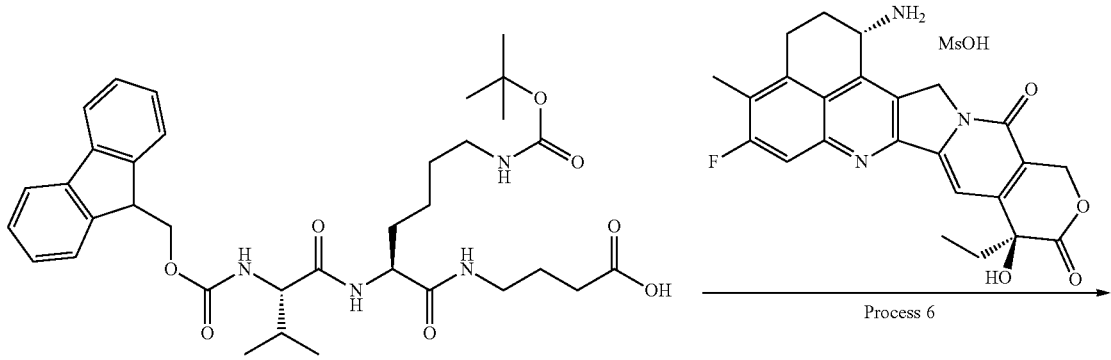
Process 6

-continued
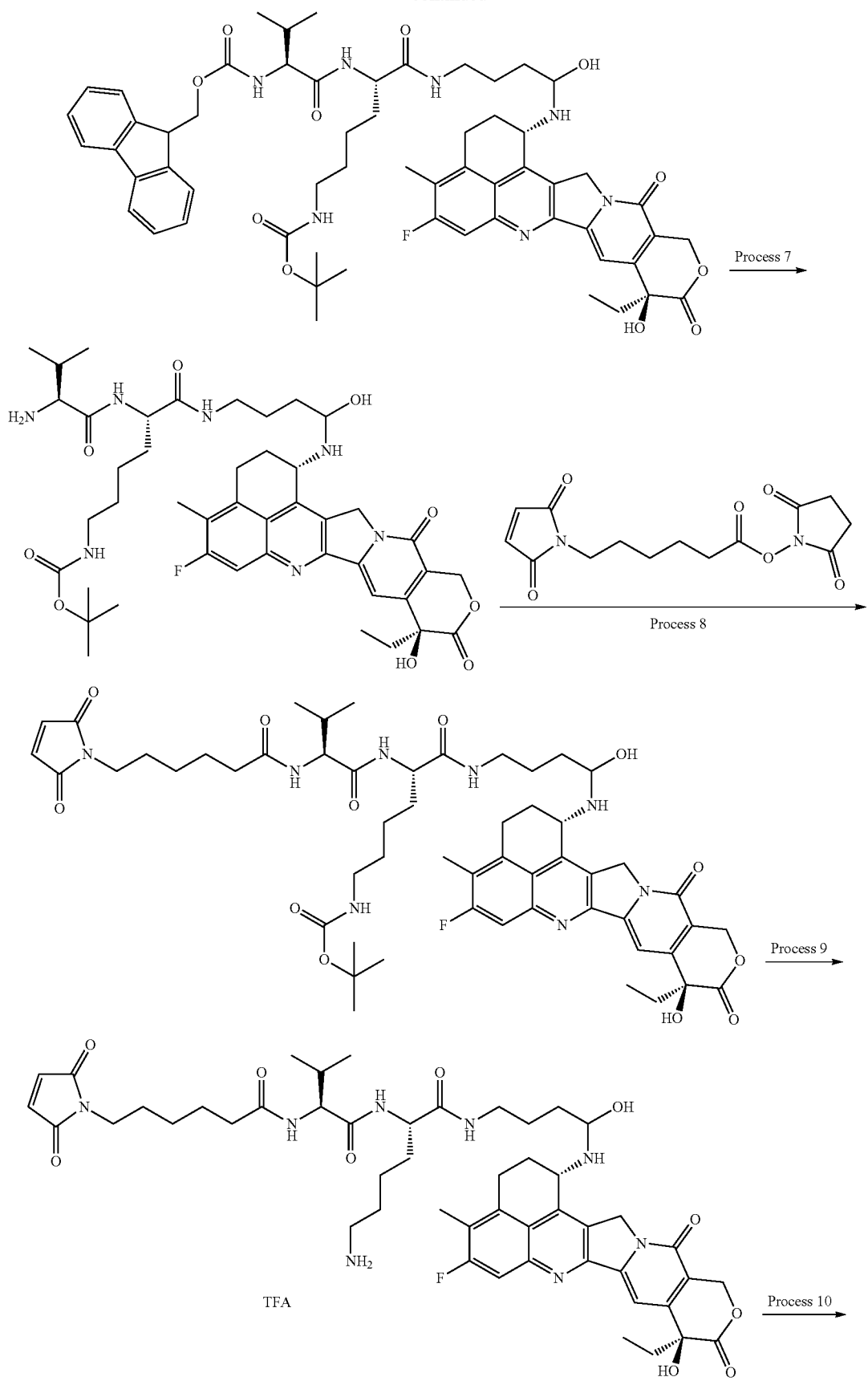

-continued

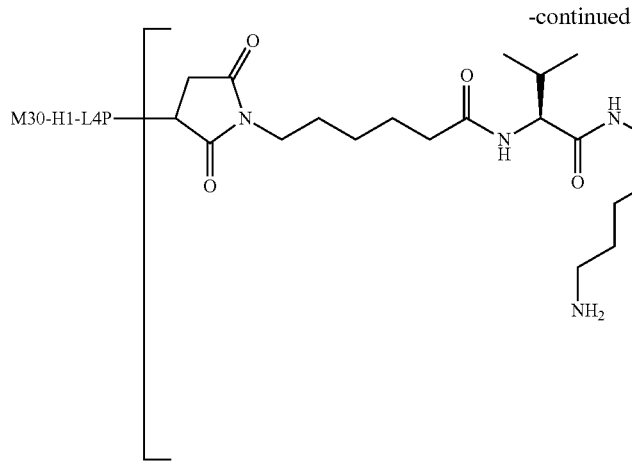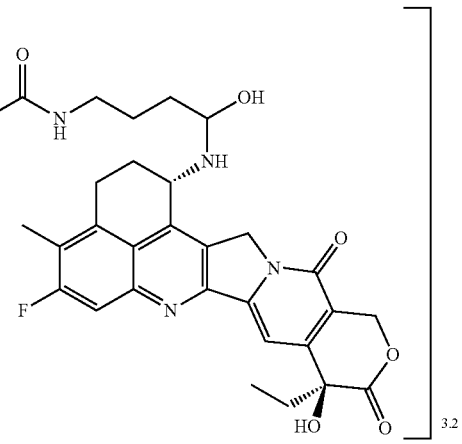

Process 1: tert-Butyl 4-({N⁶-(tert-butoxycarbonyl)-N²-[(9H-fluoren-9-ylmethoxy)carbonyl]-L-lysyl}amino) butanoate To an N,N-dimethylformamide (10.0 mL) solution of N-(tert-butoxycarbonyl)-N^α-[(9H-fluoren-9-ylmethoxy)carbonyl]-L-lysine (1.00 g, 2.14 mmol), N-hydroxysuccinimide (0.370 g, 3.20 mmol), and tert-butyl 4-aminobutanoic acid ester hydrochloride (0.830 g, 4.27 mmol), 1-ethyl-3-(3-dimethylaminopropyl)carbodiimide hydrochloride (0.610 g, 3.20 mmol) and N,N-diisopropylethylamine (0.410 ml, 2.35 mmol) were added and stirred at room temperature for 3 days. The reaction solution was diluted with ethyl acetate and washed with an aqueous solution of 10% citric acid and a saturated aqueous solution of sodium hydrogen carbonate, and saturated brine, and then the organic layer was dried over anhydrous magnesium sulfate. The solvent was removed under reduced pressure to yield the titled compound as a colorless solid (1.35 g, quantitative).

¹H-NMR (400 MHz, DMSO-d₆) δ: 1.14-1.42 (4H, m), 1.36 (9H, s), 1.37 (9H, s), 1.48-1.67 (4H, m), 2.18 (2H, t, J=7.6 Hz), 2.84-2.93 (2H, m), 2.99-3.11 (2H, m), 3.84-3.94 (1H, m), 4.18-4.30 (3H, m), 6.76 (1H, t, J=5.4 Hz), 7.33 (2H, t, J=7.3 Hz), 7.39-7.45 (3H, m), 7.73 (2H, dd, J=7.3, 2.7 Hz), 7.85-7.92 (3H, m).

Process 2: Tert-butyl 4-([N⁶-(tert-butoxycarbonyl)-L-lysyl]amino)butanoate

To an N,N-dimethylformamide (8.00 mL) solution of the compound (1.35 g, 2.22 mmol) obtained in Process 1 above, piperidine (2.00 mL) was added and stirred at room temperature for 1.5 hours. The solvent was removed under reduced pressure to yield a mixture containing the titled compound. The mixture was used for the next reaction without further purification.

Process 3: N-[(9H-fluoren-9-ylmethoxy)carbonyl]-L-valyl-N⁶-(tert-butoxycarbonyl)-N-(4-tert-butoxy-4-oxobutyl)-L-lysinamide To an N,N-dimethylformamide (30.0 mL) solution of the mixture (2.22 mmol) obtained in Process 2 above, N-[(9H-fluoren-9-ylmethoxy)carbonyl]-L-valine (1.13 g, 3.32 mmol), N-hydroxysuccinimide (0.310 g, 2.66 mmol), and 1-ethyl-3-(3-dimethylaminopropyl)carbodiimide hydrochloride (0.550 g, 2.88 mmol) were added and stirred at room temperature for 18 hours. The reaction solution was diluted with ethyl acetate and washed with a saturated aqueous solution of sodium hydrogen carbonate and saturated brine, and then the organic layer was dried over anhydrous magnesium sulfate. The solvent was removed under reduced pressure and the residues obtained were purified by silica gel column chromatography [chloroform-chloroform:methanol=9:1 (v/v)] to yield the titled compound as a colorless solid (0.363 g, 23%).

¹H-NMR (400 MHz, DMSO-d₆) δ: 0.84 (6H, t, J=6.0 Hz), 1.12-1.64 (8H, m), 1.34 (9H, s), 1.38 (9H, s), 1.90-2.04 (1H, m), 2.17 (2H, t, J=7.3 Hz), 2.79-2.90 (2H, m), 2.99-3.09 (2H, m), 3.83-3.91 (1H, m), 4.08-4.44 (4H, m), 6.71 (1H, t, J=5.4 Hz), 7.32 (2H, t, J=7.3 Hz), 7.42 (3H, t, J=7.3 Hz), 7.74 (2H, t, J=7.0 Hz), 7.85-7.91 (4H, m).

MS (ESI) m/z: 709 (M+H)⁺

Process 4: N-[(9H-fluoren-9-ylmethoxy)carbonyl]-L-valyl-N-(3-carboxypropyl)-L-lysinamide formate To the compound (0.363 mg, 0.512 mmol) obtained in Process 3 above, formic acid (10.0 ml) was added and stirred at room temperature for 4 hours. The solvent was removed under reduced pressure to yield the titled compound. The compound was used for the next reaction without further purification.

Process 5: N-[(9H-fluoren-9-ylmethoxy)carbonyl]-L-valyl-N⁶-(tert-butoxycarbonyl)-N-(3-carboxypropyl)-L-lysinamide To 1,4-dioxane (5.00 mL) suspension of the compound (0.512 mmol) obtained in Process 4 above, a saturated aqueous solution of sodium hydrogen carbonate (20.0 ml) and di-tert-butyl dicarbonate (0.178 ml, 0.769 mmol) were added and stirred at room temperature for 3 hours. The reaction solution was diluted with ethyl acetate and washed with an aqueous solution of 10% citric acid and saturated brine, and then the organic layer was dried over anhydrous magnesium sulfate. The solvent was removed under reduced pressure to yield the titled compound as a colorless solid (0.295 g, 88%).

¹H-NMR (400 MHz, DMSO-d₆) δ: 0.84 (6H, t, J=6.7 Hz), 1.13-1.39 (4H, m), 1.35 (9H, s), 1.48-1.62 (4H, m), 1.91-2.04 (1H, m), 2.20 (2H, t, J=7.3 Hz), 2.80-2.89 (2H, m), 2.99-3.11 (2H, m), 3.87 (1H, dd, J=8.5, 6.7 Hz), 4.06-4.35

(4H, m), 6.71 (1H, t, J=6.0 Hz), 7.32 (2H, t, J=7.6 Hz), 7.39-7.46 (3H, m), 7.74 (2H, t, J=7.6 Hz), 7.83-7.94 (4H, m).
MS (ESI) m/z: 653 (M+H)$^+$

Process 6: N-[(9H-fluoren-9-ylmethoxy)carbonyl]-L-valyl-N$^6$-(tert-butoxycarbonyl)-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)-L-lysinamide Mesylate of the compound (4) (0.240 g, 0.452 mmol) was reacted in the same manner as Process 1 of Example 1 by using the compound (0.295 g, 0.452 mmol) obtained in Process 5 above instead of 4-(tert-butoxycarbonylamino) butanoic acid to yield the titled compound as a pale orange solid (0.208 g, 43%).
MS (ESI) m/z: 1071 (M+H)$^+$ Process 7: L-Valyl-N$^6$-(tert-butoxycarbonyl)-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)-L-lysinamide The compound (0.208 g, 0.194 mmol) obtained in Process 6 above was reacted in the same manner as Process 2 to yield a mixture containing the titled compound. The mixture was used for the next reaction without further purification.

Process 8: N-[6-(2,5-dioxo-2,5-dihydro-1H-pyrrol-1-yl)hexanoyl]-L-valyl-N$^6$-(tert-butoxycarbonyl)-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)-L-lysinamide The mixture (0.194 mmol) obtained in Process 7 above was reacted in the same manner as Process 3 of Example 2 to yield the titled compound as a pale yellow solid (0.133 g, 56%).
$^1$H-NMR (400 MHz, DMSO-d$_6$) δ: 0.77 (6H, t, J=5.7 Hz), 0.87 (3H, t, J=7.3 Hz), 1.14-1.71 (10H, m), 1.35 (9H, s), 1.77-1.95 (3H, m), 2.02-2.23 (7H, m), 2.40 (3H, s), 2.84 (3H, q, J=6.4 Hz), 3.05 (2H, d, J=6.7 Hz), 3.17 (2H, s), 3.26-3.39 (3H, m), 4.01-4.16 (2H, m), 5.15 (1H, d, J=18.7 Hz), 5.24 (1H, d, J=18.7 Hz), 5.36-5.48 (2H, m), 5.51-5.60 (1H, m), 6.52 (1H, s), 6.72 (1H, t, J=6.0 Hz), 6.99 (2H, s), 7.31 (1H, s), 7.71-7.85 (5H, m), 8.41 (1H, d, J=9.1 Hz).
MS (ESI) m/z: 1041 (M+H)$^+$ Process 9: N-[6-(2,5-dioxo-2,5-dihydro-1H-pyrrol-1-yl)hexanoyl]-L-valyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)-L-lysinamide trifluoroacetate To a dichloromethane (10.0 ml) solution of the compound (0.110 mg, 0.106 mmol) obtained in Process 8 above, trifluoroacetic acid (4.00 ml) was added and stirred at room temperature for 5 hours. The solvent was removed under reduced pressure to yield the titled compound as a pale yellow solid (70.0 mg, 64%).
$^1$H-NMR (400 MHz, DMSO-d$_6$) δ: 0.76-0.81 (6H, m), 0.87 (3H, t, J=7.3 Hz), 1.12-1.31 (4H, m), 1.39-1.56 (8H, m), 1.57-1.74 (3H, m), 1.79-1.96 (3H, m), 2.06-2.18 (7H, m), 2.40 (3H, s), 2.70-2.80 (2H, m), 3.01-3.10 (2H, m), 3.13-3.22 (2H, m), 4.04 (1H, t, J=7.6 Hz), 4.10-4.20 (1H, m), 5.15 (1H, d, J=18.7 Hz), 5.24 (1H, d, J=18.7 Hz), 5.36-5.47 (2H, m), 5.52-5.60 (1H, m), 6.53 (1H, s), 7.00 (2H, s), 7.32 (1H, s), 7.61 (3H, brs), 7.75-7.88 (4H, m), 8.43 (1H, d, J=8.5 Hz).
MS (ESI) m/z: 941 (M+H)$^+$ Process 10: Antibody-Drug Conjugate (33)

By using the M30-H1-L4P antibody produced in Reference Example 2 and the compound obtained in Process 9 above, the titled antibody-drug conjugate was obtained in the same manner as Process 2 of Example 29. Antibody concentration: 12.0 mg/mL, antibody yield: 8.4 mg (67%), and average number of conjugated drug molecules (n) per antibody molecule: 3.2.

Example 35 Antibody-Drug Conjugate (34)

[Formula 104]

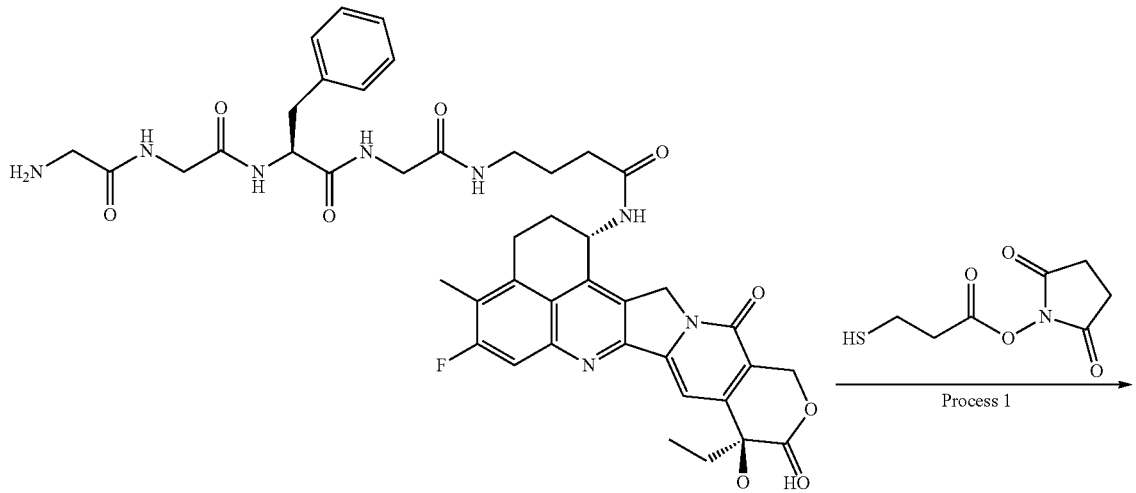

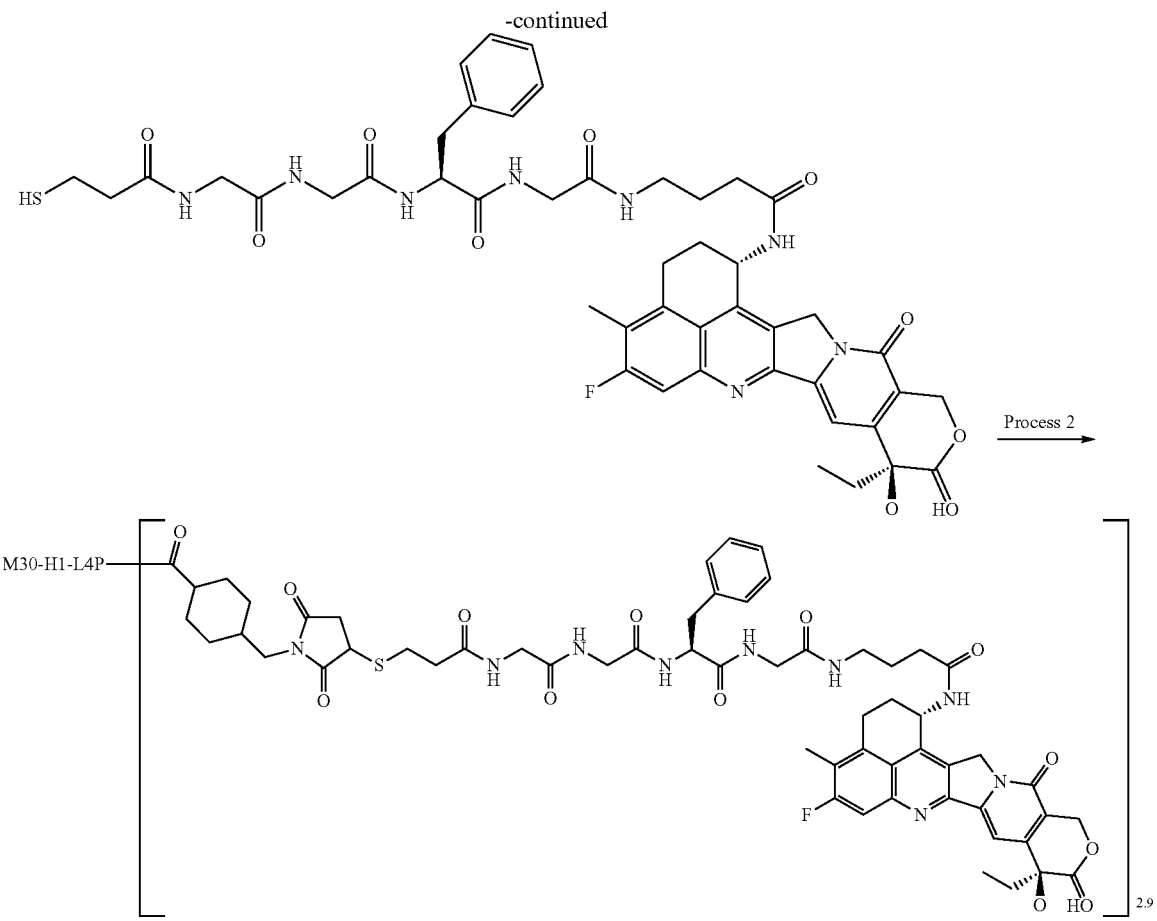

Process 1: N-(3-sulfanylpropanoyl)glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (84.0 mg, 0.100 mmol) obtained in Process 2 of Example 2 was reacted in the same manner as Process 3 of Example 2 by using N-succinimidyl 3-mercaptopropionate instead of N-succinimidyl 6-maleimide hexanoate to yield the titled compound as a pale yellow solid (61.2 mg, 66%).

$^1$H-NMR (DMSO-D$_6$) δ: 0.87 (3H, t, J=7.4 Hz), 1.77-1.66 (2H, m), 1.79-1.92 (2H, m), 2.07-2.24 (4H, m), 2.31-2.47 (3H, m), 2.40 (3H, s), 2.59-2.69 (2H, m), 2.78 (1H, dd, J=13.7, 9.8 Hz), 2.98-3.13 (3H, m), 3.14-3.23 (2H, m), 3.54-3.79 (6H, m), 4.40-4.50 (1H, m), 5.20 (2H, dd, J=36.8, 19.2 Hz), 5.36-5.47 (2H, m), 5.52-5.63 (1H, m), 6.54 (1H, s), 7.14-7.28 (5H, m), 7.31 (1H, s), 7.68-7.74 (1H, m), 7.80 (1H, d, J=10.9 Hz), 8.03-8.09 (1H, m), 8.13 (1H, d, J=7.8 Hz), 8.19-8.29 (2H, m), 8.46 (1H, d, J=8.6 Hz).

MS (ESI) m/z: 927 (M+H)$^+$

Process 2: Antibody-Drug Conjugate (34)

SMCC derivatization of antibody: The M30-H1-L4P antibody produced in Reference Example 2 was prepared to have antibody concentration of 20 mg/mL by replacing the medium with PBS6.5/EDTA by using the Common procedure C-2 and Common procedure B (as absorption coefficient at 280 nm, 1.61 mLmg$^{-1}$ cm$^{-1}$ was used). The solution (0.25 mL) was placed in a 1.5 mL tube, charged with DMSO solution (0.0063 mL; which corresponds to about 2.55 equivalents per antibody molecule) containing 27.6 mM succinimidyl-4-(N-maleimidomethyl)cyclohexane-1-carboxylate (SMCC, Thermo Fisher Scientific Inc.) at room temperature, and reacted at room temperature for 2 hours. This reaction solution was subjected to purification using the Common procedure D-2 to yield 0.7 mL of a solution containing about 5 mg of the SMCC-derivatized antibody.

Conjugation between antibody and drug linker: After adding DMSO (0.045 mL) and a DMSO solution containing 10 mM of the compound obtained in Process 1 (0.015 mL; which corresponds to about 2.4 equivalents per antibody molecule) to the above solution at room temperature, it was stirred by using a tube rotator (MTR-103, manufactured by AS ONE Corporation) for conjugating the drug linker to the antibody at room temperature for 16 hours.

Purification: The above solution was subjected to purification using the Common procedure D-1 (ABS was used as buffer solution) to yield 3.5 mL of a solution containing the titled antibody-drug conjugate. After that, the solution was concentrated by the Common procedure A.

Physicochemical characterization: By using the Common procedure E (as molar absorption coefficient, ε$_{A,280}$=235300 (estimated calculation value), ε$_{A,370}$=0 (estimated calculation value), ε$_{D,280}$=5000 (measured average value), and ε$_{D,370}$=19000 (measured average value) were used), the following characteristic values were obtained.

Antibody concentration: 3.85 mg/mL, antibody yield: 0.8 mg (16%), and average number of conjugated drug molecules (n) per antibody molecule: 2.9.

Example 36 Antibody-Drug Conjugate (35)

Conjugation between antibody and drug linker: After adding DMSO (0.03 mL) and a DMSO solution containing 10 mM of the compound obtained in Process 1 of Example 35 (0.03 mL; which corresponds to about 4.8 equivalents per antibody molecule) to the above solution at room temperature, it was stirred by using a tube rotator (MTR-103,

[Formula 105]

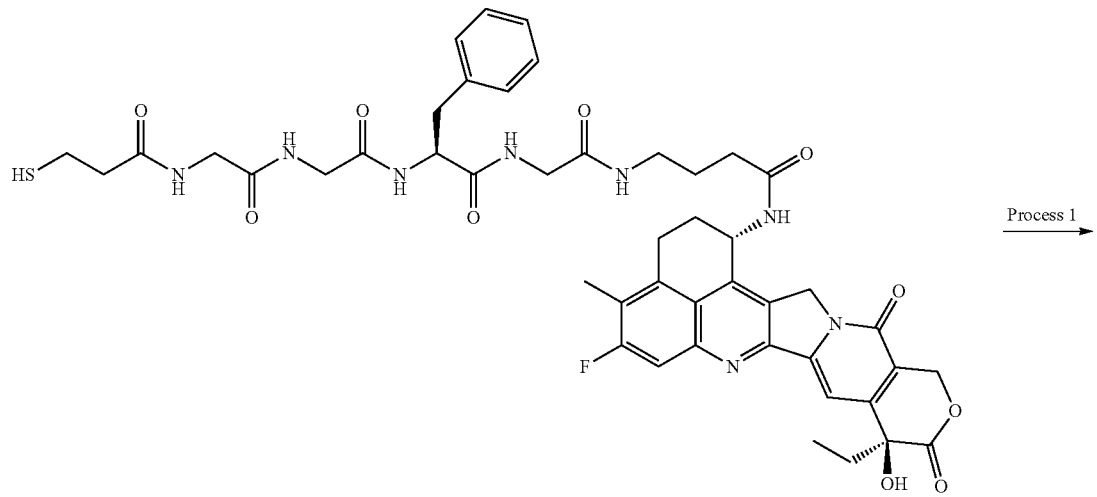

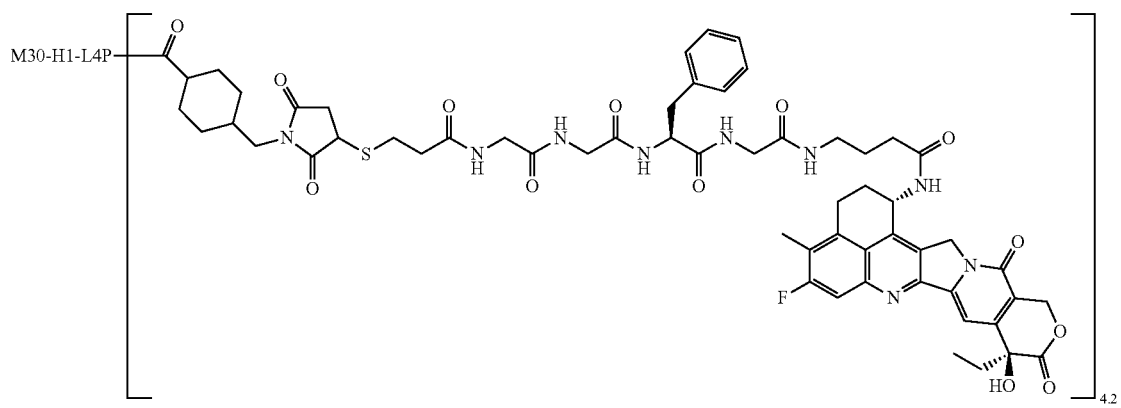

Process 1: Antibody-Drug Conjugate (35)

SMCC derivatization of antibody: The M30-H1-L4P antibody produced in Reference Example 2 was prepared to have antibody concentration of 20 mg/mL by replacing the medium with PBS6.5/EDTA by using the Common procedure C-2 and Common procedure B (as absorption coefficient at 280 nm, 1.61 mLmg$^{-1}$ cm$^{-1}$ was used). The solution (0.25 mL) was placed in a 1.5 mL tube, charged with DMSO solution (0.0125 mL; which corresponds to about 5.1 equivalents per antibody molecule) containing 27.6 mM succinimidyl-4-(N-maleimidomethyl)cyclohexane-1-carboxylate (SMCC, Thermo Fisher Scientific Inc.) at room temperature, and reacted at room temperature for 2 hours. This reaction solution was subjected to purification using the Common procedure D-2 to yield 0.7 mL of a solution containing about 5 mg of the SMCC-derivatized antibody.

manufactured by AS ONE Corporation) for conjugating the drug linker to the antibody at room temperature for 16 hours.

Purification: The above solution was subjected to purification using the Common procedure D-1 (ABS was used as buffer solution) to yield 3.5 mL of a solution containing the titled antibody-drug conjugate. After that, the solution was concentrated by the Common procedure A.

Physicochemical characterization: By using the Common procedure E (as molar absorption coefficient, $\varepsilon_{A,280}$=235300 (estimated calculation value), $\varepsilon_{A,370}$=0 (estimated calculation value), $\varepsilon_{D,280}$=5000 (measured average value), and $\varepsilon_{D,370}$=19000 (measured average value) were used), the following characteristic values were obtained.

Antibody concentration: 2.43 mg/mL, antibody yield: 0.5 mg (10%), and average number of conjugated drug molecules (n) per antibody molecule: 4.2.

Example 37 Antibody-Drug Conjugate (36)

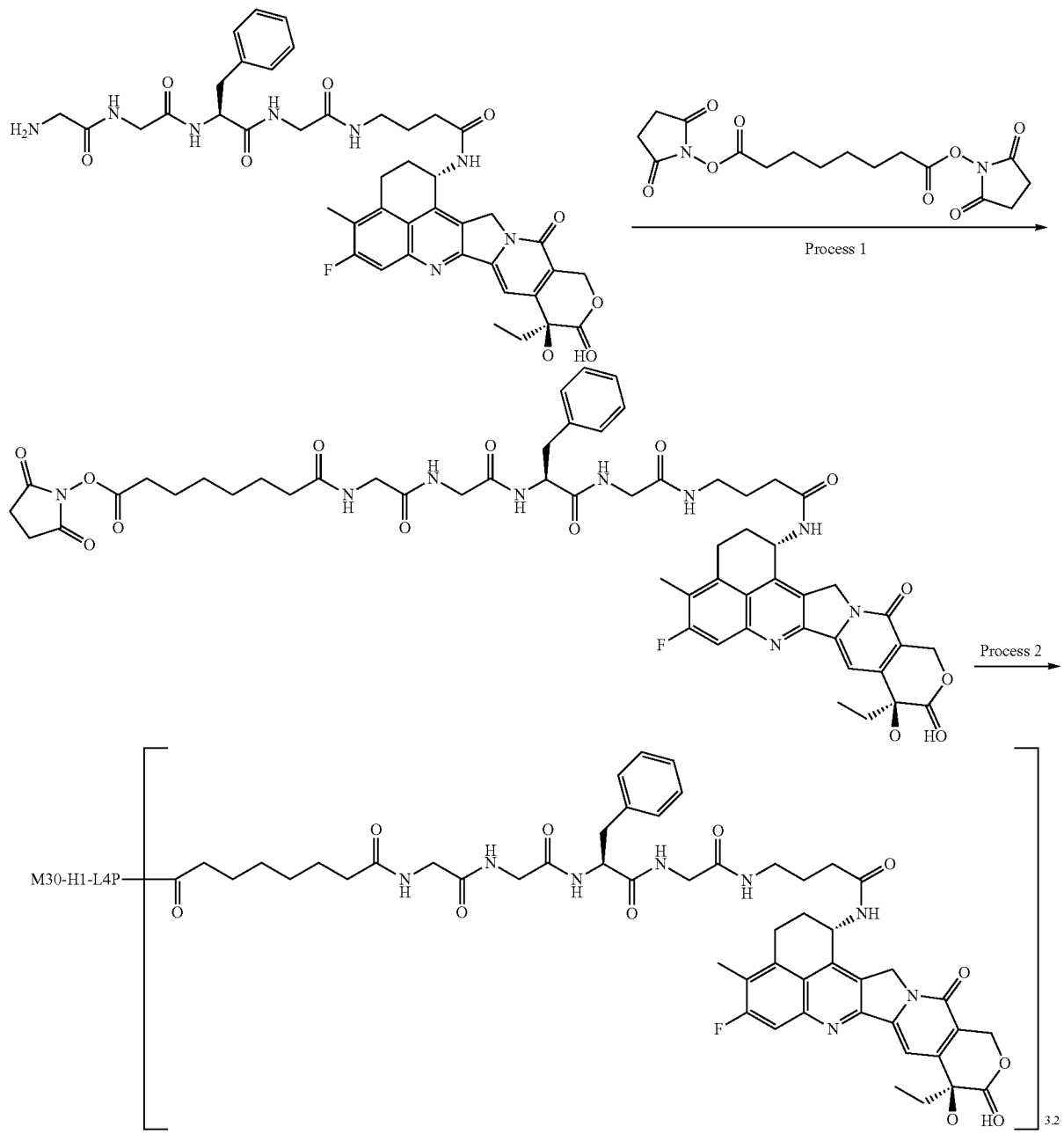

Process 1: N-{8-[(2,5-dioxopyrrolidin-1-yl)oxy]-8-oxooctanoyl}glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (84.0 mg, 0.100 mmol) obtained in Process 2 of Example 2 was reacted in the same manner as Process 3 of Example 2 by using di(N-succinimidyl) suberate instead of N-succinimidyl 6-maleimide hexanoate to yield the titled compound as a pale yellow solid (77.1 mg, 71%).

$^1$H-NMR (DMSO-D$_6$) δ: 0.87 (3H, t, J=7.2 Hz), 1.21-1.38 (4H, m), 1.43-1.50 (2H, m), 1.55-1.63 (2H, m), 1.68-1.76 (2H, m), 1.80-1.91 (2H, m), 2.07-2.22 (6H, m), 2.40 (3H, s), 2.60-2.67 (2H, m), 2.76-2.84 (5H, m), 2.97-3.22 (5H, m), 3.56-3.76 (6H, m), 4.40-4.50 (1H, m), 5.20 (2H, q, J=18.8 Hz), 5.37-5.48 (2H, m), 5.53-5.62 (1H, m), 6.54 (1H, s), 7.15-7.28 (5H, m), 7.31 (1H, s), 7.71 (1H, t, J=5.5 Hz), 7.80 (1H, d, J=10.9 Hz), 8.04 (1H, t, J=5.9 Hz), 8.09 (1H, t, J=5.9 Hz), 8.14 (1H, d, J=7.8 Hz), 8.26 (1H, t, J=5.9 Hz), 8.47 (1H, d, J=8.6 Hz).

MS (ESI) m/z: 1092 (M+H)$^+$

Process 2: Antibody-Drug Conjugate (36)

Conjugation between antibody and drug linker: The M30-H1-L4P antibody produced in Reference Example 2 was prepared to have antibody concentration of 20 mg/mL by replacing the medium with PBS6.5/EDTA by using the Common procedure C-2 and Common procedure B (as absorption coefficient at 280 nm, 1.61 mLmg$^{-1}$ cm$^{-1}$ was used). The solution (0.25 mL) was placed in a 1.5 mL tube, charged with a DMSO solution containing 10 mM of the compound obtained in above Process 1 (0.025 mL; which corresponds to about 3.7 equivalents per antibody molecule) at room temperature, and stirred by using a tube rotator (MTR-103, manufactured by AS ONE Corporation) for conjugating the drug linker to the antibody at room temperature for 16 hours.

Purification: The above solution was subjected to purification using the Common procedure D-1 (ABS was used as buffer solution) to yield 3.5 mL of a solution containing the titled antibody-drug conjugate. After that, the solution was concentrated by the Common procedure A.

Physicochemical characterization: By using the Common procedure E (as molar absorption coefficient, $\varepsilon_{A,280}$=235300 (estimated calculation value), $\varepsilon_{A,370}$=0 (estimated calculation value), $\varepsilon_{D,280}$=5000 (measured average value), and $\varepsilon_{D,370}$=19000 (measured average value) were used), the following characteristic values were obtained.

Antibody concentration: 6.25 mg/mL, antibody yield: 1.3 mg (26%), and average number of conjugated drug molecules (n) per antibody molecule: 3.2.

Example 38 Antibody-Drug Conjugate (37)

[Formula 107]

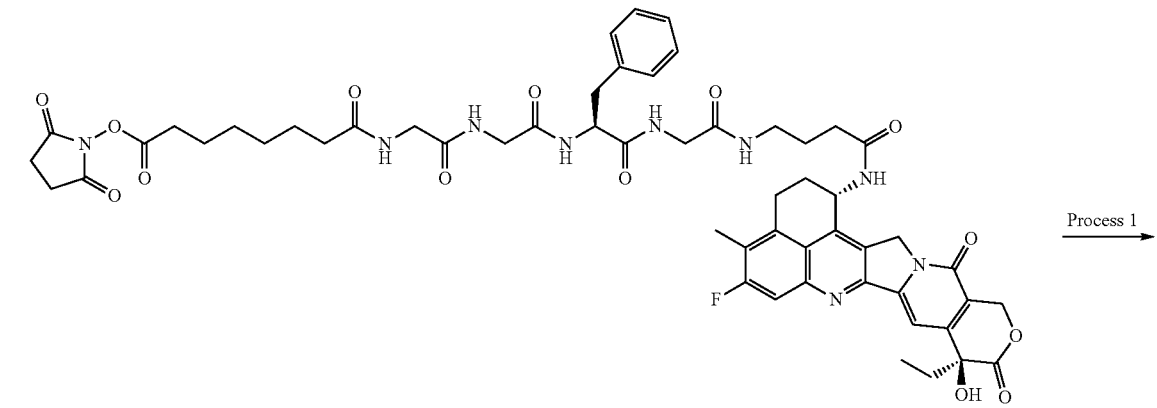

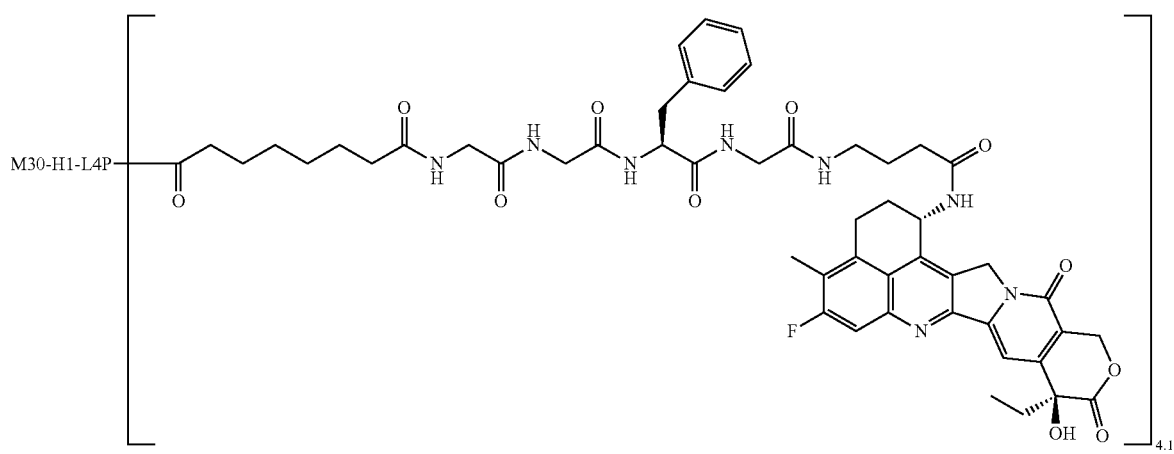

Process 1: Antibody-Drug Conjugate (37)

Conjugation between antibody and drug linker: The M30-H1-L4P antibody produced in Reference Example 2 was prepared to have antibody concentration of 20 mg/mL by replacing the medium with PBS6.5/EDTA by using the Common procedure C-2 and Common procedure B (as absorption coefficient at 280 nm, 1.61 mLmg$^{-1}$ cm$^{-1}$ was used). The solution (0.5 mL) was placed in a 1.5 mL tube, thereafter charged with a DMSO solution containing DMSO (0.025 mL) and 10 mM of the compound obtained in Process 1 of Example 37 (0.025 mL; which corresponds to about 7.4 equivalents per antibody molecule) at room temperature, and stirred by using a tube rotator (MTR-103, manufactured by AS ONE Corporation) for conjugating the drug linker to the antibody at room temperature for 16 hours.

Purification: The above solution was subjected to purification using the Common procedure D-1 (ABS was used as buffer solution) to yield 3.5 mL of a solution containing the titled antibody-drug conjugate. After that, the solution was concentrated by the Common procedure A.

Physicochemical characterization: By using the Common procedure E (as molar absorption coefficient, $\varepsilon_{A,280}=235300$ (estimated calculation value), $\varepsilon_{A,370}=0$ (estimated calculation value), $\varepsilon_{D,280}=5000$ (measured average value), and $\varepsilon_{D,370}=19000$ (measured average value) were used), the following characteristic values were obtained.

Antibody concentration: 4.36 mg/mL, antibody yield: 0.9 mg (18%), and average number of conjugated drug molecules (n) per antibody molecule: 4.1.

Example 39 Antibody-Drug Conjugate (38)

Common procedure C-2 and Common procedure B (as absorption coefficient at 280 nm, 1.75 mLmg$^{-1}$ cm$^{-1}$ was used). The solution (0.4 mL, 4 mg of the antibody) was placed in a 1.5 mL tube, thereafter charged with DMSO (0.017 mL) and a DMSO solution containing 10 mM of the compound obtained in Process 1 of Example 37 (0.023 mL; which corresponds to 9 equivalents per antibody molecule) at room temperature, and stirred by using a tube rotator (MTR-103, manufactured by AS ONE Corporation) for conjugating the drug linker to the antibody at room temperature for 4 hours.

Purification: The above solution was subjected to purification using the Common procedure D-1 (ABS was used as buffer solution) to yield 2.5 mL of a solution containing the titled antibody-drug conjugate.

Physicochemical characterization: By using the Common procedure E (as molar absorption coefficient, $\varepsilon_{A,280}=270400$ (estimated calculation value), $\varepsilon_{A,370}=0$ (estimated calculation value), $\varepsilon_{D,280}=2670$ (measured value), and

[Formula 108]

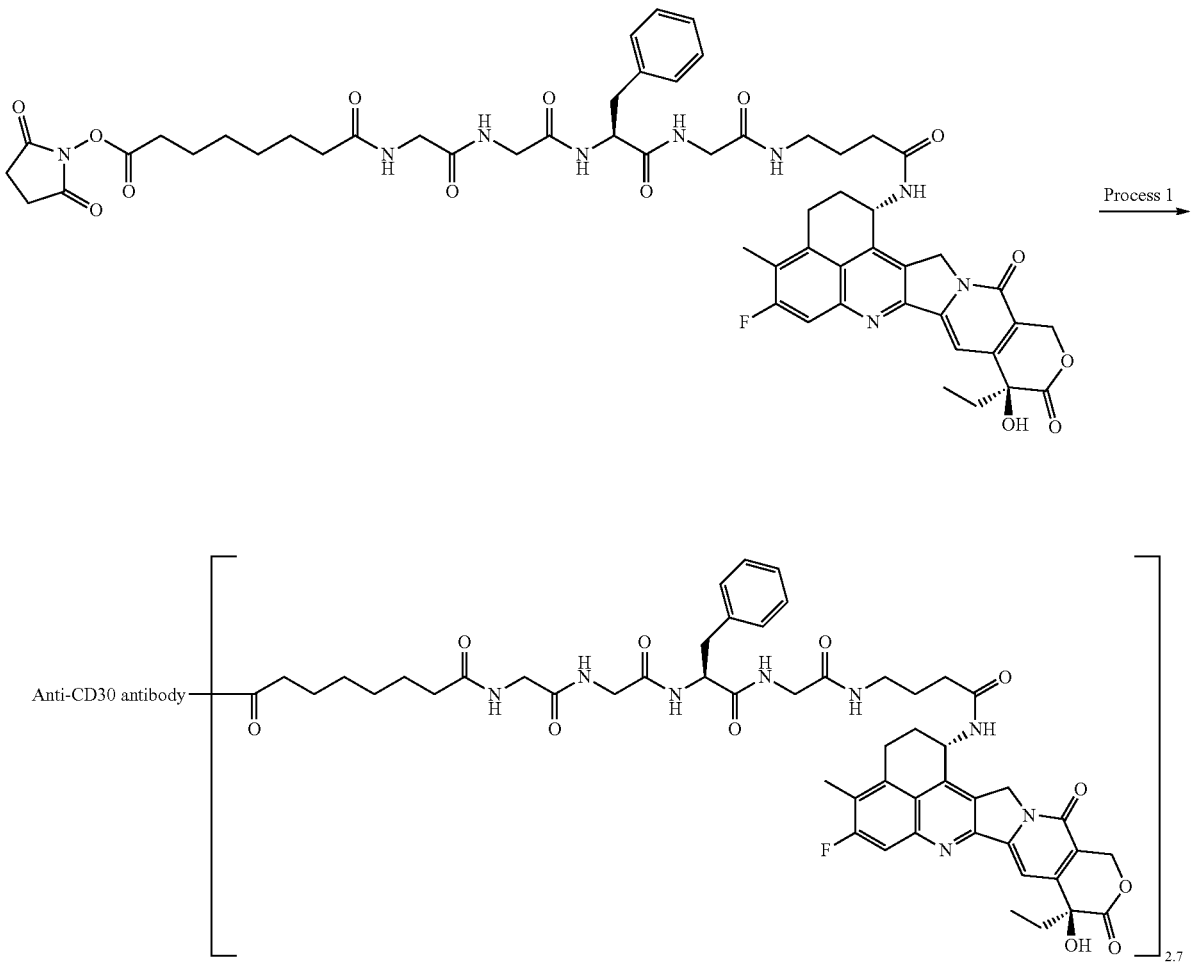

Process 1: Antibody-Drug Conjugate (38)

Conjugation between antibody and drug linker: The anti-CD30 antibody produced in Reference Example 3 was prepared to have antibody concentration of 10 mg/mL by replacing the medium with PBS6.5/EDTA by using the $\varepsilon_{D,370}=15820$ (measured value) were used), the following characteristic values were obtained.

Antibody concentration: 0.55 mg/mL, antibody yield: 1.4 mg (34%), and average number of conjugated drug molecules (n) per antibody molecule: 2.7.

Example 40 Antibody-Drug Conjugate (39)

Process 1

[Formula 109]

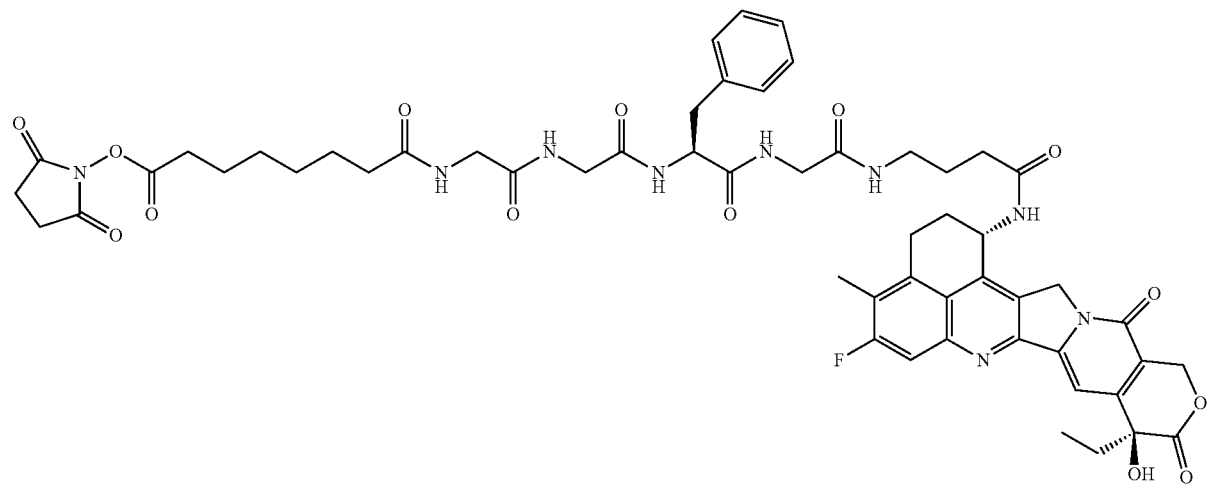

Process 1: Antibody-Drug Conjugate (39)

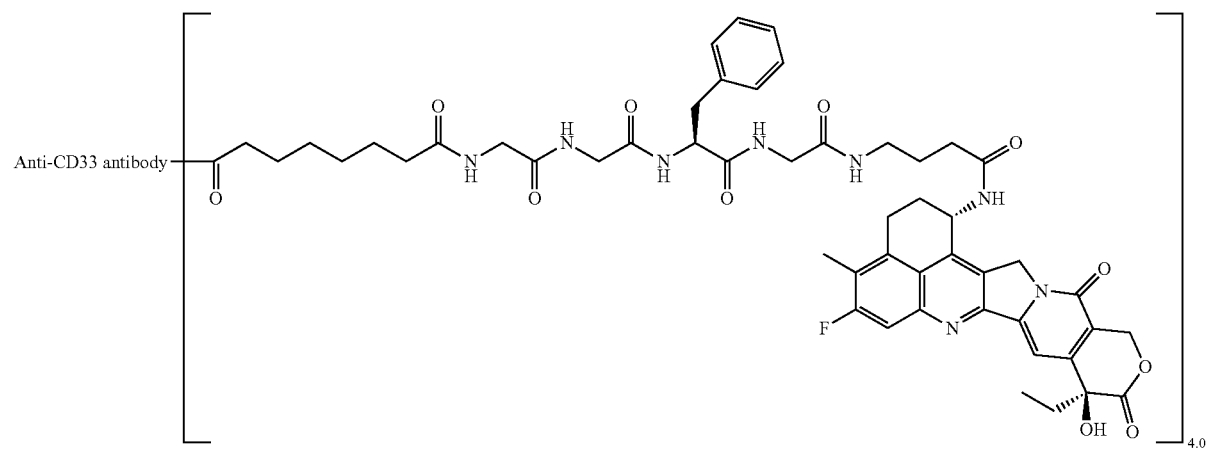

Conjugation between antibody and drug linker: The anti-CD33 antibody produced in Reference Example 4 was prepared to have antibody concentration of 10 mg/mL by replacing the medium with PBS6.5/EDTA by using the Common procedure C-2 and Common procedure B (as absorption coefficient at 280 nm, 1.66 mLmg$^{-1}$ cm$^{-1}$ was used). The solution (0.4 mL, 4 mg of the antibody) was placed in a 1.5 mL tube, thereafter charged with DMSO (0.017 mL) and a DMSO solution containing 10 mM of the compound obtained in Process 1 of Example 37 (0.023 mL; which corresponds to 9 equivalents per antibody molecule) at room temperature, and stirred by using a tube rotator (MTR-103, manufactured by AS ONE Corporation) for conjugating the drug linker to the antibody at room temperature for 4 hours.

Purification: The above solution was subjected to purification using the Common procedure D-1 (ABS was used as buffer solution) to yield 2.5 mL of a solution containing the titled antibody-drug conjugate.

Physicochemical characterization: By using the Common procedure E (as molar absorption coefficient, $\varepsilon_{A,280}=256400$ (estimated calculation value), $\varepsilon_{A,370}=0$ (estimated calculation value), $\varepsilon_{D,280}=2670$ (measured value), and $\varepsilon_{D,370}=15820$ (measured value) were used), the following characteristic values were obtained.

Antibody concentration: 0.93 mg/mL, antibody yield: 2.3 mg (58%), and average number of conjugated drug molecules (n) per antibody molecule: 4.0.

Example 41 Antibody-Drug Conjugate (40)

Process 1

[Formula 110]

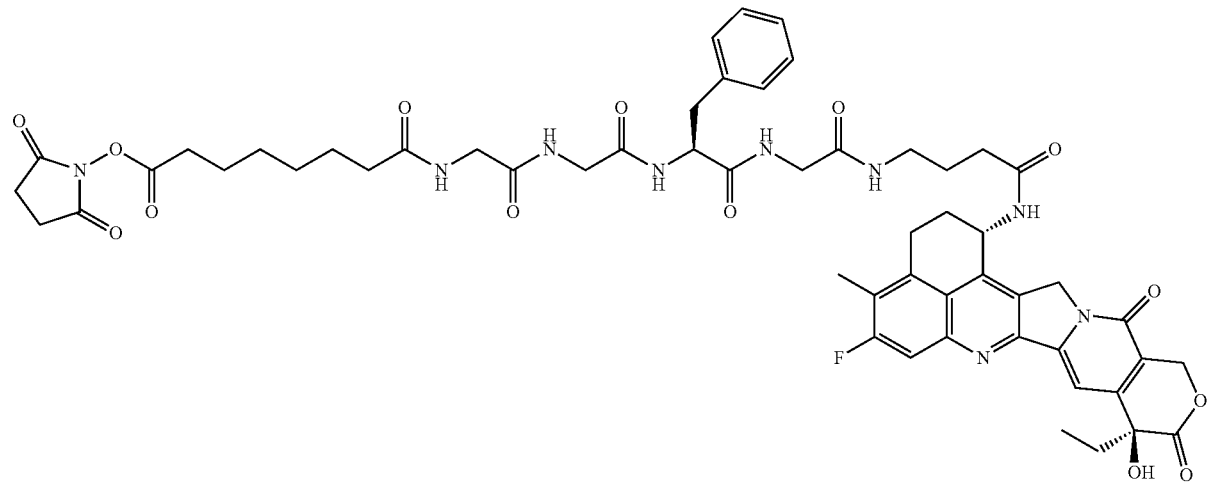

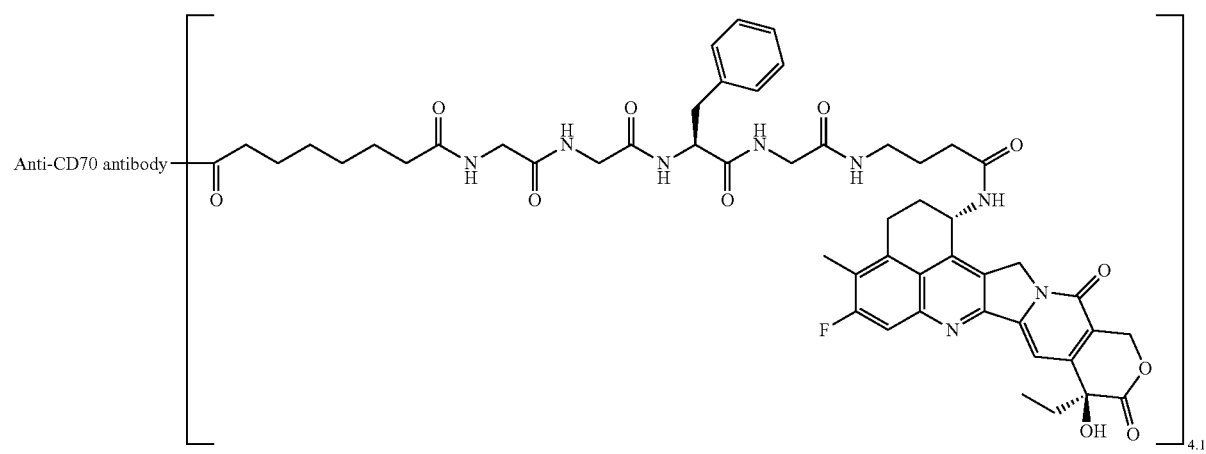

Process 1: Antibody-Drug Conjugate (40)

Conjugation between antibody and drug linker: The anti-CD70 antibody produced in Reference Example 5 was prepared to have antibody concentration of 10 mg/mL by replacing the medium with PBS6.5/EDTA by using the Common procedure C-2 and Common procedure B (as absorption coefficient at 280 nm, 1.69 mLmg$^{-1}$ cm$^{-1}$ was used). The solution (0.4 mL, 4 mg of the antibody) was placed in a 1.5 mL tube, thereafter charged with DMSO (0.017 mL) and a DMSO solution containing 10 mM of the compound obtained in Process 1 (0.023 mL; which corresponds to 9 equivalents per antibody molecule) of Example 37 at room temperature, and stirred by using a tube rotator (MTR-103, manufactured by AS ONE Corporation) for conjugating the drug linker to the antibody at room temperature for 4 hours.

Purification: The above solution was subjected to purification using the Common procedure D-1 (ABS was used as buffer solution) to yield 2.5 mL of a solution containing the titled antibody-drug conjugate.

Physicochemical characterization: By using the Common procedure E (as molar absorption coefficient, $\varepsilon_{A,280}=262400$ (estimated calculation value), $\varepsilon_{A,370}=0$ (estimated calculation value), $\varepsilon_{D,280}=2670$ (measured value), and $\varepsilon_{D,370}=15820$ (measured value) were used), the following characteristic values were obtained.

Antibody concentration: 1.04 mg/mL, antibody yield: 2.6 mg (65%), and average number of conjugated drug molecules (n) per antibody molecule: 4.1.

Example 42 2-(2-Aminoethoxy)-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]acetamide

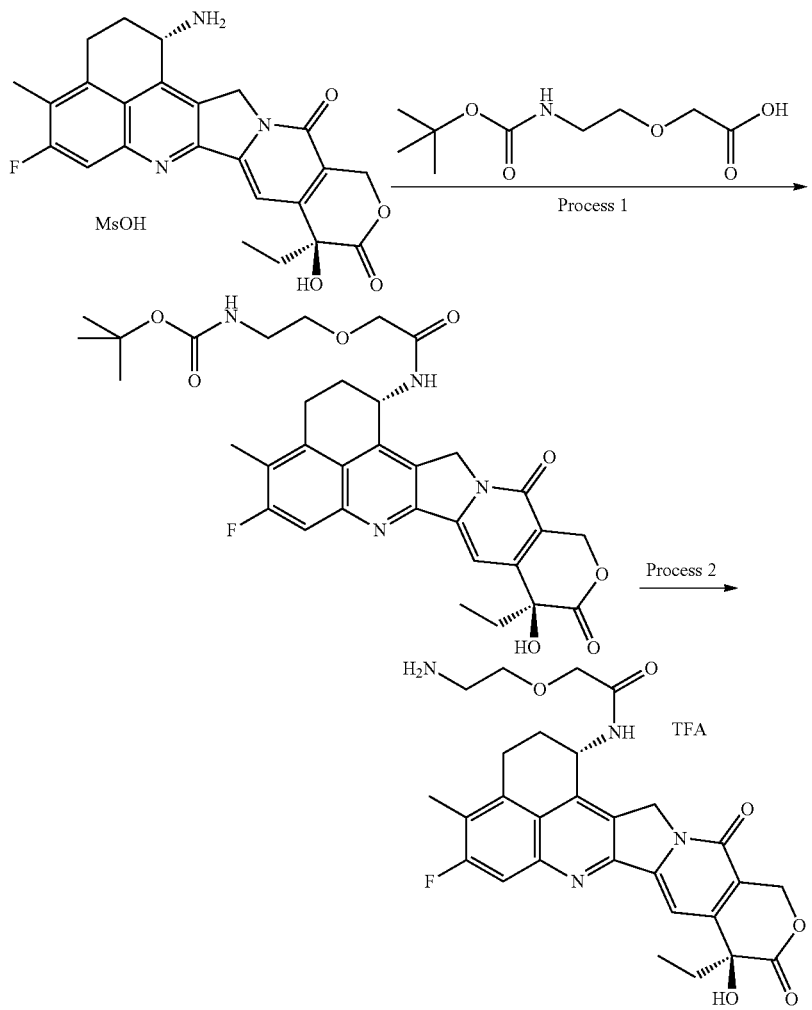

Process 1: tert-Butyl [2-(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)ethyl]carbamate Mesylate of the compound (4) (3.10 g, 5.47 mol) was reacted in the same manner as Process 1 of Example 1 by using {2-[(tert-butoxycarbonyl)amino]ethoxy}acetic acid (J. Med. Chem., 1992, vol. 35, pp. 2928) (1.55 g, 6.01 mmol) instead of 4-(tert-butoxycarbonylamino)butanoic acid to yield the titled compound as a pale yellow solid (2.56 g, 73%).

$^1$H-NMR (400 MHz, DMSO-$d_6$) δ: 0.87 (3H, t, J=7.3 Hz), 1.26 (9H, s), 1.81-1.91 (2H, m), 2.13-2.22 (2H, m), 2.40 (3H, s), 3.08-3.26 (4H, m), 3.43-3.53 (2H, m), 4.00 (1H, d, J=15.1 Hz), 4.05 (1H, d, J=15.1 Hz), 5.14 (1H, d, J=18.7 Hz), 5.22 (1H, d, J=18.7 Hz), 5.40 (1H, d, J=16.6 Hz), 5.44 (1H, d, J=16.6 Hz), 5.59-5.66 (1H, m), 6.53 (1H, s), 6.86 (1H, t, J=5.4 Hz), 7.31 (1H, s), 7.79 (1H, d, J=10.9 Hz), 8.49 (1H, d, J=9.1 Hz).

MS (APCI) m/z: 637 (M+H)$^+$

[Formula 111]

Process 2: 2-(2-Aminoethoxy)-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]acetamide The compound (1.50 g, 2.36 mol) obtained in Process 1 above was reacted in the same manner as Process 2 of Example 1 to yield trifluorohydrochloride of the titled compound as a pale yellow solid (1.50 g, quantitative). This compound was confirmed in the tumor of a cancer-bearing mouse that received the antibody-drug conjugate (41).

$^1$H-NMR (400 MHz, DMSO-$d_6$) δ: 0.87 (3H, t, J=7.5 Hz), 1.81-1.92 (2H, m), 2.15-2.23 (2H, m), 2.41 (3H, s), 3.05 (2H, t, J=5.1 Hz), 3.15-3.23 (2H, m), 3.71 (2H, t, J=5.1 Hz), 4.10 (2H, s), 5.19 (1H, d, J=18.7 Hz), 5.24 (1H, d, J=18.7 Hz), 5.43 (2H, s), 5.58-5.66 (1H, m), 6.55 (1H, s), 7.33 (1H, s), 7.73-7.84 (4H, m), 8.55 (1H, d, J=9.1 Hz).

MS (APCI) m/z: 537 (M+H)$^+$

Example 43 Antibody-Drug Conjugate (41)
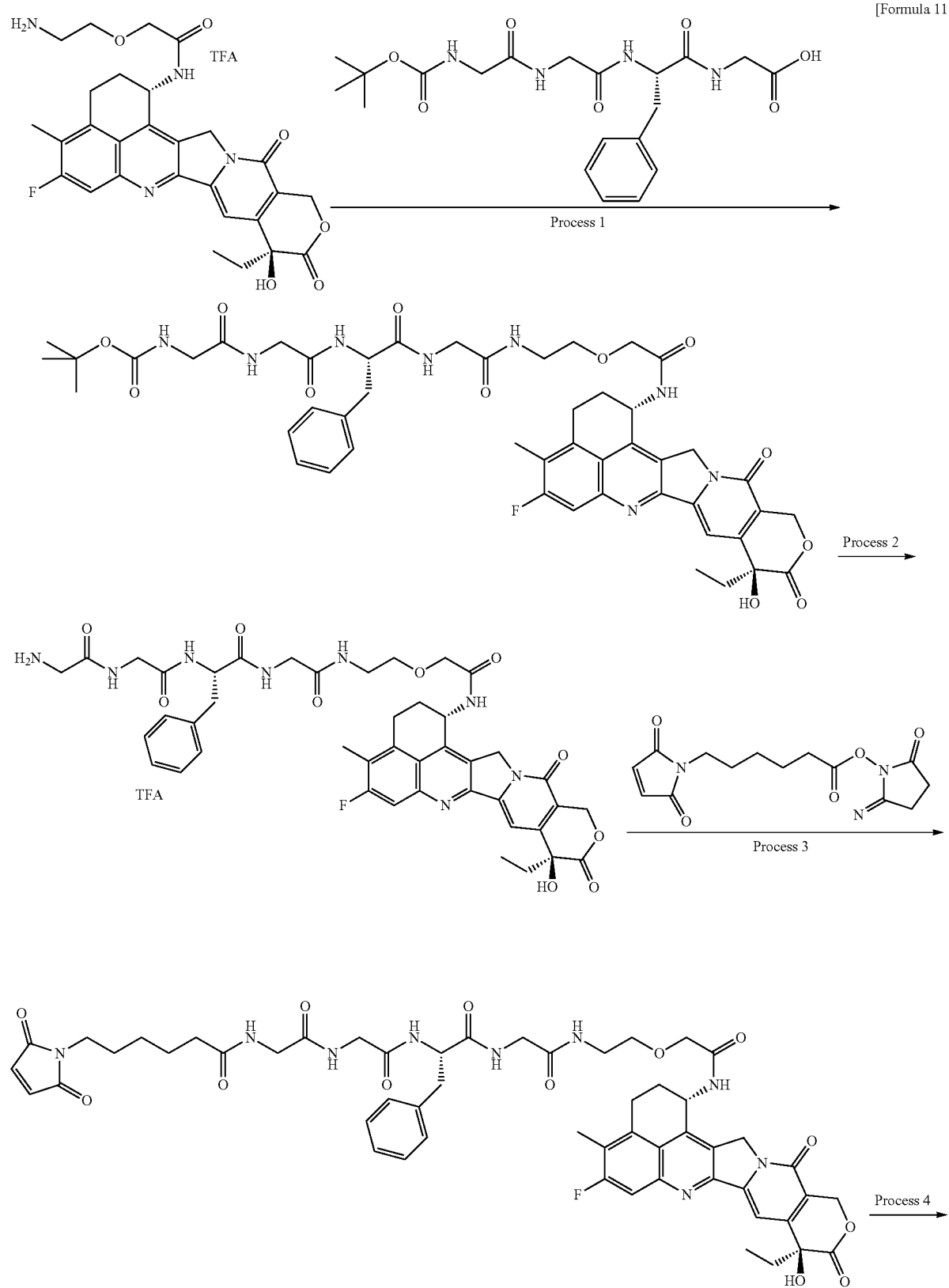
[Formula 112]

-continued

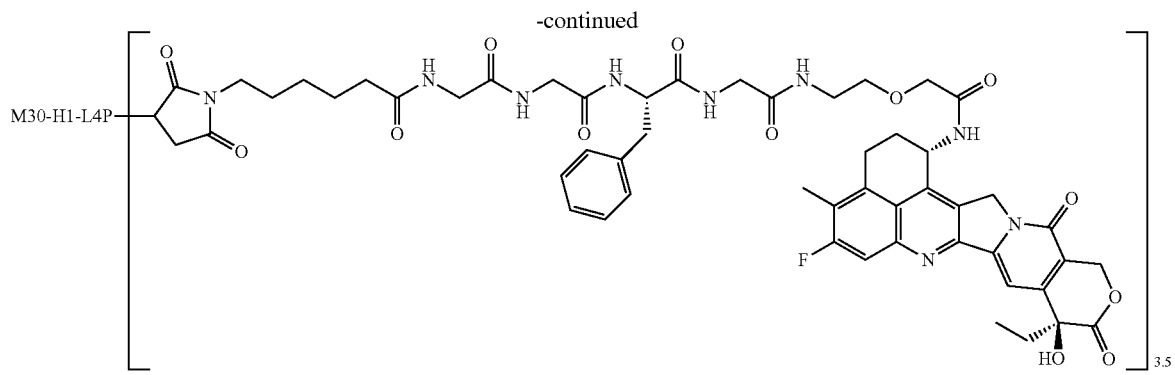

Process 1: N-(tert-butoxycarbonyl)glycylglycyl-L-phenylalanyl-N-[2-(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)ethyl]glycinamide The compound (554 mg, 0.85 mmol) of Example 42 was reacted in the same manner as Process 1 of Example 2 to yield the titled compound (775 mg, 95%).

$^{1}$H-NMR (400 MHz, DMSO-$d_6$) δ: 0.85 (3H, t, J=7.3 Hz), 1.36 (9H, s), 1.78-1.89 (2H, m), 2.13-2.22 (2H, m), 2.39 (3H, s), 2.71 (1H, dd, J=13.4, 9.8 Hz), 2.95 (1H, dd, J=13.4, 4.3 Hz), 3.09-3.23 (1H, m), 3.23-3.32 (2H, m), 3.40-3.62 (8H, m), 3.73 (1H, dd, J=16.5, 5.5 Hz), 4.03 (2H, s), 4.39-4.47 (1H, m), 5.17 (1H, d, J=18.9 Hz), 5.25 (1H, d, J=18.9 Hz), 5.41 (1H, d, J=16.8 Hz), 5.45 (1H, d, J=16.8 Hz), 5.57-5.64 (1H, m), 6.54 (1H, s), 6.99 (1H, t, J=5.8 Hz), 7.13-7.26 (5H, m), 7.31 (1H, s), 7.76-7.82 (2H, m), 7.90 (1H, t, J=5.2 Hz), 8.13 (1H, d, J=7.9 Hz), 8.27 (1H, t, J=5.8 Hz), 8.49 (1H, d, J=8.5 Hz).

MS (APCI) m/z: 955 (M+H)$^{+}$

Process 2: Glycylglycyl-L-phenylalanyl-N-[2-(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)ethyl]glycinamide trifluoroacetate The compound (630 mg, 0.659 mmol) obtained in Process 1 above was reacted in the same manner as Process 2 of Example 2 to yield the titled compound (588 mg, 92%).

$^{1}$H-NMR (400 MHz, DMSO-$d_6$) δ: 0.86 (3H, t, J=7.3 Hz), 1.79-1.90 (2H, m), 2.13-2.22 (2H, m), 2.39 (3H, s), 2.71 (1H, dd, J=13.4, 10.1 Hz), 2.99 (1H, dd, J=13.4, 4.3 Hz), 3.09-3.23 (1H, m), 3.24-3.32 (3H, m), 3.41-3.71 (7H, m), 3.86 (1H, dd, J=16.8, 5.8 Hz), 4.04 (2H, s), 4.52 (1H, td, J=9.0, 4.1 Hz), 5.17 (1H, d, J=18.9 Hz), 5.25 (1H, d, J=18.9 Hz), 5.41 (1H, d, J=16.5 Hz), 5.45 (1H, d, J=16.5 Hz), 5.56-5.65 (1H, m), 6.55 (1H, s), 7.13-7.26 (5H, m), 7.32 (1H, s), 7.80 (1H, d, J=11.0 Hz), 7.87-8.01 (4H, m), 8.29-8.36 (2H, m), 8.46-8.55 (2H, m).

MS (APCI) m/z: 855 (M+H)$^{+}$

Process 3: N-[6-(2,5-dioxo-2,5-dihydro-1H-pyrrol-1-yl)hexanoyl]glycylglycyl-L-phenylalanyl-N-[2-(2-{[(1S,9S)-9-ethyl-5-fluoro-9-hydroxy-4-methyl-10,13-dioxo-2,3,9,10,13,15-hexahydro-1H,12H-benzo[de]pyrano(3',4':6,7]indolizino[1,2-b]quinolin-1-yl]amino}-2-oxoethoxy)ethyl]glycinamide The compound (240 mg, 0.247 mmol) obtained in Process 2 above was reacted in the same manner as Process 3 of Example 2 to yield the titled compound (162 mg, 62%).

$^{1}$H-NMR (400 MHz, DMSO-$d_6$) δ: 0.86 (3H, t, J=7.6 Hz), 1.13-1.22 (2H, m), 1.40-1.51 (4H, m), 1.78-1.90 (2H, m), 2.09 (2H, t, J=7.6 Hz), 2.14-2.21 (2H, m), 2.39 (3H, s), 2.74 (1H, dd, J=13.6, 9.7 Hz), 2.96 (1H, dd, J=13.6, 4.5 Hz), 3.08-3.24 (1H, m), 3.24-3.30 (1H, m), 3.33-3.40 (4H, m), 3.47-3.68 (7H, m), 3.72 (1H, dd, J=16.6, 5.7 Hz), 4.03 (2H, s), 4.42 (1H, td, J=8.6, 4.2 Hz), 5.17 (1H, d, J=18.7 Hz), 5.25 (1H, d, J=18.7 Hz), 5.40 (1H, d, J=17.2 Hz), 5.44 (1H, d, J=17.2 Hz), 5.57-5.64 (1H, m), 6.52 (1H, s), 6.99 (2H, s), 7.13-7.25 (5H, m), 7.31 (1H, s), 7.74-7.81 (2H, m), 7.99 (1H, t, J=5.7 Hz), 8.03-8.11 (2H, m), 8.22 (1H, t, J=5.7 Hz), 8.47 (1H, d, J=9.1 Hz).

MS (APCI) m/z: 1048 (M+H)$^{+}$

Process 4: Antibody-Drug Conjugate (41)

By using the M30-H1-L4P antibody produced in Reference Example 2 and the compound obtained in Process 3 above, the titled antibody-drug conjugate was obtained in the same manner as Process 2 of Example 29. Antibody concentration: 12.0 mg/mL, antibody yield: 8.4 mg (67%), and average number of conjugated drug molecules (n) per antibody molecule: 3.5.

Example 44 Antibody-Drug Conjugate (42)

[Formula 113]

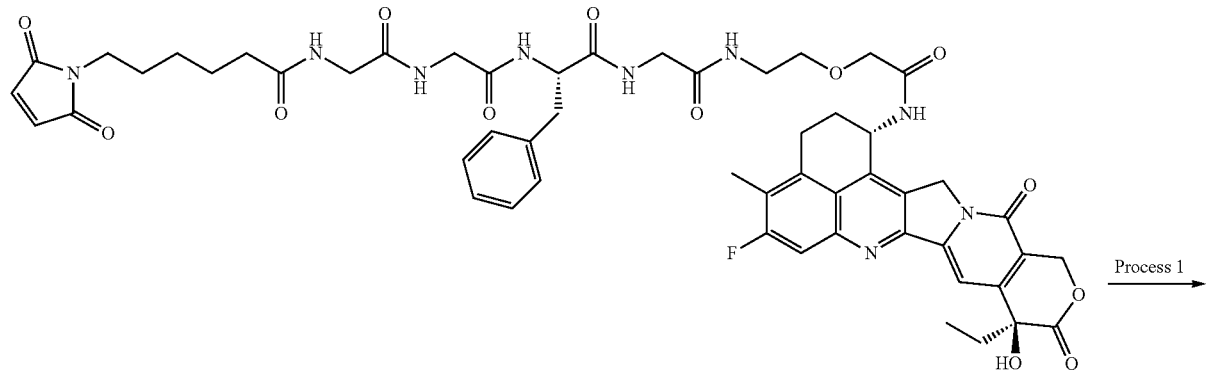

Process 1

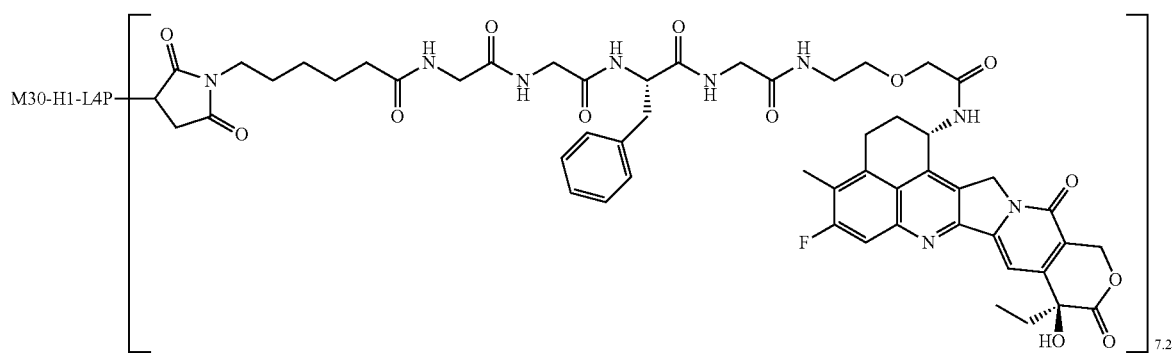

Process 1: Antibody-Drug Conjugate (42)

By using the M30-H1-L4P antibody produced in Reference Example 2 and the compound obtained in Process 3 of Example 43, the titled antibody-drug conjugate was obtained in the same manner as Process 1 of Example 5.

Antibody concentration: 0.83 mg/mL, antibody yield: 4.98 mg (40%), and average number of conjugated drug molecules (n) per antibody molecule: 7.2.

Example 45 Antibody-Drug Conjugate (43)

[Formula 114]

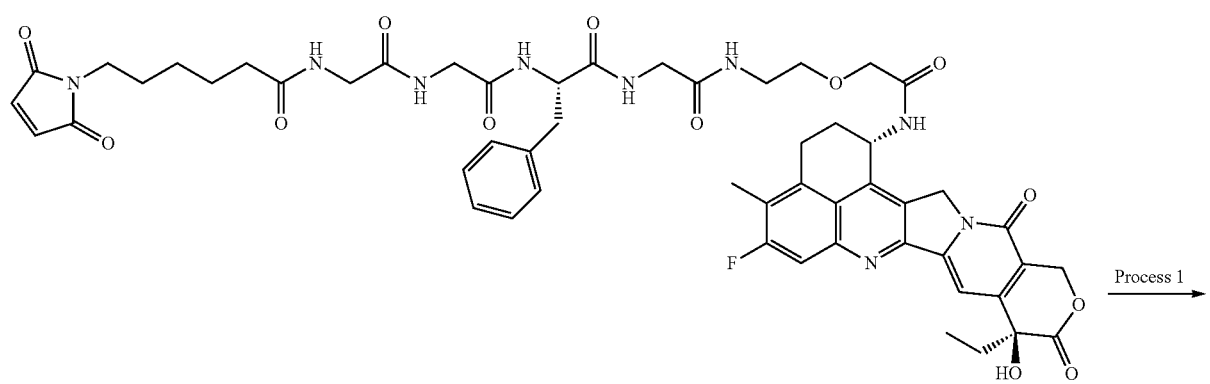

Process 1

-continued

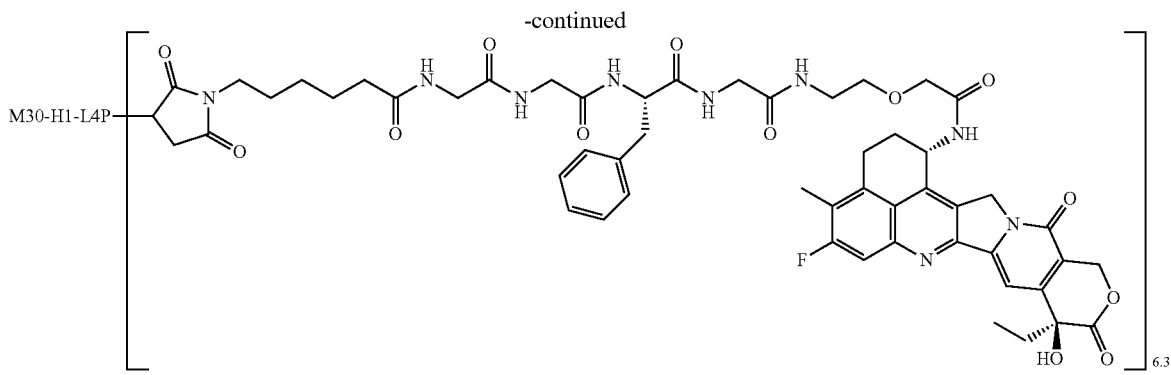

Process 1: Antibody-Drug Conjugate (43)

By using the M30-H1-L4P antibody produced in Reference Example 2 and the compound obtained in Process 3 of Example 43, the titled antibody-drug conjugate was obtained in the same manner as Process 1 of Example 4.

Antibody concentration: 1.06 mg/mL, antibody yield: 6.36 mg (51%), and average number of conjugated drug molecules (n) per antibody molecule: 6.3.

Example 46 Antibody-Drug Conjugate (44)

[Formula 115]

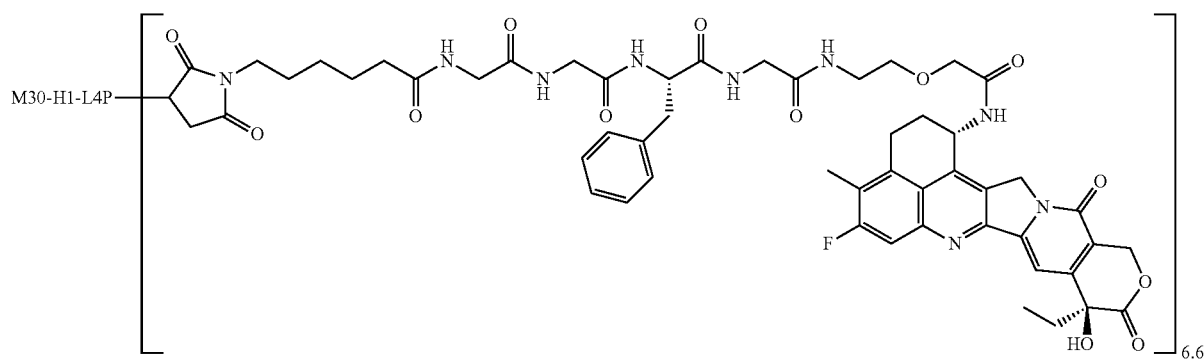

Almost the whole amounts of the antibody-drug conjugates of Examples 44 and 45 were mixed and the solution was concentrated by the Common procedure A to yield the titled antibody-drug conjugate.

Antibody concentration: 10.0 mg/mL, antibody yield: 10.21 mg, and average number of conjugated drug molecules (n) per antibody molecule: 6.6.

Example 47 Antibody-Drug Conjugate (45)

[Formula 116]

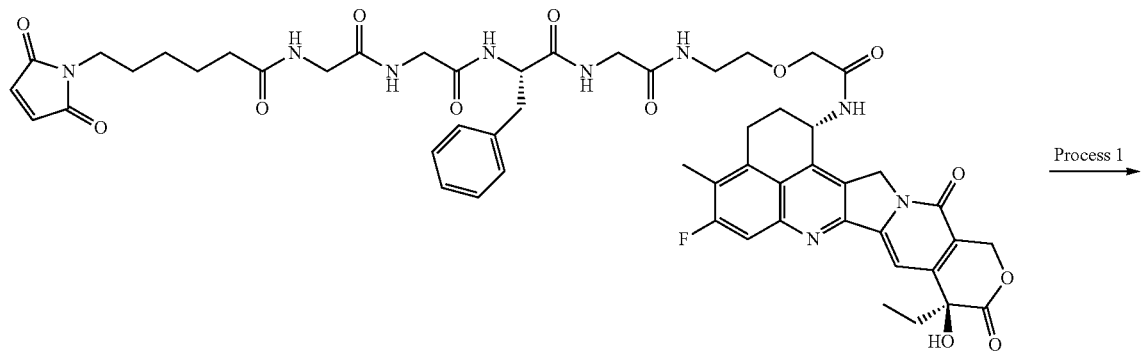

Process 1 ⟶

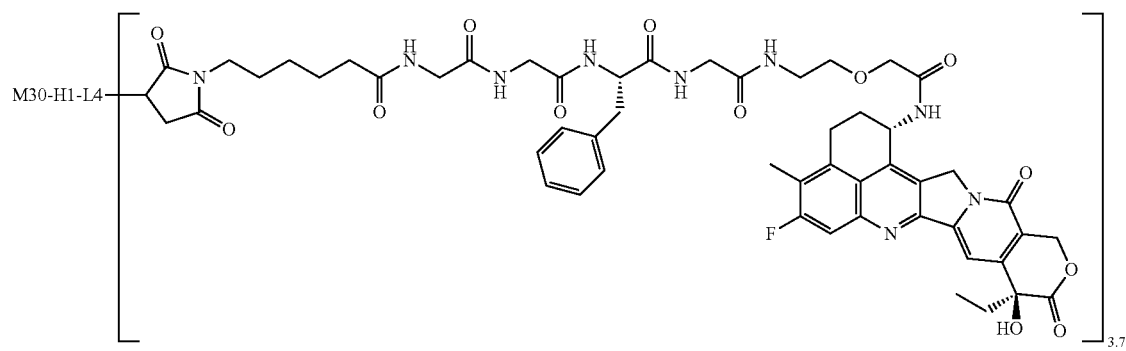

Process 1: Antibody-Drug Conjugate (45)

Reduction of the antibody: The M30-H1-L4 antibody produced in Reference Example 1 was prepared to have antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (1.25 mL, 12.5 mg of the antibody) was placed in a 1.5 mL tube and charged with an aqueous solution of 10 mM TCEP (Tokyo Chemical Industry Co., Ltd.) (0.0287 mL; 3.4 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding dimethyl sulfoxide (0.0267 mL) and a dimethyl sulfoxide solution containing 10 mM of the compound obtained in Process 3 of Example 43 (0.0439 mL; 5.2 equivalents per antibody molecule) to the above solution at room temperature, it was incubated for conjugating the drug linker to the antibody in a water bath at 15° C. for 1 hour. Next, an aqueous solution (0.0066 mL) of 100 mM NAC (Sigma-Aldrich Co. LLC) was added thereto and incubated to terminate the raction of drug linker at room temperature for another 20 minutes. Purification: The above solution was subjected to purification using the Common procedure D-1 (ABS was used as buffer solution) described in Production method 1 to yield 6 mL of a solution containing the titled antibody-drug conjugate. After that, the solution was concentrated by the Common procedure A.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,200}$=5193 (measured value), and $\varepsilon_{D,370}$=20347 (measured value) were used), the following characteristic values were obtained.

Antibody concentration: 10.0 mg/mL, antibody yield: 9.3 mg (74%), and average number of conjugated drug molecules (n) per antibody molecule: 3.7.

Example 48 Antibody-Drug Conjugate (46)

[Formula 117]

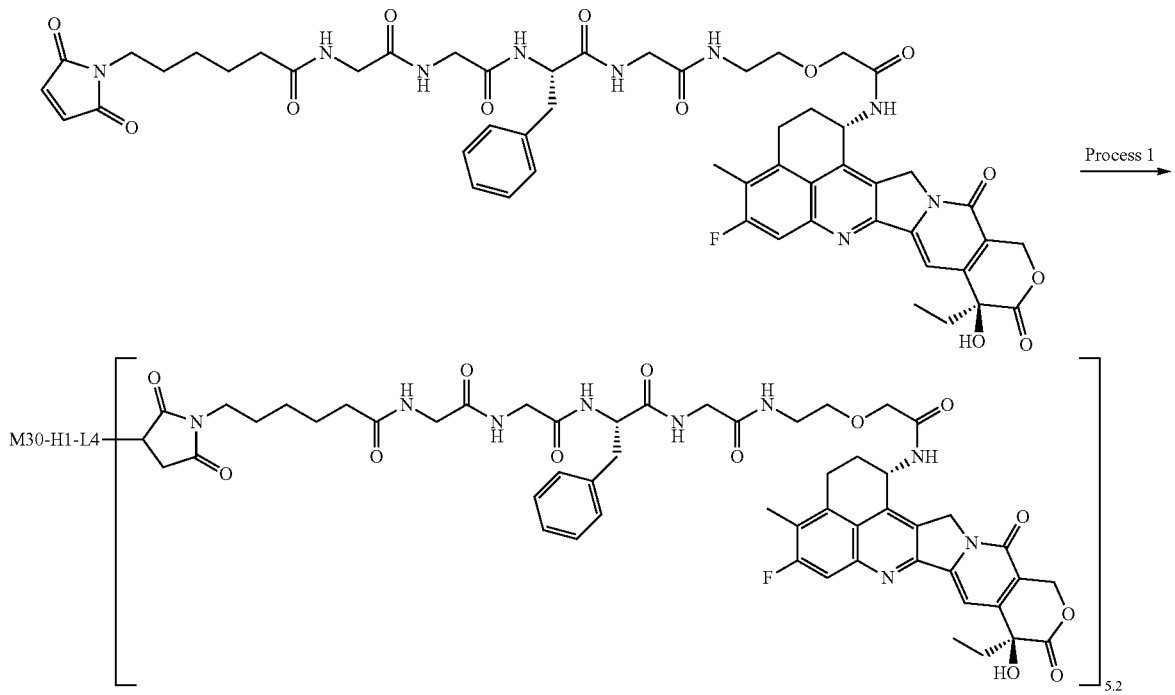

Process 1: Antibody-Drug Conjugate (46)

Reduction of the antibody: The M30-H1-L4 antibody produced in Reference Example 1 was prepared to have antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (1.25 mL, 12.5 mg of the antibody) was placed in a 1.5 mL tube and charged with an aqueous solution of 10 mM TCEP (Tokyo Chemical Industry Co., Ltd.) (0.0439 mL; 5.2 equivalents per antibody molecule) (0.0287 mL; 3.4 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding a dimethyl sulfoxide solution (0.0726 mL; 8.6 equivalents per antibody molecule) containing 10 mM of the compound obtained in Process 3 of Example 43 to the above solution at room temperature, it was incubated for conjugating the drug linker to the antibody in a water bath at 15° C. for 1 hour. Next, an aqueous solution (0.011 mL) of 100 mM NAC (Sigma-Aldrich Co. LLC) was added thereto and incubated to terminate the raction of drug linker at room temperature for another 20 minutes.

Purification: The above solution was subjected to purification using the Common procedure D-1 (ABS was used as buffer solution) described in Production method 1 to yield 6 mL of a solution containing the titled antibody-drug conjugate. After that, the solution was concentrated by the Common procedure A.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,280}$=5193 (measured value), and $\varepsilon_{D,370}$=20347 (measured value) were used), the following characteristic values were obtained.

Antibody concentration: 10.0 mg/mL, antibody yield: 7.8 mg (62%), and average number of conjugated drug molecules (n) per antibody molecule: 5.2.

Example 49 N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alaninamide

[Formula 118]

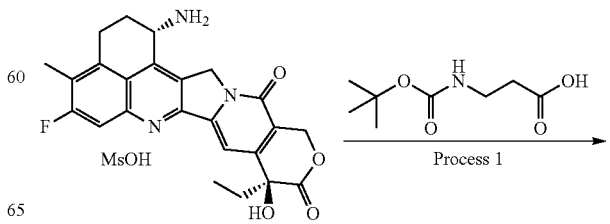

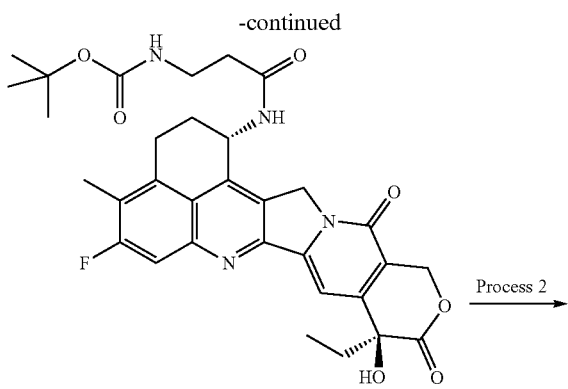

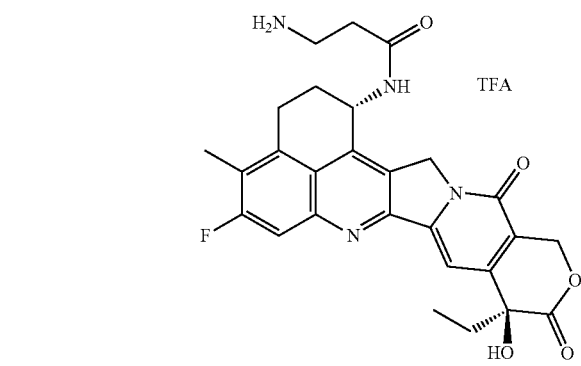

Process 1: tert-Butyl (3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-3-oxopropyl)carbamate Mesylate of the compound (4) (500 mg, 0.941 mmol) was reacted in the same manner as Process 1 of Example 1 by using N-(tert-butoxycarbonyl)-β-alanine instead of 4-(tert-butoxycarbonylamino)butanoic acid to yield the titled compound as a yellow-brown solid (616 mg, quantitative).

$^1$H-NMR (400 MHz, DMSO-$d_6$) δ: 0.87 (3H, t, J=7.2 Hz), 1.29 (9H, s), 1.86 (2H, dt, J=15.1, 7.3 Hz), 2.04-2.22 (2H, m), 2.31 (2H, t, J=6.8 Hz), 2.40 (3H, s), 3.10-3.26 (4H, m), 5.15 (1H, d, J=18.8 Hz), 5.26 (1H, d, J=19.2 Hz), 5.42 (2H, dd, J=18.8, 16.4 Hz), 5.57 (1H, dt, J=8.5, 4.2 Hz), 6.53 (1H, s), 6.78 (1H, t, J=5.5 Hz), 7.30 (1H, s), 7.80 (1H, d, J=11.0 Hz), 8.46 (1H, d, J=8.6 Hz).

MS (ESI) m/z: 607 (M+H)$^+$

Process 2: N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alaninamide The compound obtained in Process 1 above was reacted in the same manner as Process 2 of Example 1 to yield trifluoroacetate of the titled compound as a yellow solid (499 mg, 86%).

$^1$H-NMR (400 MHz, DMSO-$d_6$) δ: 0.87 (3H, t, J=7.2 Hz), 1.86 (2H, dquin, J=14.6, 7.2, 7.2, 7.2, 7.2 Hz), 2.06-2.27 (1H, m), 2.41 (3H, s), 2.46-2.57 (2H, m), 3.08 (2H, t, J=6.8 Hz), 3.14-3.24 (2H, m), 5.22 (1H, d, J=18.8 Hz), 5.29 (1H, d, J=18.8 Hz), 5.43 (2H, s), 5.58 (1H, dt, J=8.5, 4.5 Hz), 6.55 (1H, s), 7.32 (1H, s), 7.74 (3H, brs), 7.82 (1H, d, J=11.0 Hz), 8.67 (1H, d, J=8.6 Hz).

MS (ESI) m/z: 507 (M+H)$^+$

Example 50 Antibody-Drug Conjugate (47)

[Formula 119]

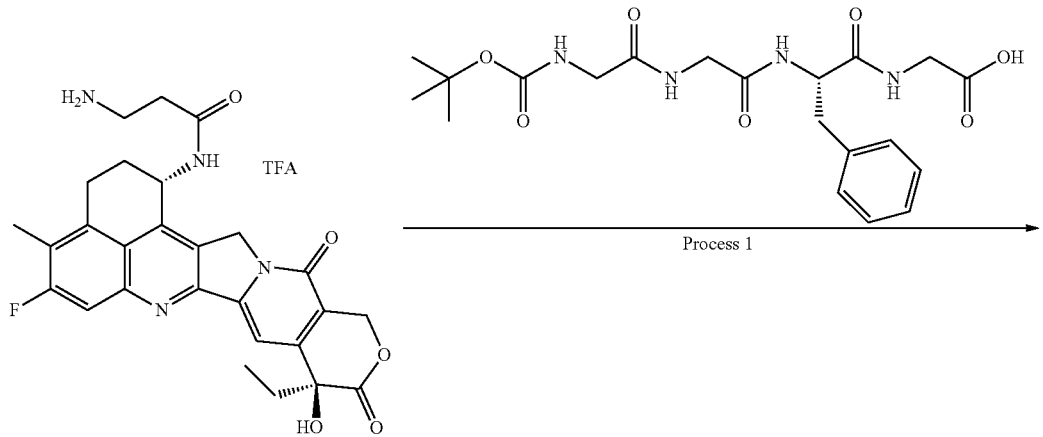

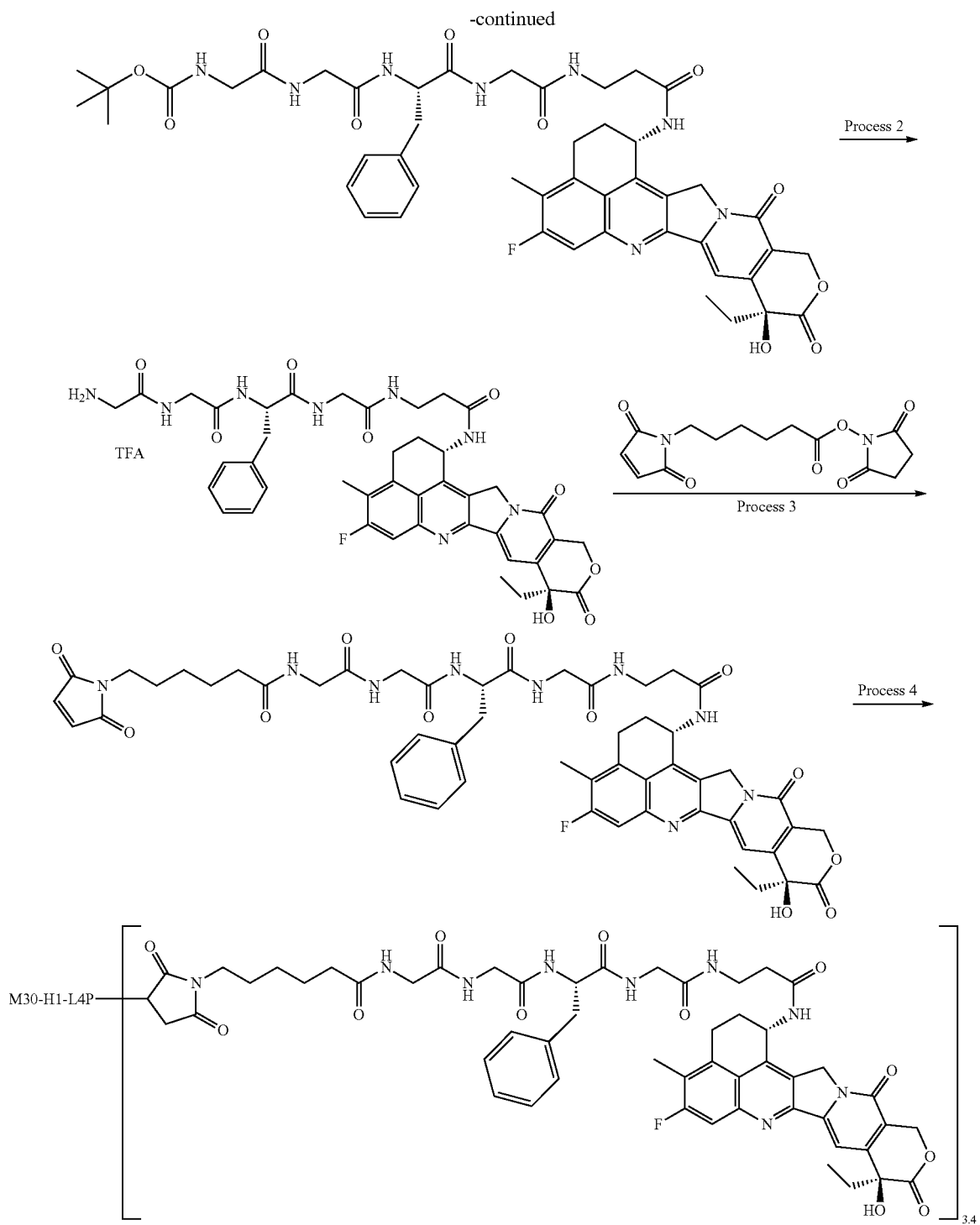

Process 1: N-(tert-butoxycarbonyl)glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alaninamide The compound (484 mg, 0.780 mmol) of Example 49 was reacted in the same manner as Process 1 of Example 2 to yield the titled compound as a pale yellow solid (626 mg, 87%).

$^1$H-NMR (400 MHz, DMSO-$d_6$) δ: 0.87 (3H, t, J=7.4 Hz), 1.27-1.42 (9H, m), 1.77-1.93 (2H, m), 2.06-2.22 (2H, m), 2.36 (2H, t, J=7.2 Hz), 2.40 (3H, d, J=1.6 Hz), 2.44-2.54 (2H, m), 2.76 (1H, dd, J=14.5, 10.2 Hz), 3.02 (1H, dd, J=13.9, 4.5 Hz), 3.12-3.22 (2H, m), 3.52 (6H, d, J=6.3 Hz), 4.42-4.54 (1H, m), 5.19 (1H, d, J=19.2 Hz), 5.26 (1H, d, J=18.4 Hz), 5.42 (1H, dd, J=18.4, 16.4 Hz), 5.57 (1H, dt, J=8.7, 4.4 Hz), 6.53 (1H, s), 6.98 (1H, t, J=5.9 Hz), 7.14-7.28 (5H, m), 7.31 (1H, s), 7.77-7.84 (1H, m), 7.91 (1H, t, J=5.5 Hz), 8.16 (1H, d, J=7.8 Hz), 8.27 (1H, t, J=5.1 Hz), 8.52 (1H, d, J=9.0 Hz).

Process 2: Glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alaninamide trifluoroacetate The compound (624 mg, 0.675 mmol) obtained in Process 1 above was reacted in the same manner as Process 2 of Example 2 to yield the titled compound as a yellow solid (626 mg, 92%).

$^1$H-NMR (400 MHz, DMSO-$d_6$) δ: 0.87 (3H, t, J=7.4 Hz), 1.86 (2H, tt, J=14.5, 7.2 Hz), 2.07-2.22 (2H, m), 2.36 (2H, t, J=7.2 Hz), 2.40 (3H, s), 2.44-2.54 (2H, m), 2.75 (1H, dd, J=13.7, 9.8 Hz), 3.04 (1H, dd, J=13.7, 4.3 Hz), 3.12-3.22 (2H, m), 3.58 (2H, d, J=4.7 Hz), 3.69 (3H, td, J=11.2, 5.7 Hz), 3.87 (1H, dd, J=17.0, 5.7 Hz), 4.54 (1H, m, J=17.8, 4.5 Hz), 5.19 (1H, d, J=19.2 Hz), 5.26 (1H, d, J=18.8 Hz), 5.43 (2H, s), 5.51-5.60 (1H, m), 6.55 (1H, s), 7.14-7.29 (5H, m), 7.32 (1H, s), 7.81 (1H, d, J=10.9 Hz), 7.88 (1H, t, J=5.7 Hz), 7.97 (3H, brs), 8.29-8.38 (2H, m), 8.50 (1H, t, J=5.7 Hz), 8.55 (1H, d, J=8.6 Hz).

MS (ESI) m/z: 825 (M+H)$^+$

Process 3: N-[6-(2,5-dioxo-2,5-dihydro-1H-pyrrol-1-yl)hexanoyl]glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alaninamide The compound (60.0 mg, 0.0646 mmol) obtained in Process 2 above was reacted in the same manner as Process 3 of Example 2 to yield the titled compound as a solid (14.0 mg, 21%).

$^1$H-NMR (400 MHz, DMSO-$d_6$) δ: 0.86 (3H, t, J=7.2 Hz), 1.12-1.22 (2H, m), 1.39-1.51 (4H, m), 1.79-1.91 (2H, m), 2.02-2.20 (2H, m), 2.07 (2H, t, J=7.4 Hz), 2.30-2.42 (4H, m), 2.40 (3H, s), 2.78 (1H, dd, J=14.1, 9.4 Hz), 3.02 (1H, dd, J=14.7, 4.9 Hz), 3.12-3.21 (2H, m), 3.26-3.42 (2H, m), 3.50-3.80 (6H, m), 4.40-4.51 (1H, m), 5.19 (1H, d, J=19.6 Hz), 5.26 (1H, d, J=19.2 Hz), 5.42 (2H, brs), 5.51-5.62 (1H, m), 6.53 (1H, s), 6.99 (2H, s), 7.13-7.28 (5H, m), 7.31 (1H, s), 7.74-7.84 (2H, m), 8.01 (1H, t, J=5.3 Hz), 8.06 (1H, t, J=5.7 Hz), 8.14 (1H, d, J=8.2 Hz), 8.25 (1H, t, J=5.7 Hz), 8.53 (1H, d, J=8.6 Hz).

MS (ESI) m/z: 1018 (M+H)$^+$

Process 4: Antibody-Drug Conjugate (47)

By using the M30-H1-L4P antibody produced in Reference Example 2 and the compound obtained in Process 3 above, the titled antibody-drug conjugate was obtained in the same manner as Process 4 of Example 2. Antibody concentration: 12.27 mg/mL, antibody yield: 8.6 mg (69%), and average number of conjugated drug molecules (n) per antibody molecule: 3.4.

Example 51 Antibody-Drug Conjugate (48)

[Formula 120]

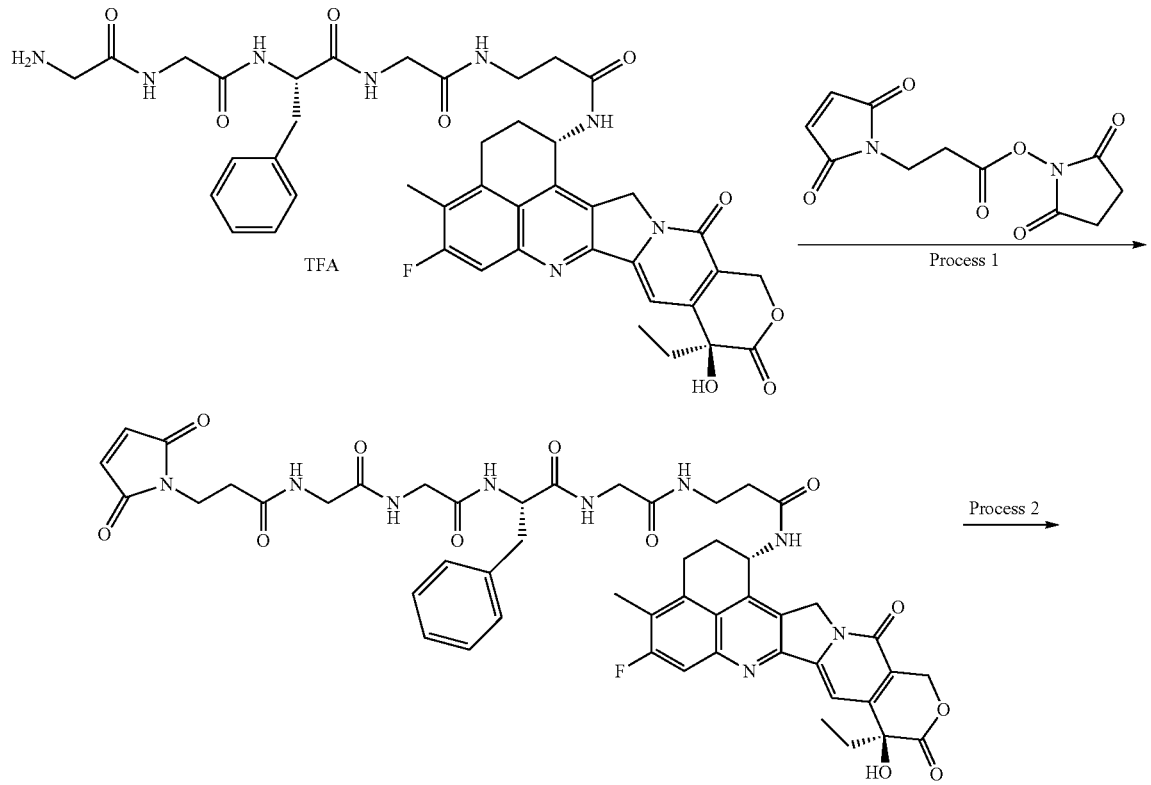

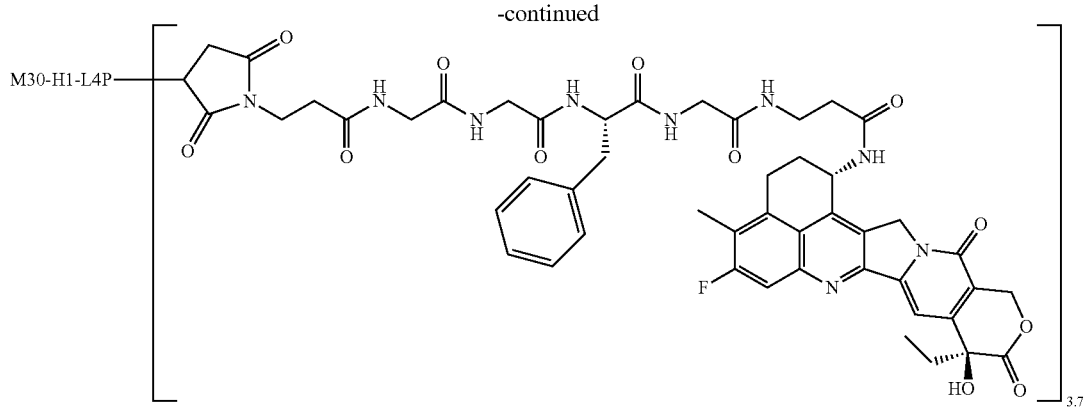

Process 1: N-[3-(2,5-dioxo-2,5-dihydro-1H-pyrrol-1-yl)propanoyl]glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alaninamide The compound (60.0 mg, 0.0646 mmol) obtained in Process 2 of Example 50 was reacted in the same manner as Process 3 of Example 2 by using N-succinimidyl 3-maleimide propanoate instead of N-succinimidyl 6-maleimide hexanoate to yield the titled compound as a pale yellow solid (36.0 mg, 57%).

$^1$H-NMR (400 MHz, DMSO-$d_6$) δ: 0.86 (3H, t, J=7.4 Hz), 1.85 (2H, dt, J=14.4, 7.5 Hz), 2.05-2.22 (2H, m), 2.40 (3H, s), 2.30-2.44 (5H, m), 2.73-2.84 (1H, m), 3.02 (1H, dd, J=13.9, 4.5 Hz), 3.17 (3H, d, J=5.1 Hz), 3.26-3.40 (2H, m), 3.41-3.81 (6H, m), 4.40-4.51 (1H, m), 5.19 (1H, d, J=19.2 Hz), 5.26 (1H, d, J=18.8 Hz), 5.42 (2H, brs), 5.52-5.61 (1H, m), 6.53 (1H, s), 6.99 (2H, s), 7.13-7.28 (5H, m), 7.31 (1H, s), 7.80 (2H, d, J=10.2 Hz), 8.03 (1H, t, J=5.5 Hz), 8.12 (1H, d, J=8.2 Hz), 8.20-8.31 (2H, m), 8.52 (1H, d, J=8.6 Hz).

MS (ESI) m/z: 976 (M+H)$^+$

Process 2: Antibody-Drug Conjugate (48)

By using the M30-H1-L4P antibody produced in Reference Example 2 and the compound obtained in Process 1 above, the titled antibody-drug conjugate was obtained in the same manner as Process 4 of Example 2. Antibody concentration: 11.59 mg/mL, antibody yield: 8.1 mg (65%), and average number of conjugated drug molecules (n) per antibody molecule: 3.7.

Example 52 Antibody-Drug Conjugate (49)

[Formula 121]

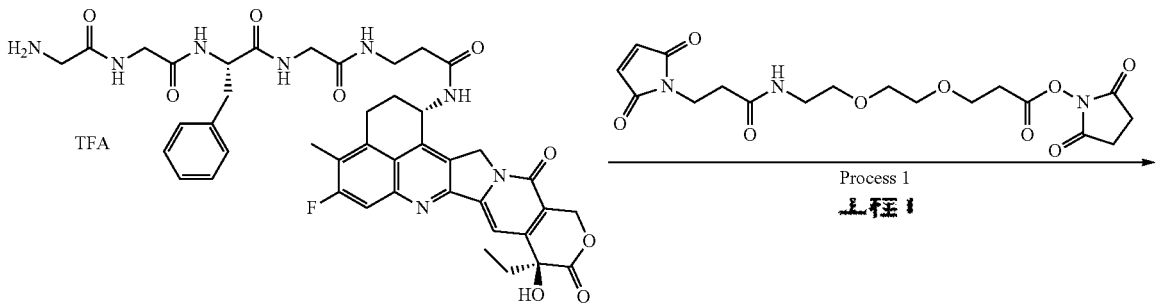

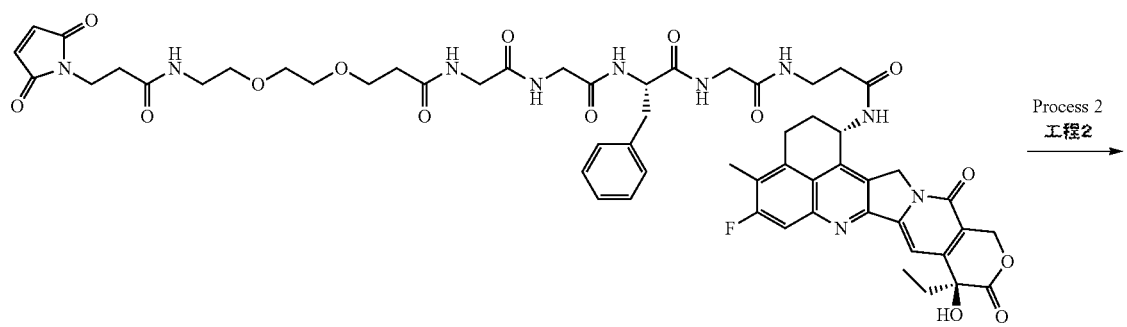

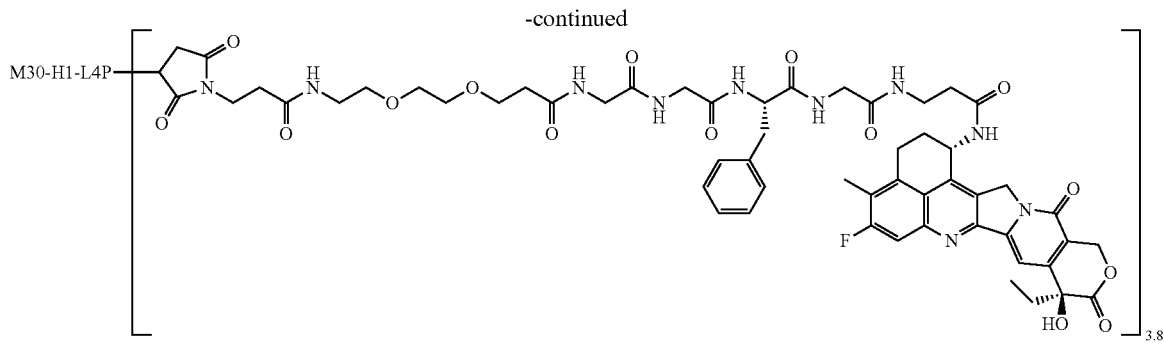
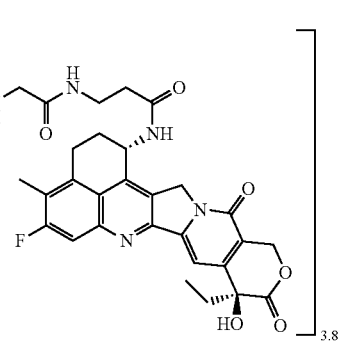

Process 1: N-{3-[2-(2-{[3-(2,5-dioxo-2,5-dihydro-1H-pyrrol-1-yl)propanoyl]amino})ethoxy]propanoyl}glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alaninamide The compound (60.0 mg, 0.0646 mmol) obtained in Process 2 of Example 50 was reacted in the same manner as Process 3 of Example 2 by using N-succinimidyl 3-(2-(2-(3-maleinimidepropanamide) ethoxy)ethoxy)propanoate instead of N-succinimidyl 6-maleimide hexanoate to yield the titled compound as a solid (23.0 mg, 31%).

$^1$H-NMR (400 MHz, DMSO-$d_6$) δ: 0.86 (3H, t, J=7.4 Hz), 1.77-1.92 (2H, m), 2.07-2.21 (2H, m), 2.27-2.42 (6H, m), 2.40 (3H, s), 2.74-2.84 (1H, m), 2.97-3.06 (1H, m), 3.09-3.21 (4H, m), 3.25-3.39 (6H, m), 3.45 (4H, s), 3.50-3.80 (8H, m), 4.41-4.51 (1H, m), 5.19 (1H, d, J=18.4 Hz), 5.26 (1H, m, J=18.4 Hz), 5.42 (2H, brs), 5.51-5.61 (1H, m), 6.54 (1H, s), 7.00 (2H, s), 7.13-7.28 (5H, m), 7.31 (1H, s), 7.74-7.87 (2H, m), 7.93-8.07 (2H, m), 8.09-8.21 (2H, m), 8.26 (1H, brs), 8.54 (1H, d, J=8.6 Hz).

MS (ESI) m/z: 1135 (M+H)$^+$

Process 2: Antibody-Drug Conjugate (49)

By using the M30-H1-L4P antibody produced in Reference Example 2 and the compound obtained in Process 1 above, the titled antibody-drug conjugate was obtained in the same manner as Process 2 of Example 29. Antibody concentration: 14.50 mg/mL, antibody yield: 10.2 mg (82%), and average number of conjugated drug molecules (n) per antibody molecule: 3.8.

Example 53 Antibody-Drug Conjugate (50)

[Formula 122]

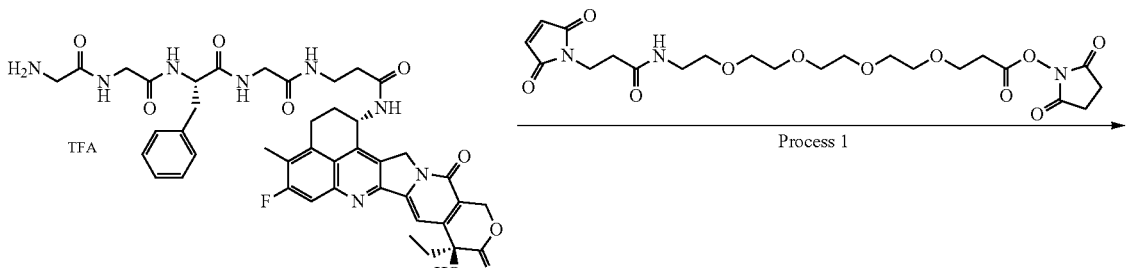

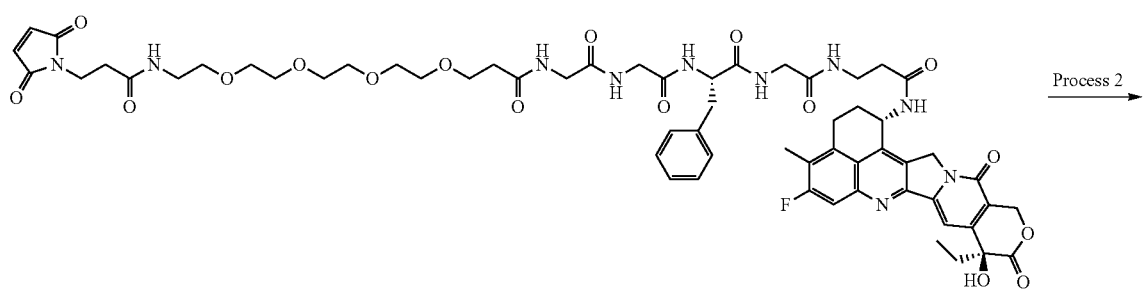

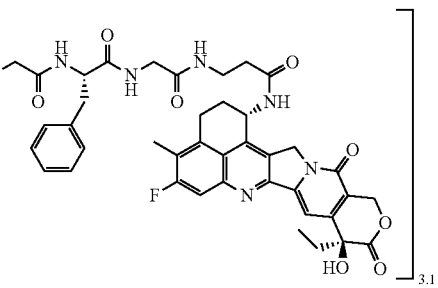

Process 1: N-[19-(2,5-dioxo-2,5-dihydro-1H-pyrrol-1-yl)-17-oxo-4,7,10,13-tetraoxa-16-azanonadecan-1-oyl]glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alaninamide The compound (60.0 mg, 0.0646 mmol) obtained in Process 2 of Example 50 was reacted in the same manner as Process 3 of Example 2 by using N-succinimidyl 1-maleinimide-3-oxo-7,10,13,16-tetraoxa-4-azanonadecanoate instead of N-succinimidyl 6-maleimide hexanoate to yield the titled compound as a solid (23.0 mg, 29%).

$^1$H-NMR (400 MHz, DMSO-$d_6$) δ: 0.86 (3H, t, J=7.0 Hz), 1.85 (2H, tt, J=14.6, 7.1 Hz), 2.06-2.22 (2H, m), 2.40 (3H, s), 2.28-2.43 (6H, m), 2.78 (1H, dd, J=13.7, 9.4 Hz), 3.02 (1H, dd, J=14.1, 3.9 Hz), 3.09-3.22 (4H, m), 3.27-3.41 (4H, m), 3.47 (12H, d, J=8.6 Hz), 3.53-3.81 (10H, m), 4.41-4.51 (1H, m), 5.19 (1H, d, J=19.2 Hz), 5.26 (1H, d, J=18.8 Hz), 5.42 (2H, brs), 5.53-5.61 (1H, m), 6.54 (1H, s), 7.00 (2H, s), 7.12-7.29 (5H, m), 7.31 (1H, s), 7.74-7.85 (2H, m), 8.03 (2H, d, J=6.6 Hz), 8.11-8.21 (2H, m), 8.27 (1H, t, J=5.9 Hz), 8.54 (1H, d, J=8.6 Hz).

MS (ESI) m/z: 1224 (M+H)$^+$

Process 2: Antibody-Drug Conjugate (50)

By using the M30-H1-L4P antibody produced in Reference Example 2 and the compound obtained in Process 1 above, the titled antibody-drug conjugate was obtained in the same manner as Process 4 of Example 2. Antibody concentration: 13.47 mg/mL, antibody yield: 9.4 mg (75%), and average number of conjugated drug molecules (n) per antibody molecule: 3.1.

Example 54 Antibody-Drug Conjugate (51)

[Formula 123]

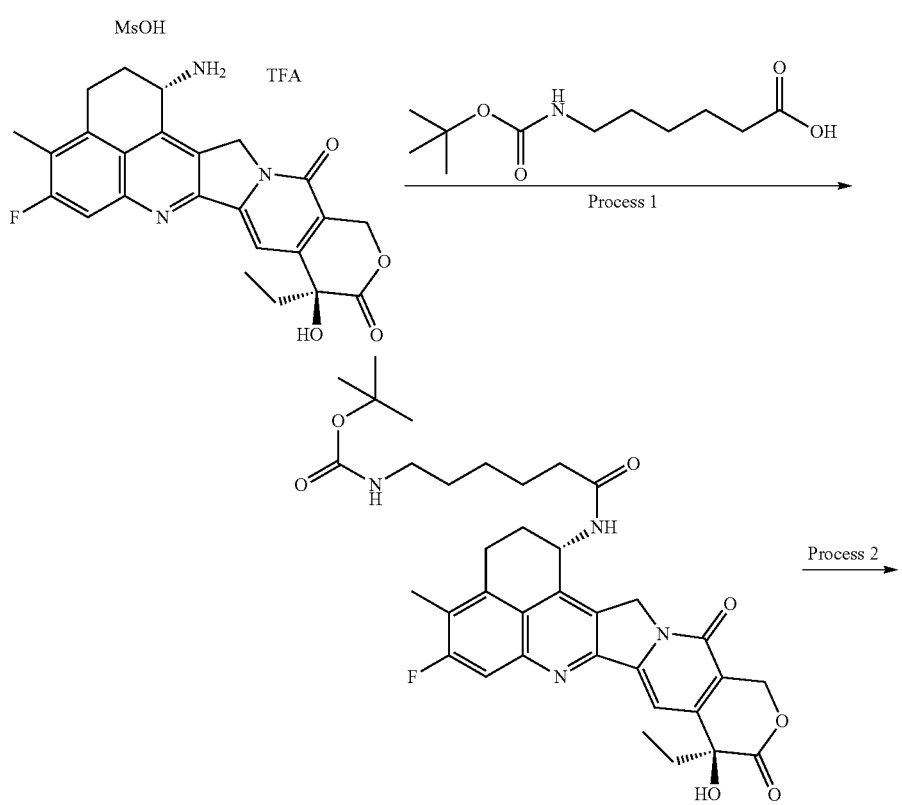

225
-continued
226
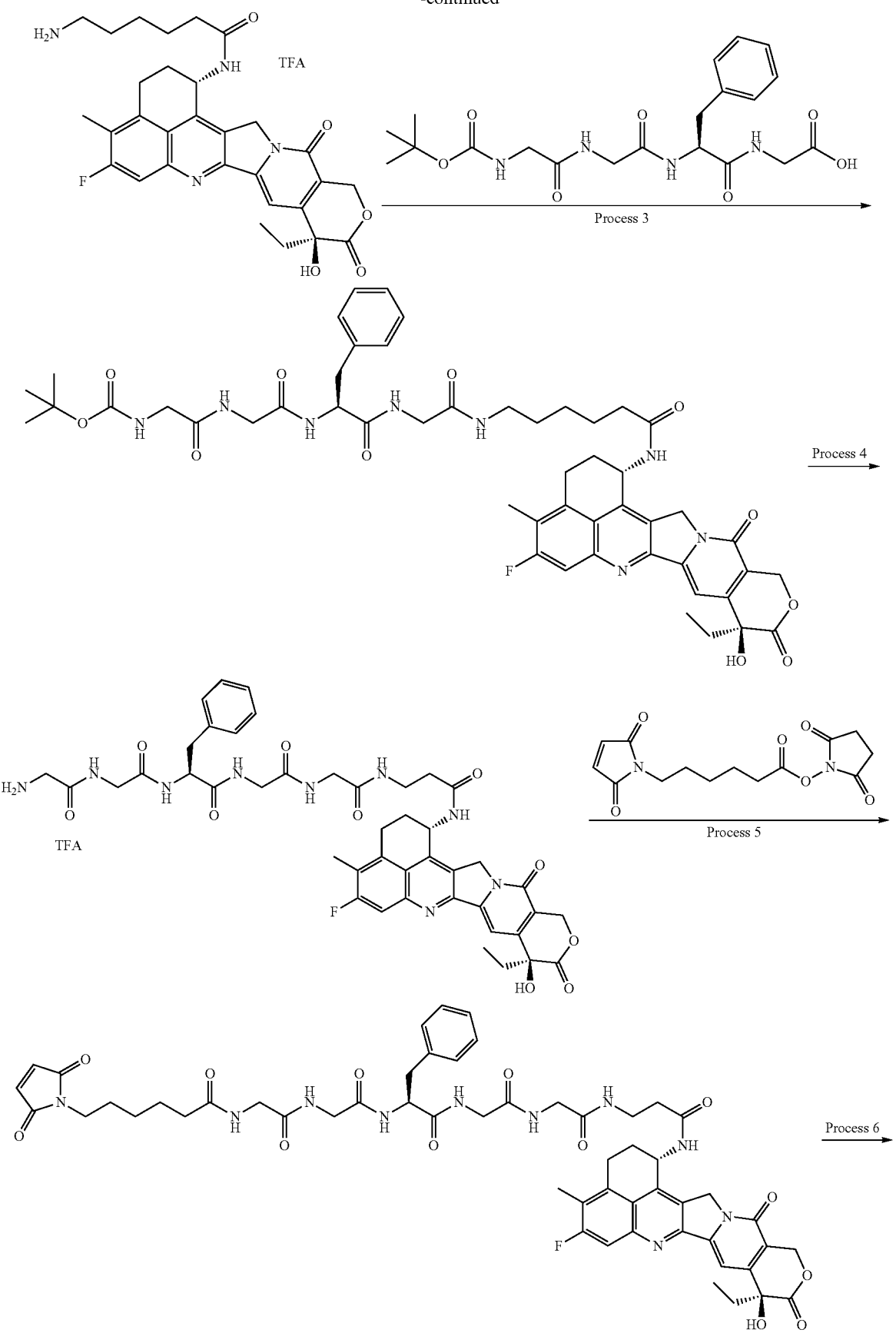

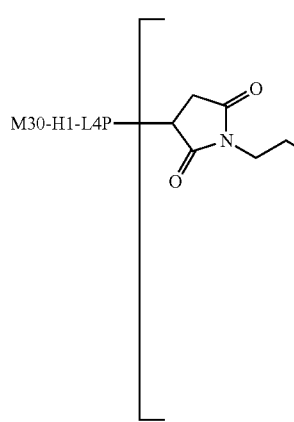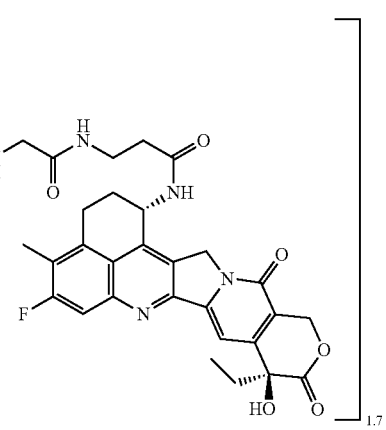

Process 1: tert-Butyl (6-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-6-oxohexyl) carbamate Mesylate of the compound (4) (0.500 g, 0.882 mmol) was reacted in the same manner as Process 1 of Example 1 by using 6-(tert-butoxycarbonylamino)hexanoic acid instead of 4-(tert-butoxycarbonylamino)butanoic acid to yield the titled compound (0.620 g, quantitative).

$^1$H-NMR (DMSO-d$_6$) δ: 0.83 (3H, t, J=7.8 Hz), 1.14-1.28 (2H, m), 1.31 (9H, s), 1.47-1.61 (2H, m), 1.75-1.89 (2H, m), 2.04-2.17 (4H, m), 2.35 (3H, s), 2.81-2.88 (2H, m), 3.09-3.16 (2H, m), 5.10 (1H, d, J=19.4 Hz), 5.16 (1H, d, J=19.4 Hz), 5.39 (2H, s), 5.48-5.55 (1H, m), 6.50 (1H, s), 6.73-6.78 (1H, m), 7.26 (1H, s), 7.74 (1H, d, J=10.9 Hz), 8.39 (1H, d, J=9.0 Hz).

Process 2: 6-Amino-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]hexanamide trifluoroacetate The compound (0.397 g, 0.611 mmol) obtained in Process 1 above was reacted in the same manner as Process 2 of Example 1 to yield the titled compound (0.342 g, 84%).

$^1$H-NMR (DMSO-d$_6$) δ: 0.88 (3H, t, J=7.2 Hz), 1.31-1.41 (2H, m), 1.52-1.70 (4H, m), 1.80-1.94 (2H, m), 2.05-2.18 (2H, m), 2.21 (2H, t, J=7.4 Hz), 2.40 (3H, s), 2.81 (2H, t, J=7.4 Hz), 3.10-3.25 (2H, m), 3.33 (2H, brs), 5.18 (1H, d, J=19.8 Hz), 5.22 (1H, d, J=19.8 Hz), 5.41 (2H, d, J=16.6 Hz), 5.45 (2H, d, J=16.6 Hz), 5.53-5.60 (1H, m), 6.55 (1H, s), 7.32 (1H, s), 7.80 (1H, d, J=10.9 Hz), 8.49 (1H, d, J=9.2 Hz).

Process 3: N-(tert-butoxycarbonyl)glycylglycyl-L-phenylalanyl-N-(6-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-6-oxohexyl) glycinamide The compound (0.170 g, 0.516 mmol) obtained in Process 2 above was reacted in the same manner as Process 1 of Example 2 to yield the titled compound (0.225 g, 91%).

$^1$H-NMR (DMSO-d$_6$) δ: 0.88 (3H, t, J=7.4 Hz), 1.43-1.70 (6H, m), 1.87 (2H, td, J=15.0, 7.4 Hz), 2.10-2.22 (3H, m), 2.28-2.37 (1H, m), 2.42 (3H, s), 2.78-2.85 (1H, m), 3.01-3.10 (3H, m), 3.15-3.22 (2H, m), 3.54-3.61 (5H, m), 3.62-3.69 (1H, m), 4.44-4.53 (1H, m), 5.17 (1H, d, J=19.2 Hz), 5.25 (1H, d, J=19.2 Hz), 5.45 (2H, s), 5.54-5.61 (1H, m), 6.55 (1H, s), 7.02 (1H, t, J=6.1 Hz), 7.11-7.28 (5H, m), 7.33 (1H, s), 7.63-7.69 (1H, m), 7.82 (1H, d, J=11.0 Hz), 7.90-7.96 (1H, m), 8.17 (1H, d, J=7.8 Hz), 8.28 (1H, t, J=5.5 Hz), 8.46 (1H, d, J=9.0 Hz).

Process 4: Glycylglycyl-L-phenylalanyl-N-(6-{[(1S,9S)-9-ethyl-5-fluoro-9-hydroxy-10,13-dioxo-2,3,9,10,13,15-hexahydro-1H,12H-benzo[de]pyrano[3',4':6,7]indolizino[1,2-b]quinolin-1-yl]amino}-6-oxohexyl)glycinamide The compound (0.105 g, 0.108 mmol) obtained in Process 3 above was reacted in the same manner as Process 2 of Example 2 to yield the titled compound (0.068 mg, 65%).

$^1$H-NMR (DMSO-d$_6$) δ: 0.89 (3H, t, J=7.4 Hz), 1.15-1.67 (6H, m), 1.79-1.97 (2H, m), 2.08-2.24 (4H, m), 2.42 (3H, s), 2.76-2.82 (1H, m), 3.00-3.10 (5H, m), 3.19 (1H, s), 3.50-3.63 (2H, m), 3.64-3.76 (3H, m), 3.84-3.92 (1H, m), 4.51-4.59 (1H, m), 5.17 (1H, d, J=19.4 Hz), 5.24 (1H, d, J=19.4 Hz), 5.44 (2H, s), 5.53-5.61 (1H, m), 6.55 (1H, brs), 7.15-7.29 (5H, m), 7.33 (1H, s), 7.72-7.78 (1H, m), 7.82 (1H, d, J=11.0 Hz), 7.96-8.08 (2H, m), 8.30-8.38 (2H, m), 8.46-8.56 (2H, m).

Process 5: N-[6-(2,5-dioxo-2,5-dihydro-1H-pyrrol-1-yl)hexanoyl]glycylglycyl-L-phenylalanyl-N-(6-{[(1S,9S)-9-ethyl-5-fluoro-9-hydroxy-10,13-dioxo-2,3,9,10,13,15-hexahydro-1H,12H-benzo[de]pyrano[3',4':6,7]indolizino[1,2-b]quinolin-1-yl]amino}-6-oxohexyl)glycinamide The compound (58 mg, 0.060 mmol) obtained in Process 4 above was reacted in the same manner as Process 3 of Example 2 to yield the titled compound (39 mg, 62%).

$^1$H-NMR (CD$_3$OD) δ: 0.99 (3H, t, J=7.4 Hz), 1.27 (2H, td, J=11.6, 6.1 Hz), 1.38-1.44 (2H, m), 1.50-1.63 (6H, m), 1.65-1.80 (2H, m), 1.89-1.98 (2H, m), 2.17-2.25 (3H, m), 2.26-2.36 (3H, m), 2.40 (3H, s), 2.95 (1H, dd, J=14.3, 9.2 Hz), 3.12 (1H, dd, J=13.7, 5.7 Hz), 3.15-3.25 (4H, m), 3.44 (2H, t, J=7.2 Hz), 3.65 (1H, d, J=17.2 Hz), 3.76 (1H, d, J=17.2 Hz), 3.79-3.86 (4H, m), 4.43 (1H, dd, J=8.9, 6.0 Hz), 5.10 (1H, d, J=18.9 Hz), 5.25 (1H, d, J=18.9 Hz), 5.35 (1H, d, J=16.6 Hz), 5.56 (1H, d, J=16.0 Hz), 5.60-5.64 (1H, m), 6.76 (2H, s), 7.12-7.24 (6H, m), 7.58 (1H, s), 7.60 (1H, d, J=10.9 Hz), 7.68 (1H, t, J=5.7 Hz).

MS (ESI) m/z: 1060 (M+H)+

Process 6: Antibody-Drug Conjugate (51)

Reduction of the antibody: The M30-H1-L4P antibody produced in Reference Example 2 was prepared to have antibody concentration of 10 mg/mL with PBS6.0/EDTA by using the Common procedure B (as absorption coefficient at 280 nm, 1.61 was used) and Common procedure C-1 described in Production method 1. The solution (1.0 mL) was collected into a 1.5 mL tube and charged with an aqueous solution of 10 mM TCEP (Tokyo Chemical Industry Co., Ltd.) (0.0147 mL; 2.3 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour. Conjugation between antibody and drug linker: After incubating the solution at 22° C. for 10 minutes, a dimethyl sulfoxide solution containing 10 mM of the compound obtained in above Process 5 (0.0295 mL; 4.6 equivalents per antibody molecule) was added thereto and incubated for conjugating the drug linker to the antibody at 22° C. for 40 minutes. Next, an aqueous solution (0.00590 mL; 9.2 equivalents per antibody molecule) of 100 mM NAC (Sigma-Aldrich Co. LLC) was added thereto and incubated to terminate the raction of drug linker at 22° C. for another 20 minutes.

Purification: The above solution was subjected to purification using the Common procedure D-1 (PBS7.4 was used as buffer solution) described in Production method 1 to yield 6 mL of a solution containing the titled antibody-drug conjugate.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,280}$=5000 (measured average value), and $\varepsilon_{D,370}$=19000 (measured average value) were used), the following characteristic values were obtained.

Antibody concentration: 0.97 mg/mL, antibody yield: 5.82 mg (58%), and average number of conjugated drug molecules (n) per antibody molecule: 1.7.

Example 55 Antibody-Drug Conjugate (52)

[Formula 124]

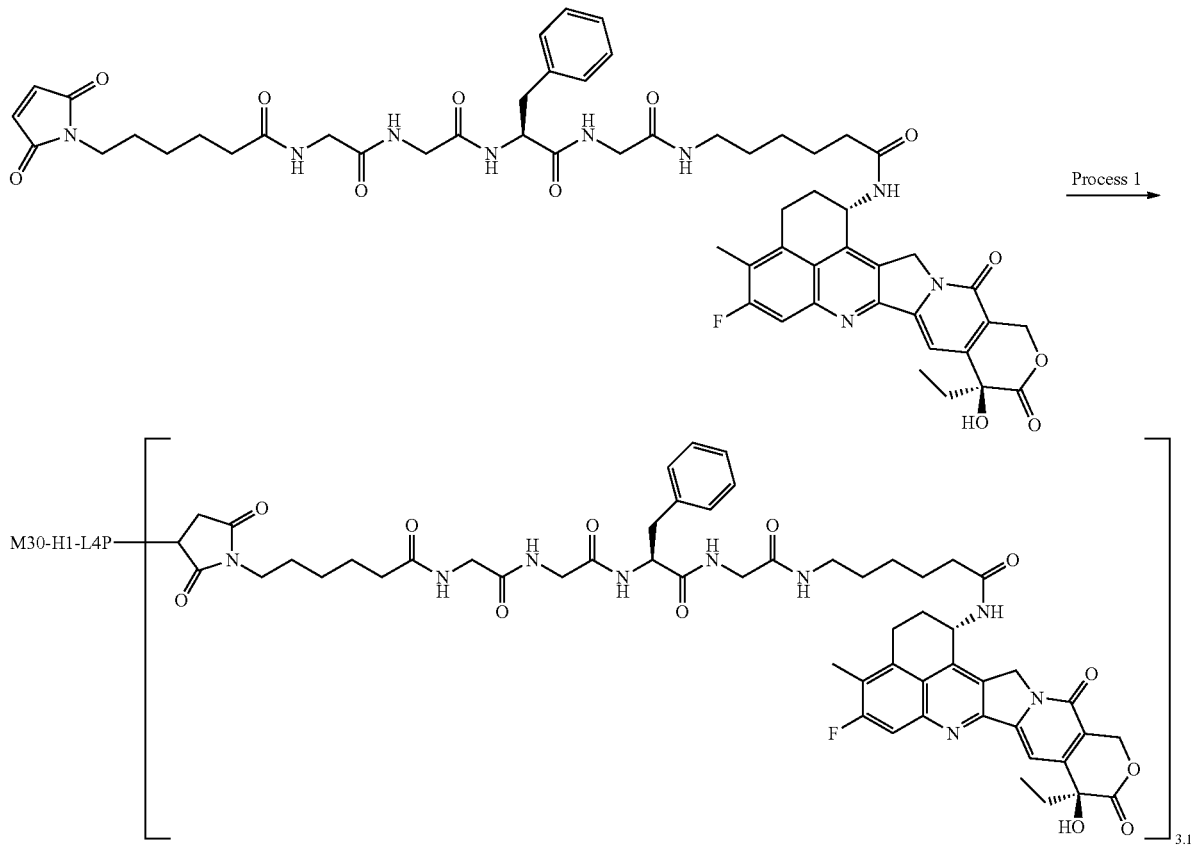

Process 1: Antibody-Drug Conjugate (52)

Reduction of the antibody: The M30-H1-L4P antibody produced in Reference Example 2 was prepared to have antibody concentration of 10 mg/mL with PBS6.0/EDTA by using the Common procedure B (as absorption coefficient at 280 nm, 1.61 was used) and Common procedure C-1 described in Production method 1. The solution (1.0 mL) was collected into a 1.5 mL tube and charged with an aqueous solution of 10 mM TCEP (Tokyo Chemical Industry Co., Ltd.) (0.0295 mL; 4.6 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour. Conjugation between antibody and drug linker: After incubating the above solution at 22° C. for 10 minutes, a dimethyl sulfoxide solution containing 10 mM of the compound obtained in Process 5 of Example 54 (0.0590 mL; 9.2 equivalents per antibody molecule) was added thereto and incubated for conjugating the drug linker to the antibody at 22° C. for 40 minutes. Next, an aqueous solution (0.0118 mL; 18.4 equivalents per antibody molecule) of 100 mM NAC (Sigma-Aldrich Co. LLC) was added thereto and incubated to terminate the raction of drug linker at 22° C. for another 20 minutes. Purification: The above solution was subjected to purification using the Common procedure D-1 (PBS7.4 was used as buffer solution) described in Production method 1 to yield 6 mL of a solution containing the titled antibody-drug conjugate.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,280}$=5000 (measured average value), and $\varepsilon_{D,370}$=19000 (measured average value) were used), the following characteristic values were obtained.

Antibody concentration: 0.94 mg/mL, antibody yield: 5.64 mg (56%), and average number of conjugated drug molecules (n) per antibody molecule: 3.1.

Example 56 Antibody-Drug Conjugate (53)

[Formula 125]

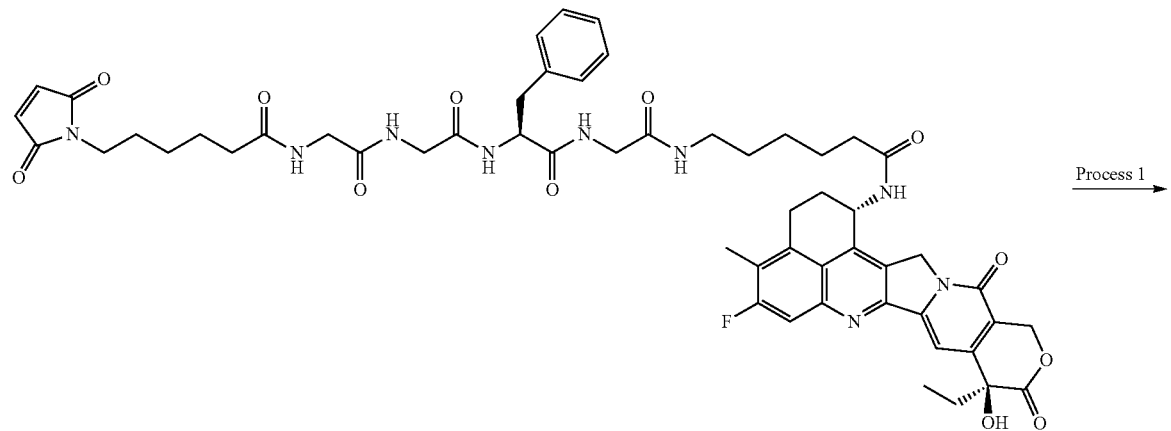

Process 1

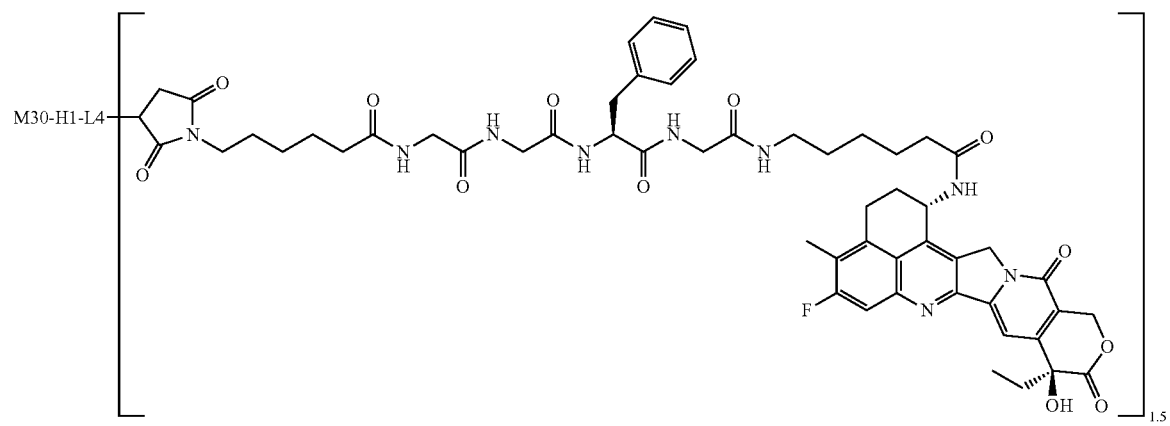

Process 1: Antibody-Drug Conjugate (53)

Reduction of the antibody: The M30-H1-L4 antibody produced in Reference Example 1 was prepared to have antibody concentration of 10 mg/mL with PBS6.0/EDTA by using the Common procedure B (as absorption coefficient at 280 nm, 1.61 was used) and Common procedure C-1 described in Production method 1. The solution (1.0 mL) was collected into a 1.5 mL tube and charged with an aqueous solution of 10 mM TCEP (Tokyo Chemical Industry Co., Ltd.) (0.0147 mL; 2.3 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour. Conjugation between antibody and drug linker: After incubating the above solution at 22° C. for 10 minutes, a dimethyl sulfoxide solution containing 10 mM of the compound obtained in Process 5 of Example 54 (0.0295 mL; 4.6 equivalents per antibody molecule) was added thereto and incubated for conjugating the drug linker to the antibody at 22° C. for 40 minutes. Next, an aqueous solution (0.00590 mL; 9.2 equivalents per antibody molecule) of 100 mM NAC (Sigma-Aldrich Co. LLC) was added thereto and incubated to terminate the raction of drug linker at 22° C. for another 20 minutes. Purification: The above solution was subjected to purification using the Common procedure D-1 (PBS7.4 was used as buffer solution) described in Production method 1 to yield 6 mL of a solution containing the titled antibody-drug conjugate.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,280}$=5000 (measured average value), and $\varepsilon_{D,370}$=19000 (measured average value) were used), the following characteristic values were obtained.

Antibody concentration: 1.22 mg/mL, antibody yield: 7.32 mg (73%), and average number of conjugated drug molecules (n) per antibody molecule: 1.5.

Example 57 Antibody-Drug Conjugate (54)

[Formula 126]

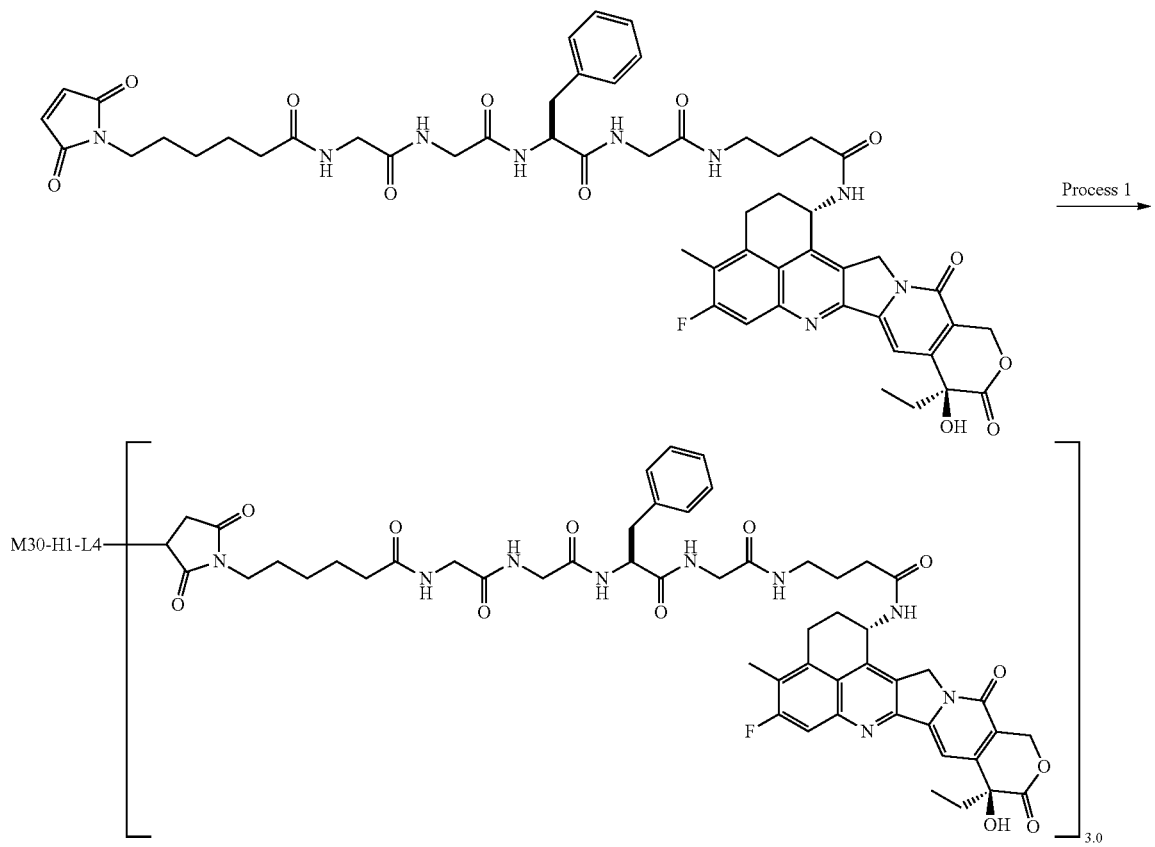

Process 1: Antibody-Drug Conjugate (54)

Reduction of the antibody: The M30-H1-L4 antibody produced in Reference Example 1 was prepared to have antibody concentration of 10 mg/mL with PBS6.0/EDTA by using the Common procedure B (as absorption coefficient at 280 nm, 1.61 was used) and Common procedure C-1 described in Production method 1. The solution (1.0 mL) was collected into a 1.5 mL tube and charged with an aqueous solution of 10 mM TCEP (Tokyo Chemical Industry Co., Ltd.) (0.0295 mL; 4.6 equivalents per antibody molecule) and an aqueous solution of 1 M dipotassium hydrogen phosphate (Nacalai Tesque, Inc.; 0.050 mL). After confirming that the solution had pH of 7.4±0.1, the disulfide bond at hinge part in the antibody was reduced by incubating at 37° C. for 1 hour. Conjugation between antibody and drug linker: After incubating the above solution at 22° C. for 10 minutes, a dimethyl sulfoxide solution containing 10 mM of the compound obtained in Process 5 of Example 54 (0.0590 mL; 9.2 equivalents per antibody molecule) was added thereto and incubated for conjugating the drug linker to the antibody at 22° C. for 40 minutes. Next, an aqueous solution (0.0118 mL; 18.4 equivalents per antibody molecule) of 100 mM NAC (Sigma-Aldrich Co. LLC) was added thereto and incubated to terminate the raction of drug linker at 22° C. for another 20 minutes. Purification: The above solution was subjected to purification using the Common procedure D-1 (PBS7.4 was used as buffer solution) described in Production method 1 to yield 6 mL of a solution containing the titled antibody-drug conjugate.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,280}$=5000 (measured average value), and $\varepsilon_{D,370}$=19000 (measured average value) were used), the following characteristic values were obtained.

Antibody concentration: 1.06 mg/mL, antibody yield: 6.36 mg (64%), and average number of conjugated drug molecules (n) per antibody molecule: 3.0.

Example 58 Antibody-Drug Conjugate (55)

[Formula 127]

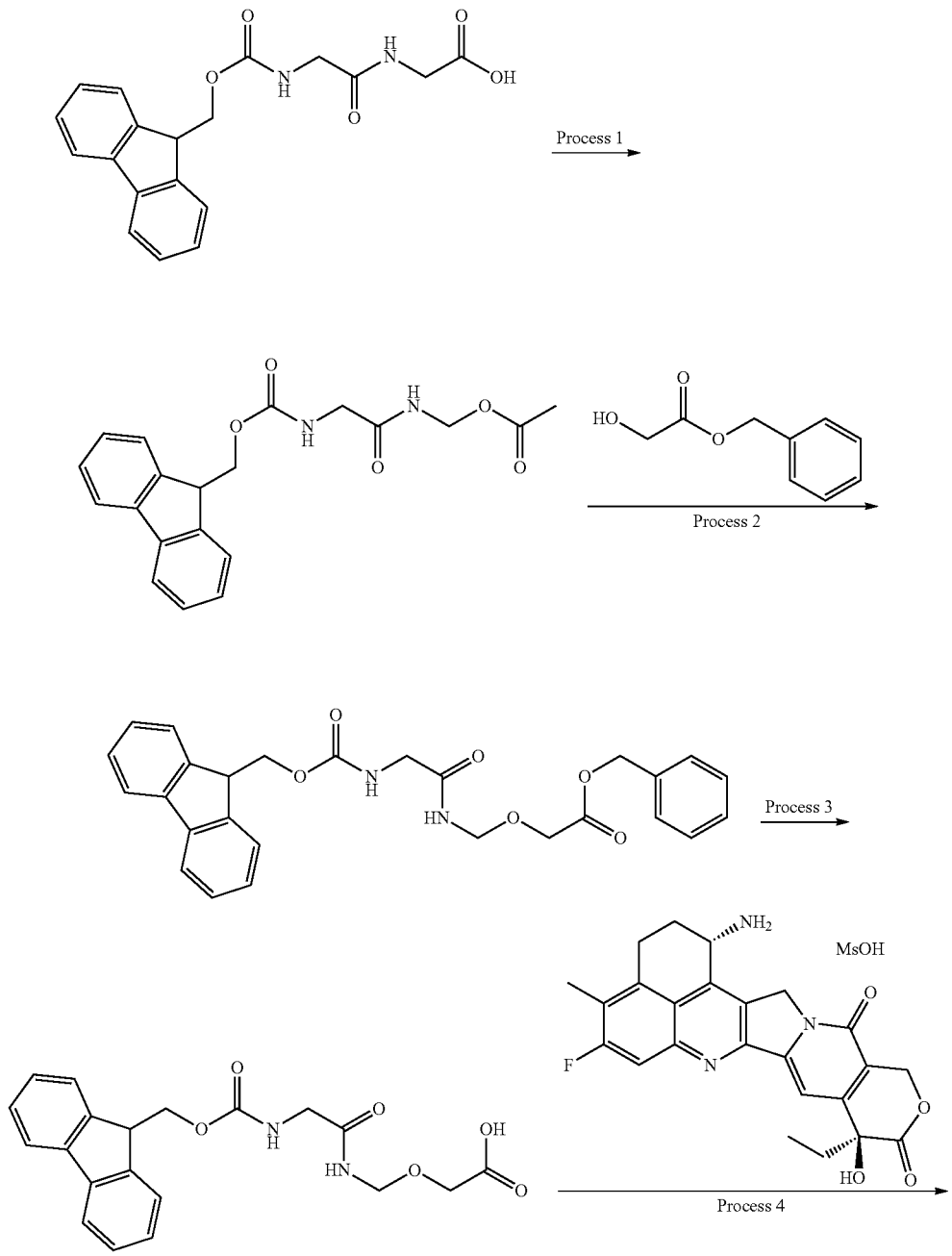

237 238
-continued
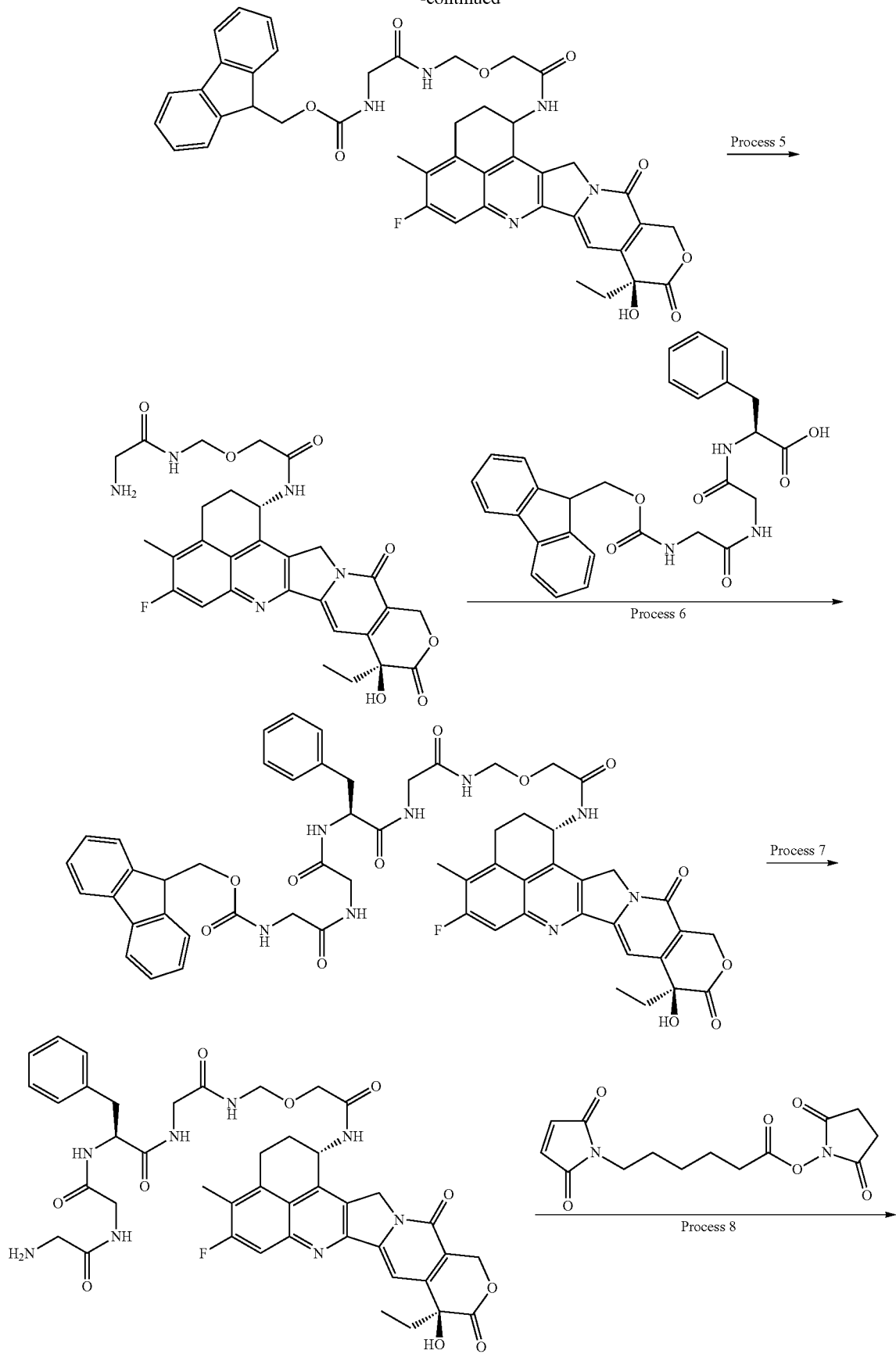

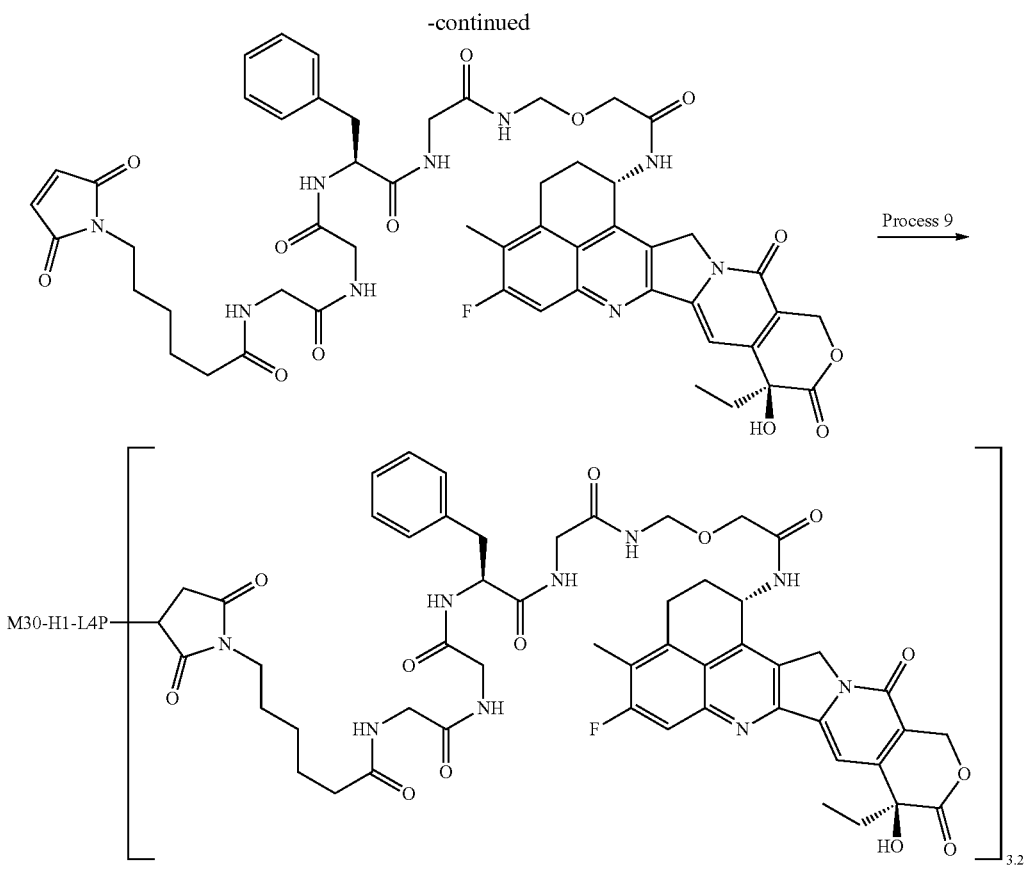

Process 1: ({N-[(9H-fluoren-9-ylmethoxy)carbonyl]glycyl}amino)methyl acetate

To a mixture containing N-9-fluorenylmethoxycarbonyl-glycylglycine (4.33 g, 12.2 mmol), tetrahydrofuran (120 ml), and toluene (40.0 ml), cooled to room temperature, the insolubles were removed by filtration through Celite, and concentrated under reduced pressure. The residues obtained were dissolved in ethyl acetate and washed with water and saturated brine, and then the organic layer was dried over anhydrous magnesium sulfate. After the solvent was removed under reduced pressure, the residues obtained were purified by silica gel column chromatography [hexane:ethyl acetate=9:1 (v/v)–ethyl acetate] to yield the titled compound as a colorless solid (3.00 g, 67%).

$^1$H-NMR (400 MHz, CDCl$_3$) δ: 2.07 (3H, s), 3.90 (2H, d, J=5.1 Hz), 4.23 (1H, t, J=7.0 Hz), 4.46 (2H, d, J=6.6 Hz), 5.26 (2H, d, J=7.0 Hz), 5.32 (1H, brs), 6.96 (1H, brs), 7.32 (2H, t, J=7.3 Hz), 7.41 (2H, t, J=7.3 Hz), 7.59 (2H, d, J=7.3 Hz), 7.77 (2H, d, J=7.3 Hz).

Process 2: Benzyl [({N-[(9H-fluoren-9-ylmethoxy)carbonyl]glycyl}amino)methoxy]acetate To a tetrahydrofuran (40.0 mL) solution of the compound (3.68 g, 10.0 mmol) obtained in Process 1 above and benzyl glycolate (4.99 g, 30.0 mmol), potassium tert-butoxide (2.24 g, 20.0 mmol) was added at 0° C. and stirred at room temperature for 15 minutes. The reaction solution was charged with ethyl acetate and water at 0° C. and extracted with ethyl acetate and chloroform. The obtained organic layer was dried over sodium sulfate and filtered. The solvent was removed under reduced pressure. The residues obtained were dissolved in dioxane (40.0 mL) and water (10.0 mL), charged with sodium hydrogen carbonate (1.01 g, 12.0 mmol) and 9-fluorenylmethyl chloroformate (2.59 g, 10.0 mmol), and stirred at room temperature for 2 hours. The reaction solution was charged with water and extracted with ethyl acetate. The obtained organic layer was dried over sodium sulfate and filtered. The solvent was removed under reduced pressure and the residues obtained were purified by silica gel column chromatography [hexane:ethyl acetate=100:0 (v/v)–0:100] to yield the titled compound in colorless oily substance (1.88 g, 40%).

$^1$H-NMR (400 MHz, CDCl$_3$) δ: 3.84 (2H, d, J=5.5 Hz), 4.24 (3H, t, J=6.5 Hz), 4.49 (2H, d, J=6.7 Hz), 4.88 (2H, d, J=6.7 Hz), 5.15-5.27 (1H, m), 5.19 (2H, s), 6.74 (1H, brs), 7.31-7.39 (7H, m), 7.43 (2H, t, J=7.4 Hz), 7.61 (2H, d, J=7.4 Hz), 7.79 (2H, d, J=7.4 Hz).

Process 3: [({N-[(9H-fluoren-9-ylmethoxy)carbonyl]glycyl}amino)methoxy]acetic Acid The compound (1.88 g, 3.96 mmol) obtained in Process 2 above was dissolved in ethanol (40.0 mL) and ethyl acetate (20.0 ml). After adding palladium carbon catalyst (376 mg), it was stirred under hydrogen atmosphere at room temperature for 2 hours. The insolubles were removed by filtration through Celite, and the solvent was removed under reduced pressure to yield the titled compound as a colorless solid (1.52 g, quantitative).

$^1$H-NMR (400 MHz, DMSO-d$_6$) δ: 3.62 (2H, d, J=6.3 Hz), 3.97 (2H, s), 4.18-4.32 (3H, m), 4.60 (2H, d, J=6.7 Hz), 7.29-7.46 (4H, m), 7.58 (1H, t, J=5.9 Hz), 7.72 (2H, d, J=7.4 Hz), 7.90 (2H, d, J=7.4 Hz), 8.71 (1H, t, J=6.5 Hz).

Process 4: 9H-Fluoren-9-ylmethyl(2-{[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]amino}-2-oxoethyl)carbamate Under ice cooling, to an N,N-dimethylformamide (10.0 mL) solution of mesylate of the compound (4) (0.283 g, 0.533 mmol), N-hydroxysuccinimide (61.4 mg, 0.533 mmol), and the compound (0.205 g, 0.533 mmol) obtained in Process 3 above, N,N-diisopropylethylamine (92.9 μL, 0.533 mmol) and N,N'-dicyclohexylcarbodiimide (0.143 g, 0.693 mmol) were added and stirred at room temperature for 3 days. The solvent was removed under reduced pressure and the residues obtained were purified by silica gel column chromatography [chloroform-partitioned organic layer of chloroform:methanol:water=7:3:1 (v/v/v)] to yield the titled compound as a pale brown solid (0.352 g, 82%).

$^1$H-NMR (400 MHz, DMSO-$d_6$) δ: 0.81 (3H, t, J=7.4 Hz), 1.73-1.87 (2H, m), 2.06-2.20 (2H, m), 2.34 (3H, s), 3.01-3.23 (2H, m), 3.58 (2H, d, J=6.7 Hz), 3.98 (2H, s), 4.13-4.25 (3H, m), 4.60 (2H, d, J=6.7 Hz), 5.09-5.22 (2H, m), 5.32-5.42 (2H, m), 5.50-5.59 (1H, m), 6.49 (1H, s), 7.24-7.30 (3H, m), 7.36 (2H, t, J=7.4 Hz), 7.53 (1H, t, J=6.3 Hz), 7.66 (2H, d, J=7.4 Hz), 7.75 (1H, d, J=11.0 Hz), 7.84 (2H, d, J=7.4 Hz), 8.47 (1H, d, J=8.6 Hz), 8.77 (1H, t, J=6.7 Hz).
MS (ESI) m/z: 802 (M+H)$^+$

Process 5: N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide To an N,N-dimethylformamide (11.0 mL) solution of the compound (0.881 g, 1.10 mmol) obtained in Process 4 above, piperidine (1.1 mL) was added and stirred at room temperature for 2 hours. The solvent was removed under reduced pressure to yield a mixture containing the titled compound. The mixture was used for the next reaction without further purification.

Process 6: N-[(9H-fluoren-9-ylmethoxy)carbonyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide Under ice cooling, to an N,N-dimethylformamide (50.0 mL) solution of the mixture (0.439 mmol) obtained in Process 5 above, N-hydroxysuccinimide (0.101 g, 0.878 mmol), and N-[(9H-fluoren-9-ylmethoxy)carbonyl]glycylglycyl-L-phenylalanine (the compound described in Japanese Patent Laid-Open No. 2002-60351) (0.440 g, 0.878 mmol), N,N'-dicyclohexylcarbodiimide (0.181 g, 0.878 mmol) was added and stirred at room temperature for 4 days. The solvent was removed under reduced pressure and the residues obtained were purified by silica gel column chromatography [chloroform-chloroform:methanol=9:1 (v/v)] to yield the titled compound as a pale orange solid (0.269 g, 58%).
MS (ESI) m/z: 1063 (M+H)$^+$ Process 7: Glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide To an N,N-dimethylformamide (4.00 mL) solution of the compound (0.269 g, 0.253 mmol) obtained in Process 6 above, piperidine (0.251 mL, 2.53 mmol) was added and stirred at room temperature for 2 hours. The solvent was removed under reduced pressure to yield a mixture containing the titled compound. The mixture was used for the next reaction without further purification.

Process 8: N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide To an N,N-dimethylformamide (10.0 mL) solution of the compound (0.253 mmol) obtained in Process 7 above, N-succinimidyl 6-maleimide hexanoate (0.156 g, 0.506 mmol) was added and stirred at room temperature for 3 days. The solvent was removed under reduced pressure and the residues obtained were purified by silica gel column chromatography [chloroform-chloroform methanol=9:1 (v/v)] to yield the titled compound as a pale yellow solid (0.100 g, 38%).

$^1$H-NMR (400 MHz, DMSO-$d_6$) δ: 0.83 (3H, t, J=7.2 Hz), 1.09-1.21 (2H, m), 1.33-1.47 (4H, m), 1.75-1.90 (2H, m), 2.00-2.23 (4H, m), 2.36 (3H, s), 2.69-2.81 (1H, m), 2.94-3.03 (1H, m), 3.06-3.22 (2H, m), 3.23-3.74 (8H, m), 3.98 (2H, s), 4.39-4.50 (1H, m), 4.60 (2H, d, J=6.7 Hz), 5.17 (2H, s), 5.39 (2H, s), 5.53-5.61 (1H, m), 6.50 (1H, s), 6.96 (2H, s), 7.11-7.24 (5H, m), 7.28 (1H, s), 7.75 (1H, d, J=11.0 Hz), 7.97 (1H, t, J=5.7 Hz), 8.03 (1H, t, J=5.9 Hz), 8.09 (1H, d, J=7.8 Hz), 8.27 (1H, t, J=6.5 Hz), 8.48 (1H, d, J=9.0 Hz), 8.60 (1H, t, J=6.5 Hz).
MS (ESI) m/z: 1034 (M+H)$^+$

Process 9: Antibody-Drug Conjugate (55)

Reduction of the antibody: The M30-H1-L4P antibody produced in Reference Example 2 was prepared to have antibody concentration of 10 mg/mL by replacing the medium with PBS6.0/EDTA by using the Common procedure C-1 and Common procedure B (as absorption coefficient at 280 nm, 1.61 mLmg$^{-1}$ cm$^{-1}$ was used) described in Production method 1. The solution (1.25 mL) was placed in a 1.5 mL polypropylene tube and charged with an aqueous solution of 10 mM TCEP (Tokyo Chemical Industry Co., Ltd.) (0.025 mL; 3.0 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding dimethyl sulfoxide (Sigma-Aldrich Co. LLC; 0.109 mL) and a dimethyl sulfoxide solution containing 10 mM of the compound obtained in above Process 8 (0.039 mL; 4.6 equivalents per antibody molecule) to the above solution at room temperature, it was stirred by using a tube rotator (MTR-103, manufactured by AS ONE Corporation) for conjugating the drug linker to the antibody at room temperature for 40 minutes. Next, an aqueous solution (0.008 mL) of 100 mM NAC (Sigma-Aldrich Co. LLC) was added thereto and stirred to terminate the raction of drug linker at room temperature for another 20 minutes.

Purification: The above solution was subjected to purification using the Common procedure D-1 (ABS was used as buffer solution) described in Production method 1 to yield 6 mL of a solution containing the titled antibody-drug conjugate. After that, the solution was concentrated by the Common procedure A described in Production method 1.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,280}$=5000 (measured average value), and $\varepsilon_{D,370}$=19000 (measured average value) were used), the following characteristic values were obtained.

Antibody concentration: 12.57 mg/mL, antibody yield: 8.8 mg (70%), and average number of conjugated drug molecules (n) per antibody molecule: 3.2.

Example 59 Antibody-Drug Conjugate (56)

dure C-1 and Common procedure B (as absorption coefficient at 280 nm, 1.61 mLmg$^{-1}$ cm$^{-1}$ was used) described in Production method 1. The solution (1.25 mL) was placed in a 1.5 mL polypropylene tube and charged with an aqueous solution of 10 mM TCEP (Tokyo Chemical Industry Co., Ltd.) (0.051 mL; 6.0 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding dimethyl sulfoxide (Sigma-Aldrich Co. LLC; 0.067 mL) a dimethyl sulfoxide solution containing and 10 mM of the compound obtained in Process 8 of Example 58 (0.085 mL; 10.0 equivalents per antibody molecule) to the above solution at room temperature, it was stirred by using a tube rotator (MTR-103, manufactured by AS ONE Corporation) for conjugating the drug linker to the antibody at room temperature for 60 minutes. Next, an aqueous solution (0.013 mL) of 100 mM NAC (Sigma-Aldrich Co. LLC) was added thereto and stirred to terminate the raction of drug linker at room temperature for another 20 minutes.

Purification: The above solution was subjected to purification using the Common procedure D-1 (ABS was used as

[Formula 128]

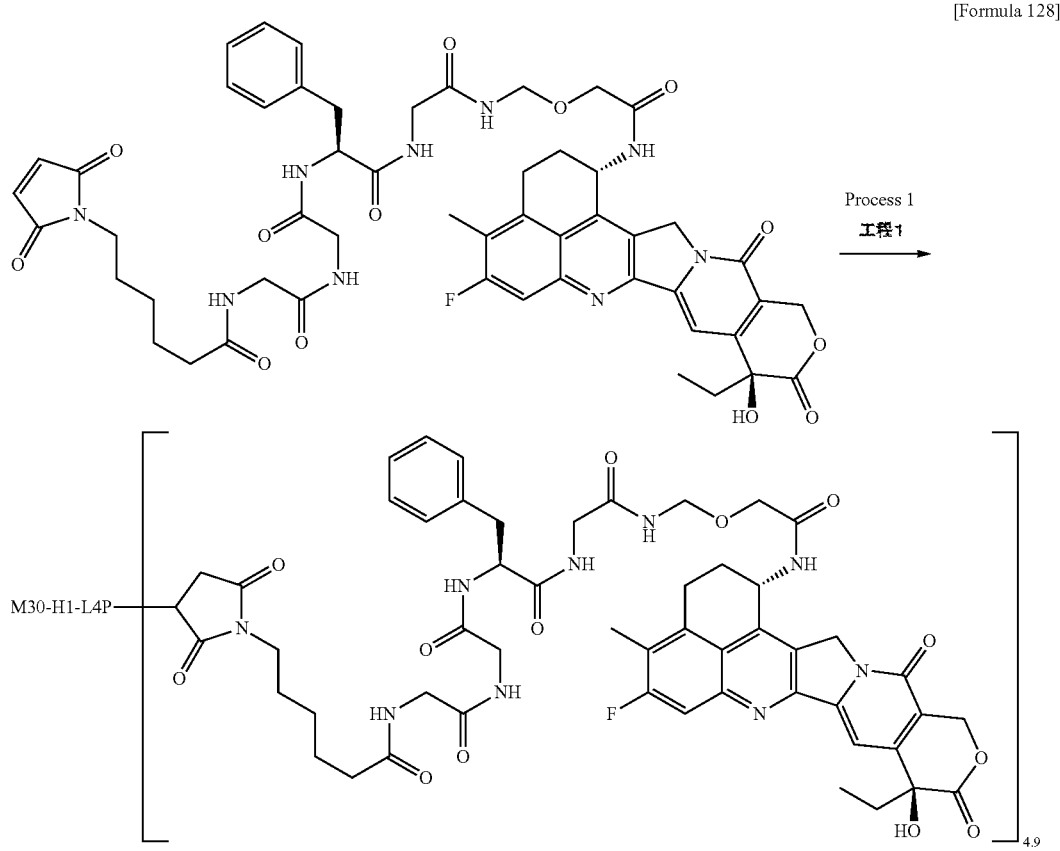

Process 1: Antibody-Drug Conjugate (56)

Reduction of the antibody: The M30-H1-L4P antibody produced in Reference Example 2 was prepared to have antibody concentration of 10 mg/mL by replacing the medium with PBS6.0/EDTA by using the Common procebuffer solution) described in Production method 1 to yield 6 mL of a solution containing the titled antibody-drug conjugate.

Physicochemical characterization: By using the Common procedure E described in Production method 1 (as molar absorption coefficient, $\varepsilon_{A,280}$=235300 (estimated calculation value), $\varepsilon_{A,370}=0$ (estimated calculation value), $\varepsilon_{D,280}=5000$ (measured average value), and $\varepsilon_{D,370}=19000$ (measured average value) were used), the following characteristic values were obtained.

Antibody concentration: 1.33 mg/mL, antibody yield: 7.98 mg (64%), and average number of conjugated drug molecules (n) per antibody molecule: 4.9.

Example 60 Antibody-Drug Conjugate (57)

Conjugation between antibody and drug linker: After adding dimethyl sulfoxide (Sigma-Aldrich Co. LLC; 0.025 mL) and a dimethyl sulfoxide solution containing 10 mM of the compound obtained in Process 8 of Example 58 (0.127 mL; 15.0 equivalents per antibody molecule) to the above solution at room temperature, it was stirred by using a tube rotator (MTR-103, manufactured by AS ONE Corporation) for conjugating the drug linker to the antibody at room temperature for 60 minutes. Next, an aqueous solution (0.019 mL) of 100 mM NAC (Sigma-Aldrich Co. LLC) was

[Formula 129]

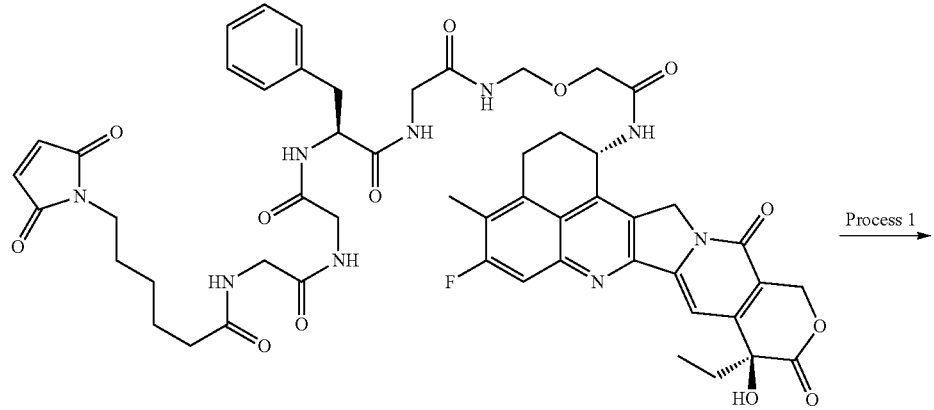

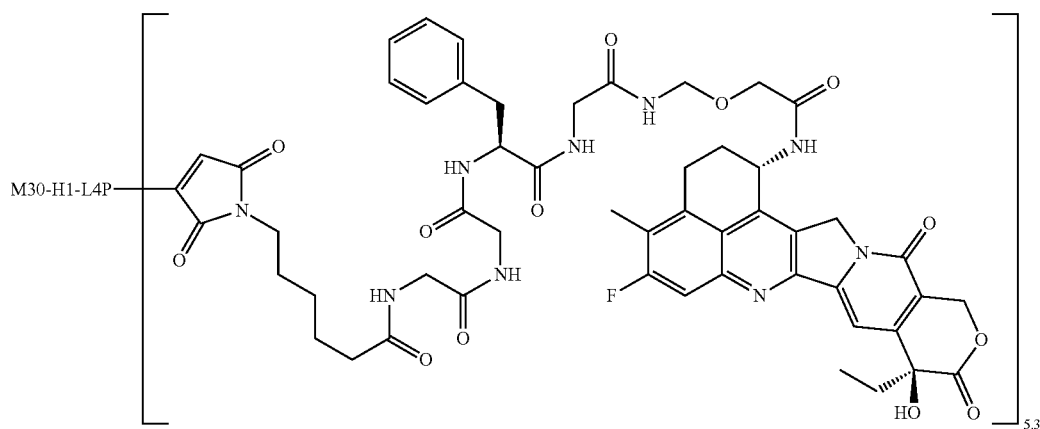

Process 1: Antibody-Drug Conjugate (57)

Reduction of the antibody: The M30-H1-L4P antibody produced in Reference Example 2 was prepared to have antibody concentration of 10 mg/mL by replacing the medium with PBS6.0/EDTA by using the Common procedure C-1 and Common procedure B (as absorption coefficient at 280 nm, 1.61 mLmg$^{-1}$ cm$^{-1}$ was used) described in Production method 1. The solution (1.25 mL) was placed in a 1.5 mL polypropylene tube and charged with an aqueous solution of 10 mM TCEP (Tokyo Chemical Industry Co., Ltd.) (0.051 mL; 6.0 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

added thereto and stirred to terminate the raction of drug linker at room temperature for another 20 minutes.

Purification: The above solution was subjected to purification using the Common procedure D-1 (ABS was used as buffer solution) described in Production method 1 to yield 6 mL of a solution containing the titled antibody-drug conjugate. After that, the solution was concentrated by the Common procedure A described in Production method 1.

Physicochemical characterization: By using the Common procedure E described in Production method 1 (as molar absorption coefficient, $\varepsilon_{A,280}=235300$ (estimated calculation value), $\varepsilon_{A,370}=0$ (estimated calculation value), $\varepsilon_{D,280}=5000$ (measured average value), and $\varepsilon_{D,370}=19000$ (measured average value) were used), the following characteristic values were obtained.

Antibody concentration: 0.91 mg/mL, antibody yield: 5.46 mg (44%), and average number of conjugated drug molecules (n) per antibody molecule: 6.3.

Example 61 Antibody-Drug Conjugate (58)

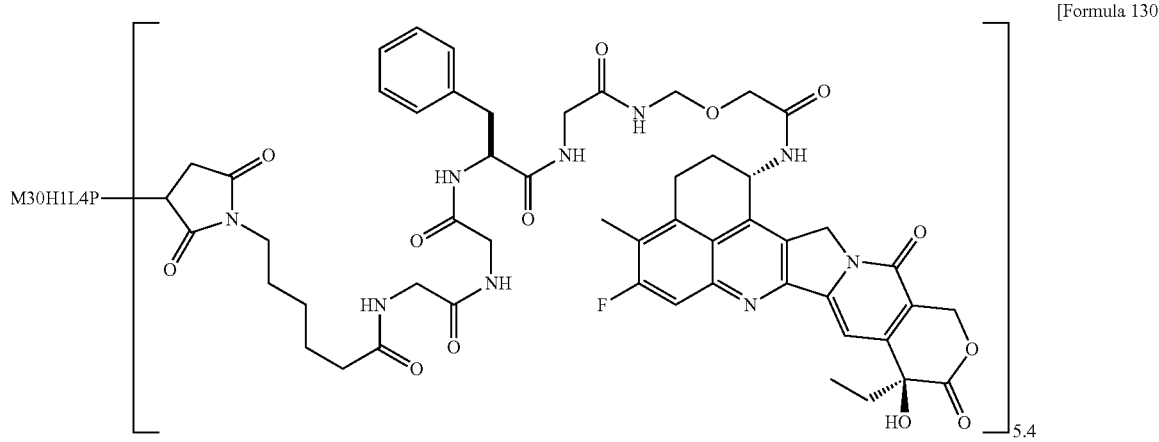

[Formula 130]

Almost the whole amounts of the antibody-drug conjugates of Examples 59 and 60 were mixed and the solution was concentrated by the Common procedure A described in Production method 1 to yield the titled antibody-drug conjugate.

Antibody concentration: 10.0 mg/mL, antibody yield: 12.30 mg, and average number of conjugated drug molecules (n) per antibody molecule: 5.4.

Example 62 Antibody-Drug Conjugate (59)

[Formula 131]

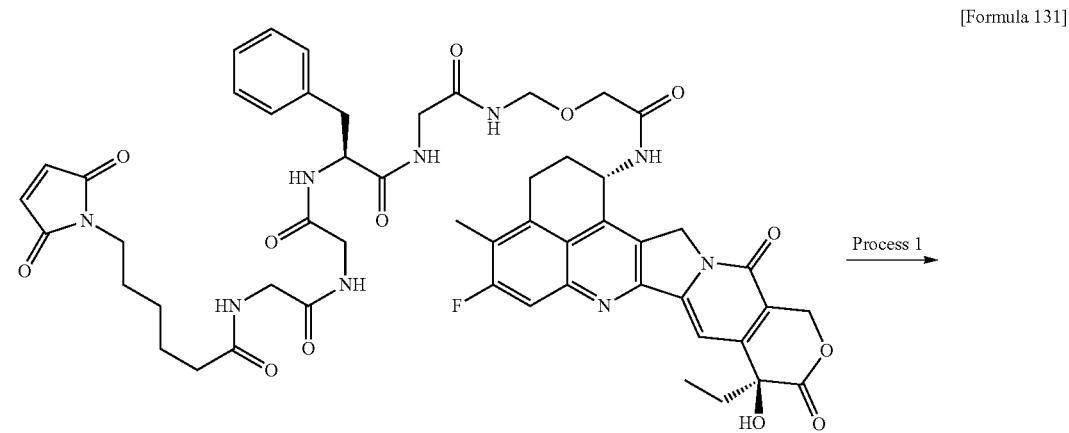

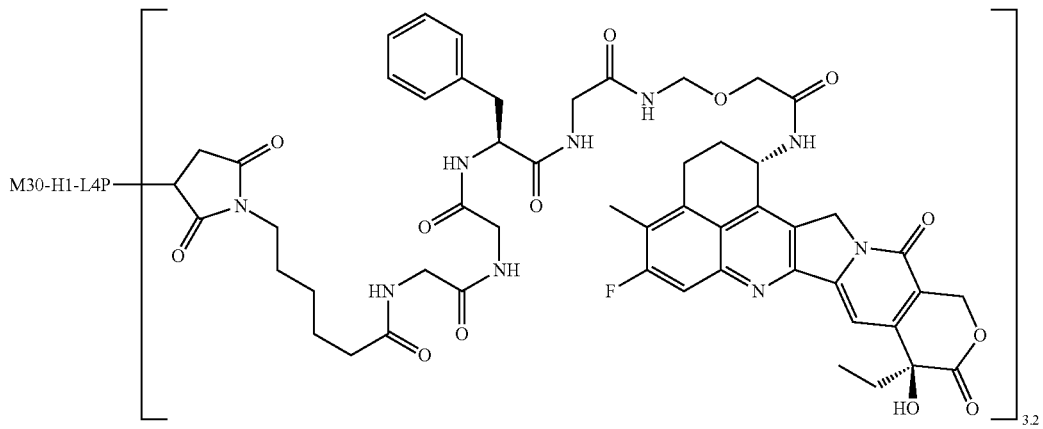

Process 1: Antibody-Drug Conjugate (59)

Reduction of the antibody: The M30-H1-L4P antibody produced in Reference Example 1 was prepared to have antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (100 mL, 1 g of the antibody) was placed in a 250 mL flask and charged with an aqueous solution of 10 mM TCEP (Tokyo Chemical Industry Co., Ltd.) (2.43 mL; 3.6 equivalents per antibody molecule) and further with an aqueous solution of 1 M dipotassium hydrogen phosphate (5 mL). After confirming that the solution had pH near 7.4 by using a pH meter, the disulfide bond at hinge part in the antibody was reduced by incubating at 37° C. for 1 hour.

Conjugation between antibody and drug linker: After adding a dimethyl sulfoxide solution containing 10 mM of the compound obtained in Process 8 of Example 58 (3.51 mL; 5.2 equivalents per antibody molecule) and dimethyl sulfoxide (2.14 mL) to the above solution at room temperature, it was stirred with a stirrer for conjugating the drug linker to the antibody in a water bath at 15° C. for 130 minutes. Next, an aqueous solution (0.547 mL) of 100 mM NAC was added thereto and further incubated to terminate the raction of drug linker at room temperature for 20 minutes.

Purification: The above solution was subjected to ultrafiltration purification using an ultrafiltration apparatus composed of an ultrafiltration membrane (Merck Japan, Pellicon XL Cassette, Biomax 50 KDa), a tube pump (Cole-Parmer International, MasterFlex Pump model 77521-40, Pump Head model 7518-00), and a tube (Cole-Parmer International, MasterFlex Tube L/S16). Specifically, while ABS was added dropwise (a total of 800 mL) as a buffer solution for purification to the reaction solution, ultrafiltration purification was performed for removing unconjugated drug linkers and other low-molecular-weight reagents, also replacing the buffer solution with ABS, and further concentrating the solution, to yield about 70 mL of a solution containing the titled antibody-drug conjugate.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,280}$=5178 (measured value), and $\varepsilon_{D,370}$=20217 (measured value) were used), the following characteristic values were obtained.

Antibody concentration: 14.2 mg/mL, antibody yield: 1.0 g (about 100%), and average number of conjugated drug molecules (n) per antibody molecule: 3.2.

Example 63 Antibody-Drug Conjugate (60)

[Formula 132]

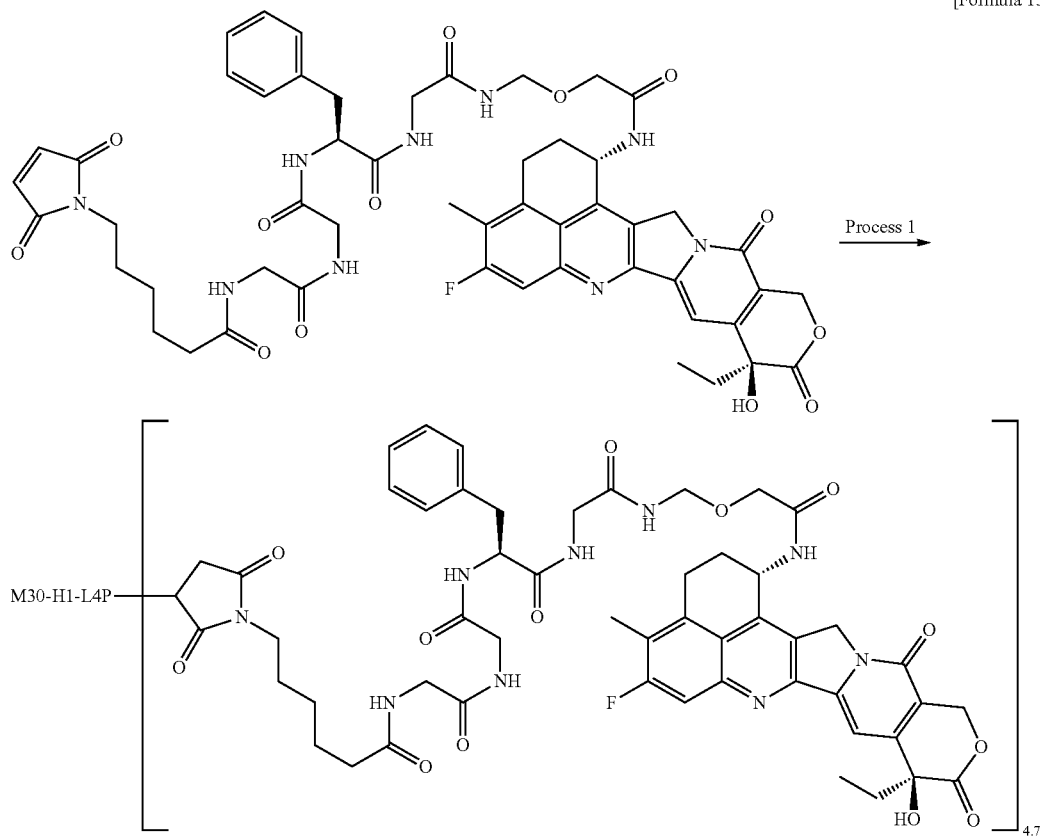

Process 1: Antibody-Drug Conjugate (60)

Reduction of the antibody: The M30-H1-L4P antibody produced in Reference Example 1 was prepared to have antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (5 mL, 50 mg of the antibody) was placed in a 15 mL tube and charged with an aqueous solution of 10 mM TCEP (Tokyo Chemical Industry Co., Ltd.) (0.075 mL; 4 equivalents per antibody molecule). After confirming that the solution had pH near 7.0 by using a pH meter, the disulfide bond at hinge part in the antibody was reduced by incubating at 37° C. for 1 hour.

Conjugation between antibody and drug linker: After adding a dimethyl sulfoxide solution containing 10 mM of the compound obtained in Process 8 of Example 58 (0.219 mL; 6.5 equivalents per antibody molecule) and dimethyl sulfoxide (0.064 mL) to the above solution, it was incubated for conjugating the drug linker to the antibody in a water bath at 15° C. for 90 minutes. Next, an aqueous solution (0.033 mL; 9.8 equivalents per antibody molecule) of 100 mM NAC was added thereto and incubated to terminate the raction of drug linker at room temperature for another 20 minutes.

Purification: The above solution was subjected to purification using the Common procedure D-1 (ABS was used as buffer solution) described in Production method 1 to yield 19 mL of a solution containing the titled antibody-drug conjugate.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,280}$=5178 (measured value), and $\varepsilon_{D,370}$=20217 (measured value) were used), the following characteristic values were obtained.

Antibody concentration: 2.19 mg/mL, antibody yield: 42 mg (83%), and average number of conjugated drug molecules (n) per antibody molecule: 4.7.

Example 64 Antibody-Drug Conjugate (61)

[Formula 133]

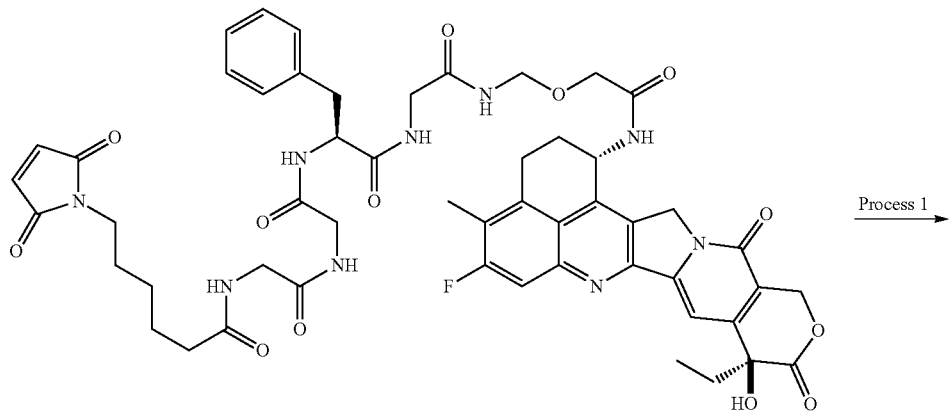

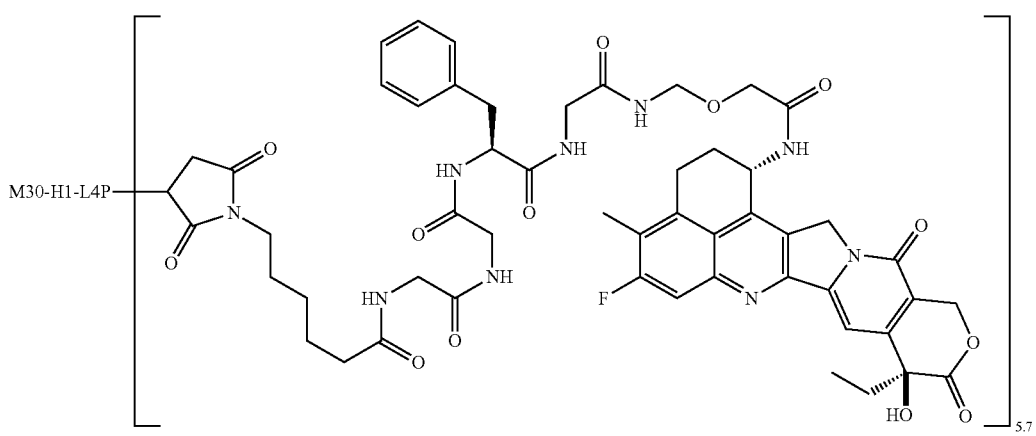

Process 1: Antibody-Drug Conjugate (61)

Reduction of the antibody: The M30-H1-L4P antibody produced in Reference Example 1 was prepared to have antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (4 mL, 40 mg of the antibody) was placed in a 15 mL tube and charged with an aqueous solution of 10 mM TCEP

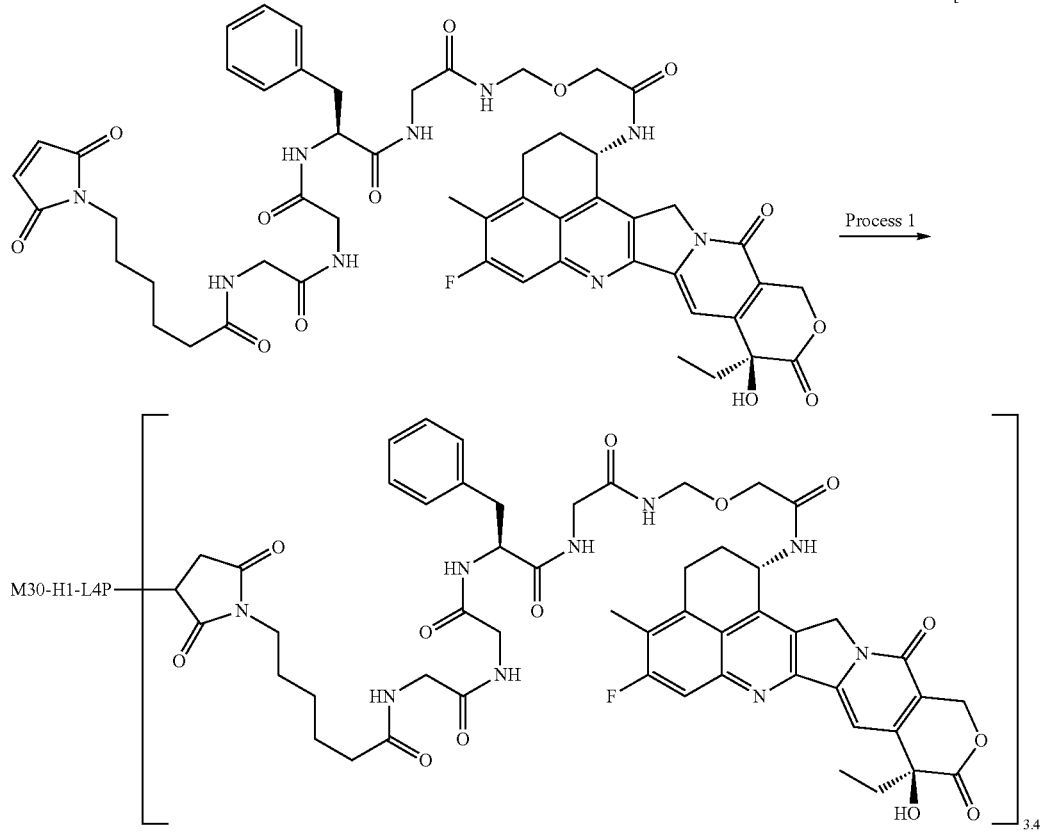

(Tokyo Chemical Industry Co., Ltd.) (0.14 mL; 5.2 equivalents per antibody molecule). After confirming that the solution had pH near 7.0 by using a pH meter, the disulfide bond at hinge part in the antibody was reduced by incubating at 37° C. for 1 hour. Conjugation between antibody and drug linker: After adding a dimethyl sulfoxide solution containing 10 mM of the compound obtained in Process 8 of Example 58 (0.232 mL; 8.6 equivalents per antibody molecule) to the above solution, it was incubated for conjugating the drug linker to the antibody in a water bath at 15° C. for 60 minutes. Next, an aqueous solution (0.035 mL; 12.9 equivalents per antibody molecule) of 100 mM NAC was added thereto and incubated to terminate the raction of drug linker at room temperature for another 20 minutes.

Purification: The above solution was subjected to purification using the Common procedure D-1 (ABS was used as buffer solution) described in Production method 1 to yield 13 mL of a solution containing the titled antibody-drug conjugate.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,280}$=5178 (measured value), and $\varepsilon_{D,370}$=20217 (measured value) were used), the following characteristic values were obtained.

Antibody concentration: 2.03 mg/mL, antibody yield: 26 mg (66%), and average number of conjugated drug molecules (n) per antibody molecule: 5.7.

Example 65 Antibody-Drug Conjugate (62)

[Formula 134]

Process 1: Antibody-Drug Conjugate (62)

Reduction of the antibody: The M30-H1-L4 antibody produced in Reference Example 1 was prepared to have antibody concentration of 10 mg/mL with PBS6.0/EDTA by using the Common procedure B (as absorption coefficient at 280 nm, 1.61 mLmg$^{-1}$ cm$^{-1}$ was used) and Common procedure C-1 described in Production method 1. The solution (1.25 mL, 12.5 mg of the antibody) was placed in a 1.5 mL tube and charged with an aqueous solution of 10 mM TCEP (Tokyo Chemical Industry Co., Ltd.) (0.0287 mL; 3.4 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding a dimethyl sulfoxide solution containing 10 mM of the compound obtained in Process 8 of Example 58 (0.0439 mL; 5.2 equivalents per antibody molecule) and dimethyl sulfoxide (0.0267 mL) to the above solution at room temperature, it was incubated for conjugating the drug linker to the antibody in a water bath at 15° C. for 1 hour. Next, an aqueous solution (0.0066 mL) of 100 mM NAC (Sigma-Aldrich Co. LLC) was added thereto and incubated to terminate the raction of drug linker at room temperature for another 20 minutes.

Purification: The above solution was subjected to purification using the Common procedure D-1 (ABS was used as buffer solution) described in Production method 1 to yield 6 mL of a solution containing the titled antibody-drug conjugate. After that, the solution was concentrated by the Common procedure A.

Physicochemical characterization: By using the Common procedure E described in Production method 1 (as molar absorption coefficient, $\varepsilon_{A,280}$=235300 (estimated calculation value), $\varepsilon_{A,370}$=0 (estimated calculation value), $\varepsilon_{D,280}$=5178 (measured value), and $\varepsilon_{D,370}$=20217 (measured value) were used), the following characteristic values were obtained.

Antibody concentration: 10.0 mg/mL, antibody yield: 7.8 mg (62%), and average number of conjugated drug molecules (n) per antibody molecule: 3.4.

Example 66 Antibody-Drug Conjugate (63)

280 nm, 1.61 mLmg$^{-1}$ cm$^{-1}$ was used) and Common procedure C-1 described in Production method 1. The solution (1.25 mL, 12.5 mg of the antibody) was placed in a 1.5 mL tube and charged with an aqueous solution of 10 mM TCEP (Tokyo Chemical Industry Co., Ltd.) (0.0439 mL; 5.2 equivalents per antibody molecule) (0.0287 mL; 3.4 equivalents per antibody molecule) and an aqueous solution of 1 M dipotassium hydrogen phosphate (Nacalai Tesque, Inc.; 0.0625 mL). After confirming that the solution had pH of 7.4±0.1, the disulfide bond at hinge part in the antibody was reduced by incubating at 37° C. for 1 hour.

Conjugation between antibody and drug linker: After adding a dimethyl sulfoxide solution containing 10 mM of the compound obtained in Process 8 of Example 58 (0.0726 mL; 8.6 equivalents per antibody molecule) to the above solution at room temperature, it was incubated for conjugating the drug linker to the antibody in a water bath at 15° C. for 1 hour. Next, an aqueous solution (0.011 mL) of 100 mM NAC (Sigma-Aldrich Co. LLC) was added thereto and incubated to terminate the raction of drug linker at room temperature for another 20 minutes.

Purification: The above solution was subjected to purification using the Common procedure D-1 (ABS was used as buffer solution) described in Production method 1 to yield 6

[Formula 135]

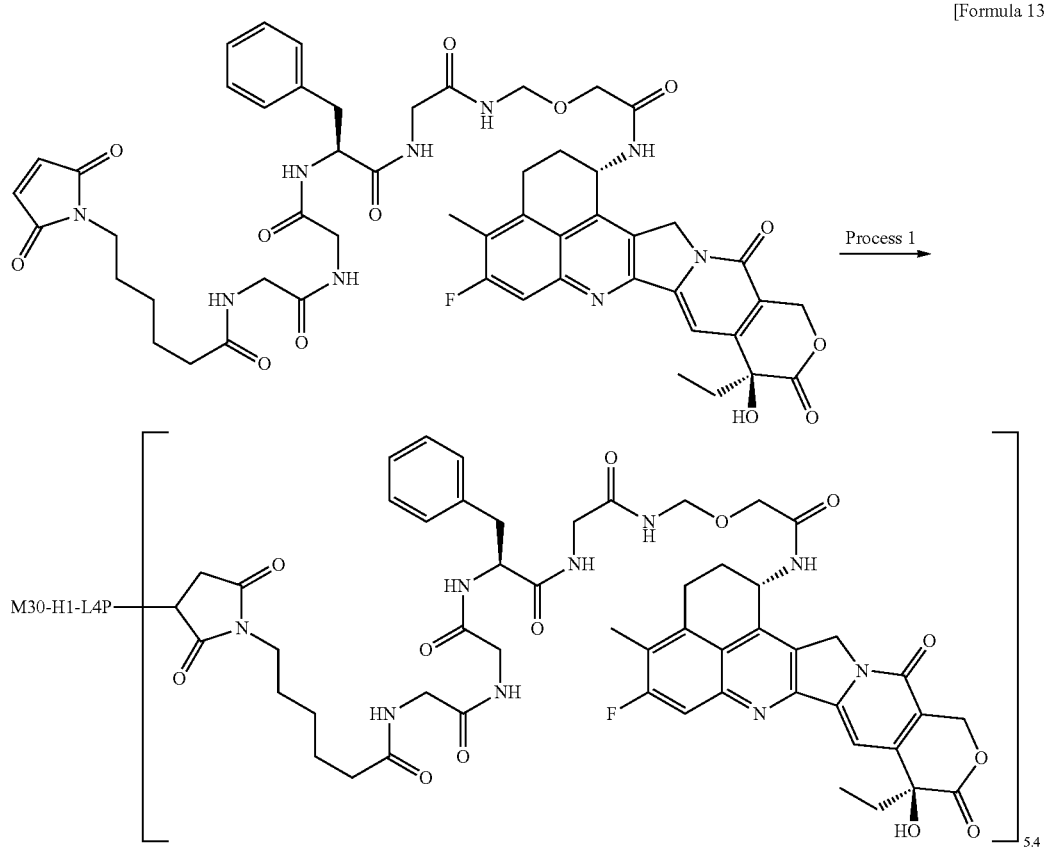

Process 1: Antibody-Drug Conjugate (63)

Reduction of the antibody: The M30-H1-L4 antibody produced in Reference Example 1 was prepared to have antibody concentration of 10 mg/mL with PBS6.0/EDTA by using the Common procedure B (as absorption coefficient at mL of a solution containing the titled antibody-drug conjugate. After that, the solution was concentrated by the Common procedure A.

Physicochemical characterization: By using the Common procedure E described in Production method 1 (as molar absorption coefficient, $\varepsilon_{A,280}$=235300 (estimated calculation value), $\varepsilon_{A,370}=0$ (estimated calculation value), $\varepsilon_{D,280}=5178$ (measured value), and $\varepsilon_{D,370}=20217$ (measured value) were used), the following characteristic values were obtained.

Antibody concentration: 10.0 mg/mL, antibody yield: 7.3 mg (58%), and average number of conjugated drug molecules (n) per antibody molecule: 5.4.

Example 67 Antibody-Drug Conjugate (64)

Conjugation between antibody and drug linker: After adding a dimethyl sulfoxide solution containing 10 mM of the compound obtained in Process 8 of Example 58 (0.0116 mL; 4.5 equivalents per antibody molecule) and dimethyl sulfoxide (0.0101 mL) to the above solution at room temperature, it was stirred by using a tube rotator (MTR-103, manufactured by AS ONE Corporation) for conjugating the drug linker to the antibody at room temperature for 1 hour. Next, an aqueous solution (0.0017 mL) of 100 mM NAC

[Formula 136]

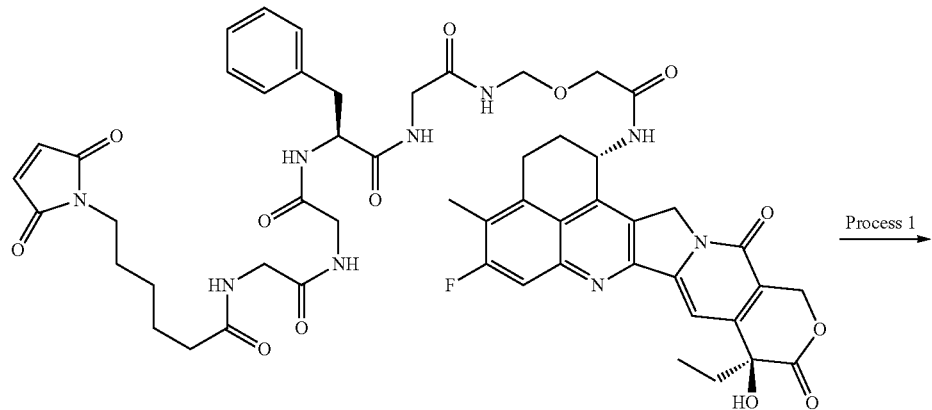

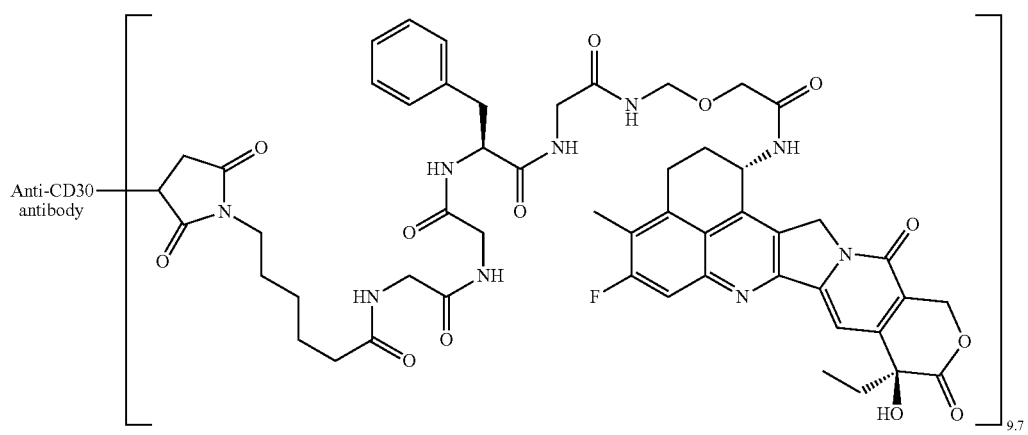

Process 1: Antibody-Drug Conjugate (64)

Reduction of the antibody: The anti-CD30 antibody produced in Reference Example 3 was prepared to have antibody concentration of 10 mg/mL with PBS6.5/EDTA by using the Common procedure B (as absorption coefficient at 280 nm, 1.75 mLmg$^{-1}$ cm$^{-1}$ was used) and Common procedure C-1 described in Production method 1. The solution (0.4 mL, 4 mg of the antibody) was placed in a 1.5 mL tube and charged with an aqueous solution of 10 mM TCEP (Tokyo Chemical Industry Co., Ltd.) (0.0065 mL; 2.5 equivalents per antibody molecule) and an aqueous solution of 1 M dipotassium hydrogen phosphate (Nacalai Tesque, Inc.; 0.0058 mL). After confirming that the solution had pH of 7.0±0.1, the disulfide bond at hinge part in the antibody was reduced by incubating at 37° C. for 1 hour.

(Sigma-Aldrich Co. LLC) was added thereto and further incubated to terminate the raction of drug linker at room temperature for 20 minutes.

Purification: The above solution was subjected to purification using the Common procedure D-1 (ABS was used as buffer solution) described in Production method 1 to yield 2.5 mL of a solution containing the titled antibody-drug conjugate.

Physicochemical characterization: By using the Common procedure E described in Production method 1 (as molar absorption coefficient, $\varepsilon_{A,280}=270400$ (estimated calculation value), $\varepsilon_{A,370}=0$ (estimated calculation value), $\varepsilon_{D,280}=5178$ (measured value), and $\varepsilon_{D,370}=20217$ (measured value) were used), the following characteristic values were obtained.

Antibody concentration: 0.96 mg/mL, antibody yield: 2.4 mg (60%), and average number of conjugated drug molecules (n) per antibody molecule: 3.7.

Example 68 Antibody-Drug Conjugate (65)

[Formula 137]

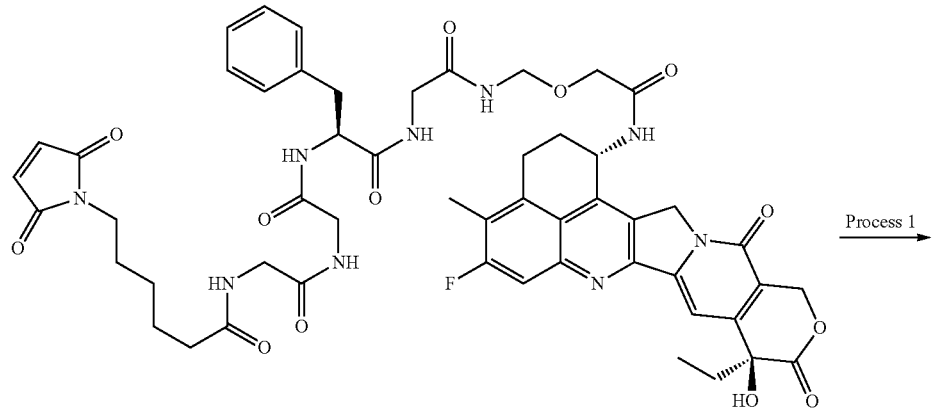

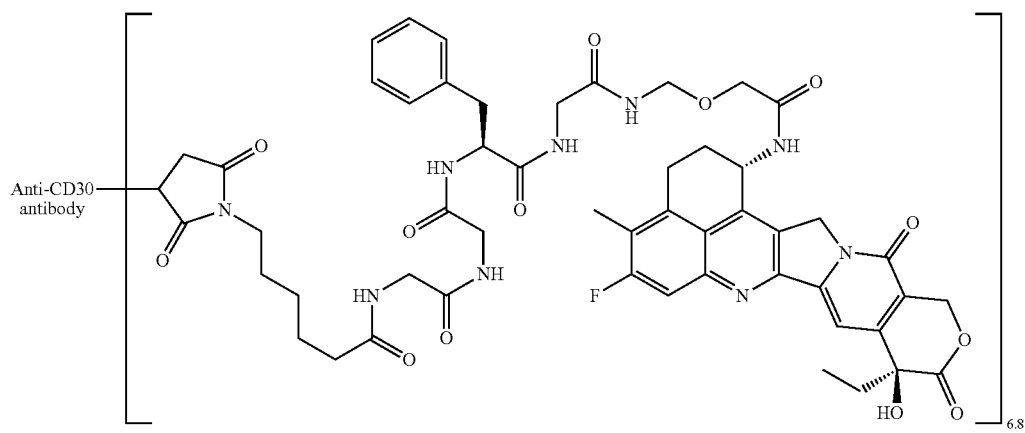

Process 1: Antibody-Drug Conjugate (65)

Reduction of the antibody: The anti-CD30 antibody produced in Reference Example 3 was prepared to have antibody concentration of 10 mg/mL with PBS6.0/EDTA by using the Common procedure B (as absorption coefficient at 280 nm, 1.75 mLmg$^{-1}$ cm$^{-1}$ was used) and Common procedure C-1 described in Production method 1. The solution (0.4 mL, 4 mg of the antibody) was placed in a 1.5 mL tube and charged with an aqueous solution of 10 mM TCEP (Tokyo Chemical Industry Co., Ltd.) (0.0129 mL; 5 equivalents per antibody molecule) and an aqueous solution of 1 M dipotassium hydrogen phosphate (Nacalai Tesque, Inc.; 0.006 mL). After confirming that the solution had pH of 7.0±0.1, the disulfide bond at hinge part in the antibody was reduced by incubating at 37° C. for 1 hour.

Conjugation between antibody and drug linker: After adding a dimethyl sulfoxide solution containing 10 mM of the compound obtained in Process 8 of Example 58 (0.0233 mL; 9 equivalents per antibody molecule) to the above solution at room temperature, it was stirred by using a tube rotator (MTR-103, manufactured by AS ONE Corporation) for conjugating the drug linker to the antibody at room temperature for 1 hour. Next, an aqueous solution (0.0035 mL) of 100 mM NAC (Sigma-Aldrich Co. LLC) was added thereto and further incubated to terminate the raction of drug linker at room temperature for 20 minutes.

Purification: The above solution was subjected to purification using the Common procedure D-1 (ABS was used as buffer solution) described in Production method 1 to yield 2.5 mL of a solution containing the titled antibody-drug conjugate.

Physicochemical characterization: By using the Common procedure E described in Production method 1 (as molar absorption coefficient, $\varepsilon_{A,280}$=270400 (estimated calculation value), $\varepsilon_{A,370}$=0 (estimated calculation value), $\varepsilon_{D,280}$=5178 (measured value), and $\varepsilon_{D,370}$=20217 (measured value) were used), the following characteristic values were obtained.

Antibody concentration: 0.39 mg/mL, antibody yield: 1.0 mg (24%), and average number of conjugated drug molecules (n) per antibody molecule: 6.8.

Example 69 Antibody-Drug Conjugate (66)

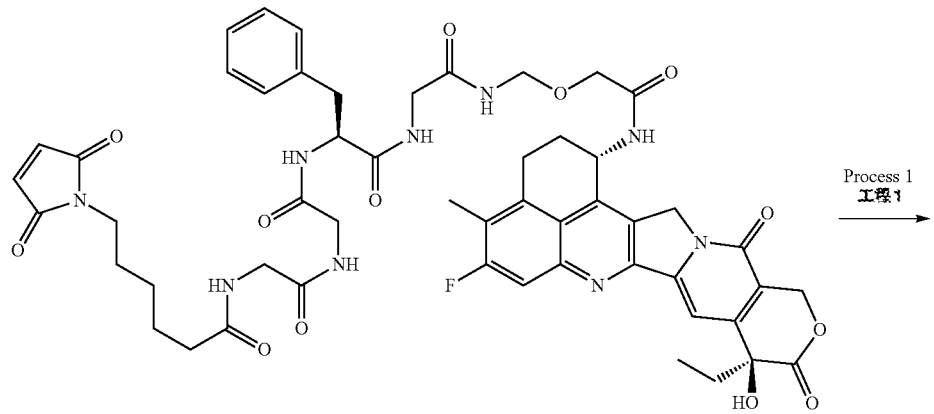

[Formula 138]

Process 1

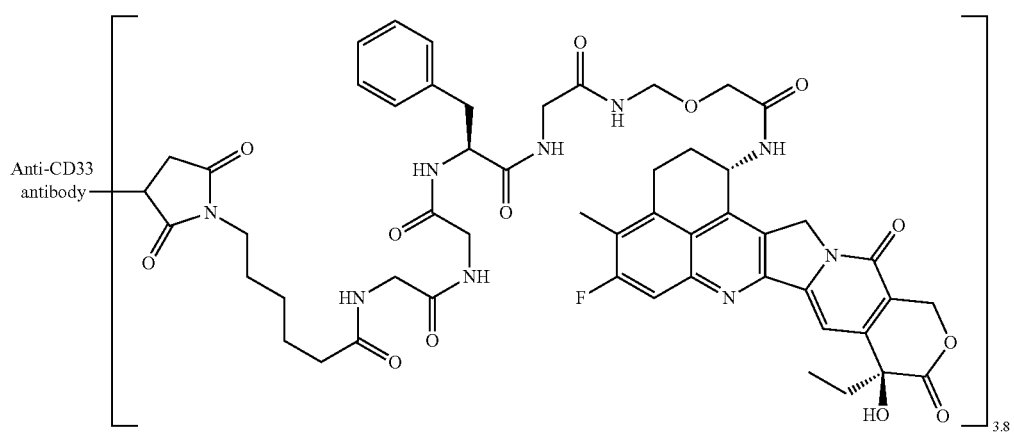

Process 1: Antibody-Drug Conjugate (66)

Reduction of the antibody: The anti-CD33 antibody produced in Reference Example 4 was prepared to have antibody concentration of 10 mg/mL with PBS6.0/EDTA by using the Common procedure B (as absorption coefficient at 280 nm, 1.66 mLmg$^{-1}$ cm$^{-1}$ was used) and Common procedure C-1 described in Production method 1. The solution (0.4 mL, 4 mg of the antibody) was placed in a 1.5 mL tube and charged with an aqueous solution of 10 mM TCEP (Tokyo Chemical Industry Co., Ltd.) (0.0065 mL; 2.5 equivalents per antibody molecule) and an aqueous solution of 1 M dipotassium hydrogen phosphate (Nacalai Tesque, Inc.; 0.0058 mL). After confirming that the solution had pH of 7.0±0.1, the disulfide bond at hinge part in the antibody was reduced by incubating at 37° C. for 1 hour.

Conjugation between antibody and drug linker: After adding a dimethyl sulfoxide solution containing 10 mM of the compound obtained in Process 8 of Example 58 (0.0116 mL; 4.5 equivalents per antibody molecule) and dimethyl sulfoxide (0.0101 mL) to the above solution at room temperature, it was stirred by using a tube rotator (MTR-103, manufactured by AS ONE Corporation) for conjugating the drug linker to the antibody at room temperature for 1 hour. Next, an aqueous solution (0.0017 mL) of 100 mM NAC (Sigma-Aldrich Co. LLC) was added thereto and further incubated to terminate the raction of drug linker at room temperature for 20 minutes.

Purification: The above solution was subjected to purification using the Common procedure D-1 (ABS was used as buffer solution) described in Production method 1 to yield 2.5 mL of a solution containing the titled antibody-drug conjugate.

Physicochemical characterization: By using the Common procedure E described in Production method 1 (as molar absorption coefficient, $\varepsilon_{A,280}$=256400 (estimated calculation value), $\varepsilon_{A,370}$=0 (estimated calculation value), $\varepsilon_{D,280}$=5178 (measured value), and $\varepsilon_{D,370}$=20217 (measured value) were used), the following characteristic values were obtained.

Antibody concentration: 1.19 mg/mL, antibody yield: 3.0 mg (74%), and average number of conjugated drug molecules (n) per antibody molecule: 3.8.

Example 70 Antibody-Drug Conjugate (67)

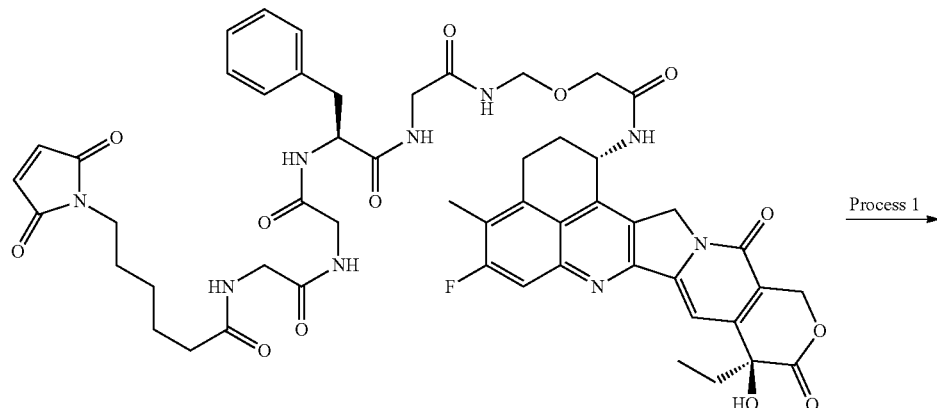

[Formula 139]

Process 1 →

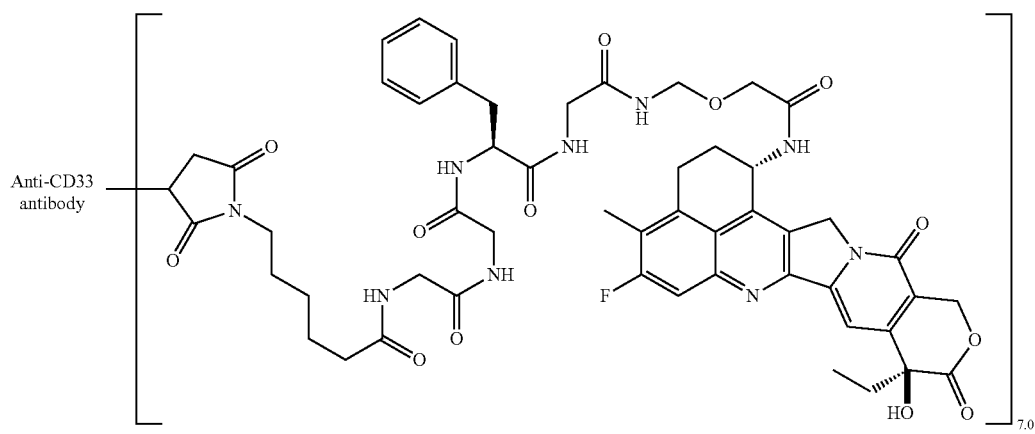

Process 1: Antibody-Drug Conjugate (67)

Reduction of the antibody: The anti-CD33 antibody produced in Reference Example 4 was prepared to have antibody concentration of 10 mg/mL with PBS6.0/EDTA by using the Common procedure B (as absorption coefficient at 280 nm, 1.66 mLmg$^{-1}$ cm$^{-1}$ was used) and Common procedure C-1 described in Production method 1. The solution (0.4 mL, 4 mg of the antibody) was placed in a 1.5 mL tube and charged with an aqueous solution of 10 mM TCEP (Tokyo Chemical Industry Co., Ltd.) (0.0129 mL; 5 equivalents per antibody molecule) and an aqueous solution of 1 M dipotassium hydrogen phosphate (Nacalai Tesque, Inc.; 0.006 mL). After confirming that the solution had pH of 7.0±0.1, the disulfide bond at hinge part in the antibody was reduced by incubating at 37° C. for 1 hour.

Conjugation between antibody and drug linker: After adding a dimethyl sulfoxide solution containing 10 mM of the compound obtained in Process 8 of Example 58 (0.0233 mL; 9 equivalents per antibody molecule) to the above solution at room temperature, it was stirred by using a tube rotator (MTR-103, manufactured by AS ONE Corporation) for conjugating the drug linker to the antibody at room temperature for 1 hour. Next, an aqueous solution (0.0035 mL) of 100 mM NAC (Sigma-Aldrich Co. LLC) was added thereto and further incubated to terminate the raction of drug linker at room temperature for 20 minutes.

Purification: The above solution was subjected to purification using the Common procedure D-1 (ABS was used as buffer solution) described in Production method 1 to yield 2.5 mL of a solution containing the titled antibody-drug conjugate.

Physicochemical characterization: By using the Common procedure E described in Production method 1 (as molar absorption coefficient, $\varepsilon_{A,280}$=256400 (estimated calculation value), $\varepsilon_{A,370}$=0 (estimated calculation value), $\varepsilon_{D,280}$=5178 (measured value), and $\varepsilon_{D,370}$=20217 (measured value) were used), the following characteristic values were obtained.

Antibody concentration: 1.24 mg/mL, antibody yield: 3.1 mg (78%), and average number of conjugated drug molecules (n) per antibody molecule: 7.0.

Example 71 Antibody-Drug Conjugate (68)

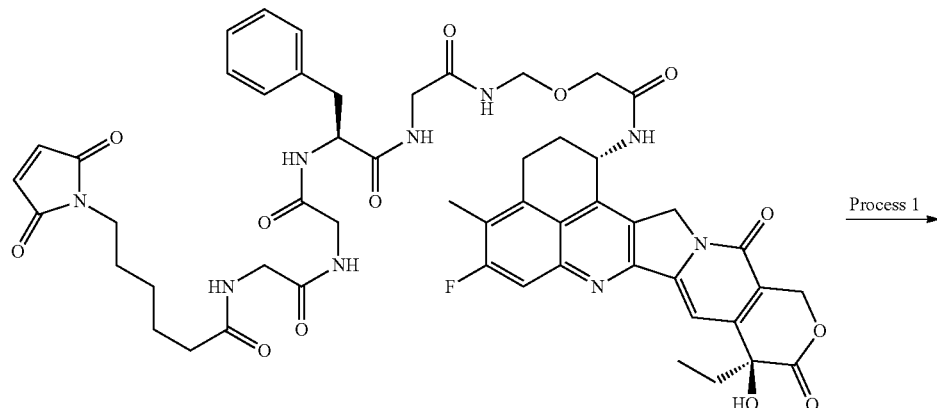

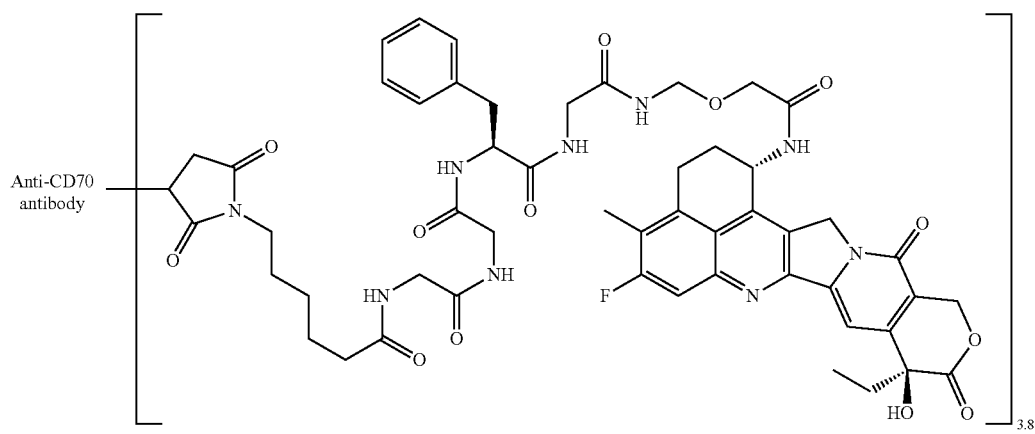

Process 1: Antibody-Drug Conjugate (68)

Reduction of the antibody: The anti-CD70 antibody produced in Reference Example 5 was prepared to have antibody concentration of 10 mg/mL with PBS6.0/EDTA by using the Common procedure B (as absorption coefficient at 280 nm, 1.69 mLmg$^{-1}$ cm$^{-1}$ was used) and Common procedure C-1 described in Production method 1. The solution (0.4 mL, 4 mg of the antibody) was placed in a 1.5 mL tube and charged with an aqueous solution of 10 mM TCEP (Tokyo Chemical Industry Co., Ltd.) (0.0065 mL; 2.5 equivalents per antibody molecule) and an aqueous solution of 1 M dipotassium hydrogen phosphate (Nacalai Tesque, Inc.; 0.0058 mL). After confirming that the solution had pH of 7.0±0.1, the disulfide bond at hinge part in the antibody was reduced by incubating at 37° C. for 1 hour.

Conjugation between antibody and drug linker: After adding a dimethyl sulfoxide solution containing 10 mM of the compound obtained in Process 8 of Example 58 (0.0116 mL; 4.5 equivalents per antibody molecule) and dimethyl sulfoxide (0.0101 mL) to the above solution at room temperature, it was stirred by using a tube rotator (MTR-103, manufactured by AS ONE Corporation) for conjugating the drug linker to the antibody at room temperature for 1 hour. Next, an aqueous solution (0.0017 mL) of 100 mM NAC (Sigma-Aldrich Co. LLC) was added thereto and further incubated to terminate the raction of drug linker at room temperature for 20 minutes.

Purification: The above solution was subjected to purification using the Common procedure D-1 (ABS was used as buffer solution) described in Production method 1 to yield 2.5 mL of a solution containing the titled antibody-drug conjugate.

Physicochemical characterization: By using the Common procedure E described in Production method 1 (as molar absorption coefficient, $\varepsilon_{A,280}$=262400 (estimated calculation value), $\varepsilon_{A,370}$=0 (estimated calculation value), $\varepsilon_{D,280}$=5178 (measured value), and $\varepsilon_{D,370}$=20217 (measured value) were used), the following characteristic values were obtained.

Antibody concentration: 1.10 mg/mL, antibody yield: 2.8 mg (69%), and average number of conjugated drug molecules (n) per antibody molecule: 3.8.

Example 72 Antibody-Drug Conjugate (69)

[Formula 141]

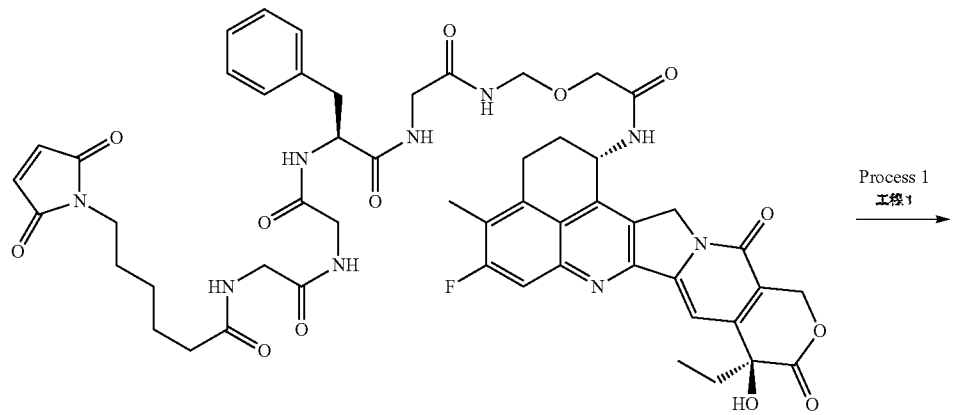

Process 1

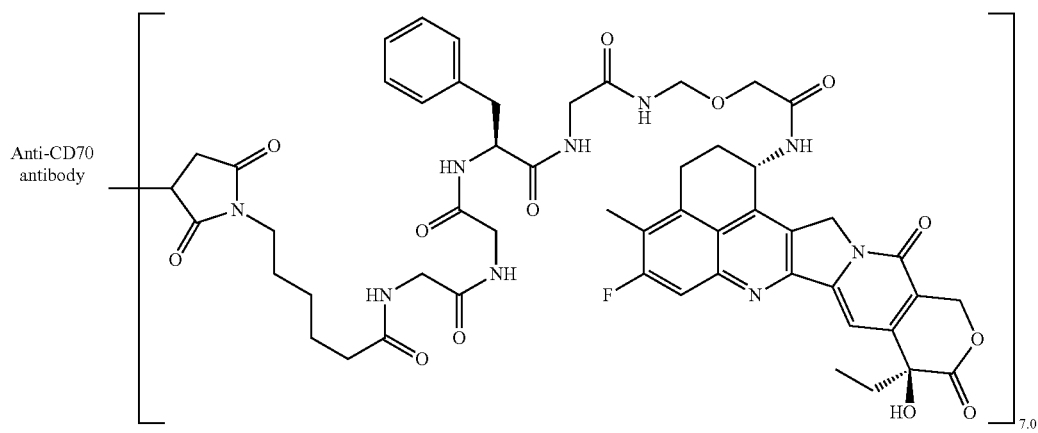

Process 1: Antibody-Drug Conjugate (69)

Reduction of the antibody: The anti-CD70 antibody produced in Reference Example 5 was prepared to have antibody concentration of 10 mg/mL with PBS6.0/EDTA by using the Common procedure B (as absorption coefficient at 280 nm, 1.69 mLmg$^{-1}$ cm$^{-1}$ was used) and Common procedure C-1 described in Production method 1. The solution (0.4 mL, 4 mg of the antibody) was placed in a 1.5 mL tube and charged with an aqueous solution of 10 mM TCEP (Tokyo Chemical Industry Co., Ltd.) (0.0129 mL; 5 equivalents per antibody molecule) and an aqueous solution of 1 M dipotassium hydrogen phosphate (Nacalai Tesque, Inc.; 0.006 mL). After confirming that the solution had pH of 7.0±0.1, the disulfide bond at hinge part in the antibody was reduced by incubating at 37° C. for 1 hour.

Conjugation between antibody and drug linker: After adding a dimethyl sulfoxide solution containing 10 mM of the compound obtained in Process 8 of Example 58 (0.0233 mL; 9 equivalents per antibody molecule) to the above solution at room temperature, it was stirred by using a tube rotator (MTR-103, manufactured by AS ONE Corporation) for conjugating the drug linker to the antibody at room temperature for 1 hour. Next, an aqueous solution (0.0035 mL) of 100 mM NAC (Sigma-Aldrich Co. LLC) was added thereto and further incubated to terminate the raction of drug linker at room temperature for 20 minutes.

Purification: The above solution was subjected to purification using the Common procedure D-1 (ABS was used as buffer solution) described in Production method 1 to yield 2.5 mL of a solution containing the titled antibody-drug conjugate.

Physicochemical characterization: By using the Common procedure E described in Production method 1 (as molar absorption coefficient, $\varepsilon_{A,280}$=262400 (estimated calculation value), $\varepsilon_{A,370}$=0 (estimated calculation value), $\varepsilon_{D,280}$=5178 (measured value), and $\varepsilon_{D,370}$=20217 (measured value) were used), the following characteristic values were obtained.

Antibody concentration: 1.16 mg/mL, antibody yield: 2.9 mg (73%), and average number of conjugated drug molecules (n) per antibody molecule: 7.0.

Example 73 Another Method for Synthesizing Compound of Process 8 of Example 58
[Formula 142]
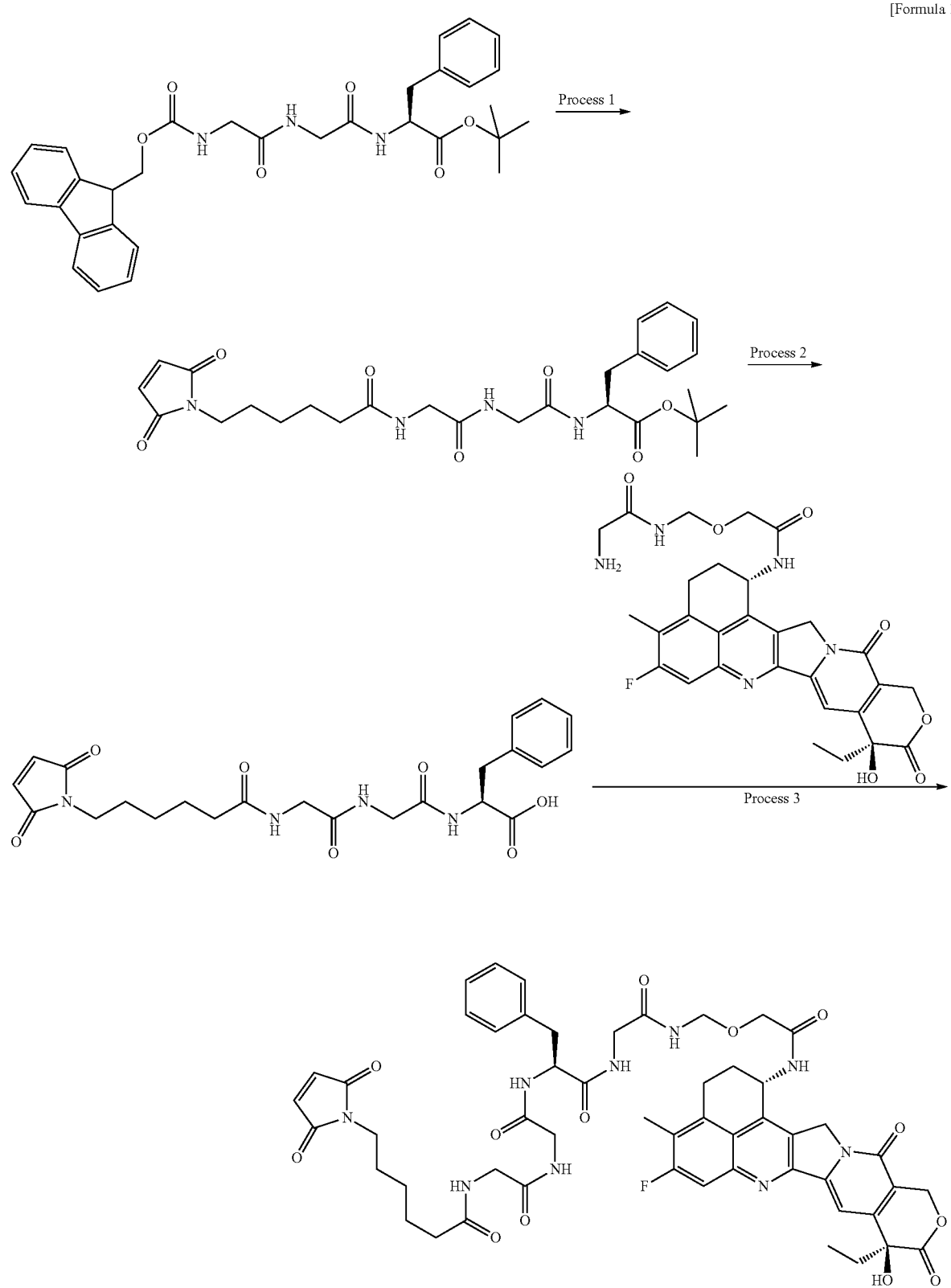

Process 1: tert-Butyl N-[6-(2,5-dioxo-2,5-dihydro-1H-pyrrol-1-yl)hexanoyl]glycylglycyl-L-phenyl alaninate Under ice cooling, to THF (12.0 ml) solution of tert-butyl N-[(9H-fluoren-9-ylmethoxy)carbonyl]glycylglycyl-L-phenyl alaninate (J. Pept. Res., 1999, vol. 53, pp. 393) (0.400 g, 0.717 mmol), 1,8-diazabicyclo[5.4.0]-7-undecene (0.400 ml) was added and stirred at room temperature for 4 days, and then N-succinimidyl 6-maleimide hexanoate (0.221 g, 0.717 mmol) was further added and stirred for 3 hours. The reaction solution was diluted with ethyl acetate and washed with an aqueous solution of 10% citric acid, a saturated aqueous solution of sodium hydrogen carbonate, and saturated brine, and then the organic layer was dried over anhydrous magnesium sulfate. After the solvent was removed under reduced pressure, the residues obtained were purified by silica gel column chromatography [chloroform-chloroform:methanol=9:1 (v/v)] to yield the titled compound as a pale yellow solid (0.295 g, 78%).

$^1$H-NMR (400 MHz, CDCl$_3$) δ: 1.28-1.36 (2H, m), 1.41 (9H, s), 1.57-1.71 (4H, m), 2.23 (2H, t, J=7.6 Hz), 3.09 (2H, d, J=6.0 Hz), 3.51 (2H, t, J=7.6 Hz), 3.85-4.02 (4H, m), 4.69-4.78 (1H, m), 6.15 (1H, t, J=4.6 Hz), 6.33 (1H, d, J=7.3 Hz), 6.60 (1H, t, J=5.0 Hz), 6.68 (2H, s), 7.10-7.16 (2H, m), 7.22-7.31 (3H, m).

MS (ESI) m/z: 529 (M+H)$^+$

Process 2: N-[6-(2,5-dioxo-2,5-dihydro-1H-pyrrol-1-yl)hexanoyl]glycylglycyl-L-phenylalanine To a dichloromethane (8.00 ml) solution of the compound (0.295 g, 0.558 mmol) obtained in Process 1 above, trifluoroacetic acid (4.00 mL) was added and stirred at room temperature for 18 hours. The solvent was removed under reduced pressure to yield the titled compound as a pale yellow solid (0.240 g, 91%).

$^1$H-NMR (400 MHz, DMSO-d$_6$) δ: 1.15-1.23 (2H, m), 1.40-1.53 (4H, m), 2.10 (2H, t, J=7.6 Hz), 2.88 (1H, dd, J=13.7, 8.9 Hz), 3.04 (1H, dd, J=13.7, 5.0 Hz), 3.35-3.43 (2H, m), 3.58-3.77 (4H, m), 4.41 (1H, td, J=7.8, 5.0 Hz), 7.00 (2H, s), 7.16-7.31 (5H, m), 8.00 (1H, t, J=5.7 Hz), 8.06 (1H, t, J=5.7 Hz), 8.13 (1H, d, J=7.8 Hz).

Process 3: N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide The compound (0.572 g, 1.21 mmol) obtained in Process 2 above was dissolved in dichloromethane (12.0 mL), charged with N-hydroxysuccinimide (0.152 g, 1.32 mmol) and 1-(3-dimethylaminopropyl)-3-ethylcarbodiimide hydrochloride (0.253 g, 1.32 mmol), and stirred for 1 hour. The reaction solution was added to an N,N-dimethylformamide (22.0 mL) solution of the mixture (1.10 mmol) obtained in Process 5 of Example 58, and stirred at room temperature for 3 hours. The reaction solution was charged with an aqueous solution of 10% citric acid and extracted with chloroform. The obtained organic layer was dried over sodium sulfate and filtered. The solvent was removed under reduced pressure and the residues obtained were purified by silica gel column chromatography [chloroform-chloroform:methanol=8:2 (v/v)] to yield the titled compound as a pale yellow solid (0.351 g, 31%). The instrumental data of the compound was the same as that of the compound of Process 8 of Example 58.

Example 74 Another Method for Synthesizing Compound of Process 8 of Example 58

[Formula 143]

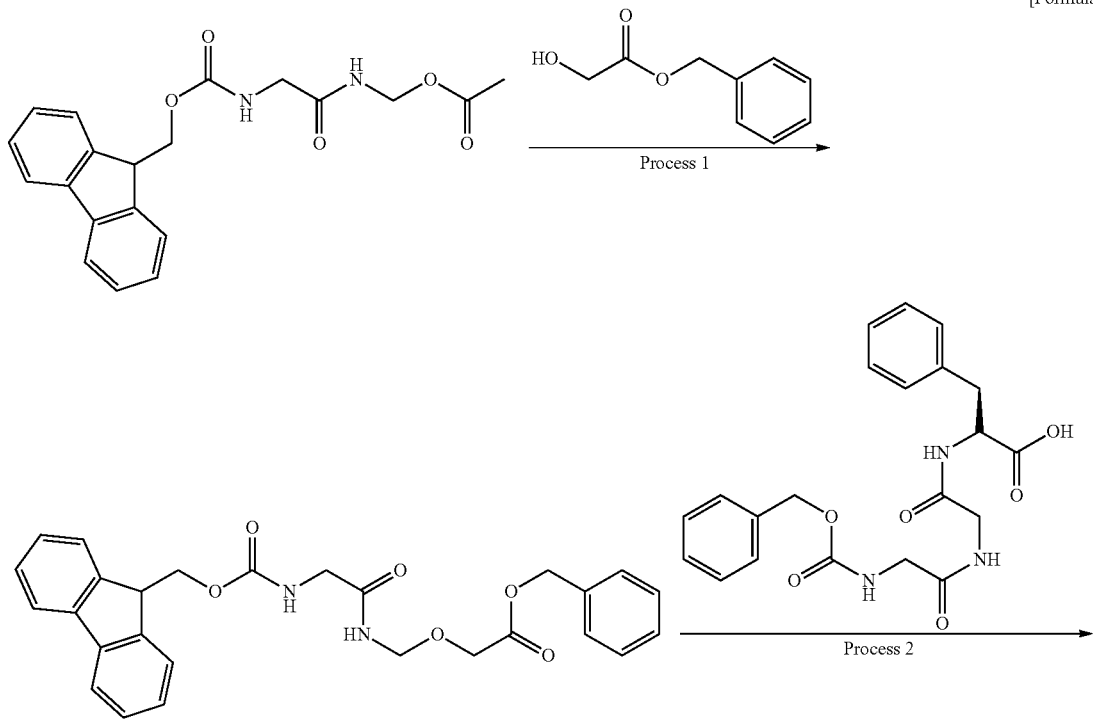

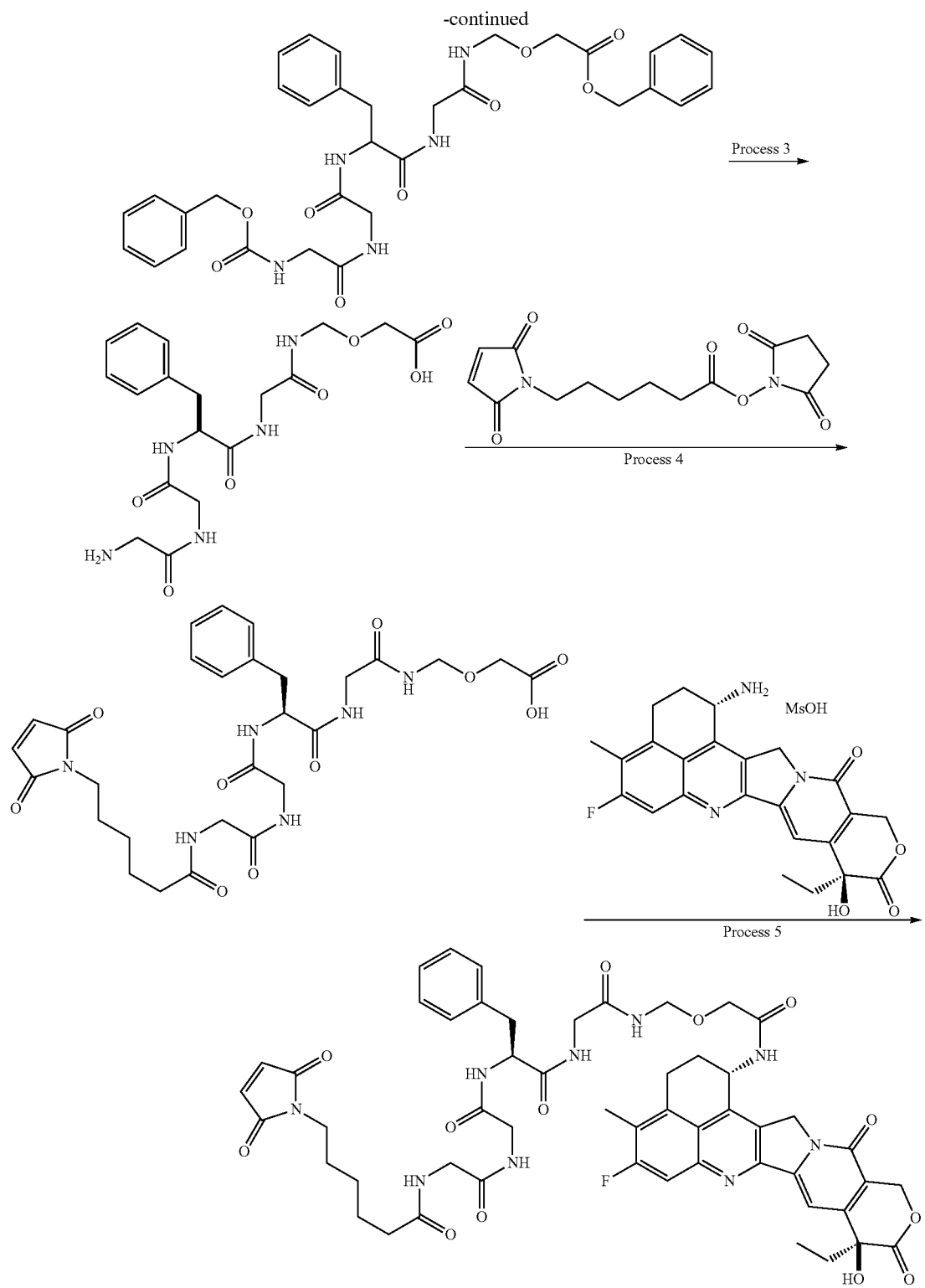

Process 1: Benzyl [({N-[(9H-fluoren-9-ylmethoxy) carbonyl]glycyl}amino)methoxy]acetate To a tetrahydrofuran (200 ml) solution of the compound (7.37 g, 20.0 mmol) obtained in Process 1 of Example 58, benzyl glycolate (6.65 g, 40.0 mmol) and p-toluene sulfonic acid monohydrate (0.381 g, 2.00 mmol) were added at 0° C. and stirred at room temperature for 2 hours and 30 minutes. The reaction solution was charged with a saturated aqueous solution of sodium hydrogen carbonate and extracted with ethyl acetate. The obtained organic layer was dried over sodium sulfate and filtered. The solvent was removed under reduced pressure and the residues obtained were purified by silica gel column chromatography [hexane:ethyl acetate=100:0 (v/v)-0:100] to yield the titled compound as a colorless solid (6.75 g, 71%). The instrumental data of the compound was the same as that of the compound of Process 2 of Example 58.

Process 2: N-[(benzyloxy)carbonyl]glycylglycyl-L-phenylalanine-N-{[(2-(benzyloxy)-2-oxoethoxy]methyl}glycinamide To an N,N-dimethylformamide (140 mL) solution of the compound (6.60 g, 13.9 mmol) obtained in Process 1 above, 1,8-diazabicyclo[5.4.0]undec-7-ene (2.22 g, 14.6 mmol) was added at 0° C. and stirred at room temperature for 15 minutes. The reaction solution was charged with an N,N-dimethylformamide (140 mL) solution of N-[(benzyloxy)carbonyl]glycylglycyl-L-phenylalanine (6.33 g, 15.3 mmol), N-hydroxysuccinimide (1.92 g, 16.7 mmol), and 1-(3-dimethylaminopropyl)-3-ethylcarbodiimide hydrochloride (3.20 g, 16.7 mmol) stirred in advance at room temperature for 1 hour, and stirred at room temperature for 4 hours. The reaction solution was charged with 0.1 N hydrochloric acid and extracted with chloroform. The obtained organic layer was dried over sodium sulfate and filtered. The solvent was removed under reduced pressure and the residues obtained were purified by silica gel column chromatography [chloroform-chloroform:methanol=8:2 (v/v)] to yield the titled compound as a colorless solid (7.10 g, 79%).

$^1$H-NMR (DMSO-D$_6$) δ: 2.78 (1H, dd, J=13.9, 9.6 Hz), 3.05 (1H, dd, J=13.9, 4.5 Hz), 3.56-3.80 (6H, m), 4.15 (2H, s), 4.47-4.55 (1H, m), 4.63 (2H, d, J=6.6 Hz), 5.03 (2H, s), 5.15 (2H, s), 7.16-7.38 (15H, m), 7.52 (1H, t, J=5.9 Hz), 8.03 (1H, t, J=5.5 Hz), 8.17 (1H, d, J=8.2 Hz), 8.36 (1H, t, J=5.7 Hz), 8.61 (1H, t, J=6.6 Hz).

Process 3: Glycylglycyl-L-phenylalanyl-N-[(carboxymethoxy)methyl]glycinamide

To an N,N-dimethylformamide (216 mL) solution of the compound (7.00 g, 10.8 mmol) obtained in Process 2 above, palladium carbon catalyst (7.00 g) was added and stirred under hydrogen atmosphere at room temperature for 24 hours. The insolubles were removed by filtration through Celite, and the solvent was removed under reduced pressure. The residues obtained were dissolved in water, the insoluble material was removed by filtration through Celite, and the solvent was removed under reduced pressure. This procedure was repeated twice to yield the titled compound as a colorless solid (3.77 g, 82%).

$^1$H-NMR (DMSO-D$_6$) δ: 2.84 (1H, dd, J=13.7, 9.8 Hz), 3.08 (1H, dd, J=13.7, 4.7 Hz), 3.50-3.72 (4H, m), 3.77-3.86 (2H, m), 3.87 (2H, s), 4.52-4.43 (1H, m), 4.61 (2H, d, J=6.6 Hz), 7.12-7.30 (5H, m), 8.43 (1H, t, J=5.9 Hz), 8.54 (1H, d, J=7.8 Hz), 8.70 (1H, t, J=6.3 Hz), 8.79 (1H, t, J=5.5 Hz).

Process 4: N-[6-(2,5-dioxo-2,5-dihydro-1H-pyrrol-1-yl)hexanoyl]glycylglycyl-L-phenylalanyl-N-[(carboxymethoxy)methyl]glycinamide To an N,N-dimethylformamide (85.0 mL) solution of the compound (3.59 g, 8.48 mmol) obtained in Process 3 above, N-succinimidyl 6-maleimide hexanoate (2.88 g, 9.33 mmol) and triethylamine (0.858 g, 8.48 mmol) were added and stirred at room temperature for 1 hour. The reaction solution was charged with 0.1 N hydrochloric acid and extracted with chloroform and a mixed solvent of chloroform and methanol [chloroform:methanol=4:1 (v/v)]. The obtained organic layer was dried over sodium sulfate and filtered. The solvent was removed under reduced pressure and the residues obtained were purified by silica gel column chromatography [chloroform-partitioned organic layer of chloroform:methanol:water=7:3:1 (v/v/v)] to yield the titled compound as a colorless solid (3.70 g, 71%).

$^1$H-NMR (DMSO-D$_6$) δ: 1.13-1.24 (2H, m), 1.42-1.53 (4H, m), 2.11 (2H, t, J=7.4 Hz), 2.80 (1H, dd, J=13.7, 9.8 Hz), 3.06 (1H, dd, J=13.9, 4.5 Hz), 3.37 (2H, t, J=7.2 Hz), 3.56-3.78 (6H, m), 3.97 (2H, s), 4.46-4.53 (1H, m), 4.61 (2H, d, J=6.3 Hz), 7.00 (2H, s), 7.15-7.29 (5H, m), 8.03-8.20 (3H, m), 8.32 (1H, t, J=5.9 Hz), 8.60 (1H, t, J=6.7 Hz).

Process 5: N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide To an N,N-dimethylformamide (40.0 mL) solution of mesylate of the compound (4) (1.14 g, 2.00 mmol), triethylamine (0.202 g, 2.00 mmol), the compound (1.48 g, 2.40 mmol) obtained in Process 4 above, and 4-(4,6-dimethoxy-1,3,5-triazin-2-yl)-4-methylmorpholinium chloride (0.993 g, 3.00 mmol) containing 16.4% water were added at 0° C. and stirred at room temperature for 1 hour. The solvent was removed under reduced pressure and the residues obtained were purified by silica gel column chromatography [chloroform-chloroform methanol=8:2 (v/v)] to yield the titled compound as a pale yellow solid (1.69 g, 82%). The instrumental data of the compound was the same as that of the compound of Process 8 of Example 58.

Example 75 N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-2-hydroxyacetamide

[Formula 144]

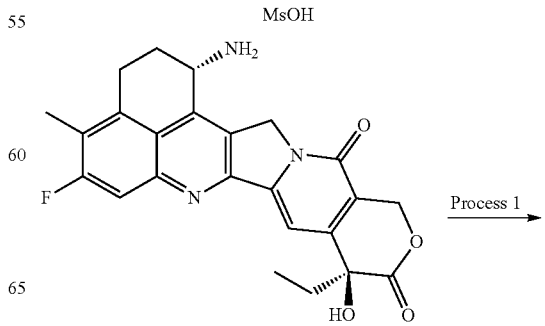

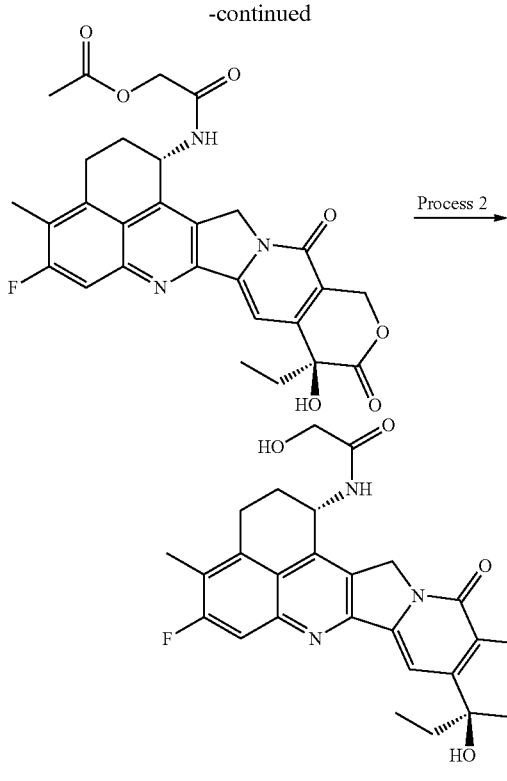

Process 1: 2-{[(1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethylacetate Under ice cooling, to an N,N-dimethylformamide (20.0 mL) suspension of mesylate of the compound (4) (0.500 g, 0.941 mmol), N,N-diisopropylethylamine (0.492 mL, 2.82 mmol) and acetoxyacetyl chloride (0.121 ml, 1.13 mmol) were added and stirred at room temperature for 1 hour. The solvent was removed under reduced pressure and the residues obtained were purified by silica gel column chromatography [chloroform-partitioned organic layer of chloroform:methanol:water=7:3:1 (v/v/v)] to yield the titled compound as a pale yellow solid (0.505 g, quantitative).

$^1$H-NMR (400 MHz, DMSO-d$_6$) δ: 0.87 (3H, t, J=7.4 Hz), 1.81-1.92 (2H, m), 2.08 (3H, s), 2.08-2.22 (2H, m), 2.41 (3H, s), 3.14-3.21 (2H, m), 4.51 (2H, dd, J=19.4, 14.7 Hz), 5.22 (2H, dd, J=40.1, 19.0 Hz), 5.43 (2H, s), 5.56-5.61 (1H, m), 6.53 (1H, s), 7.31 (1H, s), 7.81 (1H, d, J=11.0 Hz), 8.67 (1H, d, J=8.6 Hz).
MS (ESI) m/z: 536 (M+H)$^+$

Process 2: N-[(1S,9S)-9-ethyl-5-fluoro-9-hydroxy-4-methyl-10,13-dioxo-2,3,9,10,13,15-hexahydro-1H,12H-benzo[de]pyrano(3',4':6,7]indolizino[1,2-b]quinolin-1-yl]-2-hydroxyacetamide To a methanol (50.0 mL) suspension of the compound (0.504 g, 0.941 mmol) obtained in Process 1 above, tetrahydrofuran (20.0 ml) and an aqueous solution of 1 N sodium hydroxide (4.00 ml, 4.00 mmol) were added and stirred at room temperature for 1 hour. The reaction was terminated by the addition of 1 N hydrochloric acid (5.00 ml, 5.00 mmol), and the solvent was removed under reduced pressure. The residues obtained were purified by silica gel column chromatography [chloroform-partitioned organic layer of chloroform:methanol:water=7:3:1 (v/v/v)] to yield the titled compound as a pale yellow solid (0.412 g, 89%). This compound was confirmed in the tumor of a cancer-bearing mouse that received the antibody-drug conjugate (55) or (56).

$^1$H-NMR (400 MHz, DMSO-d$_6$) δ: 0.87 (3H, t, J=7.3 Hz), 1.78-1.95 (2H, m), 2.09-2.28 (2H, m), 2.39 (3H, s), 3.07-3.27 (2H, m), 3.96 (2H, d, J=6.0 Hz), 5.11-5.26 (2H, m), 5.42 (2H, s), 5.46-5.54 (1H, m), 5.55-5.63 (1H, m), 6.52 (1H, s), 7.30 (1H, s), 7.78 (1H, d, J=10.9 Hz), 8.41 (1H, d, J=9.1 Hz). MS (ESI) m/z: 494 (M+H)$^+$

Example 76 Another Method for Synthesizing Compound of Example 75

[Formula 145]

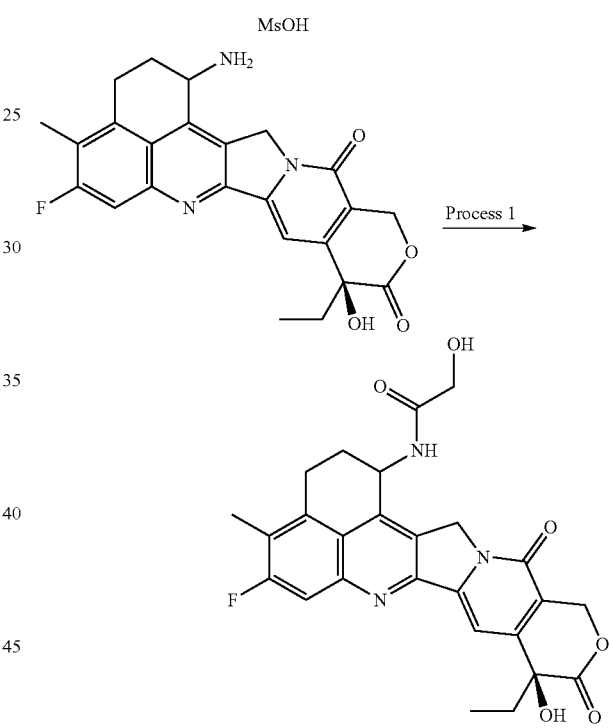

Process 1: N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-2-hydroxyacetamide Glycolic acid (0.0201 g, 0.27 mmol) was dissolved in N,N-dimethylformamide (1.0 mL), charged with N-hydroxysuccinimide (0.0302 g, 0.27 mmol) and 1-(3-dimethylaminopropyl)-3-ethylcarbodiimide hydrochloride (0.0508 g, 0.27 mmol), and stirred for 1 hour. The reaction solution was added to an N,N-dimethylformamide suspension (1.0 mL) charged with mesylate of the compound (4) (0.1 g, 0.176 mmol) and triethylamine (0.025 mL, 0.18 mmol) and stirred at room temperature for 24 hours. The solvent was removed under reduced pressure and the residues obtained were purified by silica gel column chromatography [chloroform-chloroform:methanol=10:1 (v/v)] to yield the titled compound as a pale yellow solid (0.080 g, 92%). The instrumental data of the compound was the same as that of the compound obtained in Process 2 of Example 75.

(Test Example 1) Production of Full-Length Human B7-H3 Variant 1 Expression Vector cDNA encoding human B7-H3 variant 1 was amplified by PCR reaction using cDNA synthesized from LNCaP cell (American Type Culture Collection: ATCC) total RNA as a template and the following primer set:
primer 1:
5'-ctatagggagacccaagctggctagcatgctgcgtcggcggggcag-3' (SEQ ID NO: 22) and
primer 2:
5'-aacgggccctctagactcgagcggccgctcaggctatttcttgtccat-catcttc tttgctgtcag-3' (SEQ ID NO: 23).

Next, the obtained PCR product was purified by using MagExtractor PCR & Gel cleanup (Toyobo Co., Ltd.). The purified product was further digested with restriction enzymes (NheI/NotI) and thereafter purified by using MagExtractor PCR & Gel cleanup (Toyobo Co., Ltd.). pcDNA3.1 (+) plasmid DNA (Life Technologies) was digested with the same restriction enzymes as above (NheI/NotI) and thereafter purified by using MagExtractor PCR & Gel cleanup (Toyobo Co., Ltd.).

These purified DNA solutions were mixed, further charged with Ligation high (Toyobo Co., Ltd.), and incubated for ligation at 16° C. for 8 hours.

*Escherichia coli* DH5α competent cells (Life Technologies) were transformed by the addition of the obtained reaction product.

The colonies thus obtained were subjected to colony direct PCR using PCR primers and BGH reverse primer to select candidate clones.

The obtained candidate clones were cultured in a liquid medium (LB/Amp), and plasmid DNA was extracted with MagExtractor-Plasmid-(Toyobo Co., Ltd.).

Each obtained clone was compared with the provided CDS sequence by the sequencing analysis between primer 3 (CMV promoter primer):
5'-cgcaaatgggcggtaggcgtg-3' (SEQ ID NO: 24) and
primer 4 (BGH reverse primer):
5'-tagaaggcacagtcgagg-3' (SEQ ID NO: 25)
with the obtained plasmid DNA as a template.

After confirming the sequence, the obtained clone was cultured in 200 mL of LB/Amp medium, and plasmid DNA was extracted by using VioGene Plasmid Midi V-100 kit.

The vector was designated as pcDNA3.1-B7-H3. The sequence of an ORF site of the B7-H3 variant 1 gene cloned in the vector is shown in nucleotide positions 1 to 1602 of SEQ ID NO: 26 (FIG. 16) in the Sequence Listing. Also, the amino acid sequence of the B7-H3 variant 1 is shown in SEQ ID NO: 1 in the Sequence Listing.

(Test Example 2) Preparation of CCRF-CEM Cell Stably Expressing B7-H3 Variant 1 Gene pcDNA3.1-B7-H3 produced in Test Example 1 was transfected into CCRF-CEM cells (ATCC) by electroporation using Nucleofector II (manufactured by Lonza Group Ltd.). Then, the cells were further cultured for two nights in RPMI1640 medium (Life Technologies) containing 10% fetal bovine serum (FBS) (hereinafter, referred to as 10% FBS-RPMI1640) under conditions of 37° C. and 5% $CO_2$.

After the 2-day culture, culture was started in 10% FBS-RPMI1640 containing 750 µg/mL G418 (Life Technologies) in order to select CCRF-CEM cells in which pcDNA3.1-B7-H3 was stably integrated.

After the 1-month culture, cloning was carried out by the limiting dilution method in order to yield a single cell clone. Specifically, cells having resistance to G418 were diluted into 10 cells/mL, inoculated to a 96-well plate at a concentration of 100 µL/well, and cultured, and cells allowed to proliferate were recovered from individual wells.

Flow cytometry was used for confirming B7-H3 expression in each recovered clone. Specifically, each recovered clone was washed twice with PBS containing 5% FBS, thereafter suspended by the addition of PBS containing 5% FBS and 10 µg/mL M30, and left standing at 4° C. for 30 minutes. The clone was washed twice with PBS containing 5% FBS, thereafter suspended by the addition of Fluorescein-conjugated goat IgG fraction to mouse IgG (Whole Molecule) (455493, manufactured by ICN Pharmaceuticals, Inc.) diluted 1000-fold with PBS containing 5% FBS, and left standing at 4° C. for 30 minutes. The clone was washed twice with PBS containing 5% FBS, thereafter resuspended in PBS containing 5% FBS, and detected by using a flow cytometer (FC500: Beckman Coulter, Inc.).

The CCRF-CEM cells stably expressing the B7-H3 variant 1 gene thus obtained by these procedures were designated as CEM_V1_3.1_2 cells. The parent line CCRF-CEM cells were used as a cell line lacking B7-H3 expression.

(Test Example 3) Cytotoxicity Test (1) of Antibody-Drug Conjugate

The CEM_V1_3.1_2 cells produced in Test Example 2 or CCRF-CEM cells (ATCC) were cultured in RPMI1640 (GIBCO) containing 10% fetal bovine serum (MOREGATE) (hereinafter, referred to as a medium). The CEM_V1_3.1_2 cells or CCRF-CEM cells were prepared to have a concentration of $8 \times 10^4$ cells/mL by using a medium, added at a concentration of 25 µL/well to a 96-well microplate for cell culture charged with 65 µL/well of a medium, and cultured overnight. On the next day, the M30-H1-L4 antibody, M30-H1-L4P antibody, and antibody-drug conjugate each diluted into 1000 nM, 200 nM, 40 nM, 8 nM, 1.6 nM, 0.32 nM, and 0.064 nM by using a medium were added at a concentration of 10 µL/well to the microplate. A medium was added at a concentration of 10 µL/well to test substance non-supplemented wells. The cells were cultured under 5% $CO_2$ at 37° C. for 3 days. After the culture, the microplate was taken out from the incubator and left standing at room temperature for 30 minutes. The culture solution was charged with an equal amount of CellTiter-Glo Luminescent Cell Viability Assay (Promega) and stirred. After the microplate was left standing at room temperature for 10 minutes, the amount of light emission was measured by using a plate reader (PerkinElmer). The $IC_{50}$ value was calculated according to the following equation:

$$IC_{50} \text{ (nM)} = \text{antilog}((50-d) \times (\text{LOG}_{10}b - \text{LOG}_{10}a)/(d-c) + \text{LOG}_{20}b)$$

a: Concentration a of the test substance
b: Concentration b of the test substance
c: Ratio of live cells supplemented with the test substance having the concentration a
d: Ratio of live cells supplemented with the test substance having the concentration b The concentrations a and b establish the relation a>b crossing 50% ratio of live cells.

The survival rate of cells at each concentration was calculated according to the following equation:

Survival rate of cells (%)=$a/b$×100 a: Average amount of light emission from the test substance-supplemented wells (n=2)

b: Average amount of light emission from the test substance non-supplemented wells (n=10)

The antibody-drug conjugates (5), (16), (21), (32), (44), (45), (46), (52), and (54) exhibited a cytotoxic activity of $IC_{50}$<0.1 (nM) against the CEM_V1_3.1_2 cells. The antibody-drug conjugates (1), (12), (13), (20), (28), (29), (35), (36), (37), (41), (49), and (53) exhibited a cytotoxic activity of 0.1<$IC_{50}$<1 (nM) against the cells. The antibody-drug conjugates (33), (34), (47), (48), (50), and (51) exhibited a cytotoxic activity of 1<$IC_{50}$<100 (nM) against the cells. On the other hand, none of these antibody-drug conjugates exhibited a cytotoxic activity against the CCRF-CEM cells (>100 (nM)). Neither of the M30-H1-L4 antibody nor the M30-H1-L4P antibody exhibited a cytotoxic activity against both of the cells (>100 (nM)).

(Test Example 4) Cytotoxicity Test (2) of Antibody-Drug Conjugate

Antigen-positive cells SR cells (ATCC) or antigen-negative cells Daudi cells (ATCC) were cultured in RPMI1640 (GIBCO) containing 10% fetal bovine serum (MOREGATE) (hereinafter, referred to as a medium). The SR cells or Daudi cells were prepared to have a concentration of 2.8×10$^4$ cells/mL by using a medium and added at a concentration of 90 μL/well to a 96-well microplate for cell culture. Two hours later, the anti-CD30 antibody and antibody-drug conjugates (6) and (7) each diluted into 40 nM, 8 nM, 1.6 nM, 320 pM, 64 pM, 12.8 pM, and 2.6 pM by using a medium were added at a concentration of 10 μL/well to the microplate. A medium was added at a concentration of 10 μL/well to test substance non-supplemented wells. The cells were cultured under 5% $CO_2$ at 37° C. for 3 days. After the culture, the microplate was taken out from the incubator and left standing at room temperature for 30 minutes. The culture solution was charged with an equal amount of CellTiter-Glo Luminescent Cell Viability Assay (Promega) and stirred. After the microplate was left standing at room temperature for 10 minutes, the amount of light emission was measured by using a plate reader (PerkinElmer). The $IC_{50}$ value was calculated according to the following equation:

$IC_{50}$ (nM)=antilog((50−$d$)×($LOG_{10}b$−$LOG_{10}a$)/($d$−$c$)+$LOG_{10}b$)

a: Concentration a of the test substance b: Concentration b of the test substance c: Ratio of live cells supplemented with the test substance having the concentration a d: Ratio of live cells supplemented with the test substance having the concentration b The concentrations a and b establish the relation a>b crossing 50% ratio of live cells.

The survival rate of cells at each concentration was calculated according to the following equation:

Survival rate of cells (%)=$a/b$×100 a: Average amount of light emission from the test substance-supplemented wells (n=2)

b: Average amount of light emission from the test substance non-supplemented wells (n=12)

The antibody-drug conjugates (6) and (7) exhibited a cytotoxic activity of $IC_{50}$<0.01 (nM) against the SR cells. On the other hand, the antibody-drug conjugates (6) and (7) exhibited no cytotoxic activity against the Daudi cells (>4.0 (nM)). The anti-CD30 antibody exhibited no cytotoxic activity against both of the cells (>4.0 (nM)).

(Test Example 5) Cytotoxicity Test (3) of Antibody-Drug Conjugate

Antigen-positive cells SR cells (ATCC) were cultured in RPMI1640 (GIBCO) containing 10% fetal bovine serum (MOREGATE) (hereinafter, referred to as a medium). The SR cells were prepared to have a concentration of 2.8×10$^4$ cells/mL by using a medium and added at a concentration of 90 μL/well to a 96-well microplate for cell culture. Two hours later, the anti-CD30 antibody and antibody-drug conjugates (22), (23), (38), (64), and (65) each diluted into 1000 nM, 100 nM, 10 nM, 1 nM, 100 pM, 10 pM, and 1 pM by using a medium were added at a concentration of 10 μL/well to the microplate. A medium was added at a concentration of 10 μL/well to test substance non-supplemented wells. The cells were cultured under 5% $CO_2$ at 37° C. for 6 days. After the culture, the microplate was taken out from the incubator and left standing at room temperature for 30 minutes. The culture solution was charged with an equal amount of CellTiter-Glo Luminescent Cell Viability Assay (Promega) and stirred. After the microplate was left standing at room temperature for 10 minutes, the amount of light emission was measured by using a plate reader (PerkinElmer). The $IC_{50}$ value was calculated according to the following equation:

$IC_{50}$ (nM)=antilog((50−$d$)×($LOG_{10}b$−$LOG_{10}a$)/($d$−$c$)+$LOG_{10}b$)

a: Concentration a of the test substance b: Concentration b of the test substance c: Ratio of live cells supplemented with the test substance having the concentration a d: Ratio of live cells supplemented with the test substance having the concentration b The concentrations a and b establish the relation a>b crossing 50% ratio of live cells.

The survival rate of cells at each concentration was calculated according to the following equation:

Survival rate of cells (%)=$a/b$×100 a: Average amount of light emission from the test substance-supplemented wells (n=2)

b: Average amount of light emission from the test substance non-supplemented wells (n=12) The antibody-drug conjugates (23), (38), (64), and (65) exhibited a cytotoxic activity of $IC_{50}$<0.01 (nM) against the SR cells. The antibody-drug conjugate (22) exhibited a cytotoxic activity of $IC_{50}$<0.1 (nM) against the SR cells. The anti-CD30 antibody exhibited no cytotoxic activity against the SR cells (>4.0 (nM)).

(Test Example 6) Cytotoxicity Test (4) of Antibody-Drug Conjugate

Antigen-positive cells HL-60 cells (ATCC) or antigen-negative Raji cells (ATCC) were cultured in RPMI1640 (GIBCO) containing 10% fetal bovine serum (MOREGATE) (hereinafter, referred to as a medium). The HL-60 cells or Raji cells were prepared to have a concentration of 8×10$^4$ cells/mL by using a medium and added at a concentration of 25 μL/well to a 96-well microplate for cell culture charged with 65 μL/well of a medium. The anti-CD33 antibody and antibody-drug conjugates (8) and (9) each diluted into 1000 nM, 200 nM, 40 nM, 8 nM, 1.6 nM, 0.32 nM, and 0.064 nM by using a medium were added at a concentration of 10 μL/well to the microplate. A medium was added at a concentration of 10 μL/well to test substance non-supplemented wells. The cells were cultured under 5% $CO_2$ at 37° C. for 3 days. After the culture, the microplate was taken out from the incubator and left standing at room temperature for 30 minutes. The culture solution was charged with an equal amount of CellTiter-Glo Luminescent Cell Viability Assay (Promega) and stirred. After the microplate was left standing at room temperature for 10 minutes, the amount of light emission was measured by using a plate reader (PerkinElmer). The $IC_{50}$ value was calculated according to the following equation:

$$IC_{50} \text{ (nM)} = \text{antilog}((50-d) \times (LOG_{10}b - LOG_{10}a)/(d-c) + LOG_{10}b)$$

a: Concentration a of the test substance
b: Concentration b of the test substance
c: Ratio of live cells supplemented with the test substance having the concentration a
d: Ratio of live cells supplemented with the test substance having the concentration b
The concentrations a and b establish the relation a>b crossing 50% ratio of live cells.
The survival rate of cells at each concentration was calculated according to the following equation:

$$\text{Survival rate of cells (\%)} = a/b \times 100$$

a: Average amount of light emission from the test substance-supplemented wells (n=2)
b: Average amount of light emission from the test substance non-supplemented wells (n=5)
The antibody-drug conjugates (8) and (9) exhibited a cytotoxic activity of $IC_{50}$<0.1 (nM) against the HL-60 cells. On the other hand, the antibody-drug conjugates (8) and (9) exhibited no cytotoxic activity against the Raji cells (>100 (nM)). The anti-CD33 antibody exhibited no cytotoxic activity against both of the cells (>100 (nM)).

(Test Example 7) Cytotoxicity Test (5) of Antibody-Drug Conjugate

Antigen-positive cells NOMO-1 cells (HSRRB) were cultured in RPMI1640 (GIBCO) containing 10% fetal bovine serum (MOREGATE) (hereinafter, referred to as a medium). The NOMO-1 cells were prepared to have a concentration of $2.8 \times 10^4$ cells/mL by using a medium and added at a concentration of 90 μL/well to a 96-well microplate for cell culture. Two hours later, the anti-CD33 antibody and antibody-drug conjugates (24), (25), and (67) each diluted into 1000 nM, 200 nM, 40 nM, 8 nM, 1.6 nM, 0.32 nM, and 0.064 nM by using a medium were added at a concentration of 10 μL/well to the microplate. A medium was added at a concentration of 10 μL/well to test substance non-supplemented wells. The cells were cultured under 5% $CO_2$ at 37° C. for 6 days. After the culture, the microplate was taken out from the incubator and left standing for 30 minutes at room temperature. The culture solution was charged with an equal amount of CellTiter-Glo Luminescent Cell Viability Assay (Promega) and stirred. After the microplate was left standing at room temperature for 10 minutes, the amount of light emission was measured by using a plate reader (PerkinElmer). The $IC_{50}$ value was calculated according to the following equation:

$$IC_{50} \text{ (nM)} = \text{antilog}((50-d) \times (LOG_{10}b - LOG_{10}a)/(d-c) + LOG_{10}b)$$

a: Concentration a of the test substance
b: Concentration b of the test substance
c: Ratio of live cells supplemented with the test substance having the concentration a
d: Ratio of live cells supplemented with the test substance having the concentration b
The concentrations a and b establish the relation a>b crossing 50% ratio of live cells.
The survival rate of cells at each concentration was calculated according to the following equation:

$$\text{Survival rate of cells (\%)} = a/b \times 100$$

a: Average amount of light emission from the test substance-supplemented wells (n=2)
b: Average amount of light emission from the test substance non-supplemented wells (n=5)
The antibody-drug conjugate (25) exhibited a cytotoxic activity of $IC_{50}$<0.1 (nM) against the NOMO-1 cells. The antibody-drug conjugates (24) and (67) exhibited a cytotoxic activity of $1 < IC_{50} < 100$ (nM) against the cells. The anti-CD33 antibody exhibited no cytotoxic activity against the NOMO-1 cells (>100 (nM)).

(Test Example 8) Cytotoxicity Test (6) of Antibody-Drug Conjugate

Antigen-positive cells U251 cells (ATCC) or antigen-negative cells MCF-7 cells (ATCC) were cultured in RPMI1640 (GIBCO) containing 10% fetal bovine serum (MOREGATE) (hereinafter, referred to as a medium). The U251 cells or MCF-7 cells were prepared to have a concentration of $2.8 \times 10^4$ cells/mL by using a medium, added at a concentration of 90 μL/well to a 96-well microplate for cell culture, and cultured overnight. On the next day, the anti-CD70 antibody and antibody-drug conjugates (10) and (11) each diluted into 1000 nM, 200 nM, 40 nM, 8 nM, 1.6 nM, 0.32 nM, and 0.064 nM by using a medium were added at a concentration of 10 μL/well to the microplate. A medium was added at a concentration of 10 μL/well to test substance non-supplemented wells. The cells were cultured under 5% $CO_2$ at 37° C. for 6 days. After the culture, the microplate was taken out from the incubator and left standing at room temperature for 30 minutes. The culture solution was charged with an equal amount of CellTiter-Glo Luminescent Cell Viability Assay (Promega) and stirred. After the microplate was left standing at room temperature for 10 minutes, the amount of light emission was measured by using a plate reader (PerkinElmer). The $IC_{50}$ value was calculated according to the following equation:

$$IC_{50} \text{ (nM)} = \text{antilog}((50-d) \times (LOG_{10}b - LOG_{10}a)/(d-c) + LOG_{10}b)$$

a: Concentration a of the test substance
b: Concentration b of the test substance
c: Ratio of live cells supplemented with the test substance having the concentration a
d: Ratio of live cells supplemented with the test substance having the concentration b
The concentrations a and b establish the relation a>b crossing 50% ratio of live cells.

The survival rate of cells at each concentration was calculated according to the following equation:

Survival rate of cells (%)=$a/b$×100 a: Average amount of light emission from the test substance-supplemented wells (n=2)
b: Average amount of light emission from the test substance non-supplemented wells (n=12)

The antibody-drug conjugates (10) and (11) exhibited a cytotoxic activity of $IC_{50}$<1 (nM) against the U251 cells. On the other hand, the antibody-drug conjugates (10) and (11) exhibited no cytotoxic activity against the MCF-7 cells (≥90 (nM)). The anti-CD70 antibody exhibited no cytotoxic activity against both of the cells (>100 (nM)).

(Test Example 9) Cytotoxicity Test (7) of Antibody-Drug Conjugate

Antigen-positive cells U251 cells (ATCC) were cultured in RPMI1640 (GIBCO) containing 10% fetal bovine serum (MOREGATE) (hereinafter, referred to as a medium). The U251 cells were prepared to have a concentration of 2.8×10$^4$ cells/mL by using a medium and added at a concentration of 90 μL/well to a 96-well microplate for cell culture. Two hours later, the anti-CD70 antibody and antibody-drug conjugates (26), (27), (40), (68), and (69) each diluted into 1000 nM, 200 nM, 40 nM, 8 nM, 1.6 nM, 0.32 nM, and 0.064 nM by using a medium were added at a concentration of 10 L/well to the microplate. A medium was added at a concentration of 10 μL/well to test substance non-supplemented wells. The cells were cultured under 5% $CO_2$ at 37° C. for 6 days. After the culture, the microplate was taken out from the incubator and left standing at room temperature for 30 minutes. The culture solution was charged with an equal amount of CellTiter-Glo Luminescent Cell Viability Assay (Promega) and stirred. After the microplate was left standing at room temperature for 10 minutes, the amount of light emission was measured by using a plate reader (PerkinElmer). The $IC_{50}$ value was calculated according to the following equation:

$IC_{50}$ (nM)=antilog((50−$d$)×($LOG_{10}b$−$LOG_{10}a$)/($d$−$c$)+$LOG_{10}b$)

a: Concentration a of the test substance
b: Concentration b of the test substance
c: Ratio of live cells supplemented with the test substance having the concentration a
d: Ratio of live cells supplemented with the test substance having the concentration b The concentrations a and b establish the relation a>b crossing 50% ratio of live cells.

The survival rate of cells at each concentration was calculated according to the following equation:

Survival rate of cells (%)=$a/b$×100 a: Average amount of light emission from the test substance-supplemented wells (n=2)
b: Average amount of light emission from the test substance non-supplemented wells (n=12)

The antibody-drug conjugates (26), (27), (40), and (69) exhibited a cytotoxic activity of 1<$IC_{50}$<10 (nM) against the U251 cells. The antibody-drug conjugate (68) exhibited a cytotoxic activity of 10<$IC_{50}$<100 (nM) against the cells. The anti-CD70 antibody exhibited no cytotoxic activity against the U251 cells (>100 (nM)).

(Test Example 10) Cytotoxicity Test (8) of Released Drug

A375 cells (ATCC) were cultured in DMEM (GIBCO) containing 10% fetal bovine serum (MOREGATE) (hereinafter, referred to as a medium). The A375 cells were prepared to have a concentration of 4×10$^4$ cells/mL by using a medium, added at a concentration of 25 μL/well to a 96-well microplate for cell culture (CORNING) charged with 65 μL/well of a medium, and cultured overnight. On the next day, each test substance diluted into 1000 nM, 200 nM, 40 nM, 8 nM, 1.6 nM, 0.32 nM, and 0.064 nM by using DMSO was added at a concentration of 0.5 μL/well to the microplate. DMSO was added at a concentration of 0.5 μL/well to test substance non-supplemented wells. The volume of the medium in each well was adjusted to 100 μL by the addition of 10 μL/well of a medium, and the cells were cultured under 5% $CO_2$ at 37° C. for 6 days. After the culture, the microplate was taken out from the incubator and left standing at room temperature for 30 minutes. The culture solution was charged with an equal amount of CellTiter-Glo Luminescent Cell Viability Assay (Promega) and stirred. After the microplate was left standing at room temperature for 10 minutes, the amount of light emission was measured by using a plate reader. The $IC_{50}$ value was calculated according to the following equation:

$IC_{50}$ (nM)=antilog((50−$d$)×($LOG_{10}b$−$LOG_{10}a$)/($d$−$c$)+$LOG_{10}b$)

a: Concentration a of the test substance
b: Concentration b of the test substance
c: Ratio of live cells supplemented with the test substance having the concentration a
d: Ratio of live cells supplemented with the test substance having the concentration b The concentrations a and b establish the relation a>b crossing 50% ratio of live cells.

The survival rate of cells was calculated according to the following equation:

Survival rate of cells (%)=$a/b$×100 a: Average amount of light emission from the test substance-supplemented wells (n=2)
b: Average amount of light emission from the test substance non-supplemented wells (n=10)

The compound of Example (75) and exatecan exhibited a cytotoxic activity of 0.1<$IC_{50}$<1 (nM) against the A375 cells. The compound of Example (42) exhibited a cytotoxic activity against 1<$IC_{50}$<10 (nM) against the cells. The compound of Example (1) exhibited a cytotoxic activity against 10<$IC_{50}$<100 (nM) against the cells.

(Test Example 11) Antitumor Test (1)

Mouse: 5- to 6-week-old female BALB/c nude mice (Charles River Laboratories Japan, Inc.) were acclimatized for 4 to 7 days under SPF conditions before use in the experiment. The mice were fed with sterilized solid feed (FR-2, Funabashi Farms Co., Ltd) and given sterilized tap water (prepared by the addition of 5 to 15 ppm sodium hypochlorite solution).

Assay and calculation expression: In all studies, the major axis and minor axis of tumor were measured twice a week by using an electronic digital caliper (CD-15C, Mitutoyo Corp.), and the tumor volume (mm$^3$) was calculated. The calculation expression is as shown below.

Tumor volume (mm$^3$)=½×Major axis (mm)×[Minor axis (mm)]$^2$

All of the antibody-drug conjugates were diluted with physiological saline (Otsuka Pharmaceutical Factory, Inc.) and used at a volume of 10 mL/kg for intravenous administration to the tail of each mouse. Human melanoma line A375 cells were purchased from ATCC (American Type Culture Collection). 8×10⁶ cells suspended in physiological saline were subcutaneously transplanted to the right abdomen of each female nude mouse (Day 0), and the mice were randomly grouped at Day 11. The M30-H1-L4P antibody and antibody-drug conjugate (2) were each intravenously administered at a dose of 10 mg/kg to the tail of each mouse at Days 11, 18, and 25.

The results are shown in FIG. 17. In the drawing, the line with open rhombuses depicts the results about untreated tumor, the line with open triangles depicts the effect of the M30-H1-L4P antibody, and the line with open circles depicts the effect of the antibody-drug conjugate (2).

As seen from these results, the administration of the antibody-drug conjugate (2) remarkably decreased the tumor volume, and no further tumor growth was observed after the final administration. By contrast, the administration of the M30-H1-L4P antibody resulted in the progression of tumor growth.

In addition, the mice that received the antibody-drug conjugate (2) were free from notable signs such as weight loss, suggesting that the antibody-drug conjugate (2) is low toxic and highly safe.

(Test Example 12) Antitumor Test (2)

Human melanoma line A375 cells were purchased from ATCC (American Type Culture Collection). 6×10⁶ cells suspended in physiological saline were subcutaneously transplanted to the right abdomen of each female nude mouse (Day 0), and the mice were randomly grouped at Day 18. The antibody-drug conjugate (2) was intravenously administered at each dose (0.1, 0.3, and 1.3 mg/kg) to the tail of each mouse at Days 18, 25, and 32 in a schedule of qw×3.

Figure 18:
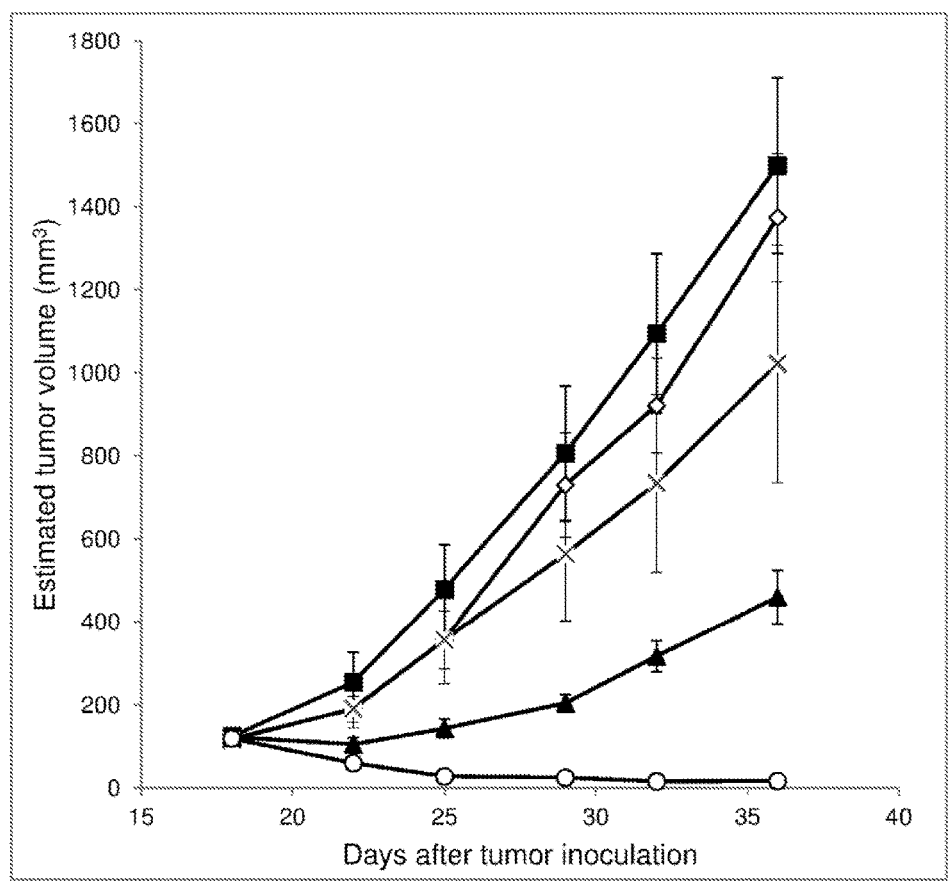
FIG. 18 shows the effect of the antibody-drug conjugate (2) on subcutaneously transplanted human melanoma line A375 cells. The line with open rhombuses depicts results about untreated tumor, the line with filled squares depicts the effect of the antibody-drug conjugate (2) administered at 0.1 mg/kg, the line with X marks depicts the effect of the antibody-drug conjugate (2) administered at 0.3 mg/kg, the line with filled triangles depicts the effect of the antibody-drug conjugate (2) administered at 1 mg/kg, and the line with open circles depicts the effect of the antibody-drug conjugate (2) administered at 3 mg/kg.

The results are shown in FIG. 18. In the drawing, the line with open rhombuses depicts the results about untreated tumor, the line with filled squares depicts the effect of the antibody-drug conjugate (2) administered at 0.1 mg/kg, the line with X marks depicts the effect of the antibody-drug conjugate (2) administered at 0.3 mg/kg, the line with filled triangles depicts the effect of the antibody-drug conjugate (2) administered at 1 mg/kg, and the line with open circles depicts the effect of the antibody-drug conjugate (2) administered at 3 mg/kg. The antibody-drug conjugate (2) was effective for shrinking tumor in a dose-dependent manner.

(Test Example 13) Antitumor Test (3)

Human non-small cell lung cancer line Calu-6 cells were purchased from ATCC (American Type Culture Collection). 5×10⁶ cells suspended in physiological saline were subcutaneously transplanted to the right abdomen of each female nude mouse (Day 0), and the mice were randomly grouped at Day 11. The M30-H1-L4P antibody and antibody-drug conjugate (2) were each intravenously administered at a dose of 10 mg/kg to the tail of each mouse at Days 11, 18, and 25 in a schedule of qw×3.

Figure 19:
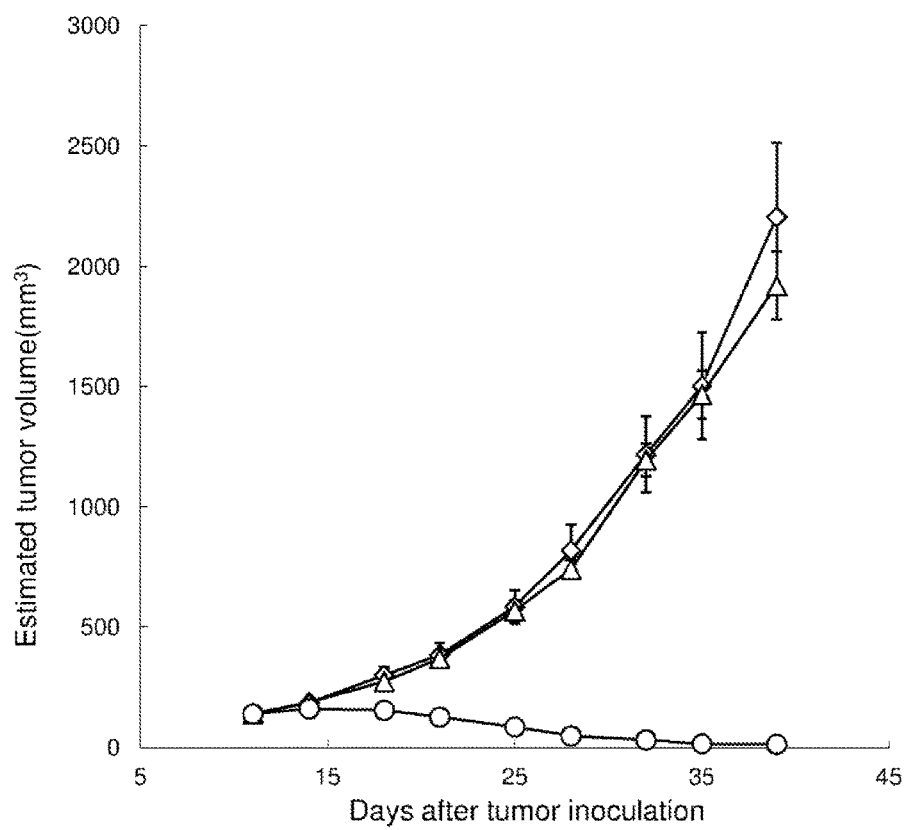
FIG. 19 shows the effect of the antibody-drug conjugate (2) on subcutaneously transplanted human non-small cell lung cancer line Calu-6 cells. The line with open rhombuses depicts results about untreated tumor, the line with open triangles depicts the effect of an M30-H1-L4P antibody, and the line with open circles depicts the effect of the antibody-drug conjugate (2).

The results are shown in FIG. 19. In the drawing, the line with open rhombuses depicts the results about untreated tumor, the line with open triangles depicts the effect of the M30-H1-L4P antibody, and the line with open circles depicts the effect of the antibody-drug conjugate (2). The administration of the antibody-drug conjugate (2) remarkably decreased the tumor volume, and no further tumor growth was observed after the final administration. By contrast, the administration of the M30-H1-L4P antibody resulted in the progression of tumor growth.

In addition, the mice that received the antibody-drug conjugate (2) were free from notable signs such as weight loss, suggesting that the antibody-drug conjugate (2) is low toxic and highly safe.

(Test Example 14) Antitumor Test (4)

Human melanoma line A375 cells were purchased from ATCC (American Type Culture Collection). 8×10⁶ cells suspended in physiological saline were subcutaneously transplanted to the right abdomen of each female nude mouse (Day 0), and the mice were randomly grouped at Day 21. The antibody-drug conjugates (1), (13), (41), and (55) were each intravenously administered at a dose of 10 mg/kg to the tail of each mouse at Day 21.

Figure 20:
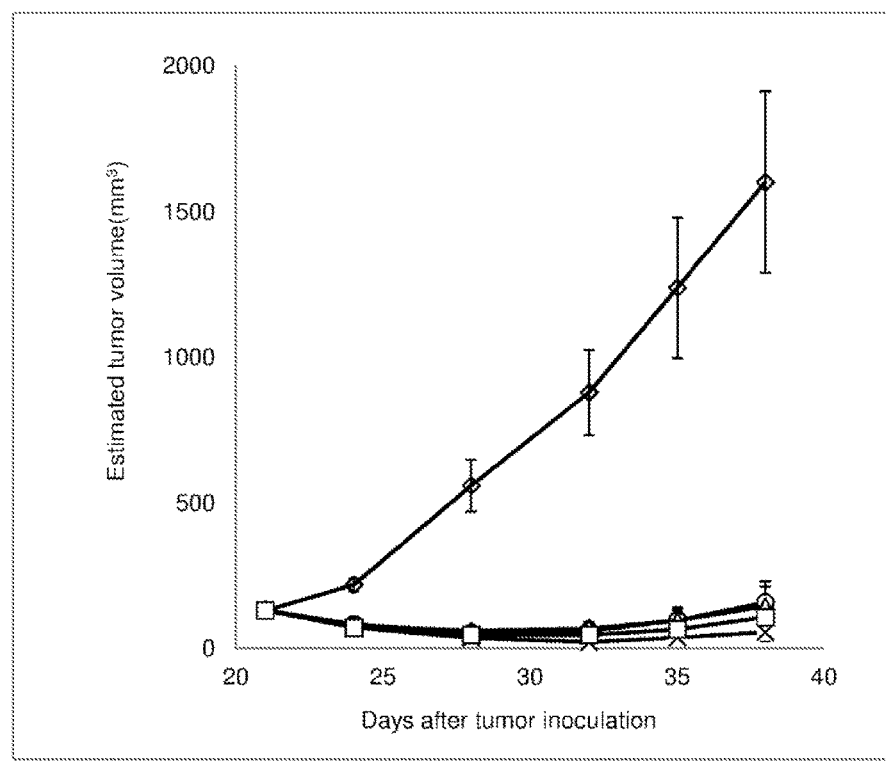
FIG. 20 shows the effects of antibody-drug conjugates (1), (13), (41), and (55) on subcutaneously transplanted human melanoma line A375 cells. In the drawing, the line with open rhombuses depicts results about untreated tumor, the line with open circles depicts the effect of the antibody-drug conjugate (1), the line with open triangles depicts the effect of the antibody-drug conjugate (13), the line with X marks depicts the effect of the antibody-drug conjugate (41), and the line with open squares depicts the effect of the antibody-drug conjugate (55).

The results are shown in FIG. 20. In the drawing, the line with open rhombuses depicts the results about untreated tumor, the line with open circles depicts the effect of the administered antibody-drug conjugate (1), the line with open triangles depicts the effect of the administered antibody-drug conjugate (13), the line with X marks depicts the effect of the administered antibody-drug conjugate (41), and the line with open squares depicts the effect of the administered antibody-drug conjugate (55). The administration of the antibody-drug conjugate (1), (13), (41), or (55) remarkably decreased the tumor volume, and all of these antibody-drug conjugates exerted a tumor growth inhibitory effect.

In addition, the mice that received the antibody-drug conjugate (1), (13), (41), or (55) were free from notable signs such as weight loss, suggesting that the antibody-drug conjugates (1), (13), (41), and (55) are low toxic and highly safe.

(Test Example 15) Antitumor Test (5)

Human non-small cell lung cancer line Calu-6 cells were purchased from ATCC (American Type Culture Collection). 5×10⁶ cells suspended in physiological saline were subcutaneously transplanted to the right abdomen of each female nude mouse (Day 0), and the mice were randomly grouped at Day 12. The antibody-drug conjugates (13), (41), and (55) were each intravenously administered at a dose of 10 mg/kg to the tail of each mouse at Day 12. As a comparative control, DE-310 was intravenously administered at a dose of 0.1 mg/kg to the tail of each mouse at Day 12. Here, the aforementioned dose of the antibody-drug conjugate was based on the amount of the antibody in the conjugate and the aforementioned dose of DE-310 was based on the amount of the drug contained therein. In this respect, the amounts of the drugs respectively contained in the antibody-drug conjugate and DE-310 were about 1:100. This means that the doses of the antibody-drug conjugate and DE-310 were equal in terms of the amounts of the drugs contained therein.

Figure 21:
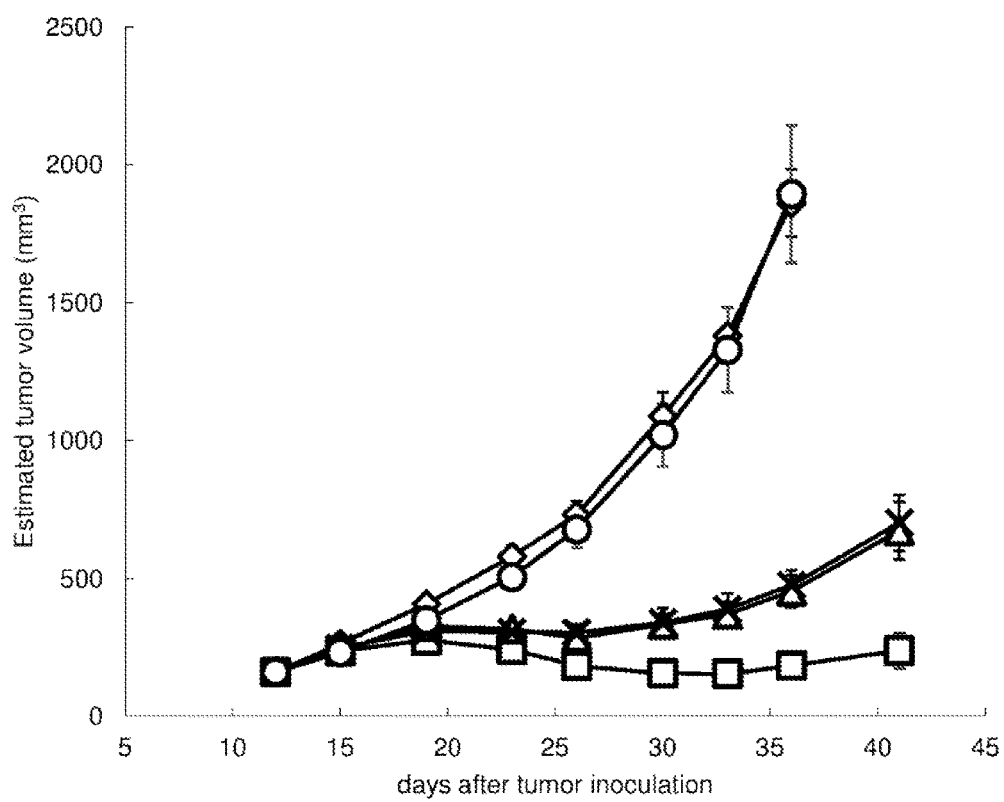
FIG. 21 shows the effects of antibody-drug conjugates (13), (41), and (55) on subcutaneously transplanted human non-small cell lung cancer line Calu-6 cells. The line with open rhombuses depicts results about untreated tumor, the line with open circles depicts the effect of DE-310, the line with open triangles depicts the effect of the antibody-drug conjugate (13), the line with X marks depicts the effect of the antibody-drug conjugate (41), and the line with open squares depicts the effect of the antibody-drug conjugate (55).

The results are shown in FIG. 21. In the drawing, the line with open rhombuses depicts the results about untreated tumor, the line with open circles depicts the effect of DE-310, the line with open triangles depicts the effect of the antibody-drug conjugate (13), the line with X marks depicts the effect of the antibody-drug conjugate (41), and the line with open squares depicts the effect of the antibody-drug conjugate (55). The administration of the antibody-drug conjugate (13), (41), or (55) remarkably decreased the tumor volume, whereas the administration of DE-310 exhibited no reduction in tumor volume.

In addition, the mice that received the antibody-drug conjugate (13), (41), or (55) were free from notable signs such as weight loss, suggesting that these antibody-drug conjugates are low toxic and highly safe.

(Test Example 16) Antitumor Test (6)

Human melanoma line A375 cells were purchased from ATCC (American Type Culture Collection). 1×10$^7$ cells suspended in physiological saline were subcutaneously transplanted to the right abdomen of each female nude mouse (Day 0), and the mice were randomly grouped at Day 11. The antibody-drug conjugates (17), (18), (19), (59), (60), and (61) were each intravenously administered at a dose of 3 mg/kg to the tail of each mouse at Days 11 and 18 in a schedule of qw×2.

Figure 22:
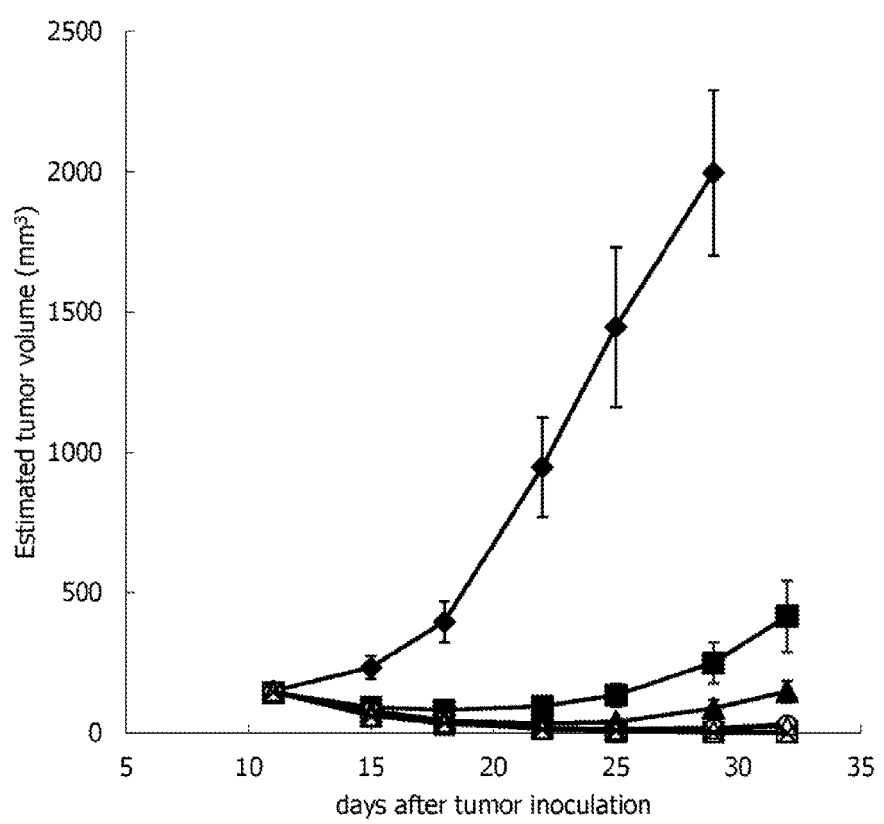
FIG. 22 shows the effects of antibody-drug conjugates (17), (18), (19), (59), (60), and (61) on subcutaneously transplanted human melanoma line A375 cells. In the drawing, the line with filled rhombuses depicts results about untreated tumor, the line with filled squares depicts the effect of the antibody-drug conjugate (17), the line with open squares depicts the effect of the antibody-drug conjugate (18), the line with open circles depicts the effect of the antibody-drug conjugate (19), the line with filled triangles depicts the effect of the antibody-drug conjugate (59), the line with open triangles depicts the effect of the antibody-drug conjugate (60), and the line with X marks depicts the effect of the antibody-drug conjugate (61).

The results are shown in FIG. 22. In the drawing, the line with filled rhombuses depicts the results about untreated tumor, the line with filled squares depicts the effect of the administered antibody-drug conjugate (17), the line with open triangles depicts the effect of the administered antibody-drug conjugate (18), the line with open circles depicts the effect of the administered antibody-drug conjugate (19), the line with filled triangles depicts the effect of the administered antibody-drug conjugate (59), the line with open squares depicts the effect of the administered antibody-drug conjugate (60), and the line with X marks depicts the effect of the administered antibody-drug conjugate (61).

The administration of the antibody-drug conjugate (17), (18), (19), (59), (60), or (61) remarkably decreased the tumor volume, and all of these antibody-drug conjugates exerted a tumor growth inhibitory effect.

In addition, the mice that received the antibody-drug conjugate (17), (18), (19), (59), (60), or (61) were free from notable signs such as weight loss, suggesting that these antibody-drug conjugates are low toxic and highly safe.

Free Text of Sequence Listing

SEQ ID NO: 1—Amino acid sequence of the B7-H3 variant 1
SEQ ID NO: 2—Amino acid sequence of the B7-H3 variant 2
SEQ ID NO: 3—Amino acid sequence of CDRH1 of the M30 antibody
SEQ ID NO: 4—Amino acid sequence of CDRH2 of the M30 antibody
SEQ ID NO: 5—Amino acid sequence of CDRH3 of the M30 antibody
SEQ ID NO: 6—Amino acid sequence of CDRL1 of the M30 antibody
SEQ ID NO: 7—Amino acid sequence of CDRL2 of the M30 antibody
SEQ ID NO: 8—Amino acid sequence of CDRL3 of the M30 antibody
SEQ ID NO: 9—Amino acid sequence of the M30-H1-type heavy chain
SEQ ID NO: 10—Amino acid sequence of the M30-H2-type heavy chain
SEQ ID NO: 11—Amino acid sequence of the M30-H3-type heavy chain
SEQ ID NO: 12—Amino acid sequence of the M30-H4-type heavy chain
SEQ ID NO: 13—Amino acid sequence of the M30-L1-type light chain
SEQ ID NO: 14—Amino acid sequence of the M30-L2-type light chain
SEQ ID NO: 15—Amino acid sequence of the M30-L3-type light chain
SEQ ID NO: 16—Amino acid sequence of the M30-L4-type light chain
SEQ ID NO: 17—Amino acid sequence of the M30-L5-type light chain
SEQ ID NO: 18—Amino acid sequence of the M30-L6-type light chain
SEQ ID NO: 19—Amino acid sequence of the M30-L7-type light chain
SEQ ID NO: 20—Amino acid sequence of a heavy chain of the M30 antibody
SEQ ID NO: 21—Amino acid sequence of a light chain of the M30 antibody
SEQ ID NO: 22—PCR primer 1
SEQ ID NO: 23—PCR primer 2
SEQ ID NO: 24—CMV promoter primer: primer 3
SEQ ID NO: 25—BGH reverse primer: primer 4
SEQ ID NO: 26—Nucleotide sequence of the B7-H3 variant 1
SEQ ID NO: 27—Amino acid sequence of a heavy chain of the anti-CD30 antibody
SEQ ID NO: 28—Amino acid sequence of a light chain of the anti-CD30 antibody
SEQ ID NO: 29—Amino acid sequence of a heavy chain of the anti-CD33 antibody
SEQ ID NO: 30—Amino acid sequence of a light chain of the anti-CD33 antibody
SEQ ID NO: 31—Amino acid sequence of a heavy chain of the anti-CD70 antibody
SEQ ID NO: 32—Amino acid sequence of a light chain of the anti-CD70 antibody

---

The invention claimed is:

1. An antibody-drug conjugate wherein an antitumor compound represented by the following formula:

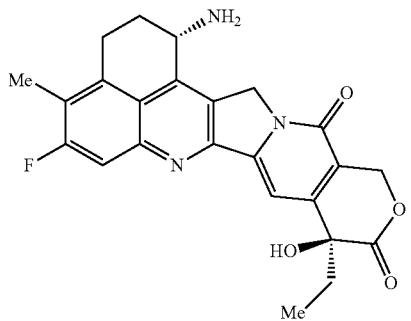

[Formula 1]

is conjugated to an antibody via a linker having a structure represented by the following formula:

-L$^1$-L$^2$-L$^P$-NH—(CH$_2$)$n^1$-L$^a$-L$^b$-L$^c$- wherein the antibody is connected to the terminal of L$^1$, the antitumor compound is connected to the terminal of L$^c$ with the nitrogen atom of the amino group at position 1 of the antitumor compound as the connecting position, wherein L$^1$ represents -(Succinimid-3-yl-N)—(CH$_2$)n$^2$-C(=O)— wherein n$^2$ represents an integer of 2 to 8, L$^2$ represents —NH—(CH$_2$—CH$_2$—O)n$^5$-CH$_2$—CH$_2$—C(=O) or a single bond, wherein n$^5$ represents an integer of 1 to 6, L$^P$ represents a tetrapeptide residue of GGFG, —NH—(CH$_2$)n$^1$-L$^a$-L$^b$-L$^c$- is —NH—(CH$_2$)$_3$—C(=O)—, —NH—CH$_2$—O—CH$_2$—C(=O)—, or —NH—(CH$_2$)$_2$—O—CH$_2$—C(=O)—, -(Succinimid-3-yl-N)— has a structure represented by the following formula:

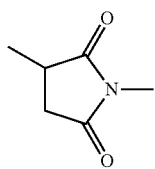

[Formula 2]

which is connected to the antibody at position 3 thereof and is connected to a methylene group in the linker structure containing this structure on the nitrogen atom at position 1.

2. The antibody-drug conjugate according to claim 1, wherein n$^2$ is an integer of 2 to 5, and L$^2$ is a single bond.

3. The antibody-drug conjugate according to claim 1, wherein n$^2$ is an integer of 2 to 5, L$^2$ is —NH—(CH$_2$CH$_2$O)n$^5$-CH$_2$—CH$_2$—C(=O)—, and n$^5$ is 2 or 4.

4. The antibody-drug conjugate according to claim 1, wherein the structure of the linker is one structure selected from the group consisting of:

-(Succinimid-3-yl-N)—CH$_2$CH$_2$—C(=O)-GGFG-NH—CH$_2$CH$_2$CH$_2$—C(=O)—(NH-DX)

-(Succinimid-3-yl-N)—CH$_2$CH$_2$CH$_2$CH$_2$CH$_2$—C(=O)-GGFG-NH—CH$_2$CH$_2$CH$_2$—C(=O)—(NH-DX)

-(Succinimid-3-yl-N)—CH$_2$CH$_2$CH$_2$CH$_2$CH$_2$—C(=O)-GGFG-NH—CH$_2$—O—CH$_2$—C(=O)—(NH-DX)

-(Succinimid-3-yl-N)—CH$_2$CH$_2$CH$_2$CH$_2$CH$_2$—C(=O)-GGFG-NH—CH$_2$CH$_2$—O—CH$_2$—C(=O)—(NH-DX)

-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX)

-(Succinimid-3-yl-N)—CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—(NH-DX)

wherein —(NH-DX) represents a group represented by the following formula:

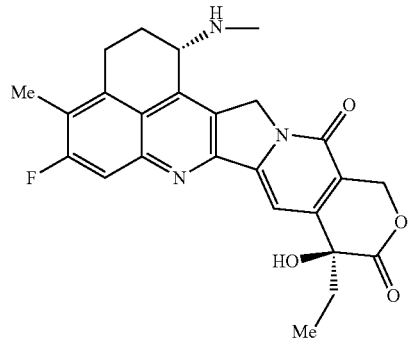

[Formula 4]

wherein the nitrogen atom of the amino group at position 1 is the connecting position, and -GGFG- represents a peptide residue of -Gly-Gly-Phe-Gly-.

5. The antibody-drug conjugate according to claim 1, wherein the structure of the linker is one structure selected from the group consisting of:

-(Succinimid-3-yl-N)—CH$_2$CH$_2$CH$_2$CH$_2$CH$_2$—C(=O)-GGFG-NH—CH$_2$—O—CH$_2$—C(=O)—(NH-DX)

-(Succinimid-3-yl-N)—CH$_2$CH$_2$CH$_2$CH$_2$CH$_2$—C(=O)-GGFG-NH—CH$_2$CH$_2$—O—CH$_2$—C(=O)—(NH-DX)

-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX)

wherein —(NH-DX) represents a group represented by the following formula:

[Formula 5]

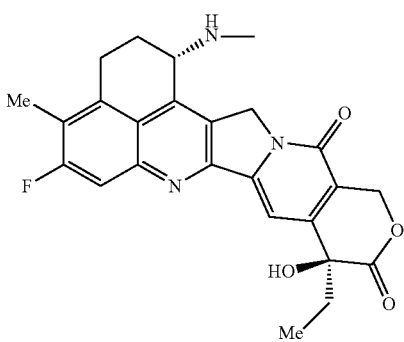

wherein the nitrogen atom of the amino group at position 1 is the connecting position.

6. The antibody-drug conjugate according to claim 1, wherein an average number of units of the selected one drug-linker structure conjugated per antibody is in a range of from 2 to 8.

7. The antibody-drug conjugate according to claim 1, wherein an average number of units of the selected one drug-linker structure conjugated per antibody is in a range of from 3 to 8.

8. The antibody-drug conjugate according to claim 1, wherein the antibody is an antibody having one or more of a property of recognizing a target cell, a property of binding to a target cell, a property of internalizing in a target cell, and a property of damaging a target cell.

9. The antibody-drug conjugate according to claim 1, wherein a cell which is targeted by the antibody-drug conjugate is a tumor cell.

10. The antibody-drug conjugate according to claim 1, wherein the antibody is an anti-A33 antibody, an anti-B7-H3 antibody, an anti-CanAg antibody, an anti-CD20 antibody, an anti-CD22 antibody, an anti-CD30 antibody, an anti-CD33 antibody, an anti-CD56 antibody, an anti-CD70 antibody, an anti-CEA antibody, an anti-Cripto antibody, an anti-EphA2 antibody, an anti-G250 antibody, an anti-MUC1 antibody, an anti-GPNMB antibody, an anti-integrin antibody, an anti-PSMA antibody, an anti-tenascin-C antibody, an anti-SLC44A4 antibody, or an anti-mesothelin antibody.

11. The antibody-drug conjugate according to claim 1, wherein the antibody is an anti-B7-H3 antibody, an anti-CD30 antibody, an anti-CD33 antibody, or an anti-CD70 antibody.

12. The antibody-drug conjugate according to claim 1, wherein the antibody is an anti-B7-H3 antibody.

13. A drug containing the antibody-drug conjugate according to claim 1, or a salt thereof.

14. An antitumor drug and/or anticancer drug containing the antibody-drug conjugate according to claim 1, or a salt thereof.

15. The antitumor drug and/or anticancer drug according to claim 14, which is applied to lung cancer, kidney cancer, urothelial cancer, colorectal cancer, prostate cancer, glioblastoma multiforme, ovarian cancer, pancreatic cancer, breast cancer, melanoma, liver cancer, bladder cancer, stomach cancer, or esophageal cancer.

16. A pharmaceutical composition containing the antibody-drug conjugate according to claim 1, or a salt thereof as an active component, and a pharmaceutically acceptable formulation component.

17. A method for treating tumor and/or cancer comprising administering the antibody-drug conjugate according to claim 1, or a salt thereof.

18. A drug-linker intermediate compound represented by the following formula:

Q—(CH$_2$)n$^Q$-C(=O)-L$^{2a}$-L$^P$-NH—(CH$_2$)n$^1$-L$^a$-L$^b$-L$^c$-(NH-DX)

wherein Q represents (maleimid-N-yl)-
n$^Q$ represents an integer of 2 to 8,
L$^{2a}$ represents —NH—(CH$_2$—CH$_2$—O)n$^5$-CH$_2$—CH$_2$—C(=O)— or a single bond,
wherein n$^5$ represents an integer of 1 to 6,
L$^P$ represents a tetrapeptide of GGFG,
—NH—(CH$_2$)n$^1$-L$^a$-L$^b$-L$^c$- is —NH—(CH$_2$)$_3$—C(=O)—, —NH—CH$_2$—O—CH$_2$—C(=O)—, or —NH—(CH$_2$)$_2$—O—CH$_2$—C(=O)—,
(maleimid-N-yl)- is a group represented by the following formula:

[Formula 10]

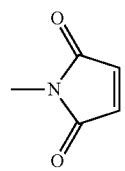

wherein the nitrogen atom is a connecting position, and

—(NH-DX) is a group represented by the following formula:

[Formula 12]

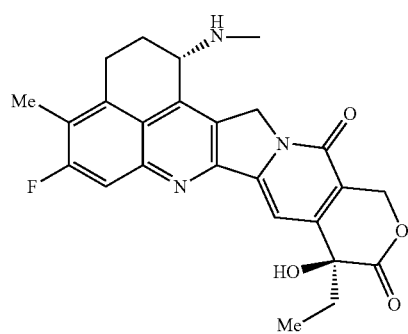

wherein the nitrogen atom of the amino group at position 1 is a connecting position.

19. The drug-linker intermediate compound according to claim 18, wherein n$^Q$ is an integer of 2 to 6.

20. The drug-linker intermediate compound according to claim 18, wherein
n$^Q$ is an integer of 2 to 5, and
L$^{2a}$ is a single bond.

21. The drug-linker intermediate compound according to claim 18, wherein
n$^Q$ is an integer of 2 to 5,
L$^{2a}$ is —NH—(CH$_2$—CH$_2$—O)n$^5$-CH$_2$—CH$_2$—C(=O)—, and
n$^5$ is an integer of 2 to 4.

22. The drug-linker intermediate compound according to claim 21, wherein $n^5$ is an integer of 2 or 4.

23. A compound of the following:

(maleimid-N-yl)-CH$_2$CH$_2$—C(=O)-GGFG-NH—CH$_2$CH$_2$CH$_2$—C(=O)—(NH-DX)

(maleimid-N-yl)-CH$_2$CH$_2$CH$_2$—C(=O)-GGFG-NH—CH$_2$CH$_2$CH$_2$—C(=O)—(NH-DX)

(maleimid-N-yl)-CH$_2$CH$_2$CH$_2$CH$_2$—C(=O)-GGFG-NH—CH$_2$CH$_2$CH$_2$—C(=O)—(NH-DX)

(maleimid-N-yl)-CH$_2$CH$_2$CH$_2$CH$_2$CH$_2$—C(=O)-GGFG-NH—CH$_2$CH$_2$CH$_2$—C(=O)—(NH-DX)

(maleimid-N-yl)-CH$_2$CH$_2$—C(=O)-GGFG-NH—CH$_2$—O—CH$_2$—C(=O)—(NH-DX)

(maleimid-N-yl)-CH$_2$CH$_2$CH$_2$—C(=O)-GGFG-NH—CH$_2$—O—CH$_2$—C(=O)—(NH-DX)

(maleimid-N-yl)-CH$_2$CH$_2$CH$_2$CH$_2$—C(=O)-GGFG-NH—CH$_2$—O—CH$_2$—C(=O)—(NH-DX)

(maleimid-N-yl)-CH$_2$CH$_2$CH$_2$CH$_2$CH$_2$—C(=O)-GGFG-NH—CH$_2$—O—CH$_2$—C(=O)—(NH-DX)

(maleimid-N-yl)-CH$_2$CH$_2$—C(=O)-GGFG-NH—CH$_2$CH$_2$—O—CH$_2$—C(=O)—(NH-DX)

(maleimid-N-yl)-CH$_2$CH$_2$CH$_2$—C(=O)-GGFG-NH—CH$_2$CH$_2$—O—CH$_2$—C(=O)—(NH-DX)

(maleimid-N-yl)-CH$_2$CH$_2$CH$_2$CH$_2$—C(=O)-GGFG-NH—CH$_2$CH$_2$—O—CH$_2$—C(=O)—(NH-DX)

(maleimid-N-yl)-CH$_2$CH$_2$CH$_2$CH$_2$CH$_2$—C(=O)-GGFG-NH—CH$_2$CH$_2$—O—CH$_2$—C(=O)—(NH-DX)

(maleimid-N-yl)-CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX) (maleimid-N-yl)-CH$_2$CH$_2$—C(=O)—NH—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—(NH-DX), or (maleimid-N-yl)-CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—(NH-DX)

wherein (maleimid-N-yl)- is a group represented by the following formula:

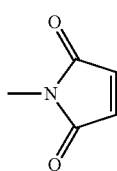

[Formula 16]

wherein the nitrogen atom is a connecting position, and —(NH-DX) is a group represented by the following formula:

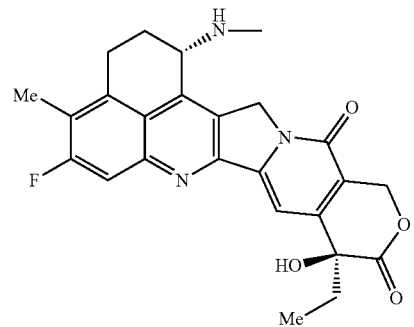

[Formula 17]

wherein the nitrogen atom of the amino group at position 1 is a connecting position.

24. A compound of the following:
(maleimid-N-yl)-CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX),
(maleimid-N-yl)-CH$_2$CH$_2$CH$_2$CH$_2$CH$_2$—C(=O)-GGFG-NH—CH$_2$—O—CH$_2$—C(=O)—(NH-DX) or
(maleimid-N-yl)-CH$_2$CH$_2$CH$_2$CH$_2$CH$_2$—C(=O)-GGFG-NH—CH$_2$CH$_2$—O—CH$_2$—C(=O)—(NH-DX), wherein (maleimid-N-yl)- is a group represented by the following formula:

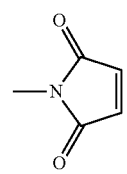

[Formula 18]

wherein the nitrogen atom is a connecting position, and —(NH-DX) is a group represented by the following formula:

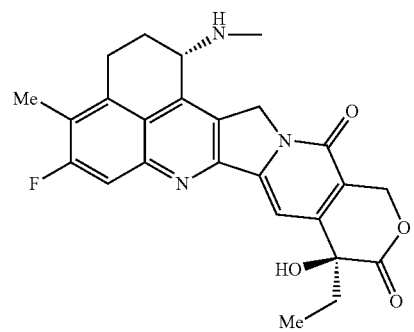

[Formula 19]

wherein the nitrogen atom of the amino group at position 1 is a connecting position.

25. A linker represented by the following formula:

-$L^2$-$L^P$-NH—(CH$_2$)$n^1$-$L^a$-$L^b$-$L^c$- for obtaining an antibody-drug conjugate in which a drug is conjugated to an antibody via the linker,
wherein $L^1$ is a connecting position for the antibody, $L^c$ is a connecting position for an antitumor compound, wherein $L^1$ represents -(Succinimid-3-yl-N)—$(CH_2)n^2$-C(=O)—, wherein $n^2$ represents an integer of 2 to 8, $L^2$ represents —NH—$(CH_2—CH_2—O)n^5$-$CH_2$—$CH_2$—C(=O) or a single bond, wherein $n^5$ represents an integer of 1 to 6, $L^P$ represents a tetrapeptide residue of GGFG, —NH—$(CH_2)n^1$-$L^a$-$L^b$-$L^c$- is —NH—$(CH_2)_3$—C(=O)—, —NH—$CH_2$—O—$CH_2$—C(=O)—, or —NH—$(CH_2)_2$—O—$CH_2$—C(=O)—, -(Succinimid-3-yl-N)— has a structure represented by the following formula:

[Formula 20]

which is connected to the antibody at position 3 thereof and is connected to a methylene group in the linker structure containing this structure on the nitrogen atom at position 1.

26. The antibody-drug conjugate according to claim 5, wherein the structure of the linker is:

-(Succinimid-3-yl-N)—$CH_2CH_2CH_2CH_2CH_2$—C(=O)-GGFG-NH—$CH_2CH_2$—O—$CH_2$—C(=O)—(NH-DX).

27. The antibody-drug conjugate according to claim 5, wherein the structure of the linker is:

-(Succinimid-3-yl-N)—$CH_2CH_2$—C(=O)—NH—$CH_2CH_2$—O—$CH_2CH_2$—O—$CH_2CH_2$—C(=O)-GGFG-NH—$CH_2CH_2CH_2$—C(=O)—(NH-DX).

28. The compound according to claim 24, wherein the structure of the compound is:

(maleimid-N-yl)-$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—(NH-DX).

29. The compound according to claim 24, wherein the structure of the compound is:

(maleimid-N-yl)-$CH_2CH_2CH_2CH_2CH_2$—C(=O)-GGFG-NH—$CH_2$—O—$CH_2$—C(=O)—(NH-DX).

30. The compound according to claim 24, wherein the structure of the compound is:

(maleimid-N-yl)-$CH_2CH_2CH_2CH_2$ $\underline{CH_2}$—C(=O)-GGFG-NH—$CH_2CH_2$—O—$CH_2$—C(=O)—(NH-DX).

31. The linker according to claim 25, which is selected from the group consisting of:

-(Succinimid-3-yl-N)—$CH_2CH_2$—C(=O)-GGFG-NH—$CH_2CH_2CH_2$—C(=O)—

-(Succinimid-3-yl-N)—$CH_2CH_2CH_2$—C(=O)-GGFG-NH—$CH_2CH_2CH_2$—C(=O)—

-(Succinimid-3-yl-N)—$CH_2CH_2CH_2CH_2$—C(=O)-GGFG-NH—$CH_2CH_2CH_2$—C(=O)—

-(Succinimid-3-yl-N)—$CH_2CH_2CH_2CH_2CH_2$—C(=O)-GGFG-NH—$CH_2CH_2CH_2$—C(=O)—

-(Succinimid-3-yl-N)—$CH_2CH_2$—C(=O)-GGFG-NH—$CH_2$—O—$CH_2$—C(=O)—

-(Succinimid-3-yl-N)—$CH_2CH_2CH_2$—C(=O)-GGFG-NH—$CH_2$—O—$CH_2$—C(=O)—

-(Succinimid-3-yl-N)—$CH_2CH_2CH_2CH_2$—C(=O)-GGFG-NH—$CH_2$—O—$CH_2$—C(=O)—

-(Succinimid-3-yl-N)—$CH_2CH_2CH_2CH_2CH_2$—C(=O)-GGFG-NH—$CH_2$—O—$CH_2$—C(=O)—

-(Succinimid-3-yl-N)—$CH_2CH_2$—C(=O)-GGFG-NH—$CH_2CH_2$—O—$CH_2$—C(=O)—

-(Succinimid-3-yl-N)—$CH_2CH_2CH_2$—C(=O)-GGFG-NH—$CH_2CH_2$—O—$CH_2$—C(=O)—

-(Succinimid-3-yl-N)—$CH_2CH_2CH_2CH_2$—C(=O)-GGFG-NH—$CH_2CH_2$—O—$CH_2$—C(=O)—

-(Succinimid-3-yl-N)—$CH_2CH_2CH_2CH_2CH_2$—C(=O)-GGFG-NH—$CH_2CH_2$—O—$CH_2$—C(=O)—

-(Succinimid-3-yl-N)—$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—

-(Succinimid-3-yl-N)—$CH_2CH_2$—C(=O)—NH—$CH_2CH_2O$—$CH_2CH_2O$—$CH_2CH_2O$—$CH_2CH_2$—C(=O)-GGFG-NH—$CH_2CH_2CH_2$—C(=O)—, and -(Succinimid-3-yl-N)—$CH_2CH_2$—C(=O)—NH—$CH_2CH_2O$—$CH_2CH_2O$—$CH_2CH_2O$—$CH_2CH_2O$—$CH_2CH_2$—C(=O)-GGFG-NH—$CH_2CH_2CH_2$—C(=O)—, wherein the left terminal is a connecting position with the antibody and the right terminal is a connecting position with the antitumor compound.

32. The linker according to claim 25, which is selected from the group consisting of:

-(Succinimid-3-yl-N)—$CH_2CH_2CH_2CH_2CH_2$—C(=O)-GGFG-NH—$CH_2$—O—$CH_2$—C(=O)—

-(Succinimid-3-yl-N)—$CH_2CH_2CH_2CH_2CH_2$—C(=O)-GGFG-NH—$CH_2CH_2$—O—$CH_2$—C(=O)—, and -(Succinimid-3-yl-N)—$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—, wherein the left terminal is a connecting position with the antibody and the right terminal is a connecting position with the antitumor compound.

33. The linker according to claim 25, which is:

-(Succinimid-3-yl-N)—$CH_2CH_2CH_2CH_2CH_2$—C(=O)-GGFG-NH—$CH_2$—O—$CH_2$—C(=O)—, wherein the left terminal is a connecting position with the antibody and the right terminal is a connecting position with the antitumor compound.

34. The linker according to claim 25, which is :

-(Succinimid-3-yl-N)—$CH_2CH_2CH_2CH_2CH_2$—C(=O)-GGFG-NH—$CH_2CH_2$—O—$CH_2$—C(=O)—, wherein the left terminal is a connecting position with the antibody and the right terminal is a connecting position with the antitumor compound.

35. The linker according to claim 25, which is:

-(Succinimid-3-yl-N)—$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—, wherein the left terminal is a connecting position with the antibody and the right terminal is a connecting position with the antitumor compound.

* * * * *

SEQUENCE LISTING

```
<160> NUMBER OF SEQ ID NOS: 32

<210> SEQ ID NO 1
<211> LENGTH: 534
<212> TYPE: PRT
<213> ORGANISM: Homo sapiens

<400> SEQUENCE: 1

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
                20                  25                  30

Val Pro Glu Asp Pro Val Val Ala Leu Val Gly Thr Asp Ala Thr Leu
            35                  40                  45
```

```
Cys Cys Ser Phe Ser Pro Glu Pro Gly Phe Ser Leu Ala Gln Leu Asn
    50              55                  60

Leu Ile Trp Gln Leu Thr Asp Thr Lys Gln Leu Val His Ser Phe Ala
65              70                  75                      80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
            115                 120                 125

Phe Gly Ser Ala Ala Val Ser Leu Gln Val Ala Ala Pro Tyr Ser Lys
        130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
                180                 185                 190

Ser Gln Met Ala Asn Glu Gln Gly Leu Phe Asp Val His Ser Ile Leu
        195                 200                 205

Arg Val Val Leu Gly Ala Asn Gly Thr Tyr Ser Cys Leu Val Arg Asn
        210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
                260                 265                 270

Glu Pro Gly Phe Ser Leu Ala Gln Leu Asn Leu Ile Trp Gln Leu Thr
        275                 280                 285

Asp Thr Lys Gln Leu Val His Ser Phe Thr Glu Gly Arg Asp Gln Gly
        290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
                340                 345                 350

Ser Leu Gln Val Ala Ala Pro Tyr Ser Lys Pro Ser Met Thr Leu Glu
        355                 360                 365

Pro Asn Lys Asp Leu Arg Pro Gly Asp Thr Val Thr Ile Thr Cys Ser
        370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
            435                 440                 445

Ala His Gly Ser Val Thr Ile Thr Gly Gln Pro Met Thr Phe Pro Pro
450                 455                 460

Glu Ala Leu Trp Val Thr Val Gly Leu Ser Val Cys Leu Ile Ala Leu
```

```
            465                 470                 475                 480
Leu Val Ala Leu Ala Phe Val Cys Trp Arg Lys Ile Lys Gln Ser Cys
                    485                 490                 495

Glu Glu Glu Asn Ala Gly Ala Glu Asp Gln Asp Gly Glu Gly Glu Gly
            500                 505                 510

Ser Lys Thr Ala Leu Gln Pro Leu Lys His Ser Asp Ser Lys Glu Asp
            515                 520                 525

Asp Gly Gln Glu Ile Ala
            530

<210> SEQ ID NO 2
<211> LENGTH: 316
<212> TYPE: PRT
<213> ORGANISM: Homo sapiens

<400> SEQUENCE: 2

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
                20                  25                  30

Val Pro Glu Asp Pro Val Val Ala Leu Val Gly Thr Asp Ala Thr Leu
            35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Arg Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Val Leu
        195                 200                 205

Arg Val Val Leu Gly Ala Asn Gly Thr Tyr Ser Cys Leu Val Arg Asn
210                 215                 220

Pro Val Leu Gln Gln Asp Ala His Gly Ser Val Thr Ile Thr Gly Gln
225                 230                 235                 240

Pro Met Thr Phe Pro Pro Glu Ala Leu Trp Val Thr Val Gly Leu Ser
                245                 250                 255

Val Cys Leu Ile Ala Leu Leu Val Ala Leu Ala Phe Val Cys Trp Arg
            260                 265                 270

Lys Ile Lys Gln Ser Cys Glu Glu Asn Ala Gly Ala Glu Asp Gln
        275                 280                 285

Asp Gly Glu Gly Glu Gly Ser Lys Thr Ala Leu Gln Pro Leu Lys His
        290                 295                 300
```

```
Ser Asp Ser Lys Glu Asp Asp Gly Gln Glu Ile Ala
305                 310                 315

<210> SEQ ID NO 3
<211> LENGTH: 5
<212> TYPE: PRT
<213> ORGANISM: Mus musculus

<400> SEQUENCE: 3

Asn Tyr Val Met His
1               5

<210> SEQ ID NO 4
<211> LENGTH: 17
<212> TYPE: PRT
<213> ORGANISM: Mus musculus

<400> SEQUENCE: 4

Tyr Ile Asn Pro Tyr Asn Asp Asp Val Lys Tyr Asn Glu Lys Phe Lys
1               5                   10                  15

Gly

<210> SEQ ID NO 5
<211> LENGTH: 13
<212> TYPE: PRT
<213> ORGANISM: Mus musculus

<400> SEQUENCE: 5

Trp Gly Tyr Tyr Gly Ser Pro Leu Tyr Tyr Phe Asp Tyr
1               5                   10

<210> SEQ ID NO 6
<211> LENGTH: 10
<212> TYPE: PRT
<213> ORGANISM: Mus musculus

<400> SEQUENCE: 6

Arg Ala Ser Ser Arg Leu Ile Tyr Met His
1               5                   10

<210> SEQ ID NO 7
<211> LENGTH: 7
<212> TYPE: PRT
<213> ORGANISM: Mus musculus

<400> SEQUENCE: 7

Ala Thr Ser Asn Leu Ala Ser
1               5

<210> SEQ ID NO 8
<211> LENGTH: 9
<212> TYPE: PRT
<213> ORGANISM: Mus musculus

<400> SEQUENCE: 8

Gln Gln Trp Asn Ser Asn Pro Pro Thr
1               5

<210> SEQ ID NO 9
<211> LENGTH: 471
<212> TYPE: PRT
<213> ORGANISM: Artificial Sequence
<220> FEATURE:
<223> OTHER INFORMATION: Humanized heavy chain of M30
```

<400> SEQUENCE: 9

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
                20                  25                  30

Pro Gly Ser Ser Val Lys Val Ser Cys Lys Ala Ser Gly Tyr Thr Phe
            35                  40                  45

Thr Asn Tyr Val Met His Trp Val Arg Gln Ala Pro Gly Gln Gly Leu
    50                  55                  60

Glu Trp Met Gly Tyr Ile Asn Pro Tyr Asn Asp Asp Val Lys Tyr Asn
65                  70                  75                  80

Glu Lys Phe Lys Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Trp Gly Tyr Tyr Gly Ser Pro Leu Tyr Tyr Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

```
Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
450             455                 460

Leu Ser Leu Ser Pro Gly Lys
465             470

<210> SEQ ID NO 10
<211> LENGTH: 471
<212> TYPE: PRT
<213> ORGANISM: Artificial Sequence
<220> FEATURE:
<223> OTHER INFORMATION: Humanized heavy chain of M30

<400> SEQUENCE: 10

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asn Tyr Val Met His Trp Val Arg Gln Ala Pro Gly Gln Gly Leu
    50                  55                  60

Glu Trp Ile Gly Tyr Ile Asn Pro Tyr Asn Asp Val Lys Tyr Asn
65              70                  75                  80

Glu Lys Phe Lys Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Trp Gly Tyr Tyr Gly Ser Pro Leu Tyr Tyr Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145             150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225             230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300
```

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 11
<211> LENGTH: 471
<212> TYPE: PRT
<213> ORGANISM: Artificial Sequence
<220> FEATURE:
<223> OTHER INFORMATION: Humanized heavy chain of M30

<400> SEQUENCE: 11

Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asn Tyr Val Met His Trp Val Lys Gln Ala Pro Gly Gln Gly Leu
    50                  55                  60

Glu Trp Ile Gly Tyr Ile Asn Pro Tyr Asn Asp Val Lys Tyr Asn
65                  70                  75                  80

Glu Lys Phe Lys Gly Lys Ala Thr Ile Thr Ala Asp Glu Ser Thr Ser
            85                  90                  95

Thr Ala Tyr Met Glu Leu Ser Ser Leu Arg Ser Glu Asp Thr Ala Val
        100                 105                 110

Tyr Tyr Cys Ala Arg Trp Gly Tyr Tyr Gly Ser Pro Leu Tyr Tyr Phe
    115                 120                 125

Asp Tyr Trp Gly Gln Gly Thr Leu Val Thr Val Ser Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

```
Thr Phe Pro Ala Val Leu Gln Ser Ser Gly Leu Tyr Ser Leu Ser Ser
            195                 200                 205

Val Val Thr Val Pro Ser Ser Leu Gly Thr Gln Thr Tyr Ile Cys
            210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
            245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
            290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Glu Glu Met Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 12
<211> LENGTH: 471
<212> TYPE: PRT
<213> ORGANISM: Artificial Sequence
<220> FEATURE:
<223> OTHER INFORMATION: Humanized heavy chain of M30

<400> SEQUENCE: 12

Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asn Tyr Val Met His Trp Val Lys Gln Ala Pro Gly Gln Gly Leu
    50                  55                  60

Glu Trp Ile Gly Tyr Ile Asn Pro Tyr Asn Asp Asp Val Lys Tyr Asn
65              70                  75                  80
```

Glu Lys Phe Lys Gly Lys Ala Thr Gln Thr Ser Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Trp Gly Tyr Tyr Gly Ser Pro Leu Tyr Tyr Phe
        115                 120                 125

Asp Tyr Trp Gly Gln Gly Thr Leu Val Thr Val Ser Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 13
<211> LENGTH: 233

```
<212> TYPE: PRT
<213> ORGANISM: Artificial Sequence
<220> FEATURE:
<223> OTHER INFORMATION: Humanized light chain of M30

<400> SEQUENCE: 13

Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Ser Arg
            35                  40                  45

Leu Ile Tyr Met His Trp Tyr Gln Gln Lys Pro Gly Gln Ala Pro Arg
    50                  55                  60

Leu Leu Ile Tyr Ala Thr Ser Asn Leu Ala Ser Gly Ile Pro Ala Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 14
<211> LENGTH: 233
<212> TYPE: PRT
<213> ORGANISM: Artificial Sequence
<220> FEATURE:
<223> OTHER INFORMATION: Humanized light chain of M30

<400> SEQUENCE: 14

Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Ser Arg
            35                  40                  45

Leu Ile Tyr Met His Trp Tyr Gln Gln Lys Pro Gly Gln Ala Pro Arg
    50                  55                  60

Leu Trp Ile Tyr Ala Thr Ser Asn Leu Ala Ser Gly Ile Pro Ala Arg
65                  70                  75                  80

Phe Ser Gly Ser Gly Ser Gly Thr Asp Tyr Thr Leu Thr Ile Ser Arg
                85                  90                  95
```

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
            115                 120                 125

Val Ala Ala Pro Ser Val Phe Ile Phe Pro Pro Ser Asp Glu Gln Leu
            130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 15
<211> LENGTH: 233
<212> TYPE: PRT
<213> ORGANISM: Artificial Sequence
<220> FEATURE:
<223> OTHER INFORMATION: Humanized light chain of M30

<400> SEQUENCE: 15

Met Val Leu Gln Thr Gln Val Phe Ile Ser Leu Leu Trp Ile Ser
1               5                   10                  15

Gly Ala Tyr Gly Gln Ile Val Leu Ser Gln Ser Pro Ala Thr Leu Ser
            20                  25                  30

Leu Ser Pro Gly Glu Arg Ala Thr Leu Thr Cys Arg Ala Ser Ser Arg
            35                  40                  45

Leu Ile Tyr Met His Trp Tyr Gln Gln Lys Pro Gly Ser Ala Pro Lys
50                  55                  60

Leu Trp Ile Tyr Ala Thr Ser Asn Leu Ala Ser Gly Ile Pro Ala Arg
65                  70                  75                  80

Phe Ser Gly Ser Gly Ser Gly Thr Ser Tyr Thr Leu Thr Ile Ser Arg
                85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
            115                 120                 125

Val Ala Ala Pro Ser Val Phe Ile Phe Pro Pro Ser Asp Glu Gln Leu
            130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 16
<211> LENGTH: 233
<212> TYPE: PRT
<213> ORGANISM: Artificial Sequence
<220> FEATURE:
<223> OTHER INFORMATION: Humanized light chain of M30

<400> SEQUENCE: 16

Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Ser Arg
            35                  40                  45

Leu Ile Tyr Met His Trp Tyr Gln Gln Lys Pro Gly Gln Ala Pro Arg
        50                  55                  60

Pro Leu Ile Tyr Ala Thr Ser Asn Leu Ala Ser Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 17
<211> LENGTH: 233
<212> TYPE: PRT
<213> ORGANISM: Artificial Sequence
<220> FEATURE:
<223> OTHER INFORMATION: Humanized light chain of M30

<400> SEQUENCE: 17

Met Val Leu Gln Thr Gln Val Phe Ile Ser Leu Leu Leu Trp Ile Ser
1               5                   10                  15

Gly Ala Tyr Gly Gln Ile Val Leu Ser Gln Ser Pro Ala Thr Leu Ser
                20                  25                  30

Leu Ser Pro Gly Glu Arg Ala Thr Leu Thr Cys Arg Ala Ser Ser Arg
            35                  40                  45

Leu Ile Tyr Met His Trp Tyr Gln Gln Lys Pro Gly Ser Ala Pro Lys

```
            50                  55                  60
Pro Trp Ile Tyr Ala Thr Ser Asn Leu Ala Ser Gly Ile Pro Ala Arg
 65                  70                  75                  80

Phe Ser Gly Ser Gly Ser Gly Thr Ser Tyr Thr Leu Thr Ile Ser Arg
                 85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 18
<211> LENGTH: 233
<212> TYPE: PRT
<213> ORGANISM: Artificial Sequence
<220> FEATURE:
<223> OTHER INFORMATION: Humanized light chain of M30

<400> SEQUENCE: 18

Met Val Leu Gln Thr Gln Val Phe Ile Ser Leu Leu Trp Ile Ser
  1               5                  10                  15

Gly Ala Tyr Gly Glu Ile Val Leu Thr Gln Ser Pro Ala Thr Leu Ser
                 20                  25                  30

Leu Ser Pro Gly Glu Arg Ala Thr Leu Ser Cys Arg Ala Ser Ser Arg
            35                  40                  45

Leu Ile Tyr Met His Trp Tyr Gln Gln Lys Pro Gly Gln Ala Pro Arg
        50                  55                  60

Pro Leu Ile Tyr Ala Thr Ser Asn Leu Ala Ser Gly Ile Pro Ala Arg
 65                  70                  75                  80

Phe Ser Gly Ser Gly Ser Gly Thr Asp Phe Thr Leu Thr Ile Ser Arg
                 85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
```

180                 185                 190
Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
        210                 215                 220

Thr Lys Ser Phe Asn Arg Gly Glu Cys
225                 230

<210> SEQ ID NO 19
<211> LENGTH: 233
<212> TYPE: PRT
<213> ORGANISM: Artificial Sequence
<220> FEATURE:
<223> OTHER INFORMATION: Humanized light chain of M30

<400> SEQUENCE: 19

Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Ser Arg
        35                  40                  45

Leu Ile Tyr Met His Trp Tyr Gln Gln Lys Pro Gly Gln Ala Pro Arg
    50                  55                  60

Pro Leu Ile Tyr Ala Thr Ser Asn Leu Ala Ser Gly Ile Pro Ala Arg
65                  70                  75                  80

Phe Ser Gly Ser Gly Ser Gly Thr Asp Tyr Thr Leu Thr Ile Ser Arg
                85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 20
<211> LENGTH: 471
<212> TYPE: PRT
<213> ORGANISM: Mus musculus

<400> SEQUENCE: 20

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

-continued

```
Pro Gly Ala Ser Val Lys Met Ser Cys Lys Ala Ser Gly Tyr Thr Phe
        35                  40                  45
Thr Asn Tyr Val Met His Trp Val Lys Gln Lys Pro Gly Gln Gly Leu
    50                  55                  60
Glu Trp Ile Gly Tyr Ile Asn Pro Tyr Asn Asp Asp Val Lys Tyr Asn
65                  70                  75                  80
Glu Lys Phe Lys Gly Lys Ala Thr Gln Thr Ser Asp Lys Ser Ser Ser
                85                  90                  95
Thr Ala Tyr Met Glu Leu Ser Ser Leu Thr Ser Glu Asp Ser Ala Val
                100                 105                 110
Tyr Tyr Cys Ala Arg Trp Gly Tyr Tyr Gly Ser Pro Leu Tyr Tyr Phe
            115                 120                 125
Asp Tyr Trp Gly Gln Gly Thr Thr Leu Thr Val Ser Ser Ala Lys Thr
        130                 135                 140
Thr Ala Pro Ser Val Tyr Pro Leu Ala Pro Val Cys Gly Asp Thr Thr
145                 150                 155                 160
Gly Ser Ser Val Thr Leu Gly Cys Leu Val Lys Gly Tyr Phe Pro Glu
                165                 170                 175
Pro Val Thr Leu Thr Trp Asn Ser Gly Ser Leu Ser Ser Gly Val His
                180                 185                 190
Thr Phe Pro Ala Val Leu Gln Ser Asp Leu Tyr Thr Leu Ser Ser Ser
            195                 200                 205
Val Thr Val Thr Ser Ser Thr Trp Pro Ser Gln Ser Ile Thr Cys Asn
        210                 215                 220
Val Ala His Pro Ala Ser Ser Thr Lys Val Asp Lys Lys Ile Glu Pro
225                 230                 235                 240
Arg Gly Pro Thr Ile Lys Pro Cys Pro Pro Cys Lys Cys Pro Ala Pro
                245                 250                 255
Asn Leu Leu Gly Gly Pro Ser Val Phe Ile Phe Pro Pro Lys Ile Lys
                260                 265                 270
Asp Val Leu Met Ile Ser Leu Ser Pro Ile Val Thr Cys Val Val Val
            275                 280                 285
Asp Val Ser Glu Asp Asp Pro Asp Val Gln Ile Ser Trp Phe Val Asn
        290                 295                 300
Asn Val Glu Val His Thr Ala Gln Thr Gln Thr His Arg Glu Asp Tyr
305                 310                 315                 320
Asn Ser Thr Leu Arg Val Val Ser Ala Leu Pro Ile Gln His Gln Asp
                325                 330                 335
Trp Met Ser Gly Lys Glu Phe Lys Cys Lys Val Asn Asn Lys Asp Leu
                340                 345                 350
Pro Ala Pro Ile Glu Arg Thr Ile Ser Lys Pro Lys Gly Ser Val Arg
            355                 360                 365
Ala Pro Gln Val Tyr Val Leu Pro Pro Pro Glu Glu Glu Met Thr Lys
        370                 375                 380
Lys Gln Val Thr Leu Thr Cys Met Val Thr Asp Phe Met Pro Glu Asp
385                 390                 395                 400
Ile Tyr Val Glu Trp Thr Asn Asn Gly Lys Thr Glu Leu Asn Tyr Lys
                405                 410                 415
Asn Thr Glu Pro Val Leu Asp Ser Asp Gly Ser Tyr Phe Met Tyr Ser
                420                 425                 430
Lys Leu Arg Val Glu Lys Lys Asn Trp Val Glu Arg Asn Ser Tyr Ser
            435                 440                 445
```

```
Cys Ser Val Val His Glu Gly Leu His Asn His His Thr Thr Lys Ser
        450                 455                 460
Phe Ser Arg Thr Pro Gly Lys
465                 470

<210> SEQ ID NO 21
<211> LENGTH: 235
<212> TYPE: PRT
<213> ORGANISM: Mus musculus

<400> SEQUENCE: 21

Met Asp Phe Leu Val Gln Ile Phe Ser Phe Leu Leu Ile Ser Ala Ser
1               5                   10                  15
Val Ile Met Ser Arg Gly Gln Ile Val Leu Ser Gln Ser Pro Thr Ile
                20                  25                  30
Leu Ser Ala Ser Pro Gly Glu Lys Val Thr Met Thr Cys Arg Ala Ser
            35                  40                  45
Ser Arg Leu Ile Tyr Met His Trp Tyr Gln Gln Lys Pro Gly Ser Ser
        50                  55                  60
Pro Lys Pro Trp Ile Tyr Ala Thr Ser Asn Leu Ala Ser Gly Val Pro
65                  70                  75                  80
Ala Arg Phe Ser Gly Ser Gly Ser Gly Thr Ser Tyr Ser Leu Thr Ile
                85                  90                  95
Ser Arg Val Glu Ala Glu Asp Ala Ala Thr Tyr Tyr Cys Gln Gln Trp
            100                 105                 110
Asn Ser Asn Pro Pro Thr Phe Gly Thr Gly Thr Lys Leu Glu Leu Lys
        115                 120                 125
Arg Ala Asp Ala Ala Pro Thr Val Ser Ile Phe Pro Pro Ser Ser Glu
130                 135                 140
Gln Leu Thr Ser Gly Gly Ala Ser Val Val Cys Phe Leu Asn Asn Phe
145                 150                 155                 160
Tyr Pro Lys Asp Ile Asn Val Lys Trp Lys Ile Asp Gly Ser Glu Arg
                165                 170                 175
Gln Asn Gly Val Leu Asn Ser Trp Thr Asp Gln Asp Ser Lys Asp Ser
            180                 185                 190
Thr Tyr Ser Met Ser Ser Thr Leu Thr Leu Thr Lys Asp Glu Tyr Glu
        195                 200                 205
Arg His Asn Ser Tyr Thr Cys Glu Ala Thr His Lys Thr Ser Thr Ser
    210                 215                 220
Pro Ile Val Lys Ser Phe Asn Arg Asn Glu Cys
225                 230                 235

<210> SEQ ID NO 22
<211> LENGTH: 46
<212> TYPE: DNA
<213> ORGANISM: Artificial Sequence
<220> FEATURE:
<223> OTHER INFORMATION: PCR primer

<400> SEQUENCE: 22
ctatagggag acccaagctg gctagcatgc tgcgtcggcg gggcag              46

<210> SEQ ID NO 23
<211> LENGTH: 66
<212> TYPE: DNA
<213> ORGANISM: Artificial Sequence
<220> FEATURE:
<223> OTHER INFORMATION: PCR primer
```

<400> SEQUENCE: 23

```
aacgggccct ctagactcga gcggccgctc aggctatttc ttgtccatca tcttctttgc    60
tgtcag                                                                66
```

<210> SEQ ID NO 24
<211> LENGTH: 21
<212> TYPE: DNA
<213> ORGANISM: Artificial Sequence
<220> FEATURE:
<223> OTHER INFORMATION: PCR primer

<400> SEQUENCE: 24

```
cgcaaatggg cggtaggcgt g                                               21
```

<210> SEQ ID NO 25
<211> LENGTH: 18
<212> TYPE: DNA
<213> ORGANISM: Artificial Sequence
<220> FEATURE:
<223> OTHER INFORMATION: PCR primer

<400> SEQUENCE: 25

```
tagaaggcac agtcgagg                                                   18
```

<210> SEQ ID NO 26
<211> LENGTH: 1815
<212> TYPE: DNA
<213> ORGANISM: Homo sapiens

<400> SEQUENCE: 26

```
atgctgcgtc ggcggggcag ccctggcatg ggtgtgcatg tgggtgcagc cctgggagca     60
ctgtggttct gcctcacagg agccctggag gtccaggtcc ctgaagaccc agtggtggca    120
ctggtgggca ccgatgccac cctgtgctgc tccttctccc ctgagcctgg cttcagcctg    180
gcacagctca acctcatctg gcagctgaca gataccaaac agctggtgca cagctttgct    240
gagggccagg accagggcag cgcctatgcc aaccgcacgg ccctcttccc ggacctgctg    300
gcacagggca acgcatccct gaggctgcag cgcgtgcgtg tggcggacga gggcagcttc    360
acctgcttcg tgagcatccg ggatttcggc agcgctgccg tcagcctgca ggtggccgct    420
ccctactcga agcccagcat gaccctggag cccaacaagg acctgcggcc aggggacacg    480
gtgaccatca cgtgctccag ctaccagggc taccctgagg ctgaggtgtt ctggcaggat    540
gggcagggtg tgccctgac tggcaacgtg accacgtcgc agatggccaa cgagcagggc    600
ttgtttgatg tgcacagcat cctgcgggtg gtgctgggtg caaatggcac ctacagctgc    660
ctggtgcgca accccgtgct gcagcaggat gcgcacagct ctgtcaccat cacaccccag    720
agaagcccca caggagccgt ggaggtccag gtccctgagg accggtggt ggccctagtg    780 ggcaccgatg ccaccctgcg ctgctccttc tcccccgagc ctggcttcag cctggcacag    840
ctcaacctca tctggcagct gacagacacc aaacagctgg tgcacagttt caccgaaggc    900
cgggaccagg gcagcgccta tgccaaccgc acggccctct cccggacct gctggcacaa    960 ggcaatgcat ccctgaggct gcagcgcgtg cgtgtggcgg acgagggcag cttcacctgc   1020
ttcgtgagca tccgggattt cggcagcgct gccgtcagcc tgcaggtggc cgctccctac   1080
tcgaagccca gcatgaccct ggagcccaac aaggacctgc ggccagggga cacggtgacc   1140
atcacgtgct ccagctaccg gggctaccct gaggctgagg tgttctggca ggatgggcag   1200
ggtgtgcccc tgactggcaa cgtgaccacg tcgcagatgg ccaacgagca gggcttgttt   1260
```

```
gatgtgcaca gcgtcctgcg ggtggtgctg ggtgcgaatg gcacctacag ctgcctggtg      1320
cgcaaccccg tgctgcagca ggatgcgcac ggctctgtca ccatcacagg gcagcctatg      1380
acattccccc cagaggccct gtgggtgacc gtggggctgt ctgtctgtct cattgcactg      1440
ctggtggccc tggctttcgt gtgctggaga aagatcaaac agagctgtga ggaggagaat      1500
gcaggagctg aggaccagga tggggaggga gaaggctcca agacagccct gcagcctctg      1560
aaacactctg acagcaaaga agatgatgga caagaaatag cctgagcggc cgccactgtg      1620
ctggatatct gcagaattcc accacactgg actagtggat ccgagctcgg taccaagctt      1680
aagtttaaac cgctgatcag cctcgactgt gccttctagt tgccagccat ctgttgtttg      1740
cccctccccc gtgccttcct tgaccctgga aggtgccact cccactgtcc tttcctaata      1800
aaatgaggaa attgc                                                      1815
```

<210> SEQ ID NO 27
<211> LENGTH: 466
<212> TYPE: PRT
<213> ORGANISM: Artificial Sequence
<220> FEATURE:
<223> OTHER INFORMATION: Heavy chain of chimeric CD30 antibody

<400> SEQUENCE: 27

Met Lys His Leu Trp Phe Phe Leu Leu Leu Val Ala Ala Pro Arg Trp
1               5                   10                  15

Val Leu Ser Gln Ile Gln Leu Gln Gln Ser Gly Pro Glu Val Val Lys
                20                  25                  30

Pro Gly Ala Ser Val Lys Ile Ser Cys Lys Ala Ser Gly Tyr Thr Phe
            35                  40                  45

Thr Asp Tyr Tyr Ile Thr Trp Val Lys Gln Lys Pro Gly Gln Gly Leu
        50                  55                  60

Glu Trp Ile Gly Trp Ile Tyr Pro Gly Ser Gly Asn Thr Lys Tyr Asn
65                  70                  75                  80

Glu Lys Phe Lys Gly Lys Ala Thr Leu Thr Val Asp Thr Ser Ser Ser
                85                  90                  95

Thr Ala Phe Met Gln Leu Ser Ser Leu Thr Ser Glu Asp Thr Ala Val
            100                 105                 110

Tyr Phe Cys Ala Asn Tyr Gly Asn Tyr Trp Phe Ala Tyr Trp Gly Gln
        115                 120                 125

Gly Thr Gln Val Thr Val Ser Ala Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

```
Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 28
<211> LENGTH: 238
<212> TYPE: PRT
<213> ORGANISM: Artificial Sequence
<220> FEATURE:
<223> OTHER INFORMATION: Light chain of chimeric CD30 antibody

<400> SEQUENCE: 28

Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Phe Asp Gly Asp Ser Tyr Met Asn Trp Tyr Gln Gln Lys Pro
    50                  55                  60

Gly Gln Pro Pro Lys Val Leu Ile Tyr Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Asp Ala Ala Thr Tyr Tyr Cys
            100                 105                 110

Gln Gln Ser Asn Gln Asp Pro Trp Thr Phe Gly Gly Gly Thr Lys Leu
        115                 120                 125

Glu Ile Lys Arg Thr Val Ala Ala Pro Ser Val Phe Ile Phe Pro Pro
    130                 135                 140
```

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 29
<211> LENGTH: 465
<212> TYPE: PRT
<213> ORGANISM: Artificial Sequence
<220> FEATURE:
<223> OTHER INFORMATION: Heavy chain of humanized CD33 antibody

<400> SEQUENCE: 29

Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
            20                  25                  30

Pro Gly Ser Ser Val Lys Val Ser Cys Lys Ala Ser Gly Tyr Thr Ile
        35                  40                  45

Thr Asp Ser Asn Ile His Trp Val Arg Gln Ala Pro Gly Gln Ser Leu
    50                  55                  60

Glu Trp Ile Gly Tyr Ile Tyr Pro Tyr Asn Gly Gly Thr Asp Tyr Asn
65                  70                  75                  80

Gln Lys Phe Lys Asn Arg Ala Thr Leu Thr Val Asp Asn Pro Thr Asn
                85                  90                  95

Thr Ala Tyr Met Glu Leu Ser Ser Leu Arg Ser Glu Asp Thr Ala Phe
            100                 105                 110

Tyr Tyr Cys Val Asn Gly Asn Pro Trp Leu Ala Tyr Trp Gly Gln Gly
        115                 120                 125

Thr Leu Val Thr Val Ser Ser Ala Ser Thr Lys Gly Pro Ser Val Phe
130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Asp Val Ser His Glu Asp
            275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
            355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
            450                 455                 460

Lys
465

<210> SEQ ID NO 30
<211> LENGTH: 238
<212> TYPE: PRT
<213> ORGANISM: Artificial Sequence
<220> FEATURE:
<223> OTHER INFORMATION: Light chain of humanized CD33 antibody

<400> SEQUENCE: 30

Met Val Leu Gln Thr Gln Val Phe Ile Ser Leu Leu Leu Trp Ile Ser
1               5                   10                  15

Gly Ala Tyr Gly Asp Ile Gln Leu Thr Gln Ser Pro Ser Thr Leu Ser
            20                  25                  30

Ala Ser Val Gly Asp Arg Val Thr Ile Thr Cys Arg Ala Ser Gln Ser
            35                  40                  45

Leu Asp Asn Tyr Gly Ile Arg Phe Leu Thr Trp Phe Gln Gln Lys Pro
    50                  55                  60

Gly Lys Ala Pro Lys Leu Leu Met Tyr Ala Ala Ser Asn Gln Gly Ser
65                  70                  75                  80

Gly Val Pro Ser Arg Phe Ser Gly Ser Gly Ser Gly Thr Glu Phe Thr
                85                  90                  95

Leu Thr Ile Ser Ser Leu Gln Pro Asp Asp Phe Ala Thr Tyr Tyr Cys
            100                 105                 110

Gln Gln Thr Lys Glu Val Pro Trp Ser Phe Gly Gln Gly Thr Lys Val
            115                 120                 125

Glu Val Lys Arg Thr Val Ala Ala Pro Ser Val Phe Ile Phe Pro Pro
            130                 135                 140

Ser Asp Glu Gln Leu Lys Ser Gly Thr Ala Ser Val Val Cys Leu Leu
145                 150                 155                 160

-continued

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 31
<211> LENGTH: 467
<212> TYPE: PRT
<213> ORGANISM: Artificial Sequence
<220> FEATURE:
<223> OTHER INFORMATION: Heavy chain of humanized CD70 antibody

<400> SEQUENCE: 31

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Lys Trp Met Gly Trp Ile Asn Thr Tyr Thr Gly Glu Pro Thr Tyr Ala
65                  70                  75                  80

Asp Ala Phe Lys Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Asp Tyr Gly Asp Tyr Gly Met Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

```
Glu Asp Pro Glu Val Lys Phe Asn Trp Tyr Val Asp Gly Val Glu Val
290                 295                 300

His Asn Ala Lys Thr Lys Pro Arg Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 32
<211> LENGTH: 238
<212> TYPE: PRT
<213> ORGANISM: Artificial Sequence
<220> FEATURE:
<223> OTHER INFORMATION: Light chain of humanized CD70 antibody

<400> SEQUENCE: 32

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Arg Ala Ser Lys Ser
        35                  40                  45

Val Ser Thr Ser Gly Tyr Ser Phe Met His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln His Ser Arg Glu Val Pro Trp Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175
```

```
Ala Leu Gln Ser Gly Asn Ser Gln Glu Ser Val Thr Glu Gln Asp Ser
            180             185             190

Lys Asp Ser Thr Tyr Ser Leu Ser Ser Thr Leu Thr Leu Ser Lys Ala
        195             200             205

Asp Tyr Glu Lys His Lys Val Tyr Ala Cys Glu Val Thr His Gln Gly
        210             215             220

Leu Ser Ser Pro Val Thr Lys Ser Phe Asn Arg Gly Glu Cys
225             230             235
```